US009511134B2

(12) United States Patent
Alexander et al.

(10) Patent No.: US 9,511,134 B2
(45) Date of Patent: Dec. 6, 2016

(54) INDUCING IMMUNE RESPONSES TO INFLUENZA VIRUS USING POLYPEPTIDE AND NUCLEIC ACID COMPOSITIONS

(75) Inventors: Jeffery L. Alexander, San Diego, CA (US); Pamuk A. Bilsel, San Diego, CA (US); Mark J. Newman, Duluth, GA (US)

(73) Assignee: Epimmune Inc., San Diego, CA (US)

( * ) Notice: Subject to any disclaimer, the term of this patent is extended or adjusted under 35 U.S.C. 154(b) by 235 days.

(21) Appl. No.: 11/802,106

(22) Filed: May 18, 2007

(65) Prior Publication Data
US 2008/0032921 A1   Feb. 7, 2008

Related U.S. Application Data

(60) Provisional application No. 60/801,065, filed on May 18, 2006, provisional application No. 60/838,859, filed on Aug. 21, 2006.

(51) Int. Cl.
| | |
|---|---|
| A61K 39/145 | (2006.01) |
| A61K 39/12 | (2006.01) |
| A61K 39/39 | (2006.01) |
| A61K 39/385 | (2006.01) |
| C07K 14/005 | (2006.01) |
| A61K 39/00 | (2006.01) |

(52) U.S. Cl.
CPC ............. *A61K 39/145* (2013.01); *A61K 39/12* (2013.01); *A61K 39/385* (2013.01); *A61K 39/39* (2013.01); *C07K 14/005* (2013.01); *A61K 2039/53* (2013.01); *A61K 2039/545* (2013.01); *A61K 2039/55505* (2013.01); *A61K 2039/55566* (2013.01); *A61K 2039/605* (2013.01); *A61K 2039/627* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| 6,534,482 B1 * | 3/2003 | Fikes et al. .................. 514/44 |
| 7,202,351 B1 | 4/2007 | Sette |
| 2004/0157780 A1 | 8/2004 | Grey et al. |
| 2007/0184526 A1 | 8/2007 | Smith et al. |
| 2007/0269456 A1 | 11/2007 | Lasher et al. |
| 2008/0003239 A1 * | 1/2008 | Duke et al. .............. 424/206.1 |
| 2008/0032921 A1 | 2/2008 | Alexander et al. |

FOREIGN PATENT DOCUMENTS

| JP | 10-298198 A | 11/1998 |
| WO | WO 94/26903 A2 | 11/1994 |
| WO | WO 95/07707 | 3/1995 |
| WO | WO 99/58658 A2 | 11/1999 |
| WO | WO 01/00225 A1 | 1/2001 |
| WO | WO 01/47541 A1 | 7/2001 |
| WO | WO 02/083714 A2 | 10/2002 |
| WO | WO 2004/031210 A2 | 4/2004 |
| WO | WO 2006/071990 A2 | 7/2006 |
| WO | WO 2007/011904 * | 1/2007 |

OTHER PUBLICATIONS

Fomsgaard et al., Induction of cytotoxic T-cell resposnes by gene gun DNA vaccination with minigenes encoding influenza A virus HA and NP CTL-epitopes, 2000, Vaccine, vol. 18, pp. 681-691.*
Dos Santos Afonso et al., The generation of recombinant influenza A viruses expressing a PB2 fusion protein requires the conservation of a packaging signal overlapping the coding and noncoding regions at the 5V end of the PB2 segment, 2005, Virology, vol. 341, pp. 34-46.*
Heinen et al., Vaccination of pigs with a DNA construct expressing an influenza virus M2-nucleoprotein fusion protein exacerbates disease after challenge with influenza A virus, 2002, Journal of General Virology, vol. 83, pp. 1851-1859.*
Neirynck et al., A universal influenza A vaccine based on the extracellular domain of the M2 protein, 1999, Nature Medicine, vol. 5, No. 10, pp. 1157-1163.*
GenBank Acession # AAA43325, Matrix protein, Oct. 16, 1993.*
Thompson,W.W., et al., "Mortality associated with influenza and respiratory syncytial virus in the United States", *JAMA* 289:179-186 American Medical Association (2003).
Nguyen-Van-Tam, J.S., et al., "The epidemiology and clinical impact of pandemic influenza", *Vaccine* 21:1762-1768 L.R. Printing Services. Ltd. (2003).
*The Lancet Infectious Diseases* 4:595 Elsevier B.V. (2004).
Nicholson, K.G., et al., "Safety and antigenicity of non-adjuvanted and MF59-adjuvanted influenza A/Duck/Singapore/97 (H5N3) vaccine: a randomised trial of two potential vaccines against H5N1 influenza", *Lancet* 357:1937-1943 Lancet Publishing Group (2001).
Treanor, J.J., et al., "Safety and immunogenicity of a recombinant hemagglutinin vaccine for H5 influenza in humans", *Vaccine* 19:1732-1737 L.R. Printing Services. Ltd. (2001).
Potter, C.W., "A history of influenza", *J Appl. Microbial.* 91:572-579 Blackwell Publishing (2001).
Hilleman, M.R., "Realities and enigmas of human viral influenza: pathogenesis, epidemiology and control", *Vaccine* 20:3068-3087 L.R. Printing Services. Ltd. (2002).
Stevens, J., et al., "Structure of the uncleaved human H1 hemagglutinin from the extinct 1918 influenza virus," *Science* 312:404 American Association for the Advancement of Science (2006).

(Continued)

Primary Examiner — Benjamin P Blumel
(74) Attorney, Agent, or Firm — Sterne, Kessler, Goldstein & Fox P.L.L.C.

(57) ABSTRACT

The present invention provides polynucleotides and polypeptides capable of enhancing the immune response of a human in need of protection against influenza virus infection by administering in vivo, into a tissue of the human, at least one polynucleotide comprising one or more regions of nucleic acid encoding an influenza protein or a fragment, variant, or derivative thereof, or at least one polypeptide encoded therefrom. The present invention also relates to identifying and preparing influenza virus epitopes and to polynucleotides and polypeptides comprising such influenza virus epitopes. The present invention also relates to compositions and methods of use in the prevention and treatment of influenza virus infection.

7 Claims, 14 Drawing Sheets

(56) References Cited

OTHER PUBLICATIONS

Gust, I.D., et al., "Planning for the next pandemic of influenza" *Rev. Med. Virol. 11*:59-70 John Wiley and Sons (2001).
Oxford, J.S., "Influenza A pandemics of the 20th century with special reference to 1918: virology, pathology and epidemiology", *Rev. Med. Viral. 10*:119-133 John Wiley and Sons (2000).
Laver, G., et al., "Pandemic influenza: its origin and control" *Microbes.Infect. 4*:1309-1316 Institut Pasteur (2002).
Tollis, M., et al., "Recent developments in avian influenza research: epidemiology and immunoprophylaxis", *Vet. J. 164*:202-215 Elsevier Ltd. (2002).
Stevens, J., et al., "Structure and receptor specificity of the hemagglutinin from an H5N1 influenza virus," *Science 303*:1866 American Association for the Advancement of Science (2004).
Wood, J.M.,et al., "From lethal virus to life-saving vaccine: developing inactivated vaccines for pandemic influenza", *Nat. Rev. Microbiol. 2*:842-847 Nature Publishing Group (2004).
Yewdell, J.W., et al., "Antigenic variation in three distinct determinants of an influenza type A haemagglutinin molecule", *Nature 279*:246-248 Nature Publishing Group (1979).
Stephenson, I., et al., "Confronting the avian influenza threat: vaccine development for a potential pandemic", *The Lancet Infectious Diseases 4*:499-509 Elsevier B.V. (2004).
Kurtz, J., et al., "Avian influenza virus isolated from a woman with conjunctivitis", *Lancet 348*:901-902 Lancet Publishing Group (1996).
Peiris, M., et al., "Human infection with influenza H9N2", *Lancet 354*:916-917 Lancet Publishing Group (1999).
Scholtissek, C., et al., "On the origin of the human influenza virus subtypes H2N2 and H3N2", *Virology 87*:13-20 Academic Press (1978).
Wells, M.A., et al., "Recovery from a viral respiratory infection, II. Passive transfer of immune spleen cells to mice with influenza pneumonia", *J. Immunol. 126*:1042-1046 The American Association of Immunologists (1981).
Yap, K.L., et al., "Cytotoxic T cells in the lungs of mice infected with an influenza A virus", *Scand. J. Immunol. 7*:73-80 Blackwell Science Ltd. (1978).
Mackenzie, C.D., et al., "Rapid recovery of lung histology correlates with clearance of influenza virus by specific CD8+ cytotoxic T cells", *Immunology 67*:375-381 Blackwell Scientific Publishers (1989).
Taylor, P.M., et al., "Influenza nucleoprotein-specific cytotoxic T-cell clones are protective in vivo", *Immunology 58*:417-420 Blackwell Scientific Publishers (1986).
Stephenson, I., et al., "Safety and antigenicity of whole virus and subunit influenza A/Hong Kong/1073/99 (H9N2) vaccine in healthy adults: phase I randomised trial", *Lancet 362*:1959-1966 Lancet Publishing Group (2003).
Kuwano, K., et al., "Cross-reactive protection against influenza A virus infections by an NS1-specific CTL clone", *Virology 178*:174-179 Academic Press (1990).
Sambhara, S., et al., "Heterosubtypic immunity against human influenza A viruses, including recently emerged avian H5 and H9 viruses, induced by FLU-ISCOM vaccine in mice requires both cytotoxic T-lymphocyte and macrophage function", *Cell Immunol. 211*:143-153 Elsevier Inc. (2001).
Okuda, K., et al., "Protective immunity against influenza A virus induced by immunization with DNA plasmid containing influenza M gene", *Vaccine 19*:3681-3691 L.R. Printing Services. Ltd. (2001).
Bender, B.S., et al., "Transgenic mice lacking class I major histocompatibility complex-restricted T cells have delayed viral clearance and increased mortality after influenza virus challenge", *J. Exp. Med. 175*:1143-1145 Rockefeller University Press (1992).
Hehme, N., et al., "Pandemic preparedness: lessons learnt from H2N2 and H9N2 candidate vaccines", *Med. Microbiol. Immunol. 191*:203-208 Springer (2002).
Fu, T.M., et al., "Dose dependence of CTL precursor frequency induced by a DNA vaccine and correlation with protective immunity against influenza virus challenge", *J. Immunol. 162*:4163-4170 The American Association of Immunologists (1999).
Ulmer, J.B., et al., "Protective CD4+ and CD8+ T cells against influenza virus induced by vaccination with nucleoprotein DNA", *J. Virol. 72*:5648-5653 American Society for Microbiology (1998).
Epstein, S.L., et al.,. "Vaccination with DNA encoding internal proteins of influenza virus does not require CD8(+) cytotoxic T lymphocytes: either CD4(+) or CD8(+) T cells can promote survival and recovery after challenge", *Int. Immunol 12*:91-101 (2000).
Langlade-Demoyen, P., et al., "Role of T cell help and endoplasmic reticulum targeting in protective CTL response against influenza virus", *Eur. J. Immunol. 33*:720-728 Oxford University Press (2003).
Anker, W.J., et al., "Cross-protection in mice after immunization with H2N2, H3N2, and H2N2 influenza virus strains", *Infect. Immun. 21*:96-101 VCH Verlagsgesellschaft mbH(1978).
Schulman, J.L., et al., "Induction of partial specific heterotypic immunity in mice by a single infection with influenza A virus", *J. Bacteriol. 89*:170-174 American Society for Microbiology (1965).
Benton, K.A., et al., "Heterosubtypic immunity to influenza A virus in mice lacking IgA, all Ig, NKT cells, or gamma delta T cells", *J. Immunol. 166*:7437-7445 The American Association of Immunologists (2001).
O'Neill, E., et al., "Heterologous protection against lethal A/HongKong/156/97 (H5N1) influenza virus infection in C57BL/6 mice", *J. Gen. Virol. 81*:2689-2696 Society for General Microbiology (2000).
Epstein, S.L., et al., "DNA vaccine expressing conserved influenza virus proteins protective against H5N1 challenge infection in mice", *Emerg. Infect. Dis. 8*:796-801 Medscape (2002).
Nguyen, H.H., et al., "Heterosubtypic immunity to lethal influenza A virus infection is associated with virus-specific CD8(+) cytotoxic T lymphocyte responses induced in mucosa-associated tissues", *Virology 254*:50-60 Academic Press (1999).
Lukacher, A.E., et al., "In vivo effector function of influenza virus-specific cytotoxic T lymphocyte clones is highly specific", *J. Exp. Med. 160*:814-826 Rockefeller University Press (1984).
Liang, S., et al., "Heterosubtypic immunity to influenza type A virus in mice. Effector mechanisms and their longevity", *J. Immunol. 152*:1653-1661 The American Association of Immunologists (1994).
Tumpey, T.M., et al., "Mucosal delivery of inactivated influenza vaccine induces B-cell-dependent heterosubtypic cross-protection against lethal influenza A H5N1 virus infection", *J. Virol. 75*:5141-5150 American Society for Microbiology (2001).
McMichael, A.J., et al., "Cytotoxic T-cell immunity to influenza", *N. Engl. J. Med. 309*:13-17 (1983).
Sonoguchi, T., et al., "Cross-subtype protection in humans during sequential, overlapping, and/or concurrent epidemics caused by H3N2 and H1N1 influenza viruses", *J. Infect. Dis. 151*:81-88 (1985).
Voeten, J.T., et al., "Antigenic drift in the influenza A virus (H3N2) nucleoprotein and escape from recognition by cytotoxic T lymphocytes", *J. Virol. 74*:6800-6807 American Society for Microbiology (2000).
Kashiwagi, T., et al., "Emergence of new influenza A viruses which carry an escape mutation of the HLA-B27-restricted CTL epitope of NP in Japan", *Microbiol. Immunol 44*:867-870 center for Academic Publications Japan (2000).
Boon, A.C., et al., "Sequence variation in a newly identified HLA-B35-restricted epitope in the influenza A virus nucleoprotein associated with escape from cytotoxic T lymphocytes", *J. Virol. 76*:2567-2572 American Society for Microbiology (2002).
Treanor, J.J., et al., "Passively transferred monoclonal antibody to the M2 protein inhibits influenza A virus replication in mice", *J. Virol. 64*:1375-1377 American Society for Microbiology (1990).
Frace, A.M., et al., "Modified M2 proteins produce heterotypic immunity against influenza A virus", *Vaccine 17*:2237-2244 L.R. Printing Services. Ltd. (1999).
Neirynck, S., et al., "A universal influenza A vaccine based on the extracellular domain of the M2 protein", *Nat. Med. 5*:1157-1163 Nature Publishing Group (1999).

(56) References Cited

OTHER PUBLICATIONS

Jegerlehner, A., et al., "Influenza A vaccine based on the extracellular domain of M2: Weak protection mediated via antibody-dependent NK cell activity", *J Immunol.* 172:5598-5605 The American Association of Immunologists (2004).

Fiers, W., et al., "A universal human influenza A vaccine", *Virus Res.* 103:173-176 Elsevier B.V. (2004).

Liu, W., et al., "Monoclonal antibodies recognizing EVETPIRN epitope of influenza A virus M2 protein could protect mice from lethal influenza A virus challenge", *Immunol. Lett.* 93:131-136 Elsevier B.V. (2004).

Fan, J., et al., "Preclinical study of influenza virus A M2 peptide conjugate vaccines in mice, ferrets, and rhesus monkeys", *Vaccine* 22:2993-3003 L.R. Printing Services. Ltd. (2004).

Jameson, J., et al., "Human CD8+ and CD4+ T lymphocyte memory to influenza A viruses of swine and avian species", *J. Immunol.* 162:7578-7583 The American Association of Immunologists (1999).

Jameson, J., et al., "Human cytotoxic T-lymphocyte repertoire to influenza A viruses", *J. Virol.* 72:8682-8689 American Society for Microbiology (1998).

Gianfrani, C., et al., "Human memory CTL response specific for influenza A virus is broad and multispecific", *Human Immunol.* 61:438-452 Elsevier B.V. (2000).

Boon, A.C., et al., "The magnitude and specificity of influenza A virus-specific cytotoxic T-lymphocyte responses in humans is related to HLA-A and -B phenotype", *J. Virol.* 76:582-590 American Society for Microbiology (2002).

Liu, M.A, "DNA vaccines: a review", *J. Intern. Med.* 253:402-410 Blackwell Publishing (2003).

Gurunathan, S., et al., "DNA vaccines: immunology, application, and optimization", *Annu. Rev. Immunol* 18:927-974 Annual Reviews (2000).

Calarota, S.A., et al., "Immune responses in asymptomatic HIV-1-infected patients after HIV-DNA immunization followed by highly active antiretroviral treatment", *J. Immunol.* 163:2330-2338 The American Association of Immunologists (1999).

Roy, M.J., et al., "Induction of antigen-specific CD8+ T cells, T helper cells, and protective levels of antibody in humans by particle-mediated administration of a hepatitis B virus DNA vaccine", *Vaccine* 19:764-778 L.R. Printing Services. Ltd. (2000).

Ugen, K.E., et al., "DNA vaccination with HIV-1 expressing constructs elicits immune responses in humans", *Vaccine* 16:1818-1821 L.R. Printing Services. Ltd. (1998).

Calarota, S.A., et al., "Gene combination raises broad human immunodeficiency virus-specific cytotoxicity", *Human Gene Therapy* 12:1623-1637 Mary Ann Liebert, Inc. (2001).

Wang, R., et al., "Induction of CD4(+) T cell-dependent CD8(+) type 1 responses in humans by a malaria DNA vaccine", *Proc. Natl. Acad. Sci. USA* 98:10817-10822 National Academy of Sciences (2001).

Sette, A., et al., "Optimizing vaccine design for cellular processing, MHC binding and TCR recognition", *Tissue Antigens* 59:443-451 Blackwell Publishing (2002).

Livingston, B., et al., "A Rational Strategy to Design Multiepitope Immunogens Based on Multiple TH Lymphocyte Epitopes", *J. Immunol.* 168:5499-5506 The American Association of Immunologists (2002).

Ishioka, G.Y., et al., "Utilization of MHC class I transgenic mice for development of minigene DNA vaccines encoding multiple HLA-restricted CTL epitopes", *J Immunol.* 162:3915-3925 The American Association of Immunologists (1999).

Livingston, B.D., et al., "Optimization of epitope processing enhances immunogenicity of multiepitope DNA vaccines", *Vaccine* 19:4652-4660 L.R. Printing Services. Ltd. (2001).

Alila, H., et al., "Expression of biologically active human insulin-like growth factor-I following intramuscular injection of a formulated plasmid in rats", *Human Gene Therapy* 8:1785-1795 Mary Ann Liebert, Inc. (1997).

Anwer, K., et al., "Synergistic Effect of Formulated Plasmid and Needle-Free Injection for Genetic Vaccines", *Pharm. Res.* 16:889-95 Plenium Publishing Corporation (1999).

Mumper, R.J., et al., "Polyvinyl derivatives as novel interactive polymers for controlled gene delivery to muscle", *Pharm. Res.* 13:701-709 Plenium Publishing Corporation (1996).

Mumper, R.J., et al., "Protective interactive noncondensing (PINC) polymers for enhanced plasmid distribution and expression in rat skeletal muscle", *J. Contr. Rel.* 52:191-203 (1998).

Lu, X., et al., "A mouse model for the evaluation of pathogenesis and immunity to influenza A (H5N1) viruses isolated from humans", *J. Virol.* 73:5903-5911 American Society for Microbiology (1999).

Katz, J.M., et al., "Pathogenesis and immunity to avian influenza A H5 viruses", *Biomed. Pharmacother.* 54:178-187 Elsevier B.V. (2000).

Vitiello, A., et al., "Analysis of the HLA-restricted influenza-specific cytotoxic T lymphocyte response in transgenic mice carrying a chimeric human-mouse class I major histocompatibility complex", *J. Exp. Med.* 173:1007-15 Rockefeller University Press (1991).

Alexander, J., et al., "Derivation of HLA-A11/Kb transgenic mice: functional CTL repertoire and recognition of human A11-restricted CTL epitopes", *J. Immunol.* 159:4753-4761 The American Association of Immunologists (1997).

Alexander, J., et al., "Derivation of HLA-B*0702 transgenic mice: functional CTL repertoire and recognition of human B*0702-restricted CTL epitopes", *Human Immunol* 64:211-223 Elsevier B.V. (2003).

Alexander, J., et al., "A decaepitope polypeptide primes for multiple CD8+ IFN-gamma and Th lymphocyte responses: evaluation of multiepitope polypeptides as a mode for vaccine delivery", *J. Immunol.* 168:6189-6198 The American Association of Immunologists (2002).

Wall, K.A., et al., "A disease-related epitope of *Torpedo* acetylcholine receptor. Residues involved in I-Ab binding, self-nonself discrimination, and TCR antagonism", *J. Immunol.* 152:4526-4536 The American Association of Immunologists (1994).

Townsend, A., et al., "Antigen recognition by class I-restricted T lymphocytes", *Annu. Rev. Immunol.* 7:601-624 Annual Reviews (1989).

Germain, R.N., et al., "The biochemistry and cell biology of antigen processing and presentation", *Annu. Rev. Immunol.* 11:403-450 Annual Reviews (1993).

Sette, A., et al., "Chemistry of peptide interactions with MHC proteins", *Current Opinion in Imunology* 4:79-86 Elsevier Ltd. (1992).

Sinigaglia, F., et al., "Defining rules for the peptide-MHC class II interaction", *Current Opinion in Immunology.* 6:52-56 Elsevier Ltd. (1994).

Engelhard,V.H., "Structure of peptides associated with MHC class I molecules", *Current Opinion in Immunology.* 6:13-23 Elsevier Ltd. (1994).

Brown, K., et al., "Three-dimensional structure of the human class II histocompatibility antigen HLA-DR1", *Nature* 364:33-39 Nature Publishing Group (1993).

Guo, H.C., et al., "Comparison of the P2 specificity pocket in three human histocompatibility antigens: HLA-A*6801, HLA-A*0201, and HLA-B*2705", *Proc. Nat. Acad. Sci. USA* 90:8053-8057 National Academy of Sciences (1993).

Guo, H.C., et al., "Different length peptides bind to HLA-Aw68 similarly at their ends but bulge out in the middle", *Nature* 360:364-366 Nature Publishing Group (1992).

Silver, M.L., et al., "Atomic structure of a human MHC molecule presenting an influenza virus peptide", *Nature* 360:367-369 Nature Publishing Group (1992).

Ressing, M.E., et al., "Detection of T helper responses, but not a f human papillomavirus-specific cytotoxic T lymphocyte responses, after peptide vaccination of patients with cervical carcinoma", *J. Immunother.* 23:255-266 Lippincott Williams & Wilkens (2000).

Madden, D.R., et al., "The three-dimensional structure of HLA-B27 at 2.1 A resolution suggests a general mechanism for tight peptide binding to MHC" *Cell* 70:1035-1048 Elsevier Inc.(1995).

(56) References Cited

OTHER PUBLICATIONS

Claas, E.C., et al., "Human influenza a H5N1 virus related to a highly pathogenic avian influenza virus" *Lancet 351*:472-477 Lancet Publishing Group (1998).
Saper, M., et al., "Refined structure of the human histocompatibility antigen HLA-A2 at 2.6 A resolution", *J. Mol. Biol. 219*:277-319 Academic Press (1991).
Ruppert, J., et al., "Prominent role of secondary anchor residues in peptide binding to HLA-A2.1 molecules", *Cell 74*:929-37 Elsevier Inc. (1993).
Parker, K.C., et al., "Scheme for ranking potential HLA-A2 binding peptides based on independent binding of individual peptide sidechains", *J. Immunol. 152*:163-175 The American Association of Immunologists (1994).
De Groot, A.S., et al., "From genome to vaccine: in silico predictions, ex vivo verification," *Vaccine 19*:4385-4395 L.R. Printing Services. Ltd. (2001).
Schueler-Furman, O., et al., "Structure-based prediction of binding peptices to MHC class I molecules: Application to a broad range of MHC alleles", *Protein Science 9*:1838-1846 (2000).
Meister, G.E., et al., "Two novel T cell epitope prediction algorithms based on MHC-binding motifs; comparison of predicted and published epitopes from Mycobacterium tuberculosis and HIV protein sequences", *Vaccine 13*:581-591 L.R. Printing Services. Ltd. (1995).
Bhasin, M., et al., "Prediction of CTL epitopes using QM, SVM and ANN techniques", *Vaccine 22*:3195-3204 L.R. Printing Services. Ltd. (2004).
Altuvia, Y., et al., "Ranking potential binding peptides to MHC molecules by a computational threading approach", *J. Mol. Biol. 249*:244-250 Academic Press (1995).
Wilson, C., et al., "Development of a DNA Vaccine Designed to Induce Cytotoxic T Lymphocyte Responses to Multiple Conserved Epitopes in HIV-1", *J. Immunol. 171*:5611-5623 The American Association of Immunologists (2003).
Gulukota, K., et al., "Two complementary methods for predicting peptide binding major histocompatibility complex molecules", *J. Mol. Biol. 267*:1258-1267 Academic Press(1997).
Kubo, R.T., et al., "Definition of specific peptide motifs for four major HLA-A alleles", *J. Immunol. 152*:3913-24 The American Association of Immunologists (1994).
Threlkeld, S.C., et al., "Degenerate and promiscuous recognition by CTL of peptides presented by the MHC class I A3-like superfamily—Implications for vaccine development", *J. Immunol. 159*:1648-1657 The American Association of Immunologists (1997).
Sidney, J., et al., "Definition of an HLA-A3-like supermotif demonstrates the overlapping peptide-binding repertoires of common HLA molecules", *Human Immunol. 45*:79-93 Elsevier B.V. (1996).
Sette, A., et al., "Nine major HLA class I supertypes account for the vast preponderance of HLA-A and -B polymorphism", *Immunogenetics 50*(3-4): 201-212 Springer (1999).
Sidney, J., et al., "Specificity and degeneracy in peptide binding to HLA-B7-like class I molecules", *J. Immunol. 157*:3480-3490 The American Association of Immunologists (1996).
Del Guercio, M.F., et al., "Binding of a peptide antigen to multiple HLA alleles allows definition of an A2-like supertype" *J. Immunol. 54*:685-693 The American Association of Immunologists (1995).
Fruci, D., et al., "Anchor residue motifs of HLA class-I-binding peptides analyzed by the direct binding of synthetic peptides to HLA class I alpha chains", *Human Immunol. 38*:187-192 (1993).
Bertoni, R., et al., "Human histocompatibility leukocyte antigen-binding supermotifs predict broadly cross-reactive cytotoxic T lymphocyte responses in patients with acute hepatitis", *J. Clin. Invest. 100*:503-513 American Association for Clinical Investigation (1997).
Khanna, R., et al., "Hierarchy of Epstein-Barr virus-specific cytotoxic T-cell responses in individuals carrying different subtypes of an HLA allele: Implications for epitope-based antiviral vaccines", *J. Virol. 71*:7429-7435 American Society for Microbiology (1997).
Bertoletti, A., et al., "Molecular features of the hepatitis B virus nucleocapsid T-cell epitope 18-27: interaction with HLA and T-cell receptor", *Hepatology 26*:1027-1034 Wiley (1997).
Fleischhauer, K., et al., "Multiple HLA-A alleles can present an immunodominant peptide of the human melanoma antigen Melan-A/MART-1 to a peptide-specific HLA-A*0201+ cytotoxic T cell line", *J. Immunol. 157*:787-297 The American Association of Immunologists (1996).
Kawashima, I., et al., "The multi-epitope approach for immunotherapy for cancer: Identification of several CTL epitopes from various tumor-associated antigens expressed on solid epithelial tumors", *Human Immunol. 59*:1-14 Elsevier B.V. (1998).
Wang, R.F., et al., "Recognition of an antigenic peptide derived from tyrosinase-related protein-2 by CTL in the context of HLA-A31 and -A33", *J. Immunol. 160*:890-897 The American Association of Immunologists (1998).
Southwood, S., et al., "Several Common HLA-DR Types Share Largely Overlapping Peptide Binding Repertoires", *J. Immunol. 160*:3363-3373 The American Association of Immunologists (1998).
Schaeffer, E.B., et al., "Relative contribution of "determinant selection" and "holes in the T-cell repertoire" to T-cell responses", *Proc. Nat. Acad. Sci. USA 86*:4649-4653 National Academy of Sciences (2000).
Currier, J.R., et al., "A panel of MHC class I restricted viral peptides for use as a quality control for vaccine trial ELISPOT assays", *J. Immunological Meth. 260*:157-172 Elsevier B.V. (2002).
Bartlett, J.A., et al., "Safety and immunogenicity of an HLA-based HIV envelope polyvalent synthetic peptide immunogen DATRI 010 study group. Division of AIDS Treatment Research Inititive", *AIDS 12*:1291-1300 Lippincott Williams & Wilkens (1998).
Pinto, L.A., et al., "HIV-specific immunity following immunization with HIV synthetic envelope peptides in asymptomatic HIV-infected patients", *AIDS 13*:2003-2012 Lippincott Williams & Wilkens (1999).
Gahéry-Ségard, H., et al., "Multiepitopic B- and T-cell responses induced in humans by a human immunodeficiency virus type 1 lipopeptide vaccine", *J. Virol. 74*:1694-1703 American Society for Microbiology (2000).
Serwold, T., et al., "Specific Proteolytic Cleavages Limit the Diversity of the Pool of Peptides Available to MHC Class I Molecules in Living Cells", *J. Immunol. 162*:4712-4719 The American Association of Immunologists (1999).
Shastri, N., et al., "Presentation of endogenous peptide/MHC class I complexes is profoundly influenced by specific C-terminal flanking residues", *J. Immunol. 155*:4339-4346 The American Association of Immunologists (1995).
Chou, K.C., "Prediction of tight turns and their types in proteins", *Anal. Biochem. 286*:1-16 Elsevier Science (2000).
Davis, N.L., et al., "Alphavirus replicon particles as candidate HIV Vaccines", *IUBMB Life 53*:209-211 Informa Healthcare (2002).
Lee, J.S., et al., "Immune protection against Staphylococcal enterotoxin-induced toxic shock by vaccination with a Venezuelan Equine Encephalitis virus replicon", *J. Infec. Dis. 185*:1192-1196 University of Chicago Press (2002).
Hevey, M., et al., "Marburg virus vaccines: comparing classical and new approaches", *Vaccine 20*:586-593 L.R. Printing Services. Ltd. (2002).
Pratt, W.D., et al., "Genetically engineered, live attenuated vaccines for Venezuelan equine encephalitis: testing in animal models. 2003", *Vaccine 21*:3854-3862 L.R. Printing Services. Ltd. (2003).
Gipson, C.L., et al., "Evaluation of Venezuelan Equine Encephalitis (VEE) replicon-based outer surface protein a (OspA) vaccines in a tick challenge mouse model of Lyme disease", *Vaccine 21*:3875-3884 L.R. Printing Services. Ltd. (2003).
Nelson, E.L., et al., "Venezuelan equine encephalitis replicon immunization overcomes intrinsic tolerance and elicits effective anti-tumor immunity to the 'self' tumor-associated antigen, neu in a rat mammary tumor model", *Breast Cancer Research and Treatment 82*:169-183 Springer (2003).
Leitner, W.W., et al., "Alphavirus-based DNA vaccine breaks immunological tolerance by activating innate antiviral pathways", *Nat. Med. 9*:33-39 Nature Publishing Group (2003).

(56) References Cited

OTHER PUBLICATIONS

Leitner, W.W., et al., "Apoptosis is essential for the increased efficacy of alphaviral replicase-based DNA vaccines", *Vaccine* 22:1537-1544 L.R. Printing Services. Ltd. (2004).
Garland, S.M., "Imiquimod", *Curr. Opin. Infect. Dis.* 16:85-89 Lippincott Williams & Wilkens (2003).
Hehme, N., H. et al., "Immunogenicity of a monovalent, aluminum-adjuvanted influenza whole virus vaccine for pandemic use", *Virus Res.* 103:163-171 Thomson Scientific (2004).
Crotty, S., et al., "Tracking human antigen-specific memory B cells: a sensitive and generalized ELISPOT system", *J. Immunological Meth.* 286:111-122 Elsevier B.V. (2004).
Fritz, J.H., et al., "The artificial antimicrobial peptide KLKLLLLLKLK induces predominantly a TH2-type immune response to co-injected antigens", *Vaccine* 22:3274-3284 L.R. Printing Services. Ltd. (2004).
Alexander, J., et al. "Development of high potency universal DR-restricted helper epitopes by modification of high affinity DR-blocking peptides", *Immunity.* 1:751-761 Elsevier Inc. (1994).
del Guercio, M.F., et al., "Potent immunogenic short linear peptide constructs composed of B cell epitopes and Pan DR T helper epitopes (PADRE®) for antibody responses in vivo", *Vaccine* 15:441-448 L.R. Printing Services. Ltd. (1997).
Alexander, J., et al., "Development of experimental carbohydrate-conjugate vaccines composed of *Streptococcus pneumoniae* capsular polysaccharides and the universal helper T-lymphocyte epitope (PADRE®)", *Vaccine* 22:2362-2367 L.R. Printing Services. Ltd. (2004).
Rosa, D.S., et al., "The pan HLA DR-binding epitope improves adjuvant-assisted immunization with a recombinant protein containing a malaria vaccine candidate", *Immunol. Lett.* 92:259-268 Elsevier B.V. (2004).
Vichier-Guerre, S., et al., "Induction of carbohydrate-specific antibodies in HLA-DR transgenic mice by a synthetic glycopeptide: a potential anti cancer vaccine for human use", *J. Peptide Res.* 62:117-124 Blackwell Publishing (2003).
International Search Report and Written Opinion of the International Search Authority issued on Jun. 26, 2008 for Intl. Appl. No. PCT/US07/11900, filed May 18, 2007.
Zhang et al., "Th-Cytotoxic T-Lymphocyte Chimeric Epitopes Extended by N-Palmitoyl Lysines Induce Herpes Simplex Virus Type 1-Specific Effector CD8+ Tc1 Responses and Protect against Ocular Infection," *J. of Virology* 79:15289-15301 American Society for Microbiology (2005).
Heinen et al., "Vaccination of pigs with a DNA construct expressing an influenza virus M2-nucleoprotein fusion protein exacerbates disease after challenge with influenza A virus," *J. of General Virology* 83:1851-1859 The Society for General Microbiology (2002).
Supplemental Search Report for European Application No. EP 07 86 7125, The Hague, Netherlands, completed on Sep. 7, 2010, 7 pages.
Gerhard et al., "Prospects for Universal Influenza Virus Vaccine," *Emerging Infectious Diseases*, vol. 12, No. 4, Apr. 2006, pp. 569-574.
Yuan, J., et al., "Langerhans Cells Derived from Genetically Modified Human CD34[+] Hemopoietic Progenitors Are More Potent Than Peptide-Pulsed Langerhans Cells for Inducing Antigen-Specific CD8[+] Cytolytic T Lymphocyte Responses," *The Journal of Immunology* 174:758-766, The American Association of Immunologists, Inc., United States (2005).
Beveridge, W.I.B., "The Chronicle of Influenza Epidemics," *Hist. Philos. Life Sci.* 13:223-234, Taylor and Francis, England (1991).
Cusi, M.G., "Applications of Influenza Virosomes as a Delivery System," *Hum. Vaccin.* 2:1-7, Landes Bioscience, United States (2006).
English language Abstract of Japanese Patent Publication No. 10-298198 A, Japanese Patent Office, Patent & Utility Model Gazette DB, Patent Abstract of Japan (1998).
Fremont, D.H., et al., "Crystal Structures of Two Viral Peptides in Complex with Murine MHC Class I H-2K$^b$," *Science* 257:919-927, American Association for the Advancement of Science, United States (1992).
Gorman, O.T., et al., "Evolutionary Processes in Influenza Viruses: Divergence, Rapid Evolution, and Stasis," *Curr. Top Microbiol. Immunol.* 176:75-97, Springer Verlag, Germany (1992).
Heinen, Paul P., et al., "Vaccination of pigs with a DNA construct expressing an influenza virus M2-nucleoprotein fusion protein exacerbates disease after challenge with influenza A virus," *Journal of General Virology* 83: 1851-1859 (2002).
Hoelscher, M.A., et al., "Development of adenoviral-vector-based pandemic influenza vaccine against antigenically distinct human H5N1 strains in mice," *The Lancet* 367:475-481, Elsevier Ltd., The Netherlands (2006).
Jurk, M., et al., "Human TLR7 or TLR8 independently confer responsiveness to the antiviral compound R-848," *Nat. Immunol.* 3:499, Nature America Inc., United States (2002).
Kuwano, K., et al., "HA2 Subunit of Influenza A H1 and H2 Subtype Viruses Induces a Protective Cross-Reactive Cytotoxic T Lymphocyte Response," *J Immunol.* 140:1264-1268, American Association of Immunologists, United States (1988).
Liu, W., et al., "Monoclonal antibodies recognizing EVETPIRN epitope of influenza A virus M2 protein could protect mice from lethal influenza A virus challenge," *Immunol. Lett.* 93:131-136, Elsevier/North-Holland Biomedical Press, The Netherlands (2004).

\* cited by examiner

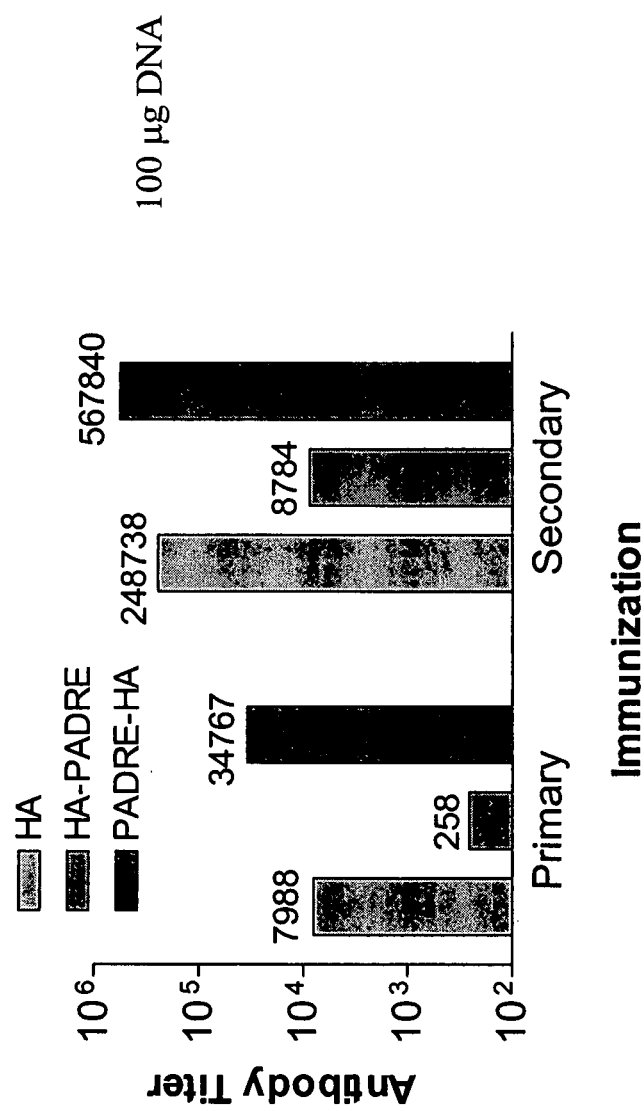
Figure 1. PADRE increases HA-Specific Antibody Responses

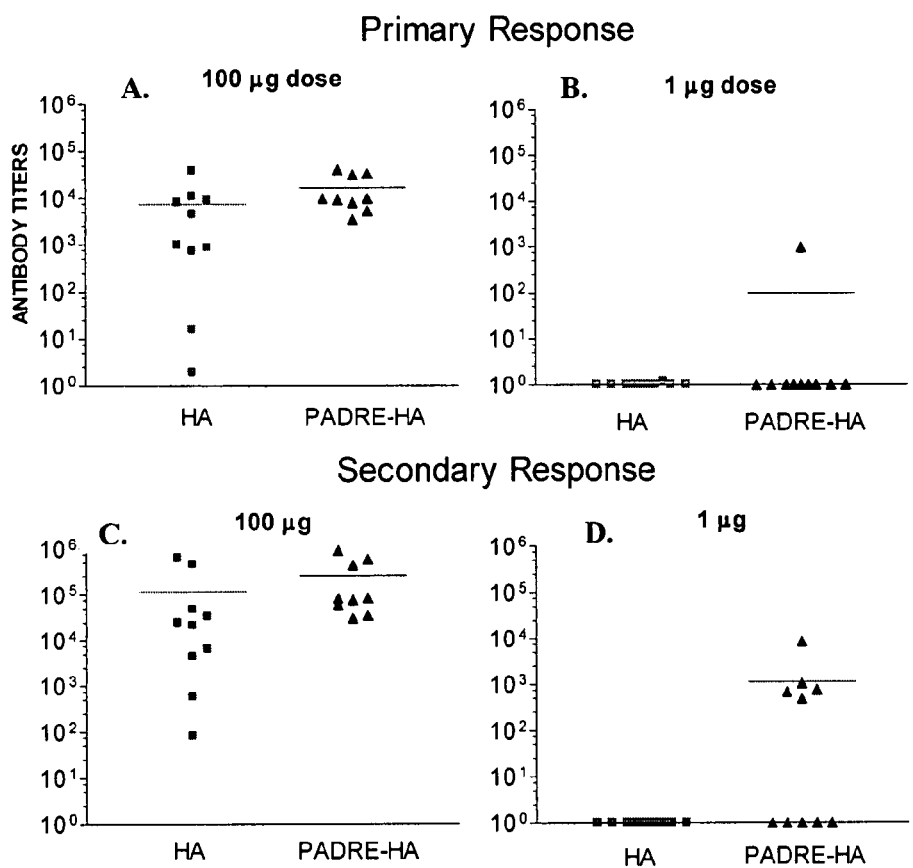
Figure 2. PADRE Increases HA-Specific Antibody Responses in Individual Animals Figure 3. HTL Human Recall Responses in Donor X753
A.
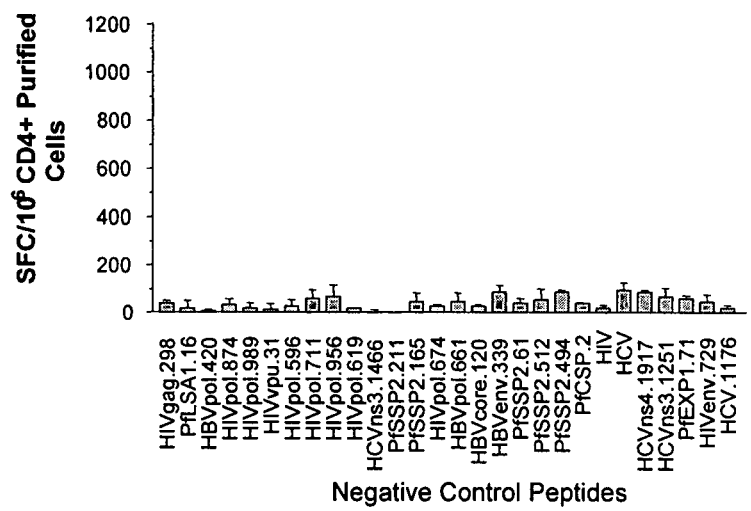
B.
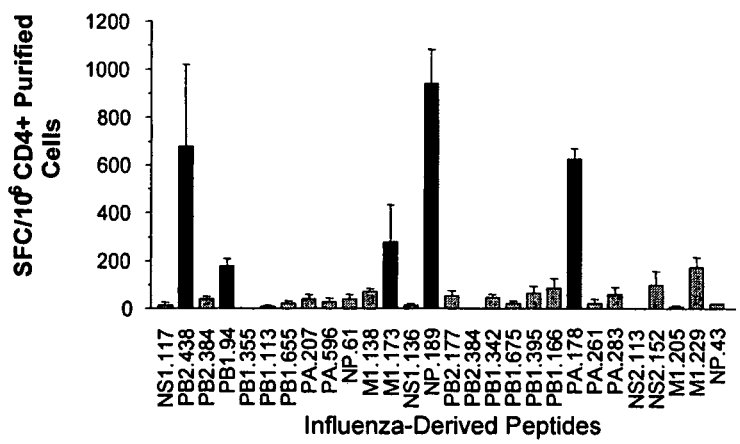

Figure 4. Immune Human Recall Responses in Donor 6018
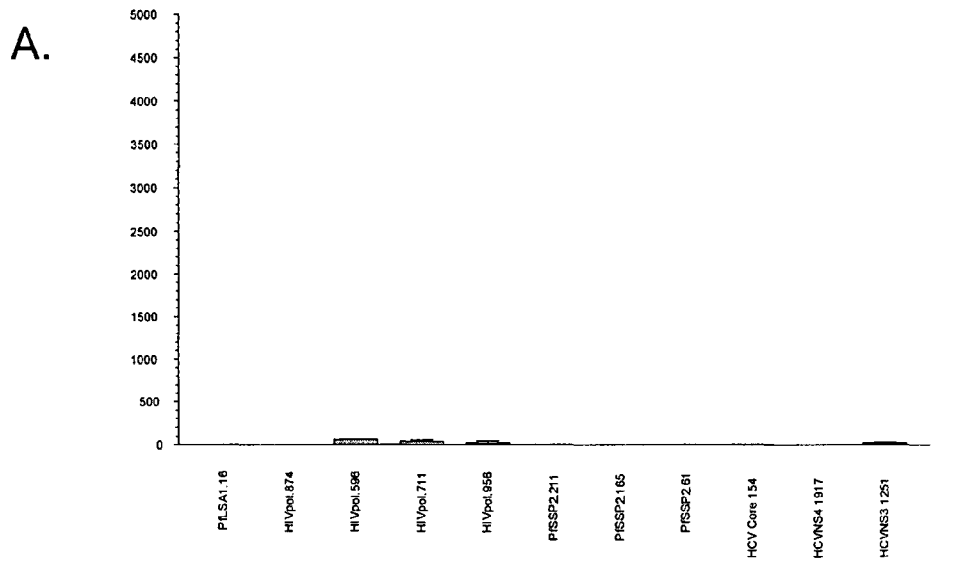
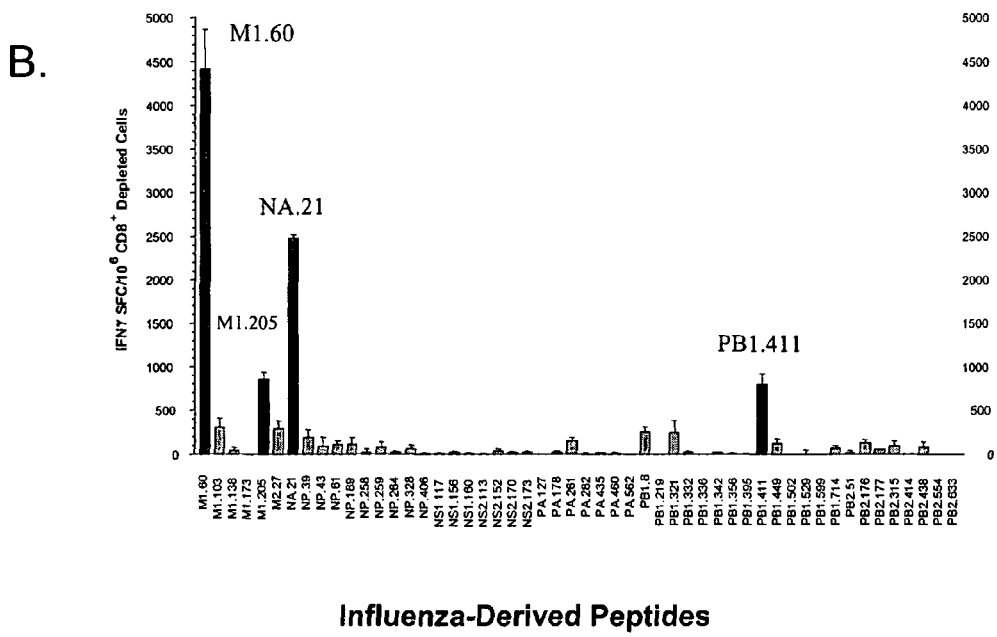

Figure 5. Immune Human Recall Responses in Donor 753
A.
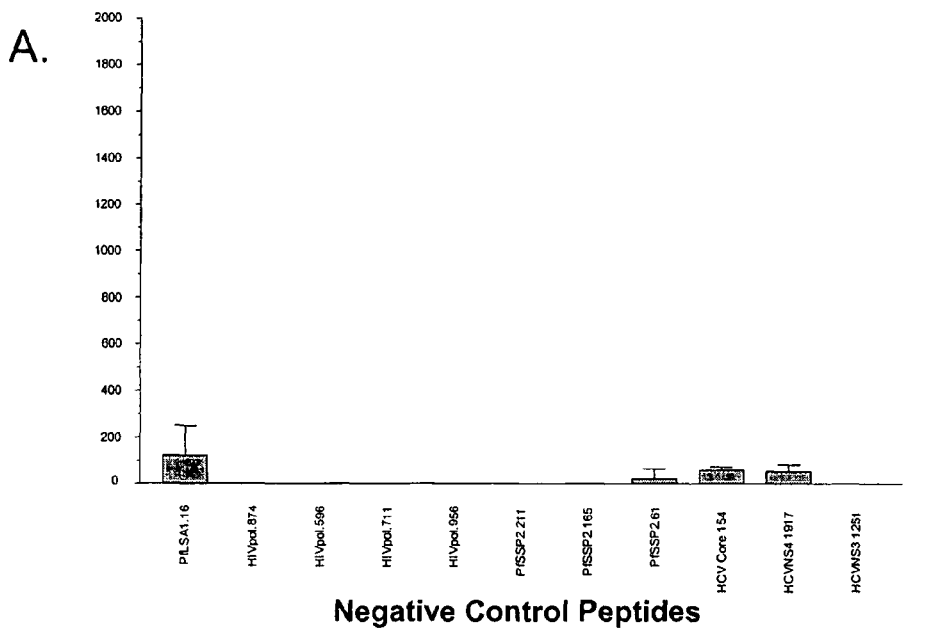
B.
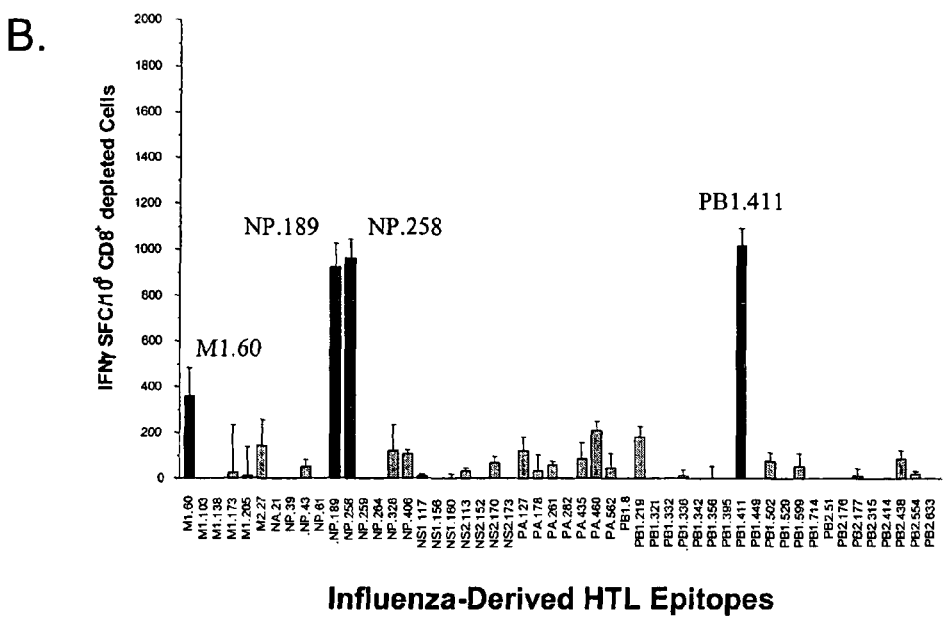

Figure 6. Immune Human Recall Responses in Donor 3501
A.
Negative Control Peptides
B.
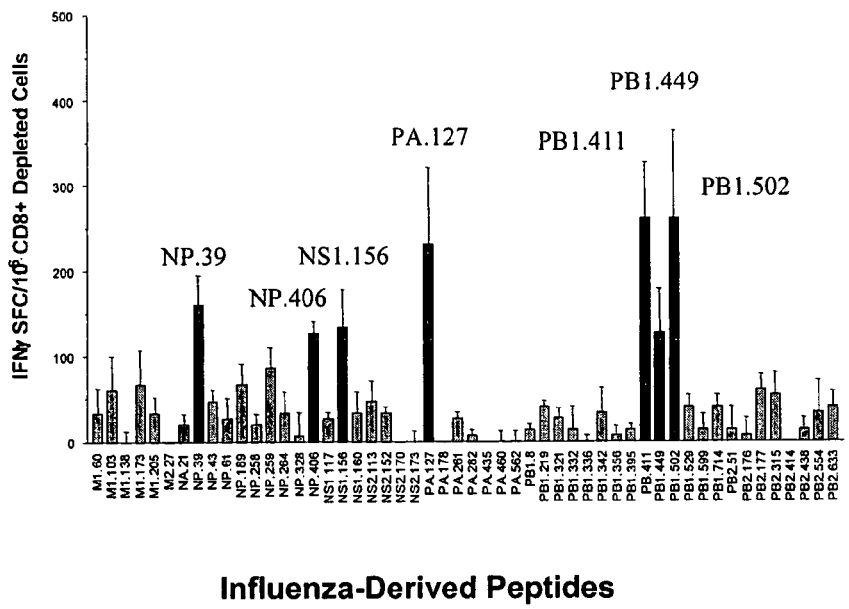
Influenza-Derived Peptides

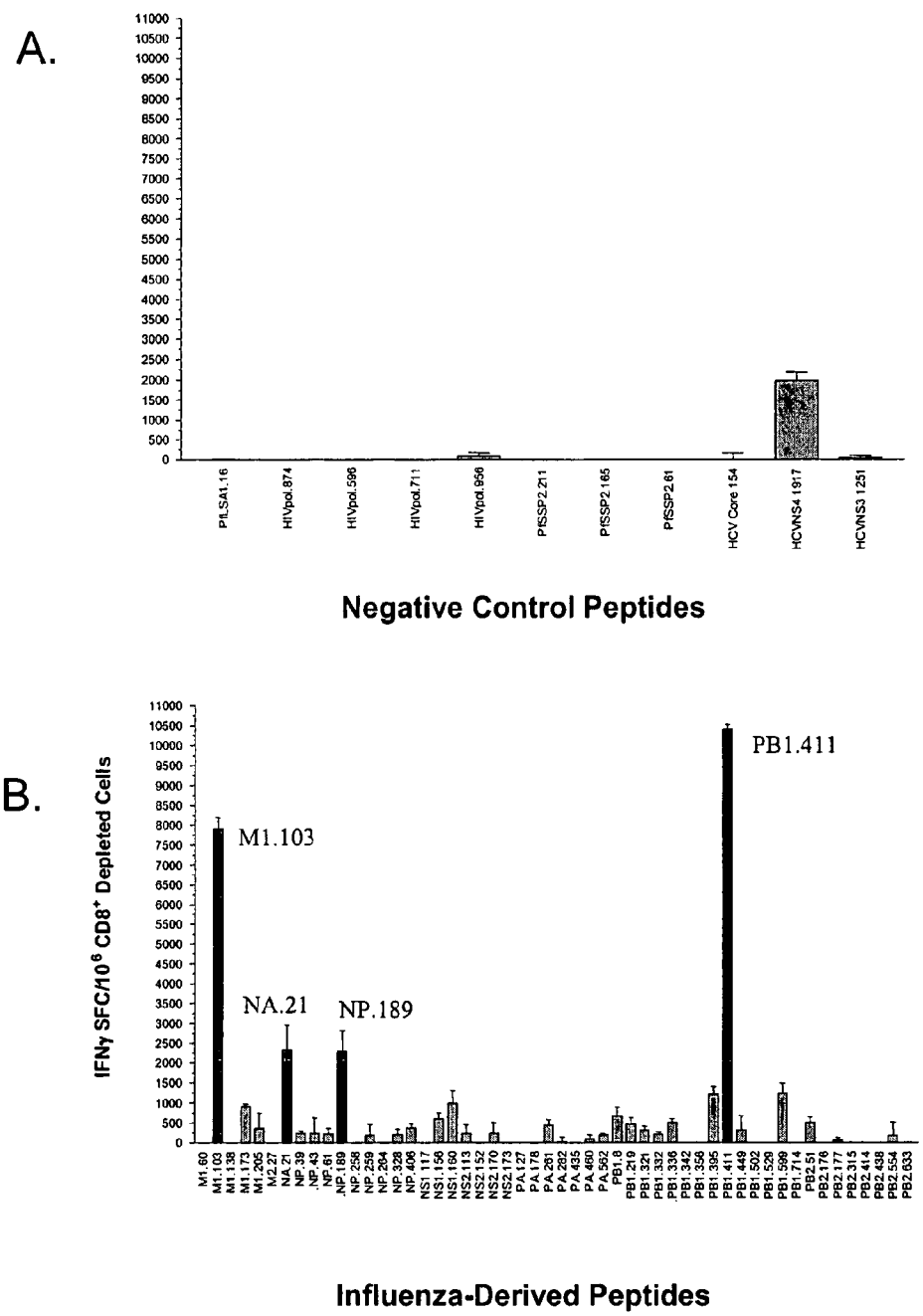
Figure 7. Immune Human Recall Responses in Donor 716

Figure 8. Immune Human Recall Responses in Donor AC08
A. 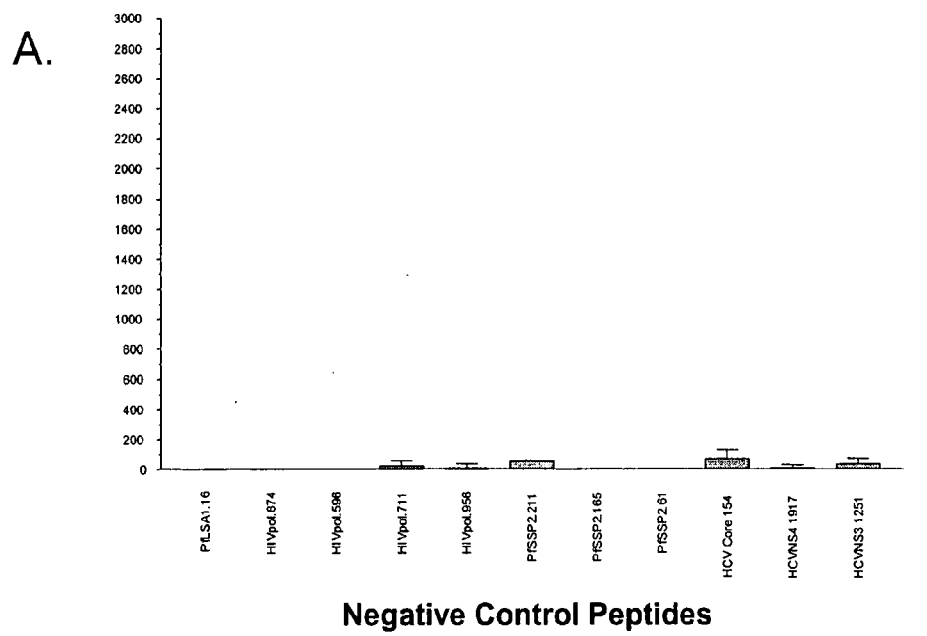
Negative Control Peptides
B. 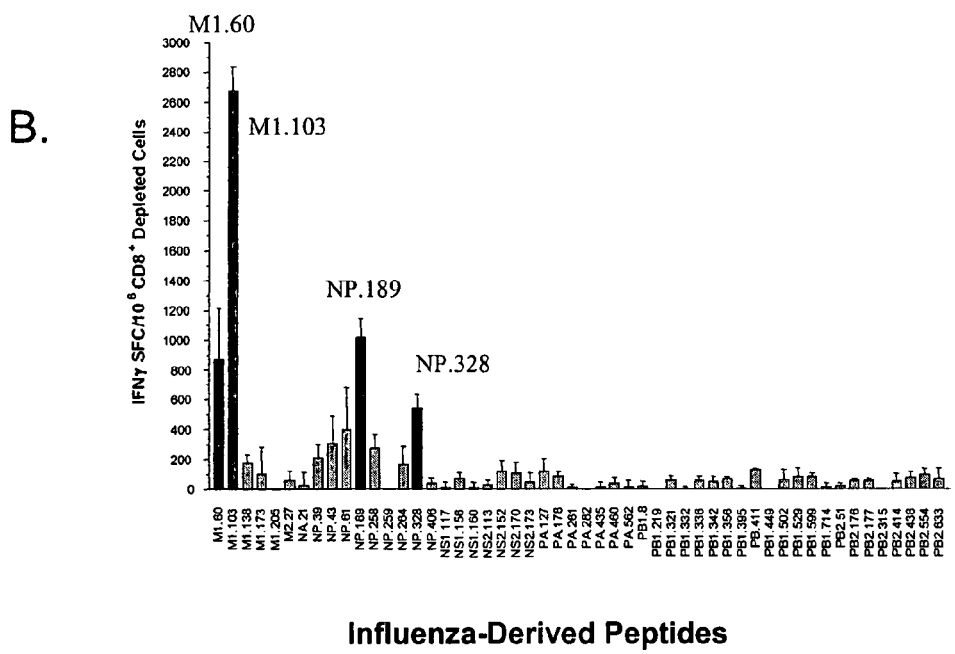
Influenza-Derived Peptides Figure 9. Immune Human Recall Responses in Donor AC02
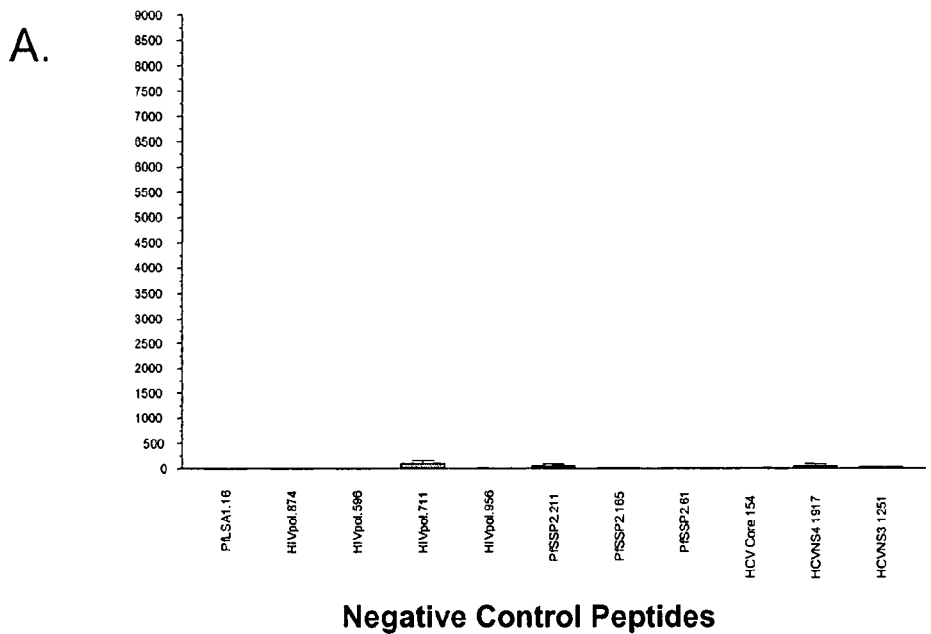
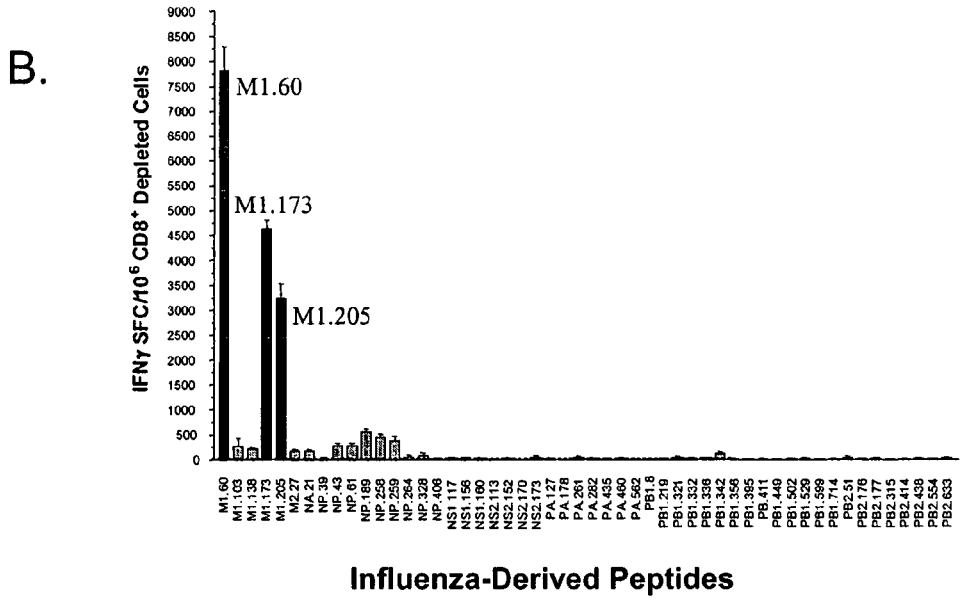

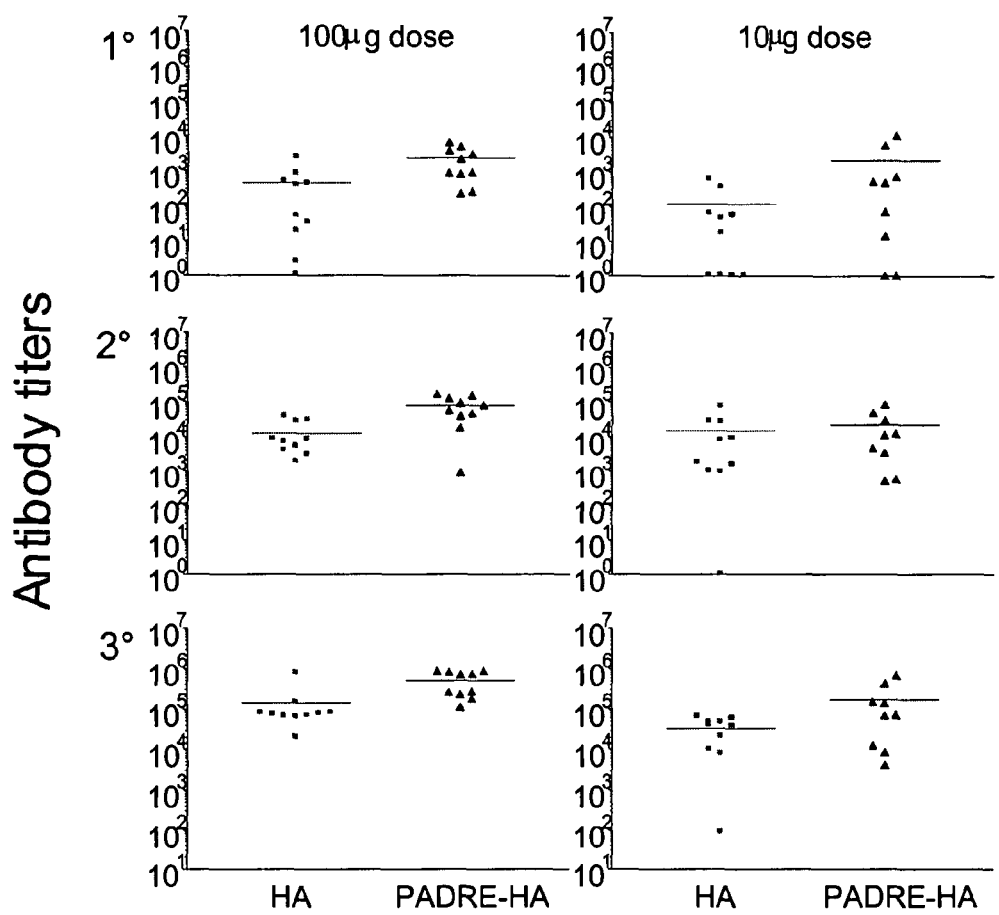
Figure 10. PADRE®-HA Immunogenicity as Measured by HA-Specific Antibody Titers Figure 11. Evaluation of Antibody Function by
Hemagglutination Inhibition and Viral Microneuralization Individual Mouse Sera (ELISA Titer x $10^5$)

| | | | | | | | | | | |
|---|---|---|---|---|---|---|---|---|---|---|
| HA | 0.64 | 0.71 | 0.68 | 0.75 | 0.77 | 1.4 | 0.61 | 0.19 | 0.77 | 0.79 |
| PADRE-HA | 1.1 | 8.7 | 1.8 | 2.5 | 7.4 | 7.1 | 8.8 | 8.0 | 2.7 | 2.2 |

Individual Mouse Sera (Microneutralization)

| | | | | | | | | | | |
|---|---|---|---|---|---|---|---|---|---|---|
| HA | -- | -- | -- | -- | -- | -- | -- | -- | -- | -- |
| PADRE-HA | -- | 640 | -- | 160 | -- | -- | -- | -- | -- | -- |

Individual Mouse Sera (Hemagglutination Inhibition)

| | | | | | | | | | | |
|---|---|---|---|---|---|---|---|---|---|---|
| HA | 20 | -- | -- | -- | 80 | 40 | -- | -- | -- | -- |
| PADRE-HA | -- | 160 | -- | 20 | -- | 80 | -- | 20 | 20 | -- |

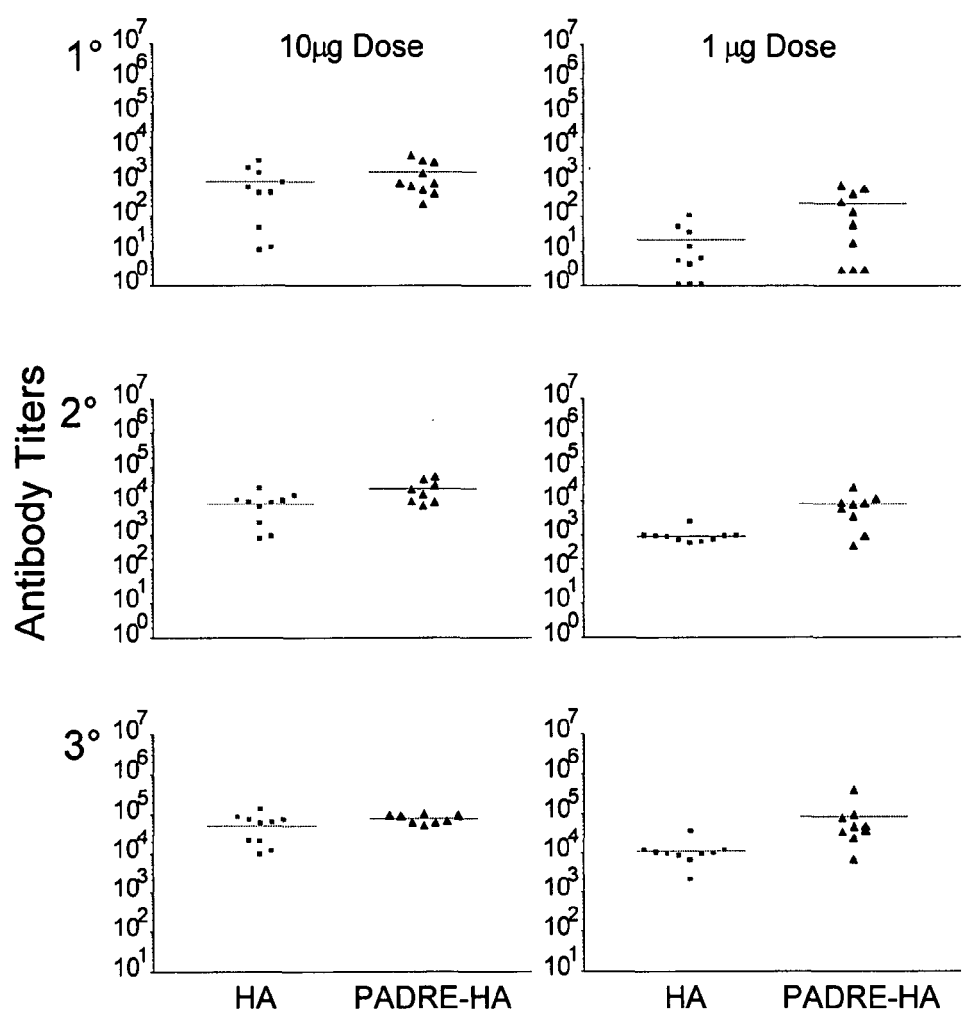
Figure 12. PADRE®-HA Recombinant Protein Immunogenicity as Measured by HA-Specific Antibody Titers with Alum Figure 13. PADRE®-HA Recombinant Protein Immunogenicity as Measured by HA-Specific Antibody Titers with Alum/Provax™
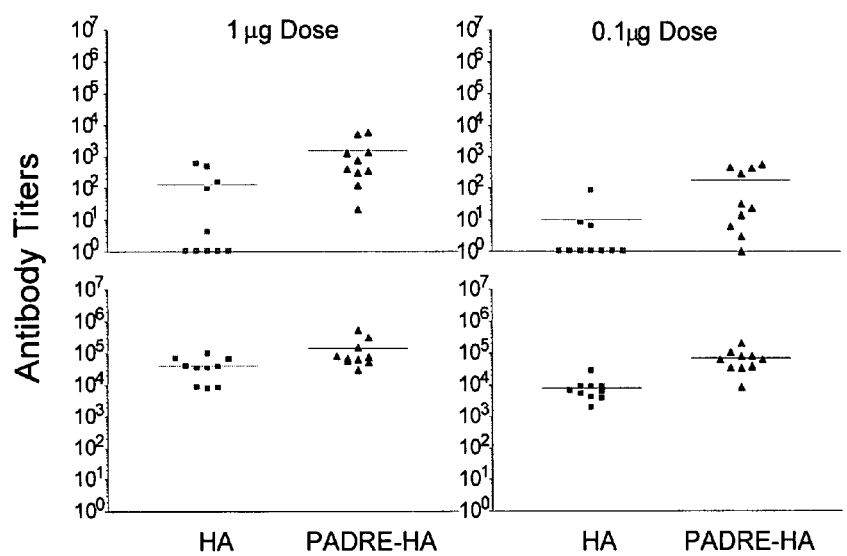

Figure 14. Schematic of PADRE®-HA and HA DNA and Protein Constructs
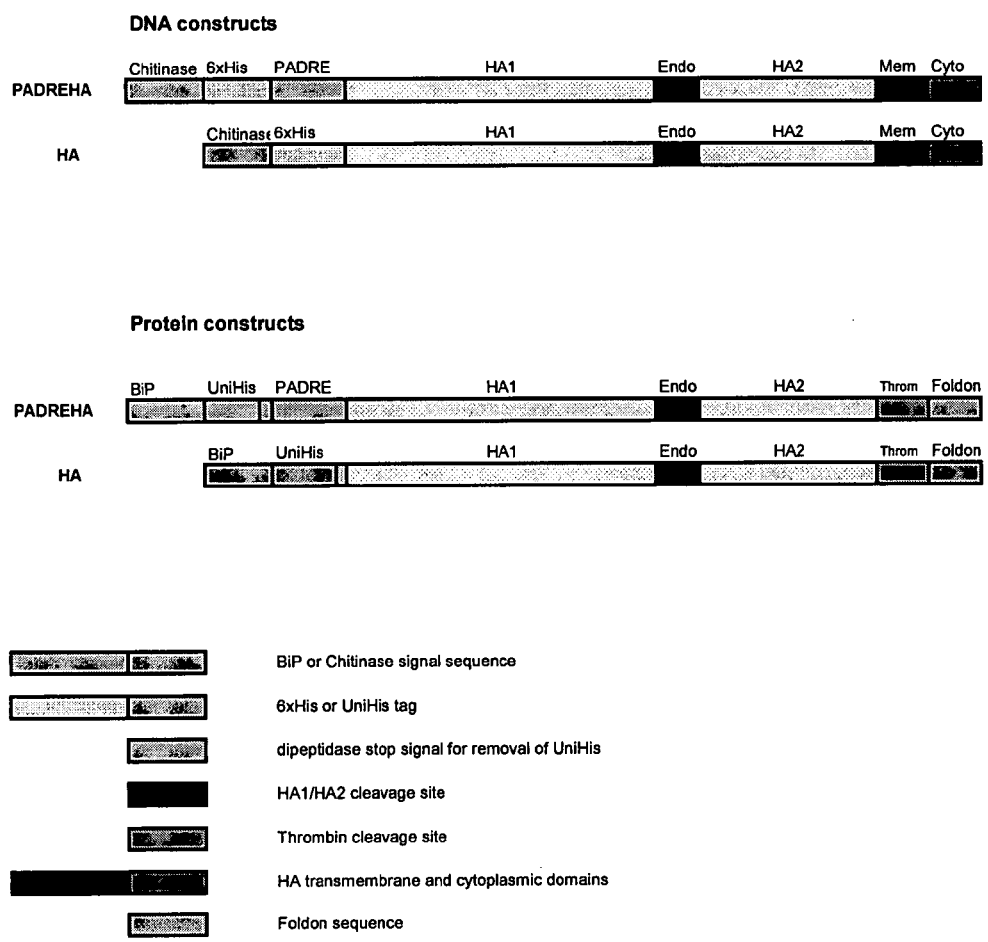

INDUCING IMMUNE RESPONSES TO INFLUENZA VIRUS USING POLYPEPTIDE AND NUCLEIC ACID COMPOSITIONS

CROSS-REFERENCES TO RELATED APPLICATIONS

This application claims priority to provisional application 60/838,859, filed Aug. 21, 2006 and to provisional application 60/801,065, filed May 18, 2006, each of which is herein incorporated by reference.

REFERENCE TO A SEQUENCE LISTING SUBMITTED ON A COMPACT DISC

This application includes a "Sequence Listing," which is provided as an electronic document on a compact disc (CD-R). This compact disc contains the file "Sequence Listing.txt" (129,024 bytes, created on May 18, 2007), which is herein incorporated by reference in its entirety.

BACKGROUND OF THE INVENTION

The present invention relates to influenza virus vaccine compositions and methods of treating or preventing influenza infection and disease in mammals. Influenza is caused by an RNA virus of the myxovirus group. Influenza viruses can be classified into three types (A, B and C), based on antigenic differences in the nucleoprotein and the matrix protein. Type A, which includes several subtypes, causes widespread epidemics and global pandemics. Type B causes regional epidemics. Influenza C is less severe and has been isolated from humans and pigs. Type C causes sporadic cases and minor, local outbreaks. Influenza A viruses can be further classified based on the viral surface proteins hemagglutinin (HA or H) and neuraminidase (NA or N). There are sixteen known H subtypes and nine known N subtypes of Type A viruses; while there is only one known H subtype and one N subtype of Type B viruses. Typical nomenclature identifies an influenza virus by both proteins, e.g., H3N2.

Type A and B influenza viruses each contain 8 RNA segments, while type C only has 7 RNA segments. Influenza A is most important and is very pathogenic for man, as well as for animals, for example pigs and horses. Type B influenza causes disease in humans. These virus types are distinguished in part on the basis of differences in two structural proteins, the nucleoprotein, found in the center of the virus, and the matrix protein, which forms the viral shell. The virus is transmitted through the air, mainly in droplets expelled during coughing and sneezing. The influenza viruses cause an infection of the respiratory tract, which is usually accompanied with coughing, high fever and myalgia.

Although an influenza infection does not often lead to the death of the infected individual, the morbidity can be severe. As a consequence thereof influenza epidemics may lead to substantial economic loss. Furthermore, influenza infection can be more dangerous for certain groups of individuals, such as those having suffered from a heart attack, CARA patients or the elderly. A vaccine against influenza is therefore highly desirable.

Influenza Epidemiology and Virology

Pandemics of influenza A viruses continue to occur at sporadic intervals in human populations. Three have occurred in the twentieth century alone in 1918, 1957 and 1968[6-8]. These worldwide pandemics are noted for their high mortality with rates approaching 30-50%[9]. For example, it is estimated that 20-40 million people died in the 1918 pandemic and at least 1.5 million people in the 1957 and 1968 outbreaks combined[10]. Whether a pandemic occurs from an act of nature or from the deliberate release of a novel influenza strain with pandemic potential, the extent of world travel will ensure the rapid global spread of the pandemic agent. Such an event could result in worldwide deaths totaling in the millions and severely impact health care systems such that economies and governments of smaller countries could collapse[9,11].

The capacity of the influenza virus to cause disease in a recurring manner is due to a complex set of factors that include: 1) the presence of an established reservoir of influenza A viruses of different subtypes in shorebirds and waterfowl; 2) the ability of avian influenza viruses to recombine with influenza viruses of other animals, most notably swine[12], a process termed 'antigenic shift'; 3) accumulation of mutations in viral gene products caused by a lack of proofreading activity of the viral RNA polymerase, a process termed 'antigenic drift'. These reassortment and mutation events combine to cause the well-characterized antigenic variability in the two surface glycoproteins of the virus, hemagglutinin (HA) and neuraminidase (NA)[13-15] which provides the virus a mechanism for escaping immune responses, particularly neutralizing antibodies, induced as the result of previous infections or vaccinations. Antigenic shift, which occurs only among influenza A viruses, results in major antigenic change introducing viruses with a new gene segment(s). Antigenic shift can occur when an animal influenza A virus is transmitted directly to humans, such as the transmission of the H1N1 from swine-to-human[16] or the transmission of the H5N1, H7N7 or H9N2 variants from avian to human[17,18]. Alternatively, a virus may acquire a new gene segment(s) as a result of genetic reassortment between animal and human influenza A viruses, the cause of the 1957 H2N2 and 1968 H3N2 pandemics[19].

Since 1997, several novel avian subtypes have crossed the so-called species barrier from domestic poultry to humans and have caused a spectrum of mild to severe and even fatal human disease. In 1997, 18 cases of human infection with highly pathogenic avian H5N1 influenza viruses, including 6 deaths were documented in Hong Kong following outbreaks of disease in domestic poultry. Avian H5N1 viruses reemerged in Hong Kong and from Dec. 30, 2003 to Mar. 17, 2004, there were 12 human cases of confirmed H5N1 influenza in Thailand and 23 in Vietnam, including 23 deaths. As of May 2006, approximately 115 deaths have been attributed to H5N1 infection. The H5N1 strain does not jump easily from birds to humans or between humans. However since the human virus, H3N2, can coexist with avian influenza viruses and is widespread in pigs from southeast China, reassortment has the potential to occur with a highly pathogenic human-to-human transmissible H5N1 being the result. Although these wholly avian viruses were associated with only limited human-to-human transmission, their repeated emergence in humans highlights the potential for the generation of an avian-human reassortant virus with the potential for spread in the human population. Thus, the development of effective vaccines against these avian subtypes is of the highest public health priority.

Vaccine production must rely on surveillance programs to predict the influenza subtypes likely to have global impact on human health. The time required to produce subtype-matched vaccines, composed of inactivated or 'split' virions, typically requires a minimum of 6-8 months. In the face of a serious influenza virus pandemic caused by a viral subtype, this lag time could allow for national or international spread with excessive morbidity and mortality.

Virus Structures

An influenza virus is roughly spherical, but it can also be elongated or irregularly shaped. Inside the virus, eight segments of single-stranded RNA contain the genetic instructions for making the virus. The most striking feature of the virus is a layer of spikes projecting outward over its surface. There are two different types of spikes: one is composed of the molecule hemagglutinin (HA), the other of neuraminidase (NA). The HA molecule allows the virus to "stick" to a cell, initiating infection. The NA molecule allows newly formed viruses to exit their host cell without sticking to the cell surface or to each other. The viral capsid is comprised of viral ribonucleic acid and several so called "internal" proteins (polymerases (PB1, PB2, and PA, matrix protein (M1) and nucleoprotein (NP)). Because antibodies against HA and NA have traditionally proved the most effective in fighting infection, much research has focused on the structure, function, and genetic variation of those molecules. Researchers are also interested in two non-structural proteins M2 and NS1; both molecules play important roles in viral infection.

Type A subtypes are described by a nomenclature system that includes the geographic site of discovery, a lab identification number, the year of discovery, and in parentheses the type of HA and NA it possesses, for example, A/Hong Kong/156/97 (H5N1). If the virus infects non-humans, the host species is included before the geographical site, as in A/Chicken/Hong Kong/G9/97 (H9N2).

Virions contain 7 segments (influenza C virus) to 8 segments (influenza A and B virus) of linear negative-sense single stranded RNA. Most of the segments of the virus genome code for a single protein. For many influenza viruses, the whole genome is now known. Genetic reassortment of the virus results from intermixing of the parental gene segments in the progeny of the viruses when a cell is co-infected by two different viruses of a given type. This phenomenon is facilitated by the segmental nature of the genome of influenza virus. Genetic reassortment is manifested as sudden changes in the viral surface antigens.

Antigenic changes in HA and NA allow the influenza virus to have tremendous variability. Antigenic drift is the term used to indicate minor antigenic variations in HA and NA of the influenza virus from the original parent virus, while major changes in HA and NA which make the new virions significantly different, are called Antigenic shift. The difference between the two phenomena is a matter of degree.

Antigenic drift (minor changes) occurs due to accumulation of point mutations in the gene which results in changes in the amino acids in the proteins. Changes which are extreme, and drastic (too drastic to be explained by mutation alone) result in antigenic shift of the virus. The segmented genomes of the influenza viruses reassort readily in double infected cells. Genetic reassortment between human and non-human influenza virus has been suggested as a mechanism for antigenic shift. Influenza is a zoonotic disease, and an important pathogen in a number of animal species, including swine, horses, and birds, both wild and domestic. Influenza viruses are transferred to humans from other species.

Because of antigenic shift and antigenic drift, immunity to an influenza virus carrying a particular HA and/or NA protein does not necessarily confer protective immunity against influenza virus strains carrying variant, or different HA and/or NA proteins. Because antibodies against HA and NA have traditionally proved the most effective in fighting influenza virus infection, much research has focused on the structure, function and genetic variation of those molecules.

Role of Cellular Immune Responses in Protection Against Influenza

Cellular immune responses are known to contribute to the control of viral replication in vivo and to mediate viral clearance. In murine models, influenza-specific $CD8^+$ cytotoxic T-lymphocytes (CTL) limit virus replication and protect against lethal virus challenge[20-27]. Recovery from infection correlated with virus-specific $CD8^+$ CTL activity[22] and lack of $CD8^+$ CTL activity was associated with delayed viral clearance and increased mortality[28]. Studies completed by Ulmer and Okuda using a DNA vaccine encoding the viral nucleoprotein and M gene proteins, respectively are particularly relevant. These vaccines induced influenza-specific $CD8^+$ CTL that provided cross-strain protection[27,29,30]. The contribution of CTL and Helper T-lymphocytes (HTL) was definitively demonstrated by adoptive transfer of $CD8^+$ and $CD4^+$ T-lymphocytes[31]. Similarly, Epstein and colleagues demonstrated that either $CD8^+$ or $CD4^+$ T-lymphocytes promoted survival in mice immunized with an experimental DNA vaccine encoding internal viral proteins[32]. Finally, virus specific HTL augment the generation of CTL and size of the CTL memory pool, an effect known to be associated with long term protection[33]. Cellular immune responses clearly contribute to the control and clearance of infection and reduce pathogenesis.

The exposure to an influenza virus of one subtype often induces immune responses that protect against infection or disease with another subtype, a phenomena referred to as Heterosubtypic Immunity (HSI)[34-37]. The mechanisms of heterosubtypic immunity appears to involve functional activity of both $CD8^+$ and $CD4^+$ T-lymphocytes[23,26,38-41], although more recently antibody responses have also been implicated[42]. HSI is not only observed using the murine models; influenza virus-specific CTL appear to provide partial protection against multiple influenza A virus strains in humans. Early human studies demonstrated that cellular immune responses play a role in controlling influenza infection[43,44]. McMichael and colleagues inoculated 63 volunteers intranasally with live unattenuated influenza A/Munich/1/79 virus and evaluated the protective effects of serum antibody and cytotoxic T-cell immunity against influenza.[43] It was found that all subjects with demonstrable T-cell responses cleared virus effectively. Sonoguchi and colleagues found that students previously infected with H3N2 virus were partially protected against subsequent infection with H1N1 subtype virus suggesting cross-subtype protection in humans during sequential epidemics. Thus, the use of vaccines to induce cellular responses against pandemic influenza virus is logical and the development of suitable vaccine technologies is warranted.

Immune system-mediated selection pressure on influenza virus can lead to CTL viral escape mutants[45-47]. While this phenomena clearly documents the importance of virus-specific CTL it also reveals a potential limitation for vaccines designed to induce CTL responses. However, the use of carefully selected epitopes in the design of a vaccine provides a means to address this problem. Selection of epitopes that are highly conserved amongst multiple viral strains is the first step and the selection of those epitopes predicted to be capable of inducing CTL responses to the majority of related epitopes is the second step.

Role of Humoral Immune Responses in Protection Against Influenza

Influenza vaccines are formulated to include human influenza strains predicted to pose the greatest risk for infectious spread. This vaccine development process requires approximately 6-8 months using conventional strains. Neutralizing antibodies induced primarily to the surface hemagglutinin protein by the conventional vaccines are highly protective. However, due to antigenic drift of the virus, the vaccines must be reformulated on a yearly basis. The danger persists that a "new" strain will emerge by antigenic shift for which the human population has little or no pre-existing immunity. Also, since vaccine production relies on embryonated chicken eggs or potentially cells in tissue culture, there are no assurances that sufficient new virus can be produced even within the 6-8 month time frame especially if the new influenza strain is lethal to birds. Pandemic influenza vaccine development would benefit by inclusion of conserved B cell epitopes capable of inducing protective immune responses. To this end, it has been reported that the external domain of the transmembrane viral M2 protein is highly conserved and that antibodies directed to this epitope are protective in mice[48-54]. The M2 protein is an integral membrane protein of influenza A virus that is expressed at the plasma membrane in virus-infected cells. Due to the low abundance of the protein in the virus, the mechanism of protection of the antibody response directed against this epitope is not mediated via viral neutralization but rather by antibody-dependent, cell-mediated cytotoxicity[51].

Conserved CTL, HTL and B-cell epitopes can be used as the basis for a vaccine designed to augment and improve prototype pandemic vaccine candidates that may be poorly immunogenic or a sub-optimal match against a pandemic strain that emerges. The advantages to using defined epitopes in vaccines are many but one advantage is that many epitopes can be incorporated into a vaccine to induce a broadly specific immune response targeting numerous viral gene products. Data from natural infection studies wherein human memory CTL specific to influenza A virus were restricted by multiple HLA Class I alleles have shown that responses within a given individual were broadly directed to epitopes within the NP, NA, HA, M1, NS1 and M2 viral proteins.

Design and Testing of Vaccines to Induce Cellular and Humoral Immune Responses:

The use of recombinant DNA technology to produce influenza vaccines offers several advantages: a recombinant DNA influenza vaccine can be produced under safer and more stringently controlled conditions; propagation with infectious influenza in eggs is not required; recombinant HA protein can be more highly purified, virtually eliminating side effects due to contaminating proteins; purification procedures for recombinant HA do not have to include virus inactivation or organic extraction of viral membrane components, therefore avoiding denaturation of antigens and additional safety concerns due to residual chemicals in the vaccine. Production of HA via recombinant DNA technology provides an opportunity to avoid the genetic heterogeneity which occurs during adaptation and passage through eggs, which should make it possible to better match vaccine stains with influenza epidemic strains, resulting in improved efficacy; and a recombinant approach may also allow for strain selection later in the year, thereby allowing time for selections based on more reliable epidemiological data.

A major obstacle to the development of vaccines that induce immune responses is the selection of a suitable delivery format. DNA plasmid vaccines and viral vectors, used either alone or together, and recombinant protein or peptides are logical vaccine delivery formats; however, each format has advantages and disadvantages. For example, DNA vaccines are readily produced and safe to administer but potency has been lacking, especially in clinical trials, requiring the administration of large (milligram) doses[59-65]. Studies completed in small animals have indicated increased vaccine potency[66-69]. Polymer formulation technology based on polyvinylpyrrolidone (PVP) can also be utilized. PVP is a nontoxic formulation excipient used to enhance DNA plasmid uptake by muscle cells[70-73]. Such vaccine design parameters can correct for at least some of the limitations of naked-DNA vaccine technology.

The use of viral vectors to deliver vaccines has raised concerns, usually related to safety and pre-existing immunity to the vector. However, AlphaVax replicons are reported to be safe, non-transmissible and there is a general lack of pre-existing immunity to the vector. Another delivery vehicle that is being evaluated is peptides in adjuvant. Generally, peptides in adjuvant have shown to be immunogenic and efficacious in humans. However, there are concerns regarding vaccine formulation wherein high numbers of peptides will need to be delivered.

Several adjuvants have been developed for the administration of influenza virus vaccines, including alum based compounds, emulsions (e.g. MF59), (lipophilic immune stimulating complexes ISCOMS) containing Quil A adjuvant) and liposomes. A development of the liposomal technique has been the use of immunopotentiating reconstituted influenza virosomes (IRIVs) as antigen delivery systems. See Mischler, R. and Metcalfe, I. C., *Vaccine* 20: B17-B23 (2002). The IRIV vaccine delivery system is comprised of spherical unilamellar vesicles comprising naturally occurring phospholipids (PL) and phosphatidylcholine (PC) and envelope phospholipids originating from influenza virus used to provide influenza virus NA and HA glycoproteins. See id. The fusion mechanism of IRIVs enables stimulation of the MHC Class I or Class II pathway, depending upon how antigens are presented to the APCs. Virosomes are able to induce either a B- or T-cell response. See id.

The use of smaller polypeptides comprising antigenic epitopes in vaccines has several advantages over current vaccines, particularly when compared to the use of whole antigens in vaccine compositions. There is evidence that the immune response to whole antigens is directed largely toward variable regions of the antigen, allowing for immune escape due to mutations. The epitopes for inclusion in an epitope-based vaccine may be selected from conserved regions of influenza antigens, which thereby reduces the likelihood of escape mutants. Furthermore, immunosuppressive epitopes that may be present in whole antigens can be avoided with the use of epitope-based vaccines.

An additional advantage of an epitope-based vaccine approach is the ability to combine selected epitopes (e.g., multiple HTL epitope epitopes), and further, to modify the composition of the epitopes, achieving, for example, enhanced immunogenicity. Accordingly, the immune response can be modulated, as appropriate, for the target disease. Similar engineering of the response is not possible with traditional approaches.

Several groups have established the mouse model as a tool for evaluating the efficacy of influenza vaccines[26-31,74,75]. The testing of vaccines comprised of epitopes restricted by HLA is a unique challenge, requiring the appropriate restriction elements. Specifically cell-surface expressed HLA Class II molecules for HTL epitopes on antigen presenting cells are required. With regard to evaluating Class II-restricted responses, HLA-DR4 mice are available commercially. Most HTL epitopes restricted to HLA Class II can bind murine H-2 IAb molecules and initiate a response[80].

Virus-specific, human leukocyte antigen (HLA) class I-restricted cytotoxic T lymphocytes (CTL) are known to play a major role in the prevention and clearance of virus infections in vivo (Oldstone, et al., *Nature* 321:239, 1989; Jamieson, et al., *J. Virol.* 61:3930, 1987; Yap, et al., *Nature* 273:238, 1978; Lukacher, et al., *J. Exp. Med.* 160:814, 1994; McMichael, et al., *N. Engl. J. Med.* 309:13, 1983; Sethi, et al., *J. Gen. Virol.* 64:443, 1983; Watari, et al., *J. Exp. Med.* 165:459, 1987; Yasukawa, et al., *J. Immunol.* 143:2051, 1989; Tigges, et al., *J. Virol.* 66:1622, 1993; Reddenhase, et al., *J. Virol.* 55:263, 1985; Quinnan, et al., *N. Engl. J. Med.* 307:6, 1982). HLA class I molecules are expressed on the surface of almost all nucleated cells. Following intracellular processing of antigens, epitopes from the antigens are presented as a complex with the HLA class I molecules on the surface of such cells. CTL recognize the peptide-HLA class I complex, which then results in the destruction of the cell bearing the HLA-peptide complex directly by the CTL and/or via the activation of non-destructive mechanisms e.g., the production of interferon, that inhibit viral replication.

Virus-specific T helper lymphocytes are also known to be critical for maintaining effective immunity in chronic viral infections. Historically, HTL responses were viewed as primarily supporting the expansion of specific CTL and B cell populations; however, more recent data indicate that HTL may directly contribute to the control of virus replication. For example, a decline in CD4+ T cells and a corresponding loss in HTL function characterize infection with HIV (Lane, et al., *N. Engl. J. Med.* 313:79, 1985). Furthermore, studies in HIV infected patients have also shown that there is an inverse relationship between virus-specific HTL responses and viral load, suggesting that HTL plays a role in controlling viremia (see, e.g., Rosenberg, et al., *Science* 278:1447, 1997).

The epitope approach, as we describe herein, allows the incorporation of various antibody, CTL and HTL epitopes, from various proteins, in a single vaccine composition. Such a composition may simultaneously target multiple dominant and subdominant epitopes and thereby be used to achieve effective immunization in a diverse population.

The technology relevant to multi-epitope ("minigene") vaccines is developing. Several independent studies have established that induction of simultaneous immune responses against multiple epitopes can be achieved. For example, responses against a large number of T cell specificities can be induced and detected. In natural situations, Doolan, et al. (*Immunity, Vol.* 7(1):97-112 (1997)) simultaneously detected recall T cell responses, against as many as 17 different *P. falciparum* epitopes using PBMC from a single donor. Similarly, Bertoni and colleagues (*J. Clin. Invest.*, 100(3):503-13 (1997)) detected simultaneous CTL responses against 12 different HBV-derived epitopes in a single donor. In terms of immunization with multi-epitope nucleic acid vaccines, several examples have been reported where multiple T cell responses were induced. For example, minigene vaccines composed of approximately ten MHC Class I epitopes in which all epitopes were immunogenic and/or antigenic have been reported. Specifically, minigene vaccines composed of 9 EBV (Thomson, et al., *Proc. Natl. Acad. Sci. USA*, 92(13):5845-49 (1995)), 7 HIV (Woodberry, et al., *J. Virol.*, 73(7):5320-25 (1999)), 10 murine (Thomson, et al., *J. Immunol.*, 160(4):1717-23 (1998)) and 10 tumor-derived (Mateo, et al., *J. Immunol.*, 163(7):4058-63 (1999)) epitopes have been shown to be active. It has also been shown that a multi-epitope DNA plasmid encoding nine different HLA-A2.1- and A11-restricted epitopes derived from HBV and HIV induced CTL against all epitopes (Ishioka, et al., *J. Immunol.*, 162(7):3915-25 (1999)).

Recently, several multi-epitope DNA plasmid vaccines specific for HIV have entered clinical trials (Nanke, et al., *Nature Med.*, 6:951-55 (2000); Wilson, C. C., et al., *J. Immunol.* 171(10):5611-23 (2003)).

Thus, vaccines containing multiple MHC Class I and Class II (i.e., HTL) epitopes can be designed, and presentation and recognition can be obtained for all epitopes. However, the immunogenicity of such multi-epitope constructs appears to be strongly influenced by a number of variables, a number of which have heretofore been unknown. For example, the immunogenicity (or antigenicity) of the same epitope expressed in the context of different vaccine constructs can vary over several orders of magnitude. Thus, there exists a need to identify strategies to optimize such multi-epitope containing vaccine constructs. Such optimization is important in terms of induction of potent immune responses and ultimately, for clinical efficacy. Accordingly, the present invention provides strategies to optimize antigenicity and immunogenicity of multi-epitope vaccines encompassing a certain number of epitopes. The present invention also provides optimized multi-epitope containing vaccines, particularly minigene vaccines, generated in accordance with these strategies.

BRIEF SUMMARY OF THE INVENTION

The present invention is directed to enhancing the immune response of a vertebrate in need of protection against influenza virus infection by administering in vivo, into a tissue of the vertebrate, at least one polynucleotide, wherein the polynucleotide comprises a nucleic acid sequence of a coding region operably encoding an influenza virus polypeptide, or fragment, variant, or derivative thereof and a pan-DR binding epitope (e.g. PADRE®). The polynucleotide of the present invention can further comprise one or more nucleic acids encoding a helper T lymphocyte (HTL) epitope.

In certain embodiments, the invention provides a polynucleotide comprising (a) a nucleic acid encoding zero to ten HTL epitopes; (b) a nucleic acid encoding a pan-DR binding epitope; (c) a nucleic acid encoding an influenza virus hemagglutinin (HA) sequence, or fragment thereof; and (d) optionally, a nucleic acid encoding an influenza matrix protein 2 external (M2e) sequence, or fragment thereof. In other embodiments, the invention provides a polynucleotide comprising (a) a nucleic acid encoding zero to ten HTL epitopes; (b) a nucleic acid encoding a pan-DR binding epitope; (c) a nucleic acid encoding an influenza virus matrix protein 2 external (M2e) sequence, or fragment thereof; and (d) optionally, a nucleic acid encoding an influenza virus hemagglutinin (HA) sequence, or fragment thereof. In further embodiments, the polynucleotide of the invention encodes a polypeptide comprising the pan-DR-binding epitope AKFVAAWTLKAAA (SEQ ID NO:1). In certain embodiments, the pan-DR binding epitope may be located on either the 5' or 3' end of the polynucleotide encoding an influenza virus hemagglutinin sequence, or fragment thereof, or positioned within an influenza virus hemagglutinin sequence, or fragment thereof as a straight insertion between influenza amino acids or as a replacement of influenza amino acids. In further embodiments, the nucleic acids of (a), (b), (c), and optionally (d), can be arranged in any order relative to one another.

In certain embodiments, the polynucleotide comprises a nucleic acid encoding zero to seven HTL epitopes. In other embodiments, the polynucleotide comprises a nucleic acid encoding zero to five HTL epitopes. In further embodiments, the polynucleotide comprises a nucleic acid encoding zero to four HTL epitopes. In further embodiments, the polynucleotide comprises a nucleic acid encoding zero to three HTL epitopes. In further embodiments, the polynucleotide comprises a nucleic acid encoding zero to two HTL epitopes. In further embodiments, the polynucleotide comprises a nucleic acid encoding zero to one HTL epitopes.

The polynucleotide of the invention can comprise a nucleic acid of a coding region operably encoding any influenza polypeptide or fragment, variant, or, derivative thereof, including, but not limited to, HA, NA, NP, PA, PB1, PB2, NS1, NS2, M1 or M2 proteins or fragments (e.g., M2e), variants or derivatives thereof. A polynucleotide of the invention can also encode a derivative fusion protein, wherein two or more nucleic acid fragments, at least one of which encodes an influenza polypeptide or fragment, variant, or derivative thereof, are joined in frame to encode a single polypeptide, e.g., HA fused to M2e. Additionally, a polynucleotide of the invention can further comprise a heterologous nucleic acid or nucleic acid fragment. Such heterologous nucleic acid or nucleic acid fragment may encode a heterologous polypeptide fused in frame with the polynucleotide encoding the influenza virus polypeptide, e.g., a hepatitis B core protein or a secretory signal peptide. Preferably, the polynucleotide encodes an influenza polypeptide or fragment, variant, or derivative thereof comprising at least one immunogenic epitope of influenza virus, wherein the epitope elicits a B-cell (antibody) response, a T-cell response, or both.

In certain embodiments, the invention provides a polypeptide comprising (a) a polypeptide encoding zero to ten HTL epitopes; (b) a pan-DR binding epitope; (c) an influenza virus hemagglutinin (HA) sequence, or fragment thereof; and (d) optionally, an influenza matrix protein 2 external (M2e) sequence, or fragment thereof. In other embodiments, the invention provides a polypeptide comprising (a) a polypeptide having from zero to ten HTL epitopes; (b) a pan-DR binding epitope; (c) an influenza virus matrix protein 2 external (M2e) sequence, or fragment thereof; and (d) optionally, an influenza virus hemagglutinin (HA) sequence, or fragment thereof. In polypeptide embodiments, the pan-DR-binding epitope comprises the amino acid sequence $a_1$KXVAAWTLKAA$a_2$ (SEQ ID NO:2), where "X" is selected from the group consisting of cyclohexylalanine, phenylalanine, and tyrosine; and "$a_1$" is either D-alanine or L-alanine; and "$a_2$" is either D-alanine or L-alanine. In alternative embodiments, the pan-DR binding epitope may be located on the N- or C-terminus of the polypeptide of the present invention, or positioned within an influenza sequence as a straight insertion between influenza amino acids or as a replacement of influenza amino acids. In further embodiments, polypeptides of (a), (b), (c), and optionally (d), can be arranged in any order relative to one another.

Similarly, the isolated influenza polypeptide, fragment, variant, or derivative thereof to be delivered (either a recombinant protein, a purified subunit, or viral vector expressing an isolated influenza polypeptide, or in the form of an inactivated influenza vaccine) can be any isolated influenza virus polypeptide or fragment, variant, or derivative thereof, including but not limited to the HA, NA, NP, PA, PB1, PB2, NS1, NS2, M1 or M2 proteins or fragments (e.g., M2e), variants or derivatives thereof. In certain embodiments, a derivative protein can be a fusion protein, where the fusion protein contains a pan-DR binding epitope (e.g., M2e-PADRE®-HA). In other embodiments, the isolated influenza polypeptide or fragment, variant, or derivative thereof can be fused to a heterologous protein, e.g., a secretory signal peptide or the hepatitis B virus core protein. Preferably, the isolated influenza polypeptide or fragment, variant, or derivative thereof comprises at least one immunogenic epitope of influenza virus, wherein the antigen elicits a B-cell antibody response, a T-cell antibody response, or both. In further embodiments, the isolated influenza polypeptide or fragment, variant, or derivative thereof can be fused to an HTL epitope from an influenza virus polypeptide that is capable of eliciting an immune response.

In further embodiments, the influenza HA sequence is from an influenza strain selected from the group consisting of: Human A/Viet Nam/1203/2004 (H5N1), Human A/Hong Kong/156/97 (H5N1), Human A/Hong Kong/483/97 (H5N1), Human A/Hong Kong/1073/99 (H9N2), Avian A/Chicken/HK/G9/97 (H9N2), Swine A/Swine/Hong Kong/10/98 (H9N2), Avian A/FPV/Rostock/34 (H7N1), Avian A/Turkey/Italy/4620/99 (H7N1), Avian A/FPV/Weybridge/34 (H7N7), Human A/New Caledonia/20/99 (H1N1), Human A/Hong Kong/1/68 (H3N2), Human A/Shiga/25/97 (H3N2), Human A/Singapore/1/57 (H2N2), Human A/Leningrad/134/57 (H2N2), Human A/Ann Arbor/6/60 (H2N2), Human A/Brevig Mission/1/18 (H1N1), Swine A/Swine/Wisconsin/464/98 (H1N1), Human A/Netherlands/219/03 (H7N7) and Human A/Wyoming/3/2003 (H3N2). In certain other embodiments, the influenza virus sequence is an influenza HA sequence that encodes a polypeptide at least 90%, 95% or 100% identical to a known influenza strain. The HA sequence may be a full-length HA protein which consists essentially of the HA or extracellular (ECD) domain (HA1 and HA2), the transmembrane (TM) domain, and the cytoplasmic (CYT) domain; or a fragment of the entire HA protein which consists essentially of the HA1 domain and the HA2 domain; or a fragment of the entire HA protein which consists essentially of the HA1, HA2 and the TM domain; or a fragment of the entire HA protein which consists essentially of the CYT domain; or a fragment of the entire HA protein which consists essentially of the TM domain; or a fragment of the entire HA protein which consists essentially of the HA1 domain; or a fragment of the entire HA protein which consists essentially of the HA2 domain. The HA sequence may also include an HA1/HA2 cleavage site. The HA1/HA2 cleavage site is preferably located between the HA1 and HA2 sequences, but also can be arranged in any order relative to the other sequences of the polynucleotide or polypeptide construct.

In certain preferred embodiments, the influenza HA sequence is from a pathogenic virus strain.

Table 5 on page 151 shows an alignment of M2e sequences from representative influenza virus subtype isolates as compared to a conserved human M2e sequence that is 23 amino acids in length. Positions 10, 13, 15, 17, and 19, highlighted in grey, indicate positions where amino acid substitutions can be made. In some embodiments, the M2e sequence is selected from the M2e sequences set forth in Table 5. Table 6 on page 152 shows five pairs of sequences, the first of each pair corresponding to an M2e sequence from a representative influenza virus subtype, and the second of each pair corresponding to an M2e sequence from a representative influenza virus subtype linked to a PADRE® sequence at the N-terminus. Preferred embodiments of the invention include an M2e or PADRE®-M2e sequence selected from the group consisting of sequences set forth in Table 6. In further embodiments, the M2e sequence contains amino acid substitutions at positions 10, 13, 15, 17 and/or 19. More specifically, the amino acid substitutions correspond to the following: isoleucine at position 10 is substituted with a threonine at position 10, a glutamic acid at position 13 is substituted with glycine, a glycine at position 15 is substituted with glutamic acid, an arginine at position 17 is substituted with a lysine, and/or a glutamine at position 19 is substituted with a serine, a proline at position 9 is substituted with a leucine or histidine, an aspartic acid at position 18 is substituted with a glycine, a serine at position 20 is substituted with an aspargine, a serine at position 19 is substituted with a leucine and/or a serine at position 1 is substituted with a valine.

In addition, the invention provides consensus amino acid sequences for influenza virus polypeptides, domains, fragments, variants or derivatives thereof, including, but not limited to the HA, NA, NP, PA, PB1, PB2, NS1, NS2, M1 or M2 proteins or fragments (e.g. M2e), variants or derivatives thereof. Polynucleotides which encode the consensus polypeptides or fragments, variants or derivatives thereof, are also embodied in this invention. Such polynucleotides can be obtained by known methods, for example by back-translation of the amino acid sequence and PCR synthesis of the corresponding polynucleotide as described below.

In addition, the influenza virus polypeptide, fragments, variants or derivatives thereof can be a fragment of a full-length influenza virus polypeptide and/or can be altered so as to, for example, remove from the polypeptide non-desired protein motifs present in the polypeptide or virulence factors associated with the polypeptide. For example, the polypeptide could be altered so as not to encode a membrane anchoring region that would prevent release of the polypeptide from the cell.

In certain embodiments, the polynucleotide of the invention comprises a spacer sequence between one and eight amino acids in length, where the spacer optimizes HTL epitope processing and minimizes junctional epitopes. In preferred embodiments, the spacer is selected from the group consisting of G, P and N, and encodes an amino acid sequence selected from the group consisting of: an amino acid sequence comprising or consisting of GPGPG (SEQ ID NO:3), an amino acid sequence comprising or consisting of PGPGP (SEQ ID NO:4), an amino acid sequence comprising or consisting of (GP)n (SEQ ID NO: 173), an amino acid sequence comprising or consisting of (PG)n (SEQ ID NO:174), an amino acid sequence comprising or consisting of (GP)nG (SEQ ID NO:175), and an amino acid sequence comprising or consisting of (PG)nP (SEQ ID NO:176), where n is an integer between zero and eleven.

In further embodiments of the present invention, the nucleic acid encoding the influenza virus HA sequence, or fragment thereof is flanked by or linked to a spacer. According to the present invention, the nucleic acid sequence encoding PADRE® epitope and/or the nucleic acid sequence encoding each HTL epitope can also be flanked by or linked to a spacer.

In further embodiments, the HTL epitope is an influenza epitope selected from the group of epitopes as set forth in Table 3. In preferred embodiments, the HTL epitope of the present invention is an influenza epitope selected from the group of epitopes as set forth in Table 4. Certain HTL epitopes in Table 4 were reevaluated for binding affinity. These results are set forth in Table 7. In additional embodiments, the HTL epitope is one derived from a non-influenza protein such as tetanus toxoid (TT), diphtheria toxoid (DT), the circumsporozoite protein of *Plasmodium falciparum*, the outer membrane complex of *Neiserria meningitidis*, Hepatitis B Surface Antigen, Hepatitis B Core Antigen, keyhole limpet hemocyanin, Rotavirus capsid protein or LI protein.

Additional polypeptides of the present invention include HA, M2e or other influenza polypeptides, or fragments, or variants thereof, interrupted by the PADRE® sequence, or having the PADRE® sequence positioned at the N-terminus or C-terminus of the polypeptide, or fragment, or variant thereof. An HA, M2e or other influenza polypeptide "interrupted" by the PADRE® sequence corresponds to a polypeptide where the PADRE® sequence is inserted at any position along the HA or other influenza polypeptide sequence, and more preferably inserted on the N- or C-terminus of an HA or other influenza polypeptide domain. For example, polypeptides of the present invention include, but are not limited to a polypeptide comprising the HA extracellular (ECD) domain and PADRE®, the HA transmembrane (TM) domain and PADRE®, or the HA cytoplasmic (CYT) domain and PADRE®, as well as polypeptides comprising HA ECD, HA TM and PADRE®; polypeptides comprising HA TM, HA CYT and PADRE®; and polypeptides comprising HA ECD, HA CYT domains and PADRE®, where the PADRE® is positioned at the N-terminus or the C-terminus of the polypeptide, or where the polypeptide is interrupted by PADRE® sequence. Additional polynucleotides of the present invention include nucleic acid sequences encoding the polypeptides set forth above.

A further example of a polypeptide of the present invention is a polypeptide comprising an HA, M2e or influenza polypeptide, or fragment, variant or derivative thereof, as set further above and optionally one to ten polypeptides consisting of an HTL epitope. The one or more HTL epitopes of the present invention may be positioned at the N-terminus or C-terminus of the HA, M2e or influenza polypeptide, or fragment, variant, or derivative thereof. Representative influenza HTL epitopes according to the invention can found at Table 3. Preferred influenza HTL epitopes of the present invention can be found at Table 4. HTL epitopes selected from Table 4 that were reevaluated for binding as shown in Table 7 are also epitopes of the present invention. Additional polynucleotides of the present invention include nucleic acid sequences encoding the polypeptides set forth above.

In certain embodiments, the polynucleotide further comprises a nucleic acid encoding a targeting sequence located at the N-terminus of said construct. In further embodiments, the targeting sequence is selected from the group consisting of: an Ig kappa signal sequence, a tissue plasminogen activator signal sequence, an insulin signal sequence, an endoplasmic reticulum signal sequence, a LAMP-1 lysosomal targeting sequence, a LAMP-2 lysosomal targeting sequence, an HLA-DM lysosomal targeting sequence, an HLA-DM-association sequence of HLA-DO, an Ig-a cytoplasmic domain, Ig-ss cytoplasmic domain, a li protein, an influenza matrix protein, an HCV antigen, and a yeast Ty protein, a baculovirus signal sequence, a BiP signal sequence, a chitinase signal sequence or a prokaryotic signal sequence. In a preferred embodiment a chitinase or a BiP signal sequence are at the N-terminus of the construct. However, the chitinase and/or BiP can also be at the C-terminus or arranged in any order relative to the other sequences of the polynucleotide or polypeptide construct.

In certain embodiments, the polynucleotide further comprises a thrombin cleavage site and/or a trimerization sequence. In particular, the trimerization sequence may be a "foldon" sequence. According to the present invention, the polynucleotide can comprise a thrombin and a foldon sequence located at the C-terminus of said construct. The invention also contemplates the use of a thrombin cleavage and/or foldon sequence arranged in any order relative to the other sequences of the polynucleotide or polypeptide sequence. In one preferred embodiment, the thrombin cleavage site is located between the foldon sequence and the PADRE®-HA or HA sequence.

In a preferred embodiment of the invention, the polynucleotide includes a chitinase signal sequence, a HIS tag, optionally a PADRE® sequence and an HA sequence. The HA sequence can include a wild-type or mutant HA1/HA2 cleavage site and/or the membrane and/or cytoplasmic HA domains.

In another preferred embodiment, the polynucleotide includes a Bip signal sequence, a HIS tag, optionally a PADRE® sequence, an HA sequence, a thrombin cleavage signal, and a foldon sequence. The HA sequence can include a wild-type or a mutant HA1/HA2 cleavage site.

Nucleic acids and fragments thereof of the present invention can be altered from their native state in one or more of the following ways. First, a nucleic acid or fragment thereof which encodes an influenza virus polypeptide can be a fragment which encodes only a portion of a full-length polypeptide, and/or can be mutated so as to, for example, remove from the encoded polypeptide non-desired protein motifs present in the encoded polypeptide or virulence factors associated with the encoded polypeptide. For example, the nucleic acid sequence could be mutated so as not to encode a membrane anchoring region that would prevent release of the polypeptide from the cell as with, e.g., M2e. Upon delivery, the polynucleotide of the invention is incorporated into the cells of the vertebrate in vivo, and a prophylactically or therapeutically effective amount of an immunologic epitope of an influenza virus is produced in vivo. Alternatively, epitopes may be modified (to create analogs thereof) to increase their immunogenicity as compared to native epitopes.

The present invention further provides polypeptides encoded by the polynucleotides described above, a vector comprising the polynucleotides described above as well as immunogenic compositions comprising the polynucleotides and/or polypeptides described above. In certain other embodiments, the present invention is directed to a cell comprising polynucleotides, polypeptides, or immunogenic compositions as described above. In certain other embodiments, a composition comprises two or more polypeptides as described above, where the polypeptides are different from each other.

In certain other embodiments, the invention provides immunogenic compositions comprising at least one polynucleotide of the present invention, or a polypeptide encoded by at least one polynucleotide of the present invention, where the polynucleotide comprises a nucleic acid sequence of a coding region operably encoding an influenza virus polypeptide, fragment, variant, or derivative thereof and a pan-DR binding epitope (e.g. PADRE®) and/or one or more nucleic acids encoding a helper T lymphocyte (HTL) epitope. Such compositions can further comprise, for example, carriers, excipients, transfection facilitating agents, lipids, liposomes, virosomes and/or adjuvants as described herein.

In certain embodiments, immunogenic compositions can further comprise, for example, carriers, excipients, transfection facilitating agents, lipids, liposomes and/or adjuvants as described herein. In certain other embodiments, immunogenic compositions can further comprise a virosome. For example, the PADRE®-HA protein may be inserted into a virosome lipid bilayer. In further embodiments, the virosome is an immunopotentiating reconstituted influenza virosome (IRIV).

The compositions of the invention can be univalent, bivalent, trivalent or multivalent. A univalent composition will comprise only one polynucleotide of the present invention, or a polypeptide encoding the polynucleotide of the present invention, where the polynucleotide comprises a nucleic acid sequence of a coding region encoding an influenza virus polypeptide or a fragment, variant, or derivative thereof, a PADRE® epitope and, optionally, an HTL epitope and/or a second influenza virus polypeptide or a fragment, variant, or derivative thereof. A bivalent composition will comprise, either in polynucleotide or polypeptide form, two different influenza virus polypeptides, fragments, variants, or derivatives thereof, each capable of eliciting an immune response. The polynucleotide(s) of the composition can encode two influenza virus polypeptides or alternatively, the polynucleotide can encode only one influenza virus polypeptide and the second influenza virus polypeptide would be provided by an isolated influenza virus polypeptide of the invention as in, for example, a single formulation heterologous prime-boost vaccine composition. In the case where both influenza virus polypeptides of a bivalent composition are delivered in polynucleotide form, the nucleic acid fragments operably encoding those influenza virus polypeptides need not be on the same polynucleotide, but can be on two different polynucleotides. A trivalent or further multivalent composition will comprise three influenza virus polypeptides or fragments, variants or derivatives thereof, either in isolated form or encoded by one or more polynucleotides of the invention.

The present invention further provides plasmids and other polynucleotide constructs for delivery of nucleic acid fragments of the invention to a vertebrate, e.g., a human, which provide expression of influenza virus polypeptides, or fragments, variants, or derivatives thereof. The present invention further provides carriers, excipients, transfection-facilitating agents, immunogenicity-enhancing agents, e.g., adjuvants, or other agent or agents to enhance the transfection, expression or efficacy of the administered gene and its gene product.

In one embodiment, a multivalent composition comprises a single polynucleotide, e.g., plasmid, comprising one or more nucleic acid regions operably encoding influenza polypeptides or fragments, variants, or derivatives thereof. Reducing the number of polynucleotides, e.g., plasmids, in the compositions of the invention can have significant impacts on the manufacture and release of product, thereby reducing the costs associated with manufacturing the compositions. There are a number of approaches to include more than one expressed antigen coding sequence on a single plasmid. These include, for example, the use of Internal Ribosome Entry Site (IRES) sequences, dual promoters/expression cassettes, and fusion proteins.

The present invention is further directed to enhancing the immune response of a vertebrate in need of protection against influenza virus infection by administering, in vivo, into a tissue of the vertebrate, a polynucleotide, a polypeptide, or a composition as described above. The isolated polypeptide can be, for example, a purified subunit, a recombinant protein, a viral vector expressing an isolated influenza virus polypeptide, or can be an inactivated or attenuated influenza virus, such as those present in conventional influenza virus vaccines. According to either method, the polynucleotide is incorporated into the cells of the vertebrate in vivo, and an immunologically effective amount of an immunogenic epitope of the encoded influenza virus polypeptide, or a fragment, variant, or derivative thereof, is produced in vivo. When utilized, an isolated influenza virus polypeptide or a fragment, variant, or derivative thereof is also administered in an immunologically effective amount.

The invention also provides methods for enhancing the immune response of a vertebrate to influenza virus infection by administering to the tissues of a vertebrate one or more polypeptides, domains, fragments, or variants thereof of the present invention or one or more polynucleotides encoding one or more polypeptides, domains, fragments, or variants thereof of the present invention.

BRIEF DESCRIPTION OF THE DRAWINGS

FIG. 1. PADRE® increases HA-Specific Antibody Responses. Levels of antibody titer were measured after primary and secondary immunization of HLA-DR transgenic mice with HA, HA-PADRE®, and PADRE®-HA fusion constructs. The mice were immunized as follows: Groups of ten HLA-DR4 transgenic mice 8-16 weeks old (Taconic, Hudson, N.Y.) were immunized by injecting 50 μl bilaterally into the tibialis anterior muscle 100 μg total (high dose) and 1 μg total (low dose) plasmid DNA diluted in PBS and bled 4 wk later. The mice were subsequently immunized with the same dose of immunogen a second time and bled two weeks later to measure secondary immune responses. Following retroorbital bleeding, sera were individually analyzed or pooled to measure combined antibody responses. Antibody titers were measured by an enzyme-linked immunosorbent assays as follows: Hemagglutinin (HA)-specific antibody titers were measured by coating 96-well, flat-bottom plates (Immunol II, Dynatech, Boston, Mass.) with 100 μl of 2 μg/ml of HA antigen in PBS (Protein Sciences, Bridgeport, Conn.). Subsequently, the plates were blocked with 10% FBS in PBS followed by addition of serial ten-fold dilutions of individual or pooled sera, diluted in 1% BSA, 0.05% Tween 20 in PBS, from the immunized mice. The plates were incubated 1 h at 37° C., washed with PBS, 0.05% Tween 20, and then incubated for 2 h at room temperature with HRP-rat anti-mouse IgG (Caltag, Burlingame, Calif.). Plates were washed and then incubated with avidin DH-HRP (Vectastain ABC kit, Vector Laboratories, Burlingame, Calif.). Antibody titers were defined as the reciprocal of the serum dilution yielding 0.3 OD units (45) nm).

FIGS. 2A-D. PADRE® increases HA-Specific Antibody Responses in Individual Animals. Results of antibody titer levels corresponding to the primary response in individual animals immunized with 100 μg (FIG. 2A) or 1 μg (FIG. 2B) of HA or PADRE®-HA. Results of antibody titer levels corresponding to the secondary response in individual animals immunized with 100 μg (FIG. 2C) or 1 μg (FIG. 2D) of HA or PADRE®-HA. Immunization of animals and subsequent measurements of HA specific antibody titers using enzyme-linked immunosorbent assays were performed as described above.

FIGS. 3A-B. HTL Human Recall Responses in Donor X753. Immune responses in Donor X753 using a panel of negative control HTL epitope-containing peptides (FIG. 3A) and a panel of HTL epitope-containing peptides derived from internal flu proteins, NS1, NS2, PB1, PB2, PA, NP, M1 and M2 (FIG. 3B). Assays were performed as described in Example 6 below. The sequences of the HTL epitopes used in the experiment correspond to the nomenclature of the influenza HTL candidates in Tables 3 and 4.

FIGS. 4A-B. Immune Human Recall Responses in Donor 753. Immune responses in Donor 753 using a panel of negative control peptides derived from HIV and HCV (FIG. 4A) and a panel of peptides derived from influenza (FIG. 4B). Data are shown as spot forming cells/million CD4+ PBMC. Assays were performed as described in Example 6 below. The sequences of the influenza peptides used in the experiment correspond to the nomenclature in Tables 3-4 and 7.

FIGS. 5A-B. Immune Human Recall Responses in Donor 6018. Immune responses in Donor 6018 using a panel of negative control peptides derived from HIV and HCV (FIG. 5A) and a panel of peptides derived from influenza (FIG. 5B). Data are shown as spot forming cells/million CD4+ PBMC. Assays were performed as described in Example 6 below. The sequences of the influenza peptides used in the experiment correspond to the nomenclature in Tables 3-4 and 7.

FIGS. 6A-B Immune Human Recall Responses in Donor 716. Immune responses in Donor 716 using a panel of negative control peptides derived from HIV and HCV (FIG. 6A) and a panel of peptides derived from influenza (FIG. 6B). Data are shown as spot forming cells/million CD4+ PBMC. Assays were performed as described in Example 6 below. The sequences of the influenza peptides used in the experiment correspond to the nomenclature in Tables 3-4 and 7.

FIGS. 7A-B. Immune Human Recall Responses in Donor AC08. Immune responses in Donor AC08 using a panel of negative control peptides derived from HIV and HCV (FIG. 7A) and a panel of peptides derived from influenza (FIG. 7B). Data are shown as spot forming cells/million CD4+ PBMC. Assays were performed as described in Example 6 below. The sequences of the influenza peptides used in the experiment correspond to the nomenclature in Tables 3-4 and 7.

FIGS. 8A-B. Immune Human Recall Responses in Donor AC02. Immune responses in Donor AC02 using a panel of negative control peptides derived from HIV and HCV (FIG. 8A) and a panel of peptides derived from influenza (FIG. 8B). Data are shown as spot forming cells/million CD4+ PBMC. Assays were performed as described in Example 6 below. The sequences of the influenza peptides used in the experiment correspond to the nomenclature in Tables 3-4 and 7.

FIGS. 9A-B. Immune Human Recall Responses in Donor 3501. Immune responses in Donor 3501 using a panel of negative control peptides derived from HIV and HCV (FIG. 9A) and a panel of peptides derived from influenza (FIG. 9B). Data are shown as spot forming cells/million CD4+ PBMC. Assays were performed as described in Example 6 below. The sequences of the influenza peptides used in the experiment correspond to the nomenclature in Tables 3-4 and 7.

FIG. 10. PADRE®-HA immunogenicity as measured by HA-specific antibody titers. Results of antibody titer levels in individual animals immunized with 100 μg or 10 μg of HA or PADRE®-HA. Each triangle represents the immune response of a single mouse immunized with PADRE®-HA while each square represents the immune response of a single mouse immunized with HA.

FIG. 11. Evaluation of antibody function by hemagglutination inhibition and viral microneutralization. Immune sera from PADRE®-HA and HA immunized mice (Sera evaluated is indicated in the previous figure, following 3rd immunization and using 100 μg dose) were next evaluated for the antibody capacity to inhibit the agglutination of horse red blood cells (hemagglutination inhibition) and to inhibit the growth of virus (Microneutralization).

FIG. 12. PADRE®-HA Recombinant Protein Immunogenicity as Measured by HA-Specific Antibody Titers with Alum. Animals were immunized with 1 μg or 0.1 μg of HA or PADRE®-HA recombinant protein delivered with alum as an adjuvant. Assays were performed as described in Example 11 below. Each triangle represents the immune response of a single mouse immunized with PADRE®-HA while each square represents the immune response of a single mouse immunized with HA. Antibody titers are given as the reciprocal of the dilution giving an OD reading of 0.3 at 450 nM.

FIG. 13. PADRE®-HA Recombinant Protein Immunogenicity as Measured by HA-Specific Antibody Titers with Alum/Provax™. Animals were immunized with 1 μg or 0.11 g of HA or PADRE®-HA recombinant protein delivered with alum and Provax™ as an adjuvant. Assays were performed as described in Example 12 below. Each triangle represents the immune response of a single mouse immunized with PADRE®-HA while each square represents the immune response of a single mouse immunized with HA. Antibody titers are given as the reciprocal of the dilution giving an OD reading of 0.3 at 450 nM.

FIG. 14. Schematic of PADRE®-HA and HA DNA and Protein Constructs.

DETAILED DESCRIPTION OF THE INVENTION

The present invention is directed to compositions and methods for enhancing the immune response of a vertebrate in need of protection against influenza virus infection by administering in vivo, into a tissue of a vertebrate, at least one polynucleotide or at least one polypeptide encoded by such a polynucleotide, comprising or encoded by one or more nucleic acid fragments, where each nucleic acid fragment is a fragment of a coding region operably encoding an influenza virus polypeptide, or a fragment, variant, or derivative thereof in cells of the vertebrate in need of protection. The polynucleotide or polypeptide also comprises a nucleic acid sequence encoding a pan-DR binding epitope (e.g. PADRE®) or the peptide encoded therein and optionally one or more nucleic acids encoding a sequence that comprises a helper T lymphocyte (HTL) epitope or the polypeptide encoded therein.

The present invention is also directed to administering in vivo, into a tissue of the vertebrate the above described polynucleotide and at least one isolated influenza polypeptide, or a fragment, variant, or derivative thereof. The isolated influenza polypeptide or fragment, variant, or derivative thereof can be, for example, a recombinant protein, a purified subunit protein, a protein expressed and carried by a heterologous live or inactivated or attenuated viral vector expressing the protein, or can be an inactivated influenza, such as those present in conventional, commercially available, inactivated influenza vaccines. According to either method, the polynucleotide is incorporated into the cells of the vertebrate in vivo, and an immunologically effective amount of the influenza protein, or fragment or variant encoded by the polynucleotide is produced in vivo. The isolated protein or fragment, variant, or derivative thereof is also administered in an immunologically effective amount. The polynucleotide can be administered to the vertebrate in need thereof either prior to, at the same time (simultaneously), or subsequent to the administration of the isolated influenza polypeptide or fragment, variant, or derivative thereof.

Non-limiting examples of influenza polypeptides within the scope of the invention include, but are not limited to, HA, NA, NP, PA, PB1, PB2, NS1, NS2, M1 or M2 polypeptides, and fragments, e.g., M2e derivatives, and variants thereof. Nucleotide and amino acid sequences of influenza polypeptides from a wide variety of influenza types and subtypes are known in the art. The nucleotide sequences and polypeptide sequences set forth below comprise wild-type HA sequences. For example, the amino acid sequence corresponding to the mature HA protein of Influenza A/Vietnam/1203/2004 (H5N1) is available in GenBank (Accession Number AAT73274), and has the following sequence, referred to herein as SEQ ID NO: 5:

DQICIGYHANNSTEQVDTIMEKNVTVTHAQDILEKKHNGKLCDLDGVKPL

ILRDCSVAGWLLGNPMCDEFINVPEWSYIVEKANPVNDLCYPGDFNDYEE

LKHLLSRINHFEKIQIIPKSSWSSHEASLGVSSACPYQGKSSFFRNVVWL

IKKNSTYPTIKRSYNNTNQEDLLVLWGIHHPNDAAEQTKLYQNPTTYISV

GTSTLNQRLVPRIATRSKVNGQSGRMEFFWTILKPNDAINFESNGNFIAP

EYAYKIVKKGDSTIMKSELEYGNCNTKCQTPMGAINSSMPFHNIHPLTIG

ECPKYVKSNRLVLATGLRNSPQRERRRKKRGLFGAIAGFIEGGWQGMVDG

WYGYHHSNEQGSGYAADKESTQKAIDGVTNKVNSIIDKMNTQFEAVGREF

NNLERRIENLNKKMEDGFLDVWTYNAELLVLMENERTLDFHDSNVKNLYD

KVRLQLRDNAKELGNGCFEFYHKCDNECMESVRNGTYDYPQYSEEARLKR

EEISGVKLESIGIYQILSIYSTVASSLALAIMVAGLSLWMCSNGSLQCR

Polypeptides of the present invention also include the extracellular domain (ECD) of the HA protein, for example, of Influenza A/Vietnam/1203/2004 (H5N1), having the following sequence, referred to herein as SEQ ID NO: 6:

DQICIGYHANNSTEQVDTIMEKNVTVTHAQDILEKKHNGKLCDLDGVKPL

ILRDCSVAGWLLGNPMCDEFINVPEWSYIVEKANPVNDLCYPGDFNDYEE

LKHLLSRINHFEKIQIIPKSSWSSHEASLGVSSACPYQGKSSFFRNVVWL

IKKNSTYPTIKRSYNNTNQEDLLVLWGIHHPNDAAEQTKLYQNPTTYISV

GTSTLNQRLVPRIATRSKVNGQSGRMEFFWTILKPNDAINFESNGNFIAP

EYAYKIVKKGDSTIMKSELEYGNCNTKCQTPMGAINSSMPFHNIHPLTIG

ECPKYVKSNRLVLATGLRNSPQRERRRKKRGLFGAIAGFIEGGWQGMVDG

WYGYHHSNEQGSGYAADKESTQKAIDGVTNKVNSIIDKMNTQFEAVGREF

NNLERRIENLNKKMEDGFLDVWTYNAELLVLMENERTLDFHDSNVKNLYD

KVRLQLRDNAKELGNGCFEFYHKCDNECMESVRNGTYDYPQYSEEARLKR

EEISGVKLESIGIYQ

Polypeptides of the present invention may further include the transmembrane domain (TM) of the HA protein, for example, of Influenza A/Vietnam/1203/2004 (H5N1) having the sequence ILSIYSTVASSLALAIMVAGL (SEQ ID NO: 7) and/or the cytoplasmic domain (CYT) of the HA protein, for example, of Influenza A/Vietnam/1203/2004 (H5N1) having the sequence SLWMCSNGSLQCR (SEQ ID NO:8).

Additional HA sequences of the present invention correspond to isolated wild-type HA sequences from influenza A and influenza B strains as disclosed in Tables 1 and 2. Wild-type HA sequences from influenza strains can also be found at http://www.flu.lanl.gov/search/index.html?form_page=search.

Additional polypeptides of the present invention include polypeptides comprising the ECD domain, the TM domain, or the CYT domain of the HA sequences set forth above, and any combinations thereof, including, but not limited to HA polypeptides comprising the ECD, TM and CYT domains; polypeptides comprising both the ECD and TM domains; polypeptides comprising both the TM and CYT domains; and polypeptides comprising the ECD and CYT domains. Polypeptides of the present invention can optionally comprise a N-terminal sequence, for example, residues 1-16 of the HA sequence available in Genbank (Accession Number AAT73274), which corresponds to the natural signal sequence and/or other appropriate signal sequences known in the art.

Polynucleotides of the present invention can comprise a heterologous signal sequence, a His-tag sequence, a wild-type HA sequence and/or a PADRE® sequence. For example, the polynucleotide sequence of an exemplary HA construct comprising a heterologous signal sequence, a His-tag sequence, and a wild-type HA sequence of the present invention is as follows, referred to herein as SEQ ID NO: 9:

```
GGATCCGAATTCACCATGCCGCTCTACAAATTGCTAAACGTGTTATGGTT
AGTCGCTGTGTCCAACGCGATTCCTGGCAGCTATTACCATCACCATCACC
ATCACGACTACGATATTCCGACGACCGAAAACTTGTATTTTCAAGGCGCG
GATCAAATTTGTATAGGTTACCATGCGAACAATAGCACGGAACAAGTAGA
TACCATTATGGAAAAGAACGTGACAGTTACACATGCGCAGGACATTTTGG
AAAAAAAGCACAATGGAAAGTTGTGTGATCTTGACGGGGTCAAACCACTA
ATCTTACGTGACTGTTCAGTGGCGGGTTGGTTGTTAGGCAACCCGATGTG
CGATGAATTTATTAATGTACCGGAGTGGTCATATATCGTGGAAAAAGCCA
ACCCCGTTAACGACTTGTGTTATCCTGGTGATTTTAATGACTACGAGGAA
TTAAAACACTTGCTGTCACGTATCAATCACTTTGAGAAAATACAAATAAT
```

-continued
```
CCGCTGAACAGACAAAATTATATCAAAACCCCACTACCTACATTTCAGTA
GGCACGAGTACGCTGAACCAGCGCCTTGTGCCACGAATAGCCACTAGGTC
TAAGGTTAATGGCCAGTCTGGTCGCATGGAATTTTTCTGGACTATACTCA
AACCTAACGATGCTATCAACTTTGAGTCTAATGGCAACTTTATTGCCCCT
GAATACGCGTATAAGATTGTTAAAAAGGGCGATTCGACGATTATGAAATC
GGAACTCGAATATGGTAATTGCAACACCAAATGTCAAACTCCCATGGGCG
CTATTAACAGCTCCATGCCATTTCACAATATTCACCCGTTGACTATAGGC
GAATGTCCAAAATATGTGAAGTCCAATCGCTTGGTACTCGCCACCGGCTT
GAGGAATAGCCCGCAACGTGAGAGACGGAGAAAAAAGCGGGGATTGTTTG
GCGCCATCGCCGGATTTATAGAAGGTGGCTGGCAAGGAATGGTGGATGGC
TGGTATGGATACCACCATTCCAACGAACAAGGTTCAGGCTACGCGGCAGA
CAAAGAATCTACTCAAAAAGCAATAGACGGCGTGACAAATAAAGTAAATA
GTATAATTGACAAAATGAATACGCAGTTTGAAGCCGTCGGCCGTGAGTTC
AATAACCTGGAGCGCAGAATTGAAAATCTAAACAAAAAGATGGAGGACGG
GTTTTTAGACGTTTGGACGTACAATGCAGAATTGTTAGTTTTGATGGAAA
ACGAACGCACCTTGGATTTTCACGACTCGAACGTTAAAAACCTGTACGAT
AAAGTCCGACTGCAATTACGCGATAATGCAAAAGAACTGGGAAACGGCTG
CTTCGAATTTTATCATAAATGCGACAATGAATGCATGGAATCTGTACGAA
ATGGTACATACGACTATCCCCAATACTCGGAGGAAGCGCGTCTAAAACGC
GAAGAGATTAGCGGGGTGAAATTAGAGAGTATTGGAATTTACCAAATTTT
GAGCATTTATAGCACCGTTGCATCGAGTCTTGCGTTGGCAATAATGGTCG
CGGGCTTATCTTTGTGGATGTGCAGCAACGGAAGCCTTCAATGTAGATAA
CTGCAGAAGCTTTAA
```

The amino acid sequence of this exemplary HA construct described above is as follows (highlighted portion corresponds to heterologous signal sequence and His-tag sequence), referred to herein as SEQ ID NO:10:

```
GSEFTMPLYKLLNVLWLVAVSNAIPGSYYHHHHHHDYDIPTTENLYFQGADQICIGYHANNSTEQVDTIMEK
NVTVTHAQDILEKKHNGKLCDLDGVKPLILRDCSVAGWLLGNPMCDEFINVPEWSYIVEKANPVNDLCYPGD
FNDYEELKHLLSRINHFEKIQIIPKSSWSSHEASLGVSSACPYQGKSSFFRNVVWLIKKNSTYPTIKRSYNN
TNQEDLLVLWGIHHPNDAAEQTKLYQNPTTYISVGTSTLNQRLVPRIATRSKVNGQSGRMEFFWTILKPNDA
INFESNGNFIAPEYAYKIVKKGDSTIMKSELEYGNCNTKCQTPMGAINSSMPFHNIHPLTIGECPKYVKSNR
LVLATGLRNSPQRERRRKKRGLFGAIAGFIEGGWQGMVDGWYGYHHSNEQGSGYAADKESTQKAIDGVTNKV
NSIIDKMNTQFEAVGREFNNLERRIENLNKKMEDGFLDVWTYNAELLVLMENERTLDFHDSNVKNLYDKVRL
QLRDNAKELGNGCFEFYHKCDNECMESVRNGTYDYPQYSEEARLKREEISGVKLESIGIYQILSIYSTVASS
LALAIMVAGLSLWMCSNGSLQCR
```

The polynucleotide sequence of an exemplary HA-PADRE® construct of the present invention is as follows, referred to herein as SEQ ID NO: 11:

```
GGATCCGAATTCACCATGCCGCTCTACAAATTGCTAAACGTGTTATGGTT
AGTCGCTGTGTCCAACGCGATTCCTGGCAGCTATTACCATCACCATCACC
```

-continued
```
CCCCAAATCTTCCTGGAGTAGCCATGAGGCTTCGTTGGGCGTGAGTAGCG
CCTGCCCCTACCAAGGCAAATCGAGTTTTTTCCGAAACGTGGTATGGCTA
ATAAAAAGAACTCGACGTACCCGACGATCAAAAGATCGTATAACAATAC
GAACCAGGAAGACTTGCTTGTCTTGTGGGGTATCCACCATCCGAACGACG
```

```
ATCACGACTACGATATTCCGACGACCGAAAACTTGTATTTTCAAGGCGCG

GATCAAATTTGTATAGGTTACCATGCGAACAATAGCACGGAACAAGTAGA

TACCATTATGGAAAAGAACGTGACAGTTACACATGCGCAGGACATTTTGG

AAAAAAAGCACAATGGAAAGTTGTGTGATCTTGACGGGGTCAAACCACTA

ATCTTACGTGACTGTTCAGTGGCGGGTTGGTTGTTAGGCAACCCGATGTG

CGATGAATTTATTAATGTACCGGAGTGGTCATATATCGTGGAAAAAGCCA

ACCCCGTTAACGACTTGTGTTATCCTGGTGATTTTAATGACTACGAGGAA

TTAAAACACTTGCTGTCACGTATCAATCACTTTGAGAAAATACAAATAAT

CCCCAAATCTTCCTGGAGTAGCCATGAGGCTTCGTTGGGCGTGAGTAGCG

CCTGCCCCTACCAAGGCAAATCGAGTTTTTTCCGAAACGTGGTATGGCTA

ATAAAAAAGAACTCGACGTACCCGACGATCAAAAGATCGTATAACAATAC

GAACCAGGAAGACTTGCTTGTCTTGTGGGTATCCACCATCCGAACGACG

CCGCTGAACAGACAAAATTATATCAAAACCCCACTACCTACATTTCAGTA

GGCACGAGTACGCTGAACCAGCGCCTTGTGCCACGAATAGCCACTAGGTC

TAAGGTTAATGGCCAGTCTGGTCGCATGGAATTTTTCTGGACTATACTCA

AACCTAACGATGCTATCAACTTTGAGTCTAATGGCAACTTTATTGCCCCT

GAATACGCGTATAAGATTGTTAAAAAGGGCGATTCGACGATTATGAAATC

GGAACTCGAATATGGTAATTGCAACACCAAATGTCAAACTCCCATGGGCG

CTATTAACAGCTCCATGCCATTTCACAATATTCACCCGTTGACTATAGGC

GAATGTCCAAAATATGTGAAGTCCAATCGCTTGGTACTCGCCACCGGCTT

GAGGAATAGCCCGCAACGTGAGAGACGGAGAAAAAAGCGGGGATTGTTTG

GCGCCATCGCCGGATTTATAGAAGGTGGCTGGCAAGGAATGGTGGATGGC

TGGTATGGATACCACCATTCCAACGAACAAGGTTCAGGCTACGCGGCAGA

CAAAGAATCTACTCAAAAAGCAATAGACGGCGTGACAAATAAAGTAAATA

GTATAATTGACAAAATGAATACGCAGTTTGAAGCCGTCGGCCGTGAGTTC

AATAACCTGGAGCGCAGAATTGAAAATCTAAACAAAAAGATGGAGGACGG

GTTTTTAGACGTTTGGACGTACAATGCAGAATTGTTAGTTTTGATGGAAA

ACGAACGCACCTTGGATTTTCACGACTCGAACGTTAAAAACCTGTACGAT

AAAGTCCGACTGCAATTACGCGATAATGCAAAAGAACTGGGAAACGGCTG

CTTCGAATTTTATCATAAATGCGACAATGAATGCATGGAATCTGTACGAA

ATGGTACATACGACTATCCCCAATACTCGGAGGAAGCGCGTCTAAAACGC

GAAGAGATTAGCGGGGTGAAATTAGAGAGTATTGGAATTTACCAAATTTT

GAGCATTTATAGCACCGTTGCATCGAGTCTTGCGTTGGCAATAATGGTCG

CGGGCTTATCTTTGTGGATGTGCAGCAACGGAAGCCTTCAATGTAGAGCA

AAATTTGTGGCCGCGTGGACACTGAAAGCTGCGGCTTAACTGCAGAAGCT

TTAA
```

The amino acid sequence of this exemplary HA-PADRE® construct described above is as follows (highlighted portion corresponds to heterologous signal sequence and His-tag sequence; underlined portion corresponds to PADRE® sequence), referred to herein as SEQ ID NO:12:

```
                                                  D
QICIGYHANNSTEQVDTIMEKNVTVTTHAQDILEKKHNGKLCDLDGVKPLI

LRDCSVAGWLLGNPMCDEFINVPEWSYIVEKANPVNDLCPGDFNDYEELKH

LLSRINHFEKIQIIPKSSWSSHEASLGVSSACPYQGKSSFFRNVVWLIKKN

STYPTIKRSYNNTNQEDLLVLWGIHHPNDAAEQTKLYQNPTTYISVGTSTL

NQRLVPRIATRSKVNGQSGRMEFFWTILKPNDAINFESNGNFIAPEYAYKI

VKKGDSTIMKSELEYGNCNTKCQTPMGAINSSMPFHNIHPLTIGECPKYVK

SNRLVLATGLRNSPQRERRRKKRGLFGAIAGFIEGGWQGMVDGWYGYHHSN

EQGSGYAADKESTQKAIDGVTNKVNSIIDKMNTQFEAVGREFNNLERRIEN

LNKKMEDGFLDVWTYNAELLVLMENERTLDFHDSNVKNLYDKVRLQLRDNA

KELGNGCFEFYHKCDNECMESVRNGTYDYPQYSEEARLKREEISGVKLESI

GIYQILSIYSTVASSLALAIMVAGLSLWMCSNGSLQCRAKFVAAWTLKAAA
```

The polynucleotide sequence of an exemplary PADRE®-HA construct of the present invention is as follows, referred to herein as SEQ ID NO: 13:

```
GGATCCGAATTCACCATGCCGCTCTACAAATTGCTAAACGTGTTATGGTT

AGTCGCTGTGTCCAACGCGATTCCTGGCAGCTATTACCATCACCATCACC

ATCACGACTACGATATTCCGACGACCGAAAACTTGTATTTTCAAGGCGCG

GCAAAATTTGTGGCCGCGTGGACACTGAAAGCTGCGGCTGATCAAATTTG

TATAGGTTACCATGCGAACAATAGCACGGAACAAGTAGATACCATTATGG

AAAAGAACGTGACAGTTACACATGCGCAGGACATTTTGGAAAAAAAGCAC

AATGGAAAGTTGTGTGATCTTGACGGGGTCAAACCACTAATCTTACGTGA

CTGTTCAGTGGCGGGTTGGTTGTTAGGCAACCCGATGTGCGATGAATTTA

TTAATGTACCGGAGTGGTCATATATCGTGGAAAAAGCCAACCCCGTTAAC

GACTTGTGTTATCCTGGTGATTTTAATGACTACGAGGAATTAAAACACTT

GCTGTCACGTATCAATCACTTTGAGAAAATACAAATAATCCCCAAATCTT

CCTGGAGTAGCCATGAGGCTTCGTTGGGCGTGAGTAGCGCCTGCCCCTAC

CAAGGCAAATCGAGTTTTTTCCGAAACGTGGTATGGCTAATAAAAAAGAA

CTCGACGTACCCGACGATCAAAAGATCGTATAACAATACGAACCAGGAAG

ACTTGCTTGTCTTGTGGGTATCCACCATCCGAACGACGCCGCTGAACAG

ACAAAATTATATCAAAACCCCACTACCTACATTTCAGTAGGCACGAGTAC

GCTGAACCAGCGCCTTGTGCCACGAATAGCCACTAGGTCTAAGGTTAATG

GCCAGTCTGGTCGCATGGAATTTTTCTGGACTATACTCAAACCTAACGAT

GCTATCAACTTTGAGTCTAATGGCAACTTTATTGCCCCTGAATACGCGTA

TAAGATTGTTAAAAAGGGCGATTCGACGATTATGAAATCGGAACTCGAAT

ATGGTAATTGCAACACCAAATGTCAAACTCCCATGGGCGCTATTAACAGC

TCCATGCCATTTCACAATATTCACCCGTTGACTATAGGCGAATGTCCAAA

ATATGTGAAGTCCAATCGCTTGGTACTCGCCACCGGCTTGAGGAATAGCC

CGCAACGTGAGAGACGGAGAAAAAAGCGGGGATTGTTTGGCGCCATCGCC

GGATTTATAGAAGGTGGCTGGCAAGGAATGGTGGATGGCTGGTATGGATA
```

-continued

```
CCACCATTCCAACGAACAAGGTTCAGGCTACGCGGCAGACAAAGAATCTA

CTCAAAAAGCAATAGACGGCGTGACAAATAAAGTAAATAGTATAATTGAC

AAAATGAATACGCAGTTTGAAGCCGTCGGCCGTGAGTTCAATAACCTGGA

GCGCAGAATTGAAAATCTAAACAAAAAGATGGAGGACGGGTTTTTAGACG

TTTGGACGTACAATGCAGAATTGTTAGTTTTGATGGAAAACGAACGCACC

TTGGATTTTCACGACTCGAACGTTAAAAACCTGTACGATAAAGTCCGACT

GCAATTACGCGATAATGCAAAAGAACTGGGAAACGGCTGCTTCGAATTTT

ATCATAAATGCGACAATGAATGCATGGAATCTGTACGAAATGGTACATAC

GACTATCCCCAATACTCGGAGGAAGCGCGTCTAAAACGCGAAGAGATTAG

CGGGGTGAAATTAGAGAGTATTGGAATTTACCAAATTTTGAGCATTTATA

GCACCGTTGCATCGAGTCTTGCGTTGGCAATAATGGTCGCGGGCTTATCT

TTGTGGATGTGCAGCAACGGAAGCCTTCAATGTAGATAACTGCAGAAGCT

TTAA
```

The amino acid sequence of this exemplary PADRE®-HA construct described above is as follows (highlighted portion corresponds to heterologous signal sequence and His-tag sequence; underlined portion corresponds to PADRE® sequence), referred to herein as SEQ ID NO:14:

```
░░░░░░░░░░░░░░░░░░░░░░░░░░░░░░░░░░░░░░░░░░░░░░AA

KFVAAWTLKAAADQICIGYHANNSTEQVDTIMEKNVTVTHAQDILEKKHNG

KLCDLDGVKPLILRDCSVAGWLLGNPMCDEFINVPEWSYIVEKANPVNDLC

YPGDFNDYEELKHLLSRINHFEKIQIIPKSSWSSHEASLGVSSACPYQGKS

SFFRNVVWLIKKNSTYPTIKRSYNNTNQEDLLVLWGIHHPNDAAEQTKLYQ

NPTTYISVGTSTLNQRLVPRIATRSKVNGQSGRMEFFWTILKPNDAINFES

NGNFIAPEYAYKIVKKGDSTIMKSELEYGNCNTKCQTPMGAINSSMPFHNI

HPLTIGECPKYVKSNRLVLATGLRNSPQRERRRKKRGLFGAIAGFIEGGWQ

GMVDGWYGYHHSNEQGSGYAADKESTQKAIDGVTNKVNSIIDKMNTQFEAV

GREFNNLERRIENLNKKMEDGFLDVWTYNAELLVLMENERTLDFHDSNVKN

LYDKVRLQLRDNAKELGNGCFEFYHKCDNECMESVRNGTYDYPQYSEEARL

KREEISGVKLESIGIYQILSIYSTVASSLALAIMVAGLSLWMCSNGSLQCR
```

Polynucleotides of the present invention can also comprise a HIS tag. The HIS tag can be a 6×HIS tag of the sequence or can be a HIS tag of the sequence MKHQHQHQHQHQHQ (SEQ ID NO: 176). The HIS tag can optionally be followed or proceeded by a sequence to allow for removal of the HIS tag. The sequence may, for example be a stop signal that follows the HIS tag and includes a basic amino acid in the first position adjacent to the HIS tag or a proline at the second or third position after the HIS tag. In particular, the stop sequence may be a dipeptidase stop signal of the sequence AP, GPG or GPGPG (SEQ ID NO:3). The dipeptidase stop signal may allow for removal of the HIS tag by a dipeptidase. The HIS tag also can optionally be adjacent to a TEV protease cleavage site. In a preferred embodiment the sequence that allows for removal of the HIS tag is located between the PADRE®-HA or HA sequence and the HIS tag. The HIS tag is preferably located on the N-terminus of the PADRE®-HA or HA sequence, but can be arranged in any order relative to the other sequences.

Polynucleotides of the present invention also can include a cleavage site. Optionally, the cleavage site can be located between the HA1 and HA1 sequences. The cleavage site can be, for example the endogenous cleavage site of H5 of A/Vietnam/1203/2004 HA polybasic cleavage site PQRERRRKKRGLFGAI (SEQ ID NO: 186), which is expected to be cleaved during secretion. The cleavage site can also be a mutated version of the cleavage site with the sequence PQRETQGLFGAI (SEQ ID NO:187), which is not expected to be cleaved. The cleavage site can also be a thrombin cleavage site, for example, of the sequence, SSGRLVPRGSPGS (SEQ ID NO:178). The cleavage site can also be a TEV protease cleavage site, for example, of the sequence DYDIPTTENLYFQGA (SEQ ID NO: 188).

Polynucleotides of the present invention can also include a trimerizing sequence. Influenza HA is expressed as a trimeric membrane bound protein with a C-terminal cytosolic tail. In general, proteins embedded in the membrane are more difficult to purify and are expressed in much less quantities compared to proteins that are secreted as soluble proteins. Therefore, some constructs of the present invention are designed to encode only the HA ectodomain (without membrane and cytoplasmic regions) to allow for efficient secretion of the recombinant protein. However, as the trimeric structure of HA is important for its antigenicity, a trimerizing sequence ('foldon') from the bacteriophage T4 fibritin can be added in place of the transmembrane and cytoplasmic domains. The fold-on sequence has been shown to facilitate the trimerization of influenza HA[155-156] as well as collagen. The fold-on may enhance formation of a stable trimer to ensure that antibodies raised against the recombinant truncated protein crossreact with the native HA.

Polynucleotides of the present invention can comprise a signal sequence, a HIS-tag sequence and optionally a TEV protease cleavage site, optionally a PADRE® sequence, an HA1 sequence, an HA1/HA2 cleavage site, an HA2 sequence, an HA transmembrane sequence and an HA cytoplasmic domain. For example, an exemplary example of such a polynucleotide that includes a PADRE® sequence is as follows, referred to herein as SEQ ID NO:182:

```
ATGCCGCTCTACAAATTGCTAAACGTGTTATGGTTAGTCGCTGTGTCCAA
CGCGATTCCTGGCAGCTATTACCATCACCATCACCATCACGACTACGATA
TTCCGACGACCGAAAACTTGTATTTTCAAGGCGCGGCAAAATTTGTGGCC
GCGTGGACACTGAAAGCTGCGGCTGATCAAATTTGTATAGGTTACCATGC
GAACAATAGCACGGAACAAGTAGATACCATTATGGAAAAGAACGTGACAG
TTACACATGCGCAGGACATTTTGGAAAAAAAGCACAATGGAAAGTTGTGT
GATCTTGACGGGGTCAAACCACTAATCTTACGTGACTGTTCAGTGGCGGG
TTGGTTGTTAGGCAACCCGATGTGCGATGAATTTATTAATGTACCGGAGT
GGTCATATATCGTGGAAAAAGCCAACCCCGTTAACGACTTGTGTTATCCT
GGTGATTTTAATGACTACGAGGAATTAAAACACTTGCTGTCACGTATCAA
TCACTTTGAGAAAATACAAATAATCCCCAAATCTTCCTGGAGTAGCCATG
AGGCTTCGTTGGGCGTGAGTAGCGCCTGCCCCTACCAAGGCAAATCGAGT
TTTTTCCGAAACGTGGTATGGCTAATAAAAAAGAACTCGACGTACCCGAC
```

-continued
```
GATCAAAAGATCGTATAACAATACGAACCAGGAAGACTTGCTTGTCTTGT

GGGGT

The amino acid sequence of this exemplary construct described above is as follows, referred to herein as SEQ ID NO: 181 (in which aa 1-24 correspond to a chitinase signal sequence, aa 25-30 correspond to a 6×HIS tag, aa 31-45 correspond to a TEV protease cleavage site and aa 46-594 correspond to A/Vietnam/1203/2004 HA seq (Acc #AAT73274).

```
MPLYKLLNVLWLVAVSNAIPGSYYHHHHHHDYDIPTTENLYFQGADQICI
GYHANNSTEQVDTIMEKNVTVTHAQDILEKKHNGKLCDLDGVKPLILRDC
SVAGWLLGNPMCDEFINVPEWSYIVEKANPVNDLCYPGDFNDYEELKHLL
SRINHFEKIQIIPKSSWSSHEASLGVSSACPYQGKSSFFRNVVWLIKKNS
TYPTIKRSYNNTNQEDLLVLWGIHHPNDAAEQTKLYQNPTTYISVGTSTL
NQRLVPRIATRSKVNGQSGRMEFFWTILKPNDAINFESNGNFIAPEYAYK
IVKKGDSTIMKSELEYGNCNTKCQTPMGAINSSMPFHNIHPLTIGECPKY
VKSNRLVLATGLRNSPQRERRRKKRGLFGAIAGFIEGGWQGMVDGWYGYH
HSNEQGSGYAADKESTQKAIDGVTNKVNSIIDKMNTQFEAVGREFNNLER
RIENLNKKMEDGFLDVWTYNAELLVLMENERTLDFHDSNVKNLYDKVRLQ
LRDNAKELGNGCFEFYHKCDNECMESVRNGTYDYPQYSEEARLKREEISG
VKLESIGIYQILSIYSTVASSLALAIMVAGLSLWMCSNGSLQCR
```

Polynucleotides of the present invention can comprise a signal sequence, a HIS-tag sequence, optionally a PADRE® sequence, an HA1 sequence, an HA1/HA2 cleavage site, an HA2 sequence, thrombin cleavage site and a foldon sequence. For example, an exemplary example of such a polynucleotide that includes a PADRE® sequence is as follows, referred to herein as SEQ ID NO:173:

```
ATGAAGTTGTGCATCTTGCTGGCCGTCGTGGCCTTCGTGGGCCTGTCGCT
GGGCATGAAGCACCAACACCAACATCAACATCAACATCAACATCAAGCCC
CCGCAAAATTTGTGGCCGCGTGGACACTGAAAGCTGCGGCTGATCAAATT
TGTATAGGTTACCATGCGAACAATAGCACGGAACAAGTAGATACCATTAT
GGAAAAGAACGTGACAGTTACACATGCGCAGGACATTTTGGAAAAAAAGC
ACAATGGAAAGTTGTGTGATCTTGACGGGGTCAAACCACTAATCTTACGT
GACTGTTCAGTGGCGGGTTGGTTGTTAGGCAACCCGATGTGCGATGAATT
TATTAATGTACCGGAGTGGTCATATATCGTGGAAAAAGCCAACCCCGTTA
ACGACTTGTGTTATCCTGGTGATTTTAATGACTACGAGGAATTAAAACAC
TTGCTGTCACGTATCAATCACTTTGAGAAAATACAAATAATCCCCAAATC
TTCCTGGAGTAGCCATGAGGCTTCGTTGGGCGTGAGTAGCGCCTGCCCCT
ACCAAGGCAAATCGAGTTTTTTCCGAAACGTGGTATGGCTAATAAAAAAG
AACTCGACGTACCCGACGATCAAAAGATCGTATAACAATACGAACCAGGA
AGACTTGCTTGTCTTGTGGGGTATCCACCATCCGAACGACGCCGCTGAAC
AGACAAAATTATATCAAAACCCCACTACCTACATTTCAGTAGGCACGAGT
ACGCTGAACCAGCGCCTTGTGCCACGAATAGCCACTAGGTCTAAGGTTAA
TGGCCAGTCTGGTCGCATGGAATTTTTCTGGACTATACTCAAACCTAACG
ATGCTATCAACTTTGAGTCTAATGGCAACTTTATTGCCCCTGAATACGCG
```

-continued

```
TATAAGATTGTTAAAAAGGGCGATTCGACGATTATGAAATCGGAACTCGA
ATATGGTAATTGCAACACCAAATGTCAAACTCCCATGGGCGCTATTAACA
GCTCCATGCCATTTCACAATATTCACCCGTTGACTATAGGCGAATGTCCA
AAATATGTGAAGTCCAATCGCTTGGTACTCGCCACCGGCTTGAGGAATAG
CCCGCAACGTGAGAGACGGAGAAAAAAGCGGGGATTGTTTGGCGCCATCG
CCGGATTTATAGAAGGTGGCTGGCAAGGAATGGTGGATGGCTGGTATGGA
TACCACCATTCCAACGAACAAGGTTCAGGCTACGCGGCAGACAAAGAATC
TACTCAAAAAGCAATAGACGGCGTGACAAATAAAGTAAATAGTATAATTG
ACAAAATGAATACGCAGTTTGAAGCCGTCGGCCGTGAGTTCAATAACCTG
GAGCGCAGAATTGAAAATCTAAACAAAAAGATGGAGGACGGGTTTTTAGA
CGTTTGGACGTACAATGCAGAATTGTTAGTTTTGATGGAAAACGAACGCA
CCTTGGATTTTCACGACTCGAACGTTAAAAACCTGTACGATAAAGTCCGA
CTGCAATTACGCGATAATGCAAAAGAACTGGGAAACGGCTGCTTCGAATT
TTATCATAAATGCGACAATGAATGCATGGAATCTGTACGAAATGGTACAT
ACGACTATCCCCAATACTCGGAGGAAGCGCGTCTAAAACGCGAAGAGATT
AGCAGTGGCCGCCTGGTGCCCCGCGGCAGCCCCGGCAGCGGCTACATCCC
CGAGGCCCCCCGCGATGGCCAGGCCTACGTGCGCAAGGATGGCGAGTGG
TGCTGCTGAGCACCTTCCTG
```

The amino acid sequence of this exemplary construct described above is as follows, referred to herein as SEQ ID NO:174 (in which aa 1-18 correspond to a Bip signal sequence, aa 19-32 correspond to a HIS tag, aa 33-34 correspond to a dipeptidase stop signal, aa 35-47 correspond to PADRE®, aa 552-563 correspond to a thrombin cleavage site and aa 564-590 correspond to a foldon sequence.

```
MKLCILLAVVAFVGLSLGMKHQHQHQHQHQHQAPAKFVAAWTLKAAADQI
CIGYHANNSTEQVDTIMEKNVTVTHAQDILEKKHNGKLCDLDGVKPLILR
DCSVAGWLLGNPMCDEFINVPEWSYIVEKANPVNDLCYPGDFNDYEELKH
LLSRINHFEKIQIIPKSSWSSHEASLGVSSACPYQGKSSFFRNVVWLIKK
NSTYPTIKRSYNNTNQEDLLVLWGIHHPNDAAEQTKLYQNPTTYISVGTS
TLNQRLVPRIATRSKVNGQSGRMEFFWTILKPNDAINFESNGNFIAPEYA
YKIVKKGDSTIMKSELEYGNCNTKCQTPMGAINSSMPFHMIHPLTIGECP
KYVKSNRLVLATGLRNSPQRERRRKKRGLFGAIAGFIEGGWQGMVDGWYG
YHHSNEQGSGYAADKESTQKAIDGVTNKVNSIIDKMNTQFEAVGREFNNL
ERRIENLNKKMEDGFLDVWTYNAELLVLMENERTLDFHDSNVKNLYDKVR
LQLRDNAKELGNGCFEFYHKCDNECMESVRNGTYDYPQYSEEARLKREEI
SSGRLVPRGSPGSGYIPEAPRDGQAYVRKDGEWVLLSTFL
```

An exemplary example of such a polynucleotide that does not include a PADRE® sequence is as follows, referred to herein as SEQ ID NO: 184:

```
ATGAAGTTGTGCATCTTGCTGGCCGTCGTGGCCTTCGTGGGCCTGTCGCT
GGGCATGAAGCACCAACACCAACATCAACATCAACATCAACATCAAGCCC
```

-continued
CCGATCAAATTTGTATAGGTTACCATGCGAACAATAGCACGGAACAAGTA

GATACCATTATGGAAAAGAACGTGACAGTTACACATGCGCAGGACATTTT

GGAAAAAAAGCACAATGGAAAGTTGTGTGATCTTGACGGGGTCAAACCAC

TAATCTTACGTGACTGTTCAGTGGCGGGTTGGTTGTTAGGCAACCCGATG

TGCGATGAATTTATTAATGTACCGGAGTGGTCATATATCGTGGAAAAAGC

CAACCCCGTTAACGACTTGTGTTATCCTGGTGATTTTAATGACTACGAGG

AATTAAAACACTTGCTGTCACGTATCAATCACTTTGAGAAAATACAAATA

ATCCCCAAATCTTCCTGGAGTAGCCATGAGGCTTCGTTGGGCGTGAGTAG

CGCCTGCCCCTACCAAGGCAAATCGAGTTTTTTCCGAAACGTGGTATGGC

TAATAAAAAAGAACTCGACGTACCCGACGATCAAAAGATCGTATAACAAT

ACGAACCAGGAAGACTTGCTTGTCTTGTGGGGTATCCACCATCCGAACGA

CGCCGCTGAACAGACAAAATTATATCAAAACCCCACTACCTACATTTCAG

TAGGCACGAGTACGCTGAACCAGCGCCTTGTGCCACGAATAGCCACTAGG

TCTAAGGTTAATGGCCAGTGTGGTCGCATGGAATTTTTCTGGACTATACT

CAAACCTAACGATGCTATCAACTTTGAGTCTAATGGCAACTTTATTGCCC

CTGAATACGCGTATAAGATTGTTAAAAAGGGCGATTCGACGATTATGAAA

TCGGAACTCGAATATGGTAATTGCAACACCAAATGTCAAACTCCCATGGG

CGCTATTAACAGCTCCATGCCATTTCACAATATTCACCCGTTGACTATAG

GCGAATGTCCAAATATGTGAAGTCCAATCGCTTGGTACTCGCCACCGGC

TTGAGGAATAGCCCGCAACGTGAGAGACGGAGAAAAAAGCGGGGATTGTT

TGGCGCCATCGCCGGATTTATAGAAGGTGGCTGGCAAGGAATGGTGGATG

GCTGGTATGGATACCACCATTCCAACGAACAAGGTTCAGGCTACGCGGCA

GACAAAGAATCTACTCAAAAAGCAATAGACGGCGTGACAAATAAAGTAA

TAGTATAATTGACAAAATGAATACGCAGTTTGAAGCCGTCGGCCGTGAGT

TCAATAACCTGGAGCGCAGAATTGAAAATCTAAACAAAAAGATGGAGGAC

GGGTTTTTAGACGTTTGGACGTACAATGCAGAATTGTTAGTTTTGATGGA

AAACGAACGCACCTTGGATTTTCACGACTCGAACGTTAAAAACCTGTACG

ATAAAGTCCGACTGCAATTACGCGATAATGCAAAAGAACTGGGAAACGGC

TGCTTCGAATTTTATCATAAATGCGACAATGAATGCATGGAATCTGTACG

AAATGGTACATACGACTATCCCCAATACTCGGAGGAAGCGCGTCTAAAAC

GCGAAGAGATTAGCAGTGGCCGCCTGGTGCCCCGCGGCAGCCCCGGCAGC

GGCTACATCCCCGAGGCCCCCCGCGATGGCCAGGCCTACGTGCGCAAGGA

TGGCGAGTGGGTGCTGCTGAGCACCTTCCTG

The amino acid sequence of this exemplary construct described above is as follows, referred to herein as SEQ ID NO:185 (in which aa 1-18 correspond to a BiP signal sequence, aa 19-32 correspond to a HIS tag, aa 33-34 correspond to a dipeptidase stop signal, aa 539-550 correspond to a thrombin cleavage site and aa 551-577 correspond to a foldon sequence.

MKLCILLAVVAFVGLSLGMKHQHQHQHQHQHQAPDQICIGYHANNSTEQV

DTIMEKNVTVTHAQDILEKKHNGKLCDLDGVKPLILRDCSVAGWLLGNPM

CDEFINVPEWSYIVEKANPVNDLCYPGDFNDYEELKHLLSRINHFEKIQI

IPKSSWSSHEASLGVSSACPYQGKSSFFRNVVWLIKKNSTYPTIKRSYNN

TNQEDLLVLWGIHHPNDAAEQTKLYQNPTTYISVGTSTLNQRLVPRIATR

SKVNGQSGRMEFFWTILKPNDAINFESNGNFIAPEYAYKIVKKGDSTIMK

SELEYGNCNTKCQTPMGAINSSMPFHNIHPLTIGECPKYVKSNRLVLATG

LRNSPQRERRRKKRGLFGAIAGFIEGGWQGMVDGWYGYHHSNEQGSGYAA

DKESTQKAIDGVTNKVNSIIDKMNTQFEAVGREFNNLERRIENLNKKMED

GFLDVWTYNAELLVLMENERTLDFHDSNVKNLYDKVRLQLRDNAKELGNG

CFEFYHKCDNECMESVRNGTYDYPQYSEEARIKREEISSGRLVPRGSPGS

GYIPEAPRDGQAYVRKDGEWVLLSTFL

In certain embodiments, the M2e polypeptides for use in the present invention correspond to the M2e polypeptides set forth in Table 5. Preferred M2e and PADRES M2e polypeptides of the present invention are set forth in Table 6.

In certain other embodiments, polypeptides of the present invention include SEQ ID NOs: 174, 181, 183 and 185.

In certain embodiments, the polynucleotide of the invention comprises a nucleic acid encoding from about zero to about ten HTL epitopes. In other embodiments, the polypeptide of the invention comprises from about zero to about ten HTL epitopes. The term "HTL epitope" refers to a peptide of defined length that can be from about 6 to about 30 amino acids in length, from about 8 to about 30 amino acids in length, from about 10 to about 30 amino acids, from about 12 to about 30 amino acids in length, from about 6 to about 25 amino acids in length, from about 8 to about 25 amino acids in length, from about 10 to about 25 amino acids, from about 12 to about 25 amino acids in length, from about 6 to about 18 amino acids in length, from about 8 to about 18 amino acids in length, from about 10 to about 18 amino acids, or from about 12 to about 18 amino acids in length, which is recognized by a particular HLA molecule. The one to ten HTL epitopes of the present invention are positioned at the N-terminus or C-terminus of the HA, M2e or influenza polypeptide, or fragment, variant, or derivative thereof. Representative influenza HTL epitopes according to the invention can found at Table 3. Preferred influenza HTL epitopes of the present invention can be found at Table 4. Certain HTL epitopes in Table 4 were reevaluated for binding affinity. These results are set forth in Table 7. Additional polynucleotides of the present invention include nucleic acid sequences encoding the polypeptides set forth above.

Additional polypeptides of the present invention further include HA, M2e or other influenza polypeptides, or fragment, variant or derivatives thereof, interrupted by a pan-DR binding epitope, preferably the PADRE® sequence, or having the pan-DR binding epitope or PADRE® sequence positioned at the N-terminus or C-terminus of the polypeptide, or fragment, variant, or derivative thereof. An HA, M2e or other influenza polypeptide "interrupted" by the pan-DR binding epitope or PADRE® sequence corresponds to a polypeptide where the pan-DR binding epitope or PADRE® sequence is inserted at any position along the HA or other influenza polypeptide sequence, and more preferably inserted at the N- or C-terminus of an HA or other influenza polypeptide domain. An insertion may leave the rest of the influenza polypeptide intact, or may replace a segment of the influenza polypeptide. For example, polypeptides of the present invention include, but are not limited to a polypeptide comprising HA ECD and PADRE®; HA TM and PADRE®; or HA CYT and PADRE®. Further polypeptides of the invention include polypeptides comprising HA ECD, HA TM and PADRE®; polypeptides comprising HA TM, HA CYT and PADRE®; and polypeptides comprising HA ECD, HA CYT and PADRE®; where the PADRE® is positioned at the N-terminus or the C-terminus of the polypeptide, or where the polypeptide is interrupted by PADRE® sequence. Additional polynucleotides of the present invention include nucleic acid sequences encoding the polypeptides set forth above.

A further example of a polypeptide of the present invention is a polypeptide comprising an HA, M2e or influenza polypeptide, or fragment, variant or derivative thereof, as set further above and optionally one to ten polypeptides each consisting of an HTL epitope.

Methods of designing and selecting HTL epitopes having an HLA-DR binding motif according to the present invention are described in Rammensee et al., "MHC ligands and peptide motifs: first listing," *Immunogenetics* 41:178-228 (1995) and Sette et al., "Prediction of major histocompatibility complex binding regions of protein antigens by sequence pattern analysis," *Proc. Natl. Acad. Sci.* 86: 3296-3300 (1989), the disclosure of each which is incorporated herein by reference in its entirety.

Methods of designing and generating a multi-epitope construct comprising an HA, M2e or influenza polypeptide, or fragment, variant or derivative thereof, and/or one or more HTL epitopes are performed according to methods of designing and using multi-epitope constructs as described in WO 01/47541 and WO 02/083714, the disclosure of each which is incorporated herein by reference in its entirety.

The present invention also provides vaccine compositions and methods for delivery of influenza virus coding sequences to a vertebrate with optimal expression and safety. These vaccine compositions are prepared and administered in such a manner that the encoded gene products are optimally expressed in the vertebrate of interest. As a result, these compositions and methods are useful in stimulating an immune response against influenza virus infection. Also included in the invention are expression systems and delivery systems.

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349 (1997)) comprising a polynucleotide. A polynucleotide may comprise a conventional phosphodiester bond or a non-conventional bond (e.g., an amide bond, such as found in peptide nucleic acids (PNA)).

The terms "nucleic acid" or "nucleic acid fragment" refer to any one or more nucleic acid segments, e.g., DNA or RNA fragments, present in a polynucleotide or construct. A nucleic acid or fragment thereof may be provided in linear (e.g., mRNA) or circular (e.g., plasmid) form as well as double-stranded or single-stranded forms. By "isolated" nucleic acid or polynucleotide is intended a nucleic acid molecule, DNA or RNA, which has been removed from its native environment. For example, a recombinant polynucleotide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the polynucleotides of the present invention. Isolated polynucleotides or nucleic acids according to the present invention further include such molecules produced synthetically.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic acids or nucleic acid fragments of the present invention can be present in a single polynucleotide construct, e.g., on a single plasmid, or in separate polynucleotide constructs, e.g., on separate (different) plasmids. Furthermore, any nucleic acid or nucleic acid fragment may encode a single influenza polypeptide or fragment, derivative, or variant thereof, e.g., or may encode more than one polypeptide, e.g., a nucleic acid may encode two or more polypeptides. In addition, a nucleic acid may include a regulatory element such as a promoter, ribosome binding site, or a transcription terminator, or may encode heterologous coding regions fused to the influenza coding region, e.g., specialized elements or motifs, such as a secretory signal peptide or a heterologous functional domain.

The terms "fragment," "variant," "derivative" and "analog" when referring to influenza virus polypeptides of the present invention include any polypeptides which retain at least some of the immunogenicity or antigenicity of the corresponding native polypeptide. Fragments of influenza virus polypeptides of the present invention include proteolytic fragments, deletion fragments and in particular, fragments of influenza virus polypeptides which exhibit increased secretion from the cell or higher immunogenicity or reduced pathogenicity when delivered to an animal, such as deletion of signal sequences or one or more domains. Polypeptide fragments further include any portion of the polypeptide which comprises an antigenic or immunogenic epitope of the native polypeptide, including linear as well as three-dimensional epitopes. Variants of influenza virus polypeptides of the present invention include fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome or genome of an organism or virus. *Genes II*, Lewin, B., ed., John Wiley & Sons, New York (1985), which is incorporated herein by reference. For example, as used herein, variations in a given gene product. When referring to influenza virus NA or HA proteins, each such protein is a "variant," in that native influenza virus strains are distinguished by the type of NA and HA proteins encoded by the virus. However, within a single HA or NA variant type, further naturally or non-naturally occurring variations such as amino acid deletions, insertions or substitutions may occur. Non-naturally occurring variants may be produced using art-known mutagenesis techniques. Variant polypeptides may comprise conservative or non-conservative amino acid substitutions, deletions or additions. Derivatives of influenza virus polypeptides of the present invention are polypeptides which have been altered so as to exhibit additional features not found on the native polypeptide. Examples include fusion proteins. An analog is another form of an influenza virus polypeptide of the present invention. An example is a proprotein which can be activated by cleavage of the proprotein to produce an active mature polypeptide.

The terms "infectious polynucleotide" or "infectious nucleic acid" are intended to encompass isolated viral polynucleotides and/or nucleic acids which are solely sufficient to mediate the synthesis of complete infectious virus particles upon uptake by permissive cells. Thus, "infectious nucleic acids" do not require pre-synthesized copies of any of the polypeptides it encodes, e.g., viral replicases, in order to initiate its replication cycle in a permissive host cell.

The terms "non-infectious polynucleotide" or "non-infectious nucleic acid" as defined herein are polynucleotides or nucleic acids which cannot, without additional added materials, e.g., polypeptides, mediate the synthesis of complete infectious virus particles upon uptake by permissive cells. An infectious polynucleotide or nucleic acid is not made "non-infectious" simply because it is taken up by a non-permissive cell. For example, an infectious viral polynucleotide from a virus with limited host range is infectious if it is capable of mediating the synthesis of complete infectious virus particles when taken up by cells derived from a permissive host (i.e., a host permissive for the virus itself). The fact that uptake by cells derived from a non-permissive host does not result in the synthesis of complete infectious virus particles does not make the nucleic acid "non-infectious." In other words, the term is not qualified by the nature of the host cell, the tissue type, or the species taking up the polynucleotide or nucleic acid fragment.

In some cases, an isolated infectious polynucleotide or nucleic acid may produce fully-infectious virus particles in a host cell population which lacks receptors for the virus particles, i.e., is non-permissive for virus entry. Thus viruses produced will not infect surrounding cells. However, if the supernatant containing the virus particles is transferred to cells which are permissive for the virus, infection will take place.

The terms "replicating polynucleotide" or "replicating nucleic acid" are meant to encompass those polynucleotides and/or nucleic acids which, upon being taken up by a permissive host cell, are capable of producing multiple, e.g., one or more copies of the same polynucleotide or nucleic acid. Infectious polynucleotides and nucleic acids are a subset of replicating polynucleotides and nucleic acids; the terms are not synonymous. For example, a defective virus genome lacking the genes for virus coat proteins may replicate, e.g., produce multiple copies of itself, but is NOT infectious because it is incapable of mediating the synthesis of complete infectious virus particles unless the coat proteins, or another nucleic acid encoding the coat proteins, are exogenously provided.

In certain embodiments, the polynucleotide, nucleic acid, or nucleic acid fragment is DNA. In the case of DNA, a polynucleotide comprising a nucleic acid which encodes a polypeptide normally also comprises a promoter and/or other transcription or translation control elements operably associated with the polypeptide-encoding nucleic acid fragment. An operable association is when a nucleic acid fragment encoding a gene product, e.g., a polypeptide, is associated with one or more regulatory sequences in such a way as to place expression of the gene product under the influence or control of the regulatory sequence(s). Two DNA fragments (such as a polypeptide-encoding nucleic acid fragment and a promoter associated with the 5' end of the nucleic acid fragment) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a nucleic acid fragment encoding a polypeptide if the promoter was capable of effecting transcription of that nucleic acid fragment. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, elements from picornaviruses (particularly an internal ribosome entry site, or IRES, also referred to as a CITE sequence).

A DNA polynucleotide of the present invention may be a circular or linearized plasmid or vector, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. Linear DNA may be advantageous in certain situations as discussed, e.g., in Cherng, J. Y., et al., *J. Control. Release* 60:343-53 (1999), and Chen, Z. Y., et al. *Mol. Ther.* 3:403-10 (2001), both of which are incorporated herein by reference. As used herein, the terms plasmid and vector can be used interchangeably.

Alternatively, DNA virus genomes may be used to administer DNA polynucleotides into vertebrate cells. In certain embodiments, a DNA virus genome of the present invention is nonreplicative, noninfectious, and/or nonintegrating. Suitable DNA virus genomes include without limitation, herpesvirus genomes, adenovirus genomes, adeno-associated virus genomes, and poxvirus genomes. References citing methods for the in vivo introduction of non-infectious virus genomes to vertebrate tissues are well known to those of ordinary skill in the art, and are cited supra.

In other embodiments, a polynucleotide of the present invention is RNA, for example, in the form of messenger RNA (mRNA). Methods for introducing RNA sequences into vertebrate cells are described in U.S. Pat. No. 5,580,859, the disclosure of which is incorporated herein by reference in its entirety.

Polynucleotides, nucleic acids, and nucleic acid fragments of the present invention may be associated with additional nucleic acids which encode secretory or signal peptides, which direct the secretion of a polypeptide encoded by a nucleic acid fragment or polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native leader sequence is used, or a functional derivative of that sequence that retains the ability to direct the secretion of the polypeptide that is operably associated with it. Alternatively, a heterologous mammalian leader sequence, or a functional derivative thereof, may be used. For example, the wild-type leader sequence may be substituted with the leader sequence of human tissue plasminogen activator (TPA) or mouse β-glucuronidase.

In accordance with one aspect of the present invention, there is provided a polynucleotide construct, for example, a plasmid, comprising a nucleic acid fragment, where the nucleic acid fragment is a fragment of a coding region operably encoding an influenza virus-derived polypeptide, where the coding region is optimized for expression in vertebrate cells, of a desired vertebrate species, e.g., humans, to be delivered to a vertebrate to be treated or immunized. Suitable influenza polypeptides, or fragments, variants, or derivatives thereof may be derived from, but are not limited to, the influenza virus HA, NA, NP, PA, PB1, PB2, NS1, NS2, M1 or M2 proteins. Additional influenza-derived coding sequences, e.g., coding for HA, NA, NP, PA, PB1, PB2, NS1, NS2, M1, M2 or M2e, may also be included on the plasmid, or on a separate plasmid, and expressed, either using native influenza virus codons or codons for expression in the vertebrate to be treated or immunized. When such a plasmid encoding one or more influenza sequences is delivered, in vivo to a tissue of the vertebrate to be treated or immunized, one or more of the encoded gene products will be expressed, i.e., transcribed and translated. The level of expression of the gene product(s) will depend to a significant extent on the strength of the associated promoter and the presence and activation of an associated enhancer element, as well as the degree of optimization of the coding region.

As used herein, the term "plasmid" refers to a construct made up of genetic material (i.e., nucleic acids). Typically a plasmid contains an origin of replication which is functional in bacterial host cells, e.g., *Escherichia coli*, and selectable markers for detecting bacterial host cells comprising the plasmid. Plasmids of the present invention may include genetic elements as described herein arranged such that an inserted coding sequence can be transcribed and translated in eukaryotic cells. Also, the plasmid may include a sequence from a viral nucleic acid. However, such viral sequences normally are not sufficient to direct or allow the incorporation of the plasmid into a viral particle, and the plasmid is therefore a non-viral vector. In certain embodiments described herein, a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides related to influenza virus polypeptides, which are used to prevent or treat, i.e., cure, ameliorate, lessen the severity of, or prevent or reduce contagion of infectious disease caused by the influenza virus.

As used herein, an "antigenic polypeptide" or an "immunogenic polypeptide" is a polypeptide which, when introduced into a vertebrate, reacts with the vertebrate's immune system molecules, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides of the present invention include, but are not limited to, e.g., HA or fragments or variants thereof, e.g., NP or fragments thereof, e.g., PB1 or fragments or variants thereof, e.g., PB2 or fragments or variants thereof, e.g., NS1 or fragments or variants thereof, e.g., NS2 or fragments or variants thereof, e.g., M1 or fragments or variants thereof, e.g., NA or fragments or variants thereof, e.g., PA or fragments or variants thereof, and e.g. M2 or fragments or variants thereof including the extracellular fragment of M2 (M2e), or e.g., any of the foregoing polypeptides or fragments fused to a heterologous polypeptide, for example, a hepatitis B core antigen. Isolated antigenic and immunogenic polypeptides of the present invention in addition to those encoded by polynucleotides of the invention, may be provided as a recombinant protein, a purified subunit, a viral vector expressing the protein, or may be provided in the form of an inactivated influenza virus vaccine, e.g., a live-attenuated virus vaccine, a heat-killed virus vaccine, etc.

An affinity threshold associated with immunogenicity in the context of HLA class II DR molecules has been delineated (see, e.g., Southwood et al. *J. Immunology* 160:3363-3373, 1998, and U.S. Ser. No. 60/087,192 filed May 29, 1998). In order to define a biologically significant threshold of DR binding affinity, a database of the binding affinities of 32 DR-restricted epitopes for their restricting element (i.e., the HLA molecule that binds the motif) was compiled. In approximately half of the cases (15 of 32 epitopes), DR restriction was associated with high binding affinities, i.e. binding affinity values of 100 nM or less. In the other half of the cases (16 of 32), DR restriction was associated with intermediate affinity (binding affinity values in the 100-1000 nM range). In only one of 32 cases was DR restriction associated with an $IC_{50}$ of 1000 nM or greater. Thus, 1000 nM can be defined as an affinity threshold associated with immunogenicity in the context of DR molecules.

By an "isolated" influenza virus polypeptide or a fragment, variant, or derivative thereof is intended an influenza virus polypeptide or protein that is not in its natural form. No particular level of purification is required. For example, an isolated influenza virus polypeptide can be removed from its native or natural environment. Recombinantly produced influenza virus polypeptides and proteins expressed in host cells are considered isolated for purposed of the invention, as are native or recombinant influenza virus polypeptides which have been separated, fractionated, or partially or substantially purified by any suitable technique, including the separation of influenza virus virions from eggs or culture cells in which they have been propagated. In addition, an isolated influenza virus polypeptide or protein can be provided as a live or inactivated viral vector expressing an isolated influenza virus polypeptide and can include those found in inactivated influenza virus vaccine compositions. Thus, isolated influenza virus polypeptides and proteins can be provided as, for example, recombinant influenza virus polypeptides, a purified subunit of influenza virus, a viral vector expressing an isolated influenza virus polypeptide, or in the form of an inactivated or attenuated influenza virus vaccine.

The term "immunogenic carrier" as used herein refers to a first polypeptide or fragment, variant, or derivative thereof which enhances the immunogenicity of a second polypeptide or fragment, variant, or derivative thereof. Typically, an "immunogenic carrier" is fused to or conjugated to the desired polypeptide or fragment thereof. An example of an "immunogenic carrier" is a recombinant hepatitis B core antigen expressing, as a surface epitope, an immunogenic epitope of interest. See, e.g., European Patent No. EP 0385610 B1, which is incorporated herein by reference in its entirety.

In the present invention, antigenic epitopes preferably contain a sequence of at least 4, at least 5, at least 6, at least 7, at least 8, at least 9, at least 10, at least 15, at least 20, at least 25, or between about 8 to about 30 amino acids contained within the amino acid sequence of an influenza virus polypeptide of the invention, e.g., an NP polypeptide, an M1 polypeptide or an M2 polypeptide. Certain polypeptides comprising immunogenic or antigenic epitopes are at least 5, 10, 15, 20, 25, 30, 35, 40, 45, 50, 55, 60, 65, 70, 75, 80, 85, 90, 95, or 100 amino acid residues in length. Antigenic as well as immunogenic epitopes may be linear, i.e., be comprised of contiguous amino acids in a polypeptide, or may be three dimensional, i.e., where an epitope is comprised of non-contiguous amino acids which come together due to the secondary or tertiary structure of the polypeptide, thereby forming an epitope.

As to the selection of peptides or polypeptides bearing an antigenic epitope (e.g., that contain a region of a protein molecule to which an antibody or T cell receptor can bind), it is well known in that art that relatively short synthetic peptides that mimic part of a protein sequence are routinely capable of eliciting an antiserum that reacts with the partially mimicked protein. See, e.g., Sutcliffe, J. G., et al., *Science* 219:660-666 (1983), which is herein incorporated by reference.

Peptides capable of eliciting an immunogenic response are frequently represented in the primary sequence of a protein, can be characterized by a set of simple chemical rules, and are confined neither to immunodominant regions of intact proteins nor to the amino or carboxyl terminals. Peptides that are extremely hydrophobic and those of six or fewer residues generally are ineffective at inducing antibodies that bind to the mimicked protein; longer peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Throughout this disclosure, "binding data" results are often expressed in terms of "$IC_{50}$." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. Assays for determining binding are described in detail, e.g., in PCT publications WO 94/20127 and WO 94/03205, the disclosure of each which is herein incorporated by reference. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand. Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide. Binding may also be determined using other assay systems including those using: live cells (e.g., Ceppellini et al., *Nature* 339:392, 1989; Christnick et al., *Nature* 352:67, 1991; Busch et al., *Int. Immunol.* 2:443, 19990; Hill et al., *J. Immunol.* 147:189, 1991; del Guercio et al., *J. Immunol.* 154:685, 1995), cell free systems using detergent lysates (e.g., Cerundolo et al., *J. Immunol.* 21:2069, 1991), immobilized purified MHC (e.g., Hill et al., *J. Immunol.* 152, 2890, 1994; Marshall et al., *J. Immunol.* 152:4946, 1994), ELISA systems (e.g., Reay et al., *EMBO J.* 11:2829, 1992), surface plasmon resonance (e.g., Khilko et al., *J. Biol. Chem.* 268:15425, 1993); high flux soluble phase assays (Hammer et al., *J. Exp. Med.* 180:2353, 1994), and measurement of class I MHC stabilization or assembly (e.g., Ljunggren et al., *Nature* 346:476, 1990; Schumacher et al., *Cell* 62:563, 1990; Townsend et al., *Cell* 62:285, 1990; Parker et al., *J. Immunol.* 149:1896, 1992).

The designation of a residue position in an epitope as the "carboxyl terminus" or the "carboxyl terminal position" refers to the residue position at the end of the epitope that is nearest to the carboxyl terminus of a peptide, which is designated using conventional nomenclature as defined below. "C+1" refers to the residue or position immediately following the C-terminal residue of the epitope, i.e., refers to the residue flanking the C-terminus of the epitope. The "carboxyl terminal position" of the epitope occurring at the carboxyl end of the multi-epitope construct may or may not actually correspond to the carboxyl terminal end of polypeptide. In preferred embodiments, the epitopes employed in the optimized multi-epitope constructs are motif-bearing epitopes and the carboxyl terminus of the epitope is defined with respect to primary anchor residues corresponding to a particular motif.

The designation of a residue position in an epitope as "amino terminus" or "amino-terminal position" refers to the residue position at the end of the epitope which is nearest to the amino terminus of a peptide, which is designated using conventional nomenclature as defined below. "N−1" refers to the residue or position immediately adjacent to the epitope at the amino terminal end (position number 1) of an epitope. The "amino terminal position" of the epitope occurring at the amino terminal end of the multi-epitope construct may or may not actually corresponds to the amino terminal end of the polypeptide. In preferred embodiments, the epitopes employed in the optimized multi-epitope constructs are motif-bearing epitopes and the amino terminus of the epitope is defined with respect to primary anchor residues corresponding to a particular motif.

A "construct" as used herein generally denotes a composition that does not occur in nature. A construct can be produced by synthetic technologies, e.g., recombinant DNA preparation and expression or chemical synthetic techniques for nucleic or amino acids. A construct can also be produced by the addition or affiliation of one material with another such that the result is not found in nature in that form. A "multi-epitope construct" can be used interchangeably with the term "minigene" or "multi-epitope nucleic acid vaccine," and comprises multiple epitope nucleic acids that encode peptide epitopes of any length that can bind to a molecule functioning in the immune system, preferably a class I HLA and a T-cell receptor or a class II HLA and a T-cell receptor. All of the epitope nucleic acids in a multi-epitope construct can encode class I HLA epitopes or class II HLA epitopes. Class I HLA-encoding epitope nucleic acids are referred to as CTL epitope nucleic acids, and class II HLA-encoding epitope nucleic acids are referred to as HTL epitope nucleic acids. Some multi-epitope constructs can have a subset of the multi-epitope nucleic acids encoding class I HLA epitopes and another subset of the multi-epitope nucleic acids encoding class II HLA epitopes. The CTL epitope nucleic acids preferably encode an epitope peptide of about eight to about thirteen amino acids in length, more preferably about eight to about eleven amino acids in length, and most preferably about nine amino acids in length. The HTL epitope nucleic acids can encode an epitope peptide of about six to about thirty, preferably seven to about twenty three, preferably about seven to about seventeen, and even more preferably about eleven to about fifteen, and most preferably about thirteen amino acids in length. The multi-epitope constructs described herein preferably include five or more, ten or more, fifteen or more, twenty or more, or twenty-five or more epitope nucleic acids. All of the epitope nucleic acids in a multi-epitope construct may be from one organism (e.g., the nucleotide sequence of every epitope nucleic acid may be present in HIV strains), or the multi-epitope construct may include epitope nucleic acids present in two or more different organisms (e.g., some epitopes from HIV and some from HCV). As described hereafter, one or more epitope nucleic acids in the multi-epitope construct may be flanked by a spacer nucleic acid.

A "multi-epitope vaccine," which is synonymous with a "polyepitopic vaccine," or a "multi-epitope construct" or "minigene" is a vaccine comprising multiple epitopes.

"Cross-reactive binding" indicates that a peptide is bound by more than one HLA molecule; a synonym is "degenerate binding."

A "cryptic epitope" elicits a response by immunization with an isolated peptide, but the response is not cross-reactive in vitro when intact whole protein that comprises the epitope is used as an antigen.

A "dominant epitope" is an epitope that induces an immune response upon immunization with a whole native antigen (see, e.g., Sercarz, et al., *Annu. Rev. Immunol.* 11:729-766, 1993). Such a response is cross-reactive in vitro with an isolated peptide epitope.

A "subdominant epitope" is an epitope which evokes little or no response upon immunization with whole antigens which comprise the epitope, but for which a response can be obtained by immunization with an isolated epitope, and this response (unlike the case of cryptic epitopes) is detected when whole protein is used to recall the response in vitro or in vivo.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vitro or in vivo, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably. It is to be appreciated, however, that isolated or purified protein or peptide molecules larger than and comprising an epitope of the invention are still within the bounds of the invention.

A "flanking residue" is a residue that is positioned next to an epitope. A flanking residue can be introduced or inserted at a position adjacent to the N-terminus or the C-terminus of an epitope.

An "immunogenic peptide" or "peptide epitope" or "epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

"Heteroclitic analogs" are defined herein as a peptide with increased potency for a specific T cell, as measured by increased responses to a given dose, or by a requirement of lesser amounts to achieve the same response. Advantages of heteroclitic analogs include that the epitopes can be more potent, or more economical (since a lower amount is required to achieve the same effect). In addition, modified epitopes might overcome antigen-specific T cell unresponsiveness (T cell tolerance).

"Human Leukocyte Antigen" or "HLA" is a human class I or class II Major Histocompatibility Complex (MHC) protein (see, e.g., Stites, et al., Immunology, 8th ed., Lange Publishing, Los Altos, Calif. (1994)).

An "HLA supertype or HLA family," as used herein, describes sets of HLA molecules grouped based on shared peptide-binding specificities. HLA class I molecules that share similar binding affinity for peptides bearing certain amino acid motifs are grouped into such HLA supertypes. The terms HLA superfamily, HLA supertype family, HLA family, and HLA xx-like molecules (where xx denotes a particular HLA type), are synonyms. HLA types, include, for example, HLA-A1, -A2, A3/A11, -A24, -B7, B44.

As used herein, "high affinity" with respect to HLA class I molecules is defined as binding with an $IC_{50}$, or $K_D$ value, of 50 nM or less; "intermediate affinity" with respect to HLA class I molecules is defined as binding with an $IC_{50}$ or $K_D$ value of between about 50 and about 500 nM. "High affinity" with respect to binding to HLA class II molecules is defined as binding with an $IC_{50}$ or $K_D$ value of 100 nM or less; "intermediate affinity" with respect to binding to HLA class II molecules is defined as binding with an $IC_{50}$ or $K_D$ value of between about 100 and about 1000 nM.

An "$IC_{50}$" is the concentration of peptide in a binding assay at which 50% inhibition of binding of a reference peptide is observed. Depending on the conditions in which the assays are run (i.e., limiting HLA proteins and labeled peptide concentrations), these values may approximate $K_D$ values.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

"Introducing" an amino acid residue at a particular position in a multi-epitope construct, e.g., adjacent, at the C-terminal side, to the C-terminus of the epitope, encompasses configuring multiple epitopes such that a desired residue is at a particular position, e.g., adjacent to the epitope, or such that a deleterious residue is not adjacent to the C-terminus of the epitope. The term also includes inserting an amino acid residue, preferably a preferred or intermediate amino acid residue, at a particular position. An amino acid residue can also be introduced into a sequence by substituting one amino acid residue for another. Preferably, such a substitution is made in accordance with analoging principles set forth, e.g., in PCT application number PCT/US00/19774.

The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

"Link" or "join" refers to any method known in the art for functionally connecting peptides, including, without limitation, recombinant fusion, covalent bonding, disulfide bonding, ionic bonding, hydrogen bonding, and electrostatic bonding.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, Fundamental Immunology, 3rd ed., Raven Press, New York, 1993.

As used herein, "middle of the peptide" is a position in a peptide that is neither an amino nor a carboxyl terminus.

A "minimal number of junctional epitopes" as used herein refers to a number of junctional epitopes that is lower than what would be created using a random selection criteria.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "supermotif" is an amino acid sequence for a peptide that provides binding specificity shared by HLA molecules encoded by two or more HLA alleles. Preferably, a supermotif-bearing peptide is recognized with high or intermediate affinity (as defined herein) by two or more HLA antigens.

The term "peptide" is used interchangeably with "oligopeptide" in the present specification to designate a series of residues, typically L-amino acids, connected one to the other, typically by peptide bonds between the α-amino and carboxyl groups of adjacent amino acids. The preferred CTL-inducing peptides of the invention are 13 residues or less in length and usually consist of between about 8 and about 11 residues, preferably 9 or 10 residues. The preferred HTL-inducing peptides are less than about 50 residues in length and usually consist of between about 6 and about 30 residues, more usually between about 12 and 25, and often between about 15 and 20 residues.

The term "HTL epitope" refers to a peptide of defined length that can be from about 6 to about 30 amino acids in length, from about 8 to about 30 amino acids in length, from about 10 to about 30 amino acids, from about 12 to about 30 amino acids in length, from about 6 to about 25 amino acids in length, from about 8 to about 25 amino acids in length, from about 10 to about 25 amino acids, from about 12 to about 25 amino acids in length, from about 6 to about 18 amino acids in length, from about 8 to about 18 amino acids in length, from about 10 to about 18 amino acids, or from about 12 to about 18 amino acids in length, which is recognized by a particular HLA molecule.

A "PanDR binding peptide or pan-DR binding epitope" is a member of a family of molecules that binds more than one HLA class II DR molecule. The pattern that defines this family of molecules can be thought of as an HLA Class II supermotif. For example, PADRE® binds to most HLA-DR molecules and stimulates in vitro and in vivo human helper T lymphocyte (HTL) responses.

A "negative binding residue" or "deleterious residue" is an amino acid which, if present at certain positions (typically not primary anchor positions) in a peptide epitope, results in decreased binding affinity of the peptide for the peptide's corresponding HLA molecule.

"Optimizing" refers to increasing the immunogenicity or antigenicity of a multi-epitope construct having at least one epitope pair by sorting epitopes to minimize the occurrence of junctional epitopes, inserting flanking residues that flank the C-terminus or N-terminus of an epitope, and inserting spacer residue to further prevent the occurrence of junctional epitopes or to provide a flanking residue. An increase in immunogenicity or antigenicity of an optimized multi-epitope construct is measured relative to a multi-epitope construct that has not been constructed based on the optimization parameters and is using assays known to those of skill in the art, e.g., assessment of immunogenicity in HLA transgenic mice, ELISPOT, inteferon-gamma release assays, tetramer staining, chromium release assays, and presentation on dendritic cells.

"Pathogenic virus strain" is used herein to refer to any virus strain that is capable of causing disease; preferably, the virus is on the current World Health Organization (WHO), Centers for Disease Control and Prevention (CDC), Food and Drug Administration (FDA) or other public health authority list of likely circulating viruses; more preferably, the virus has been indicated as one of the three annual viral strains for inclusion in an influenza annual vaccine (i.e., "seasonal strains"). This information is readily available from these agencies, e.g., at http://www.fda.gov/cber/flu/flu.htm or at http://www.who.int/csr/disease/influenza/vaccinerecommendationsl/en/index.html.

"Pharmaceutically acceptable" refers to a generally non-toxic, inert, and/or physiologically compatible composition.

"Presented to an HLA Class I processing pathway" means that the multi-epitope constructs are introduced into a cell such that they are largely processed by an HLA Class I processing pathway. Typically, multi-epitope constructs are introduced into the cells using expression vectors that encode the multi-epitope constructs. HLA Class II epitopes that are encoded by such a multi-epitope construct are also presented on Class II molecules, although the mechanism of entry of the epitopes into the Class II processing pathway is not defined.

A "primary anchor residue" or a "primary MHC anchor" is an amino acid at a specific position along a peptide sequence that is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment, for example, the primary anchor residues of an HLA class I epitope are located at position 2 (from the amino terminal position) and at the carboxyl terminal position of a 9-residue peptide epitope in accordance with the invention. The primary anchor positions for each motif and supermotif are described, for example, in Tables I and III of PCT/US00/27766, or PCT/US00/19774, the disclosure of each which is herein incorporated by reference. Preferred amino acids that can serve as in the anchors for most Class II epitopes consist of M and F in position one and V, M, S, T, A and C in position six. Tolerated amino acids that can occupy these positions for most Class II epitopes consist of L, I, V, W, and Y in position one and P, L and I in position six. The presence of these amino acids in positions one and six in Class II epitopes defines the HLA-DR1, 4, 7 supermotif. The HLA-DR3 binding motif is defined by preferred amino acids from the group of L, I, V, M, F, Y and A in position one and D, E, N, Q, S and T in position four and K, R and H in position six. Other amino acids may be tolerated in these positions but they are not preferred.

Furthermore, analog peptides can be created by altering the presence or absence of particular residues in these primary anchor positions. Such analogs are used to modulate the binding affinity of a peptide comprising a particular motif or supermotif "Promiscuous recognition" occurs where a distinct peptide is recognized by the same T cell clone in the context of various HLA molecules. Promiscuous recognition or binding is synonymous with cross-reactive binding.

A "protective immune response" or "therapeutic immune response" refers to a CTL and/or an HTL response to an antigen derived from an infectious agent or a tumor antigen, which in some way prevents or at least partially arrests disease symptoms, side effects or progression. The immune response may also include an antibody response that has been facilitated by the stimulation of helper T cells.

The term "residue" refers to an amino acid or amino acid mimetic incorporated into a peptide or protein by an amide bond or amide bond mimetic.

A "secondary anchor residue" is an amino acid at a position other than a primary anchor position in a peptide that may influence peptide binding. A secondary anchor residue occurs at a significantly higher frequency amongst bound peptides than would be expected by random distribution of amino acids at one position. The secondary anchor residues are said to occur at "secondary anchor positions." A secondary anchor residue can be identified as a residue which is present at a higher frequency among high or intermediate affinity binding peptides, or a residue otherwise associated with high or intermediate affinity binding. For example, analog peptides can be created by altering the presence or absence of particular residues in these secondary anchor positions. Such analogs are used to finely modulate the binding affinity of a peptide comprising a particular motif or supermotif. The terminology "fixed peptide" is sometimes used to refer to an analog peptide.

"Sorting epitopes" refers to determining or designing an order of the epitopes in a multi-epitope construct.

A "spacer" refers to a sequence that is inserted between two epitopes in a multi-epitope construct to prevent the occurrence of junctional epitopes and/or to increase the efficiency of processing. A multi-epitope construct may have one or more spacer nucleic acids. A spacer nucleic acid may flank each epitope nucleic acid in a construct, or the spacer nucleic acid to epitope nucleic acid ratio may be about 2 to 10, about 5 to 10, about 6 to 10, about 7 to 10, about 8 to 10, or about 9 to 10, where a ratio of about 8 to 10 has been determined to yield favorable results for some constructs.

The spacer nucleic acid may encode one or more amino acids. A spacer nucleic acid flanking a class I HLA epitope in a multi-epitope construct is preferably between one and about eight amino acids in length. A spacer nucleic acid flanking a class II HLA epitope in a multi-epitope construct is preferably greater than five, six, seven, or more amino acids in length, and more preferably five or six amino acids in length.

The number of spacers in a construct, the number of amino acids in a spacer, and the amino acid composition of a spacer can be selected to optimize epitope processing and/or minimize junctional epitopes. It is preferred that spacers are selected by concomitantly optimizing epitope processing and junctional motifs. Suitable amino acids for optimizing epitope processing are described herein. Also, suitable amino acid spacing for minimizing the number of junctional epitopes in a construct are described herein for class I and class II HLAs. For example, spacers flanking class II HLA epitopes preferably include G, P, and/or N residues as these are not generally known to be primary anchor residues (see, e.g., PCT/US00/19774). A particularly preferred spacer for flanking a class II HLA epitope includes alternating G and P residues, for example, $(GP)_n$, $(PG)_n$, $(GP)_nG$, $(PG)_nP$, and so forth, where n is an integer between one and ten, preferably two or about two, and where a specific example of such a spacer is GPGPG or PGPGP. A preferred spacer, particularly for class I HLA epitopes, comprises one, two, three or more consecutive alanine (A) residues.

In some multi-epitope constructs, it is sufficient that each spacer nucleic acid encodes the same amino acid sequence. In multi-epitope constructs having two spacer nucleic acids encoding the same amino acid sequence, the spacer nucleic acids encoding those spacers may have the same or different nucleotide sequences, where different nucleotide sequences may be preferred to decrease the likelihood of unintended recombination events when the multi-epitope construct is inserted into cells.

In other multi-epitope constructs, one or more of the spacer nucleic acids may encode different amino acid sequences. While many of the spacer nucleic acids may encode the same amino acid sequence in a multi-epitope construct, one, two, three, four, five or more spacer nucleic acids may encode different amino acid sequences, and it is possible that all of the spacer nucleic acids in a multi-epitope construct encode different amino acid sequences. Spacer nucleic acids may be optimized with respect to the epitope nucleic acids they flank by determining whether a spacer sequence will maximize epitope processing and/or minimize junctional epitopes, as described herein.

Multi-epitope constructs may be distinguished from one another according to whether the spacers in one construct optimize epitope processing or minimize junctional epitopes over another construct, and preferably, constructs may be distinguished where one construct is concomitantly optimized for epitope processing and junctional epitopes over the other. Computer assisted methods and in vitro and in vivo laboratory methods for determining whether a construct is optimized for epitope processing and junctional motifs are described herein.

"Synthetic peptide" refers to a peptide that is not naturally occurring, but is manmade using such methods as chemical synthesis or recombinant DNA technology.

A "TCR contact residue" or "T cell receptor contact residue" is an amino acid residue in an epitope that is understood to be bound by a T cell receptor; these are defined herein as not being any primary MHC anchor. T cell receptor contact residues are defined as the position/positions in the peptide where all analogs tested induce T-cell recognition relative to that induced with a wild type peptide.

The term "homology," as used herein, refers to a degree of complementarity between two nucleotide sequences. The word "identity" may substitute for the word "homology" when a nucleic acid has the same nucleotide sequence as another nucleic acid. Sequence homology and sequence identity can also be determined by hybridization studies under high stringency and/or low stringency, and disclosed herein are nucleic acids that hybridize to the multi-epitope constructs under low stringency or under high stringency. Also, sequence homology and sequence identity can be determined by analyzing sequences using algorithms and computer programs known in the art. Such methods may be used to assess whether a nucleic acid is identical or homologous to the multi-epitope constructs disclosed herein. The invention pertains in part to nucleotide sequences having 80% or more, 85% or more, 90% or more, 95% or more, 97% or more, 98% or more, or 99% or more identity to the nucleotide sequence of a multi-epitope construct disclosed herein.

As used herein, the term "stringent conditions" refers to conditions which permit hybridization between nucleotide sequences and the nucleotide sequences of the disclosed multi-epitope constructs. Suitable stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. For example, hybridization under high stringency conditions could occur in about 50% formamide at about 37° C. to 42° C. In particular, hybridization could occur under high stringency conditions at 42° C. in 50% formamide, 5×SSPE, 0.3% SDS, and 200 µg/ml sheared and denatured salmon sperm DNA or at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Hybridization could occur under reduced stringency conditions in about 35% to 25% formamide at about 30° C. to 35° C. For example, reduced stringency conditions could occur at 35° C. in 35% formamide, 5×SSPE, 0.3% SDS, and 200 µg/ml sheared and denatured salmon sperm DNA. The temperature range corresponding to a particular level of stringency can be further narrowed by calculating the purine to pyrimidine ratio of the nucleic acid of interest and adjusting the temperature accordingly. Variations on the above ranges and conditions are well known in the art.

In addition to utilizing hybridization studies to assess sequence identity or sequence homology, known computer programs may be used to determine whether a particular nucleic acid is homologous to a multi-epitope construct disclosed herein. An example of such a program is the Bestfit program (Wisconsin Sequence Analysis Package, Version 8 for Unix, Genetics Computer Group, University Research Park, 575 Science Drive, Madison, Wis. 53711), and other sequence alignment programs are known in the art and may be utilized for determining whether two or more nucleotide sequences are homologous. Bestfit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference sequence, the parameters may be set such that the percentage of identity is calculated over the full length of the reference nucleotide sequence and that gaps in homology of up to 5% of the total number of nucleotides in the reference sequence are allowed.

The nomenclature used to describe peptide compounds follows the conventional practice wherein the amino group is presented to the left (the N-terminus) and the carboxyl group to the right (the C-terminus) of each amino acid residue. When amino acid residue positions are referred to in an epitope, they are numbered in an amino to carboxyl direction with position one being the position closest to the amino terminal end of the epitope, or the peptide or protein of which it may be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three-letter or single-letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

Symbols for the amino acids are shown below.

| Single Letter Symbol | Three Letter Symbol | Amino Acids |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Amino acid "chemical characteristics" are defined as: Aromatic (F, W, Y); Aliphatic-hydrophobic (L, I, V, M); Small polar (S, T, C); Large polar (Q, N); Acidic (D, E); Basic (R, H, K); Proline; Alanine; and Glycine.

Acronyms used herein are as follows:
APC: Antigen presenting cell
CD3: Pan T cell marker
CD4: Helper T lymphocyte marker
CD8: Cytotoxic T lymphocyte marker
CFA: Complete Freund's Adjuvant
CTL: Cytotoxic T lymphocytes
DC: Dendritic cells. DC functioned as potent antigen presenting cells by stimulating cytokine release from CTL lines that were specific for a model peptide derived from hepatitis B virus (HBV). In vitro experiments using DC pulsed ex vivo with an HBV peptide epitope have stimulated CTL immune responses in vitro following delivery to naive mice.
DMSO: Dimethylsulfoxide
ELISA: Enzyme-linked immunosorbant assay
E:T: Effector:target ratio
FCS: Fetal calf serum
G-CSF: Granulocyte colony-stimulating factor
GM-CSF: Granulocyte-macrophage (monocyte)-colony stimulating factor
HBV: Hepatitis B virus
HLA: Human leukocyte antigen
HLA-DR: Human leukocyte antigen class II
HPLC: High Performance Liquid Chromatography
HTC: Helper T cells
HTL: Helper T Lymphocyte
ID: Identity
IFA: Incomplete Freund's Adjuvant
IFNγ: Interferon gamma
IL-4: Interleukin-4 cytokine
IV: Intravenous
$LU_{30\%}$: Cytotoxic activity required to achieve 30% lysis at a 100:1 (E:T) ratio
MAb: Monoclonal antibody
MLR: Mixed lymphocyte reaction
MNC: Mononuclear cells
PB: Peripheral blood
PBMC: Peripheral blood mononuclear cell
SC: Subcutaneous
S.E.M.: Standard error of the mean
QD: Once a day dosing
TCR: T cell receptor
WBC: White blood cells In particular embodiments to prevent HTL junctional epitopes, a spacer composed of amino acid residues that do not correspond to any known HLA Class II anchor residue, are used, e.g., alternating G and P residues (a GP spacer) is included between two HTL epitopes.

Another aspect of the invention, (consideration (ii) above) involves the introduction or substitution of particular amino acid residues at positions that flank epitopes, e.g., a position immediately adjacent to the C-terminus of the epitope, thereby generating multi-epitope constructs with enhanced antigenicity and immunogenicity compared to constructs that do not contain the particular residue introduced or substituted at that site, i.e., non-optimized multi-epitope constructs. The methods of optimizing multi-epitope constructs comprise a step of introducing a flanking residue, preferably K, N, G, R, or A at the C+1 position of the epitope, i.e., the position immediately adjacent to the C-terminus of the epitope. In an alternative embodiment, residues that contribute to decreased immunogenicity, i.e., negatively charged residues, e.g., D, aliphatic residues (I, L, M, V) or aromatic non-tryptophan residues, are replaced. The flanking residue can be introduced by positioning appropriate epitopes to provide the favorable flanking residue, or by inserting a specific residue.

Preparation of Multi-Epitope Constructs

Epitopes for inclusion in the multi-epitope constructs typically bear HLA Class I or Class II binding motifs as described, for example, in PCT applications PCT/US00/27766, or PCT/US00/19774. Multi-epitope constructs can be prepared according to the methods set forth in Ishioka, et al., *J Immunol* 162(7):3915-3925 (1999), for example, the disclosure of which is herein incorporated by reference.

Multiple HLA class II or class I epitopes present in a multi-epitope construct can be derived from the same antigen, or from different antigens. For example, a multi-epitope construct can contain one or more HLA epitopes that can be derived from two different antigens of the same virus or from two different antigens of different viruses. Epitopes for inclusion in a multi-epitope construct can be selected by one of skill in the art, e.g., by using a computer to select epitopes that contain HLA allele-specific motifs or supermotifs. The multi-epitope constructs of the invention also encode one or more broadly cross-reactive binding, or universal, HLA class II epitopes, i.e., pan-DR binding epitopes, e.g., PADRE®. (Epimmune, San Diego, Calif.), (described, for example, in U.S. Pat. No. 5,736,142) or a PADRE® family molecule.

Universal HLA Class II epitopes can be advantageously combined with other HLA Class I and Class II epitopes to increase the number of cells that are activated in response to a given antigen and provide broader population coverage of HLA-reactive alleles. Thus, the multi-epitope constructs of the invention can include HLA epitopes specific for an antigen, universal HLA class II epitopes, or a combination of specific HLA epitopes and at least one universal HLA class II epitope.

HLA Class I epitopes are generally about 8 to about 13 amino acids in length, in particular 8, 9, 10, or 11 amino acids in length. HLA Class II epitopes are generally about 6 to 25 amino acids in length, in particular about 13 to 21 amino acids in length. An HLA Class I or II epitope can be derived from any desired antigen of interest. The antigen of interest can be a viral antigen, surface receptor, tumor antigen, oncogene, enzyme, or any pathogen, cell or molecule for which an immune response is desired. Epitopes can be selected based on their ability to bind one or multiple HLA alleles. Epitopes that are analogs of naturally occurring sequences can also be included in the multi-epitope constructs described herein. Such analog peptides are described, for example, in PCT applications PCT/US97/03778, PCT/US00/19774, and co-pending U.S. Ser. No. 09/260,714 filed Mar. 1, 1999.

Influenza epitopes of the present invention were obtained from the H5N1 (AF036362) and H2N2 (M25924) viral protein sequences which were scanned for HLA-DR1 and -DR3 motifs using computer algorithm analysis as previously described. Approximately 1,200 sequences bearing the appropriate motifs were identified. In order to select potential epitopes that would be cross-reactive amongst a variety of influenza strains, these sequences were compared to other viral strains, typically 11 to 20, and conserved sequences were selected for peptide synthesis. Peptide binding assays were performed using peptide and purified HLA molecules. Binding analyses of 157 conserved peptides are provided in Table 3. In order to select epitopes that would be cross-reactive amongst various humans to obtain maximal population coverage, the number of vaccine candidate peptides was subsequently reduced to 53 by selecting only degenerate binding peptides demonstrating at least high to intermediate binding to greater than 60% of the purified HLA molecules tested, provided in Table 4. These 53 candidate peptides are again reduced to 1-10 HTL peptides for inclusion in the HA vaccine. The selection of these 1-10 HTL peptides is based on obtaining positive immune responses in human and mouse recall assays. A preference is also given for inclusion of peptides representing each of the 10 influenza proteins.

Multi-epitope constructs can be generated using methodology well known in the art. For example, polypeptides comprising the multi-epitope constructs can be synthesized and linked. Typically, multi-epitope constructs are constructed using recombinant DNA technology.

Expression Vectors and Construction of a Multi-Epitope Constructs

The multi-epitope constructs of the invention are typically provided as an expression vector comprising a nucleic acid encoding the multi-epitope polypeptide. Construction of such expression vectors is described, for example in PCT/US99/10646, the disclosure of which is herein incorporated by reference. The expression vectors contain at least one promoter element that is capable of expressing a transcription unit encoding the nucleic acid in the appropriate cells of an organism so that the antigen is expressed and targeted to the appropriate HLA molecule. For example, for administration to a human, a promoter element that functions in a human cell is incorporated into the expression vector.

In preferred embodiments, the invention utilizes routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994); Oligonucleotide Synthesis. A Practical Approach (Gait, ed., 1984); Kuijpers, *Nucleic Acids Research* 18(17):5197 (1994); Dueholm, *J. Org. Chem.* 59:5767-5773 (1994); Methods in Molecular Biology, volume 20 (Agrawal, ed.); and Tijssen, Laboratory Techniques in Biochemistry and Molecular Biology—Hybridization with Nucleic Acid Probes, e.g., Part I, chapter 2 "Overview of principles of hybridization and the strategy of nucleic acid probe assays" (1993)).

The nucleic acids encoding the epitopes are assembled in a construct according to standard techniques. In general, the nucleic acid sequences encoding multi-epitope polypeptides are isolated using amplification techniques with oligonucleotide primers, or are chemically synthesized. Recombinant cloning techniques can also be used when appropriate. Oligonucleotide sequences are selected which either amplify (when using PCR to assemble the construct) or encode (when using synthetic oligonucleotides to assemble the construct) the desired epitopes.

Amplification techniques using primers are typically used to amplify and isolate sequences encoding the epitopes of choice from DNA or RNA (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify epitope nucleic acid sequences directly from mRNA, from cDNA, from genomic libraries or cDNA libraries. Restriction endonuclease sites can be incorporated into the primers. Multi-epitope constructs amplified by the PCR reaction can be purified from agarose gels and cloned into an appropriate vector.

Synthetic oligonucleotides can also be used to construct multi-epitope constructs. This method is performed using a series of overlapping oligonucleotides, representing both the sense and non-sense strands of the gene. These DNA fragments are then annealed, ligated and cloned. Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.,* 12:6159-6168 (1984). Purification of oligonucleotides is by either native acrylamide gel electrophoresis or by anion-exchange HPLC as described in Pearson & Reanier, *J. Chrom.* 255:137-149 (1983).

The epitopes of the multi-epitope constructs are typically subcloned into an expression vector that contains a strong promoter to direct transcription, as well as other regulatory sequences such as enhancers and polyadenylation sites. Suitable promoters are well known in the art and described, e.g., in Sambrook et al. and Ausubel et al. Eukaryotic expression systems for mammalian cells are well known in the art and are commercially available. Such promoter elements include, for example, cytomegalovirus (CMV), Rous sarcoma virus LTR and SV40.

The expression vector typically contains a transcription unit or expression cassette that contains all the additional elements required for the expression of the multi-epitope construct in host cells. A typical expression cassette thus contains a promoter operably linked to the multi-epitope construct and signals required for efficient polyadenylation of the transcript. Additional elements of the cassette may include enhancers and introns with functional splice donor and acceptor sites.

In addition to a promoter sequence, the expression cassette can also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic cells may be used. Expression vectors containing regulatory elements from eukaryotic viruses are typically used in eukaryotic expression vectors, e.g., SV40 vectors, CMV vectors, papilloma virus vectors, and vectors derived from Epstein Bar virus.

The multi-epitope constructs of the invention can be expressed from a variety of vectors including plasmid vectors as well as viral or bacterial vectors. Examples of viral expression vectors include attenuated viral hosts, such as vaccinia or fowlpox. As an example of this approach, vaccinia virus is used as a vector to express nucleotide sequences that encode the peptides of the invention. Upon introduction into a host bearing a tumor, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848.

A wide variety of other vectors useful for therapeutic administration or immunization, e.g. adeno and adeno-associated virus vectors, retroviral vectors, non-viral vectors such as BCG (Bacille Calmette Guerin), *Salmonella typhi* vectors, detoxified anthrax toxin vectors, and the like, will be apparent to those skilled in the art.

Immunogenicity and antigenicity of the multi-epitope constructs are evaluated as described herein.

Targeting Sequences

The expression vectors of the invention may encode one or more MHC epitopes operably linked to a MHC targeting sequence, and are referred to herein as "targeting nucleic acids" or "targeting sequences." The use of a MHC targeting sequence enhances the immune response to an antigen, relative to delivery of antigen alone, by directing the peptide epitope to the site of MHC molecule assembly and transport to the cell surface, thereby providing an increased number of MHC molecule-peptide epitope complexes available for binding to and activation of T cells.

MHC Class I targeting sequences can be used in the present invention, e.g., those sequences that target an MHC Class I epitope peptide to a cytosolic pathway or to the endoplasmic reticulum (see, e.g., Rammensee et al., *Immunogenetics* 41:178-228 (1995)). For example, the cytosolic pathway processes endogenous antigens that are expressed inside the cell. Although not wishing to be bound by any particular theory, cytosolic proteins are thought to be at least partially degraded by an endopeptidase activity of a proteosome and then transported to the endoplasmic reticulum by the TAP molecule (transporter associated with processing). In the endoplasmic reticulum, the antigen binds to MHC Class I molecules. Endoplasmic reticulum signal sequences bypass the cytosolic processing pathway and directly target endogenous antigens to the endoplasmic reticulum, where proteolytic degradation into peptide fragments occurs. Such MHC Class I targeting sequences are well known in the art, and include, e.g., signal sequences such as those from Ig kappa, tissue plasminogen activator or insulin. A preferred signal peptide is the human. Ig kappa chain sequence. Endoplasmic reticulum signal sequences can also be used to target MHC Class II epitopes to the endoplasmic reticulum, the site of MHC Class I molecule assembly. MHC Class II targeting sequences can also be used in the invention, e.g., those that target a peptide to the endocytic pathway. These targeting sequences typically direct extracellular antigens to enter the endocytic pathway, which results in the antigen being transferred to the lysosomal compartment where the antigen is proteolytically cleaved into antigen peptides for binding to MHC Class II molecules. As with the normal processing of exogenous antigen, a sequence that directs a MHC Class II epitope to the endosomes of the endocytic pathway and/or subsequently to lysosomes, where the MHC Class II epitope can bind to a MHC Class II molecule, is a MHC Class II targeting sequence. For example, group of MHC Class II targeting sequences useful in the invention are lysosomal targeting sequences, which localize polypeptides to lysosomes. Since MHC Class II molecules typically bind to antigen peptides derived from proteolytic processing of endocytosed antigens in lysosomes, a lysosomal targeting sequence can function as a MHC Class II targeting sequence. Lysosomal targeting sequences are well known in the art and include sequences found in the lysosomal proteins LAMP-1 and LAMP-2 as described by August et al. U.S. Pat. No. 5,633,234, issued May 27, 1997), which is incorporated herein by reference.

Other lysosomal proteins that contain lysosomal targeting sequences include HLA-DM. HLA-DM is an endosomal/lysosomal protein that functions in facilitating binding of antigen peptides to MHC Class II molecules. Since it is located in the lysosome, HLA-DM has a lysosomal targeting sequence that can function as a MHC Class II molecule targeting sequence (Copier et al., *J. Immunol.* 157:1017-1027 (1996), which is incorporated herein by reference).

The resident lysosomal protein HLA-DO can also function as a lysosomal targeting sequence. In contrast to the above described resident lysosomal proteins LAMP-1 and HLA-DM, which encode specific Tyr-containing motifs that target proteins to lysosomes, HLA-DO is targeted to lysosomes by association with HLA-DM (Liljedahl et al., *EMBO J.*, 15:4817-4824 (1996)), which is incorporated herein by reference. Therefore, the sequences of HLA-DO that cause association with HLA-DM and, consequently, translocation of HLA-DO to lysosomes can be used as MHC Class II targeting sequences. Similarly, the murine homolog of HLA-DO, H2-DO, can be used to derive a MHC Class II targeting sequence. A MHC Class II epitope can be fused to HLA-DO or H2-DO and targeted to lysosomes.

In another example, the cytoplasmic domains of B cell receptor subunits Ig-α and Ig-β mediate antigen internalization and increase the efficiency of antigen presentation as described in, for example, Bonnerot et al., *Immunity*, 3:335-347 (1995). Therefore, the cytoplasmic domains of the Ig-α and Ig-β proteins can function as MHC Class II targeting sequences that target a MHC Class II epitope to the endocytic pathway for processing and binding to MHC Class II molecules.

Another example of a MHC Class II targeting sequence that directs MHC Class II epitopes to the endocytic pathway is a sequence that directs polypeptides to be secreted, where the polypeptide can enter the endosomal pathway. These MHC Class II targeting sequences that direct polypeptides to be secreted mimic the normal pathway by which exogenous, extracellular antigens are processed into peptides that bind to MHC Class II molecules. Any signal sequence that functions to direct a polypeptide through the endoplasmic reticulum and ultimately to be secreted can function as a MHC Class II targeting sequence so long as the secreted polypeptide can enter the endosomal/lysosomal pathway and be cleaved into peptides that can bind to MHC Class II molecules.

In another example, the Ii protein binds to MHC Class II molecules in the endoplasmic reticulum, where it functions to prevent peptides present in the endoplasmic reticulum from binding to the MHC Class II molecules. Therefore, fusion of a MHC Class II epitope to the Ii protein targets the MHC Class II epitope to the endoplasmic reticulum and a MHC Class II molecule. For example, the CLIP sequence of the Ii protein can be removed and replaced with a MHC Class II epitope sequence so that the MHC Class II epitope is directed to the endoplasmic reticulum, where the epitope binds to a MHC Class II molecule.

In some cases, antigens themselves can serve as MHC Class II or I targeting sequences and can be fused to a universal MHC Class II epitope to stimulate an immune response. Although cytoplasmic viral antigens are generally processed and presented as complexes with MHC Class I molecules, long-lived cytoplasmic proteins such as the influenza matrix protein can enter the MHC Class MHC Class II molecule processing pathway as described in, for example, Gueguen & Long, Proc. Natl. Acad. Sci. USA, 93:14692-14697 (1996). Therefore, long-lived cytoplasmic proteins can function as a MHC Class MHC Class II targeting sequence. For example, an expression vector encoding influenza matrix protein fused to a universal MHC Class I/MHC Class II epitope can be advantageously used to target influenza antigen and the universal MHC Class I/MHC Class II epitope to the MHC Class I/MHC Class II pathway for stimulating an immune response to influenza.

Other examples of antigens functioning as MHC Class I/MHC Class II targeting sequences include polypeptides that spontaneously form particles. The polypeptides are secreted from the cell that produces them and spontaneously form particles, which are taken up into an antigen-presenting cell by endocytosis such as receptor-mediated endocytosis or are engulfed by phagocytosis. The particles are proteolytically cleaved into antigen peptides after entering the endosomal/lysosomal pathway.

One such polypeptide that spontaneously forms particles is HBV surface antigen (HBV-S) as described in, for example, Diminsky et al., Vaccine 15:637-647 (1997) or Le Borgne et al., Virology, 240:304-315 (1998). Another polypeptide that spontaneously forms particles is HBV core antigen as described in, for example, Kuhrober et al., International Immunol., 9:1203-1212 (1997). Still another polypeptide that spontaneously forms particles is the yeast Ty protein as described in, for example, Weber et al., Vaccine, 13:831-834 (1995). For example, an expression vector containing HBV-S antigen fused to a universal MHC Class MHC Class II epitope can be advantageously used to target HBV-S antigen and the universal MHC Class MHC Class II epitope to the MHC Class MHC Class II pathway for stimulating an immune response to HBV.

The Minimization of Junctional Motifs

One of the considerations in designing multi-epitope constructs is the inadvertent creation of junctional epitopes when placing epitopes adjacent to each other. The presence of such epitopes in a multi-epitope construct could significantly affect performance. Strategies to guard against this undesired effect are disclosed herein for application to the development of multi-epitope vaccines. Junctional epitopes can first be minimized by sorting the epitopes to identify an order in which the numbers of junctional epitopes is minimized. Such a sorting procedure can be performed using a computer or by eye, if necessary, or depending on the number of epitopes to be included in the multi-epitope construct.

Eliminating Class II Junctional Epitopes and Testing for Class II Restricted Responses In Vivo As a further element in eliminating junctional epitopes, spacer sequences can be inserted between two epitopes that create a junctional epitope when juxtaposed.

In one embodiment, to correct the problem of junctional epitopes for HTL epitopes, a spacer of, for example, five amino acids in length is inserted between the two epitopes. The amino acid residues incorporated into such a spacer are preferably those amino acid residues that are not known to be primary anchor residues for any of the HLA Class II binding motifs. Such residues include G, P, and N. In a preferred embodiment, a spacer with the sequence GPGPG is inserted between two epitopes. Previous work has demonstrated that the GP spacer is particularly effective in disrupting Class II binding interactions (Sette et al., *J. Immunol.,* 143:1268-73 (1989)). All known human Class II binding motifs and the mouse $IA^b$ (the Class II expressed by HLA transgenic mice) do not tolerate either G or P at this main anchor positions, which are spaced four residues apart. This approach virtually guarantees that no Class II restricted epitopes can be formed as junctional epitopes.

Polypeptides are synthesized incorporating influenza-derived HTL epitopes. These epitopes are broadly cross-reactive HLA DR binding epitopes. These epitopes will also efficiently bind the murine $IA^b$ Class II molecule.

Responses against multiple influenza-derived Class II epitopes can be simultaneously induced, and IAb/DR cross-reactivity can be utilized to investigate the immunogenicity of various constructs incorporating HTL epitope candidates. Finally, appropriate spacers can be employed to effectively disrupt Class II junctional epitopes that would otherwise interfere with effective vaccine immunogenicity.

In the case of Class I restricted responses, one case of a naturally occurring junctional epitope and the consequent inhibition of epitope specific responses has been presented by McMichael and coworkers (Tussey et al., *Immunity,* 3(1):65-77 (1995)). To address the problem of junctional epitopes for Class I, similar analyses can be performed. For example, a specific computer program is employed to identify potential Class I restricted junctional epitopes, by screening for selected murine motifs and for the most common human Class I HLA A and B motifs.

Spacer sequences can also similarly be employed to prevent CTL junctional epitopes. Often, very small residues such as A or G are preferred spacer residues. G also occurs relatively infrequently as a preferred primary anchor residue (see, e.g., PCT/US00/24802) of an HLA Class I binding motif. These spacers can vary in length, e.g., spacer sequences can typically be 1, 2, 3, 4, 5, 6, 7, or 8 amino acid residues in length and are sometimes longer. Smaller lengths are often preferred because of physical constraints in producing the multi-epitope construct.

Sorting and Optimization of Multi-Epitope Constructs

To develop multi-epitope constructs using the invention, the epitopes for inclusion in the multi-epitope construct are sorted and optimized using the parameters defined herein. Sorting and optimization can be performed using a computer or, for fewer numbers of epitopes, not using a computer. Methods of sorting and optimization and disclosed in WO 02/083714, the disclosure of which is herein incorporated by reference.

Multi-epitope constructs can also be optimized by determining the structure of each construct to be considered. Macromolecular structures such as polypeptide structures can be described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

Structural predictions such as charge distribution, hydrophobic/hydrophilic region analysis, or folding predictions can be performed using sequence analysis programs known to those of skill in the art, for example, hydrophobic and hydrophilic domains can be identified (see, e.g., Kyte & Doolittle, *J. Mol. Biol.* 157:105-132 (1982) and Stryer, Biochemistry (3$^{rd}$ ed. 1988); see also any of a number of Internet based sequence analysis programs, such as those found at dot.imgen.bcm.tmc.edu.

A three-dimensional structural model of a multi-epitope construct can also be generated. This is generally performed by entering amino acid sequence to be analyzed into the computer system. The amino acid sequence represents the primary sequence or subsequence of the protein, which encodes the structural information of the protein. The three-dimensional structural model of the protein is then generated by the interaction of the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model. The tertiary structure of the protein encoded by the secondary structure is then formed on the basis of the energy terms of the secondary structure. The user can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like. Those multi-epitope constructs that are most readily accessible to the HLA processing apparatus are then selected.

Assessment of Immunogenicity of Multi-Epitope Vaccines

The development of multi-epitope constructs represents a unique challenge, because the species-specificity of the peptide binding to MHC. Different MHC types from different species tend to bind different sets of peptides (Rammensee et al., *Immunogenetics*, 41(4):178-228 (1995)). As a result, it is not possible to test in regular laboratory animals a construct composed of human epitopes. Alternatives to overcome this limitation are generally available. They include: 1) testing analogous constructs incorporating epitopes restricted by non-human MHC; 2) reliance on control epitopes restricted by non human MHC; 3) reliance on crossreactivity between human and non-human MHC; 4) the use of HLA transgenic animals; and 5) antigenicity assays utilizing human cells in vivo. The following is a brief overview of the development of the technology for analyzing antigenicity and immunogenicity.

Measuring HTL Responses

In preferred embodiments, vaccine constructs are optimized to induce Class II restricted immune responses. One method of evaluating multi-epitope constructs including Class II epitopes, is to use HLA-DR transgenic mice. Several groups have produced and characterized HLA-DR transgenic mice (Taneja V., David C. S., *Immunol Rev,* 169:67-79 (1999)).

An alternative also exists which relies on crossreactivity between certain human MHC molecules and particular MHC molecules expressed by laboratory animals. Bertoni and colleagues (Bertoni et al., *J Immunol,* 161(8):4447-55 (1998)) have noted that appreciable crossreactivity can be demonstrated between certain HLA Class I supertypes and certain PATR molecules expressed by chimpanzees. Crossreactivity between human and macaques at the level of Class II (Geluk et al., *J Exp Med,* 177(4):979-87 (1993)) and Class I molecules (Dzuris, et al., *J. Immunol., July* 1999) has also been noted. Finally, it can also be noted that the motif recognized by human HLA B7 supertype is essentially the same as the one recognized by the murine Class I $L^d$ (Rammensee et al., *Immunogenetics,* 41(4):178-228 (1995)). Of relevance to testing HLA DR restricted epitopes in mice, it has been shown by Wall et al. (Wall et al., *J. Immunol.,* 152:4526-36 (1994)) that similarities exist in the motif of DR1 and $IA^b$. We routinely breed our transgenic mice to take advantage of this fortuitous similarity. Furthermore, we have also shown that most of our peptides bind to $IA^b$, so that we use these mice for the study of CTL and HTL immunogenicity.

Measuring and Quantitating Immune Responses from Clinical Samples

A crucial element to assess vaccine performance is to evaluate its capacity to induce immune responses in vivo. Analyses of CTL and HTL responses against the immunogen, as well as against common recall antigens are commonly used and are known in the art. Assays employed included chromium release, lymphokine secretion and lymphoproliferation assays.

More sensitive techniques such as the ELISPOT assay, intracellular cytoline staining, and tetramer staining have become available in the art. It is estimated that these newer methods are 10- to 100-fold more sensitive than the common CTL and HTL assays (Murali-Krishna et al., *Immunity,* 8(2): 177-87 (1998)), because the traditional methods measure only the subset of T cells that can proliferate in vitro, and may, in fact, be representative of only a fraction of the memory T cell compartment (Ogg G. S., McMichael A. J., *Curr Opin Immunol,* 10(4):393-6 (1998)). Specifically in the case of HIV, these techniques have been used to measure antigen-specific CTL responses from patients that would have been undetectable with previous techniques (Ogg et al., *Science,* 279(5359):2103-6 (1998); Gray et al., *J Immunol,* 162(3):1780-8 (1999); Ogg et al., *J Virol,* 73(11):9153-60 (1999); Kalams et al., *J Viro;* 73(8):6721-8 (1999); Larsson et al., *AIDS,* 13(7):767-77 (1999); Come et al., *J Acquir Immune Defic Syndr Hum Retrovirol,* 20(5):442-7 (1999)).

With relatively few exceptions, direct activity of freshly isolated cells has been difficult to demonstrate by the means of traditional assays (Ogg G. S., McMichael A. J., *Curr Opin Immunol,* 10(4):393-6 (1998)). However, the increased sensitivity of the newer techniques has allowed investigators to detect responses from cells freshly isolated from infected humans or experimental animals (Murali-Krishna et al., *Immunity,* 8(2):177-87 (1998); Ogg G. S., McMichael A. J., *Curr Opin Immunol,* 10(4):393-6 (1998)). The availability of these sensitive assays, that do not depend on an in vitro restimulation step, has greatly facilitated the study of CTL function in natural infection and cancer. In contrast, assays utilized as an endpoint to judge effectiveness of experimental vaccines are usually performed in conjunction with one or more in vitro restimulation steps (Ogg G. S., McMichael A. J., *Curr Opin Immunol*, 10(4):393-6 (1998)). In fact, with few exceptions (Hanke et al., *Vaccine*, 16(4):426-35 (1998)), freshly isolated Class I-restricted CD8+ T cells have been difficult to demonstrate in response to immunization with experimental vaccines designed to elicit CTL responses. The use of sensitive assays, such as ELISPOT or in situ IFNγ ELISA, have been combined with a restimulation step to achieve maximum sensitivity; MHC tetramers are also used for this purpose.

MHC tetramers were first described in 1996 by Altman and colleagues. They produced soluble HLA-A2 Class I molecules which were folded with HIV-specific peptides containing a CTL epitope complexed together into tetramers tagged with fluorescent markers. These are used to label populations of T cells from HIV-infected individuals that recognize the epitope (Ogg G. S., McMichael A. J., *Curr Opin Immunol*, 10(4):393-6 (1998)). These cells were then quantified by flow cytometry, providing a frequency measurement for the T cells that are specific for the epitope. This technique has become very popular in HIV research as well as in other infectious diseases (Ogg G. S., McMichael A. J., *Curr Opin Immunol*, 10(4):393-6 (1998); Ogg et al., *Science*, 279(5359):2103-6 (1998); Gray et al., *J Immunol*, 162(3):1780-8 (1999); Ogg et al., *J Virol*, 73(11):9153-60 (1999); Kalams et al., *J Virol*, 73(8):6721-8 (1999)). However, HLA polymorphism can limit the general applicability of this technique, in that the tetramer technology relies on defined HLA/peptide combinations. However, it has been shown that a variety of peptides, including HIV-derived peptides, are recognized by peptide-specific CTL lines in the context of different members of the A2, A3 and B7 supertypes (Threlkeld et al., *J Immunol*, 159(4):1648-57 (1997); Bertoni et al., *J Clin Invest*, 100(3):503-13 (1997)). Taken together these observations demonstrate that a T cell receptor (TCR) for a given MHC/peptide combination can have detectable affinity for the same peptide presented by a different MHC molecule from the same supertype.

In circumstances in which efficacy of a prophylactic vaccine is primarily correlated with the induction of a long-lasting memory response, restimulation assays can be the most appropriate and sensitive measures to monitor vaccine-induced immunological responses. Conversely, in the case of therapeutic vaccines, the main immunological correlate of activity can be the induction of effector T cell function, most aptly measured by primary assays. Thus, the use of sensitive assays allows for the most appropriate testing strategy for immunological monitoring of vaccine efficacy.

Antigenicity of Multi-Epitope Constructs in Transfected Human APC's

Antigenicity assays are performed to evaluate epitope processing and presentation in human cells. An episomal vector to efficiently transfect human target cells with multi-epitope nucleic acid vaccines is used to perform such an analysis.

For example, 221 A2$K^b$ target cells were transfected with an influenza multi-epitope vaccine. The 221 A2 $K^b$ target cell expresses the A2 $K^b$ gene that is expressed in HLA transgenic mice, but expresses no endogenous Class I (Shimizu Y, DeMars R., *J Immunol*, 142(9):3320-8 (1989)). These transfected cells are assayed for their capacity to present antigen to CTL lines derived from HLA transgenic mice and specific for various HIV-derived CTL epitopes. To correct for differences in antigen sensitivity of different CTL lines, peptide dose titrations, using untransfected cells as APC, are run in parallel.

These data have several important implications. First, they suggest that different epitopes contained within a given construct may be processed and presented with differential efficiency. Second, they suggest that immunogenicity is proportional to the amount of processed epitope generated. Finally, these results provide an important validation of the use of transgenic mice for the purpose of optimization of multi-epitope vaccines destined for human use.

Methods of Administration

The invention also relates to pharmaceutical compositions comprising a pharmaceutically acceptable carrier and an expression vector of the invention or a polypeptide derived therefrom. Pharmaceutically acceptable carriers are well known in the art and include aqueous or non-aqueous solutions, suspensions and emulsions, including physiologically buffered saline, alcohol/aqueous solutions or other solvents or vehicles such as glycols, glycerol, oils such as olive oil or injectable organic esters, lipids, liposomes or virosomes.

A pharmaceutically acceptable carrier can contain physiologically acceptable compounds that act, for example, to stabilize the expression vector or increase the absorption of the expression vector. Such physiologically acceptable compounds include, for example, carbohydrates, such as glucose, sucrose or dextrans, antioxidants such as ascorbic acid or glutathione, chelating agents, low molecular weight polypeptides, antimicrobial agents, inert gases or other stabilizers or excipients. Expression vectors can additionally be complexed with other components such as peptides, polypeptides and carbohydrates. Expression vectors can also be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The invention further relates to methods of administering a pharmaceutical composition comprising an expression vector of the invention or a polypeptide derived therefrom to stimulate an immune response. The expression vectors are administered by methods well known in the art as described in, for example, Donnelly et al. (*Ann. Rev. Immunol.*, 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997). In one embodiment, the multi-epitope construct is administered as naked nucleic acid.

A pharmaceutical composition comprising an expression vector of the invention or a polypeptide derived therefrom can be administered to stimulate an immune response in a subject by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. An expression vector also can be administered as a topical spray, in which case one component of the composition is an appropriate propellant. The pharmaceutical composition also can be incorporated, if desired, into liposomes, virosomes, microspheres or other polymer matrices as described in, for example, Felgner et al., U.S. Pat. No. 5,703,055; Gregoriadis, Liposome Technology, Vols. I to III (2nd ed. 1993). Liposomes, for example, which consist of phospholipids or other lipids, are nontoxic, physiologically acceptable and metabolizable carriers that are relatively simple to make and administer. A virosome, for example, can be an immunopotentiating reconstituted influenza virosome (IRIV).

The expression vectors of the invention or a polypeptide derived therefrom can be delivered to the interstitial spaces of tissues of an animal body as described in, for example, Felgner et al., U.S. Pat. Nos. 5,580,859 and 5,703,055. Administration of expression vectors of the invention to muscle is a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

Other effective methods of administering an expression vector of the invention or a polypeptide derived therefrom to stimulate an immune response include mucosal administration as described in, for example, Carson et al., U.S. Pat. No. 5,679,647. For mucosal administration, the most effective method of administration includes intranasal administration of an appropriate aerosol containing the expression vector and a pharmaceutical composition. Suppositories and topical preparations are also effective for delivery of expression vectors to mucosal tissues of genital, vaginal and ocular sites. Additionally, expression vectors can be complexed to particles and administered by a vaccine gun.

The dosage to be administered is dependent on the method of administration and will generally be between about 0.1 µg up to about 200 µg. For example, the dosage can be from about 0.05 µg/kg to about 50 mg/kg, in particular about 0.005-5 mg/kg. An effective dose can be determined, for example, by measuring the immune response after administration of an expression vector. For example, the production of antibodies specific for the MHC Class II epitopes or MHC Class I epitopes encoded by the expression vector can be measured by methods well known in the art, including ELISA or other immunological assays. In addition, the activation of T helper cells or a CTL response can be measured by methods well known in the art including, for example, the uptake of $^3$H-thymidine to measure T cell activation and the release of $^{51}$Cr to measure CTL activity (see Examples II and III below).

The pharmaceutical compositions comprising an expression vector of the invention or a polypeptide derived therefrom can be administered to mammals, particularly humans, for prophylactic or therapeutic purposes. Diseases related to influenza virus infection can be treated or prevented using the expression vectors of the invention.

In therapeutic applications, the expression vectors of the invention or a polypeptide derived therefrom are administered to an individual already suffering from influenza virus infection or a related disease. Those in the incubation phase or acute phase of the disease can be treated with expression vectors of the invention, including those expressing all universal MHC Class II epitopes, separately or in conjunction with other treatments, as appropriate.

In therapeutic and prophylactic applications, pharmaceutical compositions comprising expression vectors of the invention or a polypeptide derived therefrom are administered to a patient in an amount sufficient to elicit an effective immune response to an antigen and to ameliorate the signs or symptoms of a disease. The amount of expression vector to administer that is sufficient to ameliorate the signs or symptoms of a disease is termed a therapeutically effective dose. The amount of expression vector sufficient to achieve a therapeutically effective dose will depend on the pharmaceutical composition comprising an expression vector of the invention, the manner of administration, the state and severity of the disease being treated, the weight and general state of health of the patient and the judgment of the prescribing physician.

The present invention also provides methods for delivering an influenza polypeptide or a fragment, variant, or derivative thereof to a human, which comprise administering to a human one or more of the compositions described herein; such that upon administration of compositions such as those described herein, an influenza polypeptide, or fragment, variant, or derivative thereof is expressed in human cells, in an amount sufficient to generate an immune response to the influenza virus or administering the influenza virus polypeptide or a fragment, variant, or derivative thereof itself to the human in an amount sufficient to generate an immune response.

The present invention further provides methods for delivering an influenza virus polypeptide or a fragment, variant, or derivative thereof to a human, which comprise administering to a vertebrate one or more of the compositions described herein; such that upon administration of compositions such as those described herein, an immune response is generated in the vertebrate.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The present invention further provides a method for generating, enhancing or modulating an immune response to an influenza virus comprising administering to a vertebrate one or more of the compositions described herein. In this method, the compositions may include one or more isolated polynucleotides comprising at least one nucleic acid fragment where the nucleic acid fragment is optionally a fragment of a coding region encoding an influenza virus polypeptide, or a fragment, variant, or derivative thereof. In another embodiment, the compositions may include both a polynucleotide as described above, and also an isolated influenza virus polypeptide, or a fragment, variant, or derivative thereof, wherein the protein is provided as a recombinant protein, in particular, a fusion protein, a purified subunit, viral vector expressing the protein, or in the form of an inactivated influenza virus vaccine. Thus, the latter compositions include both a polynucleotide encoding an influenza virus polypeptide or a fragment, variant, or derivative thereof and an isolated influenza virus polypeptide or a fragment, variant, or derivative thereof. The influenza virus polypeptide or a fragment, variant, or derivative thereof encoded by the polynucleotide of the compositions need not be the same as the isolated influenza virus polypeptide or a fragment, variant, or derivative thereof of the compositions. Compositions to be used according to this method may be univalent, bivalent, trivalent or multivalent.

The polynucleotides of the compositions may comprise a fragment of a human (or other vertebrate) coding region encoding a protein of the influenza virus, or a fragment, variant, or derivative thereof. The polynucleotides are incorporated into the cells of the vertebrate in vivo, and an antigenic amount of the influenza virus polypeptide, or fragment, variant, or derivative thereof, is produced in vivo. Upon administration of the composition according to this method, the influenza virus polypeptide or a fragment, variant, or derivative thereof is expressed in the vertebrate in an amount sufficient to elicit an immune response. Such an immune response might be used, for example, to generate antibodies to the influenza virus for use in diagnostic assays or as laboratory reagents, or as therapeutic or preventative vaccines as described herein.

The present invention further provides a method for generating, enhancing, or modulating a protective and/or therapeutic immune response to influenza virus in a vertebrate, comprising administering to a vertebrate in need of therapeutic and/or preventative immunity one or more of the compositions described herein. In this method, the compositions include one or more polynucleotides comprising at least one nucleic acid fragment, where the nucleic acid fragment is optionally a fragment of a coding region encoding an influenza virus polypeptide, or a fragment, variant, or derivative thereof. In a further embodiment, the composition used in this method includes both an isolated polynucleotide comprising at least one nucleic acid fragment, where the nucleic acid fragment is optionally a fragment of a coding region encoding an influenza virus polypeptide, or a fragment, variant, or derivative thereof; and at least one isolated influenza virus polypeptide, or a fragment, variant, or derivative thereof. Thus, the latter composition includes both an isolated polynucleotide encoding an influenza virus polypeptide or a fragment, variant, or derivative thereof and an isolated influenza virus polypeptide or a fragment, variant, or derivative thereof, for example, a recombinant protein, a purified subunit, viral vector expressing the protein, or an inactivated virus vaccine. Upon administration of the composition according to this method, the influenza virus polypeptide or a fragment, variant, or derivative thereof is expressed in the human in a therapeutically or prophylactically effective amount.

As used herein, an "immune response" refers to the ability of a vertebrate to elicit an immune reaction to a composition delivered to that vertebrate. Examples of immune responses include an antibody response or a cellular, e.g., cytotoxic T-cell, response. One or more compositions of the present invention may be used to prevent influenza infection in vertebrates, e.g., as a prophylactic vaccine, to establish or enhance immunity to influenza virus in a healthy individual prior to exposure to influenza or contraction of influenza disease, thus preventing the disease or reducing the severity of disease symptoms.

As mentioned above, compositions of the present invention can be used both to prevent influenza virus infection, and also to therapeutically treat influenza virus infection. In individuals already exposed to influenza, or already suffering from influenza disease, the present invention is used to further stimulate the immune system of the vertebrate, thus reducing or eliminating the symptoms associated with that disease or disorder. As defined herein, "treatment" refers to the use of one or more compositions of the present invention to prevent, cure, retard, or reduce the severity of influenza disease symptoms in a vertebrate, and/or result in no worsening of influenza disease over a specified period of time in a vertebrate which has already been exposed to influenza virus and is thus in need of therapy. The term "prevention" refers to the use of one or more compositions of the present invention to generate immunity in a vertebrate which has not yet been exposed to a particular strain of influenza virus, thereby preventing or reducing disease symptoms if the vertebrate is later exposed to the particular strain of influenza virus. The methods of the present invention therefore may be referred to as therapeutic vaccination or preventative or prophylactic vaccination. It is not required that any composition of the present invention provide total immunity to influenza or totally cure or eliminate all influenza disease symptoms. As used herein, a "vertebrate in need of therapeutic and/or preventative immunity" refers to an individual for whom it is desirable to treat, i.e., to prevent, cure, retard, or reduce the severity of influenza disease symptoms, and/or result in no worsening of influenza disease over a specified period of time. Vertebrates to treat and/or vaccinate include humans, apes, monkeys (e.g., owl, squirrel, cebus, rhesus, African green, patas, cynomolgus, and cercopithecus), orangutans, baboons, gibbons, and chimpanzees, dogs, wolves, cats, lions, and tigers, horses, donkeys, zebras, cows, pigs, sheep, deer, giraffes, bears, rabbits, mice, ferrets, seals, whales, ducks, geese, terns, shearwaters, gulls, turkeys, chickens, quail, pheasants, geese, starlings and budgerigars.

One or more compositions of the present invention are utilized in a "prime boost" regimen. An example of a "prime boost" regimen may be found in Yang, Z. et al. *J. Virol.* 77:799-803 (2002), which is incorporated herein by reference in its entirety. In these embodiments, one or more polynucleotide vaccine compositions of the present invention are delivered to a vertebrate, thereby priming the immune response of the vertebrate to an influenza virus, and then a second immunogenic composition is utilized as a boost vaccination. One or more compositions of the present invention are used to prime immunity, and then a second immunogenic composition, e.g., a recombinant viral vaccine or vaccines, a different polynucleotide vaccine, or one or more purified subunit isolated influenza virus polypeptides or fragments, variants or derivatives thereof is used to boost the anti-influenza virus immune response.

In one embodiment, a priming composition and a boosting composition are combined in a single composition or single formulation. For example, a single composition may comprise an isolated influenza virus polypeptide or a fragment, variant, or derivative thereof as the priming component and a polynucleotide encoding an influenza protein as the boosting component. In this embodiment, the compositions may be contained in a single vial where the priming component and boosting component are mixed together. In general, because the peak levels of expression of protein from the polynucleotide does not occur until later (e.g., 7-10 days) after administration, the polynucleotide component may provide a boost to the isolated protein component. Compositions comprising both a priming component and a boosting component are referred to herein as "combinatorial vaccine compositions" or "single formulation heterologous prime-boost vaccine compositions." In addition, the priming composition may be administered before the boosting composition, or even after the boosting composition, if the boosting composition is expected to take longer to act.

In another embodiment, the priming composition may be administered simultaneously with the boosting composition, but in separate formulations where the priming component and the boosting component are separated.

The terms "priming" or "primary" and "boost" or "boosting" as used herein may refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

In certain embodiments, one or more compositions of the present invention are delivered to a vertebrate by methods described herein, thereby achieving an effective therapeutic and/or an effective preventative immune response. More specifically, the compositions of the present invention may be administered to any tissue of a vertebrate, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a vertebrate, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the lumen of a duct of a salivary gland or liver, the desired polypeptide is expressed in the salivary gland and the liver such that the polypeptide is delivered into the blood stream of the vertebrate from each of the salivary gland or the liver. Certain modes for administration to secretory organs of a gastrointestinal system using the salivary gland, liver and pancreas to release a desired polypeptide into the bloodstream is disclosed in U.S. Pat. Nos. 5,837,693 and 6,004,944, both of which are incorporated herein by reference in their entireties.

In certain embodiments, the compositions are administered into embryonated chicken eggs or by intramuscular injection into the defeathered breast area of chicks as described in Kodihalli S. et al., Vaccine 18:2592-9 (2000), which is incorporated herein by reference in its entirety.

In certain embodiments, the compositions are administered to muscle, either skeletal muscle or cardiac muscle, or to lung tissue. Specific, but non-limiting modes for administration to lung tissue are disclosed in Wheeler, C. J., et al., *Proc. Natl. Acad. Sci. USA* 93:11454-11459 (1996), which is incorporated herein by reference in its entirety.

According to the disclosed methods, compositions of the present invention can be administered by intramuscular (i.m.), subcutaneous (s.c.), or intrapulmonary routes. Other suitable routes of administration include, but are not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), inraatrial (i.e., into the heart atrium) and sub arachnoid (i.e., into the sub arachnoid spaces of the brain) administration.

Any mode of administration can be used so long as the mode results in the expression of the desired peptide or protein, in the desired tissue, in an amount sufficient to generate an immune response to influenza virus and/or to generate a prophylactically or therapeutically effective immune response to influenza virus in a human in need of such response. Administration means of the present invention include needle injection, catheter infusion, biolistic injectors, particle accelerators (e.g., "gene guns" or pneumatic "needleless" injectors) Med-E-Jet (Vahlsing, H., et al., *J. Immunol. Methods* 171:11-22 (1994)), Pigjet (Schrijver, R., et al., *Vaccine* 15: 1908-1916 (1997)), Biojector (Davis, H., et al., *Vaccine* 12: 1503-1509 (1994); Gramzinski, R., et al., Mol. Med. 4: 109-118 (1998)), AdvantaJet (Linmayer, I., et al., Diabetes Care 9:294-297 (1986)), Medi-jector (Martins, J., and Roedl, E. J. Occup. Med. 21:821-824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., Life Sciences 65: 2193-2203 (1999)) or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M. et al., Proc. Natl. Acad. Sci. USA 96:4262-7 (1999); Hartikka, J. et al., Mol. Ther. 4:407-15 (2001); Mathiesen, I., Gene Ther. 6:508-14 (1999); Rizzuto G. et al., Hum. Gen. Ther. 11:1891-900 (2000). Each of the references cited in this paragraph is incorporated herein by reference in its entirety.

Determining an effective amount of one or more compositions of the present invention depends upon a number of factors including, for example, the antigen being expressed or administered directly, e.g., HA, NA, NP, M1 or M2, or fragments, e.g., M2e, variants, or derivatives thereof, the age and weight of the subject, the precise condition requiring treatment and its severity, and the route of administration. Based on the above factors, determining the precise amount, number of doses, and timing of doses are within the ordinary skill in the art and will be readily determined by the attending physician or veterinarian.

Compositions of the present invention may include various salts, excipients, delivery vehicles and/or auxiliary agents as are disclosed, e.g., in U.S. Patent Application Publication No. 2002/0019358, published Feb. 14, 2002, which is incorporated herein by reference in its entirety.

Furthermore, compositions of the present invention may include one or more transfection facilitating compounds that facilitate delivery of polynucleotides to the interior of a cell, and/or to a desired location within a cell. As used herein, the terms "transfection facilitating compound," "transfection facilitating agent," and "transfection facilitating material" are synonymous, and may be used interchangeably. It should be noted that certain transfection facilitating compounds may also be "adjuvants" as described infra, i.e., in addition to facilitating delivery of polynucleotides to the interior of a cell, the compound acts to alter or increase the immune response to the antigen encoded by that polynucleotide. Examples of the transfection facilitating compounds include, but are not limited to inorganic materials such as calcium phosphate, alum (aluminum sulfate), and gold particles (e.g., "powder" type delivery vehicles); peptides that are, for example, cationic, intercell targeting (for selective delivery to certain cell types), intracell targeting (for nuclear localization or endosomal escape), and ampipathic (helix forming or pore forming); proteins that are, for example, basic (e.g., positively charged) such as histones, targeting (e.g., asialoprotein), viral (e.g., Sendai virus coat protein), and pore-forming; lipids that are, for example, cationic (e.g., DMRIE, DOSPA, DC-Chol), basic (e.g., steryl amine), neutral (e.g., cholesterol), anionic (e.g., phosphatidyl serine), and zwitterionic (e.g., DOPE, DOPC); polymers such as dendrimers, star-polymers, "homogenous" poly-amino acids (e.g., poly-lysine, poly-arginine), "heterogeneous" poly-amino acids (e.g., mixtures of lysine & glycine), co-polymers, polyvinylpyrrolidinone (PVP), poloxamers (e.g. CRL 1005) and polyethylene glycol (PEG); and virosomes such as immunopotentiating reconstituted influenza virosome (IRIV). A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, et al., Biochim. Biophys. Acta 1380(3):354-368 (1988)), mechanical mixing (e.g., free moving materials in liquid or solid phase such as "polylysine+cationic lipids") (Gao and Huang, Biochemistry 35:1027-1036 (1996); Trubetskoy, et al., Biochem. Biophys. Acta 1131:311-313 (1992)), and aggregation (e.g., co-precipitation, gel forming such as in cationic lipids+polylactide, and polylysine+gelatin). Each of the references cited in this paragraph is incorporated herein by reference in its entirety.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual*, 2nd Ed., Sambrook et al., ed., Cold Spring Harbor Laboratory Press: (1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); and in Ausubel et al., *Current Protocols in Molecular Biology*, John Wiley and Sons, Baltimore, Md. (1989). Each of the references cited in this paragraph is incorporated herein by reference in its entirety.

Hemagglutination Inhibition (HAI) Assays

Preimmune and postimmune mouse sera were treated with receptor-destroying enzyme (RDE). HAI antibodies were measured against influenza rgA/Vietnam/1203/2004× A/PR/8/34 influenza (H5N1) vaccine virus. Four HA units of virus were incubated with serial dilutions of RDE-treated mouse sera for at least 30 minutes at room temperature followed by a 30 minute incubation with 0.5% horse erythrocytes. The HAI titer was recorded as the reciprocal of the highest dilution of antisera which inhibits the agglutination of horse erythrocytes.

Viral Micro Neutralization Assays

Influenza vaccine virus rgA/Vietnam/1203/2004×A/PR/8/34 (H5N1) and diluted RDE-treated mouse sera were incubated together at room temperature for 1 hour. The mixture was titrated on monolayers of Madin-Darby canine kidney (MDCK) cells grown in 96-well tissue culture plates. Plates were incubated for 3 days at 37° C. in 5% $CO_2$. At the end of 3 days, the presence of cytopathic effects on cell monolayers was evaluated. Neutralization titers were expressed as the reciprocal of the antibody dilution that completely inhibited virus infectivity in 50% of quadruplicate cultures

Mice, Immunizations and Cell Cultures

HLA DR4 transgenic mice are obtained from C. David (Mayo Clinic) or purchased from Taconic. Non-transgenic $H-2^b$ mice are purchased from Charles River Laboratories or other commercial vendors. Immunizations are performed as described in (Ishioka et al., *J Immunol,* 162(i):3915-25 (1999)). All cells are grown in culture medium consisting of RPMI 1640 medium with HEPES (Gibco Life Technologies) supplemented with 10% FBS, 4 mM L-glutamine, 50 μM 2-ME, 0.5 mM sodium pyruvate, 100 μg/ml streptomycin and 100 U/ml penicillin.

The natural crossreactivity between HLA-DR and $IA^b$ can also be exploited to test HTL responses. This evaluation provides an assessment of the antigenicity and immunogenicity of multi-epitope constructs.

Example 1

HA, HA-PADRE® and PADRE®-HA DNA Constructs

HA, HA-PADRE® and PADRE®-HA DNA constructs were designed as follows: the HA sequences were generated by PCR using overlapping complementary oligonucleotides encoding the H5 HA from A/Vietnam/1203/2004 (Accession # AAT73274). The HA sequences were backtranslated using the codon table for *Autographa Californica* polyhedrovirus. Blocks with 20 nucleotide overlap were annealed together and extended in a gene synthesis reaction (94° C., 30 sec;

58° C., 30 sec; 72° C., 1 min for 5 cycles; 94° C., 30 sec; 72° C., 1 min for 10 cycles) using the proof-reading polymerase Pfu (San Diego, Stratagene). The extended blocks were amplified by PCR (94° C., 30 sec; 58° C., 30 sec; 72° C., 2 min; 30 cycles) to synthesize full-length constructs. The gel purified PCR products were cloned into pFastBac (Carlsbad, Invitrogen) or mammalian vector pMB75.6 and confirmed by sequence analysis. A PADRE® sequence was inserted at a location 5' or 3' to the HA DNA sequence into the pFastBac or mammalian PMB75.6 vector, either prior to or subsequent to the cloning of the HA PCR product.

Example 2

Immunogenicity of HA in Transgenic Animals Using HA, HA-PADRE® and PADRE®-HA DNA Constructs Transgenic mice (HLA-DR4) were injected with 50 μl of 1 mg/ml and 0.01 mg/ml of HA, HA-PADRE® and PADRE®-HA DNA constructs in the anterior tibialis muscle of both legs. Mice were immunized two times, one month apart, with bleeds occurring 4 and 2 weeks following primary and secondary immunizations, respectively. ELISA measurements were performed using 96-well, flat-bottom plates (Immunol II, Dynatech, Boston, Mass.) coated with 1 μg recombinant hemagglutinin (Protein Sciences Corporation, Meriden, Conn.). Data are shown as antibody titers determined as the reciprocal of the serum dilution yielding 0.3 OD units (450 nM). Representative results are presented in FIG. 1, where the PADRE®-HA construct shows an increase in the immunogenicity of hemagglutinin as compared to HA alone and HA-PADRE®. Results of specific antibody responses at a high and a low dose in individual animals using HA and PADRE®-HA constructs are shown in FIGS. 2A-D.

In a similar experiment, groups of ten HLA-DR4 transgenic mice were immunized with a dose titration (100 and 10 μg/animal) of PADRE®-HA (SEQ ID NO: 180) and HA (SEQ ID NO:182) DNA vaccines. The mice were immunized three times at 3 week intervals. Two weeks following each immunization, the mice were bled and antibody titers determined by standard ELISA using 0.2 μg purified HA (Protein Sciences) to coat the wells. Antibody titers are given as the reciprocal of the dilution giving an OD reading of 0.3 at 450 nM. Results of specific antibody responses at a high and a low dose in individual animals using HA and PADRE®-HA constructs are shown in FIG. 10 and demonstrate that the use of PADRE® (PADRE®-HA) significantly augments the HA-specific antibody response relative to the HA-only vaccine.

HLA transgenic mouse will serve a valuable tool in evaluating epitope processing and presentation from DNA or viral epitope-based vaccines. These attributes also suggest that the mouse model can be used in influenza challenge studies following vaccination.

Example 3

M2e, M2e-PADRE® and PADRES-M2e DNA Constructs

The NCBI database was searched for M2e amino acid sequences for representatives of epidemic (H1N1, H3N2), past pandemic (H1N1, H2N2, H3N2) and potential future pandemic (H5N1, H7N7, H9N2) viral strains. As shown in Table 5, a distinct pattern of conserved and varied sequences was observed. Viral strains isolated from humans exhibited the conserved sequence, SLLTEVET-PIRNEWGCRCNDSSD (SEQ ID NO:15) which is proposed as a "universal" influenza vaccine. However, potential pandemic strains do not encode this conserved sequence. In contrast, a distinct pattern of sequence variation occurs in viral strains isolated from avian or swine sources, specifically at amino acid positions, 10, 13, 15, 17, and 19. For example, A/Swine/Saskatchewan/18789/02 sequence varies specifically at positions 10 (I→T), position 13 (E→G), position 15 (G→E), position 17 (R→K) and position 19 (N→S) relative to the human-derived sequence. There are other variants but generally with a subset of the same changes.

M2e sequences are cloned into pFastBac (Carlsbad, Invitrogen) or mammalian vector pMB75.6 and confirmed by sequence analysis. A PADRE® sequence is inserted at a location 5' or 3' to the M2e DNA sequence into the pFastBac or mammalian PMB75.6 vector, either prior to or subsequent to the cloning of the M2e sequence.

Example 4

Identification of Conserved HLA II Restricted Peptides Derived from Influenza Subtypes Using Established Motif Search Algorithms and HLA-Peptide Binding Assays To identify epitopes useful for vaccine design, a multidisciplinary approach is used based initially on amino acid motif searching of viral sequences to identify potential HLA Class II motifs (see Tables 3 and 4). This is followed by high throughput synthetic peptide binding assays using purified HLA molecules to determine affinity and breadth of epitope peptide binding.

Selection of influenza virus strains with potential to initiate pandemics: Influenza virus strains for this study were selected on the basis of host diversity (avian, swine, human), agents of past pandemics (H1N1, H2N2, H3N2) and capacity to cause zoonotic influenza infections of man (H5N1, H1N1, H7N7, H9N2). The selected strains are shown below.

Algorithm motif searches: Motif search algorithms are validated for the most common HLA Class II alleles but will focus on the HLA-DR1 and -DR3 supertypes because we can attain virtually 100% population coverage. The selected influenza viral sequences were scanned for motif positive amino acid sequences using the motif definitions. The peptides specific for DR1 and DR3 supertypes are produced as synthetic peptides.

Selected viral strains with potential to initiate pandemics are as follows:

| Virus Subtype | Host Origin | Virus Strain | Availability of Gene Sequences[a] | | | | | | | |
|---|---|---|---|---|---|---|---|---|---|---|
| | | | PB2 | PB1 | PA | HA | NP | NA | M | NS |
| H5N1 b) | Human | A/Hong Kong/156/97 | ■ | ■ | ■ | ■ | ■ | ■ | ■ | ■ |
| H5N1 | Human | A/Hong Kong/483/97 | ■ | ■ | ■ | ■ | ■ | ■ | ■ | ■ |

| Virus Subtype | Host Origin | Virus Strain | PB2 | PB1 | PA | HA | NP | NA | M | NS |
|---|---|---|---|---|---|---|---|---|---|---|
| H9N2 | Human | A/Hong Kong/1073/99 | ■ | ■ | ■ | ■ | ■ | ■ | ■ | ■ |
| H9N2 | Avian | A/Chicken/HK/G9/97 | ■ | ■ | ■ | ■ | ■ | ■ | ■ | ■ |
| H9N2 | Swine | A/Swine/Hong Kong/10/98 | ■ | ■ | ■ | ■ | ■ | ■ | ■ | ■ |
| H7N1 | Avian | A/FPV/Rostock/34 | ■ |   | ■ |   | ■ | ■ | ■ | ■ |
| H7N1 | Avian | A/Turkey/Italy/4620/99 |   |   |   | ■ |   |   |   |   |
| H7N7 | Avian | A/FPV/Weybridge/34 | ■ |   |   |   |   | ■ | ■ |   |
| H1N1 | Human | A/New Caledonia/20/99 |   |   |   | ■ | ■ | ■ | ■ | ■ |
| H3N2 c) | Human | A/Hong Kong/1/68 | ■ | ■ | ■ | ■ | ■ | ■ | ■ | ■ |
| H3N2 | Human | A/Shiga/25/97 | ■ | ■ | ■ | ■ | ■ | ■ | ■ | ■ |
| H2N2 d) | Human | A/Singapore/1/57 | ■ | ■ | ■ | ■ | ■ | ■ | ■ | ■ |
| H2N2 | Human | A/Leningrad/134/57 | ■ | ■ | ■ | ■ | ■ | ■ | ■ | ■ |
| H2N2 | Human | A/Ann Arbor/6/60 | ■ | ■ | ■ | ■ | ■ | ■ | ■ | ■ |
| H1N1 | Human | A/Brevig Mission/1/18 |   |   |   | ■ |   | ■ | ■ | ■ |
| H1N1 e) | Swine | A/Swine/Wisconsin/464/98 | ■ | ■ | ■ | ■ | ■ | ■ | ■ | ■ |
| H7N7 f) | Human | A/Netherlands/219/03 | ■ | ■ | ■ | ■ | ■ | ■ | ■ | ■ | a) Presence of this symbol (■) indicates that the gene sequence is available;
b) numerous cases of avian-to-human transmission and fatalities caused by H5N1;
c) The 1968 pandemic was due to a H3N2 virus;
d) The 1957 pandemic was due to H2N2 virus;
e) Classical swine H1N1 virus strain;
f) Isolated from a fatal human case.

Peptide synthesis: The class II peptides are synthesized initially as crude peptides from Mimotopes (Minneapolis, Minn./Clayton, Victoria, Australia) or Pepscan Systems B.V. (Lelystad, Netherlands). These peptides are supplied in small amounts and are typically only 50-70% pure. Larger quantities of selected peptides are synthesized, when needed, using an Applied Biosystems (Foster City, Calif.) 430A peptide synthesizer and fluoronylmethyloxy carbonyl (F-moc) solid phase methods. Peptides synthesized are typically purified to >95% homogeneity by reverse phase HPLC.

In vitro HLA-peptide epitope binding assays: High affinity binding of epitope peptides to HLA molecules is required for immune recognition and has proved to be one of the most highly predictive approaches for identifying epitopes. Capture assays based on the use of the TopCount benchtop microplate scintillation counter (Packard Instruments) allow the high throughput, sensitivity and compatibility with data automation platforms.

HLA Class II purification: The binding assay requires the use of purified HLA Class II molecules. A large number of different types of cells are available including EBV-transformed homozygous human B cell lines, mouse B cell lymphomas or mastocytomas, transfected fibroblasts or single MHC allele transfected 721.221 lines. HLA molecules are purified from cell lysates using monoclonal antibody-based affinity chromatography.

Measurement of peptide binding to HLA molecules and data analysis: The binding assay to be utilized is a competitive system that is based on the use of known $^{125}$I radiolabeled peptide ligands[112]. To determine the $IC_{50}$ of peptide binding, the concentration of test peptide yielding 50% inhibition of the binding of the radiolabeled peptide is calculated. Typical test concentrations range from 120 μg/ml-120 pg/ml. Under the conditions utilized, the measured $IC_{50}$ values are reasonable approximations of the Kd values.

Epitopes that are naturally processed and presented to the immune system using peptides are identified as high affinity binders to HLA molecules and peripheral blood mononuclear cells (PBMC) from normal human donors and HLA transgenic mice. It is necessary to address epitope immunogenicity because not all motif positive peptides are immunogenic nor is it likely that all epitopes are generated equally during infection. Typically two methods to document epitope immunogenicity and utility are used; 1) in vitro assays using PBMC from normal donors and 2) immunization studies with HLA transgenic mice. Recognition of epitope peptides by human PBMC in a recall assay is the most direct method to verify the authenticity of an epitope because responses demonstrate the epitope was generated as the course of natural infection and that the needed T-cell receptor (TCR) repertoire exists. Finally, the HLA transgenic mouse is well suited for testing vaccine constructs because the proteosome processing preferences and TCR repertoires of mice overlap significantly with humans.

Assay for recall memory influenza responses using human PBMC: Based on preliminary data presented, past studies[44], and those of others[42,43,45], responses to multiple epitopes are expected because the selection process is for immunologically conserved epitopes. The assays detecting IFN-γ are performed as described above and according to manufacturers' protocols.

It has been demonstrated that CD4$^+$ cells can promote survival to a lethal dose of influenza infection. The mechanisms that may be involved are several including their classic contribution as helpers during the generation of flu-specific CD8$^+$ CTL and antibody producing B cells. Potentially, CD4$^+$ cells following influenza infection may have an effector function and directly mediate viral clearance by IFN-γ-dependent mechanisms and/or by direct cytolytic effects on infected cells. Accordingly, HTL activity is measured as a function of IFN-γ secretion by CD4$^+$ T-lymphocytes, again using an ELISPOT assay as described. Depending on the results obtained using IFN-γ as a readout, IL-2 or TNF-γ could also be assayed using an ELISPOT format.

A collection of positive and control peptides for each supertype are required to ensure the specificity of the influenza-specific responses. Defined epitopes from various pathogens, generally HIV, HBV, HCV and *Plasmodium falciparum* can be used as negative controls assuming that the donors have not been exposed. Positive control peptides are usually derived from HCMV, EBV, and influenza. Negative and positive control peptides to be used for each supertype are identified from previous studies and the literature.

Human M2e-specific memory B cells using a novel ELISPOT system are identified. This assay has been used to demonstrate that the anthrax vaccine (AVA: BioThrax) elicits a substantial population of protective-antigen specific memory B cells[144]. The assay relies on a 6 day polyclonal [pokeweed mitogen extract (ICN), fixed S. aureus, Cowan (Sigma)] stimulation of PBMC followed by an antigen-specific ELISPOT for detection of memory B cells that have differentiated into antibody secreting cells. Specifically, 96-well filter plates (Millipore) are coated with M2e peptide followed by addition of activated PBMC. After an incubation period, the plates are subsequently washed and incubated in the presence of mouse anti-human pan IgG Fc biotin conjugated antibody (Hybridoma Reagent Laboratory). Following washing, the plates are incubated with HRP-conjugated avidin-D (Vector Laboratories) and developed using AEC (Sigma). Controls for the assay includes a non-M2e antigen negative control, such as KLH (Pierce), and a positive control which consists of detection of all IgG secreting cells by coating the plate with goat anti-human Ig. Data are expressed as frequency of M2e-specific B cells as a percentage of the total IgG+ memory B cells/$10^6$ PBMC. Poke weed mitogen (PWM) is assayed for activity. Individual lots of PWM are titrated for activity before use. It should be noted that although the M2e epitope is highly conserved, there are sequence variations that must be addressed. For example, the most conserved sequence of the human influenza A viruses is SLLTEVETPIRNEWGCRCNDSSD (SEQ ID NO:15). However, Shiver and colleagues have reported that antibodies induced by this sequence do not cross-react on M2 peptides derived from the pathogenic H5N1 virus[54]. The A/Hong Kong/483/97 has multiple sequence differences noted as underlined, SLLTEVETLTRNGWGCRCSDSSD (SEQ ID NO:209). If the M2e B cell epitope is to be used as a pandemic vaccine component then sequences from appropriate strains with a potential to initiate pandemics will need to be considered. Various influenza strains indicated in Table 5 were aligned and examined for sequence variation in the M2e epitope. Four different strains, as shown in Table 6, demonstrated sequence variation. Peptides corresponding to these strains are synthesized and used to immunize mice. Each M2e-specific antibody response induced is evaluated for the capacity to bind the four different sequences.

Immunogenicity testing of HTL and B cell epitopes in HLA transgenic and non transgenic mice: HLA-DR4 transgenic mice from Taconic, a commercial source are also utilized. Additionally, mice of the b haplotype, e.g., C57Bl/6 are utilized, to evaluate the immunogenicity of HLA-DR-restricted peptides[67,139]. The rationale for using b haplotype mice is based on the observation that the motifs recognized by DR alleles often cross-react on murine class II alleles. Immunogenicity of test epitopes are generally accomplished by immunizing mice with pools of peptides (5-10) emulsified in IFA (for CTL) and CFA (for HTL) followed by in vitro testing of splenocytes 14 days later for epitope-specific T lymphocyte responses.

Example 5

Inducing Immune Responses Against Multiple HTL Epitopes Combined with PADRE®-HA or HA-PADRE® Constructs Construction and Testing of HTL Epitope Strings:
Epitope strings encompassing 1-10 different HTL epitopes under the control of a single promoter are synthesized and incorporated into a standard plasmid, pcDNA 3.1 (Invitrogen, San Diego). To facilitate testing and optimization, each set of epitopes for a given construct is chosen to provide a balanced representation of epitopes which are already known to be immunogenic in $IA^b$ mice. In addition, all the peptides corresponding to junctions are synthesized and tested for binding to $IA^b$ and, most importantly, for binding to a panel of fourteen different DR molecules, representative of the most common DR alleles worldwide (Southwood et al., J Immunol, 160(7):3363-73 (1998)). Thus, HTL epitopes that are not directed to an antigen of interest are not created within these plasmids. However, should junctional regions with good DR binding potential (and hence, potential DR restricted immunogenicity in vivo) be detected, a spacer such as GPGPG is introduced to eliminate them. In all constructs, the number of Class I junctional motifs will also be minimized.

Experimental vaccine plasmids are tested for immunogenicity using HLA DR transgenic mice and/or mice of the H2b haplotype. Proliferation and/or cytokine production are measured (IL5, IFNγ). In a typical protocol, cardiotoxin treated mice are injected i.m. with 100 µg of each plasmid and responses evaluated eleven days later (Ishioka et al., J Immunol, 162(7):3915-25 (1999)).

Since the ultimate use of optimized constructs is a human vaccine, optimized human codons are utilized. However, to facilitate the optimization process in HLA transgenic mice, care are applied to select, whenever possible, human codons that are also optimal for mice. Human and murine codon usage is very similar. See, e.g., Codon usage database at http://www.kazusa.or.jp/codon/.

Human cells transfected with the various multi-epitope nucleic acid vaccine constructs can be used in antigenicity assays, conducted in parallel with in vivo testing in HLA transgenic mice. Any potential discrepancy between multi-epitope nucleic acid vaccine efficacy, due to the differential codon usage, is addressed by the availability of these two different assay systems.

Typically, antigenicity and immunogenicity testing of plasmid constructs is conducted in parallel. In vivo testing in transgenic mice are performed for A2, A11, and B7 HLA transgenic mice. Following a standard protocol, cardiotoxin pretreated mice are injected i.m. with 100 µg of each plasmid and responses evaluated eleven days later (Ishioka et al., J Immunol, 162(7):3915-25 (1999)). Assays will include ELISPOT from freshly isolated cells, as well as interferon gamma release. All of the above mentioned techniques are well established in the art. The simultaneous measurement of responses against epitopes is not problematic, as large colonies of transgenic mice are established for these HLA types. Groups of four to six mice are adequate to measure responses against six to ten different epitopes, in multiple readout assays.

Testing for Interactions Between PADRE®, HA, M2e sequences and HTL Epitopes
The activities described above yield small, functional blocks of epitopes, which are utilized to demonstrate simultaneous responses/antigenicity against all epitopes analyzable. These blocks are the subject to further optimization. Using these same constructs, immunodominance is assessed. The results obtained with the pool of constructs are then compared with the results obtained with the same construct, injected separately.

Example 6

Human Recall Responses in Donors

Primary interferon-gamma (IFN-γ) ELISPOT (enzyme linked immunospot) assay was used to identify candidate vaccine epitopes. Peripheral blood mononuclear cells (PBMCs) were collected by leukapheresis from healthy human donors. The PBMCs were purified using standard Ficoll-Paque (Amersham) density gradient centrifugation and subsequently frozen at $5\times10^7$ cells per ml. PBMCs were thawed and were either rested for 5 days (no peptide) or stimulated for 7 days with the appropriate peptides at 37° C. in media at $2.5\times10^6$ cells per mL. Elispot plates (Millipore IP plate) were coated with anti-human IFN-γ antibody clone 1-D1K (Mabtech, Cat# 3420-3, 1 mg/mL) and incubated overnight at 4° C. The following day, PBMCs were depleted of CD8+ cells using human DYNAbeads (DYNAL Biotec Cat# 111.47, OSLO, Norway). The depleted PBMCs with enriched CD4+ cells were then plated onto ELISPOT plates previously blocked with RPMI 1640 containing 10% FCS. Irradiated PBMCs coated with peptide were added to the plated PBMCs and the plates were incubated at 37° C. for 20 hours. The next day the plates were incubated with biotinylated mouse anti-human IFN-γ antibody and developed with Vectastain Elite Vector Cat# PK-6100 according to manufacturer's instructions. The spots were counted on an ELISPOT counter (AID). Donors were considered positive for a peptide if the number of spots was over 3 times background as determined by responses to irrelevant peptides (non influenza). Representative results are shown in FIGS. 3A-B.

In another experiment, frozen Donor PBMC were thawed and rested overnight in media containing RPMI 5% AB human serum/complete media followed by a five day expansion of peptide-specific HLA-DR-restricted HTL using a pool of approximately 10 peptides (1 μg/ml final concentration of each peptide). On day five, CD4+ T cells were enriched by removing CD8+ T cells using Dynal beads and a standard IFNγ ELISPOT performed. Negative control peptides (HIV, HCV) were used to determine background responses. Results for donor 753, 6018, 716, AC08 and AC02 are shown in FIGS. 4-8.

In another experiment, frozen Donor PBMC were thawed and rested five days in media containing RPMI 5% AB human serum/complete media. On day five, CD4+ T cells were enriched by removing CD8+ T cells using Dynal beads and a standard IFNγ ELISPOT performed. Negative control peptides (HIV, HCV) were used to determine background responses. Results for donor 3501 are shown in FIG. 9.

The Human influenza epitope-specific immune responses can be summarized as follows:

| | | | Random Human Donors | | | |
|---|---|---|---|---|---|---|
| Peptides | 3501 | 6018 | 753 | AC08 | 716 | AC02 |
| M1.60 | | Positive | Positive | Positive | | Positive |
| M1.103 | | | Positive | Positive | | |
| M1.173 | | | | | | Positive |
| M1.205 | | Positive | | | | Positive |
| NP.39 | Positive | | | | | |
| NP.189 | | Positive | Positive | Positive | | |
| NP.258 | | Positive | | | | |
| NP.328 | | | Positive | | | |
| NP.406 | Positive | | | | | |
| NS1.156 | Positive | | | | | |
| PB1.411 | Positive | Positive | Positive | | Positive | |
| PB1.449 | Positive | | | | | |
| PB1.502 | Positive | | | | | |
| PA.127 | Positive | | | | | |

Example 7

Immunogenicity Testing of Multi-Epitope HTL Constructs and Influence of Spacer Sequences A universal spacer consisting of GPGPG was developed to separate HTL epitopes, thus disrupting junctional epitopes. The logic behind the design of this spacer is that neither G nor P are used as primary anchors, positions 1 and 6 in the core region of an HTL peptide epitope, by any known murine or human MHC Class MHC Class II molecule. The gap of five amino acids introduced by this spacer separates adjacent epitopes so the amino acids of two epitopes cannot physically serve as anchors in the 1 and 6 positions. The utility of the GPGPG spacer is tested using synthetic peptides composed of $IA^b$.

The ability of multi-epitope HTL DNA-based constructs to induce an HTL response in vivo is evaluated by intramuscular immunization of $H2^{bxd}$ mice with an EP-HIV-1043-PADRE® construct. Eleven days after immunization, no booster immunizations were administered, CD4 T cells are purified from the spleen, and peptide specific HTL responses are measured in a primary γ-IFN ELISPOT assay. Overall, the HTL responses induced by DNA immunization with the multi-epitope influenza HTL construct are generally of equal or greater magnitude than the responses induced by peptide immunization.

Thus, as described above, the invention provides a novel method and system for automatically analyzing polypeptide junctions, eliminating or reducing the number of junctional epitopes, and identifying spacer combinations to optimize the efficacy of multi-epitope constructs. Those skilled in the art will know, or be able to ascertain using no more than routine experimentation, many equivalents to the specific embodiments of the invention described herein. These equivalents are intended to be encompassed by the following claims.

Example 8

Design and Optimization of Genetic DNA Plasmid and Viral Vectored Vaccines

Constructs are designed based on computer programs to optimize proteosomal processing and minimize junctional epitopes: Strategies have been developed to optimize epitope processing efficiency from multi-epitope genetic constructs and to minimize the generation of neo-epitopes generated at the junction of epitopes which may divert the immune responses from the specified desired epitopes[67,69]. The incorporation of preferred flanking amino acids to optimize proteosomal processing and a motif searching function is performed using a computer program.

DNA Vaccine production: DNA vaccine production is performed using routine methods based on primer extension with overlapping oligonucleotide PCR primers, averaging 70 nucleotides in length with 15 nucleotide overlaps[58]. The synthetic gene encoding the epitopes is cloned into the clinically accepted pMB75.6 vaccine backbone[145].

The influenza virus vaccine is formulated in various test adjuvants as described above. Other vaccine delivery formats are also utilized including DNA, AlphaVax viral vaccines and virosomes, and in particular IRIVs.

Assessment of vaccine immunogenicity: Immunogenicity testing is performed primarily using the HLA-DR4 transgenic mice from Taconic and CB6F1 (bxd haplotype) mice to measure responses specific for the influenza-derived HTL epitopes and HA-specific antibodies. Immunogenicity evaluation in mice is a useful tool to assess efficient antigen processing and epitope presentation specifically for the vaccine construct. The spacers adjacent to epitopes that are found to be suboptimally immunogenic in a vaccine construct can be modified, through site-directed mutagenesis, in one or more cycles of secondary optimization.

B-cell assays evaluating vaccines encoding or containing the B cell epitope M2e: An ELISA-based assay measuring antibodies specific for the M2e sequence are performed. M2e, the external domain of the transmembrane viral M2 protein, is highly conserved amongst various influenza strains of differing subtypes. Groups of 10 C57B1/6, CB6F1, or DR4 transgenic mice are immunized with a dose titration of PADRE®-M2e peptide, 0.1, 1, 10 µg adsorbed to 250 µg of alum (Superfos Biosector) as an example of an adjuvant suitable for humans. Alternatively, the PADRE®-M2e immunogen may be DNA. Vaccines are administered in volumes of 100 µl, two or three times at 3-4 week intervals by s.c. injection at the base of the tail. Blood samples are obtained prior to immunizations and at monthly intervals. To determine antibody titers, a standard ELISA assay are performed using 96-well Immunol II plates coated with 0.1 µg/well of the B cell epitope. As a control, mice are immunized with the B cell epitope adsorbed to alum (not linked to PADRE®). The protective capacity of the M2e-specific antibody responses are measured in the viral challenge experiments described below.

Augmentation of HA-derived HTL and antibody responses using DNA vaccines followed by HA protein immunization: Prior immunization with conserved influenza virus HTL epitopes will augment HTL and antibody responses induced using protein-based or inactivated virus-based vaccines. HLA transgenic mice are initially immunized separately or in a prime-boost format using the DNA, and peptides in adjuvant vaccines. These immunizations are followed by inoculation with various HA proteins (0.1, 1, 10 µg/mouse). The HTL and antibody responses are measured (as described above) and directly compared to mice receiving only the conventional HA vaccines. Purified baculovirus-expressed recombinant HA proteins (Protein Sciences, Inc, Meriden, Conn.) corresponding to A/Hong Kong/156/97 (H5) and A/Hong/Kong/1073/99 (H9) are used. The rationale for using H5 and H9 proteins is due to their pandemic potential as observed by transmission of these variants from avian to human[18,146].

Example 9

Evaluation of Efficacy of the Experimental Vaccines Alone and in Combination with Recombinant HA Protein Using HLA Transgenic Mice and Infectious Challenges The efficacy of vaccines composed of conserved influenza HTL and B cell epitopes are evaluated in an influenza viral challenge mouse model. For example, peptides are formulated in various adjuvants and tested for immunogenicity. If a particular adjuvant is superior in augmenting cellular and humoral responses then this adjuvant is used in the challenge studies. Initially, protection against various divergent influenza subtypes is determined by immunizing mice separately with selected DNA, peptides in adjuvant, HA proteins, inactivated and live attenuated vaccines. Doses and immunization schedules are determined according to the immunogenicity studies described above. The capacity of the influenza HTL and B cell epitope-based vaccines to afford protection is compared to the HA protein, inactivated and live attenuated vaccines. Finally, the HA protein combined with the DNA, and peptides in adjuvant vaccines using heterologous prime boost immunization schemes are evaluated for protection. Additionally, emphasis is placed on validating an immunization strategy that induces a protective immune response in the shortest amount of time which is likely an important factor to consider in the event of a pandemic influenza occurrence.

Murine influenza challenge models. Viral challenge studies are performed as previously described[75,147,148]. Initially, mice are immunized with selected vaccines or combinations using doses and immunization schedules that are most immunogenic. To determine the level of protection afforded by the various immunization strategies, immunized mice are challenged with various subtypes of influenza viruses that differ in virulence for mice including human viruses as well as avian and viruses with pandemic potential. Using a number of different subtypes will evaluate the level of protective broadly cross-reactive immunity induced by immunization of mice with the various vaccines expressing conserved HTL epitopes. The following are examples of subtypes for challenge studies: mouse adapted A/Taiwan/1/86 (H1N1); mouse-adapted A/Ann Arbor/6/60 (H2N2); mouse-adapted A/Philippines/1/82 (H3N2); highly pathogenic avian A/Hong Kong/483 (H5N1); a recent human isolate A/Hong Kong/213/03 (H5N1); A/Hong Kong/1073/99 (H9N2); and an H7N7 strain.

The 50% mouse infectious dose (MID50) and 50% lethal dose (LD50) titers are determined for the C57B1/6 mouse strain. Groups of 10-20 mice are lightly anesthetized and infected intranasally (i.n.) with approximately 100-1,000 MID50 of virus. Three and six days post-infection, 5 mice per group are sacrificed and multiple organs including nasal turbinates, lungs and brains are collected and titered in embryonated eggs or MDCK cells for the presence of infectious virus. For viruses that cause lethal disease, and additional group of ten mice are monitored for weight loss and survival over a period of 14 days post-infection.

The use of conserved HTL epitopes delivered by peptides in adjuvant and DNA viral vehicles are used to generate a protective vaccine against influenza.

Example 10

PADRE® Increases the Induction of Functional Antibody

The effect of PADRE® on immunogenicity was also analyzed by measuring antibody function. Antibodies in the immune sera from PADRE®-HA and HA immunized mice described in Example 2 and shown in FIG. 10 (following the third immunization using the 100 µg does) were evaluated for their capacity to inhibit the agglutination of horse red blood cells (hemagglutination inhibition) and to inhibit the grown of virus (Microneutralization).

Hemagglutination inhibition (HAI) is a standard technique used to evaluate HA-specific antibody responses following immunization or infection. The assay is dependent on the ability of the anti-HA antibody to inhibit the interaction between viral HA and erythrocyte sialic acid. In these experiments, pre-immune and post-immune mouse sera were treated with receptor-destroying enzyme (RDE). HAI antibodies were measured against influenza rgA/Vietnam/1203/2004×A/PR/8/34 influenza (H5N1) vaccine virus. Four HA units of virus were incubated with serial dilutions of RDE-treated mouse sera for at least 30 minutes at room temperature followed by a 60-minute incubation with 1% horse erythrocytes. The HAI titers are recorded as the reciprocal of the highest dilution of antisera which inhibited the agglutination of horse erythrocytes. Typically, immune ferret sera are used as a positive control and naïve mouse sera for the negative control. While only 3/10 animals exposed to HA induced antibodies capable of inhibiting hemagglutination, (20, 40 and 80 titer), 5/10 animals exposed to PADRE®-HA induced antibodies capable of inhibiting hemagglutination (20, 20, 20, 80 and 160 titer).

The Micorneutralization assay also used influenza vaccine virus rgA/Vietnam/1203/2004×A/PR/8/34 influenza (H5N1). The virus and diluted RDE-treated mouse sera were incubated together at room temperature for 1 hour. The mixture was titrated on monolayers of Madin-Darby canine kidney (MDCK) cells grown in 96-well tissue culture plates. After an overnight incubation, the cells were fixed and the presence of influenza A NP protein in infected cells was detected by ELISA as described in the WHO Animal influenza manual. Detection of NP protein in infected cells is more sensitive than scoring viral cytopathogenicity. Typically, immune ferret sera are used as a positive control and naïve mouse sera for the negative control. While none of the animals exposed to HA induced positive viral neutralization responses, 2/10 animals exposed to PADRE®-HA induced positive viral neutralization responses (160 and 640 titer).

The results of these experiments, as summarized in FIG. 11, demonstrate that the use of PADRE® significantly increased immunogenicity measured as a function of antibody titers and also demonstrate that PADRE® significantly increases the induction of functional antibody.

Example 11

PADRE® Increases the Immunogenicity of HA Recombinant Protein Delivered Using Alum as an Adjuvant Groups of ten HLA-DR4 transgenic mice were immunized with either PADRE®-HA (SEQ ID NO:174) or HA (SEQ ID NO:185) recombinant protein. The proteins were delivered using alum as an adjuvant. The mice were immunized with a dose titration (10 and 1 μg of recombinant protein/animal) three times at 1 month intervals. Two weeks following each immunization, the mice were bled and antibody titers determined by standard ELISA using 0.2 μg purified HA (Protein Sciences) to coat the wells. Representative results are shown in FIG. 12 and demonstrate that the use of PADRE® (PADRE®-HA) significantly augments the HA-specific antibody response relative to the HA only vaccine

Example 12

PADRE® Increases the Immunogenicity of HA Recombinant Protein Delivered Using Alum and Provax™ as an Adjuvant Groups of ten HLA-DR4 transgenic mice were immunized with either PADRE®-HA (SEQ ID NO:174) or HA (SEQ ID NO:185) recombinant protein. The proteins were delivered using alum and Provax™ as an adjuvant. The mice were immunized with a dose titration (1 and 0.1 μg of recombinant protein/animal) two times at 1 month intervals. Two weeks following each immunization, the mice were bled and antibody titers determined by standard ELISA using 0.2 μg purified HA (Protein Sciences) to coat the wells. Representative results are shown in FIG. 13 and demonstrate that the use of PADRE® (PADRE®-HA) significantly augments the HA-specific antibody response relative to the HA only vaccine.

LITERATURE CITED

1. Thompson, W. W., D. K. Shay, E. Weintraub, L. Brammer, N. Cox, L. J. Anderson, and K. Fukuda, 2003, "Mortality associated with influenza and respiratory syncytial virus in the United States", JAMA 289:179-186.

2. Nguyen-Van-Tam, J. S., and A. W. Hampson, 2003, "The epidemiology and clinical impact of pandemic influenza", Vaccine. 21:1762-1768.

3. "The Lancet Infectious Diseases", 4:595, 2004.

4. Nicholson, K. G., A. E. Colegate, A. Podda, I. Stephenson, J. Wood, E. Ypma, and M. C. Zambon, 2001, "Safety and antigenicity of non-adjuvanted and MF59-adjuvanted influenza A/Duck/Singapore/97 (H5N3) vaccine: a randomised trial of two potential vaccines against H5N1 influenza", Lancet 357:1937-1943.

5. Treanor, J. J., B. E. Wilkinson, F. Masseoud, J. Hu-Primmer, R. Battaglia, D. O'Brien, M. Wolff, G. Rabinovich, W. Blackwelder, and J. M. Katz, 2001, "Safety and immunogenicity of a recombinant hemagglutinin vaccine for H5 influenza in humans", Vaccine 19:1732-1737.

6. Potter, C. W., 2001, "A history of influenza", J. Appl. Microbiol, 91:572-579.

7. Hilleman, M. R., 2002, "Realities and enigmas of human viral influenza: pathogenesis, epidemiology and control", Vaccine 20:3068-3087.

8. Beveridge, W. I., 1991, "The chronicle of influenza epidemics", Hist. Philos. Life Sci. 13:223-234.

9. Gust, I. D., A. W. Hampson, and D. Lavanchy, 2001, "Planning for the next pandemic of influenza" Rev. Med. Virol. 11:59-70.

10. Oxford, J. S., 2000, "Influenza A pandemics of the 20th century with special reference to 1918: virology, pathology and epidemiology", Rev. Med. Virol. 10:119-133.

11. Layer, G. and E. Garman, 2002, "Pandemic influenza: its origin and control" Microbes. Infect. 4:1309-1316.

12. Tollis, M. and L. Di Trani, 2002, "Recent developments in avian influenza research: epidemiology and immunoprophylaxis", Vet. J. 164:202-215.

13. Palese, P. and J. F. Young, 1982, "Variation of influenza A, B, and C viruses", Science 215:1468-1474.

14. Gorman, O. T., W. J. Bean, and R. G. Webster, 1992, "Evolutionary processes in influenza viruses: divergence, rapid evolution, and stasis", Curr. Top. Microbiol. Immunol 176:75-97.

15. Yewdell, J. W., R. G. Webster, and W. U. Gerhard, 1979, "Antigenic variation in three distinct determinants of an influenza type A haemagglutinin molecule", Nature 279: 246-248.

16. Top, F. H., Jr. and P. K. Russell, 1977, "Swine influenza A at Fort Dix, N.J. (January-February 1976). IV, Summary and speculation. J. Infect. Dis. 136 Suppl:S376-S380.

17. Kurtz, J., R. J. Manvell, and J. Banks, 1996, "Avian influenza virus isolated from a woman with conjunctivitis", Lancet 348:901-902.

18. Peiris, M., K. Y. Yuen, C. W. Leung, K. H. Chan, P. L. Ip, R. W. Lai, W. K. Orr, and K. F. Shortridge, 1999, "Human infection with influenza H9N2", Lancet 354:916-917.

19. Scholtissek, C., W. Rohde, H. Von, V, and R. Rott, 1978, "On the origin of the human influenza virus subtypes H2N2 and H3N2", Virology 87:13-20.

20. Wells, M. A., F. A. Ennis, and P. Albrecht, 1981, "Recovery from a viral respiratory infection, II. Passive transfer of immune spleen cells to mice with influenza pneumonia", J. Immunol. 126:1042-1046.

21. Yap, K. L. and G. L. Ada, 1978, "Cytotoxic T cells in the lungs of mice infected with an influenza A virus", Scand. J. Immunol. 7:73-80.

22. Mackenzie, C. D., P. M. Taylor, and B. A. Askonas, 1989, "Rapid recovery of lung histology correlates with clearance of influenza virus by specific CD8+ cytotoxic T cells", Immunology 67:375-381.

23. Taylor, P. M. and B. A. Askonas, 1986, "Influenza nucleoprotein-specific cytotoxic T-cell clones are protective in vivo", Immunology 58:417-420.

24. Kuwano, K., M. Scott, J. F. Young, and F. A. Ennis, 1988, "HA2 subunit of influenza A H1 and H2 subtype viruses induces a protective cross-reactive cytotoxic T lymphocyte response", J. Immunol. 140:1264-1268.

25. Kuwano, K., M. Tamura, and F. A. Ennis, 1990, "Cross-reactive protection against influenza A virus infections by an NS1-specific CTL clone", Virology 178:174-179.

26. Sambhara, S., A. Kurichh, R. Miranda, T. Tumpey, T. Rowe, M. Renshaw, R. Arpino, A. Tamane, A. Kandil, O. James, B. Underdown, M. Klein, J. Katz, and D. Burt, 2001, "Heterosubtypic immunity against human influenza A viruses, including recently emerged avian H5 and H9 viruses, induced by FLU-ISCOM vaccine in mice requires both cytotoxic T-lymphocyte and macrophage function", Cell Immunol. 211:143-153.

27. Okuda, K., A. Ihata, S. Watabe, E. Okada, T. Yamakawa, K. Hamajima, J. Yang, N. Ishii, M. Nakazawa, K. Okuda, K. Ohnari, K. Nakajima, and K. Q. Xin, 2001, "Protective immunity against influenza A virus induced by immunization with DNA plasmid containing influenza M gene", Vaccine 19:3681-3691.

28. Bender, B. S., T. Croghan, L. Zhang, and P. A. Small, Jr., 1992, "Transgenic mice lacking class I major histocompatibility complex-restricted T cells have delayed viral clearance and increased mortality after influenza virus challenge", J. Exp. Med. 175:1143-1145.

29. Ulmer, J. B., J. J. Donnelly, S. E. Parker, G. H. Rhodes, P. L. Felgner, V. J. Dwarki, S. H. Gromkowski, R. R. Deck, C. M. DeWitt, A. Friedman, et al., 1993, "Heterologous protection against influenza by injection of DNA encoding a viral protein", Science 259:1745-1749.

30. Fu, T. M., L. Guan, A. Friedman, T. L. Schofield, J. B. Ulmer, M. A. Liu, and J. J. Donnelly, 1999, "Dose dependence of CTL precursor frequency induced by a DNA vaccine and correlation with protective immunity against influenza virus challenge", J. Immunol. 162:4163-4170.

31. Ulmer, J. B., T. M. Fu, R. R. Deck, A. Friedman, L. Guan, C. DeWitt, X. Liu, S. Wang, M. A. Liu, J. J. Donnelly, and M. J. Caulfield, 1998, "Protective CD4+ and CD8+ T cells against influenza virus induced by vaccination with nucleoprotein DNA", J. Virol. 72:5648-5653.

32. Epstein, S. L., A. Stack, J. A. Misplon, C. Y. Lo, H. Mostowski, J. Bennink, and K. Subbarao, 2000, "Vaccination with DNA encoding internal proteins of influenza virus does not require CD8(+) cytotoxic T lymphocytes: either CD4(+) or CD8(+) T cells can promote survival and recovery after challenge", Int. Immunol. 12:91-101.

33. Langlade-Demoyen, P., F. Garcia-Pons, P. Castiglioni, Z. Garcia, S. Cardinaud, S. Xiong, M. Gerloni, and M. Zanetti, 2003, "Role of T cell help and endoplasmic reticulum targeting in protective CTL response against influenza virus", Eur. J. Immunol. 33:720-728.

34. Anker, W. J., A. K. Bakker, and N. Masurel. 1978, "Cross-protection in mice after immunization with H2N2, H3N2, and H2N2 influenza virus strains". Infect. Immun. 21:96-101.

35. Schulman, J. L. and E. D. Kilbourne, 1965, "Induction of partial specific heterotypic immunity in mice by a single infection with influenza A virus", J. Bacteriol. 89:170-174.

36. Benton, K. A., J. A. Misplon, C. Y. Lo, R. R. Brutkiewicz, S. A. Prasad, and S. L. Epstein, 2001, "Heterosubtypic immunity to influenza A virus in mice lacking IgA, all Ig, NKT cells, or gamma delta T cells", J. Immunol. 166:7437-7445.

37. O'Neill, E., S. L. Krauss, J. M. Riberdy, R. G. Webster, and D. L. Woodland, 2000, "Heterologous protection against lethal A/HongKong/156/97 (H5N1) influenza virus infection in C57BL/6 mice", J. Gen. Virol. 81:2689-2696.

38. Epstein, S. L., T. M. Tumpey, J. A. Misplon, C. Y. Lo, L. A. Cooper, K. Subbarao, M. Renshaw, S. Sambhara, and J. M. Katz, 2002, "DNA vaccine expressing conserved influenza virus proteins protective against H5N1 challenge infection in mice", Emerg. Infect. Dis. 8:796-801.

39. Nguyen, H. H., Z. Moldoveanu, M. J. Novak, F. W. Van Ginkel, E. Ban, H. Kiyono, J. R. McGhee, and J. Mestecky, 1999, "Heterosubtypic immunity to lethal influenza A virus infection is associated with virus-specific CD8(+) cytotoxic T lymphocyte responses induced in mucosa-associated tissues", Virology 254:50-60.

40. Lukacher, A. E., V. L. Braciale, and T. J. Braciale, 1984, "In vivo effector function of influenza virus-specific cytotoxic T lymphocyte clones is highly specific", J. Exp. Med. 160:814-826.

41. Liang, S., K. Mozdzanowska, G. Palladino, and W. Gerhard, 1994, "Heterosubtypic immunity to influenza type A virus in mice. Effector mechanisms and their longevity", J. Immunol. 152:1653-1661.

42. Tumpey, T. M., M. Renshaw, J. D. Clements, and J. M. Katz, 2001, "Mucosal delivery of inactivated influenza vaccine induces B-cell-dependent heterosubtypic cross-protection against lethal influenza A H5N1 virus infection", J. Virol. 75:5141-5150.

43. McMichael, A. J., F. M. Gotch, G. R. Noble, and P. A. S. Beare, 1983, "Cytotoxic T-cell immunity to influenza", N. Engl. J. Med. 309:13-17.

44. Sonoguchi, T., H. Naito, M. Hara, Y. Takeuchi, and H. Fukumi, 1985, "Cross-subtype protection in humans during sequential, overlapping, and/or concurrent epidemics caused by H3N2 and H1N1 influenza viruses", J. Infect. Dis. 151:81-88.

45. Voeten, J. T., T. M. Bestebroer, N. J. Nieuwkoop, R. A. Fouchier, A. D. Osterhaus, and G. F. Rimmelzwaan, 2000, "Antigenic drift in the influenza A virus (H3N2) nucleoprotein and escape from recognition by cytotoxic T lymphocytes", J. Virol. 74:6800-6807.

46. Kashiwagi, T., N. Hamada, J. Iwahashi, K. Hara, T. Ueda, H. Noguchi, and T. Toyoda, 2000, "Emergence of new influenza A viruses which carry an escape mutation of the HLA-B27-restricted CTL epitope of NP in Japan", Microbiol. Immunol 44:867-870.

47. Boon, A. C., G. de Mutsert, Y. M. Graus, R. A. Fouchier, K. Sintnicolaas, A. D. Osterhaus, and G. F. Rimmelzwaan, 2002, "Sequence variation in a newly identified HLA-B35-restricted epitope in the influenza A virus nucleo- 48. Treanor, J. J., E. L. Tierney, S. L. Zebedee, R. A. Lamb, and B. R. Murphy, 1990, "Passively transferred monoclonal antibody to the M2 protein inhibits influenza A virus replication in mice", J. Virol. 64:1375-1377.

49. Frace, A. M., A. I. Klimov, T. Rowe, R. A. Black, and J. M. Katz, 1999, "Modified M2 proteins produce heterotypic immunity against influenza A virus", Vaccine 17:2237-2244.

50. Neirynck, S., T. Deroo, X. Saelens, P. Vanlandschoot, W. M. Jou, and W. Fiers, 1999, "A universal influenza A vaccine based on the extracellular domain of the M2 protein", Nat. Med. 5:1157-1163.

51. Jegerlehner, A., N. Schmitz T. Storni, and M. F. Bachmann, 2004, "Influenza A vaccine based on the extracellular domain of M2: Weak protection mediated via antibody-dependent NK cell activity", J. Immunol. 172:5598-5605.

52. Fiers, W., M. DeFilette, A. Birkett, S, Neirynck, and W. M. Jou, 2004, "A "universal' human influenza A vaccine", Virus Res. 103:173-176.

53. Wanli, L., P. Aou, Y.-H. Chen, 2004, "Monoclonal antibodies recognizing EVETPIRN epitope of influenza A virus M2 protein could protect mice from lethal influenza A virus challenge", Immunol. Lett. 93:131-136.

54. Fan, J., X. Liang, M. S. Horton, H. C. Perry, M. P. Citron, G. J. Heidecker, T. M. Fu, J. Joyce, C. T. Przysiecki, P. M. Keller, V. M. Garsky, R. Ionescu, Y. Rippeon, L. Shi, M. A. Chastain, J. H. Condra, M. E. Davies, J. Liao, E. A. Emini, and J. W. Shiver, 2004, "Preclinical study of influenza virus A M2 peptide conjugate vaccines in mice, ferrets, and rhesus monkeys", Vaccine 22:2993-3003.

55. Jameson, J., J. Cruz, M. Terajima, and F. A. Ennis, 1999, "Human CD8+ and CD4+ T lymphocyte memory to influenza A viruses of swine and avian species", J. Immunol. 162:7578-7583.

56. Jameson, J., J. Cruz, and F. A. Ennis, 1998, "Human cytotoxic T-lymphocyte repertoire to influenza A viruses", J. Virol. 72:8682-8689.

57. Gianfrani, C., C. Oseroff, J. Sidney, R. W. Chesnut, and A. Sette, 2000, "Human memory CTL response specific for influenza A virus is broad and multispecific", Hum. Immunol. 61:438-452.

58. Boon, A. C., G. de Mutsert, Y. M. Graus, R. A. Fouchier, K. Sintnicolaas, A. D. Osterhaus, and G. F. Rimmelzwaan, 2002, "The magnitude and specificity of influenza A virus-specific cytotoxic T-lymphocyte responses in humans is related to HLA-A and -B phenotype", J. Virol. 76:582-590.

59. Liu, M. A, 2003, "DNA vaccines: a review", J. Intern. Med. 253:402-410.

60. Gurunathan, S., D. M. Klinman, and R. A. Seder, 2000, "DNA vaccines: immunology, application, and optimization", Annu. Rev. Immunol 18:927-974.

61. Calarota, S. A., A. C. Leandersson, G. Bratt, J. Hinkula, D. M. Klinman, K. J. Weinhold, E. Sandstrom, and B. Wahren, 1999, "Immune responses in asymptomatic HIV-1-infected patients after HIV-DNA immunization followed by highly active antiretroviral treatment", J. Immunol. 163:2330-2338.

62. Roy, M. J., M. S. Wu, L. J. Barr, J. T. Fuller, L. G. Tussey, S. Speller, J. Culp, J. K. Burkholder, W. F. Swain, R. M. Dixon, G. Widera, R. Vessey, A. King, G. Ogg, A. Gallimore, J. R. Haynes, and F. D. Heydenburg, 2000, "Induction of antigen-specific CD8+ T cells, T helper cells, and protective levels of antibody in humans by particle-mediated administration of a hepatitis B virus DNA vaccine", Vaccine 19:764-778.

63. Ugen, K. E., S. B. Nyland, J. D. Boyer, C. Vidal, L. Lera, S. Rasheid, M. Chattergoon, M. L. Bagarazzi, R. Ciccarelli, T. Higgins, Y. Baine, R. Ginsberg, R. R. MacGregor, and D. B. Weiner, 1998, "DNA vaccination with HIV-1 expressing constructs elicits immune responses in humans", Vaccine 16:1818-1821.

64. Calarota, S. A., A. Kjerrstrom, K. B. Islam, and B. Wahren, 2001, "Gene combination raises broad human immunodeficiency virus-specific cytotoxicity", Hum. Gene Ther. 12:1623-1637.

65. Wang, R., J. Epstein, F. M. Baraceros, E. J. Gorak, Y. Charoenvit, D. J. Carucci, R. C. Hedstrom, N. Rahardjo, T. Gay, P. Hobart, R. Stout, T. R. Jones, T. L. Richie, S. E. Parker, D. L. Doolan, J. Norman, and S. L. Hoffman, 2001, "Induction of CD4(+) T cell-dependent CD8(+) type 1 responses in humans by a malaria DNA vaccine", Proc. Natl. Acad. Sci. USA 98:10817-10822.

66. Sette, A., M. Newman, B. Livingston, D. McKinney, J. Sidney, G. Ishioka, S. Tangri, J. Alexander, J. Fikes, and R. Chesnut, 2002, "Optimizing vaccine design for cellular processing, MHC binding and TCR recognition", Tissue Antigens 59:443-451.

67. Livingston, B., C. Crimi, M. Newman, Y. Higashimoto, E. Appella, J. Sidney, and A. Sette, 2002, "A Rational Strategy to Design Multiepitope Immunogens Based on Multiple TH Lymphocyte Epitopes", J. Immunol. 168:5499-5506.

68. Ishioka, G. Y., J. Fikes, G. Hermanson, B. Livingston, C. Crimi, M. Qin, M. F. del Guercio, C. Oseroff, C. Dahlberg, J. Alexander, R. W. Chesnut, and A. Sette, 1999, "Utilization of MHC class I transgenic mice for development of minigene DNA vaccines encoding multiple HLA-restricted CTL epitopes", J. Immunol. 162:3915-3925.

69. Livingston, B. D., M. Newman, C. Crimi, D. McKinney, R. Chesnut, and A. Sette, 2001, "Optimization of epitope processing enhances immunogenicity of multi-epitope DNA vaccines", Vaccine 19:4652-4660.

70. Alila, H., M. E. Coleman, H. Nitta, M. French, K. Anwer, Q. Liu, T. Meyer, J. Wang, R. J. Mumper, D. Oubari, S. D. Long, J. L. Nordstrom, and A. P. Rolland, 1997, "Expression of biologically active human insulin-like growth factor-I following intramuscular injection of a formulated plasmid in rats", Human Gene Therapy 8:1785-1795.

71. Anwer, K., K. A. Earle, M. Shi, J. Wang, R. J. Mumper, B. Proctor, K. Jansa, H. C. Ledebur, S. S. Davis, W. Eaglstein, and A. P. Rolland, 1999, "Synergistic Effect of Formulated Plasmid and Needle-Free Injection for Genetic Vaccines", Pharm. Res. 16:889-95.

72. Mumper, R. J., J. G. Duguid, K. Anwer, M. K. Barron, H. Nitta, and A. P. Rolland, 1996, "Polyvinyl derivatives as novel interactive polymers for controlled gene delivery to muscle", Pharm. Res. 13:701-709.

73. Mumper, R. J., J. Wang, S. L. Klakamp, H. Nitta, K. Anwer, F. Tagliaferri, and A. P. Rolland, 1998, "Protective interactive noncondensing (PINC) polymers for enhanced plasmid distribution and expression in rat skeletal muscle", J. Contr. Rel. 52:191-203.

74. Epstein, S. L., A. Stack, J. A. Misplon, C. Y. Lo, H. Mostowski, J. Bennink, and K. Subbarao, 2000, "Vaccination with DNA encoding internal proteins of influenza virus does not require CD8(+) cytotoxic T lymphocytes: either CD4(+) or CD8(+) T cells can promote survival and recovery after challenge", Int. Immunol 12:91-101.

75. Epstein, S. L., T. M. Tumpey, J. A. Misplon, C. Y. Lo, L. A. Cooper, K. Subbarao, M. Renshaw, S. Sambhara, and J. M. Katz, 2002, "DNA vaccine expressing conserved influenza virus proteins protective against H5N1 challenge infection in mice", Emerg. Infect. Dis. 8:796-801.

76. Vitiello, A., D. Marchesini, J. Furze, L. A. Sherman, and R. C. Chesnut, 1991, "Analysis of the HLA-restricted influenza-specific cytotoxic T lymphocyte response in transgenic mice carrying a chimeric human-mouse class I major histocompatibility complex", J. Exp. Med. 173:1007-15.

77. Alexander, J., C. Oseroff, J. Sidney, P. Wentworth, E. Keogh, G. Hermanson, F. V. Chisari, R. T. Kubo, H. M. Grey, and A. Sette, 1997, "Derivation of HLA-A11/Kb transgenic mice: functional CTL repertoire and recognition of human A11-restricted CTL epitopes", J. Immunol. 159:4753-4761.

78. Alexander, J., C. Oseroff, J. Sidney, and A. Sette, 2003, "Derivation of HLA-B*0702 transgenic mice: functional CTL repertoire and recognition of human B*0702-restricted CTL epitopes", Hum. Immunol 64:211-223.

79. Alexander, J., C. Oseroff, C. Dahlberg, M. Qin, G. Ishioka, M. Beebe, J. Fikes, M. Newman, R. W. Chesnut, P. A. Morton, K. Fok, E. Appella, and A. Sette, 2002, "A decaepitope polypeptide primes for multiple CD8+ IFN-gamma and Th lymphocyte responses: evaluation of multiepitope polypeptides as a mode for vaccine delivery", J. Immunol. 168:6189-6198.

80. Wall, K. A., J. Y. Hu, P. Currier, S. Southwood, A. Sette, and A. J. Infante, 1994, "A disease-related epitope of Torpedo acetylcholine receptor. Residues involved in I-Ab binding, self-nonself discrimination, and TCR antagonism", J. Immunol. 152:4526-4536.

81. Townsend, A. and H. Bodmer, 1989, "Antigen recognition by class I-restricted T lymphocytes", Annu. Rev. Immunol. 7:601-624.

82. Germain, R. N. and D. H. Margulies, 1993, "The biochemistry and cell biology of antigen processing and presentation", Annu. Rev. Immunol. 11:403-450.

83. Sette, A. and H. M. Grey, 1992, "Chemistry of peptide interactions with MHC proteins", Current Opinion in Immunology 4:79-86.

84. Sinigaglia, F. and J. Hammer, 1994, "Defining rules for the peptide-MHC class II interaction", Current Opinion in Immunology. 6:52-56.

85. Engelhard, V. H., 1994, "Structure of peptides associated with MHC class I molecules", Current Opinion in Immunology. 6:13-23.

86. Brown, K., T. S. Jardetzky, J. C. Gorga, L. J. Stem, J. L. Strominger, and D. C. Wiley, 1993, "Three-dimensional structure of the human class II histocompatibility antigen HLA-DR1", Nature 364:33-39.

87. Guo, H. C., D. R. Madden, M. L. Silver, T. S. Jardetzky, J. C. Gorga, J. L. Strominger, and D. C. Wiley, 1993, "Comparison of the P2 specificity pocket in three human histocompatibility antigens: HLA-A*6801, HLA-A*0201, and HLA-B*2705", Proc. Nat. Acad. Sci. USA 90:8053-8057.

88. Guo, H. C., T. S. Jardetzky, T. P. Garrett, W. S. Lane, J. L. Strominger, and D. C. Wiley, 1992, "Different length peptides bind to HLA-Aw68 similarly at their ends but bulge out in the middle", Nature 360:364-366.

89. Silver, M. L., H. C. Guo, J. L. Strominger, and D. C. Wiley, 1992, "Atomic structure of a human MHC molecule presenting an influenza virus peptide", Nature 360:367-369.

90. Matsumura, M., D. H. Fremont, P. A. Peterson, and I. A. Wilson, 1992, "Emerging principles for the recognition of peptide antigens by MHC class I molecules". Science 257: 927-934.

91. Madden, D. R., J. C. Gorga, J. L. Strominger, and D. C. Wiley, 1995, "The three-dimensional structure of HLA-B27 at 2.1 A resolution suggests a general mechanism for tight peptide binding to MHC" Cell 70:1035-1048.

92. Fremont, D. H., M. Matsumura, E. A. Stura, P. A. Peterson, and I. A. Wilson, 1992, "Crystal structures of two viral peptides in complex with murine MHC class I H-2 Kb", Science 257:919-927.

93. Sapp, M., P. J. Bjorkman, and D. C. Wiley, 1991, "Refined structure of the human histocompatibility antigen HLA-A2 at 2.6 A resolution", J. Mol. Biol. 219:277-319.

94. Ruppert, J., J. Sidney, E. Celis, R. T. Kubo, H. M. Grey, and A. Sette, 1993, "Prominent role of secondary anchor residues in peptide binding to HLA-A2.1 molecules", Cell 74:929-37.

95. Parker, K. C., M. A. Bednarek, and J. E. Coligan, 1994, "Scheme for ranking potential HLA-A2 binding peptides based on independent binding of individual peptide side-chains", J. Immunol. 152:163-175.

96. De Groot, A. S., A. Bosma, N. Chinai, J. Frost, B. M. Jesdale, M. A. Gonzalez, W. Martin, and C. Saint-Aubin, 2001, Vaccine 19:4385-4395.

97. Schueler-Furman, O., Y. Altuvia, A. Sette, and H. Margalit, 2000, "Structure-based prediction of binding peptices to MHC class I molecules: Application to a broad range of MHC alleles", Protein Science 9:1838-1846.

98. Meister, G. E., C. G. P. Roberts, J. A. Berzofsky, and A. S. DeGroot, 1995, "Two novel T cell epitope prediction algorithms based on MHC-binding motifs; comparison of predicted and published epitopes from *Mycobacterium tuberculosis* and HIV protein sequences", Vaccine 13:581-591.

99. Bhasin, M., and G. P. S. Raghava, 2004, "Prediction of CTL epitopes using QM, SVM and ANN techniques", Vaccine 22:3195-3204.

100. Altuvia, Y., O, Schueler, and H. Margalit, 1995, "Ranking potential binding peptides to MHC molecules by a computational threading approach", J. Mol. Biol. 249:244-250.

101. Methods for prediction of peptide binding to MHC molecules: a comparative study, Molecular Medicine 8:137-148.

102. Gulukota, K., J. Sidney, and A. Sette, 1997, "Two complementary methods for predicting peptide binding major histocompatibility complex molecules", J. Mol. Biol. 267:1258-1267.

103. Kubo, R. T., A. Sette, H. M. Grey, E. Appella, K. Sakaguchi, N. Z. Zhu, D. Arnott, N. Sherman, J. Shabanowitz, and H. Michel, 1994, "Definition of specific peptide motifs for four major HLA-A alleles", J. Immun. 152:3913-24.

104. Threlkeld, S. C., P. A. Wentworth, S. A. Kalams, B. M. Wilkes, D. J. Ruhl, E. Keogh, J. Sidney, S. Southwood, B. D. Walker, and A. Sette, 1997, "Degenerate and promiscuous recognition by CTL of peptides presented by the MHC class I A3-like superfamily—Implications for vaccine development", J. Immun. 159:1648-1657.

105. Sidney, J., H. M. Grey, S. Southwood, E. Celis, P. A. Wentworth, M. F. Del Guercio, R. T. Kubo, R. C. Chesnut, and A. Sette, 1996, "Definition of an HLA-A3-like supermotif demonstrates the overlapping peptide-binding repertoires of common HLA molecules", Hum. Immunol. 45:79-93.

106. Sette, A. and Sidney, J., "Nine major HLA class I supertypes account for the vast preponderance of HLA-A and -B polymorphism", Immunogenetics 50(3-4), 201-212, 1999.

107. Sidney, J., S. Southwood, M. F. Del Guercio, H. M. Grey, R. C. Chesnut, R. T. Kubo, and A. Sette, 1996, "Specificity and degeneracy in peptide binding to HLA-B7-like class I molecules", J. Immunol. 157:3480-3490.

108. Del Guercio, M. F., J. Sidney, G. Hermanson, C. Perez, H. M. Grey, R. T. Kubo, and A. Sette, 1995, "Binding of a peptide antigen to multiple HLA alleles allows definition of an A2-like supertype" J. Immunol. 54:685-693.

109. Fruci, D., P. Rovero, G. Falasca, A. Chersi, R. Sorrentino, R. Butler, N. Tanigaki, and R. Tosi, 1993, "Anchor residue motifs of HLA class-1-binding peptides analyzed by the direct binding of synthetic peptides to HLA class 1 alpha chains", Hum. Immunol. 38:187-192.

110. Bertoni, R., J. Sidney, P. Fowler, R. W. Chesnut, F. V. Chisari, and A. Sette, 1997, "Human histocompatibility leukocyte antigen-binding supermotifs predict broadly cross-reactive cytotoxic T lymphocyte responses in patients with acute hepatitis", J. Clin. Invest. 100:503-513.

111. Khanna, R., S. R. Burrows, A. Neisig, J. Neefjes, D. J. Moss, and S. L. Silins, 1997, "Hierarchy of Epstein-Barr virus-specific cytotoxic T-cell responses in individuals carrying different subtypes of an HLA allele: Implications for epitope-based antiviral vaccines", J. Virol. 71:7429-7435.

112. Bertoletti, A., S. Southwood, R. Chesnut, A. Sette, M. Falco, G. B. Ferrara, A. Penna, C. Boni, F. Fiaccadori, and C. Ferrari, 1997, "Molecular features of the hepatitis B virus nucleocapsid T-cell epitope 18-27: interaction with HLA and T-cell receptor", Hepatology 26:1027-1034.

113. Fleischhauer, K., S. Tanzarella, H. J. Wallny, C. Bordignon, and C. Traversari, 1996, "Multiple HLA-A alleles can present an immunodominant peptide of the human melanoma antigen Melan-A/MART-1 to a peptide-specific HLA-A*0201+ cytotoxic T cell line", J. Immunol. 157:787-297.

114. Kawashima, I., S. J. Hudson, V. Tsai, S. Southwood, K. Takesako, E. Appella, A. Sette, and E. Celis, 1998, "The multi-epitope approach for immunotherapy for cancer: Identification of several CTL epitopes from various tumor-associated antigens expressed on solid epithelial tumors", Hum. Immunol. 59:1-14.

115. Wang, R. F., S. L. Johnston, S. Southwood, A. Sette, and S. A. Rosenberg, 1998, "Recognition of an antigenic peptide derived from tyrosinase-related protein-2 by CTL in the context of HLA-A31 and -A33", J. Immunol. 160:890-897.

116. Southwood, S., J. Sidney, A. Kondo, M. F. Del Guercio, E. Appella, S. Hoffman, R. T. Kubo, R. W. Chesnut, H. M. Grey, and A. Sette, 1998, "Several Common HLA-DR Types Share Largely Overlapping Peptide Binding Repertoires", J. Immunol. 160:3363-3373.

117. Schaeffer, E. B., A. Sette, D. L. Johnson, M. C. Bekoff, J. A. Smith, H. M. Grey, and S. Buus, 2000, "Relative contribution of "determinant selection" and "holes in the T-cellrepertoire" to T-cell responses", Proc. Nat. Acad. Sci. USA 86:4649-4653.

118. Currier, J. R., E. G. Kuta, E. Turk, B. L. B. Earhart, L. Loomis-Price, S. Janetzki, G. Ferrari, D. L. Birx, and J. H. Cox, 2002, "A panel of MHC class I restricted viral peptides for use as a quality control for vaccine trial ELISPOT assays", J. Immunological Meth. 260:157-172.

119. Bartlett, J. A., S. S. Wasserman, C. B. Hicks, R. T. Dodge, K. J. Weinhold, C. O. Tacket, N. Ketter, A. E. Wittek, T. J. Palker, and B. F. Haynes, 1998, "Safety and immunogenicity of an HLA-based HIV envelope polyvalent synthetic peptide immunogen DATRI 010 study group. Division of AIDS Treatment Research Inititive", AIDS 12:1291-1300.

120. Pinto, L. A., J. A. Berzofsky, K. R. Fowke, R. F. Little, F. Merced-Galindez, R. Humphrey, J. Ahlers, N. Dunlop, R. B. Cohen, S. M. Steinberg, P. Nara, G. M. Shearer, and R. Yarchoan, 1999, "HIV-specific immunity following immunization with HIV synthetic envelope peptides in asymptomatic HIV-infected patients", AIDS 13:2003-2012.

121. Gahéry-Ségard, H., G. Pialoux, B. Charmeteau, S. Sermet, H. Poncelet, M. Raux, A. Tartar, J. P. Lévy, H. Gras-Masse, and J. G. Guillet, 2000, "Multiepitopic B- and T-cell responses induced in humans by a human immunodeficiency virus type 1 lipopeptide vaccine", J. Virol. 74:1694-1703.

122. Serwold, T. and N. Shastri, 1999, "Specific Proteolytic Cleavages Limit the Diversity of the Pool of Peptides Available to MHC Class I Molecules in Living Cells", J. Immunol. 162:4712-4719.

123. Shastri, N., T. Serwold, and F. Gonzalez, 1995, "Presentation of endogenous peptide/MHC class I complexes is profoundly influenced by specific C-terminal flanking residues", J. Immunol. 155:4339-4346.

124. Chou, K. C., 2000, "Prediction of tight turns and their types in proteins", Anal. Biochem. 286:1-16.

125. Davis, N. L., A. West, E. Reap, G. MacDonald, M. Collier, S. Dryga, M M Maughan, M. Connell, C. Walker, K. McGrath, C. Cecil, L. H. Ping, J. Frelinger, R. Olmstged, P. Keith, R. Swanstrom, C. Williamson, P. Johnson, D. Montefiori, and R. E. Johnston, 2002, "Alphavirus replicon particles as candidate HIV Vaccines", IUBMB Life 53:209-211.

126. Lee, J. S., B. K. Dyas, S. S, Nystrom, C. M. Lind, J. F. Smith, and R. G. Ulrich, 2002, "Immune protection against Staphylococcal enterotoxin-induced toxic shock by vaccination with a Venezuelan Equine Encephalitis virus replicon", J. Infec. Dis. 185:1192-1196.

127. Hevey, M., D. Negley, L. VanderZanden, R. F. Tammariello, J. Geisbert, C. Schmaljohn, J. F. Smith, P. B. Jahrling, and A. L. Schmaljohn, 2002, "Marburg virus vacciness: comparing classical and new approaches", Vaccine 20:586-593.

128. Pratt, W. D., N. L. Davis, R. E. Johnston, J. F. Smith, 2003, "Genetically engineered, live attenuated vaccines for Venezuelan equine encephalitis: testing in animal models. 2003", Vaccine 21:3854-3862.

129. Gipson, C. L., N. L. Davis, R. E. Johnston, and A. M. deSilva, 2003, "Evaluation of Venezuelan Equine Encephalitis (VEE) replicon-based outer surface protein A (OspA) vaccines in a tick challenge mouse model of Lyme disease", Vaccine 21:3875-3884.

130. Nelson, E. L., D. Prieto, T. G. Alexander, P. Pushko, L. A. Lofts, J. O. Rayner, K. I. Kamrud, B. Fralish, and J. F. Smith, 2003, "Venezuelan equine encephalitis replicon immunization overcomes intrinsic tolerance and elicits effective anti-tumor immunity to the 'self' tumor-associated antigen, neu in a rat mammary tumor model", Breast Cancer Research and Treatment 82:169-183.

131. Leitner, W. W., L. N. Hwang, M. J. DeVeer, A. Zhou, R. H. Silverman, B. R. G. Williams, T. W. Dubensky, H. Ying, and N. P. Restifo, 2003, "Alphavirus-based DNA vaccine breaks immunological tolerance by activating innate antiviral pathways", Nat. Med. 9:33-39.

132. Leitner, W. W., L. N. Hwang, E. S. Bergmann-Leitner, S. E. Finkelstein, S. Frank, and N. P. Restifo, 2004, "Apoptosis is essential for the increased efficacy of alphaviral replicase-based DNA vaccines", Vaccine 22:1537-1544.

133. Garland, S. M., 2003, "Imiquimod", Curr. Opin. Infect. Dis. 16:85-89.

134. Jurk, M., F. Heil, J. Vollmer, C. Schetter, A. M. Krieg, H. Wagner, F. Lipford, and S. Bauer, 2002, "Human TLR7 or TLR8 independently confer responsiveness to the antiviral compound R-848", Nat. Immunol. 3:499.

135. Tyring, S. T., IArany, I., M. A. Stanley, M. A. Tomai, R. L. Miller, M. H. Smith, D. J. McDermott and H. B. Slade, 1998, "A randomized, controlled, molecular study of condlomata acuminate clearance during treatment with imiquimod", J. Infect. Dis. 178:551-555.

136. Fritz, J. H., S. Brunner, M. L. Bimstiel, M. Buschle, A. V. Gabain, F. Mattner, and W. Zauner, 2004, "The artificial antimicrobial peptide KLKLLLLLKLK induces predominantly a TH2-type immune response to co-injected antigens", Vaccine 22:3274-3284.

137. Alexander, J., J. Sidney, S. Southwood, J. Ruppert, C. Oseroff, A. Maewal, K. Snoke, H. M. Serra, R. T. Kubo, A. Sette and 1994, "Development of high potency universal DR-restricted helper epitopes by modification of high affinity DR-blocking peptides", Immunity. 1:751-761.

138. del Guercio, M. F., J. Alexander, R. T. Kubo, T. Arrhenius, A. Maewal, E. Appella, S. L. Hoffman, T. Jones, D. Valmori, K. Sakaguchi, H. M. Grey, and A. Sette, 1997, "Potent immunogenic short linear peptide constructs composed of B cell epitopes and Pan DR T helper epitopes (PADRE®) for antibody responses in vivo", Vaccine 15:441-448.

139. Alexander, J., M. F. delGuercio, B. Frame, A. Maewal, A. Sette, M. H. Nahm, and M. J. Newman, 2004, "Development of experimental carbohydrate-conjugate vaccines composed of *Streptococcus pneumoniae* capsular polysaccharides and the universal helper T-lyphocyte epitope (PADRE®)", Vaccine 22:2362-2367.

140. Rosa, D. S., F. Tzelepis, M. G. Cunha, I. S. Soares, and M. M. Redriques, 2004, "The pan HLA DR-binding epitope improves adjuvant-assisted immunization with a recombinant protein containing a malaria vaccine candidate", Immunol. Lett. 92:259-268.

141. Vichier-Guerre, S., R. Lo-Man, L. BenMohamed, E. Deriaud, S. Kovats, C. Leclerc, and S. Bay, 2003, "Induction of carbohydrate-specific antibodies in HLA-DR transgenic mice by a synthetic glycopeptide: a potential anti cancer vaccine for human use", J. Peptide Res. 62:117-124.

142. Pamonsinlapatham, P., N. Decroix, L. Mihaila-Amrouche, A. Bouvet, and J. P. Bouvet, 2004, "Induction of a mucosal immune response to the Streptococcal M protein by intramuscular administration of a PADRE-ASREAK peptide.

143. Ressing, M. E., W. J. vanDriel, R. M. P. Brandt, G. G. Kenter, J. H. deJong, T. Bauknecht, G. J. Fleuren, P. Hoogerhout, R. Offringa, A. Sette, E. Celis, H. Grey, B. J. Trimbos, W. M. Kast, and C. J. M. Melief, 2000, "Detection of T helper responses, but not a f human papillomavirus-specific cytotoxic T lymphocyte responses, after peptide vaccination of patients with cervical carcinoma", J. Immunother. 23:255-266.

144. Crotty, S., R. D. Aubert, J. Glidewell, and R. Ahmed, 2004, "Tracking human antigen-specific memory B cells: a sensitive and generalized ELISPOT system", J. Immunological Meth. 286:111-122.

145. Wilson, C., D. M. McKinney, M. Anders, S. MaWhinney, J. Forster, C. Crimi, S. Southwood, A. Sette, R. Chesnut, M. Newman, and B. Livingston, 2003, "Development of a DNA Vaccine Designed to Induce Cytotoxic T Lymphocyte Responses to Multiple Conserved Epitopes in HIV-1", J. Immunol. 171:5611-5623.

146. Claas, E. C., A. D. Osterhaus, R. Van Beek, J. C. De Jong, G. F. Rimmelzwaan, D. A. Senne, S. Krauss, K. F. Shortridge, and R. G. Webster, 1998, "Human influenza A H5N1 virus related to a highly pathogenic avian influenza virus" Lancet 351:472-477.

147. Katz, J. M., X. Lu, A. M. Frace, T. Morken, S. R. Zaki, and T. M. Tumpey, 2000, "Pathogenesis and immunity to avian influenza A H5 viruses", Biomed. Pharmacother. 54:178-187.

148. Lu, X., T. M. Tumpey, T. Morken, S. R. Zaki, N. J. Cox, and J. M. Katz, 1999, "A mouse model for the evaluation of pathogenesis and immunity to influenza A (H5N1) viruses isolated from humans", J. Virol. 73:5903-5911.

149. Nicholson, K. G., A. E. Colegate, A. Podda, I. Stephenson, J. Wood, E. Ypma, and M. C. Zambon, 2001, "Safety and antigenicity of non-adjuvanted and MF59-adjuvanted influenza A/Duck/Singapore/97 (H5N3) vaccine: a randomised trial of two potential vaccines against H5N1 influenza", Lancet 357:1937.

150. Hehme, N., H. Engelmann, W. Kuenzel, E. Neumeier, and R. Saenger, 2004, "Immunogenicity of a monovalent, aluminum-adjuvanted influenza whole virus vaccine for pandemic use", Virus Res. 103:163-171.

151. Hehme, N., H. Engelmann, W. Kunzel, E. Neumeier, and R. Sanger, 2002, "Pandemic preparedness: lessons learnt from H2N2 and H9N2 candidate vaccines", Med. Microbiol. Immunol. 191:203-208.

152. Stephenson, I., K. G. Nicholson R. Gluck, R. Mischler, R. W. Newman, A. M. Palache, N. Q. Verlander, F. Warburton, J. M. Wood, and M. C. Zambon, 2003, "Safety and antigenicity of whole virus and subunit influenza A/Hong Kong/1073/99 (H9N2) vaccine in healthy adults: phase I randomised trial", Lancet 362:1959-1966.

153. Stephenson, I., K. G. Nicholson, J. M. Wood, M. C. Zambon, and J. M. Katz, 2004, "Confronting the avian influenza threat: vaccine development for a potential pandemic", The Lancet Infectious Diseases 4:499-509.

154. Wood, J. M., and J. S. Robertson, 2004, "From lethal virus to life-saving vaccine: developing inactivated vaccines for pandemic influenza", Nat. Rev. Microbiol. 2:842-847.

155. Stevens, J et al, 2004, "Structure and receptor specificity of the hemagglutinin from an H5N1 influenza virus," Science 303:1866.

156. Stevens, J et al, 2006, "Structure of the uncleaved human H1 hemagglutinin from the extinct 1918 influenza virus," Science 312:404.

TABLE 1

INFLUENZA TYPE A HA SEQUENCES

| Accession | Strain | Length | Year | Serotype |
|---|---|---|---|---|
| U37727 | A/NWS/G70C | 1743 | | H1N1 |
| DQ464377 | A/Egypt/2782-NAMRU3/2006 | 1640 | 2006 | H5N1 |
| DQ435202 | A/Iraq/207- | 1647 | 2006 | H5N1 |
| AB243873 | A/Aichi/133/2005 | 987 | 2005 | H3N2 |
| AB243872 | A/Aichi/143/2005 | 987 | 2005 | H3N2 |
| AB243871 | A/Aichi/145/2005 | 987 | 2005 | H3N2 |
| AB243870 | A/Aichi/164/2005 | 987 | 2005 | H3N2 |
| AB243869 | A/Aichi/165/2005 | 987 | 2005 | H3N2 |
| AB243868 | A/Aichi/166/2005 | 987 | 2005 | H3N2 |
| AB243867 | A/Aichi/167/2005 | 987 | 2005 | H3N2 |
| AB243744 | A/Aichi/168/2005 | 978 | 2005 | H1N1 |
| AB243745 | A/Aichi/169/2005 | 978 | 2005 | H1N1 |

TABLE 1-continued

INFLUENZA TYPE A HA SEQUENCES

| Accession | Strain | Length | Year | Serotype |
|---|---|---|---|---|
| AB246366 | A/Aichi/174/05 | 987 | 2005 | H3N2 |
| DQ371928 | A/Anhui/1/2005 | 1704 | 2005 | H5N1 |
| DQ371929 | A/Anhui/2/2005 | 1704 | 2005 | H5N1 |
| ISDN124629 | A/Brisbane/1/2005 | 1030 | 2005 | H3 |
| ISDN125777 | A/Brisbane/20/2005 | 1016 | 2005 | H3 |
| ISDN127299 | A/Brisbane/25/2005 | 1014 | 2005 | H3 |
| ISDN124633 | A/Brisbane/3/2005 | 1024 | 2005 | H3 |
| ISDN124628 | A/Brisbane/3/2005 | 1018 | 2005 | H3 |
| ISDN126668 | A/Brisbane/3e/2005 | 1018 | 2005 | H3N2 |
| ISDN124631 | A/Brisbane/4/2005 | 1030 | 2005 | H3 |
| ISDN127302 | A/Brisbane/48/2005 | 1016 | 2005 | H3 |
| ISDN124630 | A/Brisbane/5/2005 | 1028 | 2005 | H3N2 |
| ISDN125769 | A/Brisbane/6/2005 | 1018 | 2005 | H3 |
| ISDN121986 | A/Cambodia/JP52a/20 | 1707 | 2005 | H5N1 |
| CY007795 | A/Canterbury/01/2005 | 1721 | 2005 | H3N2 |
| CY007803 | A/Canterbury/02/2005 | 1721 | 2005 | H3N2 |
| CY007811 | A/Canterbury/03/2005 | 1721 | 2005 | H3N2 |
| CY008356 | A/Canterbury/104/200 | 1721 | 2005 | H3N2 |
| CY008556 | A/Canterbury/105/200 | 1718 | 2005 | H3N2 |
| CY009044 | A/Canterbury/124/200 | 1721 | 2005 | H3N2 |
| CY009932 | A/Canterbury/125/200 | 1721 | 2005 | H3N2 |
| CY008067 | A/Canterbury/127/200 | 1721 | 2005 | H3N2 |
| CY008075 | A/Canterbury/129/200 | 1721 | 2005 | H3N2 |
| CY007955 | A/Canterbury/16/2005 | 1721 | 2005 | H3N2 |
| CY008083 | A/Canterbury/166/200 | 1721 | 2005 | H3N2 |
| CY008364 | A/Canterbury/186/200 | 1711 | 2005 | H3N2 |
| CY008340 | A/Canterbury/20/2005 | 1721 | 2005 | H3N2 |
| CY008372 | A/Canterbury/204/200 | 1721 | 2005 | H3N2 |
| CY008564 | A/Canterbury/205/200 | 1721 | 2005 | H3N2 |
| CY008091 | A/Canterbury/206/200 | 1721 | 2005 | H3N2 |
| CY008099 | A/Canterbury/212/200 | 1721 | 2005 | H3N2 |
| CY008380 | A/Canterbury/220/200 | 1721 | 2005 | H3N2 |
| CY008572 | A/Canterbury/230/200 | 1721 | 2005 | H3N2 |
| CY008580 | A/Canterbury/233/200 | 1721 | 2005 | H3N2 |
| CY008388 | A/Canterbury/234/200 | 1721 | 2005 | H3N2 |
| CY008396 | A/Canterbury/235/200 | 1721 | 2005 | H3N2 |
| CY008404 | A/Canterbury/236/200 | 1721 | 2005 | H3N2 |
| CY008412 | A/Canterbury/237/200 | 1721 | 2005 | H3N2 |
| CY008420 | A/Canterbury/238/200 | 1721 | 2005 | H3N2 |
| CY008043 | A/Canterbury/24/2005 | 1721 | 2005 | H3N2 |
| CY008428 | A/Canterbury/242/200 | 1721 | 2005 | H3N2 |
| CY008588 | A/Canterbury/248/200 | 1717 | 2005 | H3N2 |
| CY010084 | A/Canterbury/250/200 | 1721 | 2005 | H3N2 |
| CY008596 | A/Canterbury/251/200 | 1717 | 2005 | H3N2 |
| CY008604 | A/Canterbury/253/200 | 1717 | 2005 | H3N2 |
| CY008612 | A/Canterbury/255/200 | 1717 | 2005 | H3N2 |
| CY008620 | A/Canterbury/256/200 | 1720 | 2005 | H3N2 |
| CY008628 | A/Canterbury/257/200 | 1722 | 2005 | H3N2 |
| CY008636 | A/Canterbury/258/200 | 1721 | 2005 | H3N2 |
| CY008107 | A/Canterbury/259/200 | 1721 | 2005 | H3N2 |
| CY009028 | A/Canterbury/26/2005 | 1721 | 2005 | H3N2 |
| CY008436 | A/Canterbury/260/200 | 1721 | 2005 | H3N2 |
| CY008644 | A/Canterbury/266/200 | 1721 | 2005 | H3N2 |
| CY008444 | A/Canterbury/269/200 | 1721 | 2005 | H3N2 |
| CY008652 | A/Canterbury/270/2005 | 1722 | 2005 | H3N2 |
| CY008051 | A/Canterbury/29/2005 | 1721 | 2005 | H3N2 |
| CY007963 | A/Canterbury/33/2005 | 1721 | 2005 | H3N2 |
| CY009036 | A/Canterbury/34/2005 | 1721 | 2005 | H3N2 |
| CY008348 | A/Canterbury/64/2005 | 1721 | 2005 | H3N2 |
| CY008059 | A/Canterbury/67/2005 | 1721 | 2005 | H3N2 |
| ISDN125780 | A/Christchurch/20/20 | 1018 | 2005 | H3N2 |
| ISDN127307 | A/Christchurch/64/20 | 1018 | 2005 | H3 |
| DQ265717 | A/Colorado/360/2005 | 1000 | 2005 | H3N2 |
| ISDN125771 | A/Darwin/5/2005 | 1009 | 2005 | H3 |
| DQ265706 | A/England/2005 | 1029 | 2005 | H1N1 |
| DQ265715 | A/Guam/362/2005 | 1000 | 2005 | H3N2 |
| DQ371930 | A/Guangxi/1/2005 | 1704 | 2005 | H5N1 |
| AB239125 | A/Hanoi/30408/2005 | 1776 | 2005 | H5N1 |
| ISDN129400 | A/Hanoi/30408/2005 | 1776 | 2005 | H5N1 |
| ISDN125873 | A/Indonesia/5/05 | 1729 | 2005 | H5N1 |
| DQ265714 | A/Iraq/34/2005 | 1000 | 2005 | H3N2 |
| DQ265713 | A/Italy/384/2005 | 1000 | 2005 | H3N2 |
| DQ265712 | A/Japan/1337/2005 | 1000 | 2005 | H3N2 |
| DQ265711 | A/Japan/1383/2005 | 1000 | 2005 | H3N2 |
| ISDN127351 | A/Johannesburg/122/0 | 923 | 2005 | H3N2 |
| ISDN127353 | A/Johannesburg/146/0 | 976 | 2005 | H1N1 |
| ISDN127352 | A/Johannesburg/28/05 | 976 | 2005 | H1N1 |
| ISDN127355 | A/Johannesburg/301/0 | 923 | 2005 | H3N2 |
| ISDN127310 | A/Johannesburg/479/2 | 1211 | 2005 | H1 |
| DQ265710 | A/Korea/298/2005 | 1000 | 2005 | H3N2 |
| ISDN124639 | A/Lyon | 1030 | 2005 | H3N2 |
| ISDN124640 | A/Lyon/108/2005 | 1012 | 2005 | H3 |
| ISDN124645 | A/Macau/122/2005 | 1211 | 2005 | H1N1 |
| ISDN124646 | A/Macau/227/2005 | 1215 | 2005 | H1N1 |
| ISDN127311 | A/Macau/405/2005 | 1216 | 2005 | H1 |
| ISDN126666 | A/Macau/557/2005 | 1030 | 2005 | H3N2 |
| ISDN125781 | A/Macau/577/2005 | 887 | 2005 | H3N2 |
| ISDN125782 | A/Macau/578/2005 | 1018 | 2005 | H3N2 |
| ISDN124627 | A/Macau/78/2005 | 1020 | 2005 | H3 |
| ISDN124641 | A/Malaysia/99/2005 | 1018 | 2005 | H3 |
| CY006123 | A/New | 1737 | 2005 | H3N2 |
| CY006131 | A/New | 1715 | 2005 | H3N2 |
| CY002776 | A/New | 1718 | 2005 | H3N2 |
| CY006139 | A/New | 1728 | 2005 | H3N2 |
| CY006147 | A/New | 1709 | 2005 | H3N2 |
| CY006155 | A/New | 1725 | 2005 | H3N2 |
| CY002720 | A/New | 1703 | 2005 | H3N2 |
| CY002184 | A/New | 1762 | 2005 | H3N2 |
| CY002000 | A/New | 1762 | 2005 | H3N2 |
| CY002008 | A/New | 1760 | 2005 | H3N2 |
| CY002448 | A/New | 1761 | 2005 | H3N2 |
| CY002200 | A/New | 1760 | 2005 | H3N2 |
| CY002456 | A/New | 1761 | 2005 | H3N2 |
| CY002240 | A/New | 1741 | 2005 | H3N2 |
| CY003048 | A/New | 1728 | 2005 | H3N2 |
| CY002016 | A/New | 1701 | 2005 | H3N2 |
| CY002032 | A/New | 1760 | 2005 | H3N2 |
| CY002464 | A/New | 1760 | 2005 | H3N2 |
| CY002264 | A/New | 1738 | 2005 | H3N2 |
| CY003344 | A/New | 1743 | 2005 | H3N2 |
| CY002480 | A/New | 1712 | 2005 | H3N2 |
| CY002056 | A/New | 1762 | 2005 | H3N2 |
| CY002488 | A/New | 1741 | 2005 | H3N2 |
| CY002736 | A/New | 1741 | 2005 | H3N2 |
| CY003056 | A/New | 1720 | 2005 | H3N2 |
| CY002072 | A/New | 1761 | 2005 | H3N2 |
| CY006076 | A/New | 1762 | 2005 | H3N2 |
| CY006291 | A/New | 1761 | 2005 | H3N2 |
| CY003640 | A/New | 1762 | 2005 | H3N2 |
| CY003648 | A/New | 1760 | 2005 | H3N2 |
| CY006084 | A/New | 1762 | 2005 | H3N2 |
| ISDN127300 | A/Newcastle/4/2005 | 1018 | 2005 | H3 |
| ISDN119864 | A/Norway/70/2005 | 1111 | 2005 | H3N2 |
| ISDN132203 | A/Oklahoma/369/05 | 998 | 2005 | H3N2 |
| ISDN132202 | A/Oklahoma/370/05 | 1666 | 2005 | H3N2 |
| ISDN132201 | A/Oklahoma/371/05 | 1665 | 2005 | H3N2 |
| ISDN132200 | A/Oklahoma/372/05 | 1017 | 2005 | H3N2 |
| ISDN124638 | A/Perth/1/2005 | 1025 | 2005 | H3N2 |
| ISDN127296 | A/Perth/14/2005 | 1009 | 2005 | H3 |
| ISDN127295 | A/Perth/20/2005 | 1015 | 2005 | H3 |
| ISDN127308 | A/Perth/28/2005 | 1216 | 2005 | H1 |
| ISDN125773 | A/Perth/3/2005 | 1016 | 2005 | H3 |
| ISDN127301 | A/Perth/65/2005 | 1016 | 2005 | H3 |
| DQ265708 | A/Peru/166/2005 | 1000 | 2005 | H3N2 |
| DQ265707 | A/Qatar/2039/2005 | 1000 | 2005 | H3N2 |
| ISDN127303 | A/Singapore/02/2005 | 1029 | 2005 | H3 |
| ISDN125774 | A/South | 1018 | 2005 | H3 |
| ISDN127298 | A/South | 1018 | 2005 | H3 |
| ISDN124642 | A/Taiwan/51/2005 | 1020 | 2005 | H3 |
| ISDN133140 | A/Taiwan/603/2005 | 1198 | 2005 | H1N1 |
| ISDN124634 | A/Thailand/123/2005 | 1024 | 2005 | H3 |
| ISDN124647 | A/Thailand/131/2005 | 1210 | 2005 | H1 |
| ISDN124635 | A/Thailand/141/2005 | 1017 | 2005 | H3N2 |
| ISDN124632 | A/Thailand/142/2005 | 1025 | 2005 | H3N2 |
| ISDN124626 | A/Thailand/151/2005 | 1027 | 2005 | H3 |
| ISDN125779 | A/Thailand/154/2005 | 1017 | 2005 | H3 |
| ISDN127305 | A/Thailand/196/2005 | 1016 | 2005 | H3 |
| ISDN127304 | A/Thailand/220/2005 | 1009 | 2005 | H3 |
| ISDN124644 | A/Thailand/28/2005 | 1201 | 2005 | H1N1 |
| ISDN124636 | A/Thailand/36/2005 | 1019 | 2005 | H3 |
| ISDN124637 | A/Thailand/54/2005 | 1019 | 2005 | H3N2 |
| DQ372591 | A/Thailand/NX165/20 | 1713 | 2005 | H5N1 |

TABLE 1-continued

INFLUENZA TYPE A HA SEQUENCES

| Accession | Strain | Length | Year | Serotype |
|---|---|---|---|---|
| ISDN125775 | A/Townsville/16/2005 | 1018 | 2005 | H3 |
| ISDN125776 | A/Townsville/21/2005 | 1018 | 2005 | H3 |
| ISDN125772 | A/Victoria/126/2005 | 1012 | 2005 | H3 |
| ISDN125770 | A/Victoria/503/2005 | 1012 | 2005 | H3 |
| ISDN127309 | A/Victoria/504/2005 | 1223 | 2005 | H1N1 |
| ISDN127297 | A/Victoria/533/2005 | 1016 | 2005 | H3 |
| ISDN119678 | A/Viet | 1704 | 2005 | H5N1 |
| ISDN117778 | A/Viet | 1707 | 2005 | H5N1 |
| ISDN117777 | A/Viet | 1707 | 2005 | H5N1 |
| ISDN118371 | A/Viet | 1707 | 2005 | H5N1 |
| ISDN131464 | A/Wisconsin/67/2005 | 1066 | 2005 | H3 |
| ISDN138724 | A/Wisconsin/67e5/20 | 1653 | 2005 | H3 |
| DQ174266 | A/Zhejiang/199/05 | 987 | 2005 | H3 |
| DQ174267 | A/Zhejiang/207/05 | 987 | 2005 | H3N2 |
| DQ174268 | A/Zhejiang/209/05 | 987 | 2005 | H3N2 |
| CY002954 | A/Ashburton/280/200 | 1742 | 2004 | H3N2 |
| ISDN110508 | A/Auckland/13/2004 | 1031 | 2004 | H3 |
| ISDN110513 | A/Auckland/45/2004 | 1014 | 2004 | H3N2 |
| ISDN110514 | A/Auckland/57/2004 | 1018 | 2004 | H3 |
| ISDN106206 | A/Ayatthaya/2111/200 | 1181 | 2004 | H1 |
| ISDN64766 | A/Bangkok/1158/200 | 1023 | 2004 | H3 |
| ISDN69022 | A/Bangkok/1406/200 | 1224 | 2004 | H1N1 |
| ISDN110520 | A/Bangkok/1563/200 | 1033 | 2004 | H3 |
| ISDN106207 | A/Bangkok/1940/200 | 1211 | 2004 | H1 |
| ISDN69011 | A/Bangkok/24/2004 | 1016 | 2004 | H3N2 |
| CY007291 | A/Bay of | 1721 | 2004 | H3N2 |
| CY007299 | A/Bay of | 1721 | 2004 | H3N2 |
| CY007315 | A/Bay of | 1721 | 2004 | H3N2 |
| ISDN64760 | A/Brisbane/1/2004 | 1021 | 2004 | H3N2 |
| ISDN110532 | A/Brisbane/122/2004 | 1011 | 2004 | H3 |
| ISDN110521 | A/Brisbane/25/2004 | 1036 | 2004 | H3 |
| ISDN110522 | A/Brisbane/59/2004 | 1019 | 2004 | H3N2 |
| ISDN110518 | A/Brisbane/70/2004 | 1028 | 2004 | H3N2 |
| ISDN110647 | A/California/7/2004 | 1538 | 2004 | H3 |
| ISDN110648 | A/California/7/2004 | 1538 | 2004 | H3 |
| CY007419 | A/Canterbury/100/200 | 1720 | 2004 | H3N2 |
| CY007427 | A/Canterbury/101/200 | 1721 | 2004 | H3N2 |
| CY007435 | A/Canterbury/102/200 | 1721 | 2004 | H3N2 |
| CY007443 | A/Canterbury/103/200 | 1721 | 2004 | H3N2 |
| CY007451 | A/Canterbury/104/200 | 1721 | 2004 | H3N2 |
| CY007459 | A/Canterbury/105/200 | 1730 | 2004 | H3N2 |
| CY007467 | A/Canterbury/106/200 | 1748 | 2004 | H1N1 |
| CY007475 | A/Canterbury/107/200 | 1721 | 2004 | H3N2 |
| CY007987 | A/Canterbury/108/200 | 1720 | 2004 | H3N2 |
| CY007995 | A/Canterbury/109/200 | 1721 | 2004 | H3N2 |
| CY007339 | A/Canterbury/11/2004 | 1718 | 2004 | H3N2 |
| CY007347 | A/Canterbury/12/2004 | 1721 | 2004 | H3N2 |
| CY007355 | A/Canterbury/16/2004 | 1717 | 2004 | H3N2 |
| CY007363 | A/Canterbury/17/2004 | 1717 | 2004 | H3N2 |
| CY007371 | A/Canterbury/18/2004 | 1721 | 2004 | H3N2 |
| CY007379 | A/Canterbury/19/2004 | 1721 | 2004 | H3N2 |
| CY007387 | A/Canterbury/20/2004 | 1723 | 2004 | H3N2 |
| CY007483 | A/Canterbury/201/200 | 1721 | 2004 | H3N2 |
| CY007491 | A/Canterbury/202/200 | 1721 | 2004 | H3N2 |
| CY007499 | A/Canterbury/205/200 | 1717 | 2004 | H3N2 |
| CY007507 | A/Canterbury/206/200 | 1721 | 2004 | H3N2 |
| CY007515 | A/Canterbury/207/200 | 1717 | 2004 | H3N2 |
| CY007523 | A/Canterbury/208/200 | 1716 | 2004 | H3N2 |
| CY007531 | A/Canterbury/209/200 | 1721 | 2004 | H3N2 |
| CY007395 | A/Canterbury/21/2004 | 1716 | 2004 | H3N2 |
| CY007539 | A/Canterbury/210/200 | 1721 | 2004 | H3N2 |
| CY007403 | A/Canterbury/23/2004 | 1717 | 2004 | H3N2 |
| CY007411 | A/Canterbury/24/2004 | 1714 | 2004 | H3N2 |
| CY007547 | A/Canterbury/303/200 | 1721 | 2004 | H3N2 |
| CY007555 | A/Canterbury/304/200 | 1721 | 2004 | H3N2 |
| CY008220 | A/Canterbury/305/200 | 1721 | 2004 | H3N2 |
| CY008228 | A/Canterbury/308/200 | 1721 | 2004 | H3N2 |
| CY008236 | A/Canterbury/309/200 | 1717 | 2004 | H3N2 |
| CY008244 | A/Canterbury/310/200 | 1720 | 2004 | H3N2 |
| CY007563 | A/Canterbury/311/200 | 1720 | 2004 | H3N2 |
| CY008252 | A/Canterbury/312/200 | 1717 | 2004 | H3N2 |
| CY007571 | A/Canterbury/313/200 | 1717 | 2004 | H3N2 |
| CY007579 | A/Canterbury/315/200 | 1717 | 2004 | H3N2 |
| ISDN110516 | A/Chachoengsao/1422 | 1020 | 2004 | H3N2 |
| AY947474 | A/Charlottesville/03/2 | 1568 | 2004 | H3N2 |
| ISDN69013 | A/Christchurch/10/20 | 1013 | 2004 | H3N2 |
| CY002905 | A/Christchurch/10/20 | 1737 | 2004 | H3N2 |
| ISDN110606 | A/Christchurch/104/2 | 1019 | 2004 | H3N2 |
| ISDN106208 | A/Christchurch/106/2 | 1216 | 2004 | H1N1 |
| ISDN110503 | A/Christchurch/11/20 | 1013 | 2004 | H3N2 |
| CY002906 | A/Christchurch/13/20 | 1749 | 2004 | H3N2 |
| CY002922 | A/Christchurch/14/20 | 1749 | 2004 | H3N2 |
| CY002914 | A/Christchurch/15/20 | 1749 | 2004 | H3N2 |
| ISDN110530 | A/Christchurch/178/2 | 1032 | 2004 | H3 |
| CY002946 | A/Christchurch/184/2 | 1749 | 2004 | H3N2 |
| ISDN110528 | A/Christchurch/190/2 | 1009 | 2004 | H3N2 |
| ISDN110609 | A/Christchurch/215/2 | 1026 | 2004 | H3 |
| ISDN110608 | A/Christchurch/263/2 | 1013 | 2004 | H3N2 |
| ISDN110658 | A/Christchurch/280/2 | 1030 | 2004 | H3N2 |
| CY002962 | A/Christchurch/297/2 | 1732 | 2004 | H3N2 |
| CY002904 | A/Christchurch/339/2 | 1761 | 2004 | H3N2 |
| ISDN110509 | A/Christchurch/70/20 | 1051 | 2004 | H3 |
| ISDN110510 | A/Christchurch/71/20 | 1018 | 2004 | H3 |
| CY002930 | A/Christchurch/89/20 | 1748 | 2004 | H3N2 |
| CY002938 | A/Christchurch/90/20 | 1737 | 2004 | H3N2 |
| ISDN110511 | A/Christchurch/94/20 | 1018 | 2004 | H3 |
| ISDN69016 | A/Darwin/1/2004 | 1002 | 2004 | H3N2 |
| ISDN110517 | A/Darwin/4/2004 | 1018 | 2004 | H3N2 |
| DQ265716 | A/Ecuador/1968/2004 | 1000 | 2004 | H3 |
| ISDN64769 | A/Fiji/185/2004 | 1010 | 2004 | H3 |
| DQ167297 | A/Finland/455/2004 | 984 | 2004 | H3 |
| DQ167299 | A/Finland/478/2004 | 984 | 2004 | H3 |
| DQ167300 | A/Finland/479/2004 | 984 | 2004 | H3 |
| DQ167301 | A/Finland/480/2004 | 984 | 2004 | H3 |
| DQ167302 | A/Finland/481/2004 | 984 | 2004 | H3 |
| DQ167303 | A/Finland/482/2004 | 984 | 2004 | H3 |
| DQ167304 | A/Finland/483/2004 | 984 | 2004 | H3 |
| DQ167305 | A/Finland/484/2004 | 984 | 2004 | H3 |
| DQ167306 | A/Finland/485/2004 | 984 | 2004 | H3 |
| DQ167307 | A/Finland/486/2004 | 984 | 2004 | H3 |
| AY963789 | A/Fujian/4/2004 | 1198 | 2004 | H3N2 |
| AY963790 | A/Fujian/52/2004 | 1198 | 2004 | H3N2 |
| AJ715872 | A/Hanoi/03/2004 | 1312 | 2004 | H5N1 |
| AB221027 | A/Hanoi/HN30109/20 | 950 | 2004 | H3N2 |
| AB221028 | A/Hanoi/HN30240/20 | 950 | 2004 | H3N2 |
| AB221026 | A/Hanoi/HN3069/200 | 950 | 2004 | H3N2 |
| AJ867074 | A/Hatay/2004 | 1707 | 2004 | H5N1 |
| AB221029 | A/Hung | 950 | 2004 | H3N2 |
| AB221030 | A/Hung | 955 | 2004 | H3N2 |
| AY854046 | A/Jiangsu/131/2004 | 511 | 2004 | H3N2 |
| AY851476 | A/Jiangsu/18/2004 | 266 | 2004 | H3N2 |
| AY854048 | A/Jiangsu/38/2004 | 511 | 2004 | H3N2 |
| AY854049 | A/Jiangsu/76/2004 | 511 | 2004 | H3N2 |
| AY854047 | A/Jiangsu/91/2004 | 511 | 2004 | H3N2 |
| AY851477 | A/Jiangsu/A20/2004 | 266 | 2004 | H3N2 |
| AY851474 | A/Jiangsu/A26/2004 | 266 | 2004 | H3N2 |
| AY851475 | A/Jiangsu/A29/2004 | 266 | 2004 | H3N2 |
| ISDN110772 | A/Johannesburg/1/04 | 923 | 2004 | H3N2 |
| ISDN110773 | A/Johannesburg/2/04 | 923 | 2004 | H3N2 |
| ISDN110507 | A/Johannesburg/30/20 | 1040 | 2004 | H3N2 |
| ISDN64757 | A/Lyon/21/2004 | 1019 | 2004 | H3 |
| ISDN64772 | A/Macau/103/2004 | 1010 | 2004 | H3N2 |
| ISDN64770 | A/Macau/14/2004 | 1010 | 2004 | H3N2 |
| ISDN64771 | A/Macau/214/2004 | 1026 | 2004 | H3N2 |
| ISDN64751 | A/Malaysia/1/2004 | 1011 | 2004 | H3N2 |
| ISDN69019 | A/Malaysia/1344/200 | 1013 | 2004 | H3 |
| ISDN106213 | A/Malaysia/1513/200 | 1220 | 2004 | H1N1 |
| ISDN69023 | A/Malaysia/1513/2004 | 1219 | 2004 | H1N1 |
| ISDN69015 | A/Malaysia/1522/2004 | 1008 | 2004 | H3N2 |
| ISDN110605 | A/Malaysia/1875/2004 | 1022 | 2004 | H3N2 |
| ISDN110615 | A/Malaysia/2050/2004 | 1018 | 2004 | H3N2 |
| ISDN110616 | A/Malaysia/2256/2004 | 1018 | 2004 | H3 |
| ISDN110529 | A/Malaysia/25/2004 | 1009 | 2004 | H3N2 |
| ISDN64763 | A/Malaysia/452/2004 | 1042 | 2004 | H3 |
| ISDN69020 | A/Malaysia/661/2004 | 1020 | 2004 | H3 |
| ISDN64305 | A/Malaysia/88/2004 | 1198 | 2004 | H1N1 |
| AY972829 | A/Minas Gerais/154/04 | 851 | 2004 | H3N2 |
| AY972827 | A/Minas | 832 | 2004 | H3N2 |
| AY972828 | A/Minas | 862 | 2004 | H3N2 |
| AY972831 | A/Minas | 851 | 2004 | H3N2 |
| ISDN64767 | A/Nakhon | 1013 | 2004 | H3N2 |

TABLE 1-continued

INFLUENZA TYPE A HA SEQUENCES

| Accession | Strain | Length | Year | Serotype |
|---|---|---|---|---|
| AY945264 | A/Nepal/1648/2004 | 1000 | 2004 | H3N2 |
| AY945267 | A/Nepal/1650/2004 | 1000 | 2004 | H3N2 |
| AY945269 | A/Nepal/1659/2004 | 1000 | 2004 | H3N2 |
| AY945266 | A/Nepal/1660/2004 | 1000 | 2004 | H3N2 |
| AY945265 | A/Nepal/1664/2004 | 1000 | 2004 | H3N2 |
| AY945263 | A/Nepal/1667/2004 | 1000 | 2004 | H3N2 |
| AY945288 | A/Nepal/1670/2004 | 1000 | 2004 | H3N2 |
| AY945287 | A/Nepal/1672/2004 | 1000 | 2004 | H3N2 |
| AY945286 | A/Nepal/1675/2004 | 1000 | 2004 | H3N2 |
| AY945285 | A/Nepal/1678/2004 | 1000 | 2004 | H3N2 |
| AY945284 | A/Nepal/1679/2004 | 1000 | 2004 | H3N2 |
| AY945283 | A/Nepal/1680/2004 | 1000 | 2004 | H3N2 |
| AY945282 | A/Nepal/1685/2004 | 1000 | 2004 | H3N2 |
| AY945281 | A/Nepal/1687/2004 | 1000 | 2004 | H3N2 |
| AY945268 | A/Nepal/1694/2004 | 1000 | 2004 | H3N2 |
| AY945280 | A/Nepal/1697/2004 | 1000 | 2004 | H3N2 |
| AY945279 | A/Nepal/1702/2004 | 1000 | 2004 | H3N2 |
| AY945278 | A/Nepal/1703/2004 | 1000 | 2004 | H3N2 |
| AY945277 | A/Nepal/1707/2004 | 1000 | 2004 | H3N2 |
| AY945276 | A/Nepal/1711/2004 | 1000 | 2004 | H3N2 |
| AY945275 | A/Nepal/1713/2004 | 1000 | 2004 | H3N2 |
| AY945274 | A/Nepal/1717/2004 | 1000 | 2004 | H3N2 |
| AY945273 | A/Nepal/1723/2004 | 1000 | 2004 | H3N2 |
| AY945272 | A/Nepal/1727/2004 | 1000 | 2004 | H3N2 |
| AY945271 | A/Nepal/1729/2004 | 1000 | 2004 | H3N2 |
| AY945270 | A/Nepal/1732/2004 | 1000 | 2004 | H3N2 |
| ISDN69009 | A/New | 1018 | 2004 | H3N2 |
| ISDN106214 | A/New | 1210 | 2004 | H1 |
| ISDN106215 | A/New | 1219 | 2004 | H1 |
| ISDN69010 | A/New | 1016 | 2004 | H3N2 |
| ISDN110621 | A/New | 1234 | 2004 | H1N1 |
| ISDN69021 | A/New | 1217 | 2004 | H1N1 |
| CY000761 | A/New York/10/2004 | 1760 | 2004 | H3N2 |
| CY003072 | A/New | 1737 | 2004 | H3N2 |
| CY002608 | A/New | 1703 | 2004 | H3N2 |
| CY002768 | A/New | 1711 | 2004 | H3N2 |
| CY002288 | A/New | 1727 | 2004 | H3N2 |
| CY002504 | A/New | 1709 | 2004 | H3N2 |
| CY002784 | A/New | 1711 | 2004 | H3N2 |
| CY003408 | A/New | 1704 | 2004 | H3N2 |
| CY003416 | A/New | 1721 | 2004 | H3N2 |
| CY002080 | A/New | 1710 | 2004 | H3N2 |
| CY002792 | A/New | 1728 | 2004 | H3N2 |
| CY007643 | A/New | 1720 | 2004 | H3N2 |
| DQ265709 | A/New | 1000 | 2004 | H3 |
| CY000369 | A/New York/31/2004 | 1756 | 2004 | H3N2 |
| CY002712 | A/New | 1737 | 2004 | H3N2 |
| CY000033 | A/New York/33/2004 | 1760 | 2004 | H3N2 |
| CY002408 | A/New | 1741 | 2004 | H3N2 |
| CY003032 | A/New | 1741 | 2004 | H3N2 |
| CY002416 | A/New | 1760 | 2004 | H3N2 |
| CY003336 | A/New | 1710 | 2004 | H3N2 |
| CY006115 | A/New | 1748 | 2004 | H3N2 |
| CY002176 | A/New | 1761 | 2004 | H3N2 |
| CY002584 | A/New | 1731 | 2004 | H3N2 |
| CY008188 | A/New | 1721 | 2004 | H3N2 |
| CY002424 | A/New | 1741 | 2004 | H3N2 |
| CY002432 | A/New | 1736 | 2004 | H3N2 |
| CY002728 | A/New | 1728 | 2004 | H3N2 |
| CY003040 | A/New | 1747 | 2004 | H3N2 |
| CY002440 | A/New | 1731 | 2004 | H3N2 |
| CY002192 | A/New | 1762 | 2004 | H3N2 |
| CY006435 | A/New | 1721 | 2004 | H3N2 |
| CY002208 | A/New | 1761 | 2004 | H3N2 |
| CY002216 | A/New | 1761 | 2004 | H3N2 |
| CY002224 | A/New | 1761 | 2004 | H3N2 |
| CY002232 | A/New | 1761 | 2004 | H3N2 |
| CY002592 | A/New | 1762 | 2004 | H3N2 |
| CY002024 | A/New | 1762 | 2004 | H3N2 |
| CY002600 | A/New | 1760 | 2004 | H3N2 |
| CY002248 | A/New | 1731 | 2004 | H3N2 |
| CY002256 | A/New | 1733 | 2004 | H3N2 |
| CY002472 | A/New | 1709 | 2004 | H3N2 |
| CY002040 | A/New | 1761 | 2004 | H3N2 |
| CY002048 | A/New | 1760 | 2004 | H3N2 |
| CY002064 | A/New | 1762 | 2004 | H3N2 |
| CY006371 | A/New | 1760 | 2004 | H3N2 |
| CY006379 | A/New | 1747 | 2004 | H3N2 |
| CY003656 | A/New | 1737 | 2004 | H3N2 |
| CY006179 | A/New | 1748 | 2004 | H3N2 |
| CY006092 | A/New | 1727 | 2004 | H3N2 |
| CY003664 | A/New | 1747 | 2004 | H3N2 |
| CY008164 | A/New | 1747 | 2004 | H3N2 |
| CY009252 | A/New | 1721 | 2004 | H3N2 |
| CY008908 | A/New | 1721 | 2004 | H3N2 |
| CY009260 | A/New | 1721 | 2004 | H3N2 |
| CY000889 | A/New York/5/2004 | 1761 | 2004 | H3N2 |
| CY009268 | A/New | 1721 | 2004 | H3N2 |
| CY000257 | A/New York/52/2004 | 1762 | 2004 | H3N2 |
| ISDN119760 | A/New York/55/2004 | 1621 | 2004 | H3 |
| CY001029 | A/New York/6/2004 | 1741 | 2004 | H3N2 |
| CY002760 | A/New York/68/2004 | 1737 | 2004 | H3N2 |
| CY000561 | A/New York/69/2004 | 1711 | 2004 | H3N2 |
| CY001229 | A/New York/70/2004 | 1760 | 2004 | H3N2 |
| CY008516 | A/New York/73/2004 | 1737 | 2004 | H3N2 |
| CY002280 | A/New York/98/2004 | 1718 | 2004 | H3N2 |
| ISDN110612 | A/Newcastle/1/2004 | 1033 | 2004 | H3N2 |
| ISDN110617 | A/Newcastle/2/2004 | 1033 | 2004 | H3 |
| DQ256374 | A/ningbo/318/04 | 987 | 2004 | H3N2 |
| DQ256375 | A/ningbo/397/04 | 987 | 2004 | H3N2 |
| DQ256372 | A/ningbo/65/04 | 987 | 2004 | H3N2 |
| DQ256373 | A/ningbo/93/04 | 987 | 2004 | H3N2 |
| ISDN69439 | A/Norway/807/2004 | 1722 | 2004 | H3N2 |
| ISDN110505 | A/Otago/2/2004 | 1027 | 2004 | H3N2 |
| AY972842 | A/Parana/291/04 | 991 | 2004 | H3N2 |
| AY972830 | A/Parana/298/04 | 854 | 2004 | H3N2 |
| AY972837 | A/Parana/306/04 | 992 | 2004 | H3N2 |
| AY972838 | A/Parana/308/04 | 989 | 2004 | H3N2 |
| AY972849 | A/Parana/312/04 | 706 | 2004 | H3N2 |
| AY972843 | A/Parana/313/04 | 988 | 2004 | H3N2 |
| ISDN64758 | A/Perth/1/2004 | 1018 | 2004 | H3N2 |
| ISDN110525 | A/Perth/26/2004 | 1031 | 2004 | H3 |
| ISDN110531 | A/Perth/35/2004 | 1018 | 2004 | H3N2 |
| ISDN110607 | A/Perth/45/2004 | 1025 | 2004 | H3N2 |
| ISDN110519 | A/Philippines/1290/2 | 1014 | 2004 | H3 |
| ISDN106212 | A/Philippines/936/20 | 1236 | 2004 | H1N1 |
| ISDN106211 | A/Philippines/987/20 | 1224 | 2004 | H1N1 |
| ISDN106210 | A/Prachinburi/1686/2 | 1211 | 2004 | H1 |
| ISDN110940 | A/Prachinburi/6231/2 | 1741 | 2004 | H5N1 |
| ISDN69012 | A/Prajianburi/1411/20 | 1014 | 2004 | H3N2 |
| AY972847 | A/RiodeJaneiro/17/04 | 990 | 2004 | H3N2 |
| AY972840 | A/RiodeJaneiro/26/04 | 993 | 2004 | H3N2 |
| AY972839 | A/RioGdeSul/213/04 | 990 | 2004 | H3N2 |
| AY972836 | A/RioGdoSul/211/04 | 989 | 2004 | H3N2 |
| AY972835 | A/RioGdoSul/212/04 | 989 | 2004 | H3N2 |
| AY972850 | A/RioGdoSul/214/04 | 706 | 2004 | H3N2 |
| AY972846 | A/RioGdoSul/406/04 | 989 | 2004 | H3N2 |
| AY972841 | A/RioGdoSul/411/04 | 984 | 2004 | H3N2 |
| AY972844 | A/RioGdoSul/417/04 | 990 | 2004 | H3N2 |
| ISDN110659 | A/Saraburi/1792/2004 | 1034 | 2004 | H3 |
| ISDN64753 | A/Singapore/1/2004 | 1005 | 2004 | H3N2 |
| ISDN69024 | A/Singapore/14/2004 | 1220 | 2004 | H1N1 |
| ISDN110622 | A/Singapore/14/2004 | 1234 | 2004 | H1N1 |
| ISDN69025 | A/Singapore/23/2004 | 1219 | 2004 | H1N1 |
| ISDN110515 | A/Singapore/36/2004 | 1016 | 2004 | H3N2 |
| ISDN110618 | A/Singapore/37/2004 | 1020 | 2004 | H3N2 |
| ISDN69014 | A/Singapore/4/2004 | 1017 | 2004 | H3 |
| ISDN64768 | A/Singpaore/38/2004 | 1000 | 2004 | H3N2 |
| ISDN64765 | A/Solomon | 1024 | 2004 | H3N2 |
| ISDN64764 | A/Solomon | 1019 | 2004 | H3 |
| ISDN110523 | A/South | 1035 | 2004 | H3N2 |
| AY972848 | A/StaCatarina/379/04 | 992 | 2004 | H3N2 |
| AY972845 | A/StaCatarina/380/04 | 979 | 2004 | H3N2 |
| ISDN64762 | A/Sydney/200/2004 | 1012 | 2004 | H3 |
| ISDN110611 | A/Sydney/38/2004 | 1018 | 2004 | H3N2 |
| ISDN110504 | A/Sydney/4/2004 | 1010 | 2004 | H3N2 |
| CY008212 | A/Tairawhiti/223/200 | 1721 | 2004 | H3N2 |
| CY007307 | A/Tairawhiti/369/200 | 1721 | 2004 | H3N2 |
| ISDN106209 | A/Taiwan/1559/2004 | 1231 | 2004 | H1N1 |
| ISDN110527 | A/Taiwan/1569/2004 | 1011 | 2004 | H3N2 |
| ISDN69740 | A/Taiwan/1571/2004 | 1161 | 2004 | H1N1 |
| ISDN110905 | A/Taiwan/1574/2004 | 1182 | 2004 | H1N1 |

TABLE 1-continued

INFLUENZA TYPE A HA SEQUENCES

| Accession | Strain | Length | Year | Serotype |
|---|---|---|---|---|
| DQ249261 | A/Taiwan/30005/2004 | 1762 | 2004 | H3N2 |
| DQ249262 | A/Taiwan/31001/2004 | 1762 | 2004 | H3N2 |
| AY555150 | A/Thailand/1-KAN- | 1739 | 2004 | H5N1 |
| ISDN40341 | A/Thailand/16/2004 | 1741 | 2004 | H5N1 |
| AY555153 | A/Thailand/2-SP- | 1740 | 2004 | H5N1 |
| ISDN49460 | A/Thailand/Chaiyaphum/622/2004 | 1741 | 2004 | H5N1 |
| AY786078 | A/Thailand/Kamphaengphet-Nontaburi/04 | 782 | 2004 | H5N1 |
| ISDN40918 | A/Thailand/Kan353/2 | 1741 | 2004 | H5N1 |
| AY679514 | A/Thailand/LFPN- | 1704 | 2004 | H5N1 |
| ISDN40917 | A/Thailand/SP83/200 | 1741 | 2004 | H5N1 |
| ISDN69018 | A/Victoria/101/2004 | 1020 | 2004 | H3N2 |
| ISDN110512 | A/Victoria/107/2004 | 1018 | 2004 | H3 |
| ISDN69017 | A/Victoria/110/2004 | 1021 | 2004 | H3N2 |
| ISDN110506 | A/Victoria/125/2004 | 1032 | 2004 | H3N2 |
| ISDN110533 | A/Victoria/144/2004 | 1002 | 2004 | H3 |
| ISDN110534 | A/Victoria/146/2004 | 1008 | 2004 | H3 |
| ISDN110619 | A/Victoria/500/2004 | 1020 | 2004 | H3N2 |
| ISDN110660 | A/Victoria/505/2004 | 1021 | 2004 | H3 |
| ISDN130602 | A/Victoria/507/2004 | 1004 | 2004 | H3N2 |
| ISDN110526 | A/Victoria/511/2004 | 1012 | 2004 | H3 |
| ISDN110620 | A/Victoria/511/2004 | 1033 | 2004 | H3 |
| ISDN110603 | A/Victoria/512/2004 | 1011 | 2004 | H3 |
| ISDN110604 | A/Victoria/513/2004 | 1015 | 2004 | H3 |
| ISDN110524 | A/Victoria/513/2004 | 1013 | 2004 | H3N2 |
| ISDN110610 | A/Victoria/520/2004 | 1019 | 2004 | H3N2 |
| ISDN110614 | A/Victoria/523/2004 | 1030 | 2004 | H3N2 |
| ISDN38686 | A/Viet | 1741 | 2004 | H5N1 |
| AY651333 | A/Viet | 1696 | 2004 | H5N1 |
| AY526745 | A/Viet Nam/1196/04 | 303 | 2004 | H5N1 |
| AY651334 | A/Viet | 1697 | 2004 | H5N1 |
| AY818135 | A/Viet | 1707 | 2004 | H5N1 |
| ISDN38687 | A/Viet | 1741 | 2004 | H5N1 |
| ISDN38688 | A/Viet | 1741 | 2004 | H5N1 |
| AY651335 | A/Viet | 1697 | 2004 | H5N1 |
| AY651336 | A/Viet | 1684 | 2004 | H5N1 |
| ISDN40278 | A/Viet | 1569 | 2004 | H5N1 |
| AY720950 | A/Viet Nam/DN- | 1075 | 2004 | H5N1 |
| ISDN69608 | A/Viet | 1707 | 2004 | H5N1 |
| ISDN110613 | A/Waikato/73/2004 | 1018 | 2004 | H3N2 |
| ISDN69596 | A/Wellington/1/2004 | 1012 | 2004 | H3N2 |
| ISDN64773 | A/Wellington/1/2004 | 1012 | 2004 | H3N2 |
| ISDN69270 | A/Wellington/1/2004 | 1012 | 2004 | H3N2 |
| CY009924 | A/Whanganui/127/20 | 1718 | 2004 | H3N2 |
| CY007275 | A/Whanganui/128/20 | 1721 | 2004 | H3N2 |
| CY007283 | A/Whanganui/129/20 | 1730 | 2004 | H3N2 |
| CY007323 | A/Whanganui/386/20 | 1721 | 2004 | H3N2 |
| CY007331 | A/Whanganui/417/20 | 1721 | 2004 | H3N2 |
| CY008204 | A/Whanganui/69/200 | 1721 | 2004 | H3N2 |
| AY963793 | A/Xiamen/181/2004 | 1198 | 2004 | H3N2 |
| AY963791 | A/Xiamen/70/2004 | 1198 | 2004 | H3N2 |
| AY963792 | A/Xiamen/80/2004 | 1198 | 2004 | H3N2 |
| DQ174264 | A/Zhejiang/546/04 | 987 | 2004 | H3N2 |
| DQ174265 | A/Zhejiang/550/04 | 987 | 2004 | H3N2 |
| DQ179512 | A/Bangladesh/C5- | 960 | 2003 | H3N2 |
| DQ179513 | A/Bangladesh/C5- | 960 | 2003 | H3N2 |
| DQ179515 | A/Bangladesh/C5- | 960 | 2003 | H3N2 |
| DQ179516 | A/Bangladesh/C5- | 960 | 2003 | H3N2 |
| DQ179517 | A/Bangladesh/C5- | 960 | 2003 | H3N2 |
| DQ179518 | A/Bangladesh/C5- | 960 | 2003 | H3N2 |
| DQ179519 | A/Bangladesh/C5- | 960 | 2003 | H3N2 |
| DQ179520 | A/Bangladesh/C5- | 960 | 2003 | H3N2 |
| DQ179521 | A/Bangladesh/C5- | 960 | 2003 | H3N2 |
| DQ179522 | A/Bangladesh/C5- | 960 | 2003 | H3N2 |
| DQ179523 | A/Bangladesh/C5- | 960 | 2003 | H3N2 |
| DQ179524 | A/Bangladesh/C5- | 960 | 2003 | H3N2 |
| DQ179525 | A/Bangladesh/C5- | 960 | 2003 | H3N2 |
| DQ179526 | A/Bangladesh/C5- | 960 | 2003 | H3N2 |
| DQ179527 | A/Bangladesh/C5- | 960 | 2003 | H3N2 |
| ISDN64746 | A/Brisbane/340/2003 | 1009 | 2003 | H3 |
| ISDN64752 | A/Brisbane/342/2003 | 1036 | 2003 | H3 |
| CY006923 | A/Canterbury/382/200 | 1721 | 2003 | H3N2 |
| CY006931 | A/Canterbury/384/200 | 1721 | 2003 | H3N2 |
| CY006939 | A/Canterbury/386/200 | 1721 | 2003 | H3N2 |
| CY006947 | A/Canterbury/387/200 | 1721 | 2003 | H3N2 |
| CY006955 | A/Canterbury/390/200 | 1721 | 2003 | H3N2 |
| CY006963 | A/Canterbury/391/200 | 1721 | 2003 | H3N2 |
| CY006971 | A/Canterbury/392/200 | 1721 | 2003 | H3N2 |
| CY006979 | A/Canterbury/393/200 | 1721 | 2003 | H3N2 |
| CY006987 | A/Canterbury/394/200 | 1721 | 2003 | H3N2 |
| CY006995 | A/Canterbury/395/200 | 1721 | 2003 | H3N2 |
| CY007003 | A/Canterbury/397/200 | 1722 | 2003 | H3N2 |
| CY007011 | A/Canterbury/398/200 | 1721 | 2003 | H3N2 |
| CY007019 | A/Canterbury/399/200 | 1721 | 2003 | H3N2 |
| CY009020 | A/Canterbury/400/200 | 1726 | 2003 | H3N2 |
| CY007027 | A/Canterbury/401/200 | 1719 | 2003 | H3N2 |
| CY007035 | A/Canterbury/403/200 | 1721 | 2003 | H3N2 |
| CY007043 | A/Canterbury/404/200 | 1721 | 2003 | H3N2 |
| CY007051 | A/Canterbury/405/200 | 1721 | 2003 | H3N2 |
| CY007059 | A/Canterbury/406/200 | 1721 | 2003 | H3N2 |
| CY007067 | A/Canterbury/408/200 | 1721 | 2003 | H3N2 |
| CY007819 | A/Canterbury/409/200 | 1721 | 2003 | H3N2 |
| CY007075 | A/Canterbury/410/200 | 1717 | 2003 | H3N2 |
| CY007083 | A/Canterbury/411/200 | 1722 | 2003 | H3N2 |
| CY007091 | A/Canterbury/412/200 | 1721 | 2003 | H3N2 |
| CY007099 | A/Canterbury/416/200 | 1721 | 2003 | H3N2 |
| CY007107 | A/Canterbury/417/200 | 1721 | 2003 | H3N2 |
| CY007115 | A/Canterbury/418/200 | 1721 | 2003 | H3N2 |
| CY007123 | A/Canterbury/420/200 | 1721 | 2003 | H3N2 |
| CY007131 | A/Canterbury/423/200 | 1721 | 2003 | H3N2 |
| CY007139 | A/Canterbury/424/200 | 1721 | 2003 | H3N2 |
| CY008540 | A/Canterbury/425/200 | 1714 | 2003 | H3N2 |
| CY008548 | A/Canterbury/426/200 | 1720 | 2003 | H3N2 |
| CY007147 | A/Canterbury/427/200 | 1721 | 2003 | H3N2 |
| CY007155 | A/Canterbury/428/200 | 1721 | 2003 | H3N2 |
| CY007827 | A/Canterbury/429/2003 | 1721 | 2003 | H3N2 |
| CY007163 | A/Canterbury/430/2003 | 1730 | 2003 | H3N2 |
| CY007171 | A/Canterbury/431/2003 | 1717 | 2003 | H3N2 |
| CY008196 | A/Canterbury/432/2003 | 1720 | 2003 | H3N2 |
| CY007187 | A/Canterbury/434/2003 | 1721 | 2003 | H3N2 |
| CY007195 | A/Canterbury/435/2003 | 1721 | 2003 | H3N2 |
| CY007203 | A/Canterbury/436/2003 | 1717 | 2003 | H3N2 |
| CY007211 | A/Canterbury/437/2003 | 1717 | 2003 | H3N2 |
| CY007219 | A/Canterbury/438/2003 | 1717 | 2003 | H3N2 |
| CY007227 | A/Canterbury/439/2003 | 1717 | 2003 | H3N2 |
| CY007235 | A/Canterbury/440/2003 | 1720 | 2003 | H3N2 |
| CY007243 | A/Canterbury/441/2003 | 1718 | 2003 | H3N2 |
| CY007251 | A/Canterbury/442/2003 | 1717 | 2003 | H3N2 |
| CY007259 | A/Canterbury/443/2003 | 1717 | 2003 | H3N2 |
| CY007267 | A/Canterbury/444/2003 | 1721 | 2003 | H3N2 |
| ISDN38158 | A/Christchurch/28/2003 | 989 | 2003 | H3N2 |
| AY531041 | A/Denmark/07/03 | 1701 | 2003 | H3N2 |
| AY531046 | A/Denmark/10/03 | 1701 | 2003 | H3N2 |
| AY531056 | A/Denmark/13/03 | 1701 | 2003 | H3N2 |
| AY531054 | A/Denmark/14-2/03 | 1701 | 2003 | H3N2 |
| AY531060 | A/Denmark/15-2/03 | 1701 | 2003 | H3N2 |
| AY531050 | A/Denmark/16-2/03 | 1701 | 2003 | H3N2 |
| AY531061 | A/Denmark/17-2/03 | 1701 | 2003 | H3N2 |
| AY531059 | A/Denmark/18-2/03 | 1701 | 2003 | H3N2 |
| AY531053 | A/Denmark/19-2/03 | 1701 | 2003 | H3N2 |
| AY531047 | A/Denmark/20/03 | 1701 | 2003 | H3N2 |
| AY531043 | A/Denmark/24/03 | 1701 | 2003 | H3N2 |
| AY531042 | A/Denmark/32/03 | 1701 | 2003 | H3N2 |
| AY531058 | A/Denmark/37/03 | 1701 | 2003 | H3N2 |
| AY531057 | A/Denmark/39/03 | 1701 | 2003 | H3N2 |
| AY531048 | A/Denmark/41/03 | 1701 | 2003 | H3N2 |
| AY531052 | A/Denmark/52/03 | 1701 | 2003 | H3N2 |
| AY531040 | A/Denmark/58/03 | 1701 | 2003 | H3N2 |
| AY531039 | A/Denmark/59/03 | 1701 | 2003 | H3N2 |
| AY531044 | A/Denmark/60/03 | 1701 | 2003 | H3N2 |
| AY531049 | A/Denmark/61/03 | 1701 | 2003 | H3N2 |
| AY531045 | A/Denmark/63/03 | 1701 | 2003 | H3N2 |
| AY531051 | A/Denmark/70/03 | 1701 | 2003 | H3N2 |
| AY531055 | A/Denmark/92/03 | 1701 | 2003 | H3N2 |
| ISDN64749 | A/Dunedin/11/2003 | 1021 | 2003 | H3 |
| ISDN64748 | A/Dunedin/15/2003 | 1012 | 2003 | H3 |
| ISDN64750 | A/Dunedin/24/2003 | 1024 | 2003 | H3 |
| ISDN64745 | A/Dunedin/39/2003 | 1011 | 2003 | H3N2 |
| ISDN64747 | A/Dunedin/40/2003 | 1019 | 2003 | H3 |
| AY661032 | A/Finland/170/03 | 987 | 2003 | H3N2 |

TABLE 1-continued

INFLUENZA TYPE A HA SEQUENCES

| Accession | Strain | Length | Year | Serotype |
|---|---|---|---|---|
| DQ167259 | A/Finland/170/2003 | 984 | 2003 | H3 |
| DQ167260 | A/Finland/180/2003 | 984 | 2003 | H3 |
| DQ167261 | A/Finland/272/2003 | 984 | 2003 | H3 |
| DQ167262 | A/Finland/278/2003 | 984 | 2003 | H3 |
| DQ167263 | A/Finland/285/2003 | 984 | 2003 | H3 |
| DQ167264 | A/Finland/291/2003 | 984 | 2003 | H3 |
| DQ167265 | A/Finland/293/2003 | 984 | 2003 | H3 |
| DQ167266 | A/Finland/300/2003 | 984 | 2003 | H3 |
| DQ167267 | A/Finland/301/2003 | 984 | 2003 | H3 |
| DQ167268 | A/Finland/302/2003 | 984 | 2003 | H3 |
| DQ167269 | A/Finland/303/2003 | 984 | 2003 | H3 |
| DQ167270 | A/Finland/304/2003 | 984 | 2003 | H3 |
| DQ167271 | A/Finland/305/2003 | 984 | 2003 | H3 |
| DQ167272 | A/Finland/306/2003 | 984 | 2003 | H3 |
| DQ167273 | A/Finland/308/2003 | 984 | 2003 | H3 |
| DQ167274 | A/Finland/309/2003 | 984 | 2003 | H3 |
| DQ167275 | A/Finland/310/2003 | 984 | 2003 | H3 |
| DQ167276 | A/Finland/311/2003 | 984 | 2003 | H3 |
| DQ167277 | A/Finland/312/2003 | 984 | 2003 | H3 |
| DQ167278 | A/Finland/313/2003 | 984 | 2003 | H3 |
| DQ167279 | A/Finland/314/2003 | 984 | 2003 | H3 |
| DQ167280 | A/Finland/319/2003 | 984 | 2003 | H3 |
| DQ167281 | A/Finland/320/2003 | 984 | 2003 | H3 |
| DQ167282 | A/Finland/323/2003 | 984 | 2003 | H3 |
| DQ167283 | A/Finland/338/2003 | 984 | 2003 | H3 |
| DQ167284 | A/Finland/342/2003 | 984 | 2003 | H3 |
| DQ167285 | A/Finland/358/2003 | 984 | 2003 | H3 |
| DQ167286 | A/Finland/377/2003 | 984 | 2003 | H3 |
| DQ167287 | A/Finland/402/2003 | 984 | 2003 | H3 |
| DQ167288 | A/Finland/420/2003 | 984 | 2003 | H3 |
| DQ167289 | A/Finland/430/2003 | 984 | 2003 | H3 |
| DQ167290 | A/Finland/431/2003 | 984 | 2003 | H3 |
| DQ167291 | A/Finland/432/2003 | 984 | 2003 | H3 |
| DQ167292 | A/Finland/433/2003 | 984 | 2003 | H3 |
| DQ167293 | A/Finland/434/2003 | 984 | 2003 | H3 |
| DQ167294 | A/Finland/435/2003 | 984 | 2003 | H3 |
| DQ167295 | A/Finland/437/2003 | 984 | 2003 | H3 |
| DQ167296 | A/Finland/453/2003 | 984 | 2003 | H3 |
| DQ167297 | A/Finland/465/2003 | 984 | 2003 | H3 |
| DQ179474 | A/Finland/C4-2/2003 | 960 | 2003 | H3N2 |
| DQ179494 | A/Finland/C4-22/2003 | 960 | 2003 | H3N2 |
| DQ179495 | A/Finland/C4-23/2003 | 960 | 2003 | H3N2 |
| DQ179496 | A/Finland/C4-24/2003 | 960 | 2003 | H3N2 |
| DQ179488 | A/France/C4-16/2003 | 960 | 2003 | H3N2 |
| AY963796 | A/Fujian/182/2003 | 1198 | 2003 | H3N2 |
| AY963783 | A/Fujian/219/2003 | 1198 | 2003 | H3N2 |
| AY963784 | A/Fujian/258/2003 | 1198 | 2003 | H3N2 |
| AY963785 | A/Fujian/292/2003 | 1198 | 2003 | H3N2 |
| AY963786 | A/Fujian/325/2003 | 1198 | 2003 | H3N2 |
| AY963787 | A/Fujian/447/2003 | 1198 | 2003 | H3N2 |
| AY963788 | A/Fujian/555/2003 | 1198 | 2003 | H3N2 |
| AB221020 | A/Hanoi/695/2003 | 950 | 2003 | H3N2 |
| AB221021 | A/Hanoi/ARI99/2003 | 950 | 2003 | H3N2 |
| AB221022 | A/Hanoi/BM766/2003 | 950 | 2003 | H3N2 |
| AB221023 | A/Hanoi/BM767/2003 | 950 | 2003 | H3N2 |
| AB221024 | A/Hanoi/BM768/2003 | 950 | 2003 | H3N2 |
| AB221025 | A/Hanoi/BM769/2003 | 950 | 2003 | H3N2 |
| DQ226106 | A/Hong | 1577 | 2003 | H9N2 |
| AY575869 | A/Hong Kong/212/03 | 1664 | 2003 | H5N1 |
| AB212054 | A/Hong Kong/213/03 | 1779 | 2003 | H5N1 |
| AY575870 | A/Hong | 1593 | 2003 | H5N1 |
| ISDN38262 | A/Hong | 1750 | 2003 | H5N1 |
| AY702441 | A/Ind/M/Enc/1/2003 | 876 | 2003 | H3N2 |
| AY702442 | A/Ind/M/Enc/2/2003 | 876 | 2003 | H3N2 |
| AY702440 | A/Ind/M/URI/1/2003 | 876 | 2003 | H3N2 |
| AY702443 | A/Ind/M/URI/2/2003 | 876 | 2003 | H3N2 |
| AY702447 | A/Ind/P/URI/1/2003 | 876 | 2003 | H3N2 |
| AY702445 | A/Ind/P/URI/2/2003 | 876 | 2003 | H3N2 |
| AY702444 | A/Ind/P/URI/3/2003 | 876 | 2003 | H3N2 |
| AY702446 | A/Ind/P/URI/4/2003 | 876 | 2003 | H3N2 |
| DQ179484 | A/Italy/C4-12/2003 | 960 | 2003 | H3N2 |
| DQ179492 | A/Italy/C4-20/2003 | 960 | 2003 | H3N2 |
| DQ179478 | A/Italy/C4-6/2003 | 960 | 2003 | H3N2 |
| AY851473 | A/Jiangsu/Children67/2003 | 266 | 2003 | H3N2 |
| AY389349 | A/Johannesburg/1/03 | 923 | 2003 | H3N2 |
| AY389351 | A/Johannesburg/10/03 | 923 | 2003 | H3N2 |
| AY389352 | A/Johannesburg/28/03 | 923 | 2003 | H3N2 |
| AY389353 | A/Johanneaburg/30/03 | 923 | 2003 | H3N2 |
| AY389350 | A/Johannesburg/4/03 | 923 | 2003 | H3N2 |
| AY389354 | A/Johannesburg/50/03 | 923 | 2003 | H3N2 |
| AY389355 | A/Johannesburg/64/03 | 923 | 2003 | H3N2 |
| ISDN64755 | A/Limoges/2402/2003 | 1029 | 2003 | H3 |
| ISDN38275 | A/Malaysia/1003/200 | 1208 | 2003 | H1N1 |
| ISDN38276 | A/Malaysia/643/2003 | 1200 | 2003 | H1N1 |
| ISDN38277 | A/Malaysia/687/2003 | 1203 | 2003 | H1N1 |
| CY002104 | A/Memphis/31/03 | 1718 | 2003 | H3N2 |
| AY389356 | A/Middleburg/41/03 | 923 | 2003 | H3N2 |
| AY389357 | A/Middleburg/45/03 | 923 | 2003 | H3N2 |
| DQ089635 | A/Moscow/328/2003 (CACO-2x12) | 1741 | 2003 | H3N2 |
| DQ086161 | A/Moscow/328/2003 (CACO-2x5) | 1728 | 2003 | H3N2 |
| DQ089636 | A/Moscow/328/2003 (MDCKx12) | 1755 | 2003 | H3N2 |
| DQ086160 | A/Moscow/328/2003 (MDCKx6) | 1742 | 2003 | H3N2 |
| DQ089634 | A/Moscow/343/2003 (CACO-2x12) | 1711 | 2003 | H3N2 |
| DQ086158 | A/Moscsw/343/2003 (CACO-2x8) | 1312 | 2003 | H3N2 |
| DQ089637 | A/Msscow/343/2003 (MDCKx12) | 1738 | 2003 | H3N2 |
| DQ086157 | A/Moscow/343/2003 (MDCKx8) | 1671 | 2003 | H3N2 |
| DQ086159 | A/Moscow/343/2003 | 1702 | 2003 | H3N2 |
| DQ066936 | A/Moscow/346/2003 | 586 | 2003 | H3N2 |
| DQ089638 | A/Moscow/346/2003 (CACO-2x12) | 1738 | 2003 | H3N2 |
| DQ089639 | A/Moscow/346/2003 (MDCKx12) | 1738 | 2003 | H3N2 |
| AY661033 | A/Netherlands/20/03 | 987 | 2003 | H3N2 |
| AY661035 | A/Netherlands/213/03 | 987 | 2003 | H3N2 |
| AY661036 | A/Netherlands/217/03 | 987 | 2003 | H3N2 |
| AY661034 | A/Netherlands/22/03 | 987 | 2003 | H3N2 |
| AY661037 | A/Netherlands/222/03 | 987 | 2003 | H3N2 |
| DQ179497 | A/Netherlands/C4- | 960 | 2003 | H3N2 |
| DQ179498 | A/Netherlands/C4- | 960 | 2003 | H3N2 |
| CY001021 | A/New York/1/2003 | 1760 | 2003 | H3N2 |
| CY000513 | A/New York/11/2003 | 1760 | 2003 | H3N2 |
| CY000121 | A/New York/12/2003 | 1760 | 2003 | H3N2 |
| CY000901 | A/New York/13/2003 | 1762 | 2003 | H3N2 |
| CY000909 | A/New York/14/2003 | 1760 | 2003 | H3N2 |
| CY000345 | A/New York/15/2003 | 1762 | 2003 | H3N2 |
| CY000129 | A/New York/16/2003 | 1760 | 2003 | H3N2 |
| CY001053 | A/New York/17/2003 | 1741 | 2003 | H3N2 |
| CY001061 | A/New York/18/2003 | 1741 | 2003 | H3N2 |
| CY000249 | A/New York/19/2003 | 1741 | 2003 | H3N2 |
| CY000753 | A/New | 1760 | 2003 | H3N2 |
| CY000865 | A/New | 1711 | 2003 | H3N2 |
| CY000873 | A/New | 1732 | 2003 | H3N2 |
| CY001461 | A/New | 1711 | 2003 | H3N2 |
| CY001536 | A/New | 1711 | 2003 | H3N2 |
| CY001544 | A/New | 1718 | 2003 | H3N2 |
| CY001013 | A/New | 1760 | 2003 | H3N2 |
| CY001253 | A/New | 1711 | 2003 | H3N2 |
| CY000473 | A/New York/2/2003 | 1741 | 2003 | H3N2 |
| CY001421 | A/New York/20/2003 | 1718 | 2003 | H3N2 |
| CY001373 | A/New | 1710 | 2003 | H3N2 |
| CY001160 | A/New | 1718 | 2003 | H3N2 |
| CY001469 | A/New | 1718 | 2003 | H3N2 |
| CY002520 | A/New | 1718 | 2003 | H3N2 |
| CY002352 | A/New | 1741 | 2003 | H1N2 |
| CY000353 | A/New York/21/2003 | 1760 | 2003 | H3N2 |
| CY006867 | A/New | 1731 | 2003 | H1N2 |
| CY001405 | A/New | 1761 | 2003 | H3N2 |
| CY006859 | A/New | 1721 | 2003 | H3N2 |
| CY001552 | A/New | 1711 | 2003 | H3N2 |
| CY001560 | A/New | 1722 | 2003 | H3N2 |
| CY006107 | A/New | 1735 | 2003 | H1N2 |
| CY000361 | A/New York/22/2003 | 1762 | 2003 | H3N2 |
| CY002984 | A/New | 1749 | 2003 | H1N1 |

TABLE 1-continued

INFLUENZA TYPE A HA SEQUENCES

| Accession | Strain | Length | Year | Serotype |
|---|---|---|---|---|
| CY002680 | A/New | 1748 | 2003 | H1N1 |
| CY002688 | A/New | 1771 | 2003 | H1N1 |
| CY006747 | A/New | 1711 | 2003 | H1N2 |
| CY002992 | A/New | 1746 | 2003 | H1N2 |
| CY002536 | A/New | 1740 | 2003 | H1N1 |
| CY003296 | A/New | 1727 | 2003 | H1N1 |
| CY010076 | A/New | 1737 | 2003 | H1N2 |
| CY000193 | A/New York/23/2003 | 1760 | 2003 | H3N2 |
| CY002624 | A/New | 1775 | 2003 | H1N1 |
| CY002632 | A/New | 1741 | 2003 | H1N2 |
| CY001088 | A/New York/24/2003 | 1733 | 2003 | H3N2 |
| CY000769 | A/New York/25/2003 | 1710 | 2003 | H3N2 |
| CY000137 | A/New York/26/2003 | 1762 | 2003 | H3N2 |
| CY001624 | A/New York/267/2003 | 1711 | 2003 | H3N2 |
| CY001632 | A/New York/268/2003 | 1762 | 2003 | H3N2 |
| CY001640 | A/New York/269/2003 | 1718 | 2003 | H3N2 |
| CY001112 | A/New York/27/2003 | 1760 | 2003 | H3N2 |
| CY001648 | A/New York/270/2003 | 1738 | 2003 | H3N2 |
| CY001712 | A/New York/271/2003 | 1714 | 2003 | H3N2 |
| CY002344 | A/New York/272/2003 | 1741 | 2003 | H3N2 |
| CY000009 | A/New York/28/2003 | 1760 | 2003 | H3N2 |
| CY000521 | A/New York/29/2003 | 1711 | 2003 | H3N2 |
| CY003376 | A/New | 1748 | 2003 | H1N1 |
| CY003384 | A/New | 1751 | 2003 | H1N1 |
| CY002656 | A/New | 1741 | 2003 | H1N2 |
| CY002152 | A/New | 1738 | 2003 | H1N2 |
| CY002664 | A/New | 1718 | 2003 | H1N2 |
| CY000881 | A/New York/3/2003 | 1740 | 2003 | H3N2 |
| CY000017 | A/New York/30/2003 | 1757 | 2003 | H3N2 |
| CY002360 | A/New | 1748 | 2003 | H1N2 |
| CY000025 | A/New York/32/2003 | 1760 | 2003 | H3N2 |
| CY000041 | A/New York/34/2003 | 1741 | 2003 | H3N2 |
| CY002704 | A/New | 1727 | 2003 | H1N1 |
| CY000049 | A/New York/35/2003 | 1711 | 2003 | H3N2 |
| CY006427 | A/New | 1724 | 2003 | H1N1 |
| CY000057 | A/New York/36/2003 | 1760 | 2003 | H3N2 |
| CY001293 | A/New York/37/2003 | 1732 | 2003 | H3N2 |
| CY000777 | A/New York/38/2003 | 1760 | 2003 | H3N2 |
| CY001096 | A/New York/39/2003 | 1711 | 2003 | H3N2 |
| CY002808 | A/New | 1775 | 2003 | H1N1 |
| CY000505 | A/New York/4/2003 | 1760 | 2003 | H3N2 |
| CY000145 | A/New York/40/2003 | 1760 | 2003 | H3N2 |
| CY003761 | A/New | 1748 | 2003 | H1N2 |
| CY000153 | A/New York/41/2003 | 1760 | 2003 | H3N2 |
| CY000161 | A/New York/42/2003 | 1762 | 2003 | H3N2 |
| CY000169 | A/New York/43/2003 | 1760 | 2003 | H3N2 |
| CY000177 | A/New York/44/2003 | 1762 | 2003 | H3N2 |
| CY000065 | A/New York/45/2003 | 1762 | 2003 | H3N2 |
| CY000785 | A/New York/46/2003 | 1741 | 2003 | H3N2 |
| CY000073 | A/New York/47/2003 | 1761 | 2003 | H3N2 |
| CY008868 | A/New | 1720 | 2003 | H3N2 |
| CY008876 | A/New | 1721 | 2003 | H3N2 |
| CY008884 | A/New | 1721 | 2003 | H3N2 |
| CY008892 | A/New | 1721 | 2003 | H3N2 |
| CY009244 | A/New | 1721 | 2003 | H3N2 |
| CY008900 | A/New | 1721 | 2003 | H3N2 |
| CY008916 | A/New | 1721 | 2003 | H3N2 |
| CY000081 | A/New York/48/2003 | 1760 | 2003 | H3N2 |
| CY006387 | A/New | 1731 | 2003 | H1N2 |
| CY003672 | A/New | 1748 | 2003 | H1N2 |
| CY008524 | A/New | 1724 | 2003 | H1N1 |
| CY008996 | A/New | 1727 | 2003 | H1N1 |
| CY003680 | A/New | 1737 | 2003 | H3N2 |
| CY003688 | A/New | 1729 | 2003 | H1N1 |
| CY006395 | A/New | 1715 | 2003 | H1N1 |
| CY006915 | A/New | 1748 | 2003 | H1N1 |
| CY003696 | A/New | 1748 | 2003 | H1N2 |
| CY000377 | A/New York/49/2003 | 1761 | 2003 | H3N2 |
| CY006403 | A/New | 1714 | 2003 | H1N2 |
| CY006187 | A/New | 1716 | 2003 | H1N1 |
| CY006411 | A/New | 1715 | 2003 | H1N2 |
| CY006667 | A/New | 1748 | 2003 | H1N1 |
| CY003704 | A/New | 1748 | 2003 | H1N1 |
| CY006195 | A/New | 1748 | 2003 | H1N1 |
| CY000089 | A/New York/50/2003 | 1761 | 2003 | H3N2 |
| CY001064 | A/New York/51/2003 | 1762 | 2003 | H3N2 |
| CY000265 | A/New York/53/2003 | 1762 | 2003 | H3N2 |
| CY000097 | A/New York/54/2003 | 1762 | 2003 | H3N2 |
| CY000949 | A/New York/55/2003 | 1738 | 2003 | H3N2 |
| CY001205 | A/New York/56/2003 | 1711 | 2003 | H3N2 |
| CY001512 | A/New York/58/2003 | 1760 | 2003 | H3N2 |
| CY000957 | A/New York/59/2003 | 1741 | 2003 | H3N2 |
| CY000105 | A/New | 1741 | 2003 | H3N2 |
| CY000001 | A/New | 1762 | 2003 | H3N2 |
| CY000917 | A/New | 1711 | 2003 | H3N2 |
| CY001213 | A/New York/63/2003 | 1760 | 2003 | H3N2 |
| CY000965 | A/New York/64/2003 | 1760 | 2003 | H3N2 |
| CY001221 | A/New York/65/2003 | 1741 | 2003 | H3N2 |
| CY001341 | A/New York/66/2003 | 1716 | 2003 | H3N2 |
| CY000973 | A/New York/67/2003 | 1741 | 2003 | H3N2 |
| CY001037 | A/New York/7/2003 | 1741 | 2003 | H3N2 |
| CY001045 | A/New York/8/2003 | 1760 | 2003 | H3N2 |
| CY001285 | A/New York/9/2003 | 1750 | 2003 | H3N2 |
| AY695089 | A/Ningbo/198/03 | 987 | 2003 | H3N2 |
| AY695090 | A/Ningbo/217/03 | 987 | 2003 | H3N2 |
| ISDN38160 | A/Norway/88/2003 | 1118 | 2003 | H3N2 |
| DQ059385 | A/Oklahoma/323/03 | 1701 | 2003 | H3N2 |
| ISDN48385 | A/Oklahoma/8/2003 | 1151 | 2003 | H3 |
| ISDN64756 | A/Philippines/1320/2 | 1021 | 2003 | H3 |
| ISDN64774 | A/Philippines/825/20 | 1011 | 2003 | H3N2 |
| ISDN64304 | A/Poitiers/2168/2003 | 1204 | 2003 | H1N1 |
| DQ179489 | A/Poland/C4-17/2003 | 960 | 2003 | H3N2 |
| AY389359 | A/Pretoria/16/03 | 923 | 2003 | H3N2 |
| AY389360 | A/Pretoria/17/03 | 923 | 2003 | H3N2 |
| AY389358 | A/Pretoria/2/03 | 923 | 2003 | H3N2 |
| AY972833 | A/RiodeJaneiro/107/0 | 925 | 2003 | H3N2 |
| AY972851 | A/RiodeJaneiro/346/0 | 997 | 2003 | H3N2 |
| AY972834 | A/RiodeJaneiro/98/03 | 995 | 2003 | H3N2 |
| AY972832 | A/RiodeJaneiro/99/03 | 994 | 2003 | H3N2 |
| DQ179482 | A/Scotland/C4- | 960 | 2003 | H3N2 |
| DQ179486 | A/Scotland/C4- | 960 | 2003 | H3N2 |
| DQ179487 | A/Scotland/C4- | 960 | 2003 | H3N2 |
| DQ179490 | A/Scotland/C4- | 960 | 2003 | H3N2 |
| DQ179491 | A/Scotland/C4- | 960 | 2003 | H3N2 |
| DQ179493 | A/Scotland/C4- | 960 | 2003 | H3N2 |
| DQ179499 | A/Scotland/C4- | 960 | 2003 | H3N2 |
| DQ179500 | A/Scotland/C4- | 960 | 2003 | H3N2 |
| ISDN64754 | A/Singapore/107/200 | 1005 | 2003 | H3 |
| DQ179510 | A/Singapore/C5- | 960 | 2003 | H3N2 |
| DQ179511 | A/Singapore/C5- | 960 | 2003 | H3N2 |
| DQ179514 | A/Singapore/C5- | 960 | 2003 | H3N2 |
| DQ179509 | A/Singapore/C5- | 960 | 2003 | H3N2 |
| ISDN38159 | A/South | 989 | 2003 | H3N2 |
| CY007179 | A/South Canterbury/433/2003 | 1720 | 2003 | H3N2 |
| ISDN38234 | A/Sydney/015/03 | 1154 | 2003 | H3N2 |
| ISDN64759 | A/Sydney/101/2003 | 1019 | 2003 | H3 |
| AY604817 | A/Taiwan/0040/2003 | 791 | 2003 | H3N2 |
| AY604828 | A/Taiwan/0097/2003 | 791 | 2003 | H3N2 |
| AY604823 | A/Taiwan/0122/2003 | 791 | 2003 | H3N2 |
| AY604822 | A/Taiwan/0570/2003 | 791 | 2003 | H3N2 |
| AY604827 | A/Taiwan/0572/2003 | 791 | 2003 | H3N2 |
| AY604821 | A/Taiwan/0578/2003 | 791 | 2003 | H3N2 |
| AY604820 | A/Taiwan/0583/2003 | 791 | 2003 | H3N2 |
| ISDN64761 | A/Taiwan/14/2003 | 957 | 2003 | H3 |
| AY479982 | A/Taiwan/1523/2003 | 985 | 2003 | H3N2 |
| AY604808 | A/Taiwan/1523/2003 | 494 | 2003 | H1N1 |
| AY604826 | A/Taiwan/1566/2003 | 791 | 2003 | H3N2 |
| AY604806 | A/Taiwan/1566/2003 | 494 | 2003 | H1N1 |
| AY604819 | A/Taiwan/1568/2003 | 791 | 2003 | H3N2 |
| AY604818 | A/Taiwan/2040/2003 | 791 | 2003 | H3N2 |
| DQ249259 | A/Taiwan/3640/2003 | 1762 | 2003 | H3N2 |
| AY604807 | A/Taiwan/4050/2003 | 494 | 2003 | H1N1 |
| AY604825 | A/Taiwan/4050/2003 | 791 | 2003 | H3N2 |
| AY604824 | A/Taiwan/4063/2003 | 791 | 2003 | H3N2 |
| AY604829 | A/Taiwan/7099/2003 | 791 | 2003 | H3N2 |

TABLE 1-continued

INFLUENZA TYPE A HA SEQUENCES

| Accession | Strain | Length | Year | Serotype |
|---|---|---|---|---|
| AY604830 | A/Taiwan/7100/2003 | 791 | 2003 | H3N2 |
| AB221031 | A/Tay | 950 | 2003 | H3N2 |
| AB221032 | A/Tay | 950 | 2003 | H3N2 |
| AB221033 | A/Tay | 950 | 2003 | H3N2 |
| AB221034 | A/Tay | 950 | 2003 | H3N2 |
| AB221035 | A/Tay | 979 | 2003 | H3N2 |
| ISDN48417 | A/Texas/40/2003 | 1151 | 2003 | H3 |
| ISDN48418 | A/Texas/40e/2003 | 1151 | 2003 | H3 |
| DQ179473 | A/United Kingdom/C4-1/2003 | 960 | 2003 | H3N2 |
| DQ179483 | A/United Kingdom/C4-11/2003 | 960 | 2003 | H3N2 |
| DQ179485 | A/United Kingdom/C4-13/2003 | 960 | 2003 | H3N2 |
| DQ179475 | A/United Kingdom/C4-3/2003 | 960 | 2003 | H3N2 |
| DQ179476 | A/United Kingdom/C4-4/2003 | 960 | 2003 | H3N2 |
| DQ179477 | A/United Kingdom/C4-5/2003 | 960 | 2003 | H3N2 |
| DQ179479 | A/United Kingdom/C4-7/2003 | 960 | 2003 | H3N2 |
| DQ179480 | A/United Kingdom/C4-8/2003 | 960 | 2003 | H3N2 |
| DQ179481 | A/United Kingdom/C4-9/2003 | 960 | 2003 | H3N2 |
| AY531033 | A/Wyoming/3/03 | 1701 | 2003 | H3N2 |
| ISDN38155 | A/Wyoming/3/2003 | 1050 | 2003 | H3N2 |
| ISDN38156 | A/Wyoming/3/2003 | 1050 | 2003 | H3N2 |
| AY695088 | A/Zhejiang/102/03 | 987 | 2003 | H3N2 |
| AY695084 | A/Zhejiang/78/03 | 987 | 2003 | H3N2 |
| AY695085 | A/Zhejiang/80/03 | 987 | 2003 | H3N2 |
| AY695086 | A/Zhejiang/81/03 | 987 | 2003 | H3N2 |
| AY714347 | A/Zhejiang/92/03 | 987 | 2003 | H3N2 |
| AY695087 | A/Zhejiang/95/03 | 987 | 2003 | H3N2 |
| AJ489861 | A/1352/02 | 975 | 2002 | H1N2 |
| AJ489862 | A/1660/02 | 975 | 2002 | H1N2 |
| AB117165 | A/Akita/86/2002 | 978 | 2002 | H1N1 |
| DQ179506 | A/Bangladesh/C5-6/2002 | 960 | 2002 | H3N2 |
| DQ179408 | A/Belgium/C2-11/2002 | 960 | 2002 | H3N2 |
| DQ179412 | A/Belgium/C2- | 960 | 2002 | H3N2 |
| DQ179399 | A/Belgium/C2-2/2002 | 942 | 2002 | H3N2 |
| DQ179400 | A/Belgium/C2-3/2002 | 942 | 2002 | H3N2 |
| DQ179405 | A/Belgium/C2-8/2002 | 960 | 2002 | H3N2 |
| CY007587 | A/Canterbury/01/2002 | 1721 | 2002 | H3N2 |
| CY007595 | A/Canterbury/02/2002 | 1721 | 2002 | H3N2 |
| CY008003 | A/Canterbury/04/2002 | 1721 | 2002 | H3N2 |
| CY007603 | A/Canterbury/05/2002 | 1721 | 2002 | H3N2 |
| CY008260 | A/Canterbury/06/2002 | 1714 | 2002 | H3N2 |
| CY008268 | A/Canterbury/09/2002 | 1717 | 2002 | H3N2 |
| CY008276 | A/Canterbury/10/2002 | 1717 | 2002 | H3N2 |
| CY007787 | A/Canterbury/102/200 | 1721 | 2002 | H3N2 |
| CY008011 | A/Canterbury/13/2002 | 1717 | 2002 | H3N2 |
| CY007843 | A/Canterbury/14/2002 | 1721 | 2002 | H3N2 |
| CY008284 | A/Canterbury/15/2002 | 1721 | 2002 | H3N2 |
| CY007651 | A/Canterbury/16/2002 | 1721 | 2002 | H3N2 |
| CY007659 | A/Canterbury/18/2002 | 1721 | 2002 | H3N2 |
| CY007851 | A/Canterbury/19/2002 | 1721 | 2002 | H3N2 |
| CY007859 | A/Canterbury/20/2002 | 1721 | 2002 | H3N2 |
| CY008019 | A/Canterbury/21/2002 | 1718 | 2002 | H3N2 |
| CY007667 | A/Canterbury/22/2002 | 1721 | 2002 | H3N2 |
| CY007867 | A/Canterbury/27/2002 | 1721 | 2002 | H3N2 |
| CY007875 | A/Canterbury/29/2002 | 1721 | 2002 | H3N2 |
| CY007883 | A/Canterbury/31/2002 | 1722 | 2002 | H3N2 |
| CY007891 | A/Canterbury/33/2002 | 1721 | 2002 | H3N2 |
| CY007899 | A/Canterbury/34/2002 | 1721 | 2002 | H3N2 |
| CY007675 | A/Canterbury/35/2002 | 1721 | 2002 | H3N2 |
| CY007683 | A/Canterbury/41/2002 | 1721 | 2002 | H3N2 |
| CY007915 | A/Canterbury/44/2002 | 1721 | 2002 | H3N2 |
| CY008027 | A/Canterbury/46/2002 | 1721 | 2002 | H3N2 |
| CY007691 | A/Canterbury/47/2002 | 1721 | 2002 | H3N2 |
| CY007699 | A/Canterbury/48/2002 | 1721 | 2002 | H3N2 |
| CY007707 | A/Canterbury/49/2002 | 1721 | 2002 | H3N2 |
| CY007715 | A/Canterbury/50/2002 | 1721 | 2002 | H3N2 |
| CY007723 | A/Canterbury/53/2002 | 1721 | 2002 | H3N2 |
| CY007731 | A/Canterbury/56/2002 | 1721 | 2002 | H3N2 |
| CY008035 | A/Canterbury/57/2002 | 1721 | 2002 | H3N2 |
| CY007923 | A/Canterbury/58/2002 | 1721 | 2002 | H3N2 |
| CY007739 | A/Canterbury/59/2002 | 1721 | 2002 | H3N2 |
| CY008292 | A/Canterbury/60/2002 | 1717 | 2002 | H3N2 |
| CY008300 | A/Canterbury/61/2002 | 1710 | 2002 | H3N2 |
| CY008308 | A/Canterbury/62/2002 | 1711 | 2002 | H3N2 |
| CY008316 | A/Canterbury/64/2002 | 1714 | 2002 | H3N2 |
| CY007931 | A/Canterbury/66/2002 | 1716 | 2002 | H3N2 |
| CY007747 | A/Canterbury/68/2002 | 1721 | 2002 | H3N2 |
| CY007755 | A/Canterbury/69/2002 | 1721 | 2002 | H3N2 |
| CY008324 | A/Canterbury/70/2002 | 1721 | 2002 | H3N2 |
| CY007939 | A/Canterbury/72/2002 | 1721 | 2002 | H3N2 |
| CY007763 | A/Canterbury/75/2002 | 1721 | 2002 | H3N2 |
| CY008332 | A/Canterbury/76/2002 | 1721 | 2002 | H3N2 |
| CY007947 | A/Canterbury/79/2002 | 1721 | 2002 | H3N2 |
| CY007771 | A/Canterbury/80/2002 | 1721 | 2002 | H3N2 |
| CY007779 | A/Canterbury/81/2002 | 1721 | 2002 | H3N2 |
| AY851471 | A/Changzhou/112/20 | 327 | 2002 | H1 |
| AY851472 | A/Changzhou/63/200 | 327 | 2002 | H1 |
| AY589648 | A/Cheju/274/2002 | 1653 | 2002 | H3N2 |
| AY589649 | A/Cheju/311/2002 | 1653 | 2002 | H3N2 |
| AY589650 | A/Cheonnam/323/200 | 1653 | 2002 | H3N2 |
| AY589651 | A/Cheonnam/338/200 | 1653 | 2002 | H3N2 |
| AY589652 | A/Cheonnam/340/200 | 1653 | 2002 | H3N2 |
| AY589653 | A/Cheonnam/432/200 | 1653 | 2002 | H3N2 |
| DQ179388 | A/China/C1-7/2002 | 960 | 2002 | H3N2 |
| DQ179389 | A/China/C1-8/2002 | 960 | 2002 | H3N2 |
| AY297154 | A/Chonnam/07/2002 | 1137 | 2002 | H1N1 |
| AY297156 | A/Chonnam/18/2002 | 1176 | 2002 | H1N1 |
| AY299502 | A/Chonnam/19/2002 | 1167 | 2002 | H1N1 |
| AY299498 | A/Chonnam/51/2002 | 1161 | 2002 | H1N1 |
| AY299506 | A/Chungbuk/50/2002 | 1161 | 2002 | H1N1 |
| AY589654 | A/Chungnam/447/200 | 1653 | 2002 | H3N2 |
| AY589655 | A/Daejeon/258/2002 | 1653 | 2002 | H3N2 |
| AY589656 | A/Daejeon/390/2002 | 1653 | 2002 | H3N2 |
| AJ457876 | A/Egypt/96/2002 | 976 | 2002 | H1N2 |
| AJ489852 | A/England/161/02 | 975 | 2002 | H1N1 |
| AJ489857 | A/England/18/02 | 975 | 2002 | H1N2 |
| AJ457911 | A/England/2/2002 | 1094 | 2002 | H1N2 |
| AY968041 | A/EspiritoSanto/88/02 | 991 | 2002 | H3N2 |
| DQ179402 | A/Europe/C2-5/2002 | 960 | 2002 | H3N2 |
| DQ167252 | A/Finland/1/2002 | 984 | 2002 | H3 |
| DQ167254 | A/Finland/12/2002 | 984 | 2002 | H3 |
| DQ167255 | A/Finland/13/2002 | 984 | 2002 | H3 |
| DQ167253 | A/Finland/2/2002 | 984 | 2002 | H3 |
| DQ167256 | A/Finland/22/2002 | 984 | 2002 | H3 |
| DQ167257 | A/Finland/28/2002 | 984 | 2002 | H3 |
| DQ167258 | A/Finland/51/2002 | 984 | 2002 | H3 |
| DQ179407 | A/Finland/C2-10/2002 | 960 | 2002 | H3N2 |
| DQ179409 | A/Finland/C2-12/2002 | 960 | 2002 | H3N2 |
| DQ179410 | A/Finland/C2-13/2002 | 960 | 2002 | H3N2 |
| DQ179411 | A/Finland/C2-14/2002 | 960 | 2002 | H3N2 |
| DQ179414 | A/Finland/C2-17/2002 | 960 | 2002 | H3N2 |
| DQ179403 | A/Finland/C2-6/2002 | 960 | 2002 | H3N2 |
| DQ227423 | A/Fujian/411/02-like | 1726 | 2002 | H3N2 |
| DQ227428 | A/Fujian/411/02-like | 1640 | 2002 | H3N2 |
| DQ227429 | A/Fujian/411/02-like | 1653 | 2002 | H3N2 |
| DQ227430 | A/Fujian/411/02-like | 1650 | 2002 | H3N2 |
| DQ227431 | A/Fujian/411/02-like | 1673 | 2002 | H3N2 |
| DQ227424 | A/Fujian/411/02-like | 1655 | 2002 | H3N2 |
| DQ227425 | A/Fujian/411/02-like | 1655 | 2002 | H3N2 |
| DQ227426 | A/Fujian/411/02-like | 1655 | 2002 | H3N2 |
| DQ227427 | A/Fujian/411/02-like | 1655 | 2002 | H3N2 |
| ISDN38157 | A/Fujian/411/2002 | 1042 | 2002 | H3N2 |
| AY738729 | A/Fujian/411/2002 | 591 | 2002 | H3N2 |
| AB117167 | A/Gifu-C/9/2002 | 978 | 2002 | H1N1 |
| AY299507 | A/Gwangju/55/2002 | 1179 | 2002 | H1N1 |
| AY299508 | A/Gwangju/57/2002 | 1167 | 2002 | H1N1 |
| AY299509 | A/Gwangju/58/2002 | 1176 | 2002 | H1N1 |
| AY299499 | A/Gwangju/90/2002 | 1164 | 2002 | H1N1 |
| AY377129 | A/Gyeongbuk/2/02 | 1047 | 2002 | H3N2 |
| AB221016 | A/Hanoi/184/2002 | 979 | 2002 | H3N2 |
| AB221017 | A/Hanoi/197/2002 | 979 | 2002 | H3N2 |
| AB221018 | A/Hanoi/217/2002 | 982 | 2002 | H3N2 |

TABLE 1-continued

INFLUENZA TYPE A HA SEQUENCES

| Accession | Strain | Length | Year | Serotype |
|---|---|---|---|---|
| AB221019 | A/Hanoi/235/2002 | 979 | 2002 | H3N2 |
| DQ179391 | A/Hong Kong/C1- | 960 | 2002 | H3N2 |
| DQ179392 | A/Hong Kong/C1- | 960 | 2002 | H3N2 |
| DQ179394 | A/Hong Kong/C1- | 960 | 2002 | H3N2 |
| DQ179390 | A/Hong Kong/C1- | 960 | 2002 | H3N2 |
| AY589657 | A/Incheon/260/2002 | 1653 | 2002 | H3N2 |
| DQ179418 | A/India/C3-4/2002 | 960 | 2002 | H3N2 |
| DQ179459 | A/India/C3-45/2002 | 960 | 2002 | H3N2 |
| DQ179472 | A/India/C3-58/2002 | 960 | 2002 | H3N2 |
| AJ457930 | A/Ireland/649/2002 | 1065 | 2002 | H1N1 |
| ISDN38162 | A/Ishikawa/102/2002 | 987 | 2002 | H3N2 |
| AJ457878 | A/Israel/6/2002 | 1059 | 2002 | H1N2 |
| DQ179401 | A/Israel/C2-4/2002 | 960 | 2002 | H3N2 |
| DQ179404 | A/Israel/C2-7/2002 | 960 | 2002 | H3N2 |
| DQ179406 | A/Israel/C2-9/2002 | 960 | 2002 | H3N2 |
| AB117168 | A/Iwate/33/2002 | 978 | 2002 | H1N1 |
| ISDN140348 | A/Korea/770/2002 | 1033 | 2002 | H3N2 |
| ISDN38180 | A/KUMAMOTO/102/ | 987 | 2002 | H3N2 |
| ISDN69739 | A/Kumamoto/102/200 | 987 | 2002 | H3N2 |
| AY589658 | A/Kwangju/219/2002 | 1653 | 2002 | H3N2 |
| AY589659 | A/Kwangju/243/2002 | 1653 | 2002 | H3N2 |
| AY589660 | A/Kyongbuk/320/200 | 1653 | 2002 | H3N2 |
| AY589661 | A/Kyongnam/347/200 | 1653 | 2002 | H3N2 |
| AB117170 | A/Kyoto-C/3/2002 | 978 | 2002 | H1N1 |
| AJ457861 | A/Latvia/686/2002 | 1053 | 2002 | H1N1 |
| AJ457877 | A/Madrid/1216/2002 | 1095 | 2002 | H1N1 |
| DQ179468 | A/Malaysia/C3- | 960 | 2002 | H3N2 |
| DQ179501 | A/Malaysia/C5- | 960 | 2002 | H3N2 |
| DQ179502 | A/Malaysia/C5- | 960 | 2002 | H3N2 |
| DQ179505 | A/Malaysia/C5- | 960 | 2002 | H3N2 |
| DQ179508 | A/Malaysia/C5- | 960 | 2002 | H3N2 |
| AB117171 | A/Nagoya/32/2002 | 978 | 2002 | H1N1 |
| AB117172 | A/Nara/41/2002 | 978 | 2002 | H1N1 |
| AY661031 | A/Netherlands/1/02 | 1095 | 2002 | H3N2 |
| AY661030 | A/Netherlands/120/02 | 1095 | 2002 | H3N2 |
| CY000225 | A/New | 1760 | 2002 | H3N2 |
| CY001104 | A/New | 1711 | 2002 | H3N2 |
| CY001317 | A/New | 1759 | 2002 | H3N2 |
| CY000417 | A/New | 1711 | 2002 | H3N2 |
| CY001184 | A/New | 1711 | 2002 | H3N2 |
| CY001128 | A/New | 1711 | 2002 | H3N2 |
| CY000489 | A/New | 1760 | 2002 | H3N2 |
| CY001144 | A/New | 1730 | 2002 | H3N2 |
| CY000497 | A/New | 1760 | 2002 | H3N2 |
| CY000529 | A/New | 1760 | 2002 | H3N2 |
| CY000113 | A/New | 1762 | 2002 | H3N2 |
| CY000933 | A/New | 1743 | 2002 | H3N2 |
| CY001325 | A/New | 1741 | 2002 | H3N2 |
| CY000233 | A/New | 1762 | 2002 | H3N2 |
| CY000537 | A/New | 1761 | 2002 | H3N2 |
| CY000545 | A/New | 1741 | 2002 | H3N2 |
| CY000553 | A/New | 1741 | 2002 | H3N2 |
| CY000793 | A/New | 1762 | 2002 | H3N2 |
| CY001333 | A/New | 1754 | 2002 | H3N2 |
| CY000941 | A/New | 1762 | 2002 | H3N2 |
| CY000625 | A/New | 1718 | 2002 | H3N2 |
| CY000241 | A/New | 1762 | 2002 | H3N2 |
| CY001197 | A/New | 1741 | 2002 | H3N2 |
| CY001437 | A/New | 1718 | 2002 | H3N2 |
| CY001944 | A/New | 1714 | 2002 | H3N2 |
| CY000425 | A/New | 1760 | 2002 | H3N2 |
| CY000313 | A/New | 1732 | 2002 | H3N2 |
| CY000585 | A/New | 1762 | 2002 | H3N2 |
| CY000433 | A/New | 1760 | 2002 | H3N2 |
| CY000329 | A/New | 1741 | 2002 | H3N2 |
| CY000441 | A/New | 1760 | 2002 | H3N2 |
| CY000337 | A/New | 1760 | 2002 | H3N2 |
| CY001237 | A/New | 1711 | 2002 | H3N2 |
| CY003368 | A/New | 1738 | 2002 | H1N2 |
| CY002528 | A/New | 1754 | 2002 | H1N1 |
| CY001728 | A/New | 1760 | 2002 | H3N2 |
| CY002128 | A/New | 1741 | 2002 | H3N2 |
| CY001736 | A/New | 1760 | 2002 | H3N2 |
| CY003304 | A/New | 1755 | 2002 | H1N1 |
| CY003096 | A/New | 1760 | 2002 | H3N2 |
| CY003104 | A/New | 1761 | 2002 | H3N2 |
| CY003112 | A/New | 1750 | 2002 | H3N2 |
| CY003120 | A/New | 1762 | 2002 | H3N2 |
| CY003424 | A/New | 1750 | 2002 | H3N2 |
| CY003123 | A/New | 1762 | 2002 | H3N2 |
| CY003136 | A/New | 1762 | 2002 | H3N2 |
| CY003144 | A/New | 1761 | 2002 | H3N2 |
| CY003152 | A/New | 1749 | 2002 | H3N2 |
| CY003160 | A/New | 1741 | 2002 | H3N2 |
| CY003168 | A/New | 1750 | 2002 | H3N2 |
| CY003176 | A/New | 1751 | 2002 | H3N2 |
| CY003184 | A/New | 1737 | 2002 | H3N2 |
| CY003192 | A/New | 1760 | 2002 | H3N2 |
| CY003769 | A/New | 1730 | 2002 | H1N2 |
| CY003200 | A/New | 1762 | 2002 | H3N2 |
| CY003208 | A/New | 1737 | 2002 | H3N2 |
| CY003777 | A/New | 1762 | 2002 | H3N2 |
| CY006675 | A/New | 1734 | 2002 | H1N1 |
| CY001152 | A/New York/74/2002 | 1741 | 2002 | H3N2 |
| CY001301 | A/New York/75/2002 | 1736 | 2002 | H3N2 |
| CY001429 | A/New York/76/2002 | 1711 | 2002 | H3N2 |
| CY001680 | A/New York/78/2002 | 1468 | 2002 | H1N2 |
| CY001261 | A/New York/81/2002 | 1711 | 2002 | H3N2 |
| CY000281 | A/New York/86/2002 | 1760 | 2002 | H3N2 |
| CY000393 | A/New York/87/2002 | 1711 | 2002 | H3N2 |
| CY001072 | A/New York/88/2002 | 1733 | 2002 | H3N2 |
| CY000401 | A/New York/89/2002 | 1711 | 2002 | H3N2 |
| CY000409 | A/New York/90/2002 | 1711 | 2002 | H3N2 |
| CY000209 | A/New York/91/2002 | 1760 | 2002 | H3N2 |
| CY000289 | A/New York/92/2002 | 1741 | 2002 | H3N2 |
| CY000925 | A/New York/93/2002 | 1711 | 2002 | H3N2 |
| CY000217 | A/New York/95/2002 | 1760 | 2002 | H3N2 |
| CY000297 | A/New York/96/2002 | 1711 | 2002 | H3N2 |
| CY001309 | A/New York/97/2002 | 1719 | 2002 | H3N2 |
| CY001080 | A/New York/99/2002 | 1762 | 2002 | H3N2 |
| AY138518 | A/ningbo/17/2002 | 987 | 2002 | H3N2 |
| AY138517 | A/ningbo/25/2002 | 987 | 2002 | H3N2 |
| AB117173 | A/Okinawa/225/2002 | 978 | 2002 | H1N1 |
| ISDN13326 | A/Oslo/398/2002 | 1144 | 2002 | H3N2 |
| ISDN14998 | A/Oslo/5811/2002 | 551 | 2002 | H3N2 |
| ISDN13294 | A/Oslo/669/2002 | 1144 | 2002 | H3N2 |
| DQ179429 | A/Philippines/C3- | 960 | 2002 | H3N2 |
| DQ179431 | A/Philippines/C3- | 960 | 2002 | H3N2 |
| DQ179432 | A/Philippines/C3- | 960 | 2002 | H3N2 |
| DQ179416 | A/Philippines/C3- | 671 | 2002 | H3N2 |
| DQ179434 | A/Philippines/C3- | 960 | 2002 | H3N2 |
| DQ179435 | A/Philippines/C3- | 858 | 2002 | H3N2 |
| DQ179437 | A/Philippines/C3- | 960 | 2002 | H3N2 |
| DQ179440 | A/Philippines/C3- | 960 | 2002 | H3N2 |
| DQ179441 | A/Philippines/C3- | 661 | 2002 | H3N2 |
| DQ179442 | A/Philippines/C3- | 681 | 2002 | H3N2 |
| DQ179445 | A/Philippines/C3- | 960 | 2002 | H3N2 |
| DQ179446 | A/Philippines/C3- | 960 | 2002 | H3N2 |
| DQ179447 | A/Philippines/C3- | 960 | 2002 | H3N2 |
| DQ179448 | A/Philippines/C3- | 960 | 2002 | H3N2 |
| DQ179449 | A/Philippines/C3- | 960 | 2002 | H3N2 |
| DQ179450 | A/Philippines/C3- | 960 | 2002 | H3N2 |
| DQ179453 | A/Philippines/C3- | 960 | 2002 | H3N2 |
| DQ179455 | A/Philippines/C3- | 633 | 2002 | H3N2 |
| DQ179456 | A/Philippines/C3- | 633 | 2002 | H3N2 |
| DQ179457 | A/Philippines/C3- | 960 | 2002 | H3N2 |
| DQ179458 | A/Philippines/C3- | 960 | 2002 | H3N2 |
| DQ179462 | A/Philippines/C3- | 960 | 2002 | H3N2 |
| DQ179464 | A/Philippines/C3- | 960 | 2002 | H3N2 |
| DQ179467 | A/Philippines/C3- | 960 | 2002 | H3N2 |
| DQ179470 | A/Philippines/C3- | 960 | 2002 | H3N2 |
| DQ179471 | A/Philippines/C3- | 960 | 2002 | H3N2 |
| AY299503 | A/Pusan/22/2002 | 1149 | 2002 | H1N1 |
| AY297157 | A/Pusan/23/2002 | 1158 | 2002 | H1N1 |
| AY299494 | A/Pusan/24/2002 | 1128 | 2002 | H1N1 |
| AY299504 | A/Pusan/44/2002 | 1167 | 2002 | H1N1 |
| AY299496 | A/Pusan/45/2002 | 1167 | 2002 | H1N1 |
| AY299497 | A/Pusan/46/2002 | 1176 | 2002 | H1N1 |
| AY299505 | A/Pusan/47/2002 | 1170 | 2002 | H1N1 |
| AY589647 | A/Pusan/504/2002 | 1653 | 2002 | H3N2 |
| AY968037 | A/RioGdoSul/205/02 | 1002 | 2002 | H3N2 |
| AY971011 | A/RioGdoSul/358/02 | 1008 | 2002 | H1N1 |

TABLE 1-continued

INFLUENZA TYPE A HA SEQUENCES

| Accession | Strain | Length | Year | Serotype |
|---|---|---|---|---|
| AB117174 | A/Sapporo/186/2002 | 978 | 2002 | H1N1 |
| AJ489858 | A/Scotland/15/02 | 975 | 2002 | H1N2 |
| AY297155 | A/Seoul/11/2002 | 1176 | 2002 | H1N1 |
| AY299500 | A/Seoul/13/2002 | 1167 | 2002 | H1N1 |
| AY299501 | A/Seoul/15/2002 | 1149 | 2002 | H1N1 |
| AY299495 | A/Seoul/33/2002 | 1167 | 2002 | H1N1 |
| AB117175 | A/Shiga/12/2002 | 978 | 2002 | H1N1 |
| DQ179507 | A/Singapore/C5- | 960 | 2002 | H3N2 |
| CY007907 | A/South | 1721 | 2002 | H3N2 |
| DQ179503 | A/South Korea/C5- | 960 | 2002 | H3N2 |
| DQ179504 | A/South Korea/C5- | 960 | 2002 | H3N2 |
| AY968038 | A/StaCatarina/311/02 | 998 | 2002 | H3N2 |
| AY968039 | A/StaCatarina/327/02 | 1007 | 2002 | H3N2 |
| AY968040 | A/StaCatarina/339/02 | 1002 | 2002 | H3N2 |
| AJ457909 | A/Stockholm/13/2002 | 1098 | 2002 | H1N2 |
| AY884276 | A/Stockholm/26/2002 | 1650 | 2002 | H3N2 |
| AY884280 | A/Stockholm/26/2002 | 1650 | 2002 | H3N2 |
| AY884279 | A/Stockholm/26/2002 | 1650 | 2002 | H3N2 |
| AY884277 | A/Stockholm/26/2002 | 1650 | 2002 | H3N2 |
| AY884278 | A/Stockholm/26/2002 | 1650 | 2002 | H3N2 |
| AY884281 | A/Stockholm/27/2002 | 1650 | 2002 | H3N2 |
| AY884282 | A/Stockholm/27/2002 | 1650 | 2002 | H3N2 |
| AY884283 | A/Stockholm/27/2002 | 1650 | 2002 | H3N2 |
| AY884284 | A/Stockholm/27/2002 | 1650 | 2002 | H3N2 |
| AJ517813 | A/Switzerland/3100/2 | 975 | 2002 | H1N1 |
| AJ517815 | A/Switzerland/8808/2 | 1091 | 2002 | H1N1 |
| AY604804 | A/Taiwan/0032/2002 | 494 | 2002 | H1N1 |
| AY604795 | A/Taiwan/0061/2002 | 494 | 2002 | H1N1 |
| AY604803 | A/Taiwan/0069/2002 | 494 | 2002 | H1N1 |
| AY604805 | A/Taiwan/0078/2002 | 494 | 2002 | H1N1 |
| AY604797 | A/Taiwan/0094/2002 | 494 | 2002 | H1N1 |
| AY604796 | A/Taiwan/0116/2002 | 494 | 2002 | H1N1 |
| AY604801 | A/Taiwan/0859/2002 | 494 | 2002 | H1N1 |
| AY604800 | A/Taiwan/0983/2002 | 494 | 2002 | H1N1 |
| AY604798 | A/Taiwan/1887/2002 | 494 | 2002 | H1N1 |
| AY604799 | A/Taiwan/1906/2002 | 494 | 2002 | H1N1 |
| AY604802 | A/Taiwan/1922/2002 | 494 | 2002 | H1N1 |
| DQ249260 | A/Taiwan/2985/2002 | 1775 | 2002 | H1N1 |
| AY604811 | A/Taiwan/3131/2002 | 791 | 2002 | H3N2 |
| AY604814 | A/Taiwan/3744/2002 | 791 | 2002 | H3N2 |
| AY604813 | A/Taiwan/4673/2002 | 791 | 2002 | H3N2 |
| AY604812 | A/Taiwan/4680/2002 | 791 | 2002 | H3N2 |
| AY604809 | A/Taiwan/4938/2002 | 791 | 2002 | H3N2 |
| AY604815 | A/Taiwan/4954/2002 | 791 | 2002 | H3N2 |
| AY604810 | A/Taiwan/4963/2002 | 791 | 2002 | H3N2 |
| AY604816 | A/Taiwan/5153/2002 | 791 | 2002 | H3N2 |
| DQ179461 | A/Taiwan/C3-47/2002 | 960 | 2002 | H3N2 |
| DQ179466 | A/Taiwan/C3-52/2002 | 960 | 2002 | H3N2 |
| AY947476 | A/Texas/131/2002 | 1094 | 2002 | H3N2 |
| DQ179393 | A/Thailand/C1- | 618 | 2002 | H3N2 |
| DQ179395 | A/Thailand/C1- | 960 | 2002 | H3N2 |
| DQ179396 | A/Thailand/C1- | 960 | 2002 | H3N2 |
| DQ179397 | A/Thailand/C1- | 630 | 2002 | H3N2 |
| DQ179415 | A/Thailand/C3-1/2002 | 960 | 2002 | H3N2 |
| DQ179424 | A/Thailand/C3- | 960 | 2002 | H3N2 |
| DQ179425 | A/Thailand/C3- | 960 | 2002 | H3N2 |
| DQ179426 | A/Thailand/C3- | 960 | 2002 | H3N2 |
| DQ179427 | A/Thailand/C3- | 960 | 2002 | H3N2 |
| DQ179428 | A/Thailand/C3- | 960 | 2002 | H3N2 |
| DQ179430 | A/Thailand/C3- | 960 | 2002 | H3N2 |
| DQ179433 | A/Thailand/C3- | 960 | 2002 | H3N2 |
| DQ179436 | A/Thailand/C3- | 960 | 2002 | H3N2 |
| DQ179438 | A/Thailand/C3- | 851 | 2002 | H3N2 |
| DQ179439 | A/Thailand/C3- | 960 | 2002 | H3N2 |
| DQ179443 | A/Thailand/C3- | 960 | 2002 | H3N2 |
| DQ179417 | A/Thailand/C3- | 960 | 2002 | H3N2 |
| DQ179444 | A/Thailand/C3- | 674 | 2002 | H3N2 |
| DQ179451 | A/Thailand/C3- | 960 | 2002 | H3N2 |
| DQ179452 | A/Thailand/C3- | 960 | 2002 | H3N2 |
| DQ179454 | A/Thailand/C3- | 960 | 2002 | H3N2 |
| DQ179460 | A/Thailand/C3- | 669 | 2002 | H3N2 |
| DQ179463 | A/Thailand/C3- | 960 | 2002 | H3N2 |
| DQ179419 | A/Thailand/C3- | 960 | 2002 | H3N2 |
| DQ179465 | A/Thailand/C3- | 960 | 2002 | H3N2 |
| DQ179469 | A/Thailand/C3- | 960 | 2002 | H3N2 |
| DQ179420 | A/Thailand/C3- | 960 | 2002 | H3N2 |
| DQ179421 | A/Thailand/C3- | 960 | 2002 | H3N2 |
| DQ179422 | A/Thailand/C3- | 960 | 2002 | H3N2 |
| DQ179423 | A/Thailand/C3- | 960 | 2002 | H3N2 |
| AB117176 | A/Tokushima/3/2002 | 978 | 2002 | H1N1 |
| DQ179413 | A/United Kingdom/C2-16/2002 | 960 | 2002 | H3N2 |
| AB117177 | A/Yamaguchi/12/200 | 978 | 2002 | H1N1 |
| AB117178 | A/Yamanashi/1/2002 | 978 | 2002 | H1N1 |
| AB126622 | A/Yokohama/22/2002 | 1144 | 2002 | H1N2 |
| AB126630 | A/Yokohama/47/2002 | 1144 | 2002 | H1N2 |
| AB117179 | A/Yokobama/62/2002 | 978 | 2002 | H1N1 |
| AY138516 | A/zhejiang/11/2002 | 987 | 2002 | H3N2 |
| AY138519 | A/zbejiang/8/2002 | 987 | 2002 | H3N2 |
| M489859 | A/575/01 | 975 | 2001 | H1N2 |
| AJ489860 | A/576/01 | 975 | 2001 | H1N2 |
| ISDN13440 | A/AUCKLAND/21/20 | 915 | 2001 | H1 |
| ISDN13434 | A/AUCKLAND/65/20 | 952 | 2001 | H1 |
| ISDN13432 | A/BANGKOK/31/200 | 919 | 2001 | H1 |
| DQ335992 | A/Brazil/099/01 | 975 | 2001 | H1N1 |
| DQ335993 | A/Brazil/101/01 | 975 | 2001 | H1N1 |
| DQ335994 | A/Brazil/103/01 | 975 | 2001 | H1N1 |
| DQ335995 | A/Brazil/104/01 | 975 | 2001 | H1N1 |
| DQ335996 | A/Brazil/109/01 | 975 | 2001 | H1N1 |
| DQ335997 | A/Brazil/112/01 | 975 | 2001 | H1N1 |
| DQ335998 | A/Brazil/113/01 | 975 | 2001 | H1N1 |
| DQ335999 | A/Brazil/114/01 | 975 | 2001 | H1N1 |
| DQ336000 | A/Brazil/121/01 | 975 | 2001 | H1N1 |
| DQ336001 | A/Brazil/122/01 | 975 | 2001 | H1N1 |
| DQ336006 | A/Brazil/125/01 | 984 | 2001 | H3N2 |
| DQ336002 | A/Brazil/126/01 | 975 | 2001 | H1N1 |
| DQ336003 | A/Brazil/133/01 | 975 | 2001 | H1N1 |
| DQ336004 | A/Brazil/140/01 | 975 | 2001 | H1N1 |
| AF534056 | A/Buenos | 984 | 2001 | H3N2 |
| AF503482 | A/Canada/4/2001 | 1029 | 2001 | H1N2 |
| CY010396 | A/Canterbury/01/2001 | 1746 | 2001 | H1N1 |
| CY009948 | A/Canterbury/06/2001 | 1721 | 2001 | H3N2 |
| CY009556 | A/Canterbury/07/2001 | 1721 | 2001 | H3N2 |
| CY009860 | A/Canterbury/08/2001 | 1746 | 2001 | H1N1 |
| CY009396 | A/Canterbury/10/2001 | 1721 | 2001 | H3N2 |
| CY010476 | A/Canterbury/106/200 | 1746 | 2001 | H1N1 |
| CY010308 | A/Canterbury/119/200 | 1746 | 2001 | H1N1 |
| CY010316 | A/Canterbury/125/200 | 1746 | 2001 | H1N1 |
| CY010324 | A/Canterbury/126/200 | 1737 | 2001 | H1N1 |
| CY010332 | A/Canterbury/139/200 | 1746 | 2001 | H1N1 |
| CY009588 | A/Canterbury/140/200 | 1723 | 2001 | H3N2 |
| CY010340 | A/Canterbury/144/200 | 1746 | 2001 | H1N1 |
| CY009852 | A/Canterbury/1461200 | 1721 | 2001 | H3N2 |
| CY009436 | A/Canterbury/149/200 | 1721 | 2001 | H3N2 |
| CY009980 | A/Canterbury/153/200 | 1739 | 2001 | H1N1 |
| CY010348 | A/Canterbury/155/200 | 1746 | 2001 | H1N1 |
| CY009876 | A/Canterbury/16/2001 | 1746 | 2001 | H1N1 |
| CY010148 | A/Canterbury/17/2001 | 1747 | 2001 | H1N1 |
| CY010156 | A/Canterbury/19/2001 | 1746 | 2001 | H1N1 |
| CY010764 | A/Canterbury/20/2001 | 1746 | 2001 | H1N1 |
| CY010164 | A/Canterbury/21/2001 | 1746 | 2001 | H1N1 |
| CY010772 | A/Canterbury/22/2001 | 1746 | 2001 | H1N1 |
| CY010172 | A/Canterbury/23/2001 | 1740 | 2001 | H1N1 |
| CY010180 | A/Canterbury/24/2001 | 1747 | 2001 | H1N1 |
| CY010188 | A/Canterbury/25/2001 | 1746 | 2001 | H1N1 |
| CY010196 | A/Canterbury/27/2001 | 1746 | 2001 | H1N1 |
| CY010204 | A/Canterbury/29/2001 | 1746 | 2001 | H1N1 |
| CY010212 | A/Canterbury/30/2001 | 1746 | 2001 | H1N1 |
| CY010220 | A/Canterbury/34/2001 | 1746 | 2001 | H1N1 |
| CY010228 | A/Canterbury/35/2001 | 1745 | 2001 | H1N1 |
| CY010548 | A/Canterbury/36/2001 | 1721 | 2001 | H3N2 |
| CY009412 | A/Canterbury/37/2001 | 1721 | 2001 | H3N2 |
| CY010236 | A/Canterbusy/40/2001 | 1746 | 2001 | H1N1 |
| CY009884 | A/Canterbury/41/2001 | 1746 | 2001 | H1N1 |
| CY010780 | A/Canterbury/42/2001 | 1744 | 2001 | H1N1 |
| CY009572 | A/Canterbury/43/2001 | 1721 | 2001 | H3N2 |
| CY009420 | A/Canterbury/44/2001 | 1721 | 2001 | H3N2 |
| CY010244 | A/Canterbury/45/2001 | 1747 | 2001 | H1N1 |
| CY010252 | A/Canterbury/47/2001 | 1737 | 2001 | H1N1 |
| CY010260 | A/Canterbury/48/2001 | 1747 | 2001 | H1N1 |
| CY009580 | A/Canterbury/50/2001 | 1721 | 2001 | H3N2 |

TABLE 1-continued

INFLUENZA TYPE A HA SEQUENCES

| Accession | Strain | Length | Year | Serotype |
|---|---|---|---|---|
| CY010412 | A/Canterbury/51/2001 | 1737 | 2001 | H1N1 |
| CY010268 | A/Canterbury/53/2001 | 1746 | 2001 | H1N1 |
| CY010556 | A/Canterbury/54/2001 | 1746 | 2001 | H1N1 |
| CY010276 | A/Canterbury/58/2001 | 1746 | 2001 | H1N1 |
| CY010420 | A/Canterbury/63/2001 | 1746 | 2001 | H1N1 |
| CY010284 | A/Canterbury/64/2001 | 1746 | 2001 | H1N1 |
| CY010428 | A/Canterbury/65/2001 | 1747 | 2001 | H1N1 |
| CY009956 | A/Canterbury/66/2001 | 1746 | 2001 | H1N1 |
| CY010436 | A/Canterbury/68/2001 | 1746 | 2001 | H1N1 |
| CY010444 | A/Canterbury/69/2001 | 1746 | 2001 | H1N1 |
| CY010452 | A/Canterbury/70/2001 | 1747 | 2001 | H1N1 |
| CY010460 | A/Canterbury/71/2001 | 1747 | 2001 | H1N1 |
| CY010292 | A/Canterbury/72/2001 | 1746 | 2001 | H1N1 |
| CY010300 | A/Canterbury/73/2001 | 1747 | 2001 | H1N1 |
| CY009964 | A/Canterbury/74/2001 | 1746 | 2001 | H1N1 |
| CY009972 | A/Canterbury/76/2001 | 1747 | 2001 | H1N1 |
| CY010468 | A/Canterbury/79/2001 | 1748 | 2001 | H1N1 |
| AF534055 | A/Chaco/R538/01 | 984 | 2001 | H3N2 |
| AY682833 | A/Charlottesville/6/20 | 1665 | 2001 | H1N1 |
| DQ179383 | A/China/C1-2/2001 | 960 | 2001 | H3N2 |
| DQ179384 | A/China/C1-3/2001 | 960 | 2001 | H3N2 |
| DQ179386 | A/China/C1-5/2001 | 960 | 2001 | H3N2 |
| DQ179387 | A/China/C1-6/2001 | 960 | 2001 | H3N2 |
| AF534058 | A/Cordoba/1007333/0 | 984 | 2001 | H3N2 |
| ISDN13435 | A/DARWIN/5/2001 | 979 | 2001 | H1N1 |
| AJ457865 | A/Denmark/40/2001 | 1071 | 2001 | H1N1 |
| AY063229 | A/Ecuador/2625/01 | 1032 | 2001 | H1N1 |
| AY063228 | A/Ecuador/2630/01 | 1029 | 2001 | H1N1 |
| AJ457871 | A/Egypt/101/2001 | 1092 | 2001 | H1N2 |
| AF503486 | A/Egypt/21181/2001 | 1029 | 2001 | H1N2 |
| AJ457875 | A/Egypt/84/2001 | 1092 | 2001 | H1N2 |
| AB117180 | A/Ehime/1/2001 | 978 | 2001 | H1N1 |
| AJ489853 | A/England/627/01 | 975 | 2001 | H1N2 |
| AJ489855 | A/England/689/01 | 975 | 2001 | H1N2 |
| AJ489856 | A/England/691/01 | 975 | 2001 | H1N2 |
| AY971006 | A/EspiritoSanto/141/0 | 1038 | 2001 | H1N1 |
| AY971008 | A/EspiritoSanto/39/01 | 1033 | 2001 | H1N1 |
| AY971009 | A/EspiritoSanto/45/01 | 1059 | 2001 | H1N1 |
| AY968027 | A/EspiritoSanto/452/0 | 525 | 2001 | H3N2 |
| AY968028 | A/EspiritoSanto/454/0 | 930 | 2001 | H3N2 |
| AB117181 | A/Fukui/1/2001 | 978 | 2001 | H1N1 |
| AJ457868 | A/Greece/158/2001 | 1037 | 2001 | H1N1 |
| AJ457867 | A/Greece/204/2001 | 1056 | 2001 | H1N1 |
| AJ457869 | A/Hannover/71/2001 | 1044 | 2001 | H1N1 |
| DQ397950 | A/Hiroshima/37/2001 | 1698 | 2001 | H1N1 |
| AJ457872 | A/Hong | 1088 | 2001 | H1N2 |
| DQ179385 | A/Hong Kong/C1- | 960 | 2001 | H3N2 |
| AJ457873 | A/Iceland/57/2001 | 1090 | 2001 | H1N1 |
| AF503474 | A/India/66193/2001 | 1029 | 2001 | H1N2 |
| AF503475 | A/India/77251/2001 | 1019 | 2001 | H1N2 |
| AF503478 | A/India/77267/2001 | 1029 | 2001 | H1N2 |
| AF503477 | A/India/77302/2001 | 1029 | 2001 | H1N2 |
| AF503485 | A/India/77308/2001 | 1029 | 2001 | H1N2 |
| ISDN13436 | A/INDONESIA/8148/ | 978 | 2001 | H1N1 |
| AB117182 | A/Iwate/1003/2001 | 978 | 2001 | H1N1 |
| AB117183 | A/Kagawa/243/2001 | 978 | 2001 | H1N1 |
| AB117169 | A/Kitakyusyu/793/2001 | 978 | 2001 | H1N1 |
| AJ457866 | A/latvia/2524/2001 | 1054 | 2001 | H1N1 |
| AJ457886 | A/Madrid/1082/2001 | 1083 | 2001 | H1N1 |
| AB117184 | A/Mie/1/2001 | 978 | 2001 | H1N1 |
| AJ457874 | A/Morocco/69/2001 | 976 | 2001 | H1N1 |
| AB117185 | A/Nagano/1101/2001 | 978 | 2001 | H1N1 |
| AB117186 | A/Nagoya/26/2001 | 978 | 2001 | H1N1 |
| AY851467 | A/Nanjing/Children3/ | 327 | 2001 | H1 |
| AY851468 | A/Nanjing/Children4/ | 327 | 2001 | H1 |
| AB117187 | A/Nara/13/2001 | 978 | 2001 | H1N1 |
| AY661022 | A/Netherlands/118/01 | 1095 | 2001 | H1N1 |
| AY661023 | A/Netherlands/124/01 | 1095 | 2001 | H3N2 |
| AY661024 | A/Netherlands/126/01 | 1095 | 2001 | H3N2 |
| AF534059 | A/Neuquen/1016002/ | 984 | 2001 | H3N2 |
| AF534060 | A/Neuquen/1038288/ | 984 | 2001 | H3N2 |
| AF534057 | A/Neuquen/2260/01 | 984 | 2001 | H3N2 |
| AF503484 | A/Nevada/5/2001 | 1023 | 2001 | H1N1 |
| CY000305 | A/New | 1711 | 2001 | H3N2 |
| CY000584 | A/New | 1762 | 2001 | H3N2 |
| CY000321 | A/New | 1711 | 2001 | H3N2 |
| CY001952 | A/New | 1754 | 2001 | H1N1 |
| CY002616 | A/New | 1754 | 2001 | H1N1 |
| CY006419 | A/New | 1740 | 2001 | H1N1 |
| CY010852 | A/New | 1731 | 2001 | H1N1 |
| CY003000 | A/New | 1724 | 2001 | H1N1 |
| CY003008 | A/New | 1727 | 2001 | H1N1 |
| CY006355 | A/New | 1748 | 2001 | H1N1 |
| CY003016 | A/New | 1748 | 2001 | H1N1 |
| CY001720 | A/New | 1759 | 2001 | H3N2 |
| CY002568 | A/New | 1763 | 2001 | H1N1 |
| CY002816 | A/New | 1760 | 2001 | H3N2 |
| CY003312 | A/New | 1748 | 2001 | H1N1 |
| CY006363 | A/New | 1775 | 2001 | H1N1 |
| CY003392 | A/New | 1727 | 2001 | H1N1 |
| CY003400 | A/New | 1748 | 2001 | H1N1 |
| CY008148 | A/New | 1743 | 2001 | H1N1 |
| CY002800 | A/New | 1748 | 2001 | H1N1 |
| CY006875 | A/New | 1735 | 2001 | H1N1 |
| CY002672 | A/New | 1763 | 2001 | H1N1 |
| CY002696 | A/New | 1736 | 2001 | H1N1 |
| CY003024 | A/New York/341/2001 | 1756 | 2001 | H1N1 |
| CY003320 | A/New York/342/2001 | 1747 | 2001 | H1N1 |
| CY002392 | A/New York/343/2001 | 1757 | 2001 | H1N1 |
| CY006779 | A/New York/344/2001 | 1735 | 2001 | H1N1 |
| CY002400 | A/New York/345/2001 | 1729 | 2001 | H1N1 |
| CY003328 | A/New | 1727 | 2001 | H1N1 |
| CY003080 | A/New | 1737 | 2001 | H3N2 |
| CY003088 | A/New | 1760 | 2001 | H3N2 |
| CY009236 | A/New | 1744 | 2001 | H1N1 |
| CY003464 | A/New | 1748 | 2001 | H1N1 |
| CY003472 | A/New | 1775 | 2001 | H1N1 |
| CY003288 | A/New | 1748 | 2001 | H1N1 |
| CY003833 | A/New | 1774 | 2001 | H1N1 |
| CY003480 | A/New | 1748 | 2001 | H1N1 |
| CY006171 | A/New | 1748 | 2001 | H1N1 |
| CY000481 | A/New York/71/2001 | 1761 | 2001 | H3N2 |
| CY002328 | A/New York/77/2001 | 1711 | 2001 | H3N2 |
| CY000569 | A/New York/80/2001 | 1739 | 2001 | H3N2 |
| CY000273 | A/New York/82/2001 | 1760 | 2001 | H3N2 |
| CY000185 | A/New York/83/2001 | 1741 | 2001 | H3N2 |
| CY000201 | A/New York/84/2001 | 1729 | 2001 | H3N2 |
| CY000385 | A/New York/85/2001 | 1732 | 2001 | H3N2 |
| CY001168 | A/New York/94/2001 | 1760 | 2001 | H3N2 |
| AB117189 | A/Okayama/33/2001 | 978 | 2001 | H1N1 |
| AB117190 | A/Okayama/4/2001 | 978 | 2001 | H1N1 |
| AB117191 | A/Okinawa/18/2001 | 978 | 2001 | H1N1 |
| AF503479 | A/Oman/16353/2001 | 1029 | 2001 | H1N2 |
| ISDN13364 | A/Oslo/1019/2001 | 1072 | 2001 | H1N1 |
| ISDN13346 | A/Oslo/1061/2001 | 901 | 2001 | H1N1 |
| ISDN13365 | A/Oslo/1167/2001 | 1059 | 2001 | H1N1 |
| ISDN13360 | A/Oslo/1169/2001 | 756 | 2001 | H1N1 |
| ISDN13348 | A/Oslo/1261/2001 | 901 | 2001 | H1N1 |
| ISDN13358 | A/Oslo/1512/2001 | 1059 | 2001 | H1N1 |
| ISDN13342 | A/Oslo/1581/01 | 972 | 2001 | H1N1 |
| ISDN13343 | A/Oslo/1584/01 | 971 | 2001 | H1N1 |
| ISDN13344 | A/Oslo/1586/2001 | 971 | 2001 | H1N1 |
| ISDN13353 | A/Oslo/1587/2001 | 970 | 2001 | H1N1 |
| ISDN13359 | A/Oslo/2289/2001 | 1056 | 2001 | H1N1 |
| ISDN13362 | A/Oslo/2292/2001 | 1047 | 2001 | H1N1 |
| ISDN13363 | A/Oslo/2298/2001 | 1060 | 2001 | H1N1 |
| ISDN13347 | A/Oslo/341/2001 | 901 | 2001 | H1N1 |
| ISDN13341 | A/Oslo/483/2001 | 901 | 2001 | H1N1 |
| ISDN13345 | A/Oslo/484/2001 | 901 | 2001 | H1N1 |
| ISDN13339 | A/Oslo/555/2001 | 890 | 2001 | H1N1 |
| ISDN13338 | A/Oslo/598/2001 | 901 | 2001 | H1N1 |
| ISDN13350 | A/Oslo/739/2001 | 1039 | 2001 | H1N1 |
| ISDN13357 | A/Oslo/791/2001 | 1062 | 2001 | H1N1 |
| ISDN13352 | A/Oslo/826/2001 | 1082 | 2001 | H1N1 |
| ISDN13351 | A/Oslo/847/2001 | 1042 | 2001 | H1N1 |
| ISDN13361 | A/Oslo/866/2001 | 1087 | 2001 | H1N1 |
| ISDN13355 | A/Oslo/868/2001 | 1084 | 2001 | H1N1 |

TABLE 1-continued

INFLUENZA TYPE A HA SEQUENCES

| Accession | Strain | Length | Year | Serotype |
|---|---|---|---|---|
| ISDN13356 | A/Oslo/869/2001 | 1060 | 2001 | H1N1 |
| ISDN13349 | A/Oslo/971/2001 | 1088 | 2001 | H1N1 |
| DQ179382 | A/Philippines/C1-1/2001 | 960 | 2001 | H3N2 |
| AJ457863 | A/Podgorica/4011/20 | 1050 | 2001 | H1N1 |
| AY968026 | A/RiodeJaneiro/310/0 | 672 | 2001 | H3N2 |
| AY971010 | A/RiodeJaneiro/404/0 | 1031 | 2001 | H1N1 |
| AY968029 | A/RiodeJaneiro/465/0 | 996 | 2001 | H3N2 |
| AY968030 | A/RiodeJaneiro/470/0 | 994 | 2001 | H3N2 |
| AY968031 | A/RiodeJaneiro/471/0 | 994 | 2001 | H3N2 |
| AY968032 | A/RiodeJaneiro/478/0 | 972 | 2001 | H3N2 |
| AY968034 | A/RiodeJaneiro/533/0 | 568 | 2001 | H3N2 |
| AY968035 | A/RiodeJaneiro/565/0 | 580 | 2001 | H3N2 |
| AY968036 | A/RiodeJaneiro/580/0 | 584 | 2001 | H3N2 |
| AY968033 | A/RioGdoSul/523/01 | 566 | 2001 | H3N2 |
| AJ457910 | A/Saudi | 1092 | 2001 | H1N1 |
| AJ489854 | A/Scotland/122/01 | 975 | 2001 | H1N2 |
| AF503481 | A/Singapore/63/2001 | 1029 | 2001 | H1N2 |
| AF503483 | A/Singapore/66/2001 | 1029 | 2001 | H1N2 |
| AF503480 | A/Singapore/73/2001 | 1029 | 2001 | H1N2 |
| CY009868 | A/South | 1746 | 2001 | H1N1 |
| CY010356 | A/South Canterbury/159/2001 | 1747 | 2001 | H1N1 |
| DQ179398 | A/Spain/C2-1/2001 | 942 | 2001 | H3N2 |
| AJ457888 | A/Switzerland/5684/2 | 1059 | 2001 | H1N1 |
| AJ517814 | A/Switzerland/5773/2 | 1098 | 2001 | H1N1 |
| AY625729 | A/Taiwan/0388/2001 | 791 | 2001 | H3N2 |
| AY625730 | A/Taiwan/0568/2001 | 791 | 2001 | H3N2 |
| AY625731 | A/Taiwan/0964/2001 | 791 | 2001 | H3N2 |
| AY303734 | A/Taiwan/2175/2001 | 561 | 2001 | H1N1 |
| AY303741 | A/Taiwan/3361/2001 | 561 | 2001 | H1N1 |
| AY303747 | A/Taiwan/3896/2001 | 561 | 2001 | H1N1 |
| ISDN13433 | A/TEHRAN/1/2001 | 935 | 2001 | H1N1 |
| A3457864 | A/Tehran/49/2001 | 988 | 2001 | H1N1 |
| AF503476 | A/Texas/7/2001 | 1029 | 2001 | H1N2 |
| M457870 | A/Trieste/21/2001 | 1067 | 2001 | H1N1 |
| AJ457881 | A/Vladimir/16/2001 | 1041 | 2001 | H1N1 |
| CY009564 | A/West | 1721 | 2001 | H3N2 |
| CY009404 | A/West | 1721 | 2001 | H3N2 |
| CY010404 | A/West | 1746 | 2001 | H1N1 |
| CY009428 | A/West | 1721 | 2001 | H3N2 |
| AY684125 | A/Wisconsin/12/2001 | 1075 | 2001 | H1N2 |
| AF503473 | A/Wisconsin/12/2001 | 1036 | 2001 | H1N2 |
| AY851470 | A/Wuxi/44/2001 | 327 | 2001 | H1 |
| AY851469 | A/Wuxi/57/2001 | 327 | 2001 | H1 |
| AY851464 | A/Xuzhou/02/2001 | 327 | 2001 | H1 |
| AY851465 | A/Xuzhou/06/2001 | 327 | 2001 | H1 |
| AY851466 | A/Xuzhou/36/2001 | 327 | 2001 | H1 |
| AY029287 | A/Alaska/1173/00 | 1029 | 2000 | H1N1 |
| ISDN13438 | A/AUCKLAND/3/200 | 999 | 2000 | H1N1 |
| DQ336007 | A/Brazil/003/00 | 984 | 2000 | H3N2 |
| DQ335991 | A/Brazil/006/00 | 891 | 2000 | H1N1 |
| DQ336015 | A/Brazil/006/00 | 555 | 2000 | H3N2 |
| DQ336011 | A/Brazil/008/00 | 984 | 2000 | H3N2 |
| DQ336014 | A/Brazil/009/00 | 984 | 2000 | H3N2 |
| DQ336013 | A/Brazil/010/00 | 984 | 2000 | H3N2 |
| DQ336016 | A/Brazil/011/00 | 555 | 2000 | H3N2 |
| DQ336009 | A/Brazil/012/00 | 984 | 2000 | H3N2 |
| DQ336017 | A/Brazil/013/00 | 555 | 2000 | H3N2 |
| DQ336005 | A/Brazil/015/00 | 975 | 2000 | H1N1 |
| DQ336012 | A/Brazil/015/00 | 984 | 2000 | H3N2 |
| DQ336010 | A/Brazil/024/00 | 984 | 2000 | H3N2 |
| DQ336008 | A/Brazil/049/00 | 984 | 2000 | H3N2 |
| AJ457889 | A/Brazil/202/2000 | 975 | 2000 | H1N1 |
| AF534044 | A/Buenos | 890 | 2000 | H1N1 |
| CY010132 | A/Canterbury/100/200 | 1727 | 2000 | H1N1 |
| CY008844 | A/Canterbury/101/200 | 1737 | 2000 | H1N1 |
| CY008836 | A/Canterbury/103/200 | 1717 | 2000 | H3N2 |
| CY008476 | A/Canterbury/17/2000 | 1721 | 2000 | H3N2 |
| CY009116 | A/Canterbury/2/2000 | 1721 | 2000 | H3N2 |
| CY009756 | A/Canterbury/23/2000 | 1737 | 2000 | H1N1 |
| CY010100 | A/Canterbury/27/2000 | 1746 | 2000 | H1N1 |
| CY009188 | A/Canterbury/28/2000 | 1746 | 2000 | H1N1 |
| CY009100 | A/Canterbury/3/2000 | 1721 | 2000 | H3N2 |
| CY009180 | A/Canterbury/30/2000 | 1746 | 2000 | H1N1 |
| CY009220 | A/Canterbury/32/2000 | 1746 | 2000 | H1N1 |
| CY009212 | A/Canterbury/33/2000 | 1724 | 2000 | H1N1 |
| CY009228 | A/Canterbury/34/2000 | 1746 | 2000 | H1N1 |
| CY009196 | A/Canterbury/36/2000 | 1746 | 2000 | H1N1 |
| CY009532 | A/Canterbury/37/2000 | 1725 | 2000 | H1N1 |
| CY008484 | A/Canterbury/38/2000 | 1721 | 2000 | H3N2 |
| CY008139 | A/Canterbury/39/2000 | 1721 | 2000 | H3N2 |
| CY009828 | A/Canterbury/41/2000 | 1746 | 2000 | H1N1 |
| CY008131 | A/Canterbury/42/2000 | 1721 | 2000 | H3N2 |
| CY010092 | A/Canterbury/43/2000 | 1746 | 2000 | H1N1 |
| CY009540 | A/Canterbury/5/2000 | 1746 | 2000 | H1N1 |
| CY010108 | A/Canterbury/51/2000 | 1737 | 2000 | H1N1 |
| CY010124 | A/Canterbury/54/2000 | 1746 | 2000 | H1N1 |
| CY009132 | A/Canterbury/55/2000 | 1721 | 2000 | H3N2 |
| CY008748 | A/Canterbury/56/2000 | 1717 | 2000 | H3N2 |
| CY009844 | A/Canterbury/57/2000 | 1746 | 2000 | H1N1 |
| CY010116 | A/Canterbury/58/2000 | 1722 | 2000 | H1N1 |
| CY009148 | A/Canterbury/58/2000 | 1721 | 2000 | H3N2 |
| CY009820 | A/Canterbury/60/2000 | 1746 | 2000 | H1N1 |
| CY009164 | A/Canterbury/61/2000 | 1721 | 2000 | H3N2 |
| CY010388 | A/Canterbury/63/2000 | 1746 | 2000 | H1N1 |
| CY009140 | A/Canterbury/64/2000 | 1722 | 2000 | H3N2 |
| CY009548 | A/Canterbury/65/2000 | 1746 | 2000 | H1N1 |
| CY008764 | A/Canterbury/66/2000 | 1721 | 2000 | H3N2 |
| CY009156 | A/Canterbury/67/2000 | 1721 | 2000 | H3N2 |
| CY008756 | A/Canterbury/68/2000 | 1717 | 2000 | H3N2 |
| CY009764 | A/Canterbury/7/2000 | 1737 | 2000 | H1N1 |
| CY008772 | A/Canterbury/71/2000 | 1717 | 2000 | H3N2 |
| CY008492 | A/Canterbury/73/2000 | 1736 | 2000 | H3N2 |
| CY009788 | A/Canterbury/76/2000 | 1727 | 2000 | H1N1 |
| CY009812 | A/Canterbury/78/2000 | 1737 | 2000 | H1N1 |
| CY009796 | A/Canterbury/79/2000 | 1746 | 2000 | H1N1 |
| CY010380 | A/Canterbury/8/2000 | 1727 | 2000 | H1N1 |
| CY008780 | A/Canterbury/80/2000 | 1721 | 2000 | H3N2 |
| CY008788 | A/Canterbury/81/2000 | 1721 | 2000 | H3N2 |
| CY008796 | A/Canterbury/84/2000 | 1721 | 2000 | H3N2 |
| CY008804 | A/Canterbury/85/2000 | 1721 | 2000 | H3N2 |
| CY009076 | A/Canterbury/87/2000 | 1714 | 2000 | H3N2 |
| CY009804 | A/Canterbury/87/2000 | 1737 | 2000 | H1N1 |
| CY008500 | A/Canterbury/88/2000 | 1721 | 2000 | H3N2 |
| CY008820 | A/Canterbury/89/2000 | 1717 | 2000 | H3N2 |
| CY009940 | A/Canterbury/9/2000 | 1722 | 2000 | H1N1 |
| CY008860 | A/Canterbury/90/2000 | 1721 | 2000 | H3N2 |
| CY009092 | A/Canterbury/92/2000 | 1721 | 2000 | H3N2 |
| CY008828 | A/Canterbury/93/2000 | 1717 | 2000 | H3N2 |
| CY009388 | A/Canterbury/94/2000 | 1721 | 2000 | H3N2 |
| CY010140 | A/Canterbury/95/2000 | 1728 | 2000 | H1N1 |
| CY009084 | A/Canterbury/96/2000 | 1717 | 2000 | H3N2 |
| CY008852 | A/Canterbury/98/2000 | 1721 | 2000 | H3N2 |
| CY008508 | A/Canterbury/99/2000 | 1721 | 2000 | H3N2 |
| AF534045 | A/Chaco/R112/00 | 890 | 2000 | H1N1 |
| AB117197 | A/Chiba-C/402/2000 | 981 | 2000 | H1N1 |
| AJ457887 | A/Dakar/17/2000 | 1065 | 2000 | H1N1 |
| AJ457903 | A/Denmark/39/2000 | 978 | 2000 | H1N1 |
| AJ457902 | A/Dublin/9852/00 | 1099 | 2000 | H1N1 |
| AY968024 | A/EspiritoSanto/128/0 | 1002 | 2000 | H3N2 |
| AY971005 | A/EspiritoSanto/131/0 | 987 | 2000 | H1N1 |
| AY971007 | A/EspiritoSanto/150/0 | 1035 | 2000 | H1N1 |
| AY029288 | A/Florida/904/00 | 1029 | 2000 | H1N1 |
| AY029290 | A/Hawaii/1313/00 | 1029 | 2000 | H1N1 |
| AY029289 | A/Hawaii/3948/00 | 1029 | 2000 | H1N1 |
| CY008812 | A/Hutt/82/2000 | 1714 | 2000 | H3N2 |
| AJ457904 | A/Iceland/25/2000 | 1044 | 2000 | H1N1 |
| AB117201 | A/Kagawa/8/2000 | 978 | 2000 | H1N1 |
| AB117202 | A/Kagawa/83/2000 | 978 | 2000 | H1N1 |
| AB117203 | A/Kagoshima/80/2000 | 978 | 2000 | H1N1 |
| AJ457883 | A/Kalingrad/5/2000 | 975 | 2000 | H1N1 |
| AJ457893 | A/Madagascar/57794/ | 975 | 2000 | H1N1 |
| ISDN13354 | A/Madagascar/57794/ | 970 | 2000 | H1N1 |
| AF357932 | A/Madrid/G967/00 | 519 | 2000 | H3N2 |
| AF357933 | A/Madrid/G984/00 | 519 | 2000 | H3N2 |
| AF357948 | A/Madrid/RR599/00 | 519 | 2000 | H3N2 |
| AF357950 | A/Madrid/RR607/00 | 519 | 2000 | H3N2 |
| AF357951 | A/Madrid/RR610/00 | 519 | 2000 | H3N2 |
| AF357969 | A/Madrid/SO2913/00 | 519 | 2000 | H3N2 |
| ISDNSWA011 | A/Malmoe/1/2000 | 987 | 2000 | H3N2 |
| ISDNSWA012 | A/Malmoe/2/2000 | 987 | 2000 | H3N2 |

TABLE 1-continued

INFLUENZA TYPE A HA SEQUENCES

| Accession | Strain | Length | Year | Serotype |
|---|---|---|---|---|
| AF534047 | A/Mendoza/VJ636/00 | 890 | 2000 | H1N1 |
| AY029292 | A/Misawa/1226/00 | 1029 | 2000 | H1N1 |
| AB117205 | A/Miyagi/4/2000 | 978 | 2000 | H1N1 |
| AB117209 | A/Nagoya/16/2000 | 978 | 2000 | H1N1 |
| AY851462 | A/Nanjing/06/2000 | 327 | 2000 | H1 |
| AY851463 | A/Nanjing/08/2000 | 327 | 2000 | M1 |
| CY009124 | A/Nelson | 1721 | 2000 | H3N2 |
| AY661021 | A/Netherlands/3/00 | 1095 | 2000 | H3N2 |
| AF534048 | A/Neuquen/P3D1/00 | 890 | 2000 | H1N1 |
| AY029291 | A/New Jersey/313/00 | 1029 | 2000 | H1N1 |
| CY001520 | A/New | 1760 | 2000 | H3N2 |
| CY000449 | A/New | 1741 | 2000 | H3N2 |
| CY000817 | A/New | 1760 | 2000 | H3N2 |
| CY000465 | A/New | 1760 | 2000 | H3N2 |
| CY001136 | A/New | 1711 | 2000 | H3N2 |
| CY000609 | A/New | 1762 | 2000 | H3N2 |
| CY001397 | A/New | 1739 | 2000 | H3N2 |
| CY000833 | A/New | 1731 | 2000 | H3N2 |
| CY000981 | A/New | 1760 | 2000 | H3N2 |
| CY001245 | A/New | 1760 | 2000 | H3N2 |
| CY000997 | A/New | 1759 | 2000 | H3N2 |
| CY000809 | A/New | 1711 | 2000 | H3N2 |
| CY000841 | A/New | 1741 | 2000 | H3N2 |
| CY000657 | A/New | 1760 | 2000 | H3N2 |
| CY000665 | A/New | 1760 | 2000 | H3N2 |
| CY000689 | A/New | 1711 | 2000 | H3N2 |
| CY000697 | A/New | 1736 | 2000 | H3N2 |
| CY000705 | A/New | 1760 | 2000 | H3N2 |
| CY000713 | A/New | 1760 | 2000 | H3N2 |
| CY000849 | A/New | 1760 | 2000 | H3N2 |
| CY000737 | A/New | 1760 | 2000 | H3N2 |
| CY001277 | A/New | 1741 | 2000 | H3N2 |
| CY001365 | A/New | 1759 | 2000 | H3N2 |
| CY002640 | A/New | 1748 | 2000 | H1N1 |
| CY002648 | A/New | 1724 | 2000 | H1N1 |
| CY003809 | A/New | 1737 | 2000 | H3N2 |
| CY003448 | A/New | 1750 | 2000 | H3N2 |
| CY003240 | A/New | 1750 | 2000 | H3N2 |
| CY003817 | A/New | 1737 | 2000 | H3N2 |
| CY003248 | A/New | 1737 | 2000 | H3N2 |
| CY003256 | A/New | 1761 | 2000 | H3N2 |
| CY006659 | A/New | 1721 | 2000 | H3N2 |
| CY003264 | A/New | 1747 | 2000 | H3N2 |
| CY003272 | A/New | 1737 | 2000 | H3N2 |
| CY003280 | A/New | 1737 | 2000 | H3N2 |
| CY003456 | A/New | 1748 | 2000 | H3N2 |
| CY003825 | A/New | 1748 | 2000 | H3N2 |
| AB117188 | A/Niigata/2756/2000 | 978 | 2000 | H1N1 |
| AB117211 | A/Okinawa/159/2000 | 978 | 2000 | H1N1 |
| AB117212 | A/Okinawa/51/2000 | 978 | 2000 | H1N1 |
| AB117213 | A/Osaka/972/2000 | 978 | 2000 | H1N1 |
| ISDNOS0022 | A/Oslo/6391/2000 | 1130 | 2000 | H3N2 |
| ISDN13337 | A/Oslo/7649/2000 | 901 | 2000 | H1N1 |
| ISDN13336 | A/Oslo/7701/2000 | 901 | 2000 | H1N1 |
| ISDN13335 | A/Oslo/7709/2000 | 901 | 2000 | H1N1 |
| ISDNOS0021 | A/Oslo/841/2000 | 1139 | 2000 | H3N2 |
| AF357949 | A/Oviedo/RR605/00 | 519 | 2000 | H3N2 |
| AF534049 | A/Paraguay/CS24/00 | 890 | 2000 | H1N1 |
| AY968025 | A/RiodeJaneiro/172/0 | 557 | 2000 | H3N2 |
| AY971003 | A/RiodeJaneiro/20/00 | 1026 | 2000 | H1N1 |
| AY971004 | A/RiodeJaneiro/21/00 | 1029 | 2000 | H1N1 |
| AY968023 | A/RiodeJaneiro/28/00 | 993 | 2000 | H3N2 |
| AF357947 | A/Salamanca/RR593/00 | 519 | 2000 | H3N2 |
| AF357954 | A/Salamanca/RR682/00 | 519 | 2000 | H3N2 |
| AF534050 | A/Santa Fe/R98/00 | 890 | 2000 | H1N1 |
| AB117214 | A/Sapporo/174/2000 | 978 | 2000 | H1N1 |
| AJ457862 | A/Saudi | 1042 | 2000 | H1N1 |
| AB117193 | A/Shizuoka/761/2000 | 978 | 2000 | H1N1 |
| ISDN13366 | A/SOUTH | 973 | 2000 | H1N1 |
| ISDN13376 | A/SOUTH | 975 | 2000 | H1N1 |
| ISDN13370 | A/SOUTH | 973 | 2000 | H1N1 |
| ISDN13377 | A/SOUTH | 975 | 2000 | H1N1 |
| ISDN13378 | A/SOUTH | 975 | 2000 | H1N1 |
| ISDN13371 | A/SOUTH | 973 | 2000 | H3N2 |
| ISDN13430 | A/SOUTH AUSTRALIA/24/200 | 982 | 2000 | H1 |
| ISDN13441 | A/SOUTH AUSTRALIA/8/2000 | 977 | 2000 | H1N1 |
| CY009772 | A/South | 1747 | 2000 | H1N1 |
| CY009204 | A/South | 1746 | 2000 | H1N1 |
| CY009780 | A/South | 1722 | 2000 | H1N1 |
| CY009172 | A/South Canterbury/50/2000 | 1746 | 2000 | H1N1 |
| CY009836 | A/South | 1746 | 2000 | H1N1 |
| ISDNSWA004 | A/Stockholm/2/2000 | 987 | 2000 | H3N2 |
| ISDNSWA005 | A/Stockholm/3/2000 | 987 | 2000 | H3N2 |
| ISDNSWA006 | A/Stockholm/4/2000 | 987 | 2000 | H3N2 |
| ISDNSWA007 | A/Stockholm/5/2000 | 987 | 2000 | H3N2 |
| ISDNSWA008 | A/Stockholm/7/2000 | 987 | 2000 | H3N2 |
| ISDNSWA009 | A/Stockholm/8/2000 | 987 | 2000 | H3N2 |
| ISDN13379 | A/Sydney/118/2000 | 1103 | 2000 | H3N2 |
| AY303713 | A/Taiwan/0275/2000 | 844 | 2000 | H3N2 |
| AY303717 | A/Taiwan/0379/2000 | 844 | 2000 | H3N2 |
| AY303723 | A/Taiwan/0646/2000 | 844 | 2000 | H3N2 |
| ISDN13437 | A/TAIWAN/1/2000 | 915 | 2000 | H1N1 |
| AF362803 | A/Taiwan/12/00 | 561 | 2000 | H1N1 |
| AF362806 | A/Taiwan/149/00 | 844 | 2000 | H3N2 |
| AF362779 | A/Taiwan/16/00 | 561 | 2000 | H1N1 |
| AF362780 | A/Taiwan/30/00 | 561 | 2000 | H1N1 |
| AF362818 | A/Taiwan/3083/00 | 940 | 2000 | H3N2 |
| AF362819 | A/Taiwan/3460/00 | 942 | 2000 | H3N2 |
| AF362804 | A/Taiwan/3760/00 | 940 | 2000 | H3N2 |
| AF362797 | A/Taiwan/3825/00 | 581 | 2000 | H1N1 |
| ISDN13439 | A/TEHRAN/1/2000 | 943 | 2000 | H1N1 |
| AJ457882 | A/Umea/1/2000 | 975 | 2000 | H1N1 |
| ISDNSWA014 | A/Umea/2/2000 | 987 | 2000 | H3N2 |
| ISDNSWA015 | A/Umea/3/2000 | 987 | 2000 | H3N2 |
| AF534051 | A/Uruguay/33/00 | 890 | 2000 | H1N1 |
| AF534052 | A/Uruguay/37/00 | 890 | 2000 | H1N1 |
| AF534053 | A/Uruguay/38/00 | 890 | 2000 | H1N1 |
| AF534054 | A/Uruguay/42/00 | 890 | 2000 | H1N1 |
| CY010996 | A/Wellington/2/2000 | 1739 | 2000 | H1N1 |
| CY011004 | A/Wellington/3/2000 | 1746 | 2000 | H1N1 |
| CY011012 | A/Wellington/5/2000 | 1737 | 2000 | H1N1 |
| CY011020 | A/Wellington/9/2000 | 1720 | 2000 | H3N2 |
| AB117218 | A/Yamagata/162/2000 | 978 | 2000 | H1N1 |
| AB043498 | A/Yokohama/12/2000 | 1029 | 2000 | H1N1 |
| AB117220 | A/Yokohama/24/2000 | 981 | 2000 | H1N1 |
| AB043499 | A/Yokohama/24/2000 | 1032 | 2000 | H1N1 |
| AF357952 | A/Zaragoza/RR653/00 | 519 | 2000 | H3N2 |
| AF357953 | A/Zaragoza/RR658/00 | 519 | 2000 | H3N2 |
| AB043497 | A/Aichi/102/99 | 1029 | 1999 | H1N1 |
| AB043496 | A/Aichi/94/99 | 1029 | 1999 | H1N1 |
| AF315566 | A/Athens/135/99 | 1113 | 1999 | H3N2 |
| AJ457884 | A/Auckland/176/99 | 987 | 1999 | H1N1 |
| AF534031 | A/Buenos | 1044 | 1999 | H1N1 |
| AF534030 | A/Buenos | 1044 | 1999 | H1N1 |
| AF534034 | A/Buenos | 984 | 1999 | H3N2 |
| AF534032 | A/Buenos | 984 | 1999 | H3N2 |
| AF534033 | A/Buenos | 984 | 1999 | H3N2 |
| AF501516 | A/Canada/33312/99 | 987 | 1999 | H3N2 |
| CY009108 | A/Canterbury/179/199 | 1721 | 1999 | H3N2 |
| AF534035 | A/Chaco/140/99 | 984 | 1999 | H3N2 |
| AF297094 | A/Charlottesville/10/9 | 987 | 1999 | H3N2 |
| AF297096 | A/Charlottesville/49/9 | 987 | 1999 | H3N2 |
| AF297097 | A/Charlottesville/69/9 | 987 | 1999 | H3N2 |
| AF297095 | A/Charlottesville/73/9 | 987 | 1999 | H3N2 |
| AB117195 | A/Chiba/1042/1999 | 978 | 1999 | H1N1 |
| AB117196 | A/Chiba/1108/1999 | 978 | 1999 | H1N1 |
| AF534043 | A/Cordoba/VA418/99 | 990 | 1999 | H1N1 |
| ISDNAU0013 | A/DARWIN/2/99 | 1020 | 1999 | H3N2 |
| AY968018 | A/EspiritoSanto/14/99 | 988 | 1999 | H3N2 |
| AY968017 | A/EspiritoSanto/3/99 | 973 | 1999 | H3N2 |
| AY968021 | A/EspiritoSanto/33/99 | 992 | 1999 | H3N2 |
| AF442469 | A/Finland/616/99 | 984 | 1999 | H3N2 |
| AF442456 | A/Finland/638/99 | 984 | 1999 | H3N2 |
| AF442477 | A/Finland/644/99 | 984 | 1999 | H3N2 |
| AF442473 | A/Finland/645/99 | 984 | 1999 | H3N2 |
| AF442472 | A/Finland/646/99 | 984 | 1999 | H3N2 |
| AF442460 | A/Finland/656/99 | 984 | 1999 | H3N2 |

TABLE 1-continued

INFLUENZA TYPE A HA SEQUENCES

| Accession | Strain | Length | Year | Serotype |
|---|---|---|---|---|
| AF442462 | A/Finland/657/99 | 984 | 1999 | H3N2 |
| AF442463 | A/Finland/658/99 | 984 | 1999 | H3N2 |
| AF442465 | A/Finland/659/99 | 984 | 1999 | H3N2 |
| AF442475 | A/Finland/660/99 | 984 | 1999 | H3N2 |
| AF442467 | A/Finland/661/99 | 984 | 1999 | H3N2 |
| AF442457 | A/Finland/662/99 | 984 | 1999 | H3N2 |
| AF442474 | A/Finland/663/99 | 984 | 1999 | H3N2 |
| AF442461 | A/Finland/664/99 | 984 | 1999 | H3N2 |
| AF442466 | A/Finland/665/99 | 984 | 1999 | H3N2 |
| AF442468 | A/Finland/666/99 | 984 | 1999 | H3N2 |
| AF442459 | A/Finland/678/99 | 984 | 1999 | H3N2 |
| AF442478 | A/Finland/679/99 | 984 | 1999 | H3N2 |
| AF442481 | A/Finland/680/99 | 984 | 1999 | H3N2 |
| AF442476 | A/Finland/681/99 | 984 | 1999 | H3N2 |
| AF442470 | A/Finland/682/99 | 984 | 1999 | H3N2 |
| AF442455 | A/Finland/683/99 | 984 | 1999 | H3N2 |
| AF442464 | A/Finland/684/99 | 984 | 1999 | H3N2 |
| AF442479 | A/Finland/686/99 | 984 | 1999 | H3N2 |
| AF442471 | A/Finland/694/99 | 984 | 1999 | H3N2 |
| AF442458 | A/Finland/695/99 | 984 | 1999 | H3N2 |
| AF442482 | A/Finland/697/99 | 984 | 1999 | H3N2 |
| AF442480 | A/Finland/702/99 | 984 | 1999 | H3N2 |
| AY633996 | A/France/1/00 | 972 | 1999 | H3N2 |
| AY634005 | A/France/10/00 | 987 | 1999 | H3N2 |
| AY634006 | A/France/11/00 | 987 | 1999 | H3N2 |
| AY634007 | A/France/12/00 | 987 | 1999 | H3N2 |
| AY634008 | A/France/13/00 | 987 | 1999 | H3N2 |
| AY634009 | A/France/14/00 | 987 | 1999 | H3N2 |
| AY634010 | A/France/15/00 | 987 | 1999 | H3N2 |
| AY634011 | A/France/16/00 | 987 | 1999 | H3N2 |
| AY634012 | A/France/17/00 | 987 | 1999 | H3N2 |
| AY634013 | A/France/18/00 | 987 | 1999 | H3N2 |
| AY634014 | A/France/19/00 | 987 | 1999 | H3N2 |
| AY633997 | A/France/2/00 | 987 | 1999 | H3N2 |
| AY634015 | A/France/20/00 | 987 | 1999 | H3N2 |
| AY634016 | A/France/21/00 | 987 | 1999 | H3N2 |
| AY634017 | A/France/22/00 | 987 | 1999 | H3N2 |
| AY634018 | A/France/23/00 | 987 | 1999 | H3N2 |
| AY634019 | A/France/24/00 | 987 | 1999 | H3N2 |
| AY634020 | A/France/25/00 | 987 | 1999 | H3N2 |
| AY634021 | A/France/26/00 | 987 | 1999 | H3N2 |
| AY634022 | A/France/27/00 | 987 | 1999 | H3N2 |
| AY634023 | A/France/28/00 | 987 | 1999 | H3N2 |
| AY634024 | A/France/29/00 | 987 | 1999 | H3N2 |
| AY633998 | A/France/3/00 | 987 | 1999 | H3N2 |
| AY634025 | A/France/30/00 | 987 | 1999 | H3N2 |
| AY634026 | A/France/31/00 | 987 | 1999 | H3N2 |
| AY634027 | A/France/32/00 | 987 | 1999 | H3N2 |
| AY634028 | A/France/33/00 | 987 | 1999 | H3N2 |
| AY634029 | A/France/34/00 | 987 | 1999 | H3N2 |
| AY634030 | A/France/35/00 | 987 | 1999 | H3N2 |
| AY634031 | A/France/36/00 | 987 | 1999 | H3N2 |
| AY634032 | A/France/37/00 | 987 | 1999 | H3N2 |
| AY634033 | A/France/38/00 | 987 | 1999 | H3N2 |
| AY634034 | A/France/39/00 | 987 | 1999 | H3N2 |
| AY633999 | A/France/4/00 | 987 | 1999 | H3N2 |
| AY634035 | A/France/40/00 | 987 | 1999 | H3N2 |
| AY634036 | A/France/41/00 | 987 | 1999 | H3N2 |
| AY634037 | A/France/42/00 | 987 | 1999 | H3N2 |
| AY634038 | A/France/43/00 | 987 | 1999 | H3N2 |
| AY634039 | A/France/44/00 | 987 | 1999 | H3N2 |
| AY634040 | A/France/45/00 | 987 | 1999 | H3N2 |
| AY634041 | A/France/46/00 | 987 | 1999 | H3N2 |
| AY634042 | A/France/47/00 | 987 | 1999 | H3N2 |
| AY634043 | A/France/48/00 | 987 | 1999 | H3N2 |
| AY634044 | A/France/49/00 | 987 | 1999 | H3N2 |
| AY634000 | A/France/5/00 | 987 | 1999 | H3N2 |
| AY634045 | A/France/50/00 | 987 | 1999 | H3N2 |
| AY634046 | A/France/51/00 | 987 | 1999 | H3N2 |
| AY634047 | A/France/52/00 | 987 | 1999 | H3N2 |
| AY634048 | A/France/53/00 | 987 | 1999 | H3N2 |
| AY634049 | A/France/54/00 | 987 | 1999 | H3N2 |
| AY634001 | A/France/6/00 | 987 | 1999 | H3N2 |
| AY634002 | A/France/7/00 | 987 | 1999 | H3N2 |
| AY634003 | A/France/8/00 | 987 | 1999 | H3N2 |
| AY634004 | A/France/9/00 | 987 | 1999 | H3N2 |
| AY963795 | A/Fujian/134/1999 | 1198 | 1999 | H3N2 |
| AY963782 | A/Fujian/137/1999 | 1198 | 1999 | H3N2 |
| ISDNSW001 | A/GOTHBNBURG/1/99 | 987 | 1999 | H3N2 |
| ISDNSW0019 | A/GOTHENBURG/3/99 | 987 | 1999 | H3N2 |
| AF315564 | A/Greece/109/99 | 1108 | 1999 | H3N2 |
| AF315565 | A/Greece/132/99 | 1096 | 1999 | H3N2 |
| AY043019 | A/Guangzhou/333/99 | 1488 | 1999 | H9N2 |
| AJ404626 | A/Hong Kong/1073/99 | 1714 | 1999 | H9N2 |
| AB080226 | A/Hong Kong/1073/99 | 960 | 1999 | H9N2 |
| AJ404627 | A/Hong Kong/1074/99 | 1714 | 1999 | H9N2 |
| AY035588 | A/Hong Kong/1143/99 | 1762 | 1999 | H3N2 |
| AF382320 | A/Hong Kong/1143/99 (clinical isolate) | 1762 | 1999 | H3N2 |
| AF382319 | A/Hong Kong/1143/99 (MDCK isolate) | 1762 | 1999 | H3N2 |
| AY035589 | A/Hong Kong/1144/99 | 1762 | 1999 | H3N2 |
| AF382322 | A/Hong Kong/1144/99 (clinical isolate) | 1762 | 1999 | H3N2 |
| AF382321 | A/Hong Kong/1144/99 (MDCK isolate) | 1762 | 1999 | H3N2 |
| AY035590 | A/Hong Kong/1179/99 | 1762 | 1999 | H3N2 |
| AF382324 | A/Hong Kong/1179/99 (clinical isolate) | 1762 | 1999 | H3N2 |
| AF382323 | A/Hong Kong/1179/99 (MDCK isolate) | 1762 | 1999 | H3N2 |
| AY035591 | A/Hong Kong/1180/99 | 1762 | 1999 | H3N2 |
| AF382326 | A/Hong Kong/1180/99 (clinical isolate) | 1762 | 1999 | H3N2 |
| AF382325 | A/Hong Kong/1180/99 (MDCK isolate) | 1762 | 1999 | H3N2 |
| AY035592 | A/Hong Kong/1182/99 | 1762 | 1999 | H3N2 |
| AF382328 | A/Hong Kong/1182/99 (clinical isolate) | 1762 | 1999 | H3N2 |
| AF382327 | A/Hong Kong/1182/99 (MDCK isolate) | 1762 | 1999 | H3N2 |
| AJ293926 | A/Hong Kong/1774/99 | 1699 | 1999 | H3N2 |
| AJ457880 | A/Hong Kong/2070/99 | 975 | 1999 | H1N1 |
| AB117199 | A/Ibaraki/66/1999 | 978 | 1999 | H1N1 |
| AF386634 | A/Inchon/81/99 | 987 | 1999 | H3N2 |
| AF501534 | A/Indiana/28170/99 | 987 | 1999 | H3N2 |
| AF386614 | A/Kangwon/11/99 | 987 | 1999 | H3N2 |
| AF386615 | A/Kangwon/12/99 | 987 | 1999 | H3N2 |
| AF386616 | A/Kangwon/88/99 | 987 | 1999 | H3N2 |
| AF386617 | A/Kangwon/93/99 | 987 | 1999 | H3N2 |
| AF386630 | A/Kwangju/105/99 | 987 | 1999 | H3N2 |
| AF386631 | A/Kwangju/115/99 | 987 | 1999 | H3N2 |
| AF386632 | A/Kwangju/117/99 | 987 | 1999 | H3N2 |
| AJ457905 | A/Madrid/930/99 | 1044 | 1999 | H1N1 |
| AF357931 | A/Madrid/G960/99 | 519 | 1999 | H3N2 |
| AF357944 | A/Madrid/RR444/99 | 519 | 1999 | H3N2 |
| AF357945 | A/Madrid/RR490/99 | 519 | 1999 | H3N2 |
| AF357946 | A/Madrid/RR498/99 | 519 | 1999 | H3N2 |
| AF357966 | A/Madrid/SO2447/99 | 519 | 1999 | H3N2 |
| AF357967 | A/Madrid/SO2523/99 | 519 | 1999 | H3N2 |
| AF357968 | A/Madrid/SO2531/99 | 519 | 1999 | H3N2 |
| ISDNSW001 | A/MALMO/1/99 | 987 | 1999 | H3N2 |
| ISDNSW001 | A/MALMO/2/99 | 987 | 1999 | H3N2 |
| ISDNSWA01 | A/Malmoe/3/99 | 987 | 1999 | H3N2 |
| AF534040 | A/Mar del Plata/267/99 | 984 | 1999 | H3N2 |
| CY002112 | A/Memphis/59/99 | 1741 | 1999 | H3N2 |
| AF534036 | A/Mendoza/135/99 | 984 | 1999 | H3N2 |
| AF501531 | A/Michigan/22568/99 | 987 | 1999 | H3N2 |
| AF501518 | A/Michigan/22692/99 | 987 | 1999 | H3N2 |
| AF534037 | A/Misiones/195/99 | 984 | 1999 | H3N2 |
| AB117206 | A/Miyagi/89/1999 | 978 | 1999 | H1N1 |
| DQ487341 | A/Moscow/10/99 | 1762 | 1999 | H3N2 |
| AY661019 | A/Moscow/10/99 | 1095 | 1999 | H3N2 |
| AY531035 | A/Moscow/10/99 | 1701 | 1999 | H3N2 |
| ISDN13277 | A/Mascow/10/99 | 988 | 1999 | H3N2 |
| AB117208 | A/Nagasaki/142/1999 | 978 | 1999 | H1N1 |
| AY661026 | A/Netherlands/301/99 | 1095 | 1999 | H3N2 |
| AF534039 | A/Neuquen/102/99 | 984 | 1999 | H3N2 |
| AF534038 | A/Neuquen/1381/99 | 1044 | 1999 | H1N1 |
| ISDNAU001 | A/NEW | 995 | 1999 | H3N2 |
| ISDN13401 | A/NEW CALEDONIA/11/99 | 995 | 1999 | H3N2 |

TABLE 1-continued

INFLUENZA TYPE A HA SEQUENCES

| Accession | Strain | Length | Year | Serotype |
|---|---|---|---|---|
| DQ508857 | A/New Caledonia/20/1999 | 1698 | 1999 | H1N1 |
| AJ3344014 | A/New Caledonia/20/99 | 1692 | 1999 | H1N1 |
| AY289929 | A/New Caledonia/20/99 | 1711 | 1999 | H1N1 |
| ISDNAU0001 | A/NEW CALEDONIA/20/99 | 981 | 1999 | H1N1 |
| CY001120 | A/New York/137/1999 | 1742 | 1999 | H3N2 |
| CY000989 | A/New York/138/1999 | 1711 | 1999 | H3N2 |
| CY001349 | A/New York/139/1999 | 1711 | 1999 | H3N2 |
| CY002512 | A/New York/140/1999 | 1711 | 1999 | H3N2 |
| CY000801 | A/New York/141/1999 | 1760 | 1999 | H3N2 |
| CY000633 | A/New York/143/1999 | 1744 | 1999 | H3N2 |
| CY001381 | A/New York/145/1999 | 1711 | 1999 | H3N2 |
| CY000593 | A/New York/147/1999 | 1762 | 1999 | H3N2 |
| CY000457 | A/New York/149/1999 | 1760 | 1999 | H3N2 |
| CY000601 | A/New York/151/1999 | 1761 | 1999 | H3N2 |
| CY002312 | A/New York/153/1999 | 1741 | 1999 | H3N2 |
| CY001445 | A/New York/155/1999 | 1711 | 1999 | H3N2 |
| CY000825 | A/New York/157/1999 | 1760 | 1999 | H3N2 |
| CY000617 | A/New York/161/1999 | 1732 | 1999 | H3N2 |
| CY000641 | A/New York/163/1999 | 1760 | 1999 | H3N2 |
| CY001269 | A/New York/164/1999 | 1722 | 1999 | H3N2 |
| CY000649 | A/New York/167/1999 | 1760 | 1999 | H3N2 |
| CY000673 | A/New York/171/1999 | 1730 | 1999 | H3N2 |
| CY000681 | A/New York/172/1999 | 1760 | 1999 | H3N2 |
| CY000721 | A/New York/177/1999 | 1760 | 1999 | H3N2 |
| CY000729 | A/New York/179/1999 | 1760 | 1999 | H3N2 |
| CY001176 | A/New York/181/1999 | 1760 | 1999 | H3N2 |
| CY001357 | A/New York/183/1999 | 1711 | 1999 | H3N2 |
| CY001453 | A/New York/184/1999 | 1732 | 1999 | H3N2 |
| CY000745 | A/New York/185/1999 | 1717 | 1999 | H3N2 |
| CY000857 | A/New York/186/1999 | 1711 | 1999 | H3N2 |
| CY001528 | A/New York/188/1999 | 1711 | 1999 | H3N2 |
| CY001005 | A/New York/189/1999 | 1722 | 1999 | H3N2 |
| CY001688 | A/New York/248/1999 | 1762 | 1999 | H3N2 |
| CY002552 | A/New York/252/1999 | 1718 | 1999 | H3N2 |
| CY001576 | A/New York/253/1999 | 1760 | 1999 | H3N2 |
| CY001696 | A/New York/255/1999 | 1710 | 1999 | H3N2 |
| CY001704 | A/New York/257/1999 | 1703 | 1999 | H3N2 |
| CY001592 | A/New York/259/1999 | 1711 | 1999 | H3N2 |
| CY001960 | A/New York/260/1999 | 1703 | 1999 | H3N2 |
| CY002560 | A/New York/261/1999 | 1760 | 1999 | H3N2 |
| CY001600 | A/New York/262/1999 | 1711 | 1999 | H3N2 |
| CY001413 | A/New York/263/1999 | 1741 | 1999 | H3N2 |
| CY001608 | A/New York/264/1999 | 1711 | 1999 | H3N2 |
| CY001616 | A/New York/265/1999 | 1711 | 1999 | H3N2 |
| CY002336 | A/New York/266/1999 | 1741 | 1999 | H3N2 |
| CY001744 | A/New York/277/1999 | 1739 | 1999 | H3N2 |
| CY001968 | A/New York/278/1999 | 1749 | 1999 | H3N2 |
| CY001752 | A/New York/279/1999 | 1762 | 1999 | H3N2 |
| CY001760 | A/New York/280/1999 | 1761 | 1999 | H3N2 |
| CY001768 | A/New York/282/1999 | 1762 | 1999 | H3N2 |
| CY002136 | A/New York/283/1999 | 1762 | 1999 | H3N2 |
| CY001656 | A/New York/284/1999 | 1762 | 1999 | H3N2 |
| CY002144 | A/New York/285/1999 | 1703 | 1999 | H3N2 |
| CY001664 | A/New York/286/1999 | 1715 | 1999 | H3N2 |
| CY001776 | A/New York/288/1999 | 1762 | 1999 | H3N2 |
| CY001792 | A/New York/290/1999 | 1741 | 1999 | H3N2 |
| CY001808 | A/New York/311/1999 | 1725 | 1999 | H3N2 |
| CY001824 | A/New York/314/1999 | 1762 | 1999 | H3N2 |
| CY001832 | A/New York/315/1999 | 1762 | 1999 | H3N2 |
| CY002160 | A/New York/316/1999 | 1761 | 1999 | H3N2 |
| CY001840 | A/New York/317/1999 | 1762 | 1999 | H3N2 |
| CY001848 | A/New York/318/1999 | 1728 | 1999 | H3N2 |
| CY001856 | A/New York/320/1999 | 1762 | 1999 | H3N2 |
| CY001864 | A/New York/321/1999 | 1762 | 1999 | H3N2 |
| CY002168 | A/New York/322/1999 | 1743 | 1999 | H3N2 |
| CY001872 | A/New York/323/1999 | 1762 | 1999 | H3N2 |
| CY001976 | A/New York/324/1999 | 1762 | 1999 | H3N2 |
| CY002368 | A/New York/325/1999 | 1740 | 1999 | H3N2 |
| CY007635 | A/New York/326/1999 | 1721 | 1999 | H3N2 |
| CY001880 | A/New York/327/1999 | 1762 | 1999 | H3N2 |
| CY001888 | A/New York/329/1999 | 1762 | 1999 | H3N2 |
| CY001984 | A/New York/331/1999 | 1762 | 1999 | H3N2 |
| CY001992 | A/New York/332/1999 | 1761 | 1999 | H3N2 |
| CY001896 | A/New York/333/1999 | 1762 | 1999 | H3N2 |
| CY001904 | A/New York/335/1999 | 1760 | 1999 | H3N2 |
| CY001912 | A/New York/336/1999 | 1761 | 1999 | H3N2 |
| CY001920 | A/New York/337/1999 | 1762 | 1999 | H3N2 |
| CY001928 | A/New York/338/1999 | 1762 | 1999 | H3N2 |
| CY002576 | A/New York/339/1999 | 1760 | 1999 | H3N2 |
| CY001936 | A/New York/340/1999 | 1741 | 1999 | H3N2 |
| CY002296 | A/New York/347/1999 | 1760 | 1999 | H3N2 |
| CY006163 | A/New York/397/1999 | 1710 | 1999 | H3N2 |
| CY002304 | A/New York/398/1999 | 1711 | 1999 | H3N2 |
| CY003432 | A/New York/421/1999 | 1720 | 1999 | H3N2 |
| CY003785 | A/New York/422/1999 | 1737 | 1999 | H3N2 |
| CY003793 | A/New York/423/1999 | 1728 | 1999 | H3N2 |
| CY003216 | A/New York/424/1999 | 1711 | 1999 | H3N2 |
| CY003440 | A/New York/425/1999 | 1735 | 1999 | H3N2 |
| CY003224 | A/New York/426/1999 | 1760 | 1999 | H3N2 |
| CY003232 | A/New York/427/1999 | 1747 | 1999 | H3N2 |
| CY003801 | A/New York/428/1999 | 1737 | 1999 | H3N2 |
| CY003568 | A/New York/449/1999 | 1737 | 1999 | H3N2 |
| CY003576 | A/New York/450/1999 | 1736 | 1999 | H3N2 |
| CY003584 | A/New York/451/1999 | 1737 | 1999 | H3N2 |
| CY006060 | A/New York/452/1999 | 1737 | 1999 | H3N2 |
| CY003592 | A/New York/453/1999 | 1750 | 1999 | H3N2 |
| CY003600 | A/New York/454/1999 | 1734 | 1999 | H3N2 |
| CY006068 | A/New York/455/1999 | 1737 | 1999 | H3N2 |
| CY003608 | A/New York/456/1999 | 1762 | 1999 | H3N2 |
| CY003616 | A/New York/457/1999 | 1732 | 1999 | H3N2 |
| CY003624 | A/New York/458/1999 | 1762 | 1999 | H3N2 |
| CY003632 | A/New York/459/1999 | 1758 | 1999 | H3N2 |
| CY006899 | A/New York/460/1999 | 1730 | 1999 | H3N2 |
| ISDNOS0001 | A/Oslo/102/1999 | 551 | 1999 | H3N2 |
| ISDNOS0013 | A/Oslo/1179/1999 | 843 | 1999 | H3N2 |
| ISDNOS0015 | A/Oslo/2130/99 | 855 | 1999 | H3N2 |
| ISDNOS0016 | A/Oslo/2137/99 | 1139 | 1999 | H3N2 |
| ISDNOS0017 | A/Oslo/2501/99 | 1139 | 1999 | H3N2 |
| ISDNOS0018 | A/Oslo/2512/99 | 1140 | 1999 | H3N2 |
| ISDNOS0019 | A/Oslo/3161/99 | 1140 | 1999 | H3N2 |
| ISDNOS0020 | A/Oslo/5631/99 | 1041 | 1999 | H3N2 |
| ISDNOS0012 | A/Oslo/737/1999 | 843 | 1999 | H3N2 |
| ISDNOS0003 | A/Oslo/800/1999 | 551 | 1999 | H3N2 |
| ISDNOS0004 | A/Oslo/820/1999 | 551 | 1999 | H3N2 |
| ISDNOS0005 | A/Oslo/834/1999 | 551 | 1999 | H3N2 |
| ISDNOS0006 | A/Oslo/871/1999 | 551 | 1999 | H3N2 |
| ISDNOS0002 | A/Oslo/881/1999 | 551 | 1999 | H3N2 |
| ISDNOS0007 | A/Oslo/910/1999 | 551 | 1999 | H3N2 |
| ISDNOS99 | A/Oslo/936/99 | 816 | 1999 | H3N2 |
| DQ508865 | A/Panama/2007/1999 | 1701 | 1999 | H3N2 |
| DQ487340 | A/Panama/2007/99 | 1762 | 1999 | H3N2 |
| ISDNCDA00 | A/Panama/2007/99 | 1000 | 1999 | H3N2 |
| AF501526 | A/Pennsylvania/20109/99 | 987 | 1999 | H3N2 |
| AF268313 | A/Peru/1621/99 | 1029 | 1999 | H1N1 |
| AF268312 | A/Peru/1798/99 | 1029 | 1999 | H1N1 |
| AF386633 | A/Pusan/71/99 | 987 | 1999 | H3N2 |
| AY968022 | A/RiodeJaneiro/57/99 | 560 | 1999 | H3N2 |
| AY968019 | A/RioGdoSul/21/99 | 996 | 1999 | H3N2 |
| AY968020 | A/RioGdoSul/25/99 | 997 | 1999 | H3N2 |
| AF534041 | A/Santa Fe/466/99 | 984 | 1999 | H3N2 |
| AF534042 | A/Santa Fe/9/99 | 984 | 1999 | H3N2 |
| AJ457879 | A/Saudi Arabia/13006/99 | 975 | 1999 | H1N1 |
| AB117215 | A/Sendai-H/1544/1999 | 978 | 1999 | H1N1 |
| ISDN13375 | A/SOUTH AFRICA/214/1999 | 979 | 1999 | H1N1 |
| ISDNSW000 | A/STOCKHOLM/1/99 | 987 | 1999 | H3N2 |
| ISDNSW001 | A/STOCKHOLM/10/99 | 987 | 1999 | H3N2 |
| ISDNSWA00 | A/Stockholm/11/99 | 987 | 1999 | H3N2 |
| ISDNSWA00 | A/Stockholm/12/99 | 987 | 1999 | H3N2 |
| ISDNSWA00 | A/Stockholm/13/99 | 987 | 1999 | H3N2 |
| ISDNSW000 | A/STOCKHOLM/2/99 | 987 | 1999 | H3N2 |
| ISDNSW000 | A/STOCKHOLM/3/99 | 987 | 1999 | H3N2 |
| ISDNSW000 | A/STOCKHOLM/4/99 | 987 | 1999 | H3N2 |
| ISDNSW000 | A/STOCKHOLM/6/99 | 987 | 1999 | H3N2 |
| ISDNSW000 | A/STOCKHOLM/7/99 | 987 | 1999 | H3N2 |
| ISDNSW001 | A/STOCKHOLM/8/99 | 987 | 1999 | H3N2 |
| AF362812 | A/Taiwan/1008/99 | 844 | 1999 | H3N2 |
| AF362793 | A/Taiwan/1184/99 | 561 | 1999 | H1N1 |
| AF362813 | A/Taiwan/1537/99 | 844 | 1999 | H3N2 |
| AF362817 | A/Taiwan/2548/99 | 844 | 1999 | H3N2 |
| AF362808 | A/Taiwan/389/99 | 844 | 1999 | H3N2 |

TABLE 1-continued

INFLUENZA TYPE A HA SEQUENCES

| Accession | Strain | Length | Year | Serotype |
|---|---|---|---|---|
| AF362798 | A/Taiwan/4360/99 | 561 | 1999 | H1N1 |
| AF362799 | A/Taiwan/4415/99 | 561 | 1999 | H1N1 |
| AF362788 | A/Taiwan/464/99 | 561 | 1999 | H1N1 |
| AF362800 | A/Taiwan/4845/99 | 561 | 1999 | H1N1 |
| AF362801 | A/Taiwan/4943/99 | 561 | 1999 | H1N1 |
| AF362802 | A/Taiwan/5063/99 | 561 | 1999 | H1N1 |
| AF362811 | A/Taiwan/830/99 | 844 | 1999 | H3N2 |
| AF362792 | A/Taiwan/892/99 | 561 | 1999 | H1N1 |
| ISDNAU000 | A/Tehran/83/99 | 996 | 1999 | H3N2 |
| ISDNAU000 | A/Townsville/1/99 | 1033 | 1999 | H3N2 |
| ISDNSW001 | A/UMEA/1/99 | 987 | 1999 | H3N2 |
| ISDNSWA01 | A/Umea/2/99 | 987 | 1999 | H3N2 |
| AF501529 | A/United Kingdom/26554/99 | 987 | 1999 | H3N2 |
| AF501527 | A/United Kingdom/34300/99 | 987 | 1999 | H3N2 |
| AF501533 | A/Utah/20997/99 | 987 | 1999 | H3N2 |
| AF501532 | A/Virginia/21712/99 | 987 | 1999 | H3N2 |
| AF501515 | A/Virginia/21716/99 | 987 | 1999 | H3N2 |
| AF501530 | A/Virginia/21735/99 | 987 | 1999 | H3N2 |
| AF501524 | A/Virginia/21743/99 | 987 | 1999 | H3N2 |
| AF501519 | A/Virginia/21754/99 | 987 | 1999 | H3N2 |
| AF501523 | A/Virginia/21799/99 | 987 | 1999 | H3N2 |
| AF501525 | A/Virginia/21817/99 | 987 | 1999 | H3N2 |
| AF501520 | A/Virginia/21822/99 | 987 | 1999 | H3N2 |
| AF501528 | A/Virginia/21828/99 | 987 | 1999 | H3N2 |
| AF501517 | A/Virginia/21833/99 | 987 | 1999 | H3N2 |
| AF501522 | A/Virginia/21845/99 | 987 | 1999 | H3N2 |
| AF501535 | A/Virginia/21847/99 | 987 | 1999 | H3N2 |
| AF501521 | A/Virginia/G1/99 | 987 | 1999 | H3N2 |
| AY963794 | A/Zhangzhou/51/1999 | 1198 | 1999 | H3N2 |
| AY138514 | A/zhejiang/12/99 | 987 | 1999 | H3N2 |
| AY138513 | A/zhejiang/6/99 | 987 | 1999 | H3N2 |
| AB117194 | A/Akita/161/1998 | 978 | 1998 | H1N1 |
| AF315571 | A/Athens/1/98 | 1126 | 1998 | H3N2 |
| AF316820 | A/Athens/16/98 | 1152 | 1998 | H3N2 |
| AF316817 | A/Athens/2/98 | 1126 | 1998 | H3N2 |
| AF316818 | A/Athens/7/98 | 1158 | 1998 | H3N2 |
| AF315560 | A/Athens/76/98 | 1128 | 1998 | H3N2 |
| AF315561 | A/Athens/94/98 | 1108 | 1998 | H3N2 |
| ISDNAU000 | A/AUCKLAND/18/98 | 848 | 1998 | H1N1 |
| ISDNAU000 | A/Bangkok/569/98 | 994 | 1998 | H1N1 |
| AF533712 | A/Buenos Aires/T28/98 | 984 | 1998 | H3N2 |
| AF533713 | A/Buenos Aires/V191/98 | 984 | 1998 | H3N2 |
| AF533714 | A/Buenos Aires/V235/98 | 984 | 1998 | H3N2 |
| ISDNAU000 | A/Christchurch/45/98 | 998 | 1998 | H3N2 |
| AF255023 | A/CNIC/109/98 | 988 | 1998 | H3N2 |
| AE255024 | A/CNIC/121/98 | 988 | 1998 | H3N2 |
| AF255025 | A/CNIC/125/98 | 988 | 1998 | H3N2 |
| AF255026 | A/CNIC/130/98 | 988 | 1998 | H3N2 |
| AF255027 | A/CNIC/145/98 | 988 | 1998 | H3N2 |
| AF255028 | A/CNIC/146/98 | 988 | 1998 | H3N2 |
| AF255029 | A/CNIC/149/98 | 988 | 1998 | H3N2 |
| AF255019 | A/CNIC/3/98 | 988 | 1998 | H3N2 |
| AF255020 | A/CNIC/52/98 | 988 | 1998 | H3N2 |
| AF255021 | A/CNIC/96/98 | 988 | 1998 | H3N2 |
| AF255022 | A/CNIC/97/98 | 988 | 1998 | H3N2 |
| AF533715 | A/Cordoba/V185/98 | 984 | 1998 | H3N2 |
| AF533716 | A/Cordoba/V391/98 | 984 | 1998 | H3N2 |
| AE533717 | A/Cordoba/V584/98 | 984 | 1998 | H3N2 |
| AF533718 | A/Cordoba/V651/98 | 984 | 1998 | H3N2 |
| AF386613 | A/Daegu/103/98 | 987 | 1998 | H3N2 |
| DQ167251 | A/Finland/541/98 | 984 | 1998 | H3 |
| AF311679 | A/Finland/571/98 | 984 | 1998 | H3N2 |
| AF311680 | A/Finland/572/98 | 984 | 1998 | H3N2 |
| AF311681 | A/Finland/573/98 | 984 | 1998 | H3N2 |
| AF311682 | A/Finland/574/98 | 984 | 1998 | H3N2 |
| AF311683 | A/Finland/575/98 | 984 | 1998 | H3N2 |
| AF311684 | A/Finland/576/98 | 984 | 1998 | H3N2 |
| AF311685 | A/Finland/577/98 | 984 | 1998 | H3N2 |
| AF311686 | A/Finland/578/98 | 984 | 1998 | H3N2 |
| AF311687 | A/Finland/579/98 | 984 | 1998 | H3N2 |
| AF311688 | A/Finland/582/98 | 984 | 1998 | H3N2 |
| AF311689 | A/Finland/583/98 | 975 | 1998 | H3N2 |
| AF311690 | A/Finland/584/98 | 984 | 1998 | H3N2 |
| AF311691 | A/Finland/585/98 | 984 | 1998 | H3N2 |
| AF311692 | A/Finland/586/98 | 984 | 1998 | H3N2 |
| AF311693 | A/Finland/587/98 | 984 | 1998 | H3N2 |
| AF311694 | A/Finland/589/98 | 984 | 1998 | H3N2 |
| AF311695 | A/Finland/590/98 | 984 | 1998 | H3N2 |
| AF311696 | A/Finland/592/98 | 984 | 1998 | H3N2 |
| AF311697 | A/Finland/593/98 | 984 | 1998 | H3N2 |
| AF311698 | A/Finland/594/98 | 984 | 1998 | H3N2 |
| AF357941 | A/Granada/RR334/98 | 519 | 1998 | H3N2 |
| AF357942 | A/Granada/RR356/98 | 519 | 1998 | H3N2 |
| AF316819 | A/Greece/10/98 | 1142 | 1998 | H3N2 |
| AF315562 | A/Greece/103/98 | 1088 | 1998 | H3N2 |
| AF315563 | A/Greece/106/98 | 1126 | 1998 | H3N2 |
| AF316821 | A/Greece/18/98 | 1149 | 1998 | H3N2 |
| AF315559 | A/Greece/19/98 | 1090 | 1998 | H3N2 |
| AF386778 | A/Hong Kong/1035/98 (egg isolate) | 1775 | 1998 | H1N1 |
| AF386777 | A/Hong Kong/1035/98 (MDCK isolate) | 1775 | 1998 | H1N1 |
| AF386779 | A/Hong Kong/1035/98 (original isolate) | 1262 | 1998 | H1N1 |
| AF386776 | A/Hong Kong/1035/98 (vero | 1775 | 1998 | H1N1 |
| AF387491 | A/Hong Kong/1131/98 (MDCK isolate) | 1211 | 1998 | H1N1 |
| AF386775 | A/Hong Kong/1131/98 (vero isolate) | 1775 | 1998 | H1N1 |
| AF386783 | A/Hong Kong/1134/98 | 693 | 1998 | H1N1 |
| AF386781 | A/Hong Kong/1134/98 | 1775 | 1998 | H1N1 |
| AF386782 | A/Hong Kong/1134/98 | 1306 | 1998 | H1N1 |
| AF386780 | A/Hong Kong/1134/98 (MDCK isolate) | 1775 | 1998 | H1N1 |
| AJ457885 | A/Hong Kong/4847/98 | 1041 | 1998 | H1N1 |
| AF102676 | A/Hong Kong/97/98 | 1656 | 1998 | H5N1 |
| AB043500 | A/Ibaraki/90/98 | 1029 | 1998 | H1N1 |
| ISDNAU001 | A/JOHANNESBURG/3/98 | 994 | 1998 | H3N2 |
| AJ457890 | A/Kanagawa/92/98 | 975 | 1998 | H1N1 |
| AF357930 | A/Madrid/G718/98 | 519 | 1998 | H3N2 |
| AF357959 | A/Madrid/SO1672/98 | 519 | 1998 | H3N2 |
| AF357960 | A/Madrid/SO1676/98 | 519 | 1998 | H3N2 |
| AF357961 | A/Madrid/SO1745/98 | 519 | 1998 | H3N2 |
| AF357962 | A/Madrid/SO1747/98 | 519 | 1998 | H3N2 |
| AF357963 | A/Madrid/SO1798/98 | 519 | 1998 | H3N2 |
| AF357964 | A/Madrid/SO2017/98 | 519 | 1998 | H3N2 |
| AF357965 | A/Madrid/SO2060/98 | 519 | 1998 | H3N2 |
| ISDNSW001 | A/MALMO/1/98 | 987 | 1998 | H3N2 |
| ISDNSW001 | A/MALMO/14/98 | 987 | 1998 | H3N2 |
| AY271794 | A/Memphis/31/98 | 1701 | 1998 | H3N2 |
| AJ457894 | A/Moscow/17/98 | 1041 | 1998 | H1N1 |
| AB019355 | A/Nagasaki/76/98 | 1762 | 1998 | H3N2 |
| AB019356 | A/Nagasaki/93/98 | 1762 | 1998 | H3N2 |
| AY661206 | A/Netherlands/414/98 | 1095 | 1998 | H3N2 |
| AY661207 | A/Netherlands/427/98 | 1095 | 1998 | H3N2 |
| AY661208 | A/Netherlands/462/98 | 1095 | 1998 | H3N2 |
| AY661209 | A/Netherlands/5/98 | 1095 | 1998 | H3N2 |
| AF533719 | A/Neuquen/V541/98 | 984 | 1998 | H3N2 |
| AF533720 | A/Neuquen/V690/98 | 984 | 1998 | H3N2 |
| CY001568 | A/New York/224/1998 | 1703 | 1998 | H3N2 |
| CY001477 | A/New York/240/1998 | 1703 | 1998 | H3N2 |
| CY001504 | A/New York/247/1998 | 1718 | 1998 | H3N2 |
| CY001485 | A/New York/249/1998 | 1760 | 1998 | H3N2 |
| CY001493 | A/New York/250/1998 | 1760 | 1998 | H3N2 |
| CY002544 | A/New York/251/1998 | 1718 | 1998 | H3N2 |
| CY002120 | A/New York/254/1998 | 1711 | 1998 | H3N2 |
| CY001584 | A/New York/256/1998 | 1737 | 1998 | H3N2 |
| CY001672 | A/New York/287/1998 | 1710 | 1998 | H3N2 |
| CY001784 | A/New York/289/1998 | 1760 | 1998 | H3N2 |
| CY001800 | A/New York/304/1998 | 1743 | 1998 | H3N2 |
| CY001816 | A/New York/313/1998 | 1762 | 1998 | H3N2 |
| CY002376 | A/New York/328/1998 | 1761 | 1998 | H3N2 |
| CY002384 | A/New York/330/1998 | 1742 | 1998 | H3N2 |
| CY003560 | A/New York/448/1998 | 1762 | 1998 | H3N2 |
| CY008180 | A/New York/502/1998 | 1722 | 1998 | H3N2 |
| CY008924 | A/New York/504/1998 | 1717 | 1998 | H3N2 |
| CY006787 | A/New York/506/1998 | 1721 | 1998 | H3N2 |
| CY006251 | A/New York/510/1998 | 1721 | 1998 | H3N2 |
| CY006459 | A/New York/512/1998 | 1721 | 1998 | H3N2 |

TABLE 1-continued

INFLUENZA TYPE A HA SEQUENCES

| Accession | Strain | Length | Year | Serotype |
|---|---|---|---|---|
| CY008940 | A/New York/514/1998 | 1721 | 1998 | H3N2 |
| CY006283 | A/New York/517/1998 | 1730 | 1998 | H3N2 |
| CY006475 | A/New York/518/1998 | 1721 | 1998 | H3N2 |
| CY006483 | A/New York/519/1998 | 1721 | 1998 | H3N2 |
| CY006491 | A/New York/520/1998 | 1721 | 1998 | H3N2 |
| CY006499 | A/New York/521/1998 | 1721 | 1998 | H3N2 |
| CY006515 | A/New York/523/1998 | 1723 | 1998 | H3N2 |
| CY006531 | A/New York/525/1998 | 1721 | 1998 | H3N2 |
| CY006795 | A/New York/527/1998 | 1721 | 1998 | H3N2 |
| CY006539 | A/New York/528/1998 | 1721 | 1998 | H3N2 |
| CY008948 | A/New York/529/1998 | 1721 | 1998 | H3N2 |
| CY008956 | A/New York/530/1998 | 1721 | 1998 | H3N2 |
| CY006547 | A/New York/531/1998 | 1721 | 1998 | H3N2 |
| CY006555 | A/New York/532/1998 | 1721 | 1998 | H3N2 |
| CY006563 | A/New York/533/1998 | 1721 | 1998 | H3N2 |
| CY006571 | A/New York/534/1998 | 1721 | 1998 | H3N2 |
| CY006771 | A/New York/535/1998 | 1721 | 1998 | H3N2 |
| CY009988 | A/New York/536/1998 | 1721 | 1998 | H3N2 |
| CY006803 | A/New York/538/1998 | 1717 | 1998 | H3N2 |
| CY006579 | A/New York/539/1998 | 1721 | 1998 | H3N2 |
| CY008964 | A/New York/540/1998 | 1721 | 1998 | H3N2 |
| CY006587 | A/New York/541/1998 | 1721 | 1998 | H3N2 |
| CY006595 | A/New York/542/1998 | 1721 | 1998 | H3N2 |
| CY006603 | A/New York/543/1998 | 1721 | 1998 | H3N2 |
| CY008532 | A/New York/544/1998 | 1717 | 1998 | H3N2 |
| CY006619 | A/New York/546/1998 | 1721 | 1998 | H3N2 |
| CY006635 | A/New York/548/1998 | 1721 | 1998 | H3N2 |
| CY008972 | A/New York/549/1998 | 1721 | 1998 | H3N2 |
| CY008980 | A/New York/550/1998 | 1730 | 1998 | H3N2 |
| ISDNOS0008 | A/Oslo/274/1998 | 551 | 1998 | H3N2 |
| ISDNOS0009 | A/Oslo/283/1998 | 551 | 1998 | H3N2 |
| ISDNOS0011 | A/Oslo/490/1998 | 551 | 1998 | H3N2 |
| ISDNOS0010 | A/Oslo/491/1998 | 551 | 1998 | H3N2 |
| AJ457898 | A/Ostrava/801/98 | 1041 | 1998 | H1N1 |
| AJ457892 | A/Paris/1857/98 | 1041 | 1998 | H1N1 |
| ISDNAU001 | A/PERTH/24/98 | 994 | 1998 | H3N2 |
| ISDN13402 | A/PHILIPPINES/9/98 | 952 | 1998 | H1N1 |
| AF386612 | A/Pusan/10/98 | 987 | 1998 | H3N2 |
| AF386628 | A/Pusan/68/98 | 987 | 1998 | H3N2 |
| AF533721 | A/Salta/V793/98 | 984 | 1998 | H3N2 |
| AF357943 | A/San Sebastian/RR390/98 | 519 | 1998 | H3N2 |
| AF386627 | A/Seoul/37/98 | 987 | 1998 | H3N2 |
| AF386629 | A/Seoul/95/98 | 987 | 1998 | H3N2 |
| AY043015 | A/Shantou/239/98 | 1488 | 1998 | H9N2 |
| AY043017 | A/Shaoguan/408/98 | 1488 | 1998 | H9N2 |
| AY043018 | A/Shaoguan/447/98 | 1488 | 1998 | H9N2 |
| ISDN13368 | A/SOUTH AFRICA/21/98 | 973 | 1998 | H3N2 |
| ISDN13369 | A/SOUTH AFRICA/56/98 | 973 | 1998 | H3N2 |
| ISDN13367 | A/SOUTH AFRICA/8/98 | 973 | 1998 | H3N2 |
| ISDNAU0010 | A/SOUTH AUSTRALIA/6/98 | 999 | 1998 | H3N2 |
| ISDNSW000 | A/STOCKHOLM/1/98 | 987 | 1998 | H3N2 |
| ISDNSW000 | A/STOCKHOLM/18/98 | 987 | 1998 | H3N2 |
| ISDNSW000 | A/STOCKHOLM/19/98 | 987 | 1998 | H3N2 |
| AY032978 | A/Switzerland/7729/98 | 1762 | 1998 | H3N2 |
| AF382318 | A/Switzerland/7729/98 (MDCK isolate) | 1762 | 1998 | H3N2 |
| AF362805 | A/Taiwan/118/98 | 844 | 1998 | H3N2 |
| AF139938 | A/Taiwan/20/98 | 861 | 1998 | H3N2 |
| AF139934 | A/Taiwan/21/98 | 861 | 1998 | H3N2 |
| AF362807 | A/Taiwan/293/98 | 844 | 1998 | H3N2 |
| AF139940 | A/Taiwan/346/98 | 861 | 1998 | H3N2 |
| AF362809 | A/Taiwan/423/98 | 844 | 1998 | H3N2 |
| AF139939 | A/Taiwan/45/98 | 861 | 1998 | H3N2 |
| AF362810 | A/Taiwan/464/98 | 844 | 1998 | H3N2 |
| AF362778 | A/Taiwan/5779/98 | 561 | 1998 | H1N1 |
| AB013806 | A/Tokyo/1511/98 | 710 | 1998 | H3N2 |
| AB013807 | A/Tokyo/1527/98 | 710 | 1998 | H3N2 |
| AB013808 | A/Tokyo/1539/98 | 710 | 1998 | H3N2 |
| AB013809 | A/Tokyo/1566/98 | 710 | 1998 | H3N2 |
| AB013810 | A/Tokyo/1567/98 | 710 | 1998 | H3N2 |
| AB013811 | A/Tokyo/1568/98 | 710 | 1998 | H3N2 |
| AB013812 | A/Tokyo/1569/98 | 710 | 1998 | H3N2 |
| AB013813 | A/Tokyo/1570/98 | 710 | 1998 | H3N2 |
| AF533722 | A/Tucuman/V425/98 | 984 | 1998 | H3N2 |
| AF533723 | A/Tucuman/V694/98 | 984 | 1998 | H3N2 |
| ISDNSW001 | A/UMEA/16/98 | 987 | 1998 | H3N2 |
| AF533724 | A/Ushuaia/R127/98 | 984 | 1998 | H3N2 |
| AF533725 | A/Ushuaia/R13/98 | 984 | 1998 | H3N2 |
| AF533726 | A/Ushuaia/R254/98 | 984 | 1998 | H3N2 |
| AF533727 | A/Ushuaia/R270/98 | 984 | 1998 | H3N2 |
| AF533728 | A/Ushusia/R272/98 | 984 | 1998 | H3N2 |
| AF533729 | A/Ushuaia/R274/98 | 984 | 1998 | H3N2 |
| ISDNAU000 | A/Waikato/12/98 | 1015 | 1998 | H3N2 |
| AF342821 | A/Wisconsin/10/98 | 1064 | 1998 | H1N1 |
| AB117221 | A/Yokohama/50/1998 | 978 | 1998 | H1N1 |
| AB043495 | A/Yokohama/50/98 | 1029 | 1998 | H1N1 |
| AY138515 | A/zhejiang/10/98 | 987 | 1998 | H3N2 |
| DQ174263 | A/Zhejiang/18/98 | 987 | 1998 | H3N2 |
| AF315568 | A/Athens/2/97 | 1103 | 1997 | H3N2 |
| AF315570 | A/Athens/23/97 | 1126 | 1997 | H3N2 |
| AY661201 | A/Auckland/10/97 | 1095 | 1997 | H3N2 |
| AF180578 | A/Auckland/5/97 | 987 | 1997 | H3N2 |
| AF180630 | A/Bangkok/1/97 | 987 | 1997 | H3N2 |
| AF180609 | A/Beijing/17/97 | 987 | 1997 | H3N2 |
| AF180608 | A/Beijing/62/97 | 987 | 1997 | H3N2 |
| AF180649 | A/Brazil/43/97 | 987 | 1997 | H3N2 |
| AF180648 | A/Brazil/51/97 | 987 | 1997 | H3N2 |
| AF534025 | A/Buenos Aires/A64/97 | 1044 | 1997 | H1N1 |
| AF534026 | A/Buenos Aires/T114/97 | 1044 | 1997 | H1N1 |
| AF534027 | A/Buenos Aires/T118/97 | 1044 | 1997 | H1N1 |
| AF180641 | A/California/10/97 | 987 | 1997 | H3N2 |
| AF180647 | A/Canada/101/97 | 987 | 1997 | H3N2 |
| AF180577 | A/Canada/10679/97 | 987 | 1997 | H3N2 |
| AF180576 | A/Canada/2/97 | 987 | 1997 | H3N2 |
| AF180582 | A/Canberra/5/97 | 987 | 1997 | H3N2 |
| AF180572 | A/Canberra/9/97 | 987 | 1997 | H3N2 |
| AF180623 | A/Caracas/422/97 | 987 | 1997 | H3N2 |
| AF386623 | A/Daegu/84/97 | 987 | 1997 | H3N2 |
| AJ457891 | A/Dakar/11/97 | 1041 | 1997 | H1N1 |
| AF180626 | A/Delaware/4/97 | 987 | 1997 | H3N2 |
| ISDNENG97 | A/England/731/97 | 1041 | 1997 | H3N2 |
| AF368439 | A/Finland/460/97 | 984 | 1997 | H3N2 |
| AF368440 | A/Finland/524/97 | 984 | 1997 | H3N2 |
| AF368441 | A/Finland/528/97 | 984 | 1997 | H3N2 |
| AF368442 | A/Finland/529/97 | 984 | 1997 | H3N2 |
| AF368443 | A/Finland/532/97 | 984 | 1997 | H3N2 |
| AF311676 | A/Finland/539/97 | 984 | 1997 | H3N2 |
| AF180654 | A/France/75/97 | 987 | 1997 | H3N2 |
| AF315567 | A/Greece/1/97 | 1167 | 1997 | H3N2 |
| AF315569 | A/Greece/4/97 | 1145 | 1997 | H3N2 |
| AF180631 | A/Guangzhou/66/97 | 987 | 1997 | H3N2 |
| AF180580 | A/Hawaii/1/97 | 987 | 1997 | H3N2 |
| AY661202 | A/Hong Kong/1/97 | 1095 | 1997 | H3N2 |
| AF046088 | A/Hong Kong/156/97 | 1741 | 1997 | H5N1 |
| AF036356 | A/Hong Kong/156/97 | 1690 | 1997 | H5N1 |
| AF028709 | A/Hong Kong/156/97 | 1741 | 1997 | H5N1 |
| AY661203 | A/Hong Kong/280/97 | 1095 | 1997 | H3N2 |
| AF180575 | A/Hong Kong/387/97 | 987 | 1997 | H3N2 |
| AF180571 | A/Hong Kong/391/97 | 987 | 1997 | H3N2 |
| AJ457895 | A/Hong Kong/470/97 | 1041 | 1997 | H1N1 |
| AF084279 | A/Hong Kong/481/97 | 1665 | 1997 | H5N1 |
| AF046096 | A/Hong Kong/481/97 | 1741 | 1997 | H5N1 |
| AF046098 | A/Hong Kong/482/97 | 1741 | 1997 | H5N1 |
| AF084280 | A/Hong Kong/483/97 | 1665 | 1997 | H5N1 |
| AF046097 | A/Hong Kong/483/97 | 1741 | 1997 | H5N1 |
| AF084532 | A/Hong Kong/485/97 | 1665 | 1997 | H5N1 |
| AF102681 | A/Hong Kong/485/97 | 1656 | 1997 | H5N1 |
| AF084281 | A/Hong Kong/486/97 | 1665 | 1997 | H5N1 |
| AF102671 | A/Hong Kong/486/97 | 1656 | 1997 | H5N1 |
| AF102672 | A/Hong Kong/488/97 | 1656 | 1997 | H5N1 |
| AF102677 | A/Hong Kong/491/97 | 1656 | 1997 | H5N1 |
| AF102679 | A/Hong Kong/503/97 | 1656 | 1997 | H5N1 |
| AF102675 | A/Hong Kong/507/97 | 1656 | 1997 | H5N1 |
| AF102682 | A/Hong Kong/514/97 | 1656 | 1997 | H5N1 |
| AF102673 | A/Hong Kong/516/97 | 1656 | 1997 | H5N1 |
| AF102680 | A/Hong Kong/532/97 | 1656 | 1997 | H5N1 |
| AF102674 | A/Hong Kong/538/97 | 1656 | 1997 | H5N1 |
| AF102678 | A/Hong Kong/542/97 | 1656 | 1997 | H5N1 |
| AF180598 | A/Japan/416/97 | 987 | 1997 | H3N2 |
| AF180643 | A/Johannesburg/10/97 | 987 | 1997 | H3N2 |
| AJ457897 | A/Johannesburg/159/97 | 1041 | 1997 | H1N1 |

TABLE 1-continued

INFLUENZA TYPE A HA SEQUENCES

| Accession | Strain | Length | Year | Serotype |
|---|---|---|---|---|
| AF180605 | A/Johannesburg/3/97 | 987 | 1997 | H3N2 |
| AF180642 | A/Johannesburg/9/97 | 987 | 1997 | H3N2 |
| AB043494 | A/Kamata/159/97 | 1029 | 1997 | H1N1 |
| AF386622 | A/Kangwon/78/97 | 987 | 3997 | H3N2 |
| AF180618 | A/Kentucky/2/97 | 987 | 1997 | H3N2 |
| AF180596 | A/Korea/572/97 | 987 | 1997 | H3N2 |
| AF180597 | A/Korea/671/97 | 987 | 1997 | H3N2 |
| AF180595 | A/Korea/679/97 | 987 | 1997 | H3N2 |
| AF386618 | A/Kwangju/1/97 | 987 | 1997 | H3N2 |
| AF386626 | A/Kwangju/107/97 | 987 | 1997 | H3N2 |
| AF386619 | A/Kwangju/4/97 | 987 | 1997 | H3N2 |
| AF386620 | A/Kwangju/63/97 | 987 | 3997 | H3N2 |
| AF386624 | A/Kyounggi/102/97 | 987 | 1997 | H3N2 |
| AF534028 | A/La Plata/12089/97 | 984 | 1997 | H3N2 |
| AF357939 | A/Madrid/R214/97 | 519 | 3997 | H3N2 |
| AF357958 | A/Madrid/SO1208/97 | 519 | 1997 | H3N2 |
| AF180640 | A/Minnesota/1/97 | 987 | 1997 | H3N2 |
| AF180646 | A/Moscow/2/97 | 987 | 1997 | H3N2 |
| AY661205 | A/Netherlands/300/97 | 1095 | 3997 | H3N2 |
| CY006443 | A/New York/501/1997 | 1723 | 1997 | H3N2 |
| CY006227 | A/New York/503/1997 | 1731 | 1997 | H3N2 |
| CY006235 | A/New York/505/1997 | 1728 | 1997 | H3N2 |
| CY008932 | A/New York/507/1997 | 1721 | 1997 | H3N2 |
| CY006243 | A/New York/508/1997 | 1731 | 1997 | H3N2 |
| CY006451 | A/New York/509/1997 | 1729 | 1997 | H3N2 |
| CY006259 | A/New York/511/1997 | 1722 | 1997 | H3N2 |
| CY006267 | A/New York/513/1997 | 1720 | 1997 | H3N2 |
| CY006275 | A/New York/515/1997 | 1721 | 1997 | H3N2 |
| CY006467 | A/New York/516/1997 | 1730 | 1997 | H3N2 |
| CY006507 | A/New York/522/1997 | 1730 | 1997 | H3N2 |
| CY006523 | A/New York/524/1997 | 1721 | 1997 | H3N2 |
| CY007979 | A/New York/526/1997 | 1721 | 1997 | H3N2 |
| CY006611 | A/New York/545/1997 | 1721 | 1997 | H3N2 |
| CY006627 | A/New York/547/1997 | 1721 | 1997 | H3N2 |
| CY009644 | A/New York/558/1997 | 1721 | 1997 | H3N2 |
| CY009460 | A/New York/560/1997 | 1721 | 1997 | H3N2 |
| CY009468 | A/New York/564/1997 | 1721 | 1997 | H3N2 |
| CY009652 | A/New York/566/1997 | 1721 | 1997 | H3N2 |
| CY009484 | A/New York/569/1997 | 3721 | 1997 | H3N2 |
| CY009676 | A/New York/576/1997 | 1721 | 1997 | H3N2 |
| CY009516 | A/New York/579/1997 | 1721 | 1997 | H3N2 |
| CY009692 | A/New York/581/1997 | 1721 | 1997 | H3N2 |
| CY009524 | A/New York/583/1997 | 1721 | 1997 | H3N2 |
| CY009700 | A/New York/585/1997 | 1721 | 1997 | H3N2 |
| CY009748 | A/New York/597/1997 | 1721 | 1997 | H3N2 |
| AY661210 | A/Nice/491/97 | 1095 | 1997 | H3N2 |
| AF368445 | A/Oslo/185/97 | 984 | 1997 | H3N2 |
| AF368444 | A/Oslo/21/97 | 984 | 1997 | H3N2 |
| AF368446 | A/Oslo/244/97 | 984 | 1997 | H3N2 |
| AF363502 | A/Paris/896/97 | 1704 | 1997 | H3N2 |
| AF363503 | A/Paris/906/97 | 1704 | 1997 | H3N2 |
| AF363504 | A/Paris/908/97 | 1704 | 1997 | H3N2 |
| AF180644 | A/Pennsylvania/2/97 | 987 | 1997 | H3N2 |
| AF180574 | A/Puerto Rico/1/97 | 987 | 1997 | H3N2 |
| AF180656 | A/Rhode Island/7/97 | 987 | 1997 | H3N2 |
| AF180614 | A/Russia/41/97 | 987 | 1997 | H3N2 |
| AF534029 | A/Santa Fe/5456/97 | 984 | 1997 | H3N2 |
| AF386625 | A/Seoul/104/97 | 987 | 1997 | H3N2 |
| AF386621 | A/Seoul/69/97 | 987 | 1997 | H3N2 |
| AF038270 | A/Shiga/25/97 | 984 | 1997 | H3N2 |
| AF180581 | A/South Australia/54/97 | | | |
| AF180611 | A/Spain/214/97 | 987 | 1997 | H3N2 |
| AF180583 | A/Sydney/4/97 | 987 | 1997 | H3N2 |
| ISDNASYD9 | A/Sydney/5/97 | 1646 | 1997 | H3N2 |
| AJ311466 | A/Sydney/5/97 | 1653 | 1997 | H3N2 |
| AF096312 | A/Sydney/5/97-like (isolate-25) | 982 | 1997 | H3N2 |
| AF096316 | A/Sydney/5/97-like (isolate-93) | 982 | 1997 | H3N2 |
| AF087700 | A/Sydney/5/97-like(isolate1) | 982 | 1997 | H3N2 |
| AF087701 | A/Sydney/5/97-like(isolate2) | 982 | 1997 | H3N2 |
| AF087702 | A/Sydney/5/97-like (isolate3) | 982 | 1997 | H3N2 |
| AF087703 | A/Sydney/5/97-like(isolate30) | 982 | 1997 | H3N2 |
| AF087704 | A/Sydney/5/97-like(isolate31) | 982 | 1997 | H3N2 |
| AF087705 | A/Sydney/5/97-like(isolate375) | 982 | 1997 | H3N2 |
| AF087706 | A/Sydney/5/97-like(isolate5) | 982 | 1997 | H3N2 |
| AF087707 | A/Sydney/5/97-like(isolate56) | 982 | 1997 | H3N2 |
| AF087708 | A/Sydney/5/97-like(isolate57) | 982 | 1997 | H3N2 |
| AF096313 | A/Sydney/5/97-like(isolate-27) | 982 | 1997 | H3N2 |
| AF096308 | A/Sydney/5/97-like (isolate-369) | 982 | 1997 | H3N2 |
| AF096309 | A/Sydney/5/97-like (isolate-60) | 982 | 1997 | H3N2 |
| AF096311 | A/Sydney/5/97-like (isolate-65) | 982 | 1997 | H3N2 |
| AF096306 | A/Sydney/5/97-like (isolate-83) | 982 | 1997 | H3N2 |
| AF096310 | A/Sydney/5/97-like (isolate-86) | 982 | 1997 | H3N2 |
| AF096314 | A/Sydney/5/97-like (isolate-91) | 982 | 1997 | H3N2 |
| AF096315 | A/Sydney/5/97-like (isolate-92) | 982 | 1997 | H3N2 |
| AF096307 | A/Sydney/5/97-like (isolate-96) | 982 | 1997 | H3N2 |
| AF180573 | A/Sydney/6/97 | 987 | 1997 | H3N2 |
| AF362814 | A/Taiwan/1748/97 | 844 | 1997 | H3N2 |
| AF362816 | A/Taiwan/2031/97 | 844 | 1997 | H3N2 |
| AF139935 | A/Taiwan/3351/97 | 861 | 1997 | H3N2 |
| AF362796 | A/Taiwan/3355/97 | 561 | 1997 | H1N1 |
| AY303743 | A/Taiwan/3396/97 | 844 | 1997 | H3N2 |
| AF139930 | A/Taiwan/3427/97 | 861 | 1997 | H3N2 |
| AF139933 | A/Taiwan/3469/97 | 861 | 1997 | H3N2 |
| AY303745 | A/Taiwan/3503/97 | 844 | 1997 | H3N2 |
| AF139931 | A/Taiwan/3513/97 | 861 | 1997 | H3N2 |
| AF180634 | A/Tasmania/1/97 | 987 | 1997 | H3N2 |
| AF180621 | A/Thailand/78/97 | 987 | 1997 | H3N2 |
| AF180620 | A/Thailand/79/97 | 987 | 1997 | H3N2 |
| AF180601 | A/Tianjing/51/97 | 987 | 1997 | H3N2 |
| AB014060 | A/Tokyo/70/97 | 710 | 1997 | H3N2 |
| AB014061 | A/Tokyo/71/97 | 710 | 1997 | H3N2 |
| AB014062 | A/Tokyo/72/97 | 710 | 1997 | H3N2 |
| AF180633 | A/Victoria/30/97 | 987 | 1997 | H3N2 |
| AF180632 | A/Victoria/47/97 | 987 | 1997 | H3N2 |
| ISDNAU000 | A/Victoria/605/97 | 1002 | 1997 | H3N2 |
| AF180579 | A/Wellington/3/97 | 987 | 1997 | H3N2 |
| AF357940 | A/Zaragoza/RR315/97 | 519 | 1997 | H3N2 |
| AB043493 | A/Aichi/25/96 | 1032 | 1996 | H1N1 |
| AF008723 | A/Alaska/2/96 | 987 | 1996 | H3N2 |
| AF180591 | A/Argentina/207/96 | 987 | 1996 | H3N2 |
| AF180606 | A/Argentina/39/96 | 987 | 1996 | H3N2 |
| AF180590 | A/Argentina/601/96 | 987 | 1996 | H3N2 |
| AF180629 | A/Auckland/108/96 | 981 | 1996 | H3N2 |
| AF008714 | A/Auckland/5/96 | 987 | 1996 | H3N2 |
| AF008715 | A/Auckland/9/96 | 987 | 1996 | H3N2 |
| AF180586 | A/Beijing/244/96 | 987 | 1996 | H3N2 |
| AF008732 | A/Brazil/18/96 | 987 | 1996 | H3N2 |
| AF180660 | A/Brazil/184/96 | 987 | 1996 | H3N2 |
| AF180658 | A/Brazil/3/96 | 987 | 1996 | H3N2 |
| AF180651 | A/Brazil/309/96 | 987 | 1996 | H3N2 |
| AF180659 | A/Brazil/45/96 | 987 | 1996 | H3N2 |
| AF180661 | A/Brazil/597/96 | 987 | 1996 | H3N2 |
| AF008733 | A/Brazil/8/96 | 987 | 1996 | H3N2 |
| AF180657 | A/Brazil/87/96 | 987 | 1996 | H3N2 |
| AF008720 | A/Brisbane/22/96 | 987 | 1996 | H3N2 |
| AF008716 | A/Brisbane/35/96 | 987 | 1996 | H3N2 |
| AY661197 | A/Brisbane/8/96 | 1095 | 1996 | H3N2 |
| AF534024 | A/Buenos Aires/32/96 | 984 | 1996 | H3N2 |
| AF534023 | A/Buenos Aires/37/96 | 984 | 1996 | H3N2 |
| AF534019 | A/Buenos Aires/4459/96 | 984 | 1996 | H3N2 |
| AF534020 | A/Buenos Aires/4534/96 | 984 | 1996 | H3N2 |

TABLE 1-continued

INFLUENZA TYPE A HA SEQUENCES

| Accession | Strain | Length | Year | Serotype |
|---|---|---|---|---|
| AF534021 | A/Buenos Aires/4559/96 | 984 | 1996 | H3N2 |
| AF534022 | A/Buenos Aires/4634/96 | 984 | 1996 | H3N2 |
| AF180636 | A/California/13/96 | 987 | 1996 | H3N2 |
| AF008738 | A/Canada/17/96 | 987 | 1996 | H3N2 |
| AF008742 | A/Canada/27/96 | 987 | 1996 | H3N2 |
| AF008735 | A/Canada/61/96 | 987 | 1996 | H3N2 |
| AF180624 | A/Caracas/465/96 | 987 | 1996 | H3N2 |
| AF008708 | A/Chile/2115/96 | 987 | 1996 | H3N2 |
| AF008717 | A/Christchurch/1/96 | 987 | 1996 | H3N2 |
| AF008721 | A/CNIC/35/96 | 987 | 1996 | H3N2 |
| AF180599 | A/Colombia/170/96 | 987 | 1996 | H3N2 |
| AF180616 | A/Colorado/11/96 | 987 | 1996 | H3N2 |
| AF180589 | A/Cordoba/3278/96 | 987 | 1996 | H3N2 |
| AF028020 | A/England/268/96 | 1732 | 1996 | H7N7 |
| AF368437 | A/Finland/435/96 | 984 | 1996 | H3N2 |
| AF311678 | A/Finland/445/96 | 984 | 1996 | H3N2 |
| AF368438 | A/Finland/447/96 | 984 | 1996 | H3N2 |
| AF180603 | A/Fujian/133/96 | 987 | 1996 | H3N2 |
| AF008726 | A/Fujian/47/96 | 987 | 1996 | H3N2 |
| AF038266 | A/Fukushima/114/96 | 984 | 1996 | H3N2 |
| AF008712 | A/Fukushima/114/96 (cell isolate) | 987 | 1996 | H3N2 |
| AF008713 | A/Fukushima/114/96 (egg isolate) | 987 | 1996 | H3N2 |
| AF038269 | A/Fukushima/140/96 | 984 | 1996 | H3N2 |
| AY661195 | A/Geneva/3958/96 | 1095 | 1996 | H3N2 |
| AF008737 | A/Germany/491/96 | 987 | 1996 | H3N2 |
| AF357936 | A/Granada/R192/96 | 519 | 1996 | H3N2 |
| AF357937 | A/Granada/R195/96 | 519 | 1996 | H3N2 |
| AF357938 | A/Granada/R198/96 | 519 | 1996 | H3N2 |
| AF180655 | A/Guadeloupe/39/96 | 987 | 1996 | H3N2 |
| AF180653 | A/Guam/1014/96 | 987 | 1996 | H3N2 |
| AF180619 | A/Guangdong/1/96 | 987 | 1996 | H3N2 |
| AF525217 | A/Guangdong/4/96 | 984 | 1996 | H3N2 |
| AF525799 | A/Guangdong/7/96 | 984 | 1996 | H3N2 |
| AF525686 | A/Guangdong/8/96 | 984 | 1996 | H3N2 |
| AF008709 | A/Guangzhou/11/96 | 987 | 1996 | H3N2 |
| AF008707 | A/Guangzhou/6/96 | 987 | 1996 | H3N2 |
| AF008710 | A/Guangzbou/8/96 | 987 | 1996 | H3N2 |
| AF180588 | A/Guanxi/189/96 | 987 | 1996 | H3N2 |
| AF180585 | A/Harbin/3/96 | 987 | 1996 | H3N2 |
| AF008718 | A/Hawaii/2/96 | 987 | 1996 | H3N2 |
| AY661193 | A/Hong Kong/20/96 | 1095 | 1996 | H3N2 |
| AF008711 | A/Hong Kong/357/96 | 987 | 1996 | H3N2 |
| AF180602 | A/Hong Kong/358/96 | 987 | 1996 | H3N2 |
| AF008769 | A/Hong Kong/42/96 | 987 | 1996 | H3N2 |
| AF180570 | A/Hong Kong/434/96 | 987 | 1996 | H3N2 |
| AF180615 | A/Indiana/1/96 | 987 | 1996 | H3N2 |
| AF008724 | A/Japan/99/96 | 987 | 1996 | H3N2 |
| AF180665 | A/Johannesburg/53/96 | 987 | 1996 | H3N2 |
| AJ457906 | A/Johannesburg/82/96 | 1044 | 1996 | H1N1 |
| AB043492 | A/Kamata/69/96 | 1032 | 1996 | H1N1 |
| AF008736 | A/Korea/45/96 | 987 | 1996 | H3N2 |
| AF131996 | A/Lyon/1781/96(BHK-variant)grown | 1086 | 1996 | H3N2 |
| AF131998 | A/Lyon/1781/96(egg-grown variant) | 1086 | 1996 | H3N2 |
| AF131997 | A/Lyon/1781/96(MDCK-grown variant) | 1086 | 1996 | H3N2 |
| AF131993 | A/Lyon/3043/96(BHK-grown variant) | 1032 | 1996 | H1N1 |
| AF131995 | A/Lyon/3043/96(Egg-grown variant) | 1032 | 1996 | H1N1 |
| AF131994 | A/Lyon/3043/96(MDCK-grown variant) | 1032 | 1996 | H1N1 |
| AF357929 | A/Madrid/G622/96 | 519 | 1996 | H3N2 |
| AF357934 | A/Madrid/R165/96 | 519 | 1996 | H3N2 |
| AF357935 | A/Madrid/R187/96 | 519 | 1996 | H3N2 |
| AF357955 | A/Madrid/SO1015/96 | 519 | 1996 | H3N2 |
| AF357956 | A/Madrid/SO1023/96 | 519 | 1996 | H3N2 |
| AF357957 | A/Madrid/SO1025/96 | 519 | 1996 | H3N2 |
| AF008771 | A/Memphis/1/96 | 987 | 1996 | H3N2 |
| AY282758 | A/Memphis/14/96 | 1743 | 1996 | H1N1 |
| AY282756 | A/Memphis/14/96 | 1743 | 1996 | H1N1 |
| AF180625 | A/Minnesota/1/96 | 987 | 1996 | H3N2 |
| AF180637 | A/Missouri/10/96 | 987 | 1996 | H3N2 |
| AF180645 | A/Missouri/11/96 | 987 | 1996 | H3N2 |
| AF008743 | A/Missouri/6/96 | 987 | 1996 | H3N2 |
| AF180627 | A/Montevideo/318/96 | 987 | 1996 | H3N2 |
| AB117207 | A/Nagano/6059/1996 | 981 | 1996 | H1N1 |
| AF092064 | A/Netherlands/172/96 | 987 | 1996 | H3N2 |
| AY661194 | A/Netherlands/91/96 | 1095 | 1996 | H3N2 |
| AF180617 | A/New Jersey/8/96 | 987 | 1996 | H3N2 |
| AF008770 | A/New York/28/96 | 987 | 1996 | H3N2 |
| AF180650 | A/New York/37/96 | 987 | 1996 | H3N2 |
| AF180639 | A/New York/43/96 | 987 | 1996 | H3N2 |
| AF180638 | A/New York/50/96 | 987 | 1996 | H3N2 |
| AF180612 | A/New York/55/96 | 987 | 1996 | H3N2 |
| CY010796 | A/New York/555/1996 | 1721 | 1996 | H3N2 |
| CY010604 | A/New York/561/1996 | 1721 | 1996 | H3N2 |
| CY009996 | A/New York/562/1996 | 1721 | 1996 | H3N2 |
| CY010004 | A/New York/563/1996 | 1721 | 1996 | H3N2 |
| CY009476 | A/New York/565/1996 | 1721 | 1996 | H3N2 |
| CY010012 | A/New York/567/1996 | 1721 | 1996 | H3N2 |
| CY009660 | A/New York/568/1996 | 1721 | 1996 | H3N2 |
| CY009492 | A/New York/570/1996 | 1721 | 1996 | H3N2 |
| CY010588 | A/New York/572/1996 | 1721 | 1996 | H3N2 |
| CY009500 | A/New York/573/1996 | 1721 | 1996 | H3N2 |
| CY009668 | A/New York/574/1996 | 1721 | 1996 | H3N2 |
| CY009508 | A/New York/575/1996 | 1721 | 1996 | H3N2 |
| CY010596 | A/New York/578/1996 | 1722 | 1996 | H3N2 |
| CY009684 | A/New York/580/1996 | 1721 | 1996 | H3N2 |
| CY010020 | A/New York/582/1996 | 1721 | 1996 | H3N2 |
| CY009900 | A/New York/584/1996 | 1722 | 1996 | H3N2 |
| CY009708 | A/New York/586/1996 | 1721 | 1996 | H3N2 |
| CY009716 | A/New York/587/1996 | 1721 | 1996 | H3N2 |
| CY009724 | A/New York/588/1996 | 1721 | 1996 | H3N2 |
| CY009732 | A/New York/589/1996 | 1721 | 1996 | H3N2 |
| CY009740 | A/New York/590/1996 | 1721 | 1996 | H3N2 |
| CY010028 | A/New York/591/1996 | 1721 | 1996 | H3N2 |
| CY010036 | A/New York/592/1996 | 1721 | 1996 | H3N2 |
| CY009908 | A/New York/593/1996 | 1721 | 1996 | H3N2 |
| CY010044 | A/New York/594/1996 | 1721 | 1996 | H3N2 |
| CY010052 | A/New York/595/1996 | 1721 | 1996 | H3N2 |
| CY010060 | A/New York/596/1996 | 1721 | 1996 | H3N2 |
| CY010068 | A/New York/600/1996 | 1721 | 1996 | H3N2 |
| CY010612 | A/New York/603/1996 | 1721 | 1996 | H3N2 |
| CY010628 | A/New York/608/1996 | 1721 | 1996 | H3N2 |
| CY010668 | A/New York/613/1996 | 1721 | 1996 | H3N2 |
| CY010516 | A/New York/617/1996 | 1722 | 1996 | H3N2 |
| CY010684 | A/New York/619/1996 | 1719 | 1996 | H3N2 |
| CY010692 | A/New York/622/1996 | 1721 | 1996 | H3N2 |
| CY010700 | A/New York/625/1996 | 1721 | 1996 | H3N2 |
| CY010716 | A/New York/631/1996 | 1721 | 1996 | H3N2 |
| CY010724 | A/New York/634/1996 | 1721 | 1996 | H3N2 |
| CY010732 | A/New York/637/1996 | 1721 | 1996 | H3N2 |
| CY010844 | A/New York/640/1996 | 1747 | 1996 | H1N1 |
| CY010748 | A/New York/648/1996 | 1720 | 1996 | H3N2 |
| CY010836 | A/New York/653/1996 | 1740 | 1996 | H1N1 |
| AF008727 | A/New York/9/96 | 987 | 1996 | H3N2 |
| AF038267 | A/Niigata/137/96 | 984 | 1996 | H3N2 |
| AF180610 | A/Saitama/80/96 | 987 | 1996 | H3N2 |
| AF180613 | A/Santa Fe/208/96 | 987 | 1996 | H3N2 |
| AF180600 | A/Shangdong/9/96 | 987 | 1996 | H3N2 |
| AF180607 | A/Shenzhen/157/96 | 987 | 1996 | H3N2 |
| AF008705 | A/Shenzhen/43/96 | 987 | 1996 | H3N2 |
| AY661200 | A/Singapore/1/96 | 1095 | 1996 | H3N2 |
| AY661199 | A/Singapore/1/96 | 1095 | 1996 | H3N2 |
| AY661198 | A/Singapore/1/96 | 1095 | 1996 | H3N2 |
| A1457896 | A/Singapare/15/96 | 1041 | 1996 | H1N1 |
| AF026153 | A/Taiwan/112/96(quasi-species1) | 1176 | 1996 | H1N1 |
| AF026154 | A/Taiwan/112/96 (quasi-species2) | 1176 | 1996 | H1N1 |
| AF026155 | A/Taiwan/117/96 (quasi-species1) | 1176 | 1996 | H1N1 |
| AF026156 | A/Taiwan/117/96 (quasi-species2) | 1176 | 1996 | H1N1 |
| AF026157 | A/Taiwan/117/96 (quasi-species3) | 1176 | 1996 | H1N1 |
| AF026158 | A/Taiwan/118/96 (quasi-species1) | 1176 | 1996 | H1N1 |

TABLE 1-continued

INFLUENZA TYPE A HA SEQUENCES

| Accession | Strain | Length | Year | Serotype |
|---|---|---|---|---|
| AF026159 | A/Taiwan/118/96 (quasi-species2) | 1176 | 1996 | H1N1 |
| AF026160 | A/Taiwan/118/96 (quasi-species3) | 1176 | 1996 | H1N1 |
| AF362781 | A/Taiwan/130/96 | 564 | 1996 | H1N1 |
| AF362782 | A/Taiwan/132/96 | 564 | 1996 | H1N1 |
| AF362815 | A/Taiwan/1986/96 | 844 | 1996 | H3N2 |
| AY303731 | A/Taiwan/1990/96 | 844 | 1996 | H3N2 |
| AF139937 | A/Taiwan/2034/96 | 861 | 1996 | H3N2 |
| AF362783 | A/Taiwan/211/96 | 564 | 1996 | H1N1 |
| AF139932 | A/Taiwan/2191/96 | 861 | 1996 | H3N2 |
| AF139936 | A/Taiwan/2192/96 | 861 | 1996 | H3N2 |
| AY303736 | A/Taiwan/2195/96 | 844 | 1996 | H3N2 |
| AF362784 | A/Taiwan/235/96 | 564 | 1996 | H1N1 |
| AF362785 | A/Taiwan/255/96 | 564 | 1996 | H1N1 |
| AF362786 | A/Taiwan/337/96 | 564 | 1996 | H1N1 |
| AF362787 | A/Taiwan/342/96 | 564 | 1996 | H1N1 |
| AF008730 | A/Taiwan/523/96 | 987 | 1996 | H3N2 |
| AF362820 | A/Taiwan/95/96 | 844 | 1996 | H3N2 |
| AF180594 | A/Texas/11/96 | 987 | 1996 | H3N2 |
| AF180635 | A/Texas/9/96 | 987 | 1996 | H3N2 |
| AF180652 | A/Thailand/94/96 | 987 | 1996 | H3N2 |
| AF180604 | A/Tianjing/55/96 | 987 | 1996 | H3N2 |
| AB117216 | A/Tokushima/20/1996 | 981 | 1996 | H1N1 |
| AF180587 | A/Trinidad/47/96 | 987 | 1996 | H3N2 |
| AF180593 | A/Trinidad/50/96 | 987 | 1996 | H3N2 |
| AF180592 | A/Trinidad/51/96 | 987 | 1996 | H3N2 |
| AF008739 | A/United Kingdom/897/96 | 987 | 1996 | H3N2 |
| AF017270 | A/Vienna/47/96M (MDCK isolate) | 1069 | 1996 | H3N2 |
| AF017272 | A/Vienna/47/96V (Vero isolate) | 1730 | 1996 | H3N2 |
| AF017271 | A/Vienna/81/96V (Vero isolate) | 1069 | 1996 | H3N2 |
| AF008729 | A/Washington/5/96 | 987 | 1996 | H3N2 |
| AF008719 | A/Wellington/48/96 | 987 | 1996 | H3N2 |
| AF008731 | A/Wisconsin/3/96 | 987 | 1996 | H3N2 |
| AF008706 | A/Wuzhou/19/96 | 987 | 1996 | H3N2 |
| AB117219 | A/Yamanashi/11/1996 | 981 | 1996 | H1N1 |
| AF180622 | A/Yokohama/68/96 | 987 | 1996 | H3N2 |
| U48444 | A/Akita/1/95 | 1032 | 1995 | H3N2 |
| AF008748 | A/Alaska/10/95 | 987 | 1995 | H3N2 |
| AF008744 | A/Alaska/16/95 | 987 | 1995 | H3N2 |
| AF008764 | A/Argentina/4057/95 | 987 | 1995 | H3N2 |
| ISDN13429 | A/BAYERN/7/95 | 958 | 1995 | H1N1 |
| AJ457907 | A/Bayern/7/95 | 1044 | 1995 | H1N1 |
| ISDNX127 | A/Beijing/262/95 | 1032 | 1995 | H1N1 |
| AJ457900 | A/Beijing/262/95 | 1041 | 1995 | H1N1 |
| AY289928 | A/Beijing/262/95 | 1775 | 1995 | H1N1 |
| AF008734 | A/Brazil/2/95 | 987 | 1995 | H3N2 |
| AF534013 | A/Buenos Aires/4057/95 | 1095 | 1995 | H3N2 |
| AF534014 | A/Buenos Aires/4064/95 | 1095 | 1995 | H3N2 |
| AF534015 | A/Buenos Aires/4065/95 | 1095 | 1995 | H3N2 |
| AF534016 | A/Buenos Aires/4084/95 | 1095 | 1995 | H3N2 |
| AF534017 | A/Buenos Aires/4098/95 | 1095 | 1995 | H3N2 |
| AF534018 | A/Buenos Aires/4102/95 | 1095 | 1995 | H3N2 |
| AF008789 | A/California/5/95 | 987 | 1995 | H3N2 |
| AF008779 | A/Canada/124/95 | 987 | 1995 | H3N2 |
| AF008760 | A/Canada/147/95 | 987 | 1995 | H3N2 |
| AF008751 | A/Changwon/9/95 | 987 | 1995 | H3N2 |
| AF398875 | A/Charlottesville/28/95 | 1664 | 1995 | H1N1 |
| AF398874 | A/Charlottesville/28/95 (mutant delNA-28) | 1693 | 1995 | H1N1 |
| AF398878 | A/Charlottesville/31/95 | 1668 | 1995 | H1N1 |
| AF008765 | A/CNIC/22/95 | 987 | 1995 | H3N2 |
| AF180664 | A/Delaware/3/95 | 987 | 1995 | H3N2 |
| ISDN13405 | A/ENGLAND/121/95 | 987 | 1995 | H3N2 |
| ISDN13406 | A/ENGLAND/178/95 | 987 | 1995 | H3N2 |
| ISDN13407 | A/ENGLAND/255/95 | 987 | 1995 | H3N2 |
| ISDN13408 | A/ENGLAND/258/95 | 987 | 1995 | H3N2 |
| ISDN13409 | A/ENGLAND/263/95 | 987 | 1995 | H3N2 |
| ISDN13410 | A/ENGLAND/268/95 | 987 | 1995 | H3N2 |
| ISDN13411 | A/ENGLAND/282/95 | 987 | 1995 | H3N2 |
| ISDN13412 | A/ENGLAND/286/95 | 987 | 1995 | H3N2 |
| ISDN13413 | A/ENGLAND/54/95 | 987 | 1995 | H3N2 |
| AY661183 | A/Finland/338/95 | 1095 | 1995 | H3N2 |
| AF368436 | A/Finland/338/95 | 984 | 1995 | H3N2 |
| L75989 | A/Finland/339/95 | 984 | 1995 | H3N2 |
| AY661184 | A/Finland/339/95 | 984 | 1995 | H3N2 |
| L75990 | A/Finland/363/95 | 984 | 1995 | H3N2 |
| AY377547 | A/Finland/364/95 | 984 | 1995 | H3N2 |
| L75991 | A/Finland/371/95 | 984 | 1995 | H3N2 |
| AF311677 | A/Finland/380/95 | 984 | 1995 | H3N2 |
| AY661196 | A/Finland/381/95 | 1095 | 1995 | H3N2 |
| AF180663 | A/Florida/4/95 | 987 | 1995 | H3N2 |
| AY661182 | A/Geneva/AI9509/95 | 1095 | 1995 | H3N2 |
| AF008752 | A/Germany/578652/95 | 987 | 1995 | H3N2 |
| AF008754 | A/Germany/767/95 | 987 | 1995 | H3N2 |
| U65555 | A/Gifu/2/95 | 1032 | 1995 | H3N2 |
| AF525218 | A/Guangdong/1/95 | 984 | 1995 | H3N2 |
| AF525219 | A/Guangdong/8/95 | 984 | 1995 | H3N2 |
| AF008766 | A/Guangxi/42/95 | 987 | 1995 | H3N2 |
| U48447 | A/Hebei/19/95 | 1032 | 1995 | H3N2 |
| AF008755 | A/Hong Kong/3/95 | 987 | 1995 | H3N2 |
| AY661185 | A/Hong Kong/32/95 | 1095 | 1995 | H3N2 |
| AY661186 | A/Hong Kong/38/95 | 1095 | 1995 | H3N2 |
| AF008759 | A/Hong Kong/38/95 | 987 | 1995 | H3N2 |
| AY661187 | A/Hong Kong/49/95 | 1095 | 1995 | H3N2 |
| AJ457899 | A/Hong Kong/52/95 | 1041 | 1995 | H1N1 |
| AY661189 | A/Hong Kong/55/95 | 1095 | 1995 | H3N2 |
| U65558 | A/Ibaraki/1/95 | 1032 | 1995 | H3N2 |
| AF008740 | A/Idaho/3/95 | 987 | 1995 | H3N2 |
| AF008741 | A/Idaho/4/95 | 987 | 1995 | H3N2 |
| AF008782 | A/Illinois/5/95 | 975 | 1995 | H3N2 |
| AF008707 | A/Japan/86/95 | 987 | 1995 | H3N2 |
| AF008745 | A/Johannesburg/17/95 | 987 | 1995 | H3N2 |
| AF008768 | A/Johannesburg/2/95 | 987 | 1995 | H3N2 |
| U65556 | A/Kagoshima/10/95 | 1032 | 1995 | H3N2 |
| AB043491 | A/Kamata/381/95 | 1032 | 1995 | H1N1 |
| AF008749 | A/Kwangju/1/95 | 987 | 1995 | H3N2 |
| AB117204 | A/Kyoto/1/1995 | 981 | 1995 | H1N1 |
| AF008775 | A/Louisiana/1/95 | 987 | 1995 | H3N2 |
| AF180662 | A/Louisiana/5/95 | 987 | 1995 | H3N2 |
| AY661192 | A/Lyon/2279/95 | 1095 | 1995 | H3N2 |
| AF008785 | A/Massachussetts/1/95 | 987 | 1995 | H3N2 |
| CY002272 | A/Memphis/24/95 | 1741 | 1995 | H3N2 |
| AF008746 | A/Minnesota/6/95 | 987 | 1995 | H3N2 |
| U65560 | A/Miyagi/29/95 | 1032 | 1995 | H3N2 |
| AB019354 | A/Nagasaki/48/95 | 1762 | 1995 | H3N2 |
| AB019357 | A/Nagasaki/97/95 | 1762 | 1995 | H3N2 |
| AB117210 | A/Nagoya/27/1995 | 981 | 1995 | H1N1 |
| AF180628 | A/Nanchang/813/95 | 987 | 1995 | H3N2 |
| AF008725 | A/Nanchang/933/95 | 987 | 1995 | H3N2 |
| AF008750 | A/Nebraska/11/95 | 987 | 1995 | H3N2 |
| AY661181 | A/Netherlands/1/95 | 1095 | 1995 | H3N2 |
| AY661191 | A/Netherlands/271/95 | 1095 | 1995 | H3N2 |
| AF008747 | A/Nevada/1/95 | 987 | 1995 | H3N2 |
| AF008780 | A/New Jersey/10/95 | 987 | 1995 | H3N2 |
| AF008796 | A/New York/42/95 | 987 | 1995 | H3N2 |
| CY010484 | A/New York/604/1995 | 1749 | 1995 | H1N1 |
| CY010492 | A/New York/605/1995 | 1749 | 1995 | H1N1 |
| CY010620 | A/New York/606/1995 | 1721 | 1995 | H3N2 |
| CY010500 | A/New York/607/1995 | 1735 | 1995 | H1N1 |
| CY010636 | A/New York/609/1995 | 1721 | 1995 | H3N2 |
| CY010644 | A/New York/610/1995 | 1721 | 1995 | H3N2 |
| CY010652 | A/New York/611/1995 | 1711 | 1995 | H3N2 |
| CY010660 | A/New York/612/1995 | 1721 | 1995 | H3N2 |
| CY010804 | A/New York/614/1995 | 1749 | 1995 | H3N2 |
| CY010508 | A/New York/615/1995 | 1735 | 1995 | H1N1 |
| CY010676 | A/New York/618/1995 | 1720 | 1995 | H3N2 |
| CY010524 | A/New York/620/1995 | 1725 | 1995 | H1N1 |
| CY010532 | A/New York/621/1995 | 1749 | 1995 | H1N1 |
| CY010812 | A/New York/623/1995 | 1721 | 1995 | H3N2 |
| CY010540 | A/New York/627/1995 | 1749 | 1995 | H1N1 |
| CY010708 | A/New York/628/1995 | 1721 | 1995 | H3N2 |
| CY010820 | A/New York/638/1995 | 1735 | 1995 | H1N1 |
| CY010740 | A/New York/644/1995 | 1749 | 1995 | H3N2 |
| CY010828 | A/New York/651/1995 | 1749 | 1995 | H1N1 |
| U65559 | A/Niigata/124/95 | 1032 | 1995 | H3N2 |
| AF008781 | A/Ohio/3/95 | 987 | 1995 | H3N2 |
| U65553 | A/Osaka/c1/95 | 1032 | 1995 | H3N2 |
| AF180569 | A/Paris/363/95 | 987 | 1995 | H3N2 |

TABLE 1-continued

INFLUENZA TYPE A HA SEQUENCES

| Accession | Strain | Length | Year | Serotype |
|---|---|---|---|---|
| AF180568 | A/Paris/83/95 | 987 | 1995 | H3N2 |
| AF008786 | A/Pennsylvania/15/95 | 987 | 1995 | H3N2 |
| U48445 | A/Sendai/c373/95 | 1032 | 1995 | H3N2 |
| AF008728 | A/Shanghai/9/95 | 987 | 1995 | H3N2 |
| AY289930 | A/Shenzhen/227/95 | 1689 | 1995 | H1N1 |
| U65557 | A/Shiga/20/95 | 1032 | 1995 | H3N2 |
| AF008756 | A/Singapore/27/95 | 987 | 1995 | H3N2 |
| AF008758 | A/Singapore/28/95 | 987 | 1995 | H3N2 |
| AF008783 | A/Spain/351/95 | 987 | 1995 | H3N2 |
| AF008778 | A/Spain/378/95 | 987 | 1995 | H3N2 |
| AF386774 | A/Switzerland/5389/95 (MDCK isolate) | 1778 | 1995 | H1N1 |
| AF386773 | A/Switzerland/5389/95 (vero isolate) | 1778 | 1995 | H1N1 |
| AF362794 | A/Taiwan/1190/95 | 564 | 1995 | H1N1 |
| AF362795 | A/Taiwan/2200/95 | 564 | 1995 | H1N1 |
| AF362789 | A/Taiwan/562/95 | 564 | 1995 | H1N1 |
| AF362790 | A/Taiwan/563/95 | 564 | 1995 | H1N1 |
| AF362791 | A/Taiwan/657/95 | 564 | 1995 | H1N1 |
| U65554 | A/Tochigi/44/95 | 1032 | 1995 | H3N2 |
| AY661188 | A/Victoria/75/95 | 1095 | 1995 | H3N2 |
| AF008753 | A/West Virginia/1/95 | 987 | 1995 | H3N2 |
| AF008722 | A/Wuhan/359/95 | 987 | 1995 | H3N2 |
| AY661190 | A/Wuhan/359/95 | 1095 | 1995 | H3N2 |
| AJ344022 | A/Wuhan/371/95 | 1666 | 1995 | H1N1 |
| AB043708 | A/Aichi/2/94 | 1035 | 1994 | H3N2 |
| U48446 | A/Aichi/69/94 | 1032 | 1994 | H3N2 |
| AF008825 | A/Akita/1/94 | 987 | 1994 | H3N2 |
| U48443 | A/Akita/1/94 | 1032 | 1994 | H3N2 |
| AF008790 | A/Argentina/3779/94 | 987 | 1994 | H3N2 |
| AF008792 | A/Bangkok/122/94 | 987 | 1994 | H3N2 |
| AF008762 | A/Beijing/281/94 | 987 | 1994 | H3N2 |
| AF008855 | A/California/4/94 | 987 | 1994 | H3N2 |
| Z46403 | A/England/67/94 | 1041 | 1994 | H3N2 |
| Z46404 | A/England/68/94 | 1041 | 1994 | H3N2 |
| Z46405 | A/England/7/94 | 1041 | 1994 | H3N2 |
| ISDN13404 | A/ENGLAND/79/1994 | 987 | 1994 | H3N2 |
| AF008799 | A/France/1109/94 | 987 | 1994 | H3N2 |
| AF008835 | A/France/1203/94 | 987 | 1994 | H3N2 |
| U48442 | A/Guandong/28/94 | 1032 | 1994 | H3N2 |
| AF008848 | A/Guangdong/27/94 | 987 | 1994 | H3N2 |
| AY137206 | A/Guangdong/28/94 | 984 | 1994 | H3N2 |
| AF008856 | A/Harbin/3/94 | 987 | 1994 | H3N2 |
| U48441 | A/Hebei/41/94 | 1032 | 1994 | H3N2 |
| AF008772 | A/Hong Kong/1/94 | 987 | 1994 | H3N2 |
| AY661175 | A/Hong Kong/1/94 | 1110 | 1994 | H3N2 |
| Z46407 | A/Hong Kong/1/94 | 1041 | 1994 | H3N2 |
| Z46408 | A/Hong Kong/2/94 | 1041 | 1994 | H3N2 |
| AY661204 | A/Hong Kong/55/94 | 1095 | 1994 | H3N2 |
| AF008773 | A/Hong Kong/55/94 | 987 | 1994 | H3N2 |
| AY661178 | A/Hong Kong/56/94 | 1095 | 1994 | H3N2 |
| AJ457901 | A/Hong Kong/59/94 | 1044 | 1994 | H1N1 |
| AF008774 | A/Johannesburg/33/94 | 987 | 1994 | H3N2 |
| AY661180 | A/Johannesburg/33/94 | 1041 | 1994 | H3N2 |
| AY661179 | A/Johannesburg/47/94 | 1095 | 1994 | H3N2 |
| AF008674 | A/Mexico/3255/94 | 987 | 1994 | H3N2 |
| CY006339 | A/Nanchang/0058/94 | 1721 | 1994 | H3N2 |
| CY003752 | A/Nanchang/0074/94 | 1720 | 1994 | H3N2 |
| CY007835 | A/Nanchang/A1/94 | 1721 | 1994 | H3N2 |
| CY006331 | A/Nanchang/A2/94 | 1722 | 1994 | H3N2 |
| AY661020 | A/Netherlands/18/94 | 1690 | 1994 | H3N2 |
| AF008757 | A/New Jersey/11/94 | 987 | 1994 | H3N2 |
| AF008776 | A/New Jersey/8/94 | 987 | 1994 | H3N2 |
| AF008860 | A/New York/15/94 | 987 | 1994 | H3N2 |
| AF008795 | A/New York/16/94 | 987 | 1994 | H3N2 |
| AF008791 | A/New York/17/94 | 987 | 1994 | H3N2 |
| AF008787 | A/New York/28/94 | 979 | 1994 | H3N2 |
| CY010988 | A/New York/733/1994 | 1721 | 1994 | H3N2 |
| AF008788 | A/Pennsylvania/7/94 | 980 | 1994 | H3N2 |
| AF008826 | A/Romania/160/94 | 987 | 1994 | H3N2 |
| AF008831 | A/Romania/182/94 | 987 | 1994 | H3N2 |
| AF008800 | A/Russia/46967/94 | 987 | 1994 | H3N2 |
| U65552 | A/Saga/447/94 | 1032 | 1994 | H3N2 |
| AF008859 | A/Santiago/7198/94 | 987 | 1994 | H3N2 |
| U48439 | A/Sendai/c182/94 | 1032 | 1994 | H3N2 |
| U48440 | A/Sendai/e384/94 | 1032 | 1994 | H3N2 |
| AF008763 | A/Shangdong/5/94 | 987 | 1994 | H3N2 |
| AF008794 | A/Singapore/7/94 | 987 | 1994 | H3N2 |
| AY661176 | A/South_Australia/15/94 | 1111 | 1994 | H3N2 |
| AY661177 | A/South_Australia/25/94 | 1110 | 1994 | H3N2 |
| AF008784 | A/Texas/5/94 | 987 | 1994 | H3N2 |
| AF008793 | A/Thailand/75/94 | 987 | 1994 | H3N2 |
| U77837 | A/Tottori/849AM1AL3/94 | 987 | 1994 | H3N2 |
| U77833 | A/Tottori/849AM2/94 | 987 | 1994 | H3N2 |
| U77839 | A/Tottori/849AM2AL3/94 | 987 | 1994 | H3N2 |
| U77835 | A/Tottori/849AM4/94 | 987 | 1994 | H3N2 |
| U77831 | A/Tottori/849K4/94 | 987 | 1994 | H3N2 |
| U77838 | A/Tottori/872AM1AL3/94 | 987 | 1994 | H3N2 |
| U77834 | A/Tottori/872AM2/94 | 987 | 1994 | H3N2 |
| U77840 | A/Tottori/872AM2A/3/94 | 987 | 1994 | H3N2 |
| U77836 | A/Tottori/872AM4/94 | 987 | 1994 | H3N2 |
| U77832 | A/Tottori/872K4/94 | 987 | 1994 | H3N2 |
| AF008853 | A/Ulan Ude/44/94 | 987 | 1994 | H3N2 |
| AF008832 | A/Vermont/3/94 | 987 | 1994 | H3N2 |
| AF008767 | A/Virginia/25/94 | 987 | 1994 | H3N2 |
| AF008761 | A/Washington/186/94 | 987 | 1994 | H3N2 |
| U53162 | A/Wisconsin/4754/94 | 1778 | 1994 | H1N1 |
| U53163 | A/Wisconsin/4755/94 | 1778 | 1994 | H1N1 |
| AF008858 | A/Wuzhou/1/94 | 987 | 1994 | H3N2 |
| AB043707 | A/Aichi/4/93 | 1035 | 1993 | H3N2 |
| AY661155 | A/Akita/4/93 | 1095 | 1993 | H3N2 |
| AF008838 | A/Alaska/18/93 | 987 | 1993 | H3N2 |
| AF008836 | A/Ann Arbor/3/93 | 987 | 1993 | H3N2 |
| AF008827 | A/Argentina/3105/93 | 987 | 1993 | H3N2 |
| AF008833 | A/California/5/93 | 987 | 1993 | H3N2 |
| AF008837 | A/Christchurch/8/93 | 987 | 1993 | H3N2 |
| Z46393 | A/England/1/93 | 1041 | 1993 | H3N2 |
| AF008840 | A/England/220/93 | 987 | 1993 | H3N2 |
| Z46394 | A/England/247/93 | 1041 | 1993 | H3N2 |
| Z46395 | A/England/269/93 | 1041 | 1993 | H3N2 |
| Z46396 | A/England/284/93 | 1041 | 1993 | H3N2 |
| Z46397 | A/England/286/93 | 1041 | 1993 | H3N2 |
| Z46398 | A/England/289/93 | 1041 | 1993 | H3N2 |
| Z46399 | A/England/328/93 | 1041 | 1993 | H3N2 |
| Z46400 | A/England/346/93 | 1041 | 1993 | H3N2 |
| Z46401 | A/England/347/93 | 1041 | 1993 | H3N2 |
| Z46402 | A/England/471/93 | 1041 | 1993 | H3N2 |
| AY661150 | A/Enschede/5458/93 | 1095 | 1993 | H3N2 |
| AY377546 | A/Finland/250/93 | 984 | 1993 | H3N2 |
| AY462237 | A/Finland/256/93 | 984 | 1993 | H3N2 |
| L75982 | A/Finland/263/93 | 984 | 1993 | H3N2 |
| AY377545 | A/Finland/269/93 | 984 | 1993 | H3N2 |
| AY377544 | A/Finland/270/93 | 984 | 1993 | H3N2 |
| AY377543 | A/Finland/273/93 | 984 | 1993 | H3N2 |
| L75983 | A/Finland/274/93 | 984 | 1993 | H3N2 |
| L75984 | A/Finland/276/93 | 984 | 1993 | H3N2 |
| L75985 | A/Finland/278/93 | 984 | 1993 | H3N2 |
| AF442483 | A/Finland/280/93 | 984 | 1993 | H3N2 |
| L75986 | A/Finland/292/93 | 984 | 1993 | H3N2 |
| L75987 | A/Finland/295/93 | 984 | 1993 | H3N2 |
| L75988 | A/Finland/296/93 | 984 | 1993 | H3N2 |
| AY262745 | A/Finland/300/93 | 984 | 1993 | H3N2 |
| AY377541 | A/Finland/321/93 | 984 | 1993 | H3N2 |
| AY377542 | A/Finland/331/93 | 984 | 1993 | H3N2 |
| U49722 | A/Florence/1/93 | 465 | 1993 | H3N2 |
| AF008841 | A/Georgia/3/93 | 987 | 1993 | H3N2 |
| AF008828 | A/Guangdong/25/93 | 987 | 1993 | H3N2 |
| Z46406 | A/Guangdong/25/93 | 1041 | 1993 | H3N2 |
| AF008808 | A/Guangdong/4/93 | 987 | 1993 | H3N2 |
| D30668 | A/Hebei/12/93 | 1077 | 1993 | H3N2 |
| D43788 | A/Hokkaido/1/93 | 987 | 1993 | H3N2 |
| D43789 | A/Hokkaido/2/93 | 987 | 1993 | H3N2 |
| AF008689 | A/India/236/93 | 987 | 1993 | H3N2 |
| AF008690 | A/India/237/93 | 987 | 1993 | H3N2 |
| D30669 | A/Kitakyushu/159/93 | 1086 | 1993 | H3N2 |
| AF008823 | A/Kitakyushu/93 | 987 | 1993 | H3N2 |
| AF180567 | A/Louisiana/1/93 | 987 | 1993 | H3N2 |
| AF008829 | A/Louisiana/4/93 | 987 | 1993 | H3N2 |
| AF008830 | A/Louisiana/6/93 | 987 | 1993 | H3N2 |
| AY661169 | A/Lyon/1803/93 | 1095 | 1993 | H3N2 |
| AY661170 | A/Lyon/1815/93 | 1095 | 1993 | H3N2 |
| AY661171 | A/Lyon/22686/93 | 1095 | 1993 | H3N2 |

TABLE 1-continued

INFLUENZA TYPE A HA SEQUENCES

| Accession | Strain | Length | Year | Serotype |
|---|---|---|---|---|
| AY661172 | A/Lyon/23602/93 | 1095 | 1993 | H3N2 |
| AY661168 | A/Lyon/672/93 | 1095 | 1993 | H3N2 |
| Z46411 | A/Madrid/252/93 | 1041 | 1993 | H3N2 |
| AY661143 | A/Madrid/G101/93 | 1095 | 1993 | H3N2 |
| AY661144 | A/Madrid/G102/93 | 1095 | 1993 | H3N2 |
| AY661145 | A/Madrid/G109/93 | 1095 | 1993 | H3N2 |
| AY661142 | A/Madrid/G116/93 | 1095 | 1993 | H3N2 |
| AY661147 | A/Madrid/G122/93 | 1095 | 1993 | H3N2 |
| AY661148 | A/Madrid/G130/93 | 1095 | 1993 | H3N2 |
| AY661151 | A/Madrid/G252/93 | 1095 | 1993 | H3N2 |
| AF008801 | A/Nanchang/12/93 | 987 | 1993 | H3N2 |
| CY009012 | A/Nanchang/12/93 | 1721 | 1993 | H3N2 |
| AF008802 | A/Nanchang/3332/93 | 987 | 1993 | H3N2 |
| AF008822 | A/Nanchang/3396/93 | 987 | 1993 | H3N2 |
| CY006347 | A/Nanchang/58/93 | 1721 | 1993 | H3N2 |
| AF008803 | A/Nanchang/58/93 | 987 | 1993 | H3N2 |
| AY661139 | A/Netherlands/101/93 | 1095 | 1993 | H3N2 |
| AY661140 | A/Netherlands/115/93 | 1095 | 1993 | H3N2 |
| AY661141 | A/Netherlands/126/93 | 1095 | 1993 | H3N2 |
| AY661146 | A/Netherlands/165/93 | 1095 | 1993 | H3N2 |
| AY661133 | A/Netherlands/17/93 | 1095 | 1993 | H3N2 |
| AY661149 | A/Netherlands/179/93 | 1095 | 1993 | H3N2 |
| AY661160 | A/Netherlands/241/93 | 1020 | 1993 | H3N2 |
| AY661131 | A/Netherlands/3/93 | 1095 | 1993 | H3N2 |
| AF092061 | A/Netherlands/35/93 | 987 | 1993 | H3N2 |
| AY661162 | A/Netherlands/357/93 | 1095 | 1993 | H3N2 |
| AY661164 | A/Netherlands/371/93 | 1020 | 1993 | H3N2 |
| AY661163 | A/Netherlands/372/93 | 1095 | 1993 | H3N2 |
| AF008834 | A/Netherlands/372/93 | 987 | 1993 | H3N2 |
| AY661166 | A/Netherlands/398/93 | 1095 | 1993 | H3N2 |
| AY661167 | A/Nethrlands/399/93 | 1095 | 1993 | H3N2 |
| AY661165 | A/Netherlands/440/93 | 1095 | 1993 | H3N2 |
| AF092060 | A/Netherlands/5/93 | 987 | 1993 | H3N2 |
| AF008821 | A/New York/13/93 | 987 | 1993 | H3N2 |
| AF008839 | A/New York/26/93 | 987 | 1993 | H3N2 |
| AF008845 | A/New York/3/93 | 987 | 1993 | H3N2 |
| AF008847 | A/New York/38/93 | 987 | 1993 | H3N2 |
| AF008797 | A/New York/63/93 | 987 | 1993 | H3N2 |
| AF008798 | A/New York/64/93 | 987 | 1993 | H3N2 |
| AF008807 | A/Ningxia/10/93 | 987 | 1993 | H3N2 |
| AF008849 | A/North Carolina/93 | 987 | 1993 | H3N2 |
| AY661173 | A/Oslo/2219/93 | 1095 | 1993 | H3N2 |
| AY661174 | A/Oslo/2352/93 | 1095 | 1993 | H3N2 |
| AY661132 | A/Paris/287/93 | 1095 | 1993 | H3N2 |
| AF008818 | A/Paris/688/93 | 987 | 1993 | H3N2 |
| AF008857 | A/Pennsylvania/9/93 | 987 | 1993 | H3N2 |
| AF008704 | A/Ru/31/93 | 987 | 1993 | H3N2 |
| AF008804 | A/Russia/58/93 | 987 | 1993 | H3N2 |
| Z46413 | A/Scotland/142/93 | 1041 | 1993 | H3N2 |
| Z46414 | A/Scotland/160/93 | 1041 | 1993 | H3N2 |
| Z46416 | A/Scotland/173/93 | 1041 | 1993 | H3N2 |
| Z46415 | A/Scotland/174/93 | 1041 | 1993 | H3N2 |
| Z46412 | A/Scotland/2/93 | 1041 | 1993 | H3N2 |
| AY661159 | A/Shangdong/9/93 | 1095 | 1993 | H3N2 |
| Z46417 | A/Shangdong/9/93 | 1041 | 1993 | H3N2 |
| AY661156 | A/Shiga/6/93 | 1095 | 1993 | H3N2 |
| AF008806 | A/Sichuan/4/93 | 987 | 1993 | H3N2 |
| AY661211 | A/Singapore/3/93 | 1095 | 1993 | H3N2 |
| AF008677 | A/Sophia/155/93 | 987 | 1993 | H3N2 |
| AF008701 | A/Spain/118/93 | 987 | 1993 | H3N2 |
| AF008842 | A/Spain/125/93 | 987 | 1993 | H3N2 |
| AF008843 | A/Spain/190/93 | 987 | 1993 | H3N2 |
| AF008844 | A/Stockholm/1/93 | 987 | 1993 | H3N2 |
| AY661161 | A/Stockholm/20/93 | 1095 | 1993 | H3N2 |
| AF008846 | A/Texas/57/93 | 987 | 1993 | H3N2 |
| AF008811 | A/Victoria/1/93 | 987 | 1993 | H3N2 |
| AY661157 | A/Victoria/104/93 | 1095 | 1993 | H3N2 |
| AF008854 | A/Waikato/20/93 | 987 | 1993 | H3N2 |
| AF008850 | A/Washington/26/93 | 987 | 1993 | H3N2 |
| AF008852 | A/Washington/41/93 | 987 | 1993 | H3N2 |
| AY661158 | A/Wellington/59/93 | 1095 | 1993 | H3N2 |
| AF008805 | A/Wuzhou/4/93 | 987 | 1993 | H3N2 |
| AF008851 | A/Wyoming/1/93 | 987 | 1993 | H3N2 |
| AY661152 | A/Yamagata/56/93 | 1095 | 1993 | H3N2 |
| AY661153 | A/Yamagata/61/93 | 1095 | 1993 | H3N2 |
| AY661154 | A/Yamagata/62/93 | 1095 | 1993 | H3N2 |
| AB043490 | A/Aichi/24/92 | 1032 | 1992 | H1N1 |
| AF008814 | A/Alaska/9/92 | 987 | 1992 | H3N2 |
| AY661115 | A/Amsterdam/4112/92 | 1095 | 1992 | H3N2 |
| AY661130 | A/Beijing/32/92 | 1095 | 1992 | H3N2 |
| Z46392 | A/Beijing/32/92 | 1041 | 1992 | H3N2 |
| U26830 | A/Beijing/32/92 | 1701 | 1992 | H3N2 |
| AF008812 | A/Beijing/32/92 | 987 | 1992 | H3N2 |
| AF008813 | A/Beijing/46/92 | 987 | 1992 | H3N2 |
| AF008698 | A/Beijing/47/92 | 987 | 1992 | H3N2 |
| AF008817 | A/California/271/92 | 987 | 1992 | H3N2 |
| AB043706 | A/Chiba/54/92 | 1035 | 1992 | H3N2 |
| AY661096 | A/Enschede/1285/92 | 1095 | 1992 | H3N2 |
| AY377536 | A/Finland/190/92 | 984 | 1992 | H3N2 |
| AY377537 | A/Finland/191/92 | 984 | 1992 | H3N2 |
| AY377540 | A/Finland/205/92 | 984 | 1992 | H3N2 |
| L75979 | A/Finland/211/92 | 984 | 1992 | H3N2 |
| AY661109 | A/Finland/218/92 | 1095 | 1992 | H3N2 |
| AY661110 | A/Finland/220/92 | 1095 | 1992 | H3N2 |
| L75980 | A/Finland/239/92 | 984 | 1992 | H3N2 |
| AY377539 | A/Finland/245/92 | 984 | 1992 | H3N2 |
| AY262744 | A/Finland/246/92 | 984 | 1992 | H3N2 |
| L75981 | A/Finland/247/92 | 984 | 1992 | H3N2 |
| AY661138 | A/Finland/247/92 | 1095 | 1992 | H3N2 |
| AY661111 | A/Geneva/5113/92 | 1095 | 1992 | H3N2 |
| AF008809 | A/Harbin/15/92 | 987 | 1992 | H3N2 |
| AF008815 | A/Hawaii/3/92 | 987 | 1992 | H3N2 |
| CY003712 | A/Hong Kong/14/92 | 1750 | 1992 | H3N2 |
| Z46410 | A/Hong Kong/23/92 | 1041 | 1992 | H3N2 |
| AF008824 | A/Hong Kong/23/92 | 987 | 1992 | H3N2 |
| AY661124 | A/Houston/56798/92 | 1095 | 1992 | H3N2 |
| AY661122 | A/Houston/56829/92 | 1095 | 1992 | H3N2 |
| AY661123 | A/Houston/56941/92 | 1095 | 1992 | H3N2 |
| AF008694 | A/Indonesia/3946/92 | 987 | 1992 | H3N2 |
| AF008691 | A/Kasauli/149/92 | 987 | 1992 | H3N2 |
| AY661117 | A/Madrid/G58/92 | 1095 | 1992 | H3N2 |
| AY661118 | A/Madrid/OV31/92 | 1095 | 1992 | H3N2 |
| AY661080 | A/Netherlands/819/92 | 1095 | 1992 | H3N2 |
| AY661108 | A/Netherlands/823/92 | 1095 | 1992 | H3N2 |
| AY661097 | A/Netherlands/935/92 | 1095 | 1992 | H3N2 |
| AY661125 | A/Netherlands/938/92 | 1020 | 1992 | H3N2 |
| AY661113 | A/Nijmegen/3126/92 | 1095 | 1992 | H3N2 |
| AY661114 | A/Nijmegen/3129/92 | 1095 | 1992 | H3N2 |
| AF008657 | A/Paris/1/92 | 987 | 1992 | H3N2 |
| AY661082 | A/Paris/320/92 | 1095 | 1992 | H3N2 |
| AY661083 | A/Paris/325/92 | 1095 | 1992 | H3N2 |
| AY661084 | A/Paris/407/92 | 1095 | 1992 | H3N2 |
| AY661085 | A/Paris/417/92 | 1095 | 1992 | H3N2 |
| AY661086 | A/Paris/424/92 | 1095 | 1992 | H3N2 |
| AY661087 | A/Paris/457/92 | 1095 | 1992 | H3N2 |
| AY661088 | A/Paris/467/92 | 1095 | 1992 | H3N2 |
| AY661089 | A/Paris/490/92 | 1095 | 1992 | H3N2 |
| AY661090 | A/Paris/512/92 | 1095 | 1992 | H3N2 |
| AY661091 | A/Paris/548/92 | 1095 | 1992 | H3N2 |
| AY661092 | A/Paris/564/92 | 1095 | 1992 | H3N2 |
| AY661093 | A/Paris/583/92 | 1095 | 1992 | H3N2 |
| AY661094 | A/Paris/597/92 | 1095 | 1992 | H3N2 |
| AY661095 | A/Paris/614/92 | 1095 | 1992 | H3N2 |
| AF008656 | A/Perth/1/92 | 987 | 1992 | H3N2 |
| AF008816 | A/Qingdao/53/92 | 987 | 1992 | H3N2 |
| AY661112 | A/Rotterdam/100540/92 | 1095 | 1992 | H3N2 |
| AF008819 | A/Sapporo/304/92 | 987 | 1992 | H3N2 |
| AY661129 | A/Sendai/C273/92 | 1095 | 1992 | H3N2 |
| AF008695 | A/Singapore/8/92 | 987 | 1992 | H3N2 |
| AF008680 | A/South Australia/36/92 | 987 | 1992 | H3N2 |
| AF008696 | A/South Australia/68/92 | 987 | 1992 | H3N2 |
| AY661127 | A/South_Australia/23/92 | 1095 | 1992 | H3N2 |
| AY661128 | A/South_Australia/27/92 | 1095 | 1992 | H3N2 |
| AY661126 | A/South_Australia/8/92 | 1095 | 1992 | H3N2 |
| AY661136 | A/Stockholm/12/92 | 1095 | 1992 | H3N2 |
| AY661137 | A/Stockholm/13/92 | 1095 | 1992 | H3N2 |
| AY661120 | A/Stockholm/7/92 | 1095 | 1992 | H3N2 |
| AY661121 | A/Stockholm/8/92 | 1095 | 1992 | H3N2 |
| AF055426 | A/Taiwan/2243/92 | 1032 | 1992 | H1N1 |
| D30664 | A/Tianjin/33/92 | 1078 | 1992 | H3N2 |
| AY661116 | A/Tilburg/5957/92 | 1095 | 1992 | H3N2 |
| AF008692 | A/Umea/1/92 | 987 | 1992 | H3N2 |

TABLE 1-continued

INFLUENZA TYPE A HA SEQUENCES

| Accession | Strain | Length | Year | Serotype |
|---|---|---|---|---|
| AY661134 | A/Umea/1982/92 | 1095 | 1992 | H3N2 |
| AF008693 | A/Umea/2/92 | 987 | 1992 | H3N2 |
| AY661135 | A/Umea/2000/92 | 1095 | 1992 | H3N2 |
| AF008700 | A/Victoria/29/92 | 987 | 1992 | H3N2 |
| AF008697 | A/Victoria/68/92 | 987 | 1992 | H3N2 |
| AF008699 | A/Wellington/66/92 | 987 | 1992 | H3N2 |
| D30665 | A/Yokohama/73/92 | 1092 | 1992 | H3N2 |
| D30662 | A/Brazil/2/91 | 1080 | 1991 | H3N2 |
| AF008687 | A/Brazil/91 | 987 | 1991 | H3N2 |
| AY661076 | A/Canberra/1/91 | 1095 | 1991 | H3N2 |
| AY661075 | A/England/260/91 | 1095 | 1991 | H3N2 |
| AF008688 | A/England/261/91 | 987 | 1991 | H3N2 |
| AY661081 | A/England/261/91 | 1096 | 1991 | H3N2 |
| L33747 | A/Finland/154/91 | 1032 | 1991 | H1N1 |
| L19549 | A/Finland/158/91 | 1032 | 1991 | H1N1 |
| L33748 | A/Finland/160/91 | 1032 | 1991 | H1N1 |
| L33749 | A/Finland/164/91 | 1032 | 1991 | H1N1 |
| L33780 | A/Finland/168/91 | 1032 | 1991 | H1N1 |
| L33750 | A/Finland/188/91 | 1032 | 1991 | H1N1 |
| L75978 | A/Finland/189/91 | 984 | 1991 | H1N1 |
| L33751 | A/Finland/196/91 | 1032 | 1991 | H1N1 |
| AY661077 | A/Geneva/6447/91 | 1095 | 1991 | H3N2 |
| L33745 | A/Groningen/9938/91 | 1032 | 1991 | H1N1 |
| L33746 | A/Groningen/9939/91 | 1032 | 1991 | H1N1 |
| L20101 | A/Hawaii/1/91 (egg | 987 | 1991 | H3N2 |
| L20102 | A/Hawaii/1/91 (MDCK, original isolate) | 987 | 1991 | H3N2 |
| AF008681 | A/Indiana/3/91 | 987 | 1991 | H3N2 |
| AF008810 | A/Indonesia/3109/91 | 987 | 1991 | H3N2 |
| AB043705 | A/Kamata/14/91 | 1035 | 1991 | H3N2 |
| AF008659 | A/Kasauli/206/91 | 987 | 1991 | H3N2 |
| L33480 | A/Leningrad/109/91 | 1032 | 1991 | H1N1 |
| L33481 | A/Leningrad/133/91 | 1032 | 1991 | H1N1 |
| AY661098 | A/Lyon/1149/91 | 1095 | 1991 | H3N2 |
| AY661099 | A/Lyon/1182/91 | 1095 | 1991 | H3N2 |
| AY661105 | A/Lyon/chu23672/91 | 1095 | 1991 | H3N2 |
| AY661106 | A/Lyon/chu24103/91 | 1095 | 1991 | H3N2 |
| AY661107 | A/Lyon/chu24222/91 | 1095 | 1991 | H3N2 |
| AY661100 | A/Lyon/ons1189/91 | 1095 | 1991 | H3N2 |
| AY661103 | A/Lyon/ons1276/91 | 1095 | 1991 | H3N2 |
| AY661104 | A/Lyon/ons1337/91 | 1095 | 1991 | H3N2 |
| AY661102 | A/Lyon/ons1373/91 | 1095 | 1991 | H3N2 |
| AY661101 | A/Lyon/ons1594/91 | 1095 | 1991 | H3N2 |
| AY661079 | A/Madrid/G12/91 | 1095 | 1991 | H3N2 |
| L24362 | A/Maryland/12/91 | 1738 | 1991 | H1N1 |
| Z54288 | A/Mongolia/111/91 | 1708 | 1991 | H1N1 |
| Z54289 | A/Mongolia/162/91 | 1711 | 1991 | H1N1 |
| AB043489 | A/Nagano/92/91 | 1032 | 1991 | H1N1 |
| L33744 | A/Netherlands/813/91 | 1032 | 1991 | H1N1 |
| AY661078 | A/Netherlands/816/91 | 1095 | 1991 | H3N2 |
| AF008702 | A/Paris/80/91 | 987 | 1991 | H3N2 |
| AF008679 | A/Pennsylvania/9/91 | 987 | 1991 | H3N2 |
| L19017 | A/Qingdao/28/91 | 1032 | 1991 | H1N1 |
| L33743 | A/Seoul/20/91 | 1032 | 1991 | H1N1 |
| AF386608 | A/Seoul/23/91 | 987 | 1991 | H3N2 |
| AF386609 | A/Seoul/44/91 | 987 | 1991 | H3N2 |
| AF008678 | A/Seoul/45/91 | 987 | 1991 | H3N2 |
| AF386610 | A/Seoul/46/91 | 987 | 1991 | H3N2 |
| AF386611 | A/Seoul/47/91 | 987 | 1991 | H3N2 |
| AF386606 | A/Seoul/50/91 | 987 | 1991 | H3N2 |
| D49967 | A/Shiga/2/91 | 1011 | 1991 | H3N2 |
| AF008682 | A/Shiga/2/91 | 987 | 1991 | H3N2 |
| AF008661 | A/Singapore/1/91 | 987 | 1991 | H3N2 |
| AF008675 | A/South Dakota/1/91 | 987 | 1991 | H3N2 |
| AY661119 | A/Stockholm/20/91 | 1095 | 1991 | H3N2 |
| AF008703 | A/Taiwan/1143/91 | 987 | 1991 | H3N2 |
| DQ508889 | A/Texas/36/1991 | 1701 | 1991 | H1N1 |
| AJ457908 | A/Texas/36/91 | 1044 | 1991 | H1N1 |
| ISDN13427 | A/Texas/36/91 | 976 | 1991 | H1N1 |
| AY289927 | A/Texas/36/91 | 1778 | 1991 | H1N1 |
| CY009316 | A/Texas/36/91 | 1749 | 1991 | H1N1 |
| L33758 | A/Umea/2/91 | 1032 | 1991 | H1N1 |
| L33482 | A/Vilnus/48/91 | 1032 | 1991 | H1N1 |
| AF180666 | A/Virginia/1/91 | 987 | 1991 | H3N2 |
| AF008676 | A/Washington/15/91 | 987 | 1991 | H3N2 |
| D30663 | A/Washington/15/91 | 1096 | 1991 | H3N2 |

TABLE 1-continued

INFLUENZA TYPE A HA SEQUENCES

| Accession | Strain | Length | Year | Serotype |
|---|---|---|---|---|
| L19022 | A/Arszona/1/90 | 1032 | 1990 | H1N1 |
| D49965 | A/Bangkok/139/90 | 1018 | 1990 | H3N2 |
| D49966 | A/Bangkok/144/90 | 1107 | 1990 | H3N2 |
| L75976 | A/Finland/133/90 | 984 | 1990 | H3N2 |
| L75977 | A/Finland/144/90 | 984 | 1990 | H3N2 |
| L19018 | A/Goroka/2/90 | 1032 | 1990 | H1N1 |
| Z46409 | A/Hong Kong/34/90 | 1041 | 1990 | H3N2 |
| AF008658 | A/Hong Kong/34/90 | 987 | 1990 | H3N2 |
| D13583 | A/Ibaraki/1/90 | 329 | 1990 | H3N2 |
| L20103 | A/Indiana/1/90 (egg isolate) | 987 | 1990 | H3N2 |
| L20104 | A/Indiana/1/90 (MDCK, original isolates) | 987 | 1990 | H3N2 |
| L19027 | A/Maasachussetts/1/90 | 1032 | 1990 | H1N1 |
| CY003064 | A/Memphis/1/90 | 1763 | 1990 | H3N2 |
| AY661069 | A/Memphis/2/90 | 1095 | 1990 | H3N2 |
| AY661070 | A/Memphis/5/90 | 1095 | 1990 | H3N2 |
| CY008740 | A/Memphis/7/90 | 1721 | 1990 | H3N2 |
| AF008683 | A/Puerto Rico/1190 | 987 | 1990 | H3N2 |
| AY661072 | A/Seoul/1/90 | 1095 | 1990 | H3N2 |
| AF386607 | A/Seoul/22/90 | 987 | 1990 | H3N2 |
| AF008660 | A/Shanghai/24/90 | 987 | 1990 | H3N2 |
| AY661074 | A/Shanghai/24/90 | 1095 | 1990 | H3N2 |
| AF008686 | A/Shangbai/6/90 | 987 | 1990 | H3N2 |
| L20110 | A/Singapore/10/90 (egg, MDCK isolates) | 1032 | 1990 | H1N1 |
| L20111 | A/Singapore/10/90 (original specimen) | 1032 | 1990 | H1N1 |
| L20112 | A/Singapore/11/90 (egg isolate) | 1032 | 1990 | H1N1 |
| L20113 | A/Singapore/11/90 (original, MDCK isolates) | 1032 | 1990 | H1 |
| L20116 | A/Singapore/12/90 (egg isolate) | 1032 | 1990 | H1N1 |
| L20117 | A/Singapore/12/90 (original, MDCK isolates) | 1032 | 1990 | H1N1 |
| L20106 | A/Singapore/3/90 (egg isolate) | 1032 | 1990 | H1N1 |
| L20107 | A/Singapore/3/90 (original, MDCK isolates) | 1032 | 1990 | H1N1 |
| L19026 | A/Singapore/6/90 | 1032 | 1990 | H1N1 |
| L20108 | A/Singapore/6/90 (egg isolate) | 1032 | 1990 | H1N1 |
| L20109 | A/Singapore/6/90 (original, MDCK isolates) | 1032 | 1990 | H1N1 |
| L19013 | A/Stockholm/26/90 | 1032 | 1990 | H1N1 |
| D13584 | A/Suita/1/90 | 329 | 1990 | H3N2 |
| L19020 | A/Texas/22/90 | 1032 | 1990 | H1N1 |
| AY661073 | A/Victoria/2/90 | 1690 | 1990 | H3N2 |
| AY661071 | A/Atlanta/211/89 | 1095 | 1989 | H3N2 |
| D49962 | A/Bangkok/235/89 | 1049 | 1989 | H3N2 |
| D49961 | A/Beijing/352/89 | 1113 | 1989 | H3N2 |
| D43786 | A/Beijing/352/89 | 987 | 1989 | H3N2 |
| X75800 | A/Beijing/352/89(high growth reassortant NIB26) | 1086 | 1989 | H3N2 |
| DQ508833 | A/Beijing/353/1989 | 1701 | 1989 | H3N2 |
| AF008684 | A/Beijing/353/89 | 987 | 1989 | H3N2 |
| L76036 | A/Beijing/353/89 | 984 | 1989 | H3N2 |
| U97740 | A/Beijing/353/89 | 1714 | 1989 | H3N2 |
| Z46391 | A/Beijing/353/89 | 1041 | 1989 | H3N2 |
| AY661066 | A/Beijing/353/89 | 1690 | 1989 | H3N2 |
| L19000 | A/Beijing/4/89 | 987 | 1989 | H3N2 |
| L18994 | A/Beijing/4/89 (clone | 987 | 1989 | H3N2 |
| AF008662 | A/Beijing/57/89 | 987 | 1989 | H3N2 |
| AF008672 | A/Czechoslovakia/19/89 | 987 | 1989 | H3N2 |
| L19028 | A/Czechoslovakia/2/89 | 1032 | 1989 | H1N1 |
| AF008664 | A/England/648/89 | 987 | 1989 | H3N2 |
| L75975 | A/Finland/110/89 | 984 | 1989 | H3N2 |
| L33756 | A/Finland/91/89 | 1032 | 1989 | H1N1 |
| L19016 | A/France/6908/89 | 1032 | 1989 | H1N1 |
| AY661057 | A/Geneva/5007/89 | 1095 | 1989 | H3N2 |
| AF008667 | A/Guangdong/16/89 | 987 | 1989 | H3N2 |
| L19004 | A/Guangdong/39/89 | 987 | 1989 | H3N2 |
| L18996 | A/Guangdong/39/89 (clone GHYM) | 987 | 1989 | H3N2 |

TABLE 1-continued

INFLUENZA TYPE A HA SEQUENCES

| Accession | Strain | Length | Year | Serotype |
|---|---|---|---|---|
| L18998 | A/Guangdong/39/89 (clone X105) | 987 | 1989 | H3N2 |
| D49963 | A/Guizhou/54/89 | 1023 | 1989 | H3N2 |
| AF008665 | A/Guizhou/54/89 | 987 | 1989 | H3N2 |
| L19006 | A/Harbin/1/89 | 1032 | 1989 | H1N2 |
| D10163 | A/Hebei/24/89 | 1032 | 1989 | H1N2 |
| D49960 | A/Hokkaido/20189 | 1022 | 1989 | H3N2 |
| AY661059 | A/Hong Kong/1/89 | 1690 | 1989 | H3N2 |
| AB043488 | A/Nagano/1669189 | 1032 | 1989 | H1N1 |
| AY661067 | A/Netherlands/620/89 | 1095 | 1989 | H3N2 |
| AY661068 | A/Netherlands/650/89 | 1095 | 1989 | H3N2 |
| ISDN13403 | A/Netherlands/738189 | 1095 | 1989 | H3N2 |
| AY661029 | A/Netherlands/738/89 | 1095 | 1989 | H3N2 |
| D49964 | A/OMS/7026/89 | 1020 | 1989 | H3N2 |
| AF38660 | 5A/Seoul/16/89 | 987 | 1989 | H3N2 |
| AF008669 | A/Shanghai/1/89 | 987 | 1989 | H3N2 |
| AF008668 | A/Shanghai/16/89 | 987 | 1989 | H3N2 |
| AF008663 | A/Sichuan/18/89 | 987 | 1989 | H3N2 |
| L20114 | A/Singapore/12/89 (egg isolate) | 987 | 1989 | H3N2 |
| L20115 | A/Singapore/12/89 (original specimen) | 987 | 1989 | H3N2 |
| L20118 | A/Singapore/13/89 (egg isolate) | 987 | 1989 | H3N2 |
| L20119 | A/Singapore/13/89 (original specimen) | 987 | 1989 | H3N2 |
| AY661060 | A/Singapore/34/89 | 1095 | 1989 | H3N2 |
| AY661061 | A/Singapore/35/89 | 1095 | 1989 | H3N2 |
| AY661062 | A/Singapore/36/89 | 1095 | 1989 | H3N2 |
| AY661063 | A/Singapore/40/89 | 1095 | 1989 | H3N2 |
| AY661064 | A/Singapore/53/89 | 1095 | 1989 | H3N2 |
| D13573 | A/Suita/1/89 | 1778 | 1989 | H1N1 |
| D13574 | A/Suita/1/89(R) | 1778 | 1989 | H1N1 |
| AY661065 | A/Victoria/1/89 | 1095 | 1989 | H3N2 |
| AF008673 | A/Victoria/5/89 | 987 | 1989 | H3N2 |
| AY661058 | A/Wellington/5/89 | 1095 | 1989 | H3N2 |
| L19005 | A/Xianfeng/3/89 | 1032 | 1989 | H1N2 |
| D31949 | A/Yamagata/32/89 | 1032 | 1989 | H1N1 |
| AJ252129 | A/Berlin/6188 | 1759 | 1988 | H3N2 |
| L19021 | A/Canada/7/88 | 1032 | 1988 | H1N1 |
| AF008880 | A/Chiba/38/88 | 987 | 1988 | H3N2 |
| AF008905 | A/Christchurch/2/88 | 987 | 1988 | H3N2 |
| AJ252131 | A/Cottbus/42/88 | 1759 | 1988 | H3N2 |
| L19015 | A/Czechoslovakia/2/88 | 1032 | 1988 | H1N1 |
| L19001 | A/England/427/88 | 987 | 1988 | H3N2 |
| AF204238 | A/England/427/88 | 1038 | 1988 | H3N2 |
| AY661055 | A/England/427/88 | 1690 | 1988 | H3N2 |
| L18997 | A/England/427/88 (clone X103) | 987 | 1988 | H3N2 |
| AF008671 | A/England/428/88 | 987 | 1988 | H3N2 |
| L19011 | A/Fiji/2/88 | 1032 | 1988 | H1N1 |
| L33487 | A/Finland/70/88 | 1032 | 1988 | H1N1 |
| L33752 | A/Finland/72/88 | 1032 | 1988 | H1Nt |
| L33753 | A/Finland/73/88 | 1032 | 1988 | H1N1 |
| L33754 | A/Finland/74/88 | 1032 | 1988 | H1N1 |
| L33755 | A/Finland/75/88 | 1032 | 1988 | HiNt |
| L19019 | A/France/15/88 | 1032 | 1988 | H1N1 |
| L19014 | A/Fukushima/1/88 | 1032 | 1988 | H1N1 |
| L19008 | A/Harbin/1/88 | 1032 | 1988 | H1N2 |
| D43787 | A/Hokkaido/1/88 | 987 | 1988 | H3N2 |
| CY003512 | A/Hong Kong/2/88 | 1757 | 1988 | H3N2 |
| AF008881 | A/Kobe/768/88 | 987 | 1988 | H3N2 |
| CY003352 | A/Memphis/13/88 | 1711 | 1988 | H3N2 |
| CY008732 | A/Memphis/15/88 | 1721 | 1988 | H3N2 |
| CY008724 | A/Memphis/5/88 | 1721 | 1988 | H3N2 |
| CY010756 | A/Memphis/8/1988 | 1721 | 1988 | H3N2 |
| Z54287 | A/Mongolia/153/88 | 1728 | 1988 | H1N1 |
| AY661054 | A/Netherlands/450/88 | 1690 | 1988 | H3N2 |
| X59778 | A/NIB/4/88 | 1068 | 1988 | H1N1 |
| D13572 | A/Osaka/930/88 | 424 | 1988 | H1N1 |
| AF386604 | A/Seoul/11/88 | 987 | 1988 | H3N2 |
| L19024 | A/Sichuan/4/88 | 1032 | 1988 | H1N1 |
| L19025 | A/South Carolina/6/88 | 1032 | 1988 | H1N1 |
| AY661056 | A/Stockholm/12/88 | 1690 | 1988 | H3N2 |
| AF008907 | A/Texas/39989/88 | 987 | 1988 | H3N2 |
| AF008909 | A/Uruguay/3/88 | 987 | 1988 | H3N2 |
| L19023 | A/Victoria/43/88 | 1032 | 1988 | H1N1 |
| AF008890 | A/Colorado/2/87 | 987 | 1987 | H3N2 |
| L33485 | A/Finland/45/87 | 1032 | 1987 | H1N1 |
| L33486 | A/Finland/53/87 | 1032 | 1987 | H1N1 |
| AF008883 | A/Guangdong/9/87 | 987 | 1987 | H3N2 |
| AF008889 | A/Guizhou/1/87 | 987 | 1987 | H3N2 |
| AF008862 | A/Guizhou/3/87 | 987 | 1987 | H3N2 |
| CY003544 | A/Hong Kong/7/87 | 1738 | 1987 | H3N2 |
| AB043487 | A/Kamata/85/87 | 1032 | 1987 | H1N1 |
| AF008885 | A/Los Angeles/87 | 987 | 1987 | H3N2 |
| AF008887 | A/Qingdao/10/87 | 987 | 1987 | H3N2 |
| AF008886 | A/Shanghai/11/87 | 987 | 1987 | H3N2 |
| L19412 | A/Shanghai/11/87/high yield | 987 | 1987 | H3N2 |
| L19413 | A/Shanghai/11/87/low yield | 987 | 1987 | H3N2 |
| L19414 | A/Shanghai/11/87/X99/high yielding reassortant | 987 | 1987 | H3N2 |
| L19415 | A/Shanghai/11/87/X99a/ high yield reassortant | 987 | 1987 | H3N2 |
| L19416 | A/Shanghai/11/87/X99aE | 987 | 1987 | H3N2 |
| D49959 | A/Sichuan/2/87 | 1018 | 1987 | H3N2 |
| D21173 | A/Sichuan/2/87 | 987 | 1987 | H3N2 |
| AF008884 | A/Sichuan/2/87 | 987 | 1987 | H3N2 |
| D13582 | A/Sichuan/2/87 | 329 | 1987 | H3N2 |
| M33748 | A/SL/2/87 | 1095 | 1987 | H1N1 |
| AF008882 | A/Sydney/1/87 | 987 | 1987 | H3N2 |
| AF008878 | A/Tokyo/1275/87 | 987 | 1987 | H3N2 |
| AF008879 | A/Tokyo/1276/87 | 987 | 1987 | H3N2 |
| AF008888 | A/Victoria/7/87 | 987 | 1987 | H3N2 |
| M57644 | A/Wyoming/3/87 | 1035 | 1987 | H3N2 |
| AY661053 | A/Colorado/2/86 | 1690 | 1986 | H3N2 |
| AF008897 | A/Czechoslovakia/4/86 | 987 | 1986 | H3N2 |
| M57632 | A/Equador/4/86 | 1035 | 1986 | H3N2 |
| L33483 | A/Finland/42/86 | 1032 | 1986 | H1N1 |
| DQ508849 | A/Leningrad/360/1986 | 1701 | 1986 | H3N2 |
| AF008903 | A/Leningrad/360/86 | 987 | 1986 | H3N2 |
| CY002752 | A/Memphis/1/86 | 1742 | 1986 | H3N2 |
| CY008716 | A/Memphis/11/86 | 1721 | 1986 | H3N2 |
| M21648 | A/Memphis/6/86 | 1653 | 1986 | H3N2 |
| CY002088 | A/Memphis/66/86 | 1762 | 1986 | H3N2 |
| D00406 | A/Singapore/6/86 (egg isolate) | 1032 | 1986 | H1N1 |
| DQ508873 | A/Taiwan/01/1986 | 1701 | 1986 | H1N1 |
| D00407 | A/Taiwan/1/86 | 1032 | 1986 | H1N1 |
| X17224 | A/Taiwan/1/86 | 1044 | 1986 | H1N1 |
| L19012 | A/Trinidad/2/86 | 1032 | 1986 | H1N1 |
| D13571 | A/Yamagata/120/86 | 424 | 1986 | H1N1 |
| D00841 | A/Yamagata/120/86 | 1156 | 1986 | H1N1 |
| AF008901 | A/Bangkok/25/85 | 987 | 1985 | H3N2 |
| AF008899 | A/Bangkok/85 | 987 | 1985 | H3N2 |
| AF405211 | A/Baylor5B/85 | 1050 | 1985 | H3N2 |
| AF008908 | A/Cheng-mei/4/85 | 987 | 1985 | H3N2 |
| AF008895 | A/Christchurch/1/85 | 987 | 1985 | H3N2 |
| AF008896 | A/Christchurch/4/85 | 987 | 1985 | H3N2 |
| AF008875 | A/Connecticut/4/85 | 986 | 1985 | H3N2 |
| AF008876 | A/Fukuoka/C29/85 | 987 | 1985 | H3N2 |
| D13581 | A/Fukuoka/C29/85 | 329 | 1985 | H3N2 |
| AY661051 | A/Guildford/V728/85 | 1095 | 1985 | H3N2 |
| AF008900 | A/Gumma/346/85 | 987 | 1985 | H3N2 |
| CY003520 | A/Hong Kong/24/85 | 1762 | 1985 | H3N2 |
| CY003504 | A/Hong Kong/6/85 | 1750 | 1985 | H3N2 |
| CY003536 | A/Hong Kong/7/85 | 1762 | 1985 | H3N2 |
| M57631 | A/Houston/24269/85 | 1035 | 1985 | H3N2 |
| CY009068 | A/Memphis/2/85 | 1721 | 1985 | H3N2 |
| CY008668 | A/Memphis/25/85 | 1721 | 1985 | H3N2 |
| CY008452 | A/Memphis/5/85 | 1717 | 1985 | H3N2 |
| CY008708 | A/Memphis/7/85 | 1721 | 1985 | H3N2 |
| AF008872 | A/Michigan/1/85 | 987 | 1985 | H3N2 |
| AF008893 | A/Mississippi/1/85 | 987 | 1985 | H3N2 |
| L19003 | A/Mississippi/1/85 (clone X-87) | 987 | 1985 | H3N2 |
| Z54286 | A/Mongolia/231/85 | 1731 | 1985 | H1N1 |
| AY661049 | A/Netherlands/330/85 | 1095 | 1985 | H3N2 |
| AF008873 | A/New Jersey/4/85 | 987 | 1985 | H3N2 |
| AY661052 | A/Stockholm/10/85 | 1095 | 1985 | H3N2 |

TABLE 1-continued

INFLUENZA TYPE A HA SEQUENCES

| Accession | Strain | Length | Year | Serotype |
|---|---|---|---|---|
| AF008865 | A/Stockholm/4/85 | 987 | 1985 | H3N2 |
| AF008898 | A/Stockholm/8/85 | 987 | 1985 | H3N2 |
| AF008874 | A/Texas/24752/85 | 987 | 1985 | H3N2 |
| AF008891 | A/Texas/24753/85 | 987 | 1985 | H3N2 |
| AF008892 | A/Texas/25784/85 | 987 | 1985 | H3N2 |
| AF008866 | A/Texas/25887/85 | 987 | 1985 | H3N2 |
| AF008906 | A/Tonga/23/85 | 987 | 1985 | H3N2 |
| AF008864 | A/USSR/26/85 | 987 | 1985 | H3N2 |
| AY661050 | A/Wellington/4/85 | 1095 | 1985 | H3N2 |
| AF092063 | A/Wellington/4/85 | 987 | 1985 | H3N2 |
| AF008902 | A/Yamagata/96/85 | 987 | 1985 | H3N2 |
| AF008877 | A/Yamaneshi/497/85 | 987 | 1985 | H3N2 |
| AF008904 | A/Yokohama/C5/85 | 987 | 1985 | H3N2 |
| AF008863 | A/Alaska/8/84 | 986 | 1984 | H3N2 |
| S62154 | A/Alma Ata/1417/84 | 1778 | 1984 | H1N1 |
| AF008867 | A/Caen/1/84 | 987 | 1984 | H3N2 |
| L33490 | A/Finland/1/84 | 1032 | 1984 | H1N1 |
| L33491 | A/Finland/4/84 | 1032 | 1984 | H1N1 |
| L33492 | A/Finland/5/84 | 1032 | 1984 | H1N1 |
| L33493 | A/Finland/9/84 | 1032 | 1984 | H1N1 |
| CY006323 | A/Hong Kong/4/84 | 1726 | 1984 | H3N2 |
| CY003744 | A/Hong Kong/7/84 | 1714 | 1984 | H3N2 |
| CY008172 | A/Nanjing/28/84 | 1722 | 1984 | H3N2 |
| AF008871 | A/Texas/17988/84 | 987 | 1984 | H3N2 |
| AF008869 | A/Texas/18088/84 | 987 | 1984 | H3N2 |
| AF008870 | A/Texas/18733/84 | 987 | 1984 | H3N2 |
| D13570 | A/Bangkok/10/83 | 424 | 1983 | H1N1 |
| AF405207 | A/Baylor1B/83 | 991 | 1983 | H3N2 |
| AF405209 | A/Baylor3A/83 | 1050 | 1983 | H3N2 |
| AF405210 | A/Baylor4A/83 | 1050 | 1983 | H3N2 |
| X17221 | A/CHR/157/83 | 1752 | 1983 | H1N1 |
| A1289702 | A/Fiji/15899/83 | 1779 | 1983 | H1N1 |
| CY003720 | A/Hong Kong26/83 | 1720 | 1983 | H3N2 |
| CY006315 | A/Hong Kong/14/83 | 1721 | 1983 | H3N2 |
| CY003736 | A/Hong Kong/5/83 | 1721 | 1983 | H3N2 |
| CY010948 | A/Memphis/12/1983 | 1749 | 1983 | H1N1 |
| CY010956 | A/Memphis/15/1983 | 1749 | 1983 | H1N1 |
| CY010964 | A/Memphis/16/1983 | 1749 | 1983 | H1N1 |
| CY010972 | A/Memphis/17/1983 | 1749 | 1983 | H1N1 |
| CY010980 | A/Memphis/18/1983 | 1749 | 1983 | H1N1 |
| CY010916 | A/Memphis/3/1983 | 1750 | 1983 | H1N1 |
| CY009052 | A/Memphis/33/83 | 1717 | 1983 | H3N2 |
| CY010924 | A/Memphis/4/1983 | 1750 | 1983 | H1N1 |
| CY010932 | A/Memphis/7/1983 | 1750 | 1983 | H1N1 |
| CY010940 | A/Memphis/8/1983 | 1750 | 1983 | H1N1 |
| CY006851 | A/Nanjing/36/83 | 1731 | 1983 | H3N2 |
| M59324 | A/Ohio/101/83 (isolate A) | 1032 | 1983 | H1N1 |
| M59325 | A/Ohio/101/83 (isolate C) | 1032 | 1983 | H1N1 |
| M59326 | A/Ohio/101/83 (isolate D) | 1032 | 1983 | H1N1 |
| M59327 | A/Ohio/101/83 (isolate F) | 1029 | 1983 | H1N1 |
| M59328 | A/Ohio/201/83 | 1029 | 1983 | H1N1 |
| AF008868 | A/Oita/3/83 | 987 | 1983 | H3N2 |
| AY661016 | A/Oslo/13676/83 | 1095 | 1983 | H3N2 |
| AF201846 | A/Praha/2/83 (HI minus) | 1091 | 1983 | H3N2 |
| AF201845 | A/Praha/2/83 (HI plus) | 1091 | 1983 | H3N2 |
| AF008894 | A/Texas/12764/83 | 987 | 1983 | H3N2 |
| AF008861 | A/Texas/12835/83 | 987 | 1983 | H3N2 |
| CY010364 | A/Baylor/11515/82 | 1749 | 1982 | H1N1 |
| CY009620 | A/Baylor/11735/82 | 1733 | 1982 | H1N1 |
| AY661015 | A/Bilthoven/10684/82 | 1095 | 1982 | H3N2 |
| U77830 | A/Christ Hospital/231/82 | 987 | 1982 | H3N2 |
| L33489 | A/Finland/1/82 | 1032 | 1982 | H1N1 |
| CY006052 | A/Hong Kong/1/82 | 1762 | 1982 | H3N2 |
| CY006755 | A/Nanjing/2/82 | 1721 | 1982 | H3N2 |
| AY661025 | A/Netherlands/233/82 | 1095 | 1982 | H3N2 |
| AY661048 | A/Netherlands/241/82 | 1095 | 1982 | H3N2 |
| AF233691 | A/Philippines/2/82 | 1091 | 1982 | H3N2 |
| U08858 | A/Philippines/2/82 | 1685 | 1982 | H3N2 |
| U08905 | A/Philippines/2/82 | 1685 | 1982 | H3N2 |
| L19002 | A/Philippines/2/82 (clone X79) | 987 | 1982 | H3N2 |
| U08859 | A/Philippines/2/82/BS | 1685 | 1982 | H3N2 |
| ISDNPH282 | A/Phillipines/2/82 | 987 | 1982 | H3N2 |
| M57630 | A/Alabama/1/81 | 1035 | 1981 | H3N2 |
| AF405206 | A/Baylor1A/81 | 1050 | 1981 | H3N2 |
| AF405208 | A/Baylor2A/81 | 991 | 1981 | H3N2 |
| AF201844 | A/Belgium/2/81 | 1091 | 1981 | H3N2 |
| AY661014 | A/Bilthoven/4791/81 | 1095 | 1981 | H3N2 |
| CY007627 | A/Memphis/1/81 | 1721 | 1981 | H3N2 |
| X00031 | A/England/333/80 | 1074 | 1980 | H1N1 |
| CY006043 | A/Hong Kong/45/80 | 1749 | 1980 | H3N2 |
| CY003488 | A/Hong Kong/46/80 | 1737 | 1980 | H3N2 |
| X00030 | A/India/6263/80 | 1048 | 1980 | H1N1 |
| CY008660 | A/Memphis/1/80 | 1721 | 1980 | H3N2 |
| CY008468 | A/Memphis/3/80 | 1730 | 1980 | H3N2 |
| CY007619 | A/Memphis/4/80 | 1717 | 1980 | H3N2 |
| CY010908 | A/Memphis/7/1980 | 1750 | 1980 | H1N1 |
| CY006891 | A/Memphis/9/80 | 1717 | 1980 | H3N2 |
| CY006203 | A/Nanjing/13/80 | 1721 | 1980 | H3N2 |
| AY661047 | A/Netherlands/209/80 | 1095 | 1980 | H3N2 |
| AF405212 | A/Oregon/4/80 | 1050 | 1980 | H3N2 |
| AY661046 | A/Rotterdam/577/80 | 1095 | 1980 | H3N2 |
| ISDNSH80 | A/Shanghai/31/80 | 987 | 1980 | H3N2 |
| DQ508825 | A/Bangkok/01/1979 | 1701 | 1979 | H3N2 |
| AF201843 | A/Bangkok/1/79 | 1091 | 1979 | H3N2 |
| J02092 | A/Bangkok/1/79 | 1653 | 1979 | H3N2 |
| ISDNBK179 | A/Bangkok/1/79 | 987 | 1979 | H3N2 |
| ISDNBK279 | A/Bangkok/2/79 | 987 | 1979 | H3N2 |
| M38353 | A/Kiev/59/79 | 1778 | 1979 | H1N1 |
| X86657 | A/Brazil/11/78 | 1072 | 1978 | H1N1 |
| X00028 | A/Brazil/11/78 | 1068 | 1978 | H1N1 |
| X86654 | A/Brazil/11/78(X-71) escape variant 1 | 1072 | 1978 | H1N1 |
| X86655 | A/Brazil/11/78(X-71) escape variant 2 | 1072 | 1978 | H1N1 |
| X86656 | A/Brazil/11/78(X-71) escape variant 3 | 1072 | 1978 | H1N1 |
| L33757 | A/Finland/20/78 | 1032 | 1978 | H1N1 |
| L33484 | A/Finland/44/78 | 1032 | 1978 | H1N1 |
| L33488 | A/Finland/92/78 | 1032 | 1978 | H1N1 |
| AY672090 | A/Hong Kong/301/78 | 648 | 1978 | H7N1 |
| X00029 | A/Lackland/3/78 | 773 | 1978 | H1N1 |
| CY010868 | A/Memphis/10/1978 | 1750 | 1978 | H1N1 |
| CY010876 | A/Memphis/11/1978 | 1750 | 1978 | H1N1 |
| CY006699 | A/Memphis/12/78 | 1721 | 1978 | H3N2 |
| CY010884 | A/Memphis/13/1978 | 1750 | 1978 | H1N1 |
| CY010892 | A/Memphis/15/1978 | 1750 | 1978 | H1N1 |
| CY010900 | A/Memphis/17/1978 | 1750 | 1978 | H1N1 |
| CY006707 | A/Memphis/18/78 | 1721 | 1978 | H3N2 |
| CY007611 | A/Memphis/19/78 | 1717 | 1978 | H3N2 |
| CY006691 | A/Memphis/2/78 | 1721 | 1978 | H3N2 |
| AY661045 | A/Amsterdam/1609/77 | 1095 | 1977 | H3N2 |
| AY661011 | A/Bilthoven/3895/77 | 1095 | 1977 | H3N2 |
| X05907 | A/England/321/77 | 1762 | 1977 | H3N2 |
| CY009292 | A/Hong Kong/117/77 | 1750 | 1977 | H1N1 |
| CY006731 | A/Memphis/1/77 | 1721 | 1977 | H3N2 |
| CY008115 | A/Memphis/2/77 | 1721 | 1977 | H3N2 |
| CY006739 | A/Memphis/3/77 | 1721 | 1977 | H3N2 |
| CY008123 | A/Memphis/4/77 | 1721 | 1977 | H3N2 |
| CY006843 | A/Memphis/5/77 | 1721 | 1977 | H3N2 |
| CY006763 | A/Nanjing/49/77 | 1724 | 1977 | H3N2 |
| AY661012 | A/Rotterdam/5828/77 | 1095 | 1977 | H3N2 |
| AY661013 | A/Rotterdam/8179/77 | 1095 | 1977 | H3N2 |
| ISDNTX77 | A/Texas/1/77 | 987 | 1977 | H3N2 |
| AF450246 | A/Texas/1/77 | 1000 | 1977 | H3N2 |
| DQ508897 | A/USSR/90/1977 | 1701 | 1977 | H1N1 |
| K01331 | A/USSR/90/77 | 1026 | 1977 | H1N1 |
| CY010372 | A/USSR/90/77 | 1750 | 1977 | H1N1 |
| X00027 | A/USSR/90/77 | 1064 | 1977 | H1N1 |
| K01330 | A/USSR/90/77 (recomb) | 1701 | 1977 | H1N1 |
| M38312 | A/USSR/90/77 (recomb) | 1779 | 1977 | H1N1 |
| CY009284 | A/USSR/92/77 | 1750 | 1977 | H1N1 |
| AY661006 | A/Bilthoven/1761/76 | 1095 | 1976 | H3N2 |
| AY661007 | A/Bilthoven/2271/76 | 1095 | 1976 | H3N2 |
| AY661008 | A/Bilthoven/5029/76 | 1095 | 1976 | H3N2 |
| AY661009 | A/Bilthoven/5657/76 | 1093 | 1976 | H3N2 |
| AY661044 | A/Bilthoven/628/76 | 1095 | 1976 | H3N2 |
| AY661010 | A/Bilthoven/6545/76 | 1095 | 1976 | H3N2 |
| CY006883 | A/Memphis/103/76 | 1724 | 1976 | H3N2 |
| CY009060 | A/Memphis/105/76 | 1724 | 1976 | H3N2 |
| CY008692 | A/Memphis/106/76 | 1724 | 1976 | H3N2 |
| CY008700 | A/Membis/108/76 | 1724 | 1976 | H3N2 |

TABLE 1-continued

INFLUENZA TYPE A HA SEQUENCES

| Accession | Strain | Length | Year | Serotype |
|---|---|---|---|---|
| CY006835 | A/Memphis/110/76 | 1724 | 1976 | H3N2 |
| CY006723 | A/Memphis/137/76 | 1724 | 1976 | H3N2 |
| CY006044 | A/Beijing/39/75 | 1764 | 1975 | H3N2 |
| AY661043 | A/Bilthoven/2600/75 | 1690 | 1975 | H3N2 |
| AY661028 | A/Bilthoven/2813/75 | 1095 | 1975 | H3N2 |
| ISDNENG75 | A/England/864/75 | 987 | 1975 | H3N2 |
| CY003728 | A/Hong Kong/43/75 | 1725 | 1975 | H3N2 |
| ISDNMC75 | A/Mayo Clinic/1/75 | 987 | 1975 | H3N2 |
| ISDNSN75 | A/Singapore/4/75 | 987 | 1975 | H3N2 |
| ISDNTOK75 | A/Tokyo/1/75 | 987 | 1975 | H3N2 |
| V01086 | A/Victoria/3/75 | 1768 | 1975 | H3N2 |
| ISDNVIC75 | A/Victoria/3/75 | 987 | 1975 | H3N2 |
| V01098 | A/Victoria/3/75 (recomb) | 1768 | 1975 | H3N2 |
| AY661018 | A/Bilthoven/5146/74 | 1095 | 1974 | H3N2 |
| AY661042 | A/Bilthoven/5930/74 | 1690 | 1974 | H3N2 |
| AY661017 | A/Bilthoven/5931/74 | 1095 | 1974 | H3N2 |
| AY661027 | A/Bilthoven/7398/74 | 1095 | 1974 | H3N2 |
| AY661005 | A/Bilthoven/9459/74 | 1095 | 1974 | H3N2 |
| CY003496 | A/Hong Kong/14/74 | 1738 | 1974 | H3N2 |
| CY006907 | A/Hong Kong/49/74 | 1740 | 1974 | H3N2 |
| CY006715 | A/Memphis/101/74 | 1724 | 1974 | H3N2 |
| CY006819 | A/Memphis/102/74 | 1724 | 1974 | H3N2 |
| CY006827 | A/Memphis/103/74 | 1724 | 1974 | H3N2 |
| AY661004 | A/Bilthoven/3517/73 | 1095 | 1973 | H3N2 |
| AY661002 | A/Bilthoven/552/73 | 1095 | 1973 | H3N2 |
| AY661003 | A/Bilthoven/748/73 | 1095 | 1973 | H3N2 |
| AF201842 | A/Dunedin/4/73 | 1091 | 1973 | H3N2 |
| CY003528 | A/Hong Kong/11/73 | 1740 | 1973 | H3N2 |
| CY009004 | A/Hong Kong/33/73 | 1740 | 1973 | H3N2 |
| CY006811 | A/Memphis/3/73 | 1724 | 1973 | H3N2 |
| AF092062 | A/Port Chalmers/1/73 | 987 | 1973 | H3N2 |
| ISDNPC73 | A/Port Chalmers/1/73 | 987 | 1973 | H3N2 |
| CY009348 | A/Port Chalmers/73 | 1724 | 1973 | H3N2 |
| AY661041 | A/Bilthoven/21793/72 | 1690 | 1972 | H3N2 |
| AY661000 | A/Bilthoven/23290/72 | 1095 | 1972 | H3N2 |
| AY661001 | A/Bilthoven/23337/72 | 1095 | 1972 | H3N2 |
| AY660999 | A/Bilthoven/6022/72 | 1095 | 1972 | H3N2 |
| AF201875 | A/England/42/72 | 1091 | 1972 | H3N2 |
| ISDNENG72 | A/England/42/72 | 987 | 1972 | H3N2 |
| AF380346 | A/England/42/72.var | 531 | 1972 | H3N2 |
| CY009356 | A/England/72 | 1723 | 1972 | H3N2 |
| CY007971 | A/Guandong/243/72 | 1733 | 1972 | H3N2 |
| CY006307 | A/Hong Kong/50/72 | 1724 | 1972 | H3N2 |
| CY003552 | A/Hong Kong/6/72 | 1740 | 1972 | H3N2 |
| CY008676 | A/Memphis/101/72 | 1724 | 1972 | H3N2 |
| ISDNMEM7 | A/Memphis/102/72 | 987 | 1972 | H3N2 |
| CY002096 | A/Memphis/102/72 | 1741 | 1972 | H3N2 |
| V01089 | A/Memphis/102/72 | 1653 | 1972 | H3N2 |
| CY008460 | A/Memphis/103/72 | 1724 | 1972 | H3N2 |
| CY008684 | A/Memphis/105/72 | 1724 | 1972 | H3N2 |
| CY002744 | A/Memphis/109/72 | 1748 | 1972 | H3N2 |
| DQ508929 | A/Udorn/307/1972 | 1701 | 1972 | H3N2 |
| M54895 | A/Udorn/307/72 | 1765 | 1972 | H3N2 |
| K00991 | a/udorn/72 | 54 | 1972 | H3N2 |
| CY009636 | A/Udorn/72 | 1724 | 1972 | H3N2 |
| J02538 | A/Udorn/72 (3' fragment in HA-SV40 recomb) | 158 | 1972 | H3N2 |
| M25045 | A/Udorn/72 clone pFV88, 3' end) | 59 | 1972 | |
| M25043 | A/Udorn/72 (clone pFV88, 5' end) | 85 | 1972 | H3N2 |
| M25044 | A/Udorn/72 (clone pFV92, 5' end) | 53 | 1972 | H3N2 |
| AY660997 | A/Bilthoven/21438/71 | 1095 | 1971 | H3N2 |
| AY660998 | A/Bilthoven/21801/71 | 1095 | 1971 | H3N2 |
| AY660996 | A/Bilthoven/6449/71 | 1095 | 1971 | H3N2 |
| ISDNHK71 | A/Hong Kong/107/71 | 987 | 1971 | H3N2 |
| CY006683 | A/Hong Kong/46/71 | 1727 | 1971 | H3N2 |
| CY002496 | A/Memphis/1/71 | 1741 | 1971 | H3N2 |
| J02132 | A/Memphis/1/71 | 1765 | 1971 | H3N2 |
| CY006219 | A/Memphis/2/71 | 1724 | 1971 | H3N2 |
| AY660995 | A/Bilthoven/2668/70 | 1095 | 1970 | H3N2 |
| AY660994 | A/Bilthoven/93/70 | 1094 | 1970 | H3N2 |
| K03338 | A/Queensland/7/70 | 984 | 1970 | H3N2 |
| AY660993 | A/Bilthoven/17938/69 | 1095 | 1969 | H3N2 |
| AY661040 | A/Bilthoven/808/69 | 1095 | 1969 | H3N2 |
| AY660992 | A/Bilthoven/908/69 | 1095 | 1969 | H3N2 |
| K03335 | A/England/878/69 | 984 | 1969 | H3N2 |
| AJ289703 | A/England/939/69 (from recomb, clone7a) | 1765 | 1969 | H3N2 |
| CY006299 | A/Hong Kong/3/69 | 1742 | 1969 | H3N2 |
| M55059 | A/Aichi/2/68 (recomb) | 1763 | 1968 | H3N2 |
| V01085 | A/Aichi/2/68 (recomb) | 1765 | 1968 | H3N2 |
| CY008156 | A/Beijing/1/68 | 1743 | 1968 | H3N2 |
| AY209988 | A/Berkeley/1/68 | 1020 | 1968 | H2N2 |
| L11125 | A/Berkeley/1/68 | 1773 | 1968 | H2N2 |
| AY661038 | A/Bilthoven/15793/68 | 1095 | 1968 | H3N2 |
| AY661039 | A/Bilthoven/16190/68 | 1095 | 1968 | H3N2 |
| AY660991 | A/Bilthoven/16398/68 | 1095 | 1968 | H3N2 |
| AF201874 | A/Hong Kong/1/68 | 1091 | 1968 | H3N2 |
| AF348176 | A/Hong Kong/1/68 | 1736 | 1968 | H3N2 |
| AF348177 | A/HongKong/1/68 (isolate MA12) | 1736 | 1968 | H3N2 |
| AF348178 | A/Hong Kong/1/68 (isolate MA20) | 1736 | 1968 | H3N2 |
| AF348179 | A/Hong Kong/1/68 (isolate MA20C) | 1736 | 1968 | H3N2 |
| AY209989 | A/Korea/426/68 | 1020 | 1968 | H2N2 |
| L11133 | A/Korea/426/68 | 1773 | 1968 | H2N2 |
| CY006211 | A/Memphis/1/68 | 1722 | 1968 | H3N2 |
| V01103 | A/NT/60168/29C | 1765 | 1968 | H3N2 |
| J02135 | A/NT/60168/29C | 1765 | 1968 | H3N2 |
| AY209978 | A/Ann Arbor/7/67 | 1020 | 1967 | H2N2 |
| AY209979 | A/Cordoba/522/67 | 1020 | 1967 | H2N2 |
| AY209980 | A/England/10/67 | 1020 | 1967 | H2N2 |
| AY209981 | A/Georgia/1/67 | 1020 | 1967 | H2N2 |
| AY209982 | A/Johannesburg/567/67 | 1020 | 1967 | H2N2 |
| AY209986 | A/Montevideo/2208/67 | 1020 | 1967 | H2N2 |
| AY209983 | A/Panama/1/67 | 1020 | 1967 | H2N2 |
| AY209984 | A/Poland/5/67 | 1020 | 1967 | H2N2 |
| AY209985 | A/Taiwan/1/67 | 1020 | 1967 | H2N2 |
| AY209987 | A/Tokyo/3/67 | 1020 | 1967 | H2N2 |
| AY209974 | A/Berkeley/1/66 | 1020 | 1966 | H2N2 |
| AY209975 | A/California/1/66 | 1020 | 1966 | H2N2 |
| AY209976 | A/Canada/1/66 | 1020 | 1966 | H2N2 |
| AY209977 | A/Panama/1/66 | 1020 | 1966 | H2N2 |
| AY209970 | A/Albany/1/65 | 1020 | 1965 | H2N2 |
| D13579 | A/Izumi/5/65 | 1773 | 1965 | H2N2 |
| D13580 | A/Izumi/5/65(R) | 1773 | 1965 | H2N2 |
| D13578 | A/Kaizuka/2/65 | 394 | 1965 | H2N2 |
| AY209971 | A/Kumamoto/1/65 | 1020 | 1965 | H2N2 |
| D13577 | A/Kumamoto/1/65 | 394 | 1965 | H2N2 |
| AY209972 | A/New Jersey/3/65 | 1020 | 1965 | H2N2 |
| AY209973 | A/Pittsburgh/2/65 | 1020 | 1965 | H2N2 |
| L11126 | A/Berlin/3/64 | 1773 | 1964 | H2N2 |
| AY209967 | A/England/12/64 | 1020 | 1964 | H2N2 |
| AY209968 | A/Murakami/4/64 | 1020 | 1964 | H2N2 |
| AY209969 | A/Taiwan/1/64 | 1020 | 1964 | H2N2 |
| DQ508881 | A/Taiwan/1964 | 1689 | 1964 | H2N2 |
| AY209963 | A/Albany/1/63 | 1020 | 1963 | H2N2 |
| AY209964 | A/Georgia/1/63 | 1020 | 1963 | H2N2 |
| AY209965 | A/Great Lakes/3/63 | 1020 | 1963 | H2N2 |
| AY209966 | A/Netherlands/65/63 | 1020 | 1963 | H2N2 |
| AY209959 | A/Japan/170/62 | 1020 | 1962 | H2N2 |
| AY209960 | A/Netherlands/60/62 | 1020 | 1962 | H2N2 |
| AY209961 | A/Taiwan/1/62 | 1020 | 1962 | H2N2 |
| AY209962 | A/Yokosuka/3/62 | 1020 | 1962 | H2N2 |
| AY209955 | A/England/1/61 | 1020 | 1961 | H2N2 |
| AY209956 | A/Panama/1/61 | 1020 | 1961 | H2N2 |
| AY209957 | A/SaoPaolo/1/61 | 1020 | 1961 | H2N2 |
| AY209958 | A/Yale/1/61 | 1020 | 1961 | H2N2 |
| AF270721 | A/Ann Arbor/6/60 | 1017 | 1960 | H2N2 |
| AY209954 | A/Philippines/2/60 | 1020 | 1960 | H2N2 |
| L11134 | A/Krasnodar/101/59 | 1773 | 1959 | H2N2 |
| AF270727 | A/Ohio/2/59 | 1017 | 1959 | H2N2 |
| AF270725 | A/Sao Paolo/3/59 | 1017 | 1959 | H2N2 |
| AF270726 | A/Victoria/15681/59 | 1017 | 1959 | H2N2 |
| AF270723 | A/Albany/6/58 | 1017 | 1958 | H2N2 |
| AF270724 | A/Malaya/16/58 | 1017 | 1958 | H2N2 |
| D13576 | A/Adachi/2/57 | 394 | 1957 | H2N2 |
| AF270720 | A/Albany/7/57 | 1017 | 1957 | H2N2 |
| AY209952 | A/Chile/13/57 | 1020 | 1957 | H2N2 |

TABLE 1-continued

INFLUENZA TYPE A HA SEQUENCES

| Accession | Strain | Length | Year | Serotype |
|---|---|---|---|---|
| AF270728 | A/Chile/6/57 | 1017 | 1957 | H2N2 |
| AF270719 | A/Davis/1/57 | 1017 | 1957 | H2N2 |
| AF305218 | A/Denver/1/57 | 215 | 1957 | H1N1 |
| CY008988 | A/Denver/57 | 1746 | 1957 | H1N1 |
| AF270716 | A/El Salvador/2/57 | 1017 | 1957 | H2N2 |
| L20406 | A/Japan/305+/57 | 1773 | 1957 | H2N2 |
| L20407 | A/Japan/305−/57 | 1773 | 1957 | H2N2 |
| AY209953 | A/Japan/305/57 | 1020 | 1957 | H2N2 |
| AY643086 | A/Japan/305/57 | 1662 | 1957 | H2N2 |
| DQ508841 | A/Japan/305/57 | 1689 | 1957 | H2N2 |
| J02127 | A/Japan/305/57 | 1773 | 1957 | H2N2 |
| AY643085 | A/Japan/305/57-MA | 1752 | 1957 | H2N2 |
| AY643087 | A/Japan/305/57-MA, ABT-315675 resistant | 1674 | 1957 | H2N2 |
| AB056699 | A/Kayano/57 | 1773 | 1957 | H2N2 |
| AF270717 | A/Leningrad/134/57 | 1017 | 1957 | H2N2 |
| D13575 | A/Okuda/57 | 394 | 1957 | H2N2 |
| AF270722 | A/RI/5+/57 | 1017 | 1957 | H2N2 |
| L20408 | A/RI/5+/57 | 1773 | 1957 | H2N2 |
| J02154 | A/ri/5−/57 | 367 | 1957 | H2N2 |
| L20409 | A/RI/5−/57 | 1773 | 1957 | H2N2 |
| AF270718 | A/RI/5−/57 | 1017 | 1957 | H2N2 |
| AB043486 | A/Saga/2/57 | 1029 | 1957 | H1N1 |
| L20410 | A/Singapore/1/57 | 1773 | 1957 | H2N2 |
| L11142 | A/Singapore/1/57 | 1773 | 1957 | H2N2 |
| CY009364 | A/Connecticut/9/56 | 1738 | 1956 | H1N1 |
| AB043485 | A/Meguro/1/56 | 1032 | 1956 | H1N1 |
| AB043484 | A/Yamagishi/55 | 1032 | 1955 | H1N1 |
| CY009340 | A/Malaysia/54 | 1750 | 1954 | H1N1 |
| AB043483 | A/Taiwan/13/54 | 1032 | 1954 | H1N1 |
| AB043482 | A/Kojiya/1/52 | 1032 | 1952 | H1N1 |
| AB043480 | A/TF/15/51 | 1032 | 1951 | H1N1 |
| AB043481 | A/Tokyo/1/51 | 1032 | 1951 | H1N1 |
| CY009332 | A/Fort Worth/50 | 1749 | 1950 | H1N1 |
| AB043479 | A/Lepine/48 | 1032 | 1948 | H1N1 |
| U02085 | A/Fort Monmouth/1/47 | 1778 | 1947 | H1N1 |
| AF494250 | A/Fort Monmouth/1/47 | 1032 | 1947 | H1N1 |
| U02464 | A/Fort Monmouth/1/47 (Mouse adapted) | 1778 | 1947 | H1N1 |
| CY009612 | A/FortMonmouth/1/47 | 1750 | 1947 | H1N1 |
| AF494249 | A/Rhodes/47 | 1032 | 1947 | H1N1 |
| CY010860 | A/USA/L3/1947 | 1740 | 1947 | H1N1 |
| CY009596 | A/Cam/46 | 1750 | 1946 | H1N1 |
| AF494246 | A/DSP/43 | 1029 | 1943 | H1N1 |
| AF494251 | A/Huston/43 | 1032 | 1943 | H1N1 |
| AF494248 | A/Marton/43 | 1032 | 1943 | H1N1 |
| CY009452 | A/Weiss/43 | 1750 | 1943 | H1N1 |
| AF494247 | A/Weiss/43 | 1032 | 1943 | H1N1 |
| CY009276 | A/Bellamy/42 | 1744 | 1942 | H1N1 |
| CY009324 | A/Melbourne/35 | 1749 | 1935 | H1N1 |
| CY009444 | A/Puerto Rico/8/34 | 1746 | 1934 | H1N1 |
| ISDN13422 | A/Puerto Rico/8/34 | 1775 | 1934 | H1N1 |
| NC_002017 | A/Puerto Rico/8/34 | 1778 | 1934 | H1N1 |
| J02144 | A/Puerto Rico/8/34 (Mt | 1015 | 1934 | H1N1 |
| K00871 | A/Puerto Rico/8/34 (subgenomic RNA32 from DI virus: | 365 | 1934 | |
| K00872 | A/Puerto Rico/8/34 (subgenomic RNA33 from DI | 395 | 1934 | |
| K00877 | A/Puerto Rico/8/34 (subgenomic RNA39 from DI virus: | 439 | 1934 | H1N1 |
| J04573 | A/Puerto Rico/8/34 variant PY-102-V1 | 976 | 1934 | H1N1 |
| J04574 | A/Puerto Rico/8/34 variant VM113-V1 | 983 | 1934 | H1N1 |
| AF389118 | A/Puerto Rico/8/34/Mount Sinai | 1775 | 1934 | H1N1 |
| U38242 | A/NWS/33 | 1746 | 1933 | H1 |
| U08903 | A/NWS/33 | 1746 | 1933 | H1N1 |
| DQ508905 | A/Wilson-Smith/1933 | 1698 | 1933 | H1N1 |
| CY009604 | A/Wilson-Smith/33 | 1749 | 1933 | H1N1 |
| U08904 | A/WS/33 | 1746 | 1933 | H1N1 |
| J02176 | A/WSN/33 | 1775 | 1933 | H1N1 |
| AY184806 | A/London/1/1919 | 563 | 1919 | H1N1 |
| AF116575 | A/Brevig Mission/1/1918 | 1220 | 1918 | H1N1 |
| AY184805 | A/London/1/1918 | 563 | 1918 | H1N1 |
| AF116576 | A/New York/1/18 | 1220 | 1918 | H1N1 |
| AF117241 | A/South Carolina/1/18 | 1701 | 1918 | H1N1 |

TABLE 2

INFLUENZA TYPE B HA SEQUENCES

| Accession | Strain | Length | Year |
|---|---|---|---|
| AB243874 | B/Aichi/186/2005 | 1038 | 2005 |
| DQ265730 | B/Alaska/1777/2005 | 1038 | 2005 |
| DQ343768 | B/Arizona/135/2005 | 1014 | 2005 |
| DQ343767 | B/Arizona/140/2005 | 1017 | 2005 |
| DQ265729 | B/Arizona/146/2005 | 1025 | 2005 |
| DQ265725 | B/Arizona/148/2005 | 1025 | 2005 |
| DQ343766 | B/Arizona/162/2005 | 1017 | 2005 |
| DQ343765 | B/Arizona/163/2005 | 1017 | 2005 |
| DQ343764 | B/Arizona/164/2005 | 1017 | 2005 |
| DQ343770 | B/Arizona/48/2005 | 1017 | 2005 |
| DQ343769 | B/Arizona/59/2005 | 1017 | 2005 |
| ISDN125747 | B/Auckland/14/2005 | 1041 | 2005 |
| ISDN125748 | B/Auckland/32/2005 | 1038 | 2005 |
| ISDN125751 | B/Auckland/50/2005 | 1030 | 2005 |
| ISDN124785 | B/Brisbane/3/2005 | 1038 | 2005 |
| ISDN125756 | B/Brisbane/5/2005 | 1038 | 2005 |
| ISDN125757 | B/Brisbane/6/2005 | 1042 | 2005 |
| ISDN126576 | B/Cape Town/472/2005 | 1038 | 2005 |
| ISDN125752 | B/Christchurch/38/2005 | 1023 | 2005 |
| DQ265723 | B/England/1716/2005 | 1038 | 2005 |
| DQ265722 | B/England/2054/2005 | 1038 | 2005 |
| DQ231538 | B/Gyeonggi/592/2005 | 1038 | 2005 |
| DQ231539 | B/Incheon/297/2005 | 1038 | 2005 |
| DQ265719 | B/Japan/1224/2005 | 1038 | 2005 |
| DQ265727 | B/Japan/1905/2005 | 1038 | 2005 |
| ISDN127354 | B/Johannesburg/27/05 | 957 | 2005 |
| ISDN126577 | B/Johannesburg/501/2005 | 1056 | 2005 |
| ISDN125758 | B/Macau/388/2005 | 1030 | 2005 |
| ISDN125759 | B/Macau/394/2005 | 1027 | 2005 |
| ISDN125745 | B/Malaysia/1008/2005 | 1041 | 2005 |
| ISDN124784 | B/Malaysia/283/2005 | 1076 | 2005 |
| ISDN125746 | B/Malaysia/419/2005 | 1041 | 2005 |
| ISDN124781 | B/Malaysia/53/2005 | 1068 | 2005 |
| DQ343795 | B/Nepal/1078/2005 | 1017 | 2005 |
| DQ343794 | B/Nepal/1079/2005 | 1017 | 2005 |
| DQ343793 | B/Nepal/1080/2005 | 1017 | 2005 |
| DQ343792 | B/Nepal/1087/2005 | 1017 | 2005 |
| DQ343791 | B/Nepal/1088/2005 | 1017 | 2005 |
| DQ343790 | B/Nepal/1089/2005 | 1017 | 2005 |
| DQ343789 | B/Nepal/1090/2005 | 1017 | 2005 |
| DQ343788 | B/Nepal/1092/2005 | 1017 | 2005 |
| DQ343787 | B/Nepal/1101/2005 | 1017 | 2005 |
| DQ343786 | B/Nepal/1103/2005 | 1017 | 2005 |
| DQ343785 | B/Nepal/1104/2005 | 1017 | 2005 |
| DQ343784 | B/Nepal/1105/2005 | 1017 | 2005 |
| DQ343783 | B/Nepal/1106/2005 | 1017 | 2005 |
| DQ343782 | B/Nepal/1108/2005 | 1017 | 2005 |
| DQ343781 | B/Nepal/1114/2005 | 1017 | 2005 |
| DQ343780 | B/Nepal/1117/2005 | 1017 | 2005 |
| DQ343779 | B/Nepal/1118/2005 | 1017 | 2005 |
| DQ343778 | B/Nepal/1120/2005 | 1017 | 2005 |
| DQ343777 | B/Nepal/1122/2005 | 1017 | 2005 |
| DQ343776 | B/Nepal/1131/2005 | 1017 | 2005 |
| DQ343775 | B/Nepal/1132/2005 | 1017 | 2005 |
| DQ343774 | B/Nepal/1136/2005 | 1017 | 2005 |
| DQ343773 | B/Nepal/1137/2005 | 1017 | 2005 |
| DQ343772 | B/Nepal/1138/2005 | 1017 | 2005 |
| DQ343771 | B/Nepal/1139/2005 | 1017 | 2005 |
| ISDN125760 | B/New Caledonia/10/2005 | 1039 | 2005 |
| ISDN133312 | B/Ohio/1/2005 | 1049 | 2005 |
| ISDN126357 | B/Ohio/1/2005 | 1041 | 2005 |
| ISDN138728 | B/Ohio/1e4/2005 | 1750 | 2005 |

TABLE 2-continued

INFLUENZA TYPE B HA SEQUENCES

| Accession | Strain | Length | Year |
|---|---|---|---|
| ISDN126575 | B/Perth/17/2005 | 1070 | 2005 |
| ISDN126579 | B/South Australia/19/2005 | 1053 | 2005 |
| ISDN125755 | B/South Australia/6/2005 | 1039 | 2005 |
| ISDN125754 | B/South Australia/9/2005 | 1042 | 2005 |
| ISDN124789 | B/Sydney/2/2005 | 1039 | 2005 |
| ISDN125753 | B/Sydney/3/2005 | 1068 | 2005 |
| ISDN124783 | B/Taiwan/136/2005 | 1041 | 2005 |
| ISDN124782 | B/Taiwan/142/2005 | 1041 | 2005 |
| ISDN124786 | B/Thailand/130/2005 | 1041 | 2005 |
| ISDN124787 | B/Thailand/137/2005 | 1038 | 2005 |
| ISDN124780 | B/Victoria/502/2005 | 1039 | 2005 |
| ISDN124788 | B/Victoria/505/2005 | 1041 | 2005 |
| ISDN124792 | B/Victoria/507/2005 | 1039 | 2005 |
| ISDN126578 | B/Victoria/517/2005 | 1041 | 2005 |
| ISDN125749 | B/Waikato/28/2005 | 1042 | 2005 |
| ISDN125750 | B/Wellington/21/2005 | 1042 | 2005 |
| ISDN124790 | B/Wellington/4/2005 | 1042 | 2005 |
| ISDN124791 | B/Wellington/9/2005 | 1038 | 2005 |
| ISDN110432 | B/Auckland/1/2004 | 1060 | 2004 |
| ISDN110431 | B/Brisbane/1/2004 | 1055 | 2004 |
| ISDN110627 | B/Brisbane/4/2004 | 1038 | 2004 |
| ISDN110628 | B/Brisbane/5/2004 | 1050 | 2004 |
| ISDN110429 | B/Christchurch/22/2004 | 1066 | 2004 |
| ISDN110625 | B/Christchurch/27/2004 | 1053 | 2004 |
| ISDN110626 | B/Christchurch/33/2004 | 1059 | 2004 |
| ISDN69105 | B/Christchurch/7/2004 | 1071 | 2004 |
| DQ265724 | B/Colorado/2597/2004 | 1038 | 2004 |
| ISDN69096 | B/Darwin/1/2004 | 1038 | 2004 |
| AJ784059 | B/England/23/04 | 1074 | 2004 |
| DQ265721 | B/Hawaii/1990/2004 | 1017 | 2004 |
| DQ265720 | B/Hawaii/1993/2004 | 1041 | 2004 |
| ISDN64310 | B/Macau/131/2004 | 1038 | 2004 |
| ISDN64311 | B/Macau/211/2004 | 1069 | 2004 |
| ISDN69098 | B/Malaysia/1228/2004 | 1066 | 2004 |
| ISDN69103 | B/Malaysia/1523/2004 | 1056 | 2004 |
| ISDN69104 | B/Malaysia/1526/2004 | 1055 | 2004 |
| ISDN110479 | B/Malaysia/1985/2004 | 1062 | 2004 |
| ISDN110480 | B/Malaysia/20/2004 | 1065 | 2004 |
| ISDN110629 | B/Malaysia/2276/2004 | 1041 | 2004 |
| ISDN126672 | B/Malaysia/2506/2004 (egg passaged) | 1074 | 2004 |
| ISDN124776 | B/Malaysia/2506/2004 (MDCK passaged) | 1071 | 2004 |
| ISDN64309 | B/Malaysia/345/2004 | 1053 | 2004 |
| AJ842082 | B/Milano/66/04 | 997 | 2004 |
| ISDN69100 | B/Nongkhai/1112/2004 | 1047 | 2004 |
| AJ784057 | B/Oslo/71/04 | 1035 | 2004 |
| AJ842066 | B/Parma/1/04 | 1000 | 2004 |
| AJ842068 | B/Parma/2/04 | 1000 | 2004 |
| AJ842073 | B/Parma/3/04 | 1000 | 2004 |
| AJ842088 | B/Parma/4/04 | 976 | 2004 |
| ISDN110434 | B/Perth/10/2004 | 1066 | 2004 |
| ISDN110435 | B/Perth/12/2004 | 1060 | 2004 |
| ISDN69101 | B/Perth/2/2004 | 1069 | 2004 |
| ISDN110481 | B/Perth/33/2004 | 1064 | 2004 |
| DQ265728 | B/Peru/1324/2004 | 1054 | 2004 |
| DQ265726 | B/Peru/1364/2004 | 1038 | 2004 |
| ISDN110630 | B/Phitsanulok/2053/2004 | 1041 | 2004 |
| ISDN69099 | B/Saraburi/173/2004 | 1038 | 2004 |
| DQ231537 | B/Seoul/1163/2004 | 1038 | 2004 |
| ISDN110437 | B/South Australia/7/2004 | 1066 | 2004 |
| ISDN110430 | B/Sydney/4/2004 | 1057 | 2004 |
| ISDN110483 | B/Sydney/6/2004 | 1040 | 2004 |
| ISDN64308 | B/Taiwan/1/2004 | 1040 | 2004 |
| ISDN65387 | B/Taiwan/202/2004 | 1039 | 2004 |
| ISDN69102 | B/Victoria/101/2004 | 1065 | 2004 |
| ISDN110433 | B/Victoria/104/2004 | 1060 | 2004 |
| ISDN110624 | B/Victoria/501/2004 | 1038 | 2004 |
| ISDN69097 | B/Victoria/501/2004 | 1039 | 2004 |
| ISDN110623 | B/Victoria/508/2004 | 1060 | 2004 |
| ISDN110478 | B/Victoria/511/2004 | 1065 | 2004 |
| ISDN110482 | B/Victoria/513/2004 | 1061 | 2004 |
| AJ784060 | B/Bangkok/460/03 | 1026 | 2003 |
| AJ784048 | B/Barcelona/215/03 | 964 | 2003 |
| AJ784053 | B/Bucharest/795/03 | 1043 | 2003 |
| AJ784058 | B/Cheju/303/03 | 1075 | 2003 |
| AY744307 | B/Finland/164/2003 | 1041 | 2003 |
| AY744308 | B/Finland/173/2003 | 1041 | 2003 |
| AY744309 | B/Finland/176/2003 | 1041 | 2003 |
| AY744310 | B/Finland/188/2003 | 1041 | 2003 |
| AY744311 | B/Finland/190/2003 | 1041 | 2003 |
| AY744312 | B/Finland/191/2003 | 1041 | 2003 |
| AY744313 | B/Finland/192/2003 | 1041 | 2003 |
| AY744314 | B/Finland/193/2003 | 1041 | 2003 |
| AY744315 | B/Finland/199/2003 | 1041 | 2003 |
| AY744334 | B/Finland/202/2003 | 1038 | 2003 |
| AY744316 | B/Finland/203/2003 | 1041 | 2003 |
| AY744317 | B/Finland/204/2003 | 1041 | 2003 |
| AY744318 | B/Finland/205/2003 | 1041 | 2003 |
| AY744319 | B/Finland/206/2003 | 1041 | 2003 |
| AY744320 | B/Finland/220/2003 | 1041 | 2003 |
| AY744335 | B/Finland/223/2003 | 1038 | 2003 |
| AY744336 | B/Finland/225/2003 | 1038 | 2003 |
| AY744321 | B/Finland/227/2003 | 1041 | 2003 |
| AY744337 | B/Finland/231/2003 | 1038 | 2003 |
| AY744322 | B/Finland/235/2003 | 1041 | 2003 |
| AY744323 | B/Finland/239/2003 | 1041 | 2003 |
| AY744324 | B/Finland/244/2003 | 1041 | 2003 |
| AY744325 | B/Finland/245/2003 | 1041 | 2003 |
| AY744326 | B/Finland/254/2003 | 1041 | 2003 |
| AY744327 | B/Finland/255/2003 | 1041 | 2003 |
| AY744328 | B/Finland/270/2003 | 1041 | 2003 |
| AY744329 | B/Finland/275/2003 | 1041 | 2003 |
| AJ784049 | B/Geneva/5079/03 | 955 | 2003 |
| AJ842056 | B/Genova/1603/03 | 1000 | 2003 |
| AJ842059 | B/Genova/2059/03 | 1000 | 2003 |
| AJ784047 | B/Israel/95/03 | 968 | 2003 |
| AJ784061 | B/Jiangsu/10/03 | 1080 | 2003 |
| ISDN48864 | B/Jiangsu/10/2003 | 1806 | 2003 |
| ISDN68444 | B/Jiangsu/10/2003 (recomb) | 1805 | 2003 |
| ISDN65460 | B/Jiangsu/10e9/2003 | 1785 | 2003 |
| ISDN40908 | B/Jilin/20/2003 | 1069 | 2003 |
| AB126835 | B/Kobe/1/2003 | 1007 | 2003 |
| AB126836 | B/Kobe/2/2003 | 1007 | 2003 |
| AB126839 | B/Kobe/25/2003 | 774 | 2003 |
| AB126840 | B/Kobe/26/2003 | 692 | 2003 |
| AB126841 | B/Kobe/28/2003 | 1004 | 2003 |
| AB126837 | B/Kobe/3/2003 | 1008 | 2003 |
| AB126838 | B/Kobe/4/2003 | 1009 | 2003 |
| AY581970 | B/Memphis/13/03 | 1758 | 2003 |
| AY581969 | B/Memphis/7/03 | 1758 | 2003 |
| AJ784046 | B/Moscow/3/03 | 895 | 2003 |
| AJ842065 | B/Parma/1/03 | 1000 | 2003 |
| AJ842067 | B/Parma/2/03 | 1000 | 2003 |
| ISDN38278 | B/Perth/201/2003 | 1063 | 2003 |
| AJ842064 | B/Perugia/4/03 | 1000 | 2003 |
| AJ842074 | B/Roma/1/03 | 1000 | 2003 |
| AJ842089 | B/Roma/2/03 | 986 | 2003 |
| AJ842090 | B/Roma/3/03 | 965 | 2003 |
| AY604779 | B/Taiwan/0002/03 | 397 | 2003 |
| AY604780 | B/Taiwan/0562/03 | 397 | 2003 |
| AY604781 | B/Taiwan/0569/03 | 397 | 2003 |
| AY604782 | B/Taiwan/0576/03 | 397 | 2003 |
| AY604783 | B/Taiwan/0610/03 | 397 | 2003 |
| AY604784 | B/Taiwan/0615/03 | 397 | 2003 |
| AY604785 | B/Taiwan/0616/03 | 397 | 2003 |
| AY604786 | B/Taiwan/0684/03 | 397 | 2003 |
| AY604787 | B/Taiwan/0699/03 | 397 | 2003 |
| AY604788 | B/Taiwan/0735/03 | 397 | 2003 |
| AY604789 | B/Taiwan/0833/03 | 397 | 2003 |
| AY604790 | B/Taiwan/1013/03 | 397 | 2003 |
| AY604791 | B/Taiwan/1574/03 | 397 | 2003 |
| AY604792 | B/Taiwan/1618/03 | 397 | 2003 |
| AY604793 | B/Taiwan/2551/03 | 397 | 2003 |
| AY604794 | B/Taiwan/3532/03 | 397 | 2003 |
| AJ842077 | B/Trieste/1/03 | 1000 | 2003 |
| AJ842078 | B/Trieste/2/03 | 1000 | 2003 |
| AB120507 | B/Yamagata/115/2003 | 1041 | 2003 |
| AB120508 | B/Yamagata/1246/2003 | 1038 | 2003 |
| AB120509 | B/Yamagata/1311/2003 | 1038 | 2003 |
| AY375988 | B/Belgium/WV106/2002 | 722 | 2002 |
| AY375989 | B/Belgium/WV107/2002 | 722 | 2002 |

TABLE 2-continued

INFLUENZA TYPE B HA SEQUENCES

| Accession | Strain | Length | Year |
|---|---|---|---|
| AY375990 | B/Belgium/WV109/2002 | 739 | 2002 |
| AY375991 | B/Belgium/WV114/2002 | 722 | 2002 |
| AY375992 | B/Belgium/WV122/2002 | 725 | 2002 |
| ISDN33924 | B/Brisbane/32/2002 | 1074 | 2002 |
| AF532531 | B/Canada/464/2002 | 1050 | 2002 |
| AY880074 | B/clinical isolate SA1 Thailand/2002 | 621 | 2002 |
| AY880082 | B/clinical isolate SA10 Thailand/2002 | 643 | 2002 |
| AY880163 | B/clinical isolate SA100 Philippines/2002 | 714 | 2002 |
| AY880164 | B/clinical isolate SA101 Philippines/2002 | 714 | 2002 |
| AY880165 | B/clinical isolate SA102 Philippines/2002 | 482 | 2002 |
| AY880166 | B/clinical isolate SA103 Philippines/2002 | 712 | 2002 |
| AY880167 | B/clinical isolate SA104 Philippines/2002 | 714 | 2002 |
| AY880168 | B/clinical isolate SA105 Philippines/2002 | 712 | 2002 |
| AY880169 | B/clinical isolate SA106 Philippines/2002 | 712 | 2002 |
| AY880170 | B/clinical isolate SA107 Philippines/2002 | 712 | 2002 |
| AY880171 | B/clinical isolate SA108 Philippines/2002 | 727 | 2002 |
| AY880172 | B/clinical isolate SA109 Philippines/2002 | 712 | 2002 |
| AY880083 | B/clinical isolate SA11 Thailand/2002 | 598 | 2002 |
| AY880173 | B/clinical isolate SA110 Philippines/2002 | 482 | 2002 |
| AY880174 | B/clinical isolate SA112 Philippines/2002 | 712 | 2002 |
| AY880175 | B/clinical isolate SA113 Philippines/2002 | 712 | 2002 |
| AY880176 | B/clinical isolate SA114 Philippines/2002 | 712 | 2002 |
| AY880177 | B/clinical isolate SA115 Philippines/2002 | 727 | 2002 |
| AY880178 | B/clinical isolate SA116 Philippines/2002 | 712 | 2002 |
| AY880084 | B/clinical isolate SA12 Thailand/2002 | 613 | 2002 |
| AY880085 | B/clinical isolate SA13 Thailand/2002 | 598 | 2002 |
| AY880086 | B/clinical isolate SA14 Thailand/2002 | 635 | 2002 |
| AY880087 | B/clinical isolate SA15 Thailand/2002 | 623 | 2002 |
| AY880088 | B/clinical isolate SA16 Thailand/2002 | 652 | 2002 |
| AY880089 | B/clinical isolate SA17 Thailand/2002 | 637 | 2002 |
| AY880090 | B/clinical isolate SA18 Thailand/2002 | 586 | 2002 |
| AY880091 | B/clinical isolate SA19 Thailand/2002 | 635 | 2002 |
| AY880075 | B/clinical isolate SA2 Thailand/2002 | 635 | 2002 |
| AY880092 | B/clinical isolate SA20 Thailand/2002 | 620 | 2002 |
| AY880093 | B/clinical isolate SA21 Thailand/2002 | 621 | 2002 |
| AY880094 | B/clinical isolate SA22 Thailand/2002 | 638 | 2002 |
| AY880095 | B/clinical isolate SA23 Thailand/2002 | 625 | 2002 |
| AY880096 | B/clinical isolate SA24 Thailand/2002 | 623 | 2002 |
| AY880097 | B/clinical isolate SA25 Thailand/2002 | 640 | 2002 |
| AY880098 | B/clinical isolate SA26 Thailand/2002 | 621 | 2002 |
| AY880099 | B/clinical isolate SA27 Thailand/2002 | 635 | 2002 |
| AY880100 | B/clinical isolate SA28 Thailand/2002 | 637 | 2002 |
| AY880101 | B/clinical isolate SA29 Thailand/2002 | 651 | 2002 |
| AY880076 | B/clinical isolate SA3 Thailand/2002 | 622 | 2002 |
| AY880102 | B/clinical isolate SA30 Thailand/2002 | 601 | 2002 |
| AY880103 | B/clinical isolate SA31 Thailand/2002 | 641 | 2002 |
| AY880104 | B/clinical isolate SA32 Thailand/2002 | 624 | 2002 |
| AY880105 | B/clinical isolate SA33 Thailand/2002 | 621 | 2002 |
| AY880106 | B/clinical isolate SA34 Thailand/2002 | 621 | 2002 |
| AY880107 | B/clinical isolate SA37 Thailand/2002 | 641 | 2002 |
| AY880108 | B/clinical isolate SA38 Philippines/2002 | 655 | 2002 |
| AY880109 | B/clinical isolate SA39 Thailand/2002 | 621 | 2002 |
| AY880110 | B/clinical isolate SA40 Thailand/2002 | 656 | 2002 |
| AY880111 | B/clinical isolate SA41 Philippines/2002 | 637 | 2002 |
| AY880112 | B/clinical isolate SA42 Philippines/2002 | 621 | 2002 |
| AY880113 | B/clinical isolate SA43 Thailand/2002 | 618 | 2002 |
| AY880114 | B/clinical isolate SA44 Thailand/2002 | 652 | 2002 |
| AY880115 | B/clinical isolate SA45 Philippines/2002 | 641 | 2002 |
| AY880116 | B/clinical isolate SA46 Philippines/2002 | 721 | 2002 |
| AY880117 | B/clinical isolate SA47 Philippines/2002 | 721 | 2002 |
| AY880077 | B/clinical isolate SA5 Thailand/2002 | 654 | 2002 |
| AY880118 | B/clinical isolate SA50 Philippines/2002 | 638 | 2002 |
| AY880119 | B/clinical isolate SA51 Philippines/2002 | 712 | 2002 |
| AY880120 | B/clinical isolate SA52 Philippines/2002 | 712 | 2002 |
| AY880121 | B/clinical isolate SA53 Philippines/2002 | 545 | 2002 |
| AY880122 | B/clinical isolate SA57 Philippines/2002 | 637 | 2002 |
| AY880123 | B/clinical isolate SA58 Philippines/2002 | 727 | 2002 |
| AY880124 | B/clinical isolate SA59 Philippines/2002 | 637 | 2002 |
| AY880078 | B/clinical isolate SA6 Thailand/2002 | 620 | 2002 |
| AY880125 | B/clinical isolate SA60 Philippines/2002 | 637 | 2002 |
| AY880126 | B/clinical isolate SA61 Philippines/2002 | 637 | 2002 |
| AY880127 | B/clinical isolate SA62 Philippines/2002 | 623 | 2002 |
| AY880128 | B/clinical isolate SA63 Philippines/2002 | 636 | 2002 |
| AY880129 | B/clinical isolate SA64 Philippines/2002 | 604 | 2002 |
| AY880130 | B/clinical isolate SA65 Philippines/2002 | 497 | 2002 |
| AY880131 | B/clinical isolate SA66 Philippines/2002 | 621 | 2002 |
| AY880132 | B/clinical isolate SA67 Philippines/2002 | 616 | 2002 |
| AY880133 | B/clinical isolate SA68 Philippines/2002 | 586 | 2002 |

TABLE 2-continued

INFLUENZA TYPE B HA SEQUENCES

| Accession | Strain | Length | Year |
|---|---|---|---|
| AY880134 | B/clinical isolate SA69 Philippines/2002 | 712 | 2002 |
| AY880079 | B/clinical isolate SA7 Thailand/2002 | 654 | 2002 |
| AY880135 | B/clinical isolate SA70 Philippines/2002 | 619 | 2002 |
| AY880136 | B/clinical isolate SA71 Philippines/2002 | 712 | 2002 |
| AY880137 | B/clinical isolate SA73 Philippines/2002 | 712 | 2002 |
| AY880138 | B/clinical isolate SA74 Philippines/2002 | 715 | 2002 |
| AY880139 | B/clinical isolate SA76 Philippines/2002 | 712 | 2002 |
| AY880140 | B/clinical isolate SA77 Philippines/2002 | 712 | 2002 |
| AY880141 | B/clinical isolate SA78 Philippines/2002 | 712 | 2002 |
| AY880142 | B/clinical isolate SA79 Philippines/2002 | 715 | 2002 |
| AY880080 | B/clinical isolate SA8 Thailand/2002 | 655 | 2002 |
| AY880143 | B/clinical isolate SA80 Philippines/2002 | 651 | 2002 |
| AY880144 | B/clinical isolate SA81 Philippines/2002 | 714 | 2002 |
| AY880145 | B/clinical isolate SA82 Philippines/2002 | 712 | 2002 |
| AY880146 | B/clinical isolate SA83 Philippines/2002 | 714 | 2002 |
| AY880147 | B/clinical isolate SA84 Philippines/2002 | 714 | 2002 |
| AY880148 | B/clinical isolate SA85 Thailand/2002 | 712 | 2002 |
| AY880149 | B/clinical isolate SA86 Thailand/2002 | 714 | 2002 |
| AY880150 | B/clinical isolate SA87 Thailand/2002 | 714 | 2002 |
| AY880151 | B/clinical isolate SA88 Thailand/2002 | 729 | 2002 |
| AY880152 | B/clinical isolate SA89 Thailand/2002 | 714 | 2002 |
| AY880081 | B/clinical isolate SA9 Thailand/2002 | 669 | 2002 |
| AY880153 | B/clinical isolate SA90 Thailand/2002 | 714 | 2002 |
| AY880154 | B/clinical isolate SA91 Thailand/2002 | 712 | 2002 |
| AY880155 | B/clinical isolate SA92 Thailand/2002 | 714 | 2002 |
| AY880156 | B/clinical isolate SA93 Thailand/2002 | 729 | 2002 |
| AY880157 | B/clinical isolate SA94 Thailand/2002 | 714 | 2002 |
| AY880158 | B/clinical isolate SA95 Philippines/2002 | 714 | 2002 |
| AY880159 | B/clinical isolate SA96 Thailand/2002 | 722 | 2002 |
| AY880160 | B/clinical isolate SA97 Philippines/2002 | 712 | 2002 |
| AY880161 | B/clinical isolate SA98 Philippines/2002 | 726 | 2002 |
| AY880162 | B/clinical isolate SA99 Philippines/2002 | 712 | 2002 |
| AY744333 | B/Finland/154/2002 | 1038 | 2002 |
| AY744303 | B/Finland/159/2002 | 1041 | 2002 |
| AY744304 | B/Finland/160/2002 | 1041 | 2002 |
| AY744305 | B/Finland/161/2002 | 1041 | 2002 |
| AY744306 | B/Finland/162/2002 | 1041 | 2002 |
| AY744332 | B/Finland/84/2002 | 1038 | 2002 |
| AY376020 | B/Finland/WV4/2002 | 722 | 2002 |
| AY376025 | B/Finland/WV5/2002 | 710 | 2002 |
| AY236436 | B/Genoa/11/02 | 1003 | 2002 |
| AY236440 | B/Genoa/12/02 | 1000 | 2002 |
| AY236463 | B/Genoa/2/02 | 1003 | 2002 |
| AY236461 | B/Genoa/21/02 | 1003 | 2002 |
| AY236449 | B/Genoa/3/02 | 1000 | 2002 |
| AY236458 | B/Genoa/33/02 | 1003 | 2002 |
| AY236437 | B/Genoa/41/02 | 1003 | 2002 |
| AY236450 | B/Genoa/48/02 | 1000 | 2002 |
| AY236441 | B/Genoa/49/02 | 1000 | 2002 |
| AY236444 | B/Genoa/5/02 | 1000 | 2002 |
| AY236465 | B/Genoa/52/02 | 1003 | 2002 |
| AY236451 | B/Genoa/53/02 | 1000 | 2002 |
| AY236464 | B/Genoa/55/02 | 1003 | 2002 |
| AY236457 | B/Genoa/56/02 | 1000 | 2002 |
| AY236447 | B/Genoa/6/02 | 1000 | 2002 |
| AY236448 | B/Genoa/65/02 | 1000 | 2002 |
| AY236460 | B/Genoa/7/02 | 1003 | 2002 |
| AY236462 | B/Genoa/8/02 | 1003 | 2002 |
| AJ842057 | B/Genova/2/02 | 1000 | 2002 |
| AJ842058 | B/Genova/20/02 | 1000 | 2002 |
| AJ842060 | B/Genova/26/02 | 1000 | 2002 |
| AJ842079 | B/Genova/30/02 | 997 | 2002 |
| AF532542 | B/Hong Kong/1115/2002 | 1052 | 2002 |
| AF532545 | B/Hong Kong/1351/2002 | 1056 | 2002 |
| AF532546 | B/Hong Kong/1434/2002 | 1052 | 2002 |
| AJ784052 | B/Hong Kong/293/02 | 1038 | 2002 |
| AY375993 | B/Israel/WV124/2002 | 729 | 2002 |
| AY375994 | B/Israel/WV126/2002 | 710 | 2002 |
| AY375995 | B/Israel/WV133/2002 | 722 | 2002 |
| AY375996 | B/Israel/WV135/2002 | 665 | 2002 |
| AY375997 | B/Israel/WV137/2002 | 725 | 2002 |
| AY375998 | B/Israel/WV142/2002 | 725 | 2002 |
| AY375999 | B/Israel/WV143/2002 | 725 | 2002 |
| AY376000 | B/Israel/WV145/2002 | 725 | 2002 |
| AY376001 | B/Israel/WV146/2002 | 725 | 2002 |
| AY376002 | B/Israel/WV150/2002 | 711 | 2002 |
| AY376003 | B/Israel/WV153/2002 | 725 | 2002 |
| AY376004 | B/Israel/WV158/2002 | 725 | 2002 |
| AY376005 | B/Israel/WV161/2002 | 725 | 2002 |
| AY376006 | B/Israel/WV166/2002 | 722 | 2002 |
| AY376007 | B/Israel/WV169/2002 | 725 | 2002 |
| AY376008 | B/Israel/WV170/2002 | 725 | 2002 |
| AY376009 | B/Israel/WV174/2002 | 725 | 2002 |
| AY376010 | B/Israel/WV183/2002 | 722 | 2002 |
| AY376011 | B/Israel/WV187/2002 | 725 | 2002 |
| AB081570 | B/Kobe/1/2002 | 987 | 2002 |
| AB081571 | B/Kobe/2/2002 | 982 | 2002 |
| AB083182 | B/Kobe/3/2002 | 979 | 2002 |
| AB083183 | B/Kobe/4/2002 | 979 | 2002 |
| AB083404 | B/Kobe/5/2002 | 978 | 2002 |
| AB196144 | B/Kobe/6/2002 | 1009 | 2002 |
| AB126842 | B/Kobe/7/2002 | 1008 | 2002 |
| AJ842080 | B/Lazio/1/02 | 997 | 2002 |
| AY581968 | B/Los Angeles/1/02 | 1758 | 2002 |
| AF532562 | B/Maryland/1/2002 | 1028 | 2002 |
| AJ842062 | B/Milano/5/02 | 1000 | 2002 |
| AJ842081 | B/Milano/6/02 | 997 | 2002 |
| AJ842063 | B/Milano/7/02 | 1000 | 2002 |
| AF532565 | B/New York/1/2002 | 1036 | 2002 |
| ISDN13304 | B/Oslo/1329/2002 | 733 | 2002 |
| AJ489312 | B/Oslo/1329/2002 | 730 | 2002 |
| AJ489313 | B/Oslo/1510/2002 | 733 | 2002 |
| ISDN13328 | B/Oslo/1510/2002 | 754 | 2002 |
| AJ489314 | B/Oslo/1846/2002 | 728 | 2002 |
| ISDN13330 | B/Oslo/1846/2002 | 727 | 2002 |
| ISDN13331 | B/Oslo/1847/2002 | 710 | 2002 |
| AJ489315 | B/Oslo/1847/2002 | 710 | 2002 |
| AJ489316 | B/Oslo/1870/2002 | 730 | 2002 |
| ISDN13332 | B/Oslo/1870/2002 | 751 | 2002 |
| AJ489317 | B/Oslo/1871/2002 | 729 | 2002 |
| ISDN13329 | B/Oslo/1871/2002 | 1072 | 2002 |
| ISDN13306 | B/Oslo/668/2002 | 1081 | 2002 |
| AJ489311 | B/Oslo/668/2002 | 1081 | 2002 |
| ISDN13333 | B/Oslo/668/2002 | 1109 | 2002 |
| AJ842083 | B/Parma/13/02 | 997 | 2002 |
| AJ842084 | B/Parma/16/02 | 997 | 2002 |
| AJ842069 | B/Parma/23/02 | 1000 | 2002 |
| AJ842070 | B/Parma/24/02 | 1000 | 2002 |
| AJ842071 | B/Parma/25/02 | 1000 | 2002 |
| AJ842072 | B/Parma/28/02 | 1000 | 2002 |

TABLE 2-continued

INFLUENZA TYPE B HA SEQUENCES

| Accession | Strain | Length | Year |
|---|---|---|---|
| AJ842085 | B/Parma/5/02 | 997 | 2002 |
| AJ842086 | B/Roma/4/02 | 997 | 2002 |
| AJ842075 | B/Roma/7/02 | 1000 | 2002 |
| AJ784056 | B/Shanghai/361/02 | 1050 | 2002 |
| ISDN38226 | B/Shanghai/361/2002 | 1038 | 2002 |
| ISDN80784 | B/Shanghai/361/2002 | 1014 | 2002 |
| AJ842076 | B/Siena/1/02 | 1000 | 2002 |
| AY376013 | B/Spain/WV22/2002 | 722 | 2002 |
| AY376014 | B/Spain/WV26/2002 | 710 | 2002 |
| AY376015 | B/Spain/WV27/2002 | 722 | 2002 |
| AY376016 | B/Spain/WV29/2002 | 722 | 2002 |
| AY376017 | B/Spain/WV33/2002 | 722 | 2002 |
| AY376018 | B/Spain/WV34/2002 | 736 | 2002 |
| AY376019 | B/Spain/WV36/2002 | 739 | 2002 |
| AY376021 | B/Spain/WV41/2002 | 710 | 2002 |
| AY376022 | B/Spain/WV42/2002 | 710 | 2002 |
| AY376023 | B/Spain/WV43/2002 | 722 | 2002 |
| AY376024 | B/Spain/WV45/2002 | 722 | 2002 |
| AY376026 | B/Spain/WV50/2002 | 722 | 2002 |
| AY376027 | B/Spain/WV51/2002 | 722 | 2002 |
| AY376028 | B/Spain/WV56/2002 | 722 | 2002 |
| AY376029 | B/Spain/WV57/2002 | 722 | 2002 |
| AY376030 | B/Spain/WV65/2002 | 722 | 2002 |
| AY376031 | B/Spain/WV66/2002 | 722 | 2002 |
| AY376032 | B/Spain/WV67/2002 | 722 | 2002 |
| AY376033 | B/Spain/WV69/2002 | 722 | 2002 |
| AY376034 | B/Spain/WV70/2002 | 722 | 2002 |
| AY376035 | B/Spain/WV73/2002 | 722 | 2002 |
| AY376036 | B/Spain/WV78/2002 | 722 | 2002 |
| AY604756 | B/Taiwan/0409/02 | 394 | 2002 |
| AY604757 | B/Taiwan/0600/02 | 397 | 2002 |
| AY604758 | B/Taiwan/0654/02 | 397 | 2002 |
| AY604759 | B/Taiwan/0702/02 | 397 | 2002 |
| AY604760 | B/Taiwan/0722/02 | 397 | 2002 |
| AY604761 | B/Taiwan/0730/02 | 397 | 2002 |
| AY604762 | B/Taiwan/0874/02 | 394 | 2002 |
| AY604767 | B/Taiwan/0879/02 | 394 | 2002 |
| AY604763 | B/Taiwan/0880/02 | 394 | 2002 |
| AY604764 | B/Taiwan/0927/02 | 394 | 2002 |
| AY604765 | B/Taiwan/0932/02 | 394 | 2002 |
| AY604766 | B/Taiwan/0993/02 | 394 | 2002 |
| AY604768 | B/Taiwan/1013/02 | 394 | 2002 |
| AY604769 | B/Taiwan/1502/02 | 394 | 2002 |
| AY604770 | B/Taiwan/1503/02 | 394 | 2002 |
| AY604771 | B/Taiwan/1534/02 | 394 | 2002 |
| AY604772 | B/Taiwan/1536/02 | 394 | 2002 |
| AY604773 | B/Taiwan/1561/02 | 394 | 2002 |
| AY604774 | B/Taiwan/1584/02 | 394 | 2002 |
| AY604775 | B/Taiwan/1949/02 | 394 | 2002 |
| AY604776 | B/Taiwan/1950/02 | 394 | 2002 |
| AY604778 | B/Taiwan/4119/02 | 394 | 2002 |
| AY604777 | B/Taiwan/4602/02 | 394 | 2002 |
| AJ784042 | B/Tehran/80/02 | 936 | 2002 |
| AY139049 | B/Texas/3/2002 | 1052 | 2002 |
| AJ842091 | B/Trento/3/02 | 895 | 2002 |
| AJ784051 | B/Trento/3/02 | 895 | 2002 |
| AJ842087 | B/Trieste/1/02 | 997 | 2002 |
| AY236443 | B/Trieste/14/02 | 1000 | 2002 |
| AY236455 | B/Trieste/15/02 | 1000 | 2002 |
| AY236438 | B/Trieste/17/02 | 1000 | 2002 |
| AY236452 | B/Trieste/18/02 | 1000 | 2002 |
| AY236446 | B/Trieste/23/02 | 1000 | 2002 |
| AY236442 | B/Trieste/24/02 | 1000 | 2002 |
| AY236456 | B/Trieste/25/02 | 1000 | 2002 |
| AY236453 | B/Trieste/27/02 | 1003 | 2002 |
| AJ784044 | B/Trieste/28/02 | 1016 | 2002 |
| AY236459 | B/Trieste/37/02 | 1003 | 2002 |
| AY236454 | B/Trieste/4/02 | 1000 | 2002 |
| AY236445 | B/Trieste/7/02 | 1000 | 2002 |
| AY236439 | B/Trieste/8/02 | 1000 | 2002 |
| AJ784055 | B/Ulan Ude/4/02 | 992 | 2002 |
| AY376012 | B/WV194/2002 | 722 | 2002 |
| AB120506 | B/Yamagata/222/2002 | 1041 | 2002 |
| AB158792 | B/Akita/27/2001 (egg isolate) | 1041 | 2001 |
| AB158793 | B/Akita/27/2001 (MDCK isolate) | 1041 | 2001 |
| AB158796 | B/Akita/27/2001 (MG−) | 1041 | 2001 |
| AB158794 | B/Akita/27/2001 (egg isolation then cloned) | 1041 | 2001 |
| AB158795 | B/Akita/27/2001 (MG+) | 1041 | 2001 |
| AB158797 | B/Akita/5/2001 (egg isolate) | 1041 | 2001 |
| AB158798 | B/Akita/5/2001 (MDCK isolate) | 1041 | 2001 |
| AF532525 | B/Argentina/69/2001 | 1043 | 2001 |
| DQ336018 | B/Brazil/110/01 | 966 | 2001 |
| AF532529 | B/Brazil/952/2001 | 976 | 2001 |
| AF532532 | B/CNIC/27/2001 | 1050 | 2001 |
| AY744331 | B/Finland/886/2001 | 1038 | 2001 |
| AF532535 | B/Hawaii/10/2001 | 1062 | 2001 |
| AF532534 | B/Hawaii/10/2001 | 1064 | 2001 |
| AF532536 | B/Hawaii/26/2001 | 1063 | 2001 |
| AF532537 | B/Hawaii/35/2001 | 1060 | 2001 |
| AF532538 | B/Hawaii/36/2001 | 1062 | 2001 |
| AF532539 | B/Hawaii/37/2001 | 1046 | 2001 |
| AF532540 | B/Hawaii/38/2001 | 924 | 2001 |
| AF532541 | B/Hawaii/9/2001 | 1050 | 2001 |
| AB158800 | B/Hiroshima/23/2001 (MDCK isolate) | 1038 | 2001 |
| AB158799 | B/Hiroshima/23/2001 (egg isolate) | 1038 | 2001 |
| AF532543 | B/Hong Kong/112/2001 | 1065 | 2001 |
| AF532544 | B/Hong Kong/123/2001 | 1056 | 2001 |
| AF532547 | B/Hong Kong/22/2001 | 1050 | 2001 |
| AF532548 | B/Hong Kong/329/2001 | 1049 | 2001 |
| AJ784045 | B/Hong Kong/330/01 | 1093 | 2001 |
| AF532549 | B/Hong Kong/330/2001 | 1064 | 2001 |
| ISDN13431 | B/Hong Kong/330/2001 | 1071 | 2001 |
| AY504610 | B/Hong Kong/330/2001 | 1885 | 2001 |
| ISDN13279 | B/Hong Kong/330/2001 | 1064 | 2001 |
| AF504618 | B/Hong Kong/330/2001 (egg-adapted) | 1885 | 2001 |
| AF532550 | B/Hong Kong/335/2001 | 1051 | 2001 |
| AF532551 | B/Hong Kong/336/2001 | 1066 | 2001 |
| AF532552 | B/HongKong/497/2001 | 1054 | 2001 |
| AF532554 | B/Hong Kong/6/2001 | 1059 | 2001 |
| AF532555 | B/Hong Kong/666/2001 | 1057 | 2001 |
| AJ784050 | B/Hong Kong/692/01 | 1033 | 2001 |
| AF532557 | B/India/7526/2001 | 1050 | 2001 |
| AF532558 | B/India/7569/2001 | 1050 | 2001 |
| AF532559 | B/India/7600/2001 | 1056 | 2001 |
| AF532560 | B/India/7605/2001 | 1050 | 2001 |
| AF532561 | B/India/77276/2001 | 1047 | 2001 |
| AY223892 | B/Johannesburg/116/01 | 955 | 2001 |
| AY223893 | B/Johannesburg/119/01 | 955 | 2001 |
| AY223894 | B/Johannesburg/123/01 | 955 | 2001 |
| AY174683 | B/Johannesburg/33/01 | 955 | 2001 |
| AY223884 | B/Johannesburg/34/01 | 955 | 2001 |
| AY223885 | B/Johannesburg/35/01 | 955 | 2001 |
| AY223886 | B/Johannesburg/36/01 | 955 | 2001 |
| AY223888 | B/Johannesburg/77/01 | 955 | 2001 |
| AY223890 | B/Johannesburg/96/01 | 955 | 2001 |
| AB071515 | B/Kobe/64/2001 | 729 | 2001 |
| AB071516 | B/Kobe/65/2001 | 721 | 2001 |
| AB083405 | B/Kobe/69/2001 | 986 | 2001 |
| AB071517 | B/Kobe/69/2001 | 1080 | 2001 |
| AB071524 | B/Kobe/69/2001 | 1079 | 2001 |
| AB071523 | B/Kobe/69/2001 | 1078 | 2001 |
| AB071521 | B/Kobe/69/2001 (subclone1) | 1078 | 2001 |
| AB071522 | B/Kobe/69/2001 (subclone2) | 1078 | 2001 |
| AB071518 | B/Kobe/79/2001 | 1078 | 2001 |
| AB071519 | B/Kobe/83/2001 | 789 | 2001 |
| AB071520 | B/Kobe/87/2001 | 1071 | 2001 |
| AF532563 | B/Malaysia/83077/2001 | 1057 | 2001 |
| AY581963 | B/Maryland/1/01 | 1755 | 2001 |
| AY581964 | B/Memphis/1/01 | 1755 | 2001 |
| AY581965 | B/Memphis/3/01 | 1755 | 2001 |
| AJ842061 | B/Milano/1/01 | 1000 | 2001 |
| AY581966 | B/Nebraska/1/01 | 1755 | 2001 |
| AY581967 | B/Nebraska/2/01 | 1755 | 2001 |
| AY139048 | B/New York/47/2001 | 1047 | 2001 |
| AF532566 | B/Oman/16291/2001 | 1057 | 2001 |
| AY139044 | B/Oman/16296/2001 | 1058 | 2001 |

TABLE 2-continued

INFLUENZA TYPE B HA SEQUENCES

| Accession | Strain | Length | Year |
|---|---|---|---|
| AY139042 | B/Oman/16299/2001 | 1061 | 2001 |
| AY139043 | B/Oman/16305/2001 | 1058 | 2001 |
| AJ489305 | B/Oslo/1072/2001 | 730 | 2001 |
| AJ489306 | B/Oslo/1862/2001 | 1081 | 2001 |
| AJ489307 | B/Oslo/1864/2001 | 730 | 2001 |
| AJ489308 | B/Oslo/2293/2001 | 730 | 2001 |
| AJ489309 | B/Oslo/2295/2001 | 730 | 2001 |
| AJ489310 | B/Oslo/2297/2001 | 1081 | 2001 |
| AJ489304 | B/Oslo/238/2001 | 730 | 2001 |
| AJ489303 | B/Oslo/47/2001 | 730 | 2001 |
| ISDN13334 | B/Oslo/47/2001 | 730 | 2001 |
| AY139046 | B/Philippines/5072/2001 | 1055 | 2001 |
| AY139045 | B/Philippines/93079/2001 | 1057 | 2001 |
| AJ419574 | B/Quebec/1/01 | 1038 | 2001 |
| AJ419575 | B/Quebec/2/01 | 1038 | 2001 |
| AJ419576 | B/Quebec/3/01 | 1038 | 2001 |
| AJ419577 | B/Quebec/4/01 | 1038 | 2001 |
| AJ419578 | B/Quebec/6/01 | 1038 | 2001 |
| AJ419579 | B/Quebec/7/01 | 1038 | 2001 |
| AJ419580 | B/Quebec/8/01 | 1038 | 2001 |
| AJ419581 | B/Quebec/9/01 | 1038 | 2001 |
| AY947470 | B/Rochester/02/2001 | 1117 | 2001 |
| AY947469 | B/Rochester/02/2001 (pre-treatment) | 1472 | 2001 |
| AB158801 | B/Shizuoka/15/2001 (egg isolate) | 1038 | 2001 |
| AB158802 | B/Shizuoka/15/2001 (MDCK isolate) | 1038 | 2001 |
| AY139034 | B/Sichuan/317/2001 | 1038 | 2001 |
| AY604753 | B/Taiwan/0114/01 | 394 | 2001 |
| AY604751 | B/Taiwan/0202/01 | 394 | 2001 |
| AY604755 | B/Taiwan/1103/01 | 394 | 2001 |
| AF363985 | B/Taiwan/1103/2001 | 559 | 2001 |
| AF492476 | B/Taiwan/114/2001 | 559 | 2001 |
| AY604754 | B/Taiwan/11515/01 | 394 | 2001 |
| AF366075 | B/Taiwan/11515/2001 | 559 | 2001 |
| AY139041 | B/Taiwan/1484/2001 | 1035 | 2001 |
| AF366076 | B/Taiwan/202/2001 | 559 | 2001 |
| AY604752 | B/Taiwan/2805/01 | 394 | 2001 |
| AF400581 | B/Taiwan/2805/2001 | 558 | 2001 |
| AY139047 | B/Taiwan/97271/2001 | 1052 | 2001 |
| AY139039 | B/Wuhan/2/2001 | 1049 | 2001 |
| AB120486 | B/Yamagata/K198/2001 | 1038 | 2001 |
| AB120487 | B/Yamagata/K246/2001 | 1038 | 2001 |
| AB120488 | B/Yamagata/K270/2001 | 1038 | 2001 |
| AB120489 | B/Yamagata/K298/2001 | 1038 | 2001 |
| AB120490 | B/Yamagata/K320/2001 | 1038 | 2001 |
| AB120491 | B/Yamagata/K354/2001 | 1038 | 2001 |
| AB120492 | B/Yamagata/K386/2001 | 1038 | 2001 |
| AB120493 | B/Yamagata/K411/2001 | 1038 | 2001 |
| AB120494 | B/Yamagata/K461/2001 | 1038 | 2001 |
| AB120495 | B/Yamagata/K490/2001 | 1038 | 2001 |
| AB120496 | B/Yamagata/K500/2001 | 1038 | 2001 |
| AB120497 | B/Yamagata/K501/2001 | 1038 | 2001 |
| AB120498 | B/Yamagata/K508/2001 | 1038 | 2001 |
| AB120499 | B/Yamagata/K513/2001 | 1038 | 2001 |
| AB120500 | B/Yamagata/K515/2001 | 1038 | 2001 |
| AB120501 | B/Yamagata/K519/2001 | 1038 | 2001 |
| AB120502 | B/Yamagata/K520/2001 | 1038 | 2001 |
| AB120503 | B/Yamagata/K521/2001 | 1038 | 2001 |
| AB120504 | B/Yamagata/K535/2001 | 1038 | 2001 |
| AB120505 | B/Yamagata/K542/2001 | 1038 | 2001 |
| AY139040 | B/Yunnan/123/2001 | 1058 | 2001 |
| AF532526 | B/Alaska/16/2000 | 1038 | 2000 |
| DQ336022 | B/Brazil/017/00 | 717 | 2000 |
| DQ336019 | B/Brazil/053/00 | 966 | 2000 |
| DQ336023 | B/Brazil/055/00 | 966 | 2000 |
| DQ336024 | B/Brazil/064/00 | 966 | 2000 |
| DQ336021 | B/Brazil/074/00 | 966 | 2000 |
| DQ336020 | B/Brazil/079/00 | 966 | 2000 |
| AF534010 | B/Buenos Aires/161/00 | 1038 | 2000 |
| AF534011 | B/Chaco/366/00 | 1038 | 2000 |
| AF534012 | B/Chaco/R113/00 | 1038 | 2000 |
| AF532530 | B/Chongqing/3/2000 | 1058 | 2000 |
| AY744330 | B/Finland/767/2000 | 1038 | 2000 |
| ISDN13280 | B/Guangdong/120/2000 | 982 | 2000 |
| AY191498 | B/Hong Kong/548/2000 | 1882 | 2000 |
| AJ784054 | B/Hong Kong/557/00 | 1036 | 2000 |
| AF532553 | B/Hong Kong/557/2000 | 1038 | 2000 |
| AB045009 | B/Kadoma/409/2000 | 1070 | 2000 |
| AF532564 | B/Nanchang/1/2000 | 1041 | 2000 |
| AB045008 | B/Osaka/1201/2000 | 1062 | 2000 |
| AJ489302 | B/Oslo/3761/2000 | 1035 | 2000 |
| AF319589 | B/Sichuan/38/2000) | 1041 | 2000 |
| AY604744 | B/Taiwan/0409/00 | 394 | 2000 |
| AY604747 | B/Taiwan/12192/00 | 394 | 2000 |
| AF363984 | B/Taiwan/12192/2000 | 559 | 2000 |
| AY604745 | B/Taiwan/1265/00 | 394 | 2000 |
| AF363983 | B/Taiwan/1265/2000 | 559 | 2000 |
| AY604746 | B/Taiwan/1293/00 | 394 | 2000 |
| AF492477 | B/Taiwan/1293/2000 | 559 | 2000 |
| AY604748 | B/Taiwan/31511/00 | 394 | 2000 |
| AF363980 | B/Taiwan/31511/2000 | 559 | 2000 |
| AY604749 | B/Taiwan/41010/00 | 394 | 2000 |
| AF363981 | B/Taiwan/41010/2000 | 559 | 2000 |
| AY604750 | B/Taiwan/4184/00 | 394 | 2000 |
| AF363982 | B/Taiwan/4184/2000 | 559 | 2000 |
| AY139037 | B/Texas/1/2000 | 1038 | 2000 |
| ISDN20057 | B/Victoria/504/2000 | 1833 | 2000 |
| AY504602 | B/Victoria/504/2000 | 1883 | 2000 |
| AY504623 | B/Victoria/504/2000 (egg adapted var 1) | 1883 | 2000 |
| AY504624 | B/Victoria/504/2000 (egg adapted var 2) | 1796 | 2000 |
| AY139038 | B/Wuhan/356/2000 | 1038 | 2000 |
| AB027406 | B/Aichi/20/99 | 1041 | 1999 |
| ISDN13384 | B/AUCKLAND/2/99 | 1049 | 1999 |
| ISDN13391 | B/BANGKOK/166/99 | 1002 | 1999 |
| ISDN13399 | B/BANGKOK/269/99 | 1069 | 1999 |
| AF532527 | B/Bangkok/34/99 | 1041 | 1999 |
| ISDN13388 | B/BANGKOK/34/99 | 1023 | 1999 |
| ISDNAU1003 | B/Bangkok/52/99 | 1035 | 1999 |
| AF532528 | B/Bangkok/54/99 | 1041 | 1999 |
| ISDN13386 | B/BRISBANE/4/99 | 1027 | 1999 |
| ISDN13392 | B/BRISBANE/5/99 | 1001 | 1999 |
| AF534008 | B/Buenos Aires/VL518/99 | 1035 | 1999 |
| ISDN13395 | B/CHRISTCHURCH/270/99 | 1027 | 1999 |
| ISDN13398 | B/CHRISTCHURCH/6/99 | 1050 | 1999 |
| AF387496 | B/Hong Kong/110/99 (MDCK isolate) | 1882 | 1999 |
| AF387497 | B/Hong Kong/110/99 (Vero isolate) | 1882 | 1999 |
| AF387499 | B/Hong Kong/147/99 (MDCK isolate) | 1882 | 1999 |
| AF387498 | B/Hong Kong/147/99 (Vero isolate) | 1882 | 1999 |
| AF387501 | B/Hong Kong/156/99 (MDCK isolate) | 1882 | 1999 |
| AF387500 | B/Hong Kong/156/99 (Vero isolate) | 1882 | 1999 |
| AF387503 | B/Hong Kong/157/99 (MDCK isolate) | 1882 | 1999 |
| AF387502 | B/Hong Kong/157/99 (Vero isolate) | 1882 | 1999 |
| AY223881 | B/Johsnnesburg/1/99 | 955 | 1999 |
| AY223895 | B/Johannesburg/163/99 | 955 | 1999 |
| AY223896 | B/Johannesburg/187/99 | 955 | 1999 |
| AY223897 | B/Johannesburg/189/99 | 955 | 1999 |
| AY223882 | B/Johannesburg/2/99 | 955 | 1999 |
| AY223887 | B/Johannesburg/41/99 | 955 | 1999 |
| AY223883 | B/Johannesburg/5/99 | 955 | 1999 |
| ISDN13282 | B/Johannesburg/5/99 | 1038 | 1999 |
| ISDN13381 | B/JOHANNESBURG/8/99 | 1032 | 1999 |
| AY223889 | B/Johannesburg/94/99 | 955 | 1999 |
| AB036449 | B/Kadoma/1076/99 | 1005 | 1999 |
| AB036446 | B/Kadoma/122/99 | 1005 | 1999 |
| AB036452 | B/Kadoma/122/99-V1 | 1049 | 1999 |
| AB071532 | B/Kadoma/122/99-V10 | 1067 | 1999 |
| AB071533 | B/Kadoma/122/99-V11 | 1077 | 1999 |
| AB036453 | B/Kadoma/122/99-V2 | 1008 | 1999 |
| AB071525 | B/Kadoma/122/99-V3 | 1074 | 1999 |
| AB071526 | B/Kadoma/122/99-V4 | 1059 | 1999 |

TABLE 2-continued

INFLUENZA TYPE B HA SEQUENCES

| Accession | Strain | Length | Year |
|---|---|---|---|
| AB071527 | B/Kadoma/122/99-V5 | 1077 | 1999 |
| AB071528 | B/Kadoma/122/99-V6 | 1079 | 1999 |
| AB071529 | B/Kadoma/122/99-V7 | 1080 | 1999 |
| AB071530 | B/Kadoma/122/99-V8 | 656 | 1999 |
| AB071531 | B/Kadoma/122/99-V9 | 1077 | 1999 |
| AB036450 | B/Kadoma/136/99 | 1046 | 1999 |
| AB036451 | B/Kadoma/506/99 | 1046 | 1999 |
| AB045010 | B/Kadoma/506/99-V1 | 1065 | 1999 |
| AB036447 | B/kadoma/642/99 | 994 | 1999 |
| AB036448 | B/Kadoma/647/99 | 1005 | 1999 |
| AY096190 | B/Kansas/22992/99 | 978 | 1999 |
| AB036864 | B/Kouchi/193/99 | 1038 | 1999 |
| AB059242 | B/Lusaka/270/99 | 1083 | 1999 |
| AB059250 | B/Lusaka/432/99 | 1083 | 1999 |
| ISDN13385 | B/MALAYSIA/37/99 | 1033 | 1999 |
| AY223898 | B/Maputo/1/99 | 955 | 1999 |
| AY223899 | B/Maputo/2/99 | 955 | 1999 |
| AF534006 | B/Mar del Plata/595/99 | 1035 | 1999 |
| AF534005 | B/Mar del Plata/VL373/99 | 1035 | 1999 |
| AF534007 | B/Mar del Plata/VL385/99 | 1035 | 1999 |
| AY581962 | B/Memphis/8/99 | 1755 | 1999 |
| AY129961 | B/Michigan/22572/99 | 978 | 1999 |
| AY112990 | B/Michigan/22587/99 | 978 | 1999 |
| AY112991 | B/Michigan/22631/99 | 978 | 1999 |
| AY096185 | B/Michigan/22659/99 | 978 | 1999 |
| AY096186 | B/Michigan/22687/99 | 908 | 1999 |
| AY096187 | B/Michigan/22691/99 | 978 | 1999 |
| AY096188 | B/Michigan/22721/99 | 978 | 1999 |
| AY112992 | B/Michigan/22723/99 | 978 | 1999 |
| AY096189 | B/Michigan/22723/99 | 978 | 1999 |
| AB036865 | B/Nagoya/20/99 | 1041 | 1999 |
| ISDN13396 | B/NEW CALEDONIA/1/99 | 1066 | 1999 |
| AY129960 | B/New York/20139/99 | 978 | 1999 |
| AJ489300 | B/Oslo/801/99 | 1035 | 1999 |
| AJ489299 | B/Oslo/805/99 | 863 | 1999 |
| ISDNOS1000 | B/Oslo/805/99 | 717 | 1999 |
| AJ489301 | B/Oslo/837/99 | 719 | 1999 |
| ISDN13390 | B/PERTH/1/99 | 1025 | 1999 |
| AF521218 | B/Pusan/250/99 | 1135 | 1999 |
| AF521226 | B/Pusan/255/99 | 1132 | 1999 |
| AF521219 | B/Pusan/270/99 | 1135 | 1999 |
| AF521217 | B/Pusan/285/99 | 1135 | 1999 |
| AJ419591 | B/Quebec/74199/99 | 1038 | 1999 |
| AJ419592 | B/Quebec/74204/99 | 1038 | 1999 |
| AJ419593 | B/Quebec/74206/99 | 1038 | 1999 |
| AB036863 | B/Saga/S172/99 | 1038 | 1999 |
| AF299385 | B/Shenzhen/423/99 | 1038 | 1999 |
| AJ784040 | B/Sichuan/379/99 | 1030 | 1999 |
| ISDN13428 | B/SICHUAN/379/99 | 1087 | 1999 |
| ISDN13281 | B/Sichuan/379/99 | 1038 | 1999 |
| AF319590 | B/Sichuan/379/99) | 1038 | 1999 |
| ISDN13397 | B/SOUTH AUSTRALIA/12/99 | 1046 | 1999 |
| ISDN13394 | B/SOUTH | 1000 | 1999 |
| AY129962 | B/South Carolina/25723/99 | 978 | 1999 |
| ISDN13389 | B/SYDNEY/203/99 | 1025 | 1999 |
| AF363979 | B/Taiwan/1243/99 | 559 | 1999 |
| AY604740 | B/Taiwan/1243/99 | 394 | 1999 |
| AY604741 | B/Taiwan/2026/99 | 394 | 1999 |
| AF148886 | B/Taiwan/2026/99 | 559 | 1999 |
| AF148887 | B/Taiwan/2027/99 | 559 | 1999 |
| AY604742 | B/Taiwan/2027/99 | 394 | 1999 |
| AY604743 | B/Taiwan/2195/99 | 394 | 1999 |
| AF148888 | B/Taiwan/2195/99 | 559 | 1999 |
| ISDNAU1002 | B/TEHRAN/102/99 | 1032 | 1999 |
| ISDN13387 | B/TOWNSVILLE/1/99 | 1041 | 1999 |
| AY096191 | B/United Kingdom/34304/99 | 978 | 1999 |
| AY096192 | B/United Kingdom/34520/99 | 978 | 1999 |
| AF534009 | B/Ushuaia/15732/99 | 1035 | 1999 |
| AY096184 | B/Utah/20975/99 | 978 | 1999 |
| ISDN13393 | B/VICTORIA/501/99 | 1000 | 1999 |
| AF387492 | B/Vienna/1/99 | 1882 | 1999 |
| AF387493 | B/Vienna/1/99 | 1882 | 1999 |
| AF387495 | B/Vienna/1/99 | 1882 | 1999 |
| AF387494 | B/Vienna/1/99 | 1882 | 1999 |
| ISDNCHB018 | B/Vienna/1/99(Verol and MDCK2 and Direct PCR isolate) | 1882 | 1999 |
| ISDN13382 | B/WAIKATO/2/99 | 1032 | 1999 |
| ISDN13383 | B/WELLINGTON/1/99 | 1032 | 1999 |
| AB027403 | B/Aichi/3/98 | 1041 | 1998 |
| AB027404 | B/Aichi/5/98 | 1041 | 1998 |
| AB027405 | B/Aichi/8/98 | 1038 | 1998 |
| AY687397 | B/Beijing/76/98 | 1759 | 1998 |
| AF100348 | B/Chiba/447/98 | 1041 | 1998 |
| AY223900 | B/Durban/39/98 | 955 | 1998 |
| AY223876 | B/Durban/43/98 | 955 | 1998 |
| AY223877 | B/Durban/44/98 | 955 | 1998 |
| AY223878 | B/Durban/52/98 | 955 | 1998 |
| AY223879 | B/Durban/55/98 | 955 | 1998 |
| AY223880 | B/Durban/56/98 | 955 | 1998 |
| AF100350 | B/Nagano/2038/98 | 1038 | 1998 |
| AY581961 | B/Nanchang/12/98 | 1755 | 1998 |
| AY581959 | B/Nanchang/6/98 | 1758 | 1998 |
| AY581960 | B/Nanchang/7/98 | 1755 | 1998 |
| AF217216 | B/Netherlands/429/98 | 1090 | 1998 |
| AJ419583 | B/Quebec/162/98 | 1038 | 1998 |
| AJ419589 | B/Quebec/173/98 | 1038 | 1998 |
| AJ419586 | B/Quebec/452/98 | 1038 | 1998 |
| AJ419584 | B/Quebec/453/98 | 1038 | 1998 |
| AJ419590 | B/Quebec/465/98 | 1038 | 1998 |
| AJ419587 | B/Quebec/51/98 | 1038 | 1998 |
| AJ419582 | B/Quebec/511/98 | 1038 | 1998 |
| AJ419585 | B/Quebec/514/98 | 1038 | 1998 |
| AJ419588 | B/Quebec/517/98 | 1038 | 1998 |
| AF100353 | B/Shiga/44/98 | 1041 | 1998 |
| AF100352 | B/Shiga/51/98 | 1041 | 1998 |
| AB029631 | B/Shiga/N18/98 | 1078 | 1998 |
| AF100351 | B/Shiga/T30/98 | 1038 | 1998 |
| AB029632 | B/Shiga/T37/98 | 1076 | 1998 |
| ISDN13400 | B/SINGAPORE/21/98 | 1055 | 1998 |
| ISDNAU1001 | B/Singapore/21/98 | 1055 | 1998 |
| ISDN13380 | B/SINGAPORE/27/98 | 1066 | 1998 |
| AB036859 | B/Tokyo/6/98 | 1038 | 1998 |
| ISDNYAM98 | B/Yamanashi/166/98 | 1041 | 1998 |
| AF100355 | B/Yamanashi/166/98 | 1038 | 1998 |
| AB027400 | B/Aichi/14/97 | 1086 | 1997 |
| AB027401 | B/Aichi/15/97 | 1086 | 1997 |
| AB027402 | B/Aichi/33/97 | 1086 | 1997 |
| AB027399 | B/Aichi/4/97 | 1083 | 1997 |
| AF100347 | B/Argentina/218/97 | 1038 | 1997 |
| AF050062 | B/Beijing/243/97 | 1086 | 1997 |
| AF534004 | B/Buenos Aires/SW16/97 | 1035 | 1997 |
| ISDNAU1000 | B/CANBERRA/5/97 | 1027 | 1997 |
| AF521221 | B/Daeku/10/97 | 1135 | 1997 |
| AF521236 | B/Daeku/45/97 | 1138 | 1997 |
| AF521237 | B/Daeku/47/97 | 1138 | 1997 |
| AF521220 | B/Daeku/9/97 | 1135 | 1997 |
| AF532533 | B/Guangzhou/7/97 | 1041 | 1997 |
| AF100349 | B/Henan/22/97 | 1041 | 1997 |
| AF100356 | B/Hiroshima/97/97 | 1038 | 1997 |
| AF129893 | B/Memphis/10/97 | 1775 | 1997 |
| AY260945 | B/Memphis/12/97 | 1808 | 1997 |
| AY260952 | B/Memphis/12/97 | 1837 | 1997 |
| AF129894 | B/Memphis/12/97 | 1775 | 1997 |
| AY581958 | B/Nanchang/15/97 | 1758 | 1997 |
| AY581956 | B/Nanchang/2/97 | 1758 | 1997 |
| AY581957 | B/Nanchang/4/97 | 1758 | 1997 |
| AF134915 | B/Nanchang/5/97 | 550 | 1997 |
| AF100354 | B/Nara/4/97 | 1041 | 1997 |
| AF217215 | B/Netherlands/1/97 | 1090 | 1997 |
| AB126834 | B/Osaka/1036/97 | 1008 | 1997 |
| AB029617 | B/Osaka/1036/97 | 1043 | 1997 |
| AB029618 | B/Osaka/1058/97 | 1083 | 1997 |
| AB029619 | B/Osaka/1059/97 | 1061 | 1997 |
| AB029620 | B/Osaka/1146/97 | 1056 | 1997 |
| AB033826 | B/Osaka/1169/97 | 1060 | 1997 |
| AF050066 | B/Osaka/491/97 | 1086 | 1997 |
| AY139036 | B/Osaka/547/97 | 1041 | 1997 |
| AB029621 | B/Osaka/710/97 | 1078 | 1997 |
| AB029622 | B/Osaka/711/97 | 1076 | 1997 |

TABLE 2-continued

INFLUENZA TYPE B HA SEQUENCES

| Accession | Strain | Length | Year |
|---|---|---|---|
| AB029623 | B/Osaka/728/97 | 1061 | 1997 |
| AB029624 | B/Osaka/755/97 | 1076 | 1997 |
| AB029625 | B/Osaka/820/97 | 1076 | 1997 |
| AB029626 | B/Osaka/837/97 | 1049 | 1997 |
| AB029627 | B/Osaka/854/97 | 1069 | 1997 |
| AB029628 | B/Osaka/983/97 | 1078 | 1997 |
| AB029629 | B/Osaka/983/97(Mutant M1) | 1071 | 1997 |
| AB029630 | B/Osaka/983/97(Mutant M2) | 1053 | 1997 |
| AB054679 | B/Osaka/983/97-V1 | 1042 | 1997 |
| AB054680 | B/Osaka/983/97-V2 | 1049 | 1997 |
| AB054681 | B/Osaka/983/97-V3 | 1045 | 1997 |
| AB054682 | B/Osaka/983/97-V4 | 1043 | 1997 |
| AB054683 | B/Osaka/983/97-V5 | 1069 | 1997 |
| AB054684 | B/Osaka/983/97-V6 | 1058 | 1997 |
| AB054685 | B/Osaka/983/97-V7 | 1056 | 1997 |
| AB054686 | B/Osaka/983/97-V8 | 1068 | 1997 |
| AF521233 | B/Seoul/16/97 | 1135 | 1997 |
| AF521231 | B/Seoul/19/97 | 1135 | 1997 |
| AF521234 | B/Seoul/28/97 | 1138 | 1997 |
| AF521232 | B/Seoul/31/97 | 1138 | 1997 |
| AJ784041 | B/Shandong/7/97 | 1052 | 1997 |
| AF486836 | B/Shangdong/7/97 | 1353 | 1997 |
| AF299384 | B/Shangdong/7/97 | 1041 | 1997 |
| ISDN13278 | B/Shangdong/7/97 | 1041 | 1997 |
| AF387505 | B/Switzerland/4291/97 | 1882 | 1997 |
| AF387504 | B/Switzerland/4291/97 | 1882 | 1997 |
| ISDNCHB036 | B/Switzerland/4291/97 (Vero2 and MDCK2 isolate) | 1882 | 1997 |
| AY139035 | B/Taiwan/217/97 | 1041 | 1997 |
| AF026162 | B/Taiwan/21706/97 | 562 | 1997 |
| AF026161 | B/Taiwan/3143/97 | 559 | 1997 |
| AF050060 | B/Alaska/12/96 | 1083 | 1996 |
| AF059978 | B/Beijing/84/96 | 1038 | 1996 |
| AF059946 | B/Brazil/241/96 | 1038 | 1996 |
| AF059913 | B/Florida/1/96 | 1035 | 1996 |
| AF059948 | B/Hawaii/1/96 | 1038 | 1996 |
| AF059976 | B/Hong Kong/65/96 | 1038 | 1996 |
| AF532556 | B/Hong Kong/70/96 | 1041 | 1996 |
| AF129904 | B/Houston/1/96 | 513 | 1996 |
| AY581953 | B/Houston/2/96 | 1755 | 1996 |
| AF131990 | B/Lyon/1271/96 | 1056 | 1996 |
| AF131991 | B/Lyon/1271/96 | 1056 | 1996 |
| AF131992 | B/Lyon/1271/96 | 1056 | 1996 |
| AF129905 | B/Memphis/19/96 | 516 | 1996 |
| AF129892 | B/Memphis/20/96 | 1375 | 1996 |
| AY581954 | B/Memphis/21/96 | 1755 | 1996 |
| AY581955 | B/Nanchang/20/96 | 1755 | 1996 |
| AF134914 | B/Nanchang/6/96 | 552 | 1996 |
| AF129906 | B/Nashville/3/96 | 552 | 1996 |
| AF059951 | B/New York/7/96 | 1038 | 1996 |
| AF059955 | B/Ohio/10/96 | 1038 | 1996 |
| AF059953 | B/Pennsylvania/1/96 | 1038 | 1996 |
| AF059959 | B/Romania/48/96 | 1038 | 1996 |
| AF059977 | B/Sapporo/1/96 | 1038 | 1996 |
| AF059982 | B/Sichuan/16/96 | 1038 | 1996 |
| AY139033 | B/Sichuan/281/96 | 1041 | 1996 |
| AF059944 | B/Taiwan/207/96 | 1038 | 1996 |
| AF059979 | B/Texas/10/96 | 1038 | 1996 |
| AF059950 | B/Texas/19/96 | 1038 | 1996 |
| AF059949 | B/Texas/30/96 | 1038 | 1996 |
| AF059947 | B/Texas/34/96 | 1038 | 1996 |
| AF050067 | B/Tokyo/942/96 | 1081 | 1996 |
| AF059954 | B/Wellington/1/96 | 1038 | 1996 |
| AB027398 | B/Aichi/10/95 | 1083 | 1995 |
| AF059945 | B/Alaska/19/95 | 1038 | 1995 |
| AF059994 | B/Argentina/4105/95 | 1038 | 1995 |
| AF059960 | B/Beijing/33/95 | 1038 | 1995 |
| AF534003 | B/Buenos Aires/9/95 | 1035 | 1995 |
| AF059997 | B/California/1/95 | 1038 | 1995 |
| AF059961 | B/California/2/95 | 1038 | 1995 |
| AF059912 | B/Connecticut/2/95 | 1035 | 1995 |
| AF299383 | B/Hebei/4/95 | 1038 | 1995 |
| AF059984 | B/Hong Kong/15/95 | 1038 | 1995 |
| AF059980 | B/Hong Kong/19/95 | 1038 | 1995 |
| AF059940 | B/Illinois/1/95 | 1038 | 1995 |
| AF059942 | B/Indiana/1/95 | 1038 | 1995 |
| AF129891 | B/Memphis/18/95 | 1132 | 1995 |
| AF059999 | B/Montana/1/95 | 1038 | 1995 |
| AY581952 | B/Nanchang/15/95 | 1755 | 1995 |
| AY581951 | B/Nanchang/3/95 | 1758 | 1995 |
| AF134913 | B/Nanchang/8/95 | 557 | 1995 |
| AF059968 | B/Nebraska/1/95 | 1038 | 1995 |
| AF217217 | B/Netherlands/2/95 | 1090 | 1995 |
| AF217221 | B/Netherlands/31/95 | 1087 | 1995 |
| AF217218 | B/Netherlands/384/95 | 1090 | 1995 |
| AF060004 | B/New Mexico/1/95 | 1038 | 1995 |
| AF059941 | B/North Carolina/1/95 | 1038 | 1995 |
| AF059935 | B/Paris/386/95 | 1035 | 1995 |
| AF059966 | B/Russia/193/95 | 1038 | 1995 |
| AF059967 | B/Russia/222/95 | 1038 | 1995 |
| AF521223 | B/seoul/12/95 | 1135 | 1995 |
| AF521225 | B/Seoul/13/95 | 1135 | 1995 |
| AF521222 | B/Seoul/17/95 | 1135 | 1995 |
| AF521224 | B/Seoul/21/95 | 1135 | 1995 |
| AF060005 | B/Shanghai/10/95 | 1038 | 1995 |
| AF059964 | B/Shiga/T13/95 | 1038 | 1995 |
| AF059956 | B/Taiwan/512/95 | 1038 | 1995 |
| AF059943 | B/Texas/12/95 | 1038 | 1995 |
| AF059952 | B/Thailand/154/95 | 1038 | 1995 |
| AF059969 | B/Tokushima/24/95 | 1038 | 1995 |
| AF059981 | B/Washington/13/95 | 1038 | 1995 |
| AF059957 | B/Wellington/9/95 | 1038 | 1995 |
| AF059983 | B/Wuhan/256/95 | 1038 | 1995 |
| AF059985 | B/Wuhan/299/95 | 1038 | 1995 |
| AB027397 | B/Aichi/1/94 | 1083 | 1994 |
| AF059962 | B/Alaska/3779/94 | 1038 | 1994 |
| AF059988 | B/Beijing/1/94 | 1038 | 1994 |
| AF059965 | B/Beijing/172/94 | 1038 | 1994 |
| AF059990 | B/Beijing/37/94 | 1038 | 1994 |
| AF059974 | B/California/1/94 | 1038 | 1994 |
| AF059995 | B/California/2/94 | 1038 | 1994 |
| AF059963 | B/Canada/9988/94 | 1038 | 1994 |
| AF050063 | B/Guandong/5/94 | 1086 | 1994 |
| AF060003 | B/Harbin/7/94 | 1038 | 1994 |
| AF050065 | B/Harbin/7/94 | 1083 | 1994 |
| D38649 | B/Hebei/19/94 | 1135 | 1994 |
| D38648 | B/Hebei/3/94 | 1135 | 1994 |
| AF059998 | B/India/156/94 | 1038 | 1994 |
| D38647 | B/Kagoshima/15/94 | 1138 | 1994 |
| D38646 | B/Kobe/1/94 | 1135 | 1994 |
| AF059920 | B/Mexico/3288/94 | 1035 | 1994 |
| AY581948 | B/Nanchang/195/94 | 1755 | 1994 |
| AF134912 | B/Nanchang/480/94 | 760 | 1994 |
| AY581949 | B/Nanchang/560/94 | 1758 | 1994 |
| AY581950 | B/Nanchang/630/94 | 1758 | 1994 |
| AF217222 | B/Netherlands/13/94 | 1140 | 1994 |
| AF217220 | B/Netherlands/32/94 | 1087 | 1994 |
| AF060000 | B/New York/1/94 | 1038 | 1994 |
| AF059909 | B/New York/2/94 | 1035 | 1994 |
| AF059932 | B/New York/3/94 | 1035 | 1994 |
| AF059910 | B/New York/4/94 | 1035 | 1994 |
| AF060002 | B/New York/6/94 | 1038 | 1994 |
| AF059930 | B/North Carolina/1/94 | 1035 | 1994 |
| AF059934 | B/Pennsylvania/1/94 | 1035 | 1994 |
| AF059973 | B/Shangdong/16/94 | 1038 | 1994 |
| AF059971 | B/Shanghai/2/94 | 1038 | 1994 |
| AF059972 | B/Shanghai/4/94 | 1038 | 1994 |
| AF059996 | B/Singapore/11/94 | 1038 | 1994 |
| AF059933 | B/South Carolina/1/94 | 1035 | 1994 |
| AF060006 | B/Taiwan/1197/94 | 1038 | 1994 |
| AF059970 | B/Texas/1/94 | 1038 | 1994 |
| AF059975 | B/Victoria/101/94 | 1038 | 1994 |
| AF060001 | B/Wellington/1/94 | 1038 | 1994 |
| AF059924 | B/West Virginia/1/94 | 1035 | 1994 |
| AF059923 | B/West Virginia/2/94 | 1035 | 1994 |
| AB027408 | B/Aichi/1/93 | 1083 | 1993 |
| AF059907 | B/Argentina/1/93 | 1035 | 1993 |
| AF059908 | B/Argentina/2/93 | 1035 | 1993 |
| AJ784043 | B/Beijing/184/93 | 1035 | 1993 |
| AF050061 | B/Beijing/184/93 | 1083 | 1993 |
| AF059993 | B/Beijing/184/93 | 1038 | 1993 |
| AF059992 | B/Beijing/19/93 | 1038 | 1993 |

TABLE 2-continued

INFLUENZA TYPE B HA SEQUENCES

| Accession | Strain | Length | Year |
|---|---|---|---|
| AF059989 | B/Beijing/237/93 | 1038 | 1993 |
| AF059958 | B/Beijing/24/93 | 1038 | 1993 |
| AF060007 | B/Beijing/258/93 | 1038 | 1993 |
| AF059911 | B/Connecticut/7/93 | 1035 | 1993 |
| L76318 | B/Finland/254/93 | 1035 | 1993 |
| L76319 | B/Finland/260/93 | 1035 | 1993 |
| L76320 | B/Finland/268/93 | 1035 | 1993 |
| AF050064 | B/Guandong/8/93 | 1086 | 1993 |
| AF129900 | B/Houston/2/93 | 550 | 1993 |
| AF059922 | B/Massachusetts/6/93 | 1035 | 1993 |
| AF129890 | B/Memphis/3/93 | 1105 | 1993 |
| AF129901 | B/Memphis/4/93 | 541 | 1993 |
| AF129902 | B/Memphis/5/93 | 546 | 1993 |
| D38643 | B/Mie/1/93 | 1135 | 1993 |
| AF059991 | B/Mie/1/93 | 1038 | 1993 |
| AF134911 | B/Nanchang/26/93 | 546 | 1993 |
| AF060009 | B/Nanchang/3451/93 | 1038 | 1993 |
| AF060008 | B/Nanchang/P26/93 | 1038 | 1993 |
| AF129903 | B/Nashville/107/93 | 544 | 1993 |
| AF059931 | B/New York/24/93 | 1035 | 1993 |
| AF059926 | B/Novgorod/110/93 | 1035 | 1993 |
| AF059927 | B/Oregon/1/93 | 1035 | 1993 |
| D38644 | B/Osaka/c19/93 | 1138 | 1993 |
| AF059916 | B/Tokushima/101/93 | 1035 | 1993 |
| D38645 | B/Tokushima/101/93 | 1135 | 1993 |
| AF059938 | B/Beijing/10/92 | 1035 | 1992 |
| AF059986 | B/Beijing/201/92 | 1038 | 1992 |
| AF059939 | B/Beijing/36/92 | 1035 | 1992 |
| AF059919 | B/California/5/92 | 1035 | 1992 |
| AY581947 | B/Guangzhou/86/92 | 1755 | 1992 |
| AF059917 | B/Hawaii/1/92 | 1035 | 1992 |
| AF129899 | B/Houston/1/92 | 549 | 1992 |
| AF059914 | B/Oita/14/92 | 1035 | 1992 |
| AF059915 | B/Oita/15/92 | 1035 | 1992 |
| AF129898 | B/Sichuan/8/92 | 529 | 1992 |
| AF059987 | B/Sichuan/8/92 | 1038 | 1992 |
| AF059918 | B/Washington/2/92 | 1035 | 1992 |
| AF059925 | B/Washington/3/92 | 1035 | 1992 |
| AB027396 | B/Aichi/1/91 | 1080 | 1991 |
| AF059921 | B/Cordoba/2979/91 | 1035 | 1991 |
| L76315 | B/Finland/162/91 | 1035 | 1991 |
| L76316 | B/Finland/172/91 | 1035 | 1991 |
| L76317 | B/Finland/184/91 | 1035 | 1991 |
| AF059936 | B/Guangdong/4/91 | 1035 | 1991 |
| AF129896 | B/Houston/1/91 | 1008 | 1991 |
| L76322 | B/Khazkov/224/91 | 1035 | 1991 |
| L76324 | B/Leningrad/129/91 | 1035 | 1991 |
| L76325 | B/Leningrad/148/91 | 1035 | 1991 |
| AY581946 | B/Nashville/45/91 | 1752 | 1991 |
| AF129897 | B/Nashville/48/91 | 500 | 1991 |
| AF059928 | B/New York/39/91 | 1035 | 1991 |
| AF059937 | B/Qingdao/102/91 | 1035 | 1991 |
| AF521229 | B/Seoul/37/91 | 1135 | 1991 |
| AF521227 | B/Seoul/38/91 | 1135 | 1991 |
| AF521235 | B/Seoul/40/91 | 1135 | 1991 |
| AF521228 | B/Seoul/41/91 | 1135 | 1991 |
| AF059929 | B/Singapore/4/91 | 1035 | 1991 |
| M65174 | B/Texas/1/91 | 1080 | 1991 |
| M76984 | B/USSR/Novogorod/21/91 | 1086 | 1991 |
| AB027395 | B/Aichi/5/90 | 1080 | 1990 |
| M65165 | B/Bangkok/163/90 | 1080 | 1990 |
| L76314 | B/Czechoslovakia/69/90 | 1041 | 1990 |
| L19643 | B/Finland/145/90 | 1041 | 1990 |
| L19644 | B/Finland/147/90 | 1041 | 1990 |
| L19645 | B/Finland/149/90 | 1041 | 1990 |
| L19642 | B/Finland/150/90 | 1041 | 1990 |
| L19641 | B/Finland/151/90 | 1041 | 1990 |
| L76321 | B/Hannover/2/90 | 1041 | 1990 |
| L76323 | B/Lissabon/2/90 | 1041 | 1990 |
| L76326 | B/Minsk/318/90 | 1041 | 1990 |
| M76983 | B/Moscow/2/90 | 1080 | 1990 |
| L76327 | B/Netherland/2781/90 | 1041 | 1990 |
| L76328 | B/Netherland/6357/90 | 1041 | 1990 |
| L76329 | B/Netherland/800/90 | 1035 | 1990 |
| L76330 | B/Netherland/801/90 | 1035 | 1990 |
| M65170 | B/New York/3/90 | 1080 | 1990 |
| X73421 | B/NIB/48/90 | 1043 | 1990 |
| AY581945 | B/Panama/45/90 | 1752 | 1990 |
| M65171 | B/Panama/45/90 | 1080 | 1990 |
| M65173 | B/Paris/329/90 | 1086 | 1990 |
| L76331 | B/Stockholm/10/90 | 1041 | 1990 |
| L76332 | B/Switzerland/5219/90 | 1035 | 1990 |
| L76333 | B/Switzerland/5241/90 | 1041 | 1990 |
| L76334 | B/Switzerland/5441/90 | 1041 | 1990 |
| L76335 | B/Switzerland/5444/90 | 1041 | 1990 |
| L76336 | B/Switzerland/5812/90 | 1041 | 1990 |
| L76337 | B/Switzerland/6121/90 | 1041 | 1990 |
| M65175 | B/Texas/4/90 | 1080 | 1990 |
| L76313 | B/Czechoslovakia/16/89 | 1041 | 1989 |
| M65166 | B/Guangdong/55/89 | 1080 | 1989 |
| M65167 | B/Hong Kong/22/89 | 1080 | 1989 |
| M65169 | B/Hong Kong/9/89 | 1080 | 1989 |
| M65168 | B/India/3/89 | 1086 | 1989 |
| AF129889 | B/Memphis/3/89 | 1181 | 1989 |
| AF129895 | B/Nashville/6/89 | 550 | 1989 |
| AF217223 | B/Netherlands/580/89 | 1087 | 1989 |
| AF521230 | B/Seoul/1/89 | 1135 | 1989 |
| M65172 | B/SouthDakota/5/89 | 1080 | 1989 |
| M65176 | B/Victoria/103/89 | 1080 | 1989 |
| M65177 | B/Victoria/19/89 | 1086 | 1989 |
| M58424 | B/Aichi/5/88 | 1086 | 1988 |
| M58427 | B/Chengdu/54/88 | 1086 | 1988 |
| L19647 | B/Finland/56/88 | 1041 | 1988 |
| M58422 | B/Hong Kong/14/88 | 1080 | 1988 |
| X53060 | B/NIB/25/88 | 1145 | 1988 |
| M58426 | B/Ohio/10/88 | 1086 | 1988 |
| AF521239 | B/Seoul/12/88 | 1138 | 1988 |
| AF521238 | B/Seoul/6/88 | 1135 | 1988 |
| M58423 | B/Singapore/7/88 | 1080 | 1988 |
| M58421 | B/Taiwan/7/88 | 1080 | 1988 |
| M58425 | B/Texas/37/88 | 1086 | 1988 |
| M58419 | B/Yamagata/16/88 | 1080 | 1988 |
| M36105 | B/Yamagata/16/88 | 1035 | 1988 |
| AJ249279 | B/Beijing/1/87 | 1753 | 1987 |
| X53098 | B/Beijing/1/87 | 1884 | 1987 |
| M58418 | B/Beijing/1/87 | 1086 | 1987 |
| M36108 | B/Nagasaki/1/87 | 1041 | 1987 |
| M58420 | B/Shanghai/12/87 | 1080 | 1987 |
| M58413 | B/USSR/2/87 | 1086 | 1987 |
| M58428 | B/Victoria/2/87 | 1824 | 1987 |
| M22943 | B/Victoria/2/87 | 1094 | 1987 |
| DQ508913 | B/Ann Arbor/1/1986 | 1758 | 1986 |
| U70385 | B/Ann Arbor/1/86 | 1737 | 1986 |
| M21874 | B/Ann Arbor/1/86 | 1059 | 1986 |
| M22944 | B/Georgia/1/86 | 1100 | 1986 |
| M22945 | B/Idaho/1/86 | 1100 | 1986 |
| X13551 | B/Memphis/6/86 | 1831 | 1986 |
| U70384 | B/Canada/3/85 | 1737 | 1985 |
| L19646 | B/Finland/24/85 | 1041 | 1985 |
| M36107 | B/Ibaraki/2/85 | 1041 | 1985 |
| X13553 | B/Victoria/3/85 | 1831 | 1985 |
| AB027495 | B/Aichi/1/84 | 1080 | 1984 |
| AF299381 | B/Beijing/15/84 | 1035 | 1984 |
| AB027394 | B/Houston/18513/84 | 1035 | 1984 |
| AF101071 | B/Norway/1/84 | 1035 | 1984 |
| AF299382 | B/Shanghai/35/84 | 1041 | 1984 |
| AF299380 | B/Ningxia/45/83 | 1041 | 1983 |
| M16254 | B/NorthDakota/83 | 96 | 1983 |
| X13552 | B/USSR/100/83 | 1825 | 1983 |
| AB027393 | B/Aichi/21/82 | 1080 | 1982 |
| AB027407 | B/Aichi/4181/82 | 1035 | 1982 |
| X17222 | B/ENG/222/82 | 1830 | 1982 |
| M18384 | B/England/222/82 | 1851 | 1982 |
| AF299377 | B/Fujian/36/82 | 1035 | 1982 |
| AF299378 | B/Xuanwu/1/82 | 1035 | 1982 |
| AF299379 | B/Xuanwu/23/82 | 1041 | 1982 |
| AB027392 | B/Aichi/70/81 | 1080 | 1981 |
| M36106 | B/Fukuoka/80/81 | 1035 | 1981 |
| K02713 | B/Oregon/5/80 | 1878 | 1980 |
| AF299376 | B/Shanghai/10/80 | 1041 | 1980 |
| X00897 | B/Singapore/222/79 | 1878 | 1979 |
| AB027391 | B/Baylor/4/78 | 1035 | 1978 |

TABLE 2-continued

INFLUENZA TYPE B HA SEQUENCES

| Accession | Strain | Length | Year |
|---|---|---|---|
| AF299375 | B/Du/4/78 | 1041 | 1978 |
| AF299374 | B/Shanghai/1/77 | 1038 | 1977 |
| AB027390 | B/Aichi/7/76 | 1035 | 1976 |
| AF299372 | B/Beijing/5/76 | 1035 | 1976 |
| AF101070 | B/Kanagawa/3/76 | 1035 | 1976 |
| AF299373 | B/Shanghai/24/76 | 1035 | 1976 |
| AF299371 | B/Beijing/43/75 | 1035 | 1975 |
| AF101068 | B/Gifu/73 | 1032 | 1973 |
| AF101069 | B/Guma/73 | 1032 | 1973 |
| M10298 | B/Hong Kong/8/73 | 1783 | 1973 |
| K00425 | B/Hong Kong/8/73 | 1875 | 1973 |
| AB027389 | B/Yamagata/1/73 | 1032 | 1973 |
| DQ508921 | B/Hong Kong/05/1972 | 1749 | 1972 |
| AF299369 | B/Hong Kong/5/72 | 1032 | 1972 |
| AF305219 | B/Hong Kong/5/72 | 384 | 1972 |
| AF299370 | B/Hunan/4/72 | 1032 | 1972 |
| AF101067 | B/Osaka/70 | 1035 | 1970 |
| AB027388 | B/Victoria/70 | 1038 | 1970 |
| AB027387 | B/Russia/69 | 1038 | 1969 |
| ISDNCHB028 | B/Russia/69 (egg isolate) | 1882 | 1969 |
| AF101066 | B/Bangkok/64 | 1038 | 1964 |
| M22946 | B/Singapore/64 | 1097 | 1964 |
| AB027386 | B/Thailand/62 | 1032 | 1962 |
| K00424 | B/Maryland/59 | 1882 | 1959 |
| M22947 | B/GreatLakes/54 | 1091 | 1954 |
| X13550 | B/Bonn/43 | 1822 | 1943 |
| J02093 | B/Lee/40 | 1882 | 1940 |
| NC_002207 | B/Lee/40 | 1882 | 1940 |

TABLE 3

DR binding results of candidate Influenza peptides

| Sequence | SEQ ID NO | Source | Strain | Strain Conservancy | DRB1 *0101 | DRB1 *0301 | DRB1 *0401 | DRB1 *0404 | DRB1 *0405 | DRB1 *0701 | DRB1 *0802 | DRB1 *1101 | DRB1 *1302 | DRB1 *1501 | DRB4 *0101 | DRB5 *0101 | No. of HLA-DR alleles IC50 < 1000 nM |
|---|---|---|---|---|---|---|---|---|---|---|---|---|---|---|---|---|---|
| MEKIVLLFAIVSLVKSD | 16 | Flu.HA.1 | H5N1 | | 285 | | 712 | | | | | | 848 | 176 | 2660 | | 4 |
| VSLVKSDQICIGYHA | 17 | Flu.HA.11 | H5N1 | | — | 511 | 513 | | | | | | 175 | 14,472 | 32 | | 4 |
| KSSFPRNVVWLIKKN | 18 | Flu.HA.156 | H5N1 | | 46 | | 474 | | | | | | 20 | 832 | — | | 4 |
| VVWLIKKNSTYPTIKR | 19 | Flu.HA.163 | H5N1 | | 464 | | 289 | | | | | | 14 | 99 | 1665 | | 4 |
| QTKLYQNPTTYISVGT | 20 | Flu.HA.203 | H5N1 | | 3766 | | 139 | | | | | | 18 | 60 | 1666 | | 3 |
| PTTYISVGTSTLNQRL | 21 | Flu.HA.210 | H5N1 | | 190 | | 59 | | | | | | 957 | 1724 | 522 | | 4 |
| RMEFFWTILKPNDAI | 22 | Flu.HA.241 | H5N1 | | 62 | | 259 | | | | | | 644 | 10,283 | 9680 | | 3 |
| WTILKPNDAINFESN | 23 | Flu.HA.246 | H5N1 | | 131 | | 1583 | | | | | | 31 | 4982 | 3337 | | 2 |
| CPKYVKSNRLVLATGL | 24 | Flu.HA.318 | H5N1 | | 2758 | 2919 | 868 | | | | | | 48 | 230 | 287 | | 4 |
| NRLVLATGLRNSPQR | 25 | Flu.HA.325 | H5N1 | | 69 | | 645 | | | | | | 4173 | 386 | 735 | | 4 |
| ELLVLMENERTLDFHDS | 26 | Flu.HA.443 | H5N1 | | 567 | 636 | 499 | | | | | | 919 | 264 | 241 | | 6 |
| LLVLMENERTLDFHD | 27 | Flu.HA.444 | H5N1 | 11/11 | | 64 | | | | | | | | | | | 1 |
| ISGVKLESIGIYQILSI | 28 | Flu.HA.519 | H5N1 | | 406 | — | 3110 | | | | | | 408 | 9.2 | 16 | | 4 |
| IYQILSIYSTVASSLA | 29 | Flu.HA.529 | H5N1 | | 55 | | 89 | | | | | | 13 | 4.7 | 18 | | 5 |
| ILSIYSTVASSLALAI | 30 | Flu.HA.532 | H5N1 | | 11 | | 91 | | | | | | 7.6 | 20 | 824 | | 5 |
| SGPLKAEIAQRLEDV | 31 | Flu.M1.20 | H5N1 | | 6.8 | 170 | 1976 | | | | | | 32 | | | | 3 |
| EALMEWLKTRPILSP | 32 | Flu.M1.43 | H5N1 | 14/16 | 9.5 | | 891 | | | | | | 380 | 18 | 5513 | | 4 |
| MEWLKTRPILSPLTK | 33 | Flu.M1.46 | H5N1 | 16/17 | 52 | | 528 | | | | | | 3875 | 111 | 7944 | | 3 |
| TRPILSPLTKGILGF | 34 | Flu.M1.51 | H5N1 | 15/17 | 423 | | — | | | | | | 292 | 140 | 192 | | 4 |
| KGILGFVFTLTVPSE | 35 | Flu.M1.60 | H5N1 | 16/17 | 28 | | 5.6 | | | | | | 10 | 129 | 767 | | 5 |
| YRKLKREITFHGAKE | 36 | Flu.M1.103 | H5N1 | 10/17 | 67 | | 21 | | | | | | — | 253 | 79 | | 4 |

TABLE 3-continued

DR binding results of candidate Influenza peptides

| Sequence | SEQ ID NO | Source | Strain | Strain Conservancy | IC$_{50}$ nM to purified HLA DRB1 *0101 | DRB1 *0301 | DRB1 *0401 | DRB1 *0404 | DRB1 *0405 | DRB1 *0701 | DRB1 *0802 | DRB1 *1101 | DRB1 *1302 | DRB1 *1501 | DRB4 *0101 | DRB5 *0101 | No. of HLA-DR alleles IC50 < 1000 nM |
|---|---|---|---|---|---|---|---|---|---|---|---|---|---|---|---|---|---|
| MGTVTTEVALGLVCA | 37 | Flu.M1.138 | | | 58 | 348 | 321 | 355 | 10,093 | 924 | | 11,317 | 769 | 142 | 1589 | 7609 | 7 |
| CEQIADSQHRSHRQM | 38 | Flu.M1.154 | H2N2 | | — | 804 | — | — | — | | | | — | | | | 1 |
| NPLIRHENRMVLAST | 39 | Flu.M1.173 | | | 17 | 40 | 779 | 31 | 1588 | 298 | | 32 | 6.1 | 2.8 | 690 | 3691 | 9 |
| AMEVASQARQMVQAM | 40 | Flu.M1.205 | | | 641 | 833 | 4252 | 1561 | 263 | 424 | | 1406 | 185 | 310 | 759 | 786 | 8 |
| SAGLKDDLIENLQAY | 41 | Flu.M1.229 | | | 10,693 | 64 | 8653 | 976 | — | 1640 | | — | 7041 | 769 | — | — | 3 |
| DPLVVAASIIGILHL | 42 | Flu.M2.27 | | 8/15 | 113 | | 127 | | | | | | 1532 | 2345 | 169 | | 3 |
| PESMREEYRKEQQSA | 43 | Flu.M2.72 | H2N2 | | | 1108 | | | | | | | | | | | 0 |
| SLMLQIGNMISIWVSHS | 44 | Flu.NA.21 | H5N1 | | 36 | | 480 | | | | | | 44 | 34 | 746 | | 5 |
| IGNMISIWVSHSIHTG | 45 | Flu.NA.26 | H5N1 | | 1047 | | 925 | | | | | | 5950 | 81 | 817 | | 3 |
| NTNFLTEKAVASVKLA | 46 | Flu.NA.51 | H5N1 | | 106 | 12,325 | 1193 | | | | | | 125 | 47 | 2060 | | 3 |
| WAVYSKDNSIRIGSK | 47 | Flu.NA.77 | H5N1 | | 5397 | 291 | 1599 | | | | | | 36 | 642 | 19,463 | | 3 |
| GDVFVIREPFISCSHL | 48 | Flu.NA.92 | H5N1 | | 656 | | 3922 | | | | | | 9846 | 119 | 165 | | 3 |
| RTFFLTQGALLNDKHS | 49 | Flu.NA.110 | H5N1 | | 16 | | 251 | | | | | | 3205 | 790 | 2323 | | 3 |
| TQGALLNDKHSNGTVKD | 50 | Flu.NA.115 | H5N1 | | — | 177 | 18,966 | | | | | | 468 | 822 | — | | 3 |
| NGTVKDRSPHRTLMS | 51 | Flu.NA.126 | H5N1 | | 581 | | 17,939 | | | | | | 7932 | 267 | 8876 | | 2 |
| VAVLKYNGIITDTIKSW | 52 | Flu.NA.183 | H5N1 | | 3393 | | 319 | | | | | | 169 | 19 | 289 | | 4 |
| YNGIITDTIKSWRNNI | 53 | Flu.NA.188 | H5N1 | | 1723 | 515 | 1569 | | | | | | 370 | 31 | 476 | | 4 |
| NNILRTQESECACVN | 54 | Flu.NA.201 | H5N1 | | 147 | | 291 | | | | | | 558 | 1746 | 323 | | 4 |
| HKIFKMEKGKVVKSVEL | 55 | Flu.NA.233 | H5N1 | | 64 | 4531 | 555 | | | | | | 1406 | 119 | 269 | | 4 |
| VKSVELDAPNYHYEE | 56 | Flu.NA.244 | H5N1 | | — | 65 | 487 | | | | | | 197 | — | 1561 | | 3 |
| NLEYQIGYICSGVFG | 57 | Flu.NA.289 | H5N1 | | 1130 | | 975 | | | | | | 41 | 13 | 354 | | 4 |
| IGRFYIQMCTELKLS | 58 | Flu.NP.39 | | 9/11 | 64 | | 175 | | | | | | — | 246 | 985 | | 4 |

TABLE 3-continued

DR binding results of candidate Influenza peptides

| Sequence | SEQ ID NO | Source strain | Strain Con-ser-vancy | DRB1 *0101 | DRB1 *0301 | DRB1 *0401 | DRB1 *0404 | DRB1 *0405 | DRB1 *0701 | DRB1 *0802 | DRB1 *1101 | DRB1 *1302 | DRB1 *1501 | DRB4 *0101 | DRB5 *0101 | No. of HLA-DR alleles IC50 < 1000 nM |
|---|---|---|---|---|---|---|---|---|---|---|---|---|---|---|---|---|
| YIQMCTELKLSDYEG | 59 Flu.NP.43 | | | 320 | 368 | 392 | 1640 | 2694 | 5370 | | 5842 | 15,372 | 594 | — | 80 | 5 |
| EGRLIQNSITIERMV | 60 Flu.NP.56 | | 7/11 | 452 | 298 | 782 | | | | | | 55 | 3075 | 15 | | 4 |
| QNSITIERMVLSAFD | 61 Flu.NP.61 | | 7/11 | 891 | 298 | 517 | 411 | 5839 | 806 | | 4231 | 839 | 1201 | 39 | — | 7 |
| VLSAPDERRNRYLEE | 62 Flu.NP.70 | H5N1 | | 17,598 | 768 | 8451 | — | — | | | | — | | | | 1 |
| RELILYDKEEIRRIW | 63 Flu.NP.109 | H5N1 | | 10,705 | 59 | — | 1798 | — | | | | 7943 | | | | 1 |
| LILYDKEEIRRIWRQ | 64 Flu.NP.111 | H5N1 | | 7181 | 22 | 12,414 | 262 | 7501 | | | | 3102 | | | | 2 |
| VGTMVMELIRMIKRG | 65 Flu.NP.189 | | | 22 | 16 | 1092 | 13 | 1997 | 495 | | 32 | 256 | 738 | 10 | 25 | 9 |
| QKAMMDQVRESRNPG | 66 Flu.NP.238 | H5N1 | | 17,577 | 450 | 856 | 1826 | 13,072 | | | | 10,540 | | | | 2 |
| DLIFLARSALILRGS | 67 Flu.NP.258 | | 11/11 | 25 | | 365 | | | | | | 14 | 17 | 3293 | | 4 |
| LIFLARSALILRGSV | 68 Flu.NP.259 | | 11/11 | 8.8 | | 1449 | | | | | | 17 | 23 | 747 | | 4 |
| RSALILRGSVAHKSC | 69 Flu.NP.264 | | 11/11 | 30 | | 304 | | | | | | 252 | 227 | 850 | | 5 |
| KSQLVWMACHSAAFE | 70 Flu.NP.328 | | 9/11 | 122 | | 479 | | | | | | 5109 | 479 | 142 | | 4 |
| AGQISVQPTFSVQRN | 71 Flu.NP.406 | | 9/12 | 18 | | 48 | | | | | | 30 | 9.4 | 44 | | 5 |
| GSYFFGDNAEEYDN | 72 Flu.NP.488 | H5N1 | | — | 139 | 1947 | — | 65 | | | | — | | | | 2 |
| LDRLRRDQKSLRGRG | 73 Flu.NS1.36 | H5N1 | | 800 | 83 | 2532 | 925 | 7513 | | | | 1477 | | | | 3 |
| VERILKEESDEALKM | 74 Flu.NS1.68 | H2N2 | | 1045 | | 679 | 572 | — | | | | 5065 | | | | 2 |
| ASRYLTDMTIEEMSR | 75 Flu.NS1.89 | H2N2 | | 5189 | 356 | 67 | 522 | 5214 | | | | — | | | | 3 |
| LTDMTIEEMSRDWFM | 76 Flu.NS1.93 | H2N2 | | 6035 | 649 | — | 10,092 | 8793 | | | | — | | | | 1 |
| LEEMSRDWLMLIPKQ | 77 Flu.NS1.98 | H5N1 | | — | 170 | 10,940 | 5987 | 1717 | | | | 301 | | | | 2 |
| SLCIRMDQAIMDKDI | 78 Flu.NS1.117 | | | 5413 | 58 | 701 | 217 | 82 | 5552 | | 16,837 | 53 | 2357 | 153 | 8320 | 7 |
| QAIMDKDIILKANFS | 79 Flu.NS1.124 | H5N1 | | 265 | 131 | 2231 | 310 | 2948 | | | | 846 | | | | 3 |
| NFSVIFDRLETLILL | 80 Flu.NS1.136 | | | 2279 | 892 | 943 | 579 | 515 | 604 | | 8778 | 415 | 6935 | 4064 | 15,214 | 7 |

TABLE 3-continued

DR binding results of candidate Influenza peptides

| Sequence | SEQ ID NO | Source | Strain Con-ser-vancy | DRB1 *0101 | DRB1 *0301 | DRB1 *0401 | DRB1 *0404 | DRB1 *0405 | DRB1 *0701 | DRB1 *0802 |

TABLE 3-continued

DR binding results of candidate Influenza peptides

| Sequence | SEQ ID NO | Source | strain | Strain Conser-vancy | DRB1 *0101 | DRB1 *0301 | DRB1 *0401 | DRB1 *0404 | DRB1 *0405 | DRB1 *0701 | DRB1 *0802 | DRB TABLE 3-continued DR binding results of candidate Influenza peptides

| Sequence | SEQ ID NO | Source | Strain Conservancy | DRB1 *0101 | DRB1 *0301 | DRB1 *0401 | DRB1 *0404 | DRB1 *0405 | DRB1 *0701 | DRB1 *0802 | DR TABLE 3-continued DR binding results of candidate Influenza peptides IC₅₀ nM to purified HLA

| Sequence | SEQ ID NO | Source strain | Strain Conservancy | DRB1*0101 | DRB1*0301 | DRB1*0401 | DRB1*0404 | DRB1*0405 | DRB1*0701 | DRB1*0802 | DRB1*1101 | DRB1*1302 | DRB1*1501 | DRB4*0101 | DRB5*0101 | No. of HLA-DR alleles IC50<1000 nM |
|---|---|---|---|---|---|---|---|---|---|---|---|---|---|---|---|---|
| LRNLMS1SRTREILT | 147 | Flu.PB2.10 H2N2 | | 613 | 978 | 4972 | 170 | 9689 | — | — | — | 5.4 | — | — | — | 4 |
| KWMMAMKYPITADKR | 148 | Flu.PB2.51 | 14/14 | 415 | 5884 | — | 182 | 8335 | 114 | 13 | 19 | 6773 | 198 | 1257 | 101 | 7 |
| KYPITADKRIMEMIP | 149 | Flu.PB2.57 H5N1 | 13/14 | — | 48 | 9393 | 2288 | — | — | — | — | 68 | — | — | — | 2 |
| DRVMVSPLAVTWWNR | 150 | Flu.PB2.90 | | 93 | — | 7017 | 407 | 16,005 | 6169 | 3555 | 3148 | 833 | 2353 | 384 | 8887 | 4 |
| PVHFRNQVKIRRRVD | 151 | Flu.PB2.135 H5N1 | 14/14 | 2969 | 458 | 1296 | 5976 | 6039 | — | — | — | 359 | — | — | — | 2 |
| DVIMEVFPNEVGAR | 152 | Flu.PB2.164 | 14/14 | 1912 | 18,877 | 1099 | 441 | 19,230 | 3606 | — | — | 608 | 856 | 1591 | — | 3 |
| GARILTSESQLTITK | 153 | Flu.PB2.176 | 10/14 | 46 | 967 | 103 | 65 | 5479 | 376 | — | 4800 | 19 | 19 | 1181 | 7735 | 7 |
| ARILTSESQLTITKE | 154 | Flu.PB2.177 | | 51 | 139 | 182 | 92 | 1221 | 297 | — | 5247 | 34 | 94 | 1146 | 1462 | 7 |
| QLTITKEKKEELQDC | 155 | Flu.PB2.185 H2N2 | | — | 298 | — | 14,872 | — | — | — | — | 11,111 | — | — | — | 1 |
| MVAYMLERELVRKTR | 156 | Flu.PB2.205 H5N1 | | 97 | 878 | 166 | 499 | 5538 | — | — | — | 2082 | — | — | — | 4 |
| GGEVNDDVDQSLII | 157 | Flu.PB2.250 H5N1 | | — | 347 | 2164 | 458 | — | — | — | — | 2498 | — | — | — | 2 |
| KAAMGLRISSSFSFG | 158 | Flu.PB2.315 | 10/14 | 37 | 501 | 47 | 4.2 | 452 | 3.9 | 466 | 398 | 2.5 | 1.1 | 79 | 45 | 12 |
| LIQLIVSGRDEQSIA | 159 | Flu.PB2.384 | | 3225 | 53 | 83 | 90 | 460 | — | — | 2012 | 4680 | 420 | 9.9 | 1720 | 6 |
| AMVFSQEDCMIKAVR | 160 | Flu.PB2.404 H5N1 | | 11,048 | 718 | 3279 | 336 | 6780 | — | — | — | 9197 | — | — | — | 2 |
| IKAVRGDLNFVNRAN | 161 | Flu.PB2.414 | | 729 | 123 | 75 | 17 | 5101 | 8,077 | — | 1914 | 264 | 517 | 515 | 11,460 | 8 |
| LRHFQKDAKVLFQNW | 162 | Flu.PB2.438 | | 153 | 51 | 1431 | 1348 | 9917 | 578 | — | 318 | 240 | 207 | 979 | 1412 | 7 |
| MIGILPDMTPSTEMS | 163 | Flu.PB2.463 H5N1 | | — | 137 | 31 | 142 | 12,806 | — | — | — | 1542 | — | — | — | 3 |
| VSKMGVDEYSSTERV | 164 | Flu.PB2.483 H5N1 | | — | 1021 | — | — | — | — | — | — | 1851 | — | — | — | 0 |
| RVVVSIDRFLRVRDQ | 165 | Flu.PB2.496 H5N1 | | 1863 | 67 | 111 | 400 | 2053 | — | — | — | 8.1 | — | — | — | 4 |
| QWIIRNWETVKIQWS | 166 | Flu.PB2.554 | 12/14 | 47 | 4422 | 49 | 16 | 124 | 24 | 1573 | 729 | 8.8 | 2.2 | 49 | 156 | 10 |
| RMQFSSLTVNVRGSG | 167 | Flu.PB2.633 | 13/14 | 9.2 | 9323 | 33 | 71 | 988 | 310 | 833 | 437 | 149 | 102 | 3725 | 7.5 | 10 |
| AGALTEDPDEGTAGV | 168 | Flu.PB2.675 H5N1 | | — | 735 | 12,423 | 2231 | 10,118 | — | — | — | 1087 | — | — | — | 1 |

TABLE 3-continued

DR binding results of candidate Influenza peptides

| Sequence | SEQ ID NO | Source | Strain | Strain Conservancy | IC$_{50}$ nM to purified HLA DRB1 *0101 | DRB1 *0301 | DRB1 *0401 | DRB1 *0404 | DRB1 *0405 | DRB1 *0701 | DRB1 *0802 | DRB1 *1101 | DRB1 *1302 | DRB1 *1501 | DRB4 *0101 | DRB5 *0101 | No. of HLA-DR alleles IC50 < 1000 nM |
|---|---|---|---|---|---|---|---|---|---|---|---|---|---|---|---|---|---|
| ESAVLRGFLILGKED | 169 | Flu.PB2.690 | | 10/14 | 8.4 | — | 13,205 | 110 | 7101 | 2471 | 803 | 1034 | — | 39 | 1278 | 303 | 5 |
| FLILGKEDRRYGPAL | 170 | Flu.PB2.697 | H2N2 | | 8388 | 565 | 1739 | — | — | | | | 118 | | | | 2 |
| NVLIGQGDVVLVMKR | 171 | Flu.PB2.726 | | 11/14 | 616 | 164 | 1982 | 918 | 4849 | 7156 | 1085 | 403 | 361 | 3331 | 6786 | 4199 | 5 |
| DSSILTDSQTATKRI | 172 | Flu.PB2.743 | H5N1 | | 10,469 | 36 | 773 | 698 | 3022 | | | | 318 | | | | 4 |

TABLE 4

DR binding results of preferred candidate Influenza peptides

| Sequence | SEQ ID NO | Source | Strain | Strain Conservancy | IC50 nM to purified HLA DRB1 *0101 | DRB1 *0301 | DRB1 *0401 | DRB1 *0404 | DRB1 *0405 | DRB1 *0701 | DRB1 *0802 | DRB1 *1101 | DRB1 *1302 | DRB1 *1501 | DRB4 *0101 | DRB5 *0101 | No. of HLA-DR alleles IC50 < 1000 M |
|---|---|---|---|---|---|---|---|---|---|---|---|---|---|---|---|---|---|
| IYQILSIYSTVASSLA | 29 | Flu.HA.529 | H5N1 | | 55 | | 89 | | | | | | 13 | 4.7 | 18 | | 5 |
| ILSIYSTVASSLALAI | 30 | Flu.HA.532 | H5N1 | | 11 | | 91 | | | | | | 7.6 | 20 | 824 | | 5 |
| KGILGFVFTLTVPSE | 35 | Flu.M1.60 | | 16/17 | 28 | | 5.6 | | | | | | 10 | 129 | 767 | | 5 |
| YRKLKREITFHGAKE | 36 | Flu.M1.103 | | 10/17 | 67 | | 21 | | | | | | — | 253 | 79 | | 4 |
| MGTVTTEVALGLVCA | 37 | Flu.M1.138 | | | 58 | 348 | 321 | 355 | 10,093 | 924 | | 11,317 | 769 | 142 | 1589 | 7609 | 7 |
| NPLIRHENRMVLAST | 39 | Flu.M1.173 | | 17 | 40 | 779 | 31 | 1588 | 298 | | 32 | 6.1 | 2.8 | 690 | 3691 | 9 | |
| AMEVASQARQMVQAM | 40 | Flu.M1.205 | | | 641 | 833 | 4252 | 1561 | 263 | 424 | | 1406 | 185 | 310 | 759 | 786 | 8 |
| DPLVVAASIIGILHL | 42 | Flu.M2.27 | | 8/15 | 113 | | 127 | | | | | | 1532 | 2345 | 169 | | 3 |
| SLMLQIGNMISIWVSHS | 44 | Flu.NA.21 | H5N1 | | 36 | | 480 | | | | | | 44 | 34 | 746 | | 5 |
| IGRFYIQMCTELKLS | 58 | Flu.NP.39 | | 9/11 | 64 | | 175 | | | | | | — | 246 | 985 | | 4 |
| YIQMCTELKLSDYEG | 59 | Flu.NP.43 | | | 320 | 368 | 392 | 1640 | 2694 | 5370 | | 5842 | 15,372 | 594 | — | 80 | 5 |
| QNSITIERMVLSAFD | 61 | Flu.NP.61 | | 7/11 | 891 | 298 | 517 | 411 | 5839 | 806 | | 4231 | 839 | 1201 | 39 | — | 7 |
| VGTMVMELIRMIKRG | 65 | Flu.NP.189 | | | 22 | 16 | 1092 | 131997 | 495 | | 32 | 256 | 738 | 10 | 25 | 9 | |
| DLIFLARSALILRGS | 67 | Flu.NP.258 | | 11/11 | 25 | | 365 | | | | | | 14 | 17 | 3293 | | 4 |
| LIFLARSALILRGSV | 68 | Flu.NP.259 | | 11/11 | 8.8 | | 1449 | | | | | | 17 | 23 | 747 | | 4 |
| RSALILRGSVAHKSC | 69 | Flu.NP.264 | | 11/11 | 30 | | 304 | | | | | | 252 | 227 | 850 | | 5 |
| KSQLVWMACHSAAFE | 70 | Flu.NF.328 | | 9/11 | 122 | | 479 | | | | | | 5109 | 479 | 142 | | 4 |
| AGQISVQPTFSVQRN | 71 | Flu.NP.406 | | 9/12 | 18 | | 48 | | | | | | 30 | 9.4 | 44 | | 5 |
| EGAIVGEISPLPSLP | 81 | Flu.NS1.156 | | 12/15 | 85 | | 48 | | | | | | 274 | 357 | 513 | | 5 |
| VGEISPLPSLPGHTD | 82 | Flu.NS1.160 | | 7/15 | 14 | | 31 | | | | | | 10,938 | 38 | 141 | | 4 |
| SLKLYRDSLGEAVMR | 84 | Flu.NS2.113 | | | 11 | 46 | 903 | 996 | 5993 | 790 | | 14,799 | 800 | 19 | — | 14,398 | 7 |
| IRWLIEEVRHRLRIT | 86 | Flu.NS2.152 | | | 137 | 73 | 1045 | 3841 | 3511 | 877 | | 703 | 932 | 189 | 2944 | 39 | 7 |

TABLE 4-continued

DR binding results of preferred candidate Influenza peptides

| Sequence | SEQ ID NO | Source | Strain | Strain Conser-vancy | DRB1 *0101 | DRB1 *0301 | DRB1 *0401 | DRB1 *0404 | DRB1 *0405 | DRB1 *0701 | DRB1 *0802 | DRB1 *1101 | DRB1 *1302 | DRB1 *1501 | DRB4 *0101 | DRB5 *0101 | No. of HLA-DR alleles IC50 < 1000 M |
|---|---|---|---|---|---|---|---|---|---|---|---|---|---|---|---|---|---|
| | | | | | $IC_{50}$ nM to purified HLA | | | | | | | | | | | | |
| FEQITFMQALQLLLE | 87 | Flu.NS2.170 | | 8/13 | 5.3 | | 739 | | | | | | 326 | 7.0 | 406 | | 5 |
| TTFMQALQLLLEVEQ | 88 | Flu.NS2.173 | | 8/13 | 22 | | 1779 | | | | | | 260 | 145 | 143 | | 4 |
| RREVHIYYLEKANKI | 94 | Flu.PA.127 | | 8/11 | 34 | — | 63 | 181 | 1490 | 23 | 95 | 96 | 150 | 4.5 | 5.0 | 25 | 10 |
| LFTIRQEMASRGLWD | 96 | Flu.PA.178 | | | 25 | 523 | 53 | 3.8 | 768 | 3317 | | 890 | 304 | 237 | 15 | 43 | 10 |
| EPFLKTTPRPLRLPD | 98 | Flu.PA.261 | | | 17 | 373 | 961 | 2021 | 11,834 | 51 | | 131 | 412 | 570 | 7660 | 62 | 8 |
| RSKFLLMDALKLSIED | 99 | Flu.PA.282 | | 10/11 | 1.1 | 125 | 53 | 14 | 35 | 25 | 96 | 49 | 110 | 1.2 | 639 | 16 | 12 |
| VAPIEHIASMRRNYF | 104 | Flu.PA.435 | | 9/11 | 375 | 114 | 503 | 41 | 7658 | 543 | 643 | 70 | 221 | 147 | 529 | 4.1 | 11 |
| EYIMIKGVYINTALLN | 106 | Flu.PA.460 | | 10/11 | 22 | 3758 | 1064 | 67 | 425 | 1041 | 133 | 2732 | 7.0 | 70 | 1337 | 585 | 7 |
| RPMFLYVRTNGTSKI | 109 | Flu.PA.562 | | 9/11 | 5.1 | 10,682 | 7.3 | 6.7 | 400 | 15 | 12 | 8.1 | 1.4 | 83 | 694 | 6.4 | 11 |
| PTLLFLKVPAQNAIST | 114 | Flu.PB1.8 | | 11/12 | 7.6 | — | 17 | 8.5 | 152 | 34 | 15 | 49 | 1380 | 285 | 64 | 50 | 10 |
| SYLIRALTLNTMTKD | 120 | Flu.PB1.219 | | 9/12 | 7.1 | 4900 | 42 | 14 | 429 | 76 | 56 | 280 | 87 | 7.5 | 3.0 | 386 | 11 |
| FLAMITYITRNQPEW | 121 | Flu.PB1.321 | | 10/12 | 7.9 | 11,559 | 126 | 64 | 200 | 590 | 65 | 59 | 174 | 74 | 1140 | 60 | 10 |
| QPEWFRNVLSIAPIMF | 122 | Flu.PB1.332 | | 9/12 | 37 | 8991 | 100 | 236 | 374 | 12 | 228 | 288 | 98 | 723 | 104 | 656 | 11 |
| FRNVLSIAPIMFSNKM | 123 | Flu.PB1.336 | | 8/12 | 9.6 | 1450 | 25 | 8.1 | 409 | 10 | 71 | 68 | 77 | 62 | 43 | 33 | 11 |
| IAPIMFSNKMARLGK | 124 | Flu.PB1.342 | | | 58 | 51 | 404 | 180 | 10,962 | 315 | | 140 | 77 | 25 | 3733 | 100 | 9 |
| KGYMFESKSMKLRTQI | 125 | Flu.PB1.356 | | 8/12 | 6.6 | 547 | 173 | 63 | 806 | 6.3 | 60 | 33 | 8.7 | 1.7 | 34 | 7.8 | 12 |
| IRPLLVEQTASLSPG | 126 | Flu.PB1.395 | | | 35 | 819 | 13 | 35 | 835 | 882 | | 5285 | 65 | 348 | 414 | 1118 | 9 |
| MMGMFNMLSTVLGVS | 127 | Flu.PB1.411 | | 12/12 | 2.7 | 9191 | 6.3 | 0.9 | 72 | 85 | 15 | 13 | 40 | 48 | 37 | 42 | 11 |
| DFALIVNAPNHEGIQ | 128 | Flu.PB1.449 | | 11/12 | 47 | — | 37 | 10 | 52 | 8663 | 295 | 153 | 9.0 | 26 | 46 | 208 | 10 |
| YGFVANFSMELPSFG | 130 | Flu.PB1.502 | | 12/12 | 4.6 | 5376 | 40 | 61 | 617 | 8.4 | 1177 | 700 | 0.91 | 17 | 2632 | 1320 | 8 |
| GVTVIKNNMINNDLGP | 133 | Flu.PB1.529 | | 11/12 | 37 | — | 956 | 180 | 457 | 153 | 239 | 17,124 | 7.6 | 8.2 | 3762 | — | 8 |
| PNLYNIRNLHIPEVC | 137 | Flu.PB1.599 | | 10/12 | 68 | — | 1159 | 8.6 | 259 | 9.7 | 71 | 1535 | 148 | 9.1 | 409 | 2309 | 8 |
| ISSMVEAMVSRARID | 145 | Flu.PB1.714 | | 8/12 | 112 | 4284 | 93 | 10 | 14,306 | 2942 | 310 | 294 | 1108 | 902 | 108 | 13 | 8 |

TABLE 4-continued

DR binding results of preferred candidate Influenza peptides

| Sequence | SEQ ID NO | Source | Strain | Strain Conser-vancy | DRB1 *0101 | DRB1 *0301 | DRB1 *0401 | DRB1 *0404 | DRB1 *0405 | DRB1 *0701 | DRB1 *0802 | DRB1 *1101 | DRB1 *1302 | DRB1 *1501 | DRB4 *0101 | DRB5 *0101 | No. of HLA-DR alleles IC50 < 1000 M |
|---|---|---|---|---|---|---|---|---|---|---|---|---|---|---|---|---|---|
| | | | | | IC$_{50}$ nM to purified HLA | | | | | | | | | | | | |
| KWMMAMKYPITADKR | 148 | Flu.PB2.51 | | 14/14 | 415 | 5884 | — | 182 | 8335 | 114 | 13 | 19 | 6773 | 198 | 1257 | 101 | 7 |
| GARILTSESQLTTTK | 153 | Flu.PB2.176 | | 10/14 | 46 | 967 | 103 | 65 | 5479 | 376 | — | 4800 | 19 | 19 | 1181 | 7735 | 7 |
| ARILTSESQLTTTKE | 154 | Flu.PB2.177 | | | 51 | 139 | 182 | 92 | 1221 | 297 | | 5247 | 34 | 94 | 1146 | 1462 | 7 |
| KAAMGLRISSSFSFG | 158 | Flu.PB2.315 | | 10/14 | 37 | 501 | 47 | 4.2 | 452 | 3.9 | 466 | 398 | 2.5 | 1.1 | 79 | 45 | 12 |
| IKAVRGDLNFVNRAN | 161 | Flu.PB2.414 | | | 729 | 123 | 75 | 17 | 510 | 18,077 | | 1914 | 264 | 517 | 515 | 11,460 | 8 |
| LRHFQKDAKVLFQNW | 162 | Flu.PB2.438 | | | 153 | 51 | 1431 | 1348 | 9917 | 578 | | 318 | 240 | 207 | 979 | 1412 | 7 |
| QWIIRNWETVKIQWS | 166 | Flu.PB2.554 | | 12/14 | 47 | 4422 | 49 | 16 | 124 | 24 | 1573 | 729 | 8.8 | 2.2 | 49 | 156 | 10 |
| RMQFSSLTVNVRGSG | 167 | Flu.PB2.633 | | 13/14 | 9.2 | 9323 | 33 | 71 | 988 | 310 | 833 | 437 | 149 | 102 | 3725 | 7.5 | 10 |

TABLE 5

M2e sequences from representative subtype isolates

| | S | L | L | T | E | V | E | T | P | I | R | N | E | W | G | C | R | C | N | D | S | S | D | SEQ ID-NO: 15 |
|---|---|---|---|---|---|---|---|---|---|---|---|---|---|---|---|---|---|---|---|---|---|---|---|---|
| Conserved Human Sequence | | | | | | | | | | | | | | | | | | | | | | | | |
| A/Wilson-Smith/33 (H1N1) | - | - | - | - | - | - | - | - | - | - | - | - | - | - | - | - | - | - | - | - | - | - | - | |
| A/New Caledonia/20/99 (H1N1) | ? | ? | ? | ? | ? | ? | ? | ? | - | - | - | - | - | - | - | - | - | - | - | - | - | - | - | |
| A/Swine Korea/S10/2004 (H1N1) | - | - | - | - | - | - | - | - | - | - | - | - | - | - | - | - | - | - | - | - | - | - | - | |
| A/Japan/305/67 (H2N2) | - | - | - | - | - | - | - | - | - | - | - | - | - | - | - | - | - | - | - | - | - | - | - | |
| A/Ann Arbor/6/60 (H2N2) | - | - | - | - | - | - | - | - | - | - | - | - | - | - | - | - | - | - | - | - | - | - | - | |
| A/Canada/720/05 (H2N2) | - | - | - | - | - | - | - | - | - | - | - | - | - | - | - | - | - | - | - | - | - | - | - | |
| A/Hong Kong/1/68 (H3N2) | - | - | - | - | - | - | - | - | - | - | - | - | - | - | - | - | - | - | - | - | - | - | - | |
| A/Charlottesville/03/2004 (H3N2) | - | - | - | - | - | - | - | - | - | - | - | - | - | - | - | - | - | - | - | - | - | - | - | |
| A/Canterbury/129/2005 (H3N2) | - | - | - | - | - | - | - | - | - | - | - | - | - | - | - | - | - | - | - | - | - | - | - | |
| A/Brevig Mission/1/1918 (H1N1) | - | - | - | - | - | - | - | - | - | - | - | - | - | - | - | - | - | - | - | - | - | - | - | 189 |
| A/Puerto Rico/8/34/Mount Sinai (H1N1) | - | - | - | - | - | - | - | - | - | - | - | - | - | - | - | - | - | - | G | - | - | - | - | 190 |
| A/Fujian/411/02-like (H3N2) | - | - | - | - | - | - | - | - | - | - | - | - | - | - | - | - | - | - | - | - | N | - | - | 191 |
| A/Swine/Saskatchewan/18789/02 (H1N1) | - | - | - | - | - | - | - | - | - | T | - | - | G | - | E | - | K | - | S | - | - | - | - | 192 |
| A/mallard/Alberta/130/2003 (H1N1) | - | - | - | - | - | - | - | - | - | T | - | - | G | - | E | - | K | - | S | - | - | - | - | |
| A/mallard/NY/6750/78 (H2N2) | - | - | - | - | - | - | - | - | - | T | - | - | G | - | E | - | K | - | S | - | - | - | - | |
| A/mallard/Potsdam/177-4/83 (H2N2) | - | - | - | - | - | - | - | - | - | T | - | - | G | - | E | - | K | - | S | - | - | - | - | |
| A/duck/Hokkaido/95/2001 (H2N2) | ? | ? | ? | ? | ? | ? | ? | ? | - | T | - | - | G | - | E | - | K | - | S | - | - | - | ? | |
| A/Duck/Korea/S9/2003 (H3N2) | - | - | - | - | - | - | - | - | - | T | - | - | G | - | E | - | K | - | S | - | - | - | - | |
| A/swine/Shandong/2/03 (H5N1) | - | - | - | - | - | - | - | - | - | T | - | - | G | - | E | - | K | - | S | - | - | - | - | |
| A/Chicken/California/0139/2001 (H6N2) | - | - | - | - | - | - | - | - | - | T | - | - | G | - | E | - | K | - | S | - | - | - | - | |
| A/Guillemot/Sweden/3/2000 (H6N2) | ? | ? | ? | - | - | - | - | - | - | T | - | - | G | - | E | - | K | - | S | - | - | - | - | |
| A/Goose/Hong Kong/W217/97 (H6N9) | - | - | - | - | - | - | - | - | - | T | - | - | G | - | E | - | K | - | S | - | - | - | - | |
| A/chicken/British Columbia/04 (H7N3) | - | - | - | - | - | - | - | - | - | T | - | - | G | - | E | - | K | - | S | - | - | - | - | |
| A/Shorebird/Delaware/9/96 (H9N2) | - | - | - | - | - | - | - | - | - | T | - | - | G | - | E | - | K | - | S | - | - | - | - | |
| A/Duck/Hong Kong/Y439/97 (H9N2) | - | - | - | - | - | - | - | - | - | T | - | - | G | - | E | - | K | - | S | - | - | - | - | |
| A/Teal/Hong Kong/W312/97 (H6N1) | - | - | - | - | - | - | - | - | L | T | - | - | G | - | E | - | K | - | S | - | - | - | - | 193 |
| A/swine/Korea/S452/2004 (H9N2) | - | - | - | - | - | - | - | - | - | T | - | - | G | - | E | - | K | - | S | - | - | - | E | 194 |
| A/Hong Kong/1073/99 (H9N2) | - | - | - | - | - | - | - | - | L | T | - | - | G | - | E | - | K | - | R | - | - | - | - | 195 |
| A/chicken/Netherlands/1/2003 (H7N7) | - | - | - | - | - | - | - | - | - | T | - | - | G | - | E | - | K | - | - | - | - | - | - | 196 |
| A/Netherlands/219/03 (H7N7) | - | - | - | - | - | - | - | - | - | T | - | - | G | - | E | - | K | - | - | - | - | - | - | |
| A/Swine/Texas/4199-2/98 (H3N2) | - | - | - | - | - | - | - | - | - | - | - | - | G | - | E | - | K | - | - | - | - | - | - | 197 |
| A/turkey/Ohio/313053/2004 (H3N2) | - | - | - | - | - | - | - | - | - | - | - | - | G | - | E | - | K | - | - | - | - | - | - | |
| A/Turkey/North Carolina/12344/03 (H3N2) | - | - | - | - | - | - | - | - | - | - | - | S | G | - | E | - | K | - | - | - | - | - | - | 198 |
| A/Goose/Guangdong/1/96 (H5N1) | - | - | - | - | - | - | - | - | - | T | K | - | - | - | E | - | K | - | S | - | - | - | - | 199 |
| A/FPV/Dobson/27 (H7N7) | - | - | - | - | - | - | - | - | - | T | - | - | G | - | E | - | S | - | S | - | - | - | - | 200 |
| A/chicken/FPV/Weybridge (H7N7) | - | - | - | - | - | - | - | - | - | T | - | - | G | - | E | - | S | - | S | - | - | - | - | |
| A/mallard/Alberta/2001 (H1N1) | ? | ? | ? | ? | ? | ? | ? | ? | - | T | - | - | G | - | E | - | - | - | S | - | - | - | - | 201 |
| A/Duck/Hunan/114/05 (H5N1) | - | - | - | - | - | - | - | - | - | T | - | - | G | - | E | - | - | - | S | - | - | - | - | |
| A/Swine/Cotes d'Armor/1482/99 (H1N1) | V | - | - | - | - | - | - | - | - | T | - | - | G | - | E | - | - | Y | S | - | - | N | - | 202 |
| A/Swine/Betzig/2/2001 (H1N1) | ? | ? | ? | ? | ? | ? | ? | ? | - | T | - | - | G | - | E | - | - | Y | S | G | - | - | - | 203 |
| A/turkey/Italy/220158/2002 (H7N3) | - | - | - | - | - | - | - | - | - | T | - | - | G | - | E | - | - | - | S | - | L | - | - | 204 |
| A/HK/2108/2003 (H9N2) | - | - | - | - | - | - | - | - | L | T | - | - | G | - | E | - | - | - | S | G | - | - | - | 205 |
| A/FPV/Rostook/34 (H7N1) | - | - | - | - | - | - | - | - | - | T | - | - | G | - | E | - | - | - | - | - | - | - | - | |
| A/Viet Nam/1203/2004 (H5N1) | - | - | - | - | - | - | - | - | - | T | - | - | - | - | E | - | - | - | S | - | - | - | - | 206 |
| A/Viet Nam/DT-036/2005 (H5N1) | - | - | - | - | - | - | - | - | - | T | - | - | - | - | E | - | - | - | S | - | - | - | - | |
| A/grebe/Novoslbirsk/29/2005 (H5N1) | - | - | - | - | - | - | - | - | - | T | - | - | - | - | E | - | - | - | S | - | - | - | - | |
| A/Bar-headed Goose/Mongolia/1/05 (H5N1) | - | - | - | - | - | - | - | - | - | T | - | - | - | - | E | - | - | - | S | - | - | - | - | |
| A/cat/Thailand/KU-02/04 (H5N1) | - | - | - | - | - | - | - | - | - | T | - | - | - | - | E | - | - | - | S | - | - | - | - | |
| A/Hong Kong/213/03 (H5N1) | - | - | - | - | - | - | - | - | H | T | - | - | - | - | E | - | - | - | S | - | - | - | - | 207 |
| A/chicken/Guangdong/174/04 (H5N1) | - | - | - | - | - | - | - | - | - | T | - | - | - | - | E | - | - | Y | S | - | - | - | - | 208 |
| A/HK/156/97 (H5N1) | - | - | - | - | - | - | - | - | L | T | - | - | G | - | E | - | K | - | S | - | - | - | - | 209 |
| A/Quail/Hong Kong/G1/97 (H9N2) | - | - | - | - | - | - | - | - | L | T | - | - | G | - | E | - | K | - | S | - | - | - | - | |
| A/Duck/Hong Kong/Y260/97 (H9N2) | - | - | - | - | - | - | - | - | H | T | - | - | G | - | E | - | K | - | S | - | - | - | - | 210 |
| A/chicken HK/FY23/03 (H9N2) | - | - | - | - | - | - | - | - | H | T | - | - | G | - | E | - | K | - | S | - | - | - | - | |
| A/Chicken HK/G9/97 (H9N2) | - | - | - | - | - | - | - | - | - | T | - | - | G | - | E | - | K | - | S | G | - | - | - | 211 |
| A/turkey/Germany/3/91 (H1N1) | - | - | - | - | - | - | - | - | - | T | - | - | G | - | E | - | K | Y | S | - | - | - | - | 212 |

TABLE 6

M2e immunogens

| M2e Immunogens: | Sequence | SEQ ID NO. |
|---|---|---|
| Human | S L L T E V E T P I R N E W G C R C N D S S D | 15 |
| PADRE-Human | A K F V A A W T L K A A A S L L T E V E T P I R N E W G C R C N D S S D | 213 |
| H5 Human/Avian | S L L T E V E T P T R N E W E C R C S D S S D | 15 |
| PADRE-H5Human/Avian | A K F V A A W T L K A A A S L L T E V E T P T R N E W E C R C S D S S D | 214 |
| 2005 Asian avian | S L L T E V E T P T R N G W E C R C S D S S D | 15 |
| PADRE-2005 Asian avian | A K F V A A W T L K A A A S L L T E V E T P T R N G W E C R C S D S S D | 215 |
| 2005 Russian avian | S L L T E V E T P T R N E W E C R Y S D S S D | 15 |
| PADRE-2005 Asian avian | A K F V A A W T L K A A A S L L T E V E T P T R N E W E C R Y S D S S D | 216 |
| H7H9 | S L L T E V E T P T R N G W E C K C S D S S D | 15 |
| PADRE-H7H9 | A K F V A A W T L K A A A S L L T E V E T P T R N G W E C K C S D S S D | 217 |

TABLE 7

DR binding results of candidate Influenza peptides

| Sequence | SEQ ID NO | Source | DRB1 *0101 | DRB1 *0301 | DRB1 *0401 | DRB1 *0404 | DRB1 *0405 | DRB1 *0701 | DRB1 *0802 | DRB1 *0901 | DRB1 *1101 | DRB1 *1302 | DRB1 *1501 | DRB4 *0101 | DRB5 *0101 | No. of HLA-DR alleles IC50 < 1000 nM |
|---|---|---|---|---|---|---|---|---|---|---|---|---|---|---|---|---|
| KGILGFVFTLTVPSE | 35 | Flu.M1.60 | 15 | 2610 | 4.8 | 1 | 6 | 11 | 33 | 33 | 37 | 10 | 127 | 356 | 2206 | 11 |
| YRKLKREITFHGAKE | 36 | Flu.M1.103 | 20 | 4633 | 13 | 20 | 951 | 976 | 47 | 432 | 28 | — | 327 | 58 | 459 | 11 |
| MGTVTTEVALGLVCA | 37 | Flu.M1.138 | 58 | 348 | 321 | 355 | — | 924 | — | 4234 | — | 769 | 142 | 1589 | 7609 | 7 |
| NPLIRHENRMVLAST | 39 | Flu.M1.173 | 17 | 40 | 779 | 31 | 1,588 | 298 | 108 | 95 | 32 | 6.1 | 2.8 | 690 | 3691 | 11 |
| AMEVASQARQMVQAM | 40 | Flu.M1.205 | 641 | 833 | 4252 | 1561 | 263 | 424 | 1142 | 1437 | 1406 | 185 | 310 | 759 | 786 | 8 |
| DPLWAASIIGILHL | 42 | Flu.M2.27 | 78 | — | 92 | 23 | 630 | 1304 | 3591 | 709 | 1804 | 1859 | 2196 | 252 | — | 6 |
| SLMLQIGNMISIWVSHS | 44 | Flu.NA.21 | 8 | 441 | 5 | 3 | 66 | 13 | 89 | 86 | 83 | 10 | 8 | 8 | 24 | 13 |
| IGRFYIQMCTELKLS | 58 | Flu.NP.39 | 43 | 842 | 192 | 264 | 487 | 424 | 130 | 113 | 880 | 640 | 172 | 990 | 78 | 13 |
| YIQMCTELKLSDYEG | 59 | Flu.NP.43 | 320 | 368 | 392 | 1640 | 2694 | 5370 | — | — | 5842 | — | 594 | — | 80 | 5 |
| QNSITIERMVLSAFD | 61 | Flu.NP.61 | 890 | 298 | 430 | 188 | 4137 | 806 | 534 | 5615 | 4231 | 1421 | 891 | 39 | — | 8 |
| VGTMVMELIRMIKRG | 65 | Flu.NP.189 | 22 | 16 | 1092 | 13 | 1997 | 495 | 47 | 8886 | 32 | 256 | 738 | 10 | 25 | 10 |
| DLIFLARSALILRGS | 67 | Flu.NP.258 | 6.8 | 857 | 315 | 8.7 | 348 | 13 | 15 | 365 | 321 | 5.9 | 8.4 | 2243 | 35 | 12 |
| LIFLARSALILRGSV | 68 | Flu.NP.259 | 5.3 | 823 | 681 | 97 | 571 | 7 | 11 | 19 | 86 | 12 | 15 | 398 | 10 | 13 |
| RSALILRGSVAHKSC | 69 | Flu.NP.264 | 13 | 1482 | 269 | 17 | 599 | 14 | 16 | 63 | 265 | 268 | 119 | 480 | 61 | 13 |
| KSQLVWMACHSAAFE | 70 | Flu.NP.328 | 35 | 1118 | 194 | 34 | 127 172 | 324 | 201 | 472 | — | 259 | 149 | 462 | 11 | 12 |
| AGQISVQPTFSVQRN | 71 | Flu.NP.406 | 12 | 1632 | 41 | 11 | 335 | 290 | — | 589 | 3744 | 55 | 9.2 | 34 | 163 | 10 |
| SLCIRMDQAIMDKDI | 78 | Flu.NS1.117 | 265 | 58 | 701 | 217 | 82 | 5552 | 8568 | 6895 | — | 53 | 2357 | 153 | 8320 | 7 |
| EGAIVGEISPLPSLP | 81 | Flu.NS1.156 | 151 | 3857 | 27 | 13 | 2323 | 572 | 886 | 1590 | 687 | 444 | 393 | 611 | 1616 | 9 |
| VGEISPLPSLPGHTD | 82 | Flu.NS1.160 | 12 | — | 16 | 8.5 | 133 | — | 241 | 2885 | 90 | — | 28 | 141 | 466 | 9 |
| SLKLYRDSLGEAVMR | 84 | Flu.NS2.113 | 11 | 46 | 903 | 996 | 5993 | 790 | — | 707 | — | 800 | 19 | — | — | 8 |
| IRWLIEEVRHRLRIT | 86 | Flu.NS2.152 | 137 | 73 | 1045 | 3841 | 3511 | 877 | 1672 | 6597 | 703 | 932 | 189 | 2944 | 39 | 7 |
| FEQITFMQALQLLLE | 87 | Flu.NS2.170 | 5.3 | 4551 | 345 | 160 | 335 | 38 | 2696 | 47 | 765 | 1083 | 9.7 | 387 | 314 | 10 |

TABLE 7-continued

DR binding results of candidate Influenza peptides

| Sequence | SEQ ID NO | Source | IC$_{50}$ nM to purified HLA DRB1 *0101 | DRB1 *0301 | DRB1 *0401 | DRB1 *0404 | DRB1 *0405 | DRB1 *0701 | DRB1 *0802 | DRB1 *0901 | DRB1 *1101 | DRB1 *1302 | DRB1 *1501 | DRB4 *0101 | DRB5 *0101 | No. of HLA-DR alleles IC50 < 1000 nM |
|---|---|---|---|---|---|---|---|---|---|---|---|---|---|---|---|---|
| ITFMQALQLLLEVEQ | 88 | Flu.NS2.173 | 13 | 2511 | 161 | 124 | 224 | 26 | 2426 | 20 | 1375 | 242 | 104 | 149 | 46 | 10 |
| RREVHIYYLEKANKI | 94 | Flu.PA.127 | 34 | — | 63 | 181 | 1490 | 23 | 95 | 851 | 96 | 150 | 4.5 | 5.0 | 25 | 11 |
| LFTIRQEMASRGLWD | 96 | Flu.PA.178 | 25 | 523 | 53 | 3.8 | 768 | 3317 | 88 | 2428 | 890 | 304 | 237 | 15 | 43 | 11 |
| EPFLKTTPRPLRLPD | 98 | Flu.PA.261 | 17 | 373 | 961 | 2021 | — | 51 | 117 | 109 | 131 | 412 | 570 | 7660 | 62 | 10 |
| RSKFLLMDALKLSIED | 99 | Flu.PA.282 | 1.1 | 125 | 53 | 14 | 35 | 25 | 96 | 15 | 49 | 110 | 1.2 | 639 | 16 | 13 |
| VAPIEHIASMRRNYF | 104 | Flu.PA.435 | 375 | 114 | 503 | 41 | 7658 | 543 | 643 | 7437 | 70 | 221 | 147 | 529 | 4.1 | 11 |
| EYIMKGWINTALLN | 106 | Flu.PA.460 | 22 | 3758 | 1064 | 67 | 425 | 1041 | 133 | 1200 | 2732 | 7.0 | 70 | 1337 | 585 | 7 |
| RPMFLYVRTNGTSKI | 109 | Flu.PA.562 | 5.1 | — | 7.3 | 6.7 | 400 | 15 | 12 | 82 | 8.1 | 1.4 | 83 | 694 | 6.4 | 12 |
| PTLLFLKVPAQNAIST | 114 | Flu.PB1.8 | 7.6 | — | 17 | 8.5 | 152 | 34 | 15 | 69 | 49 | 1380 | 285 | 64 | 50 | 11 |
| SYLIRALTLNTMTKD | 120 | Flu.PB1.219 | 7.1 | 4900 | 42 | 14 | 429 | 76 | 56 | 121 | 280 | 87 | 7.5 | 3.0 | 386 | 12 |
| FLAMITYITRNQPEW | 121 | Flu.PB1.321 | 7.9 | — | 126 | 64 | 200 | 590 | 65 | 769 | 59 | 174 | 74 | 1140 | 60 | 11 |
| QPEWFRNVLSIAPIMF | 122 | Flu.PB1.332 | 37 | 8991 | 100 | 236 | 374 | 12 | 228 | 197 | 288 | 98 | 723 | 104 | 656 | 12 |
| FRNVLSIAPIMFSNKM | 123 | Flu.PB1.336 | 9.6 | 1450 | 25 | 8.1 | 409 | 10 | 71 | 88 | 68 | 77 | 62 | 43 | 33 | 12 |
| IAPIMFSNKMARLGK | 124 | Flu.PB1.342 | 58 | 51 | 404 | 180 | — | 315 | 27 | 1836 | 140 | 77 | 25 | 3733 | 100 | 10 |
| KGYMFESKSMKLRTQI | 125 | Flu.PB1.356 | 6.6 | 547 | 173 | 63 | 806 | 6.3 | 60 | 80 | 33 | 8.7 | 1.7 | 34 | 7.8 | 13 |
| IRPLLVEGTASLSPG | 126 | Flu.PB1.395 | 35 | 819 | 13 | 35 | 835 | 882 | 1154 | 537 | 5285 | 65 | 348 | 414 | 1118 | 10 |
| MMGMFNMLSTVLGVS | 127 | Flu.PB1.411 | 2.7 | 9191 | 6.3 | 0.91 | 72 | 85 | 15 | 20 | 13 | 40 | 48 | 37 | 42 | 12 |
| DFALIVNAPNHEGIQ | 128 | Flu.PB1.449 | 47 | — | 37 | 10 | 52 | 8663 | 295 | 724 | 153 | 9.0 | 26 | 46 | 208 | 11 |
| YGFVANFSMELPSFG | 130 | Flu.PB1.502 | 4.6 | 5376 | 40 | 61 | 617 | 8.4 | 1177 | 13 | 700 | 0.91 | 17 | 2632 | 1320 | 9 |
| GV1VIKNNMINNDLGP | 133 | Flu.PB1.529 | 37 | — | 956 | 180 | 457 | 153 239 | 1880 | — | 7.6 | 8.2 | 3762 | — | 8 | |
| PNLYNIRNLHIPEVC | 137 | Flu.PB1.599 | 68 | — | 1159 | 8.6 | 259 | 9.7 | 71 | 914 | 1535 | 148 | 9.1 | 409 | 2309 | 9 |
| ISSMVEAMVSRARID | 145 | Flu.PB1.714 | 112 | 4284 | 93 | 10 | — | 2942 | 310 | 1076 | 294 | 1108 | 902 | 108 | 13 | 8 |
| KWMMAMKYPITADKR | 148 | Flu.PB2.51 | 415 | 5884 | — | 182 | 8335 | 114 | 13 | 446 | 19 | 6773 | 198 | 1257 | 101 | 8 |

TABLE 7-continued

DR binding results of candidate Influenza peptides

| Sequence | SEQ ID NO | Source | DRB1 *0101 | DRB1 *0301 | DRB1 *0401 | DRB1 *0404 | DRB1 *0405 | DRB1 *0701 | DRB1 *0802 | DRB1 *0901 | DRB1 *1101 | DRB1 *1302 | DRB1 *1501 | DRB4 *0101 | DRB5 *0101 | No. of HLA-DR alleles IC50 < 1000 nM |
|---|---|---|---|---|---|---|---|---|---|---|---|---|---|---|---|---|
| GARILTSESQLTITK | 153 | Flu.PB2.176 | 46 | 967 | 103 | 65 | 5479 | 376 | — | 300 | 4800 | 19 | 19 | 1181 | 7735 | 8 |
| ARILTSESQLTITKE | 154 | Flu.PB2.177 | 51 | 139 | 182 | 92 | 1221 | 297 | — | 557 | 5247 | 34 | 94 | 1146 | 1462 | 8 |
| KAAMGLRISSSFSFG | 158 | Flu.PB2.315 | 37 | 501 | 47 | 4.2 | 452 | 3.9 | 466 | 58 | 398 | 2.5 | 1.1 | 79 | 45 | 13 |
| IKAVRGDLNFVNRAN | 161 | Flu.PB2.414 | 729 | 123 | 75 | 17 | 510 | — | 419 | — | 1914 | 264 | 517 | 515 | — | 9 |
| LRHFQKDAKVLFQNW | 162 | Flu.PB2.438 | 153 | 51 | 1431 | 1348 | 9917 | 578 | 536 | 5727 | 318 | 240 | 207 | 979 | 1412 | 8 |
| QWIIRNWETVKIQWS | 166 | Flu.PB2.554 | 47 | 4422 | 49 | 16 | 124 | 24 | 1573 | 243 | 729 | 8.8 | 2.2 | 49 | 156 | 11 |
| RMQFSSLTVNVRGSG | 167 | Flu.PB2.633 | 9.2 | 9323 | 33 | 71 | 988 | 310 | 833 | 306 | 437 | 149 | 102 | 3725 | 7.5 | 11 |

—indicates binding affinity > 10,000 nM.

SEQUENCE LISTING

<160> NUMBER OF SEQ ID NOS: 217

<210> SEQ ID NO 1
<211> LENGTH: 13
<212> TYPE: PRT
<213> ORGANISM: Artificial Sequence
<220> FEATURE:
<223> OTHER INFORMATION: Polypeptide comprising the pan-DR-binding
      epitope

<400> SEQUENCE: 1

Ala Lys Phe Val Ala Ala Trp Thr Leu Lys Ala Ala Ala
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Polypeptide comprising the pan-DR-binding
      epitope
<220> FEATURE:
<221> NAME/KEY: MISC_FEATURE
<222> LOCATION: (1)..(1)
<223> OTHER INFORMATION: Xaa is either D-alanine or L-alanine
<220> FEATURE:
<221> NAME/KEY: MISC_FEATURE
<222> LOCATION: (3)..(3)
<223> OTHER INFORMATION: Xaa can be cyclohexylalanine, phenylalanine, or
      tyrosine
<220> FEATURE:
<221> NAME/KEY: MISC_FEATURE
<222> LOCATION: (13)..(13)
<223> OTHER INFORMATION: Xaa is either D-alanine or L-alanine

<400> SEQUENCE: 2

Xaa Lys Xaa Val Ala Ala Trp Thr Leu Lys Ala Ala Xaa
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic spacer sequence

<400> SEQUENCE: 3

Gly Pro Gly Pro Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic spacer sequence

<400> SEQUENCE: 4

Pro Gly Pro Gly Pro
1               5

<210> SEQ ID NO 5
<211> LENGTH: 549
<212> TYPE: PRT
<213> ORGANISM: Influenza A virus

<400> SEQUENCE: 5

Asp Gln Ile Cys Ile Gly Tyr His Ala Asn Asn Ser Thr Glu Gln Val
1               5                   10                  15

```
Asp Thr Ile Met Glu Lys Asn Val Thr Val Thr His Ala Gln Asp Ile
                20                  25                  30

Leu Glu Lys Lys His Asn Gly Lys Leu Cys Asp Leu Asp Gly Val Lys
             35                  40                  45

Pro Leu Ile Leu Arg Asp Cys Ser Val Ala Gly Trp Leu Leu Gly Asn
 50                  55                  60

Pro Met Cys Asp Glu Phe Ile Asn Val Pro Glu Trp Ser Tyr Ile Val
 65                  70                  75                  80

Glu Lys Ala Asn Pro Val Asn Asp Leu Cys Tyr Pro Gly Asp Phe Asn
                 85                  90                  95

Asp Tyr Glu Glu Leu Lys His Leu Leu Ser Arg Ile Asn His Phe Glu
                100                 105                 110

Lys Ile Gln Ile Ile Pro Lys Ser Ser Trp Ser Ser His Glu Ala Ser
             115                 120                 125

Leu Gly Val Ser Ser Ala Cys Pro Tyr Gln Gly Lys Ser Ser Phe Phe
 130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
                180                 185                 190

Asn Pro Thr Thr Tyr Ile Ser Val Gly Thr Ser Thr Leu Asn Gln Arg
             195                 200                 205

Leu Val Pro Arg Ile Ala Thr Arg Ser Lys Val Asn Gly Gln Ser Gly
 210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
             260                 265                 270

Asn Cys Asn Thr Lys Cys Gln Thr Pro Met Gly Ala Ile Asn Ser Ser
 275                 280                 285

Met Pro Phe His Asn Ile His Pro Leu Thr Ile Gly Glu Cys Pro Lys
 290                 295                 300

Tyr Val Lys Ser Asn Arg Leu Val Leu Ala Thr Gly Leu Arg Asn Ser
305                 310                 315                 320

Pro Gln Arg Glu Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
             340                 345                 350

Gly Tyr His His Ser Asn Glu Gln Gly Ser Gly Tyr Ala Ala Asp Lys
             355                 360                 365

Glu Ser Thr Gln Lys Ala Ile Asp Gly Val Thr Asn Lys Val Asn Ser
             370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
             420                 425                 430
```

```
Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val Lys Leu Glu Ser Ile Gly
                500                 505                 510

Ile Tyr Gln Ile Leu Ser Ile Tyr Ser Thr Val Ala Ser Ser Leu Ala
            515                 520                 525

Leu Ala Ile Met Val Ala Gly Leu Ser Leu Trp Met Cys Ser Asn Gly
            530                 535                 540

Ser Leu Gln Cys Arg
545

<210> SEQ ID NO 6
<211> LENGTH: 515
<212> TYPE: PRT
<213> ORGANISM: Influenza A virus

<400> SEQUENCE: 6

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255
```

-continued

```
Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Arg Arg Lys Lys Arg Gly Leu Phe Gly Ala Ile
            325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
            405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
    435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
            485                 490                 495

Arg Leu Lys Arg Glu Glu Ile Ser Gly Val Lys Leu Glu Ser Ile Gly
            500                 505                 510

Ile Tyr Gln
        515

<210> SEQ ID NO 7
<211> LENGTH: 21
<212> TYPE: PRT
<213> ORGANISM: Influenza A virus

<400> SEQUENCE: 7

Ile Leu Ser Ile Tyr Ser Thr Val Ala Ser Ser Leu Ala Leu Ala Ile
1               5                   10                  15

Met Val Ala Gly Leu
            20

<210> SEQ ID NO 8
<211> LENGTH: 13
<212> TYPE: PRT
<213> ORGANISM: Influenza A virus

<400> SEQUENCE: 8

Ser Leu Trp Met Cys Ser Asn Gly Ser Leu Gln Cys Arg
1               5                   10

<210> SEQ ID NO 9
```

<211> LENGTH: 1815
<212> TYPE: DNA
<213> ORGANISM: Artificial Sequence
<220> FEATURE:
<223> OTHER INFORMATION: Synthetic HA construct

<400> SEQUENCE: 9
ggatccgaat tcaccatgcc gctctacaaa ttgctaaacg tgttatggtt agtcgctgtg 60
tccaacgcga ttcctggcag ctattaccat caccatcacc atcacgacta cgatattccg 120
acgaccgaaa acttgtattt tcaaggcgcg gatcaaattt gtataggtta ccatgcgaac 180
aatagcacgg aacaagtaga taccattatg gaaaagaacg tgacagttac acatgcgcag 240
gacattttgg aaaaaaagca caatggaaag ttgtgtgatc ttgacggggt caaaccacta 300
atcttacgtg actgttcagt ggcgggttgg ttgttaggca acccgatgtg cgatgaattt 360
attaatgtac cggagtggtc atatatcgtg gaaaaagcca accccgttaa cgacttgtgt 420
tatcctggtg attttaatga ctacgaggaa ttaaaacact tgctgtcacg tatcaatcac 480
tttgagaaaa tacaaataat ccccaaatct tcctggagta gccatgaggc ttcgttgggc 540
gtgagtagcg cctgccccta ccaaggcaaa tcgagttttt tccgaaacgt ggtatggcta 600
ataaaaaaga actcgacgta cccgacgatc aaaagatcgt ataacaatac gaaccaggaa 660
gacttgcttg tcttgtgggg tatccaccat ccgaacgacg ccgctgaaca gacaaaatta 720
tatcaaaacc ccactaccta catttcagta ggcacgagta cgctgaacca gcgccttgtg 780
ccacgaatag ccactaggtc taaggttaat ggccagtctg gtcgcatgga atttttctgg 840
actatactca aacctaacga tgctatcaac tttgagtcta atggcaactt tattgcccct 900
gaatacgcgt ataagattgt taaaaagggc gattcgacga ttatgaaatc ggaactcgaa 960
tatggtaatt gcaacaccaa atgtcaaact cccatgggcg ctattaacag ctccatgcca 1020
tttcacaata ttcacccgtt gactataggc gaatgtccaa aatatgtgaa gtccaatcgc 1080
ttggtactcg ccaccggctt gaggaatagc ccgcaacgtg agagacggag aaaaaagcgg 1140
ggattgtttg gcgccatcgc cggatttata gaaggtggct ggcaaggaat ggtggatggc 1200
tggtatggat accaccattc caacgaacaa ggttcaggct acgcggcaga caaagaatct 1260
actcaaaaag caatagacgg cgtgacaaat aaagtaaata gtataattga caaaatgaat 1320
acgcagtttg aagccgtcgg ccgtgagttc aataacctgg agcgcagaat tgaaaatcta 1380
aacaaaaaga tggaggacgg gtttttagac gtttggacgt acaatgcaga attgttagtt 1440
ttgatggaaa acgaacgcac cttggatttt cacgactcga acgttaaaaa cctgtacgat 1500
aaagtccgac tgcaattacg cgataatgca aaagaactgg gaaacggctg cttcgaattt 1560
tatcataaat gcgacaatga atgcatggaa tctgtacgaa atggtacata cgactatccc 1620
caatactcgg aggaagcgcg tctaaaacgc gaagagatta gcggggtgaa attagagagt 1680
attggaattt accaaatttt gagcatttat agcaccgttg catcgagtct tgcgttggca 1740
ataatggtcg cgggcttatc tttgtggatg tgcagcaacg gaagccttca atgtagataa 1800
ctgcagaagc tttaa 1815

<210> SEQ ID NO 10
<211> LENGTH: 599
<212> TYPE: PRT
<213> ORGANISM: Artificial Sequence
<220> FEATURE:
<223> OTHER INFORMATION: Synthetic HA construct

<400> SEQUENCE: 10

```
Gly Ser Glu Phe Thr Met Pro Leu Tyr Lys Leu Leu Asn Val Leu Trp
1               5                   10                  15

Leu Val Ala Val Ser Asn Ala Ile Pro Gly Ser Tyr Tyr His His
            20                  25                  30

His His His Asp Tyr Asp Ile Pro Thr Thr Glu Asn Leu Tyr Phe Gln
        35                  40                  45

Gly Ala Asp Gln Ile Cys Ile Gly Tyr His Ala Asn Asn Ser Thr Glu
50                  55                  60

Gln Val Asp Thr Ile Met Glu Lys Asn Val Thr Val Thr His Ala Gln
65                  70                  75                  80

Asp Ile Leu Glu Lys Lys His Asn Gly Lys Leu Cys Asp Leu Asp Gly
                85                  90                  95

Val Lys Pro Leu Ile Leu Arg Asp Cys Ser Val Ala Gly Trp Leu Leu
            100                 105                 110

Gly Asn Pro Met Cys Asp Glu Phe Ile Asn Val Pro Glu Trp Ser Tyr
            115                 120                 125

Ile Val Glu Lys Ala Asn Pro Val Asn Asp Leu Cys Tyr Pro Gly Asp
    130                 135                 140

Phe Asn Asp Tyr Glu Glu Leu Lys His Leu Leu Ser Arg Ile Asn His
145                 150                 155                 160

Phe Glu Lys Ile Gln Ile Ile Pro Lys Ser Ser Trp Ser Ser His Glu
            165                 170                 175

Ala Ser Leu Gly Val Ser Ser Ala Cys Pro Tyr Gln Gly Lys Ser Ser
            180                 185                 190

Phe Phe Arg Asn Val Val Trp Leu Ile Lys Lys Asn Ser Thr Tyr Pro
            195                 200                 205

Thr Ile Lys Arg Ser Tyr Asn Asn Thr Asn Gln Glu Asp Leu Leu Val
            210                 215                 220

Leu Trp Gly Ile His His Pro Asn Asp Ala Ala Glu Gln Thr Lys Leu
225                 230                 235                 240

Tyr Gln Asn Pro Thr Thr Tyr Ile Ser Val Gly Thr Ser Thr Leu Asn
            245                 250                 255

Gln Arg Leu Val Pro Arg Ile Ala Thr Arg Ser Lys Val Asn Gly Gln
            260                 265                 270

Ser Gly Arg Met Glu Phe Phe Trp Thr Ile Leu Lys Pro Asn Asp Ala
            275                 280                 285

Ile Asn Phe Glu Ser Asn Gly Asn Phe Ile Ala Pro Glu Tyr Ala Tyr
            290                 295                 300

Lys Ile Val Lys Lys Gly Asp Ser Thr Ile Met Lys Ser Glu Leu Glu
305                 310                 315                 320

Tyr Gly Asn Cys Asn Thr Lys Cys Gln Thr Pro Met Gly Ala Ile Asn
            325                 330                 335

Ser Ser Met Pro Phe His Asn Ile His Pro Leu Thr Ile Gly Glu Cys
            340                 345                 350

Pro Lys Tyr Val Lys Ser Asn Arg Leu Val Leu Ala Thr Gly Leu Arg
            355                 360                 365

Asn Ser Pro Gln Arg Glu Arg Arg Lys Lys Arg Gly Leu Phe Gly
            370                 375                 380

Ala Ile Ala Gly Phe Ile Glu Gly Gly Trp Gln Gly Met Val Asp Gly
385                 390                 395                 400

Trp Tyr Gly Tyr His His Ser Asn Glu Gln Gly Ser Gly Tyr Ala Ala
                405                 410                 415
```

-continued

```
Asp Lys Glu Ser Thr Gln Lys Ala Ile Asp Gly Val Thr Asn Lys Val
            420                 425                 430

Asn Ser Ile Ile Asp Lys Met Asn Thr Gln Phe Glu Ala Val Gly Arg
        435                 440                 445

Glu Phe Asn Asn Leu Glu Arg Arg Ile Glu Asn Leu Asn Lys Lys Met
    450                 455                 460

Glu Asp Gly Phe Leu Asp Val Trp Thr Tyr Asn Ala Glu Leu Leu Val
465                 470                 475                 480

Leu Met Glu Asn Glu Arg Thr Leu Asp Phe His Asp Ser Asn Val Lys
                485                 490                 495

Asn Leu Tyr Asp Lys Val Arg Leu Gln Leu Arg Asp Asn Ala Lys Glu
            500                 505                 510

Leu Gly Asn Gly Cys Phe Glu Phe Tyr His Lys Cys Asp Asn Glu Cys
        515                 520                 525

Met Glu Ser Val Arg Asn Gly Thr Tyr Asp Tyr Pro Gln Tyr Ser Glu
    530                 535                 540

Glu Ala Arg Leu Lys Arg Glu Glu Ile Ser Gly Val Lys Leu Glu Ser
545                 550                 555                 560

Ile Gly Ile Tyr Gln Ile Leu Ser Ile Tyr Ser Thr Val Ala Ser Ser
                565                 570                 575

Leu Ala Leu Ala Ile Met Val Ala Gly Leu Ser Leu Trp Met Cys Ser
            580                 585                 590

Asn Gly Ser Leu Gln Cys Arg
        595
```

<210> SEQ ID NO 11
<211> LENGTH: 1854
<212> TYPE: DNA
<213> ORGANISM: Artificial Sequence
<220> FEATURE:
<223> OTHER INFORMATION: Synthetic HA-PADRE construct

<400> SEQUENCE: 11

```
ggatccgaat tcaccatgcc gctctacaaa ttgctaaacg tgttatggtt agtcgctgtg     60
tccaacgcga ttcctggcag ctattaccat caccatcacc atcacgacta cgatattccg    120
acgaccgaaa acttgtattt tcaaggcgcg gatcaaattt gtataggtta ccatgcgaac    180
aatagcacgg aacaagtaga taccattatg gaaaagaacg tgacagttac acatgcgcag    240
gacattttgg aaaaaagca caatggaaag ttgtgtgatc ttgacggggt caaaccacta    300
atcttacgtg actgttcagt ggcgggttgg ttgttaggca acccgatgtg cgatgaattt    360
attaatgtac cggagtggtc atatatcgtg gaaaaagcca accccgttaa cgacttgtgt    420
tatcctggtg attttaatga ctacgaggaa ttaaaacact tgctgtcacg tatcaatcac    480
tttgagaaaa tacaaataat ccccaaatct tcctggagta gccatgaggc ttcgttgggc    540
gtgagtagcg cctgccccta ccaaggcaaa tcgagttttt tccgaaacgt ggtatggcta    600 ataaaaaga actcgacgta cccgacgatc aaaagatcgt ataacaatac gaaccaggaa    660
gacttgcttg tcttgtgggg tatccaccat ccgaacgacg ccgctgaaca gacaaaatta    720
tatcaaaacc ccactaccta catttcagta ggcacgagta cgctgaacca gcgccttgtg    780
ccacgaatag ccactaggtc taaggttaat ggccagtctg gtcgcatgga attttctgg    840 actatactca aacctaacga tgctatcaac tttgagtcta atggcaactt tattgcccct    900
gaatacgcgt ataagattgt taaaagggc gattcgacga ttatgaaatc ggaactcgaa    960
tatggtaatt gcaacaccaa atgtcaaact cccatgggcg ctattaacag ctccatgcca   1020
```

```
tttcacaata ttcacccgtt gactataggc gaatgtccaa atatgtgaa gtccaatcgc    1080 ttggtactcg ccaccggctt gaggaatagc ccgcaacgtg agagacggag aaaaaagcgg    1140
ggattgtttg gcgccatcgc cggatttata gaaggtggct ggcaaggaat ggtggatggc    1200
tggtatggat accaccattc caacgaacaa ggttcaggct acgcggcaga caaagaatct    1260
actcaaaaag caatagacgg cgtgacaaat aaagtaaata gtataattga caaatgaat    1320 acgcagtttg aagccgtcgg ccgtgagttc aataacctgg agcgcagaat tgaaaatcta    1380
aacaaaaaga tggaggacgg ttttttagac gtttggacgt acaatgcaga attgttagtt    1440
ttgatggaaa acgaacgcac cttggatttt cacgactcga acgttaaaaa cctgtacgat    1500
aaagtccgac tgcaattacg cgataatgca aaagaactgg aaacggctg cttcgaattt     1560 tatcataaat gcgacaatga atgcatggaa tctgtacgaa atggtacata cgactatccc    1620
caatactcgg aggaagcgcg tctaaaacgc gaagagatta gcggggtgaa attagagagt    1680
attggaattt accaaatttt gagcatttat agcaccgttg catcgagtct tgcgttggca    1740
ataatggtcg cgggcttatc tttgtggatg tgcagcaacg gaagccttca atgtagagca    1800
aaatttgtgg ccgcgtggac actgaaagct gcggcttaac tgcagaagct ttaa           1854
```

<210> SEQ ID NO 12
<211> LENGTH: 612
<212> TYPE: PRT
<213> ORGANISM: Artificial Sequence
<220> FEATURE:
<223> OTHER INFORMATION: Synthetic HA-PADRE construct

<400> SEQUENCE: 12

```
Gly Ser Glu Phe Thr Met Pro Leu Tyr Lys Leu Leu Asn Val Leu Trp
1               5                   10                  15

Leu Val Ala Val Ser Asn Ala Ile Pro Gly Ser Tyr Tyr His His His
            20                  25                  30

His His His Asp Tyr Asp Ile Pro Thr Thr Glu Asn Leu Tyr Phe Gln
        35                  40                  45

Gly Ala Asp Gln Ile Cys Ile Gly Tyr His Ala Asn Asn Ser Thr Glu
    50                  55                  60

Gln Val Asp Thr Ile Met Glu Lys Asn Val Thr Val Thr His Ala Gln
65                  70                  75                  80

Asp Ile Leu Glu Lys Lys His Asn Gly Lys Leu Cys Asp Leu Asp Gly
                85                  90                  95

Val Lys Pro Leu Ile Leu Arg Asp Cys Ser Val Ala Gly Trp Leu Leu
            100                 105                 110

Gly Asn Pro Met Cys Asp Glu Phe Ile Asn Val Pro Glu Trp Ser Tyr
        115                 120                 125

Ile Val Glu Lys Ala Asn Pro Val Asn Asp Leu Cys Tyr Pro Gly Asp
    130                 135                 140

Phe Asn Asp Tyr Glu Glu Leu Lys His Leu Leu Ser Arg Ile Asn His
145                 150                 155                 160

Phe Glu Lys Ile Gln Ile Ile Pro Lys Ser Ser Trp Ser Ser His Glu
                165                 170                 175

Ala Ser Leu Gly Val Ser Ser Ala Cys Pro Tyr Gln Gly Lys Ser Ser
            180                 185                 190

Phe Phe Arg Asn Val Val Trp Leu Ile Lys Lys Asn Ser Thr Tyr Pro
        195                 200                 205

Thr Ile Lys Arg Ser Tyr Asn Asn Thr Asn Gln Glu Asp Leu Leu Val
```

```
            210                 215                 220
Leu Trp Gly Ile His His Pro Asn Asp Ala Ala Glu Gln Thr Lys Leu
225                 230                 235                 240

Tyr Gln Asn Pro Thr Thr Tyr Ile Ser Val Gly Thr Ser Thr Leu Asn
                245                 250                 255

Gln Arg Leu Val Pro Arg Ile Ala Thr Arg Ser Lys Val Asn Gly Gln
                260                 265                 270

Ser Gly Arg Met Glu Phe Phe Trp Thr Ile Leu Lys Pro Asn Asp Ala
            275                 280                 285

Ile Asn Phe Glu Ser Asn Gly Asn Phe Ile Ala Pro Glu Tyr Ala Tyr
        290                 295                 300

Lys Ile Val Lys Lys Gly Asp Ser Thr Ile Met Lys Ser Glu Leu Glu
305                 310                 315                 320

Tyr Gly Asn Cys Asn Thr Lys Cys Gln Thr Pro Met Gly Ala Ile Asn
                325                 330                 335

Ser Ser Met Pro Phe His Asn Ile His Pro Leu Thr Ile Gly Glu Cys
                340                 345                 350

Pro Lys Tyr Val Lys Ser Asn Arg Leu Val Leu Ala Thr Gly Leu Arg
            355                 360                 365

Asn Ser Pro Gln Arg Glu Arg Arg Lys Lys Arg Gly Leu Phe Gly
        370                 375                 380

Ala Ile Ala Gly Phe Ile Glu Gly Gly Trp Gln Gly Met Val Asp Gly
385                 390                 395                 400

Trp Tyr Gly Tyr His His Ser Asn Glu Gln Gly Ser Gly Tyr Ala Ala
                405                 410                 415

Asp Lys Glu Ser Thr Gln Lys Ala Ile Asp Gly Val Thr Asn Lys Val
            420                 425                 430

Asn Ser Ile Ile Asp Lys Met Asn Thr Gln Phe Glu Ala Val Gly Arg
        435                 440                 445

Glu Phe Asn Asn Leu Glu Arg Arg Ile Glu Asn Leu Asn Lys Lys Met
450                 455                 460

Glu Asp Gly Phe Leu Asp Val Trp Thr Tyr Asn Ala Glu Leu Leu Val
465                 470                 475                 480

Leu Met Glu Asn Glu Arg Thr Leu Asp Phe His Asp Ser Asn Val Lys
                485                 490                 495

Asn Leu Tyr Asp Lys Val Arg Leu Gln Leu Arg Asp Asn Ala Lys Glu
            500                 505                 510

Leu Gly Asn Gly Cys Phe Glu Phe Tyr His Lys Cys Asp Asn Glu Cys
        515                 520                 525

Met Glu Ser Val Arg Asn Gly Thr Tyr Asp Tyr Pro Gln Tyr Ser Glu
            530                 535                 540

Glu Ala Arg Leu Lys Arg Glu Glu Ile Ser Gly Val Lys Leu Glu Ser
545                 550                 555                 560

Ile Gly Ile Tyr Gln Ile Leu Ser Ile Tyr Ser Thr Val Ala Ser Ser
                565                 570                 575

Leu Ala Leu Ala Ile Met Val Ala Gly Leu Ser Leu Trp Met Cys Ser
            580                 585                 590

Asn Gly Ser Leu Gln Cys Arg Ala Lys Phe Val Ala Ala Trp Thr Leu
        595                 600                 605

Lys Ala Ala Ala
610

<210> SEQ ID NO 13
```

<211> LENGTH: 1854
<212> TYPE: DNA
<213> ORGANISM: Artificial Sequence
<220> FEATURE:
<223> OTHER INFORMATION: Synthetic PADRE-HA construct

<400> SEQUENCE: 13

| | | | | | |
|---|---|---|---|---|---|
| ggatccgaat | tcaccatgcc | gctctacaaa | ttgctaaacg | tgttatggtt | agtcgctgtg | 60 |
| tccaacgcga | ttcctggcag | ctattaccat | caccatcacc | atcacgacta | cgatattccg | 120 |
| acgaccgaaa | acttgtattt | tcaaggcgcg | gcaaaatttg | tggccgcgtg | gacactgaaa | 180 |
| gctgcggctg | atcaaatttg | tataggttac | catgcgaaca | atagcacgga | acaagtagat | 240 |
| accattatgg | aaaagaacgt | gacagttaca | catgcgcagg | acattttgga | aaaaaagcac | 300 |
| aatggaaagt | tgtgtgatct | tgacggggtc | aaaccactaa | tcttacgtga | ctgttcagtg | 360 |
| gcgggttggt | tgttaggcaa | cccgatgtgc | gatgaattta | ttaatgtacc | ggagtggtca | 420 |
| tatatcgtgg | aaaaagccaa | ccccgttaac | gacttgtgtt | atcctggtga | ttttaatgac | 480 |
| tacgaggaat | taaaacactt | gctgtcacgt | atcaatcact | ttgagaaaat | acaaataatc | 540 |
| cccaaatctt | cctggagtag | ccatgaggct | tcgttgggcg | tgagtagcgc | ctgcccctac | 600 |
| caaggcaaat | cgagtttttt | ccgaaacgtg | gtatggctaa | taaaaaagaa | ctcgacgtac | 660 |
| ccgacgatca | aaagatcgta | taacaatacg | aaccaggaag | acttgcttgt | cttgtggggt | 720 |
| atccaccatc | cgaacgacgc | cgctgaacag | acaaaattat | atcaaaaccc | cactacctac | 780 |
| atttcagtag | gcacgagtac | gctgaaccag | cgccttgtgc | acgaatagc | cactaggtct | 840 |
| aaggttaatg | gccagtctgg | tcgcatggaa | ttttctgga | ctatactcaa | acctaacgat | 900 |
| gctatcaact | ttgagtctaa | tggcaacttt | attgcccctg | aatacgcgta | taagattgtt | 960 |
| aaaaagggcg | attcgacgat | tatgaaatcg | gaactcgaat | atggtaattg | caacaccaaa | 1020 |
| tgtcaaactc | ccatgggcgc | tattaacagc | tccatgccat | ttcacaatat | tcacccgttg | 1080 |
| actataggcg | aatgtccaaa | atatgtgaag | tccaatcgct | tggtactcgc | caccggcttg | 1140 |
| aggaatagcc | cgcaacgtga | gagacggaga | aaaaagcggg | gattgtttgg | cgccatcgcc | 1200 |
| ggatttatag | aaggtggctg | gcaaggaatg | gtggatggcg | gtatggata | ccaccattcc | 1260 |
| aacgaacaag | gttcaggcta | cgcggcagac | aaagaatcta | ctcaaaaagc | aatagacggc | 1320 |
| gtgacaaata | aagtaaatag | tataattgac | aaaatgaata | cgcagtttga | agccgtcggc | 1380 |
| cgtgagttca | ataacctgga | gcgcagaatt | gaaaatctaa | acaaaaagat | ggaggacggg | 1440 |
| ttttagacg | tttggacgta | caatgcagaa | ttgttagttt | tgatggaaaa | cgaacgcacc | 1500 |
| ttggattttc | acgactcgaa | cgttaaaaac | ctgtacgata | agtccgact | gcaattacgc | 1560 |
| gataatgcaa | aagaactggg | aaacggctgc | ttcgaatttt | atcataaatg | cgacaatgaa | 1620 |
| tgcatggaat | ctgtacgaaa | tggtacatac | gactatcccc | aatactcgga | ggaagcgcgt | 1680 |
| ctaaaacgcg | aagagattag | cggggtgaaa | ttagagagta | ttggaattta | ccaaatttg | 1740 |
| agcatttata | gcaccgttgc | atcgagtctt | gcgttggcaa | taatggtcgc | gggcttatct | 1800 |
| ttgtggatgt | gcagcaacgg | aagccttcaa | tgtagataac | tgcagaagct | ttaa | 1854 |

<210> SEQ ID NO 14
<211> LENGTH: 612
<212> TYPE: PRT
<213> ORGANISM: Artificial Sequence
<220> FEATURE:
<223> OTHER INFORMATION: Synthetic PADRE-HA construct

<400> SEQUENCE: 14

```
Gly Ser Glu Phe Thr Met Pro Leu Tyr Lys Leu Leu Asn Val Leu Trp
1               5                   10                  15

Leu Val Ala Val Ser Asn Ala Ile Pro Gly Ser Tyr Tyr His His
            20                  25                  30

His His His Asp Tyr Asp Ile Pro Thr Thr Glu Asn Leu Tyr Phe Gln
        35                  40                  45

Gly Ala Ala Lys Phe Val Ala Ala Trp Thr Leu Lys Ala Ala Ala Asp
50                  55                  60

Gln Ile Cys Ile Gly Tyr His Ala Asn Asn Ser Thr Glu Gln Val Asp
65                  70                  75                  80

Thr Ile Met Glu Lys Asn Val Thr Val Thr His Ala Gln Asp Ile Leu
                85                  90                  95

Glu Lys Lys His Asn Gly Lys Leu Cys Asp Leu Asp Gly Val Lys Pro
                100                 105                 110

Leu Ile Leu Arg Asp Cys Ser Val Ala Gly Trp Leu Leu Gly Asn Pro
            115                 120                 125

Met Cys Asp Glu Phe Ile Asn Val Pro Glu Trp Ser Tyr Ile Val Glu
        130                 135                 140

Lys Ala Asn Pro Val Asn Asp Leu Cys Tyr Pro Gly Asp Phe Asn Asp
145                 150                 155                 160

Tyr Glu Glu Leu Lys His Leu Leu Ser Arg Ile Asn His Phe Glu Lys
                165                 170                 175

Ile Gln Ile Ile Pro Lys Ser Ser Trp Ser Ser His Glu Ala Ser Leu
                180                 185                 190

Gly Val Ser Ser Ala Cys Pro Tyr Gln Gly Lys Ser Ser Phe Phe Arg
            195                 200                 205

Asn Val Val Trp Leu Ile Lys Lys Asn Ser Thr Tyr Pro Thr Ile Lys
        210                 215                 220

Arg Ser Tyr Asn Asn Thr Asn Gln Glu Asp Leu Leu Val Leu Trp Gly
225                 230                 235                 240

Ile His His Pro Asn Asp Ala Ala Glu Gln Thr Lys Leu Tyr Gln Asn
                245                 250                 255

Pro Thr Thr Tyr Ile Ser Val Gly Thr Ser Thr Leu Asn Gln Arg Leu
                260                 265                 270

Val Pro Arg Ile Ala Thr Arg Ser Lys Val Asn Gly Gln Ser Gly Arg
            275                 280                 285

Met Glu Phe Phe Trp Thr Ile Leu Lys Pro Asn Asp Ala Ile Asn Phe
        290                 295                 300

Glu Ser Asn Gly Asn Phe Ile Ala Pro Glu Tyr Ala Tyr Lys Ile Val
305                 310                 315                 320

Lys Lys Gly Asp Ser Thr Ile Met Lys Ser Glu Leu Glu Tyr Gly Asn
                325                 330                 335

Cys Asn Thr Lys Cys Gln Thr Pro Met Gly Ala Ile Asn Ser Ser Met
                340                 345                 350

Pro Phe His Asn Ile His Pro Leu Thr Ile Gly Glu Cys Pro Lys Tyr
            355                 360                 365

Val Lys Ser Asn Arg Leu Val Leu Ala Thr Gly Leu Arg Asn Ser Pro
        370                 375                 380

Gln Arg Glu Arg Arg Arg Lys Lys Arg Gly Leu Phe Gly Ala Ile Ala
385                 390                 395                 400

Gly Phe Ile Glu Gly Gly Trp Gln Gly Met Val Asp Gly Trp Tyr Gly
                405                 410                 415
```

Tyr His His Ser Asn Glu Gln Gly Ser Gly Tyr Ala Ala Asp Lys Glu
            420                 425                 430

Ser Thr Gln Lys Ala Ile Asp Gly Val Thr Asn Lys Val Asn Ser Ile
    435                 440                 445

Ile Asp Lys Met Asn Thr Gln Phe Glu Ala Val Gly Arg Glu Phe Asn
450                 455                 460

Asn Leu Glu Arg Arg Ile Glu Asn Leu Asn Lys Lys Met Glu Asp Gly
465                 470                 475                 480

Phe Leu Asp Val Trp Thr Tyr Asn Ala Glu Leu Leu Val Leu Met Glu
                485                 490                 495

Asn Glu Arg Thr Leu Asp Phe His Asp Ser Asn Val Lys Asn Leu Tyr
            500                 505                 510

Asp Lys Val Arg Leu Gln Leu Arg Asp Asn Ala Lys Glu Leu Gly Asn
            515                 520                 525

Gly Cys Phe Glu Phe Tyr His Lys Cys Asp Asn Glu Cys Met Glu Ser
            530                 535                 540

Val Arg Asn Gly Thr Tyr Asp Tyr Pro Gln Tyr Ser Glu Glu Ala Arg
545                 550                 555                 560

Leu Lys Arg Glu Glu Ile Ser Gly Val Lys Leu Glu Ser Ile Gly Ile
                565                 570                 575

Tyr Gln Ile Leu Ser Ile Tyr Ser Thr Val Ala Ser Ser Leu Ala Leu
            580                 585                 590

Ala Ile Met Val Ala Gly Leu Ser Leu Trp Met Cys Ser Asn Gly Ser
            595                 600                 605

Leu Gln Cys Arg
    610

<210> SEQ ID NO 15
<211> LENGTH: 23
<212> TYPE: PRT
<213> ORGANISM: Influenza A virus

<400> SEQUENCE: 15

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 16
<211> LENGTH: 17
<212> TYPE: PRT
<213> ORGANISM: Artificial Sequence
<220> FEATURE:
<223> OTHER INFORMATION: Influenza epitope

<400> SEQUENCE: 16

Met Glu Lys Ile Val Leu Leu Phe Ala Ile Val Ser Leu Val Lys Ser
1               5                   10                  15

Asp

<210> SEQ ID NO 17
<211> LENGTH: 15
<212> TYPE: PRT
<213> ORGANISM: Artificial Sequence
<220> FEATURE:
<223> OTHER INFORMATION: Influenza epitope

<400> SEQUENCE: 17

Val Ser Leu Val Lys Ser Asp Gln Ile Cys Ile Gly Tyr His Ala

```
1               5              10              15
```

<210> SEQ ID NO 18
<211> LENGTH: 15
<212> TYPE: PRT
<213> ORGANISM: Artificial Sequence
<220> FEATURE:
<223> OTHER INFORMATION: Influenza epitope

<400> SEQUENCE: 18

```
Lys Ser Ser Phe Phe Arg Asn Val Val Trp Leu Ile Lys Lys Asn
1               5                  10                  15
```

<210> SEQ ID NO 19
<211> LENGTH: 16
<212> TYPE: PRT
<213> ORGANISM: Artificial Sequence
<220> FEATURE:
<223> OTHER INFORMATION: Influenza epitope

<400> SEQUENCE: 19

```
Val Val Trp Leu Ile Lys Lys Asn Ser Thr Tyr Pro Thr Ile Lys Arg
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Influenza epitope

<400> SEQUENCE: 20

```
Gln Thr Lys Leu Tyr Gln Asn Pro Thr Thr Tyr Ile Ser Val Gly Thr
1               5                   10                  15
```

<210> SEQ ID NO 21
<211> LENGTH: 16
<212> TYPE: PRT
<213> ORGANISM: Artificial Sequence
<220> FEATURE:
<223> OTHER INFORMATION: Influenza epitope

<400> SEQUENCE: 21

```
Pro Thr Thr Tyr Ile Ser Val Gly Thr Ser Thr Leu Asn Gln Arg Leu
1               5                   10                  15
```

<210> SEQ ID NO 22
<211> LENGTH: 15
<212> TYPE: PRT
<213> ORGANISM: Artificial Sequence
<220> FEATURE:
<223> OTHER INFORMATION: Influenza epitope

<400> SEQUENCE: 22

```
Arg Met Glu Phe Phe Trp Thr Ile Leu Lys Pro Asn Asp Ala Ile
1               5                  10                  15
```

<210> SEQ ID NO 23
<211> LENGTH: 15
<212> TYPE: PRT
<213> ORGANISM: Artificial Sequence
<220> FEATURE:
<223> OTHER INFORMATION: Influenza epitope

<400> SEQUENCE: 23

```
Trp Thr Ile Leu Lys Pro Asn Asp Ala Ile Asn Phe Glu Ser Asn
1               5                  10                  15
```

```
<210> SEQ ID NO 24
<211> LENGTH: 16
<212> TYPE: PRT
<213> ORGANISM: Artificial Sequence
<220> FEATURE:
<223> OTHER INFORMATION: Influenza epitope

<400> SEQUENCE: 24

Cys Pro Lys Tyr Val Lys Ser Asn Arg Leu Val Leu Ala Thr Gly Leu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Influenza epitope

<400> SEQUENCE: 25

Asn Arg Leu Val Leu Ala Thr Gly Leu Arg Asn Ser Pro Gln Arg
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Influenza epitope

<400> SEQUENCE: 26

Glu Leu Leu Val Leu Met Glu Asn Glu Arg Thr Leu Asp Phe His Asp
1               5                   10                  15

Ser

<210> SEQ ID NO 27
<211> LENGTH: 15
<212> TYPE: PRT
<213> ORGANISM: Artificial Sequence
<220> FEATURE:
<223> OTHER INFORMATION: Influenza epitope

<400> SEQUENCE: 27

Leu Leu Val Leu Met Glu Asn Glu Arg Thr Leu Asp Phe His Asp
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Influenza epitope

<400> SEQUENCE: 28

Ile Ser Gly Val Lys Leu Glu Ser Ile Gly Ile Tyr Gln Ile Leu Ser
1               5                   10                  15

Ile

<210> SEQ ID NO 29
<211> LENGTH: 16
<212> TYPE: PRT
<213> ORGANISM: Artificial Sequence
<220> FEATURE:
<223> OTHER INFORMATION: Influenza epitope

<400> SEQUENCE: 29
```

-continued

Ile Tyr Gln Ile Leu Ser Ile Tyr Ser Thr Val Ala Ser Ser Leu Ala
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Influenza epitope

<400> SEQUENCE: 30

Ile Leu Ser Ile Tyr Ser Thr Val Ala Ser Ser Leu Ala Leu Ala Ile
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Influenza epitope

<400> SEQUENCE: 31

Ser Gly Pro Leu Lys Ala Glu Ile Ala Gln Arg Leu Glu Asp Val
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Influenza epitope

<400> SEQUENCE: 32

Glu Ala Leu Met Glu Trp Leu Lys Thr Arg Pro Ile Leu Ser Pro
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Influenza epitope

<400> SEQUENCE: 33

Met Glu Trp Leu Lys Thr Arg Pro Ile Leu Ser Pro Leu Thr Lys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Influenza epitope

<400> SEQUENCE: 34

Thr Arg Pro Ile Leu Ser Pro Leu Thr Lys Gly Ile Leu Gly Phe
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Influenza epitope

<400> SEQUENCE: 35

```
Lys Gly Ile Leu Gly Phe Val Phe Thr Leu Thr Val Pro Ser Glu
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Influenza epitope

<400> SEQUENCE: 36

Tyr Arg Lys Leu Lys Arg Glu Ile Thr Phe His Gly Ala Lys Glu
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Influenza epitope

<400> SEQUENCE: 37

Met Gly Thr Val Thr Thr Glu Val Ala Leu Gly Leu Val Cys Ala
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Influenza epitope

<400> SEQUENCE: 38

Cys Glu Gln Ile Ala Asp Ser Gln His Arg Ser His Arg Gln Met
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Influenza epitope

<400> SEQUENCE: 39

Asn Pro Leu Ile Arg His Glu Asn Arg Met Val Leu Ala Ser Thr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Influenza epitope

<400> SEQUENCE: 40

Ala Met Glu Val Ala Ser Gln Ala Arg Gln Met Val Gln Ala Met
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Influenza epitope

<400> SEQUENCE: 41

Ser Ala Gly Leu Lys Asp Asp Leu Ile Glu Asn Leu Gln Ala Tyr
```

```
1               5                  10                 15
```

<210> SEQ ID NO 42
<211> LENGTH: 15
<212> TYPE: PRT
<213> ORGANISM: Artificial Sequence
<220> FEATURE:
<223> OTHER INFORMATION: Influenza epitope

<400> SEQUENCE: 42

```
Asp Pro Leu Val Val Ala Ala Ser Ile Ile Gly Ile Leu His Leu
1               5                  10                 15
```

<210> SEQ ID NO 43
<211> LENGTH: 15
<212> TYPE: PRT
<213> ORGANISM: Artificial Sequence
<220> FEATURE:
<223> OTHER INFORMATION: Influenza epitope

<400> SEQUENCE: 43

```
Pro Glu Ser Met Arg Glu Glu Tyr Arg Lys Glu Gln Gln Ser Ala
1               5                  10                 15
```

<210> SEQ ID NO 44
<211> LENGTH: 17
<212> TYPE: PRT
<213> ORGANISM: Artificial Sequence
<220> FEATURE:
<223> OTHER INFORMATION: Influenza epitope

<400> SEQUENCE: 44

```
Ser Leu Met Leu Gln Ile Gly Asn Met Ile Ser Ile Trp Val Ser His
1               5                  10                 15

Ser
```

<210> SEQ ID NO 45
<211> LENGTH: 16
<212> TYPE: PRT
<213> ORGANISM: Artificial Sequence
<220> FEATURE:
<223> OTHER INFORMATION: Influenza epitope

<400> SEQUENCE: 45

```
Ile Gly Asn Met Ile Ser Ile Trp Val Ser His Ser Ile His Thr Gly
1               5                  10                 15
```

<210> SEQ ID NO 46
<211> LENGTH: 16
<212> TYPE: PRT
<213> ORGANISM: Artificial Sequence
<220> FEATURE:
<223> OTHER INFORMATION: Influenza epitope

<400> SEQUENCE: 46

```
Asn Thr Asn Phe Leu Thr Glu Lys Ala Val Ala Ser Val Lys Leu Ala
1               5                  10                 15
```

<210> SEQ ID NO 47
<211> LENGTH: 15
<212> TYPE: PRT
<213> ORGANISM: Artificial Sequence
<220> FEATURE:
<223> OTHER INFORMATION: Influenza epitope

<400> SEQUENCE: 47

Trp Ala Val Tyr Ser Lys Asp Asn Ser Ile Arg Ile Gly Ser Lys
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Influenza epitope

<400> SEQUENCE: 48

Gly Asp Val Phe Val Ile Arg Glu Pro Phe Ile Ser Cys Ser His Leu
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Influenza epitope

<400> SEQUENCE: 49

Arg Thr Phe Phe Leu Thr Gln Gly Ala Leu Leu Asn Asp Lys His Ser
1               5                   10                  15

<210> SEQ ID NO 50
<211> LENGTH: 17
<212> TYPE: PRT
<213> ORGANISM: Artificial Sequence
<220> FEATURE:
<223> OTHER INFORMATION: Influenza epitope

<400> SEQUENCE: 50

Thr Gln Gly Ala Leu Leu Asn Asp Lys His Ser Asn Gly Thr Val Lys
1               5                   10                  15

Asp

<210> SEQ ID NO 51
<211> LENGTH: 15
<212> TYPE: PRT
<213> ORGANISM: Artificial Sequence
<220> FEATURE:
<223> OTHER INFORMATION: Influenza epitope

<400> SEQUENCE: 51

Asn Gly Thr Val Lys Asp Arg Ser Pro His Arg Thr Leu Met Ser
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: Influenza epitope

<400> SEQUENCE: 52

Val Ala Val Leu Lys Tyr Asn Gly Ile Ile Thr Asp Thr Ile Lys Ser
1               5                   10                  15

Trp

<210> SEQ ID NO 53
<211> LENGTH: 16
<212> TYPE: PRT
<213> ORGANISM: Artificial Sequence
<220> FEATURE:
<223> OTHER INFORMATION: Influenza epitope

<400> SEQUENCE: 53

Tyr Asn Gly Ile Ile Thr Asp Thr Ile Lys Ser Trp Arg Asn Asn Ile
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Influenza epitope

<400> SEQUENCE: 54

Asn Asn Ile Leu Arg Thr Gln Glu Ser Glu Cys Ala Cys Val Asn
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: Influenza epitope

<400> SEQUENCE: 55

His Lys Ile Phe Lys Met Glu Lys Gly Lys Val Val Lys Ser Val Glu
1               5                   10                  15

Leu

<210> SEQ ID NO 56
<211> LENGTH: 15
<212> TYPE: PRT
<213> ORGANISM: Artificial Sequence
<220> FEATURE:
<223> OTHER INFORMATION: Influenza epitope

<400> SEQUENCE: 56

Val Lys Ser Val Glu Leu Asp Ala Pro Asn Tyr His Tyr Glu Glu
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Influenza epitope

<400> SEQUENCE: 57

Asn Leu Glu Tyr Gln Ile Gly Tyr Ile Cys Ser Gly Val Phe Gly
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Influenza epitope

<400> SEQUENCE: 58

Ile Gly Arg Phe Tyr Ile Gln Met Cys Thr Glu Leu Lys Leu Ser
1               5                   10                  15

<210> SEQ ID NO 59
<211> LENGTH: 15
<212> TYPE: PRT
<213> ORGANISM: Artificial Sequence
<220> FEATURE:

```
<223> OTHER INFORMATION: Influenza epitope

<400> SEQUENCE: 59

Tyr Ile Gln Met Cys Thr Glu Leu Lys Leu Ser Asp Tyr Glu Gly
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Influenza epitope

<400> SEQUENCE: 60

Glu Gly Arg Leu Ile Gln Asn Ser Ile Thr Ile Glu Arg Met Val
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: Influenza epitope

<400> SEQUENCE: 61

Gln Asn Ser Ile Thr Ile Glu Arg Met Val Leu Ser Ala Phe Asp
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: Influenza epitope

<400> SEQUENCE: 62

Val Leu Ser Ala Phe Asp Glu Arg Arg Asn Arg Tyr Leu Glu Glu
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Influenza epitope

<400> SEQUENCE: 63

Arg Glu Leu Ile Leu Tyr Asp Lys Glu Glu Ile Arg Arg Ile Trp
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Influenza epitope

<400> SEQUENCE: 64

Leu Ile Leu Tyr Asp Lys Glu Glu Ile Arg Arg Ile Trp Arg Gln
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Influenza epitope
```

```
<400> SEQUENCE: 65

Val Gly Thr Met Val Met Glu Leu Ile Arg Met Ile Lys Arg Gly
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Influenza epitope

<400> SEQUENCE: 66

Gln Lys Ala Met Met Asp Gln Val Arg Glu Ser Arg Asn Pro Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Influenza epitope

<400> SEQUENCE: 67

Asp Leu Ile Phe Leu Ala Arg Ser Ala Leu Ile Leu Arg Gly Ser
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Influenza epitope

<400> SEQUENCE: 68

Leu Ile Phe Leu Ala Arg Ser Ala Leu Ile Leu Arg Gly Ser Val
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Influenza epitope

<400> SEQUENCE: 69

Arg Ser Ala Leu Ile Leu Arg Gly Ser Val Ala His Lys Ser Cys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Influenza epitope

<400> SEQUENCE: 70

Lys Ser Gln Leu Val Trp Met Ala Cys His Ser Ala Ala Phe Glu
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Influenza epitope
```

```
<400> SEQUENCE: 71

Ala Gly Gln Ile Ser Val Gln Pro Thr Phe Ser Val Gln Arg Asn
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Influenza epitope

<400> SEQUENCE: 72

Gly Ser Tyr Phe Phe Gly Asp Asn Ala Glu Glu Tyr Asp Asn
1               5                   10

<210> SEQ ID NO 73
<211> LENGTH: 15
<212> TYPE: PRT
<213> ORGANISM: Artificial Sequence
<220> FEATURE:
<223> OTHER INFORMATION: Influenza epitope

<400> SEQUENCE: 73

Leu Asp Arg Leu Arg Arg Asp Gln Lys Ser Leu Arg Gly Arg Gly
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Influenza epitope

<400> SEQUENCE: 74

Val Glu Arg Ile Leu Lys Glu Glu Ser Asp Glu Ala Leu Lys Met
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Influenza epitope

<400> SEQUENCE: 75

Ala Ser Arg Tyr Leu Thr Asp Met Thr Ile Glu Glu Met Ser Arg
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Influenza epitope

<400> SEQUENCE: 76

Leu Thr Asp Met Thr Ile Glu Glu Met Ser Arg Asp Trp Phe Met
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Influenza epitope

<400> SEQUENCE: 77
```

```
Leu Glu Glu Met Ser Arg Asp Trp Leu Met Leu Ile Pro Lys Gln
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Influenza epitope

<400> SEQUENCE: 78

Ser Leu Cys Ile Arg Met Asp Gln Ala Ile Met Asp Lys Asp Ile
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Influenza epitope

<400> SEQUENCE: 79

Gln Ala Ile Met Asp Lys Asp Ile Ile Leu Lys Ala Asn Phe Ser
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Influenza epitope

<400> SEQUENCE: 80

Asn Phe Ser Val Ile Phe Asp Arg Leu Glu Thr Leu Ile Leu Leu
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Influenza epitope

<400> SEQUENCE: 81

Glu Gly Ala Ile Val Gly Glu Ile Ser Pro Leu Pro Ser Leu Pro
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Influenza epitope

<400> SEQUENCE: 82

Val Gly Glu Ile Ser Pro Leu Pro Ser Leu Pro Gly His Thr Asp
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Influenza epitope

<400> SEQUENCE: 83
```

Asp Ile Leu Met Arg Met Ser Lys Met Gln Leu Gly Ser Ser Ser
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Influenza epitope

<400> SEQUENCE: 84

Ser Leu Lys Leu Tyr Arg Asp Ser Leu Gly Glu Ala Val Met Arg
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Influenza epitope

<400> SEQUENCE: 85

Val Met Arg Met Gly Asp Leu His Ser Leu Gln Asn Arg Asn Gly
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Influenza epitope

<400> SEQUENCE: 86

Ile Arg Trp Leu Ile Glu Glu Val Arg His Arg Leu Arg Ile Thr
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Influenza epitope

<400> SEQUENCE: 87

Phe Glu Gln Ile Thr Phe Met Gln Ala Leu Gln Leu Leu Leu Glu
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Influenza epitope

<400> SEQUENCE: 88

Ile Thr Phe Met Gln Ala Leu Gln Leu Leu Leu Glu Val Glu Gln
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Influenza epitope

<400> SEQUENCE: 89

Ala Leu Gln Leu Leu Phe Glu Val Glu Gln Glu Ile Arg Thr Phe

```
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Influenza epitope

<400> SEQUENCE: 90

Gln Leu Leu Leu Glu Val Glu Gln Glu Ile Arg Thr Phe Ser Phe
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Influenza epitope

<400> SEQUENCE: 91

Leu Phe Glu Val Glu Gln Glu Ile Arg Thr Phe Ser Phe Gln Leu
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Influenza epitope

<400> SEQUENCE: 92

Phe Asn Pro Met Ile Val Glu Leu Ala Glu Lys Thr Met Lys Glu
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Influenza epitope

<400> SEQUENCE: 93

Gly Glu Ser Ile Ile Val Glu Leu Asp Asp Pro Asn Ala Leu Leu
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Influenza epitope

<400> SEQUENCE: 94

Arg Arg Glu Val His Ile Tyr Tyr Leu Glu Lys Ala Asn Lys Ile
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Influenza epitope

<400> SEQUENCE: 95

Asp Tyr Thr Leu Asp Glu Glu Ser Arg Ala Arg Ile Lys Thr Arg
1               5                   10                  15
```

<210> SEQ ID NO 96
<211> LENGTH: 15
<212> TYPE: PRT
<213> ORGANISM: Artificial Sequence
<220> FEATURE:
<223> OTHER INFORMATION: Influenza epitope

<400> SEQUENCE: 96

Leu Phe Thr Ile Arg Gln Glu Met Ala Ser Arg Gly Leu Trp Asp
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Influenza epitope

<400> SEQUENCE: 97

Arg Phe Glu Ile Thr Gly Thr Met Arg Arg Leu Ala Asp Gln Ser
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Influenza epitope

<400> SEQUENCE: 98

Glu Pro Phe Leu Lys Thr Thr Pro Arg Pro Leu Arg Leu Pro Asp
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Influenza epitope

<400> SEQUENCE: 99

Arg Ser Lys Phe Leu Leu Met Asp Ala Leu Lys Leu Ser Ile Glu Asp
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Influenza epitope

<400> SEQUENCE: 100

Leu Gln Asp Ile Glu Asn Glu Glu Lys Ile Pro Arg Thr Lys Asn
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Influenza epitope

<400> SEQUENCE: 101

Leu Lys Gln Tyr Asp Ser Asp Glu Pro Glu Leu Arg Ser Leu Ser
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Influenza epitope

<400> SEQUENCE: 102

Ser Ile Trp Ile Glu Leu Asp Glu Ile Gly Glu Asp Val Ala Pro
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Influenza epitope

<400> SEQUENCE: 103

Leu Asp Glu Ile Gly Glu Asp Val Ala Pro Ile Glu His Ile Ala
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Influenza epitope

<400> SEQUENCE: 104

Val Ala Pro Ile Glu His Ile Ala Ser Met Arg Arg Asn Tyr Phe
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Influenza epitope

<400> SEQUENCE: 105

Arg Asn Tyr Phe Thr Ala Glu Val Ser His Cys Arg Ala Thr Glu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Influenza epitope

<400> SEQUENCE: 106

Glu Tyr Ile Met Lys Gly Val Tyr Ile Asn Thr Ala Leu Leu Asn
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Influenza epitope

<400> SEQUENCE: 107

Arg Ser His Leu Arg Asn Asp Thr Asp Val Val Asn Phe Val Ser
1               5                   10                  15

```
<210> SEQ ID NO 108
<211> LENGTH: 15
<212> TYPE: PRT
<213> ORGANISM: Artificial Sequence
<220> FEATURE:
<223> OTHER INFORMATION: Influenza epitope

<400> SEQUENCE: 108

Val Asn Phe Val Ser Met Glu Phe Ser Leu Thr Asp Pro Arg Leu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Influenza epitope

<400> SEQUENCE: 109

Arg Pro Met Phe Leu Tyr Val Arg Thr Asn Gly Thr Ser Lys Ile
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Influenza epitope

<400> SEQUENCE: 110

Gly Met Glu Met Arg Arg Cys Leu Leu Gln Ser Leu Gln Gln Ile
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Influenza epitope

<400> SEQUENCE: 111

Glu Ser Met Ile Glu Ala Glu Ser Ser Val Lys Glu Lys Asp Met
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Influenza epitope

<400> SEQUENCE: 112

Leu Glu Gly Phe Ser Ala Glu Ser Arg Lys Leu Leu Leu Val Val
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Influenza epitope

<400> SEQUENCE: 113

Glu Glu Cys Leu Ile Asn Asp Pro Trp Val Leu Leu Asn Ala Ser
1               5                   10                  15

<210> SEQ ID NO 114
```

```
<211> LENGTH: 16
<212> TYPE: PRT
<213> ORGANISM: Artificial Sequence
<220> FEATURE:
<223> OTHER INFORMATION: Influenza epitope

<400> SEQUENCE: 114

Pro Thr Leu Leu Phe Leu Lys Val Pro Ala Gln Asn Ala Ile Ser Thr
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Influenza epitope

<400> SEQUENCE: 115

Ala Met Ala Phe Leu Glu Glu Ser His Pro Gly Ile Phe Glu Asn
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Influenza epitope

<400> SEQUENCE: 116

Thr Met Glu Val Ile Gln Gln Thr Arg Val Asp Lys Leu Thr Gln
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Influenza epitope

<400> SEQUENCE: 117

Leu Ile Asp Phe Leu Lys Asp Val Met Glu Ser Met Asp Lys Glu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Influenza epitope

<400> SEQUENCE: 118

Lys Glu Glu Met Glu Ile Thr Thr His Phe Gln Arg Lys Arg Arg
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Influenza epitope

<400> SEQUENCE: 119

Thr Lys Lys Met Val Thr Gln Arg Thr Ile Gly Lys Lys Lys Gln
1               5                   10                  15

<210> SEQ ID NO 120
<211> LENGTH: 15
```

```
<212> TYPE: PRT
<213> ORGANISM: Artificial Sequence
<220> FEATURE:
<223> OTHER INFORMATION: Influenza epitope

<400

```
<213> ORGANISM: Artificial Sequence
<220> FEATURE:
<223> OTHER INFORMATION: Influenza epitope

<400> SEQUENCE: 126

Ile Arg Pro Leu Leu Val Glu Gly Thr Ala Ser Leu Ser Pro Gly
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Influenza epitope

<400> SEQUENCE: 127

Met Met Gly Met Phe Asn Met Leu Ser Thr Val Leu Gly Val Ser
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Influenza epitope

<400> SEQUENCE: 128

Asp Phe Ala Leu Ile Val Asn Ala Pro Asn His Glu Gly Ile Gln
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Influenza epitope

<400> SEQUENCE: 129

Leu Val Gly Ile Asn Met Ser Lys Lys Lys Ser Tyr Ile Asn Arg
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Influenza epitope

<400> SEQUENCE: 130

Tyr Gly Phe Val Ala Asn Phe Ser Met Glu Leu Pro Ser Phe Gly
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Influenza epitope

<400> SEQUENCE: 131

Val Ala Asn Phe Ser Met Glu Leu Pro Ser Phe Gly Val Ser Gly
1               5                   10                  15

<210> SEQ ID NO 132
<211> LENGTH: 15
<212> TYPE: PRT
<213> ORGANISM: Artificial Sequence
```

-continued

```
<220> FEATURE:
<223> OTHER INFORMATION: Influenza epitope

<400> SEQUENCE: 132

Leu Pro Ser Phe Gly Val Ser Gly Ile Asn Glu Ser Ala Asp Met
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Influenza epitope

<400> SEQUENCE: 133

Gly Val Thr Val Ile Lys Asn Asn Met Ile Asn Asn Asp Leu Gly Pro
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Influenza epitope

<400> SEQUENCE: 134

Asn Asn Met Ile Asn Asn Asp Leu Gly Pro Ala Thr Ala Gln Met
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Influenza epitope

<400> SEQUENCE: 135

Leu Gln Leu Phe Ile Lys Asp Tyr Arg Tyr Thr Tyr Arg Cys His
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Influenza epitope

<400> SEQUENCE: 136

Ala Gly Leu Leu Val Ser Asp Gly Gly Pro Asn Leu Tyr Asn Ile
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Influenza epitope

<400> SEQUENCE: 137

Pro Asn Leu Tyr Asn Ile Arg Asn Leu His Ile Pro Glu Val Cys
1               5                   10                  15

<210> SEQ ID NO 138
<211> LENGTH: 15
<212> TYPE: PRT
<213> ORGANISM: Artificial Sequence
<220> FEATURE:
```

```
<223> OTHER INFORMATION: Influenza epitope

<400> SEQUENCE: 138

Trp Glu Leu Met Asp Glu Asp Tyr Gln Gly Arg Leu Cys As

```
<400> SEQUENCE: 144

Arg Arg Pro Val Gly Ile Ser Ser Met Val Glu Ala Met Val Ser
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Influenza epitope

<400> SEQUENCE: 145

Ile Ser Ser Met Val Glu Ala Met Val Ser Arg Ala Arg Ile Asp
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Influenza epitope

<400> SEQUENCE: 146

Val Ser Arg Ala Arg Ile Asp Ala Arg Ile Asp Phe Glu Ser Gly
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Influenza epitope

<400> SEQUENCE: 147

Leu Arg Asn Leu Met Ser Gln Ser Arg Thr Arg Glu Ile Leu Thr
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Influenza epitope

<400> SEQUENCE: 148

Lys Trp Met Met Ala Met Lys Tyr Pro Ile Thr Ala Asp Lys Arg
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Influenza epitope

<400> SEQUENCE: 149

Lys Tyr Pro Ile Thr Ala Asp Lys Arg Ile Met Glu Met Ile Pro
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Influenza epitope
```

```
<400> SEQUENCE: 150

Asp Arg Val Met Val Ser Pro Leu Ala Val Thr Trp Trp Asn Arg
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Influenza epitope

<400> SEQUENCE: 151

Pro Val His Phe Arg Asn Gln Val Lys Ile Arg Arg Arg Val Asp
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Influenza epitope

<400> SEQUENCE: 152

Asp Val Ile Met Glu Val Val Phe Pro Asn Glu Val Gly Ala Arg
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Influenza epitope

<400> SEQUENCE: 153

Gly Ala Arg Ile Leu Thr Ser Glu Ser Gln Leu Thr Ile Thr Lys
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Influenza epitope

<400> SEQUENCE: 154

Ala Arg Ile Leu Thr Ser Glu Ser Gln Leu Thr Ile Thr Lys Glu
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Influenza epitope

<400> SEQUENCE: 155

Gln Leu Thr Ile Thr Lys Glu Lys Lys Glu Glu Leu Gln Asp Cys
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Influenza epitope

<400> SEQUENCE: 156
```

```
Met Val Ala Tyr Met Leu Glu Arg Glu Leu Val Arg Lys Thr Arg
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Influenza epitope

<400> SEQUENCE: 157

Gly Gly Glu Val Arg Asn Asp Asp Val Asp Gln Ser Leu Ile Ile
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Influenza epitope

<400> SEQUENCE: 158

Lys Ala Ala Met Gly Leu Arg Ile Ser Ser Ser Phe Ser Phe Gly
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Influenza epitope

<400> SEQUENCE: 159

Leu Ile Gln Leu Ile Val Ser Gly Arg Asp Glu Gln Ser Ile Ala
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Influenza epitope

<400> SEQUENCE: 160

Ala Met Val Phe Ser Gln Glu Asp Cys Met Ile Lys Ala Val Arg
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Influenza epitope

<400> SEQUENCE: 161

Ile Lys Ala Val Arg Gly Asp Leu Asn Phe Val Asn Arg Ala Asn
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Influenza epitope

<400> SEQUENCE: 162
```

```
Leu Arg His Phe Gln Lys Asp Ala Lys Val Leu Phe Gln Asn Trp
1               5                   10                  15
```

<210> SEQ ID NO 163
<211> LENGTH: 15
<212> TYPE: PRT
<213> ORGANISM: Artificial Sequence
<220> FEATURE:
<223> OTHER INFORMATION: Influenza epitope

<400> SEQUENCE: 163

```
Met Ile Gly Ile Leu Pro Asp Met Thr Pro Ser Thr Glu Met Ser
1               5                   10                  15
```

<210> SEQ ID NO 164
<211> LENGTH: 15
<212> TYPE: PRT
<213> ORGANISM: Artificial Sequence
<220> FEATURE:
<223> OTHER INFORMATION: Influenza epitope

<400> SEQUENCE: 164

```
Val Ser Lys Met Gly Val Asp Glu Tyr Ser Ser Thr Glu Arg Val
1               5                   10                  15
```

<210> SEQ ID NO 165
<211> LENGTH: 15
<212> TYPE: PRT
<213> ORGANISM: Artificial Sequence
<220> FEATURE:
<223> OTHER INFORMATION: Influenza epitope

<400> SEQUENCE: 165

```
Arg Val Val Ser Ile Asp Arg Phe Leu Arg Val Arg Asp Gln
1               5                   10                  15
```

<210> SEQ ID NO 166
<211> LENGTH: 15
<212> TYPE: PRT
<213> ORGANISM: Artificial Sequence
<220> FEATURE:
<223> OTHER INFORMATION: Influenza epitope

<400> SEQUENCE: 166

```
Gln Trp Ile Ile Arg Asn Trp Glu Thr Val Lys Ile Gln Trp Ser
1               5                   10                  15
```

<210> SEQ ID NO 167
<211> LENGTH: 15
<212> TYPE: PRT
<213> ORGANISM: Artificial Sequence
<220> FEATURE:
<223> OTHER INFORMATION: Influenza epitope

<400> SEQUENCE: 167

```
Arg Met Gln Phe Ser Ser Leu Thr Val Asn Val Arg Gly Ser Gly
1               5                   10                  15
```

<210> SEQ ID NO 168
<211> LENGTH: 15
<212> TYPE: PRT
<213> ORGANISM: Artificial Sequence
<220> FEATURE:
<223> OTHER INFORMATION: Influenza epitope

<400> SEQUENCE: 168

```
Ala Gly Ala Leu Thr Glu Asp Pro Asp Glu Gly Thr Ala Gly Val
```

```
<210> SEQ ID NO 169
<211> LENGTH: 15
<212> TYPE: PRT
<213> ORGANISM: Artificial Sequence
<220> FEATURE:
<223> OTHER INFORMATION: Influenza epitope

<400> SEQUENCE: 169

Glu Ser Ala Val Leu Arg Gly Phe Leu Ile Leu Gly Lys Glu Asp
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Influenza epitope

<400> SEQUENCE: 170

Phe Leu Ile Leu Gly Lys Glu Asp Arg Arg Tyr Gly Pro Ala Leu
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Influenza epitope

<400> SEQUENCE: 171

Asn Val Leu Ile Gly Gln Gly Asp Val Val Leu Val Met Lys Arg
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Influenza epitope

<400> SEQUENCE: 172

Asp Ser Ser Ile Leu Thr Asp Ser Gln Thr Ala Thr Lys Arg Ile
1               5                   10                  15

<210> SEQ ID NO 173
<211> LENGTH: 1770
<212> TYPE: DNA
<213> ORGANISM: Artificial Sequence
<220> FEATURE:
<223> OTHER INFORMATION: Synthetic PADRE HA foldon sequence

<400> SEQUENCE: 173
atgaagttgt gcatcttgct ggccgtcgtg gccttcgtgg gcctgtcgct gggcatgaag       60
caccaacacc aacatcaaca tcaacatcaa catcaagccc cgcaaaatt tgtggccgcg       120 tggacactga agctgcggc tgatcaaatt tgtataggtt accatgcgaa caatagcacg       180
gaacaagtag ataccattat ggaaagaaac gtgacagtta cacatgcgca ggacattttg       240 gaaaaaagc acaatggaaa gttgtgtgat cttgacgggg tcaaaccact aatcttacgt       300
gactgttcag tggcgggttg gttgttaggc aacccgatgt gcgatgaatt tattaatgta       360
ccggagtggt catatatcgt ggaaaaagcc aaccccgtta acgacttgtg ttatcctggt       420
gattttaatg actacgagga attaaaacac ttgctgtcac gtatcaatca ctttgagaaa       480
```

```
atacaaataa tccccaaatc ttcctggagt agccatgagg cttcgttggg cgtgagtagc    540
gcctgcccct accaaggcaa atcgagtttt ttccgaaacg tggtatggct aataaaaaag    600
aactcgacgt acccgacgat caaaagatcg tataacaata cgaaccagga agacttgctt    660
gtcttgtggg gtatccacca tccgaacgac gccgctgaac agacaaaatt atatcaaaac    720
cccactacct acatttcagt aggcacgagt acgctgaacc agcgccttgt gccacgaata    780
gccactaggt ctaaggttaa tggccagtct ggtcgcatgg aattttttctg gactatactc   840 aaacctaacg atgctatcaa ctttgagtct aatggcaact ttattgcccc tgaatacgcg    900
tataagattg ttaaaaaggg cgattcgacg attatgaaat cggaactcga atatggtaat    960
tgcaacacca atgtcaaac tcccatgggc gctattaaca gctccatgcc atttcacaat   1020
attcacccgt tgactatagg cgaatgtcca aaatatgtga agtccaatcg cttggtactc   1080
gccaccggct tgaggaatag cccgcaacgt gagagacgga gaaaaaagcg gggattgttt   1140
ggcgccatcg ccggatttat agaaggtggc tggcaaggaa tggtggatgg ctggtatgga   1200
taccaccatt ccaacgaaca aggttcaggc tacgcggcag acaagaatc tactcaaaaa    1260 gcaatagacg gcgtgacaaa taagtaaat agtataattg acaaaatgaa tacgcagttt    1320
gaagccgtcg gccgtgagtt caataacctg gagcgcagaa ttgaaaatct aaacaaaaag   1380
atggaggacg ggttttttaga cgtttggacg tacaatgcag aattgttagt tttgatggaa   1440
aacgaacgca ccttggattt tcacgactcg aacgttaaaa acctgtacga taaagtccga   1500
ctgcaattac gcgataatgc aaaagaactg ggaaacggct gcttcgaatt ttatcataaa   1560
tgcgacaatg aatgcatgga atctgtacga aatggtacat acgactatcc ccaatactcg   1620
gaggaagcgc gtctaaaacg cgaagagatt agcagtggcc gcctggtgcc ccgcggcagc   1680
cccggcagcg gctacatccc cgaggccccc cgcgatggcc aggcctacgt gcgcaaggat   1740
ggcgagtggg tgctgctgag caccttcctg                                    1770
```

<210> SEQ ID NO 174
<211> LENGTH: 590
<212> TYPE: PRT
<213> ORGANISM: Artificial Sequence
<220> FEATURE:
<223> OTHER INFORMATION: Synthetic PADRE HA foldon sequence

<400> SEQUENCE: 174

```
Met Lys Leu Cys Ile Leu Leu Ala Val Val Ala Phe Val Gly Leu Ser
1               5                   10                  15

Leu Gly Met Lys His Gln His Gln His Gln His Gln His Gln His Gln
            20                  25                  30

Ala Pro Ala Lys Phe Val Ala Ala Trp Thr Leu Lys Ala Ala Ala Asp
        35                  40                  45

Gln Ile Cys Ile Gly Tyr His Ala Asn Asn Ser Thr Glu Gln Val Asp
    50                  55                  60

Thr Ile Met Glu Lys Asn Val Thr Val Thr His Ala Gln Asp Ile Leu
65                  70                  75                  80

Glu Lys Lys His Asn Gly Lys Leu Cys Asp Leu Asp Gly Val Lys Pro
                85                  90                  95

Leu Ile Leu Arg Asp Cys Ser Val Ala Gly Trp Leu Leu Gly Asn Pro
            100                 105                 110

Met Cys Asp Glu Phe Ile Asn Val Pro Glu Trp Ser Tyr Ile Val Glu
        115                 120                 125
```

```
Lys Ala Asn Pro Val Asn Asp Leu Cys Tyr Pro Gly Asp Phe Asn Asp
    130                 135                 140

Tyr Glu Glu Leu Lys His Leu Leu Ser Arg Ile Asn His Phe Glu Lys
145                 150                 155                 160

Ile Gln Ile Ile Pro Lys Ser Ser Trp Ser Ser His Glu Ala Ser Leu
                165                 170                 175

Gly Val Ser Ser Ala Cys Pro Tyr Gln Gly Lys Ser Ser Phe Phe Arg
                180                 185                 190

Asn Val Val Trp Leu Ile Lys Lys Asn Ser Thr Tyr Pro Thr Ile Lys
        195                 200                 205

Arg Ser Tyr Asn Asn Thr Asn Gln Glu Asp Leu Leu Val Leu Trp Gly
    210                 215                 220

Ile His His Pro Asn Asp Ala Ala Glu Gln Thr Lys Leu Tyr Gln Asn
225                 230                 235                 240

Pro Thr Thr Tyr Ile Ser Val Gly Thr Ser Thr Leu Asn Gln Arg Leu
                245                 250                 255

Val Pro Arg Ile Ala Thr Arg Ser Lys Val Asn Gly Gln Ser Gly Arg
                260                 265                 270

Met Glu Phe Phe Trp Thr Ile Leu Lys Pro Asn Asp Ala Ile Asn Phe
            275                 280                 285

Glu Ser Asn Gly Asn Phe Ile Ala Pro Glu Tyr Ala Tyr Lys Ile Val
290                 295                 300

Lys Lys Gly Asp Ser Thr Ile Met Lys Ser Glu Leu Glu Tyr Gly Asn
305                 310                 315                 320

Cys Asn Thr Lys Cys Gln Thr Pro Met Gly Ala Ile Asn Ser Ser Met
                325                 330                 335

Pro Phe His Asn Ile His Pro Leu Thr Ile Gly Glu Cys Pro Lys Tyr
            340                 345                 350

Val Lys Ser Asn Arg Leu Val Leu Ala Thr Gly Leu Arg Asn Ser Pro
            355                 360                 365

Gln Arg Glu Arg Arg Arg Lys Lys Arg Gly Leu Phe Gly Ala Ile Ala
    370                 375                 380

Gly Phe Ile Glu Gly Gly Trp Gln Gly Met Val Asp Gly Trp Tyr Gly
385                 390                 395                 400

Tyr His His Ser Asn Glu Gln Gly Ser Gly Tyr Ala Ala Asp Lys Glu
                405                 410                 415

Ser Thr Gln Lys Ala Ile Asp Gly Val Thr Asn Lys Val Asn Ser Ile
            420                 425                 430

Ile Asp Lys Met Asn Thr Gln Phe Glu Ala Val Gly Arg Glu Phe Asn
            435                 440                 445

Asn Leu Glu Arg Arg Ile Glu Asn Leu Asn Lys Lys Met Glu Asp Gly
    450                 455                 460

Phe Leu Asp Val Trp Thr Tyr Asn Ala Glu Leu Leu Val Leu Met Glu
465                 470                 475                 480

Asn Glu Arg Thr Leu Asp Phe His Asp Ser Asn Val Lys Asn Leu Tyr
                485                 490                 495

Asp Lys Val Arg Leu Gln Leu Arg Asp Asn Ala Lys Glu Leu Gly Asn
                500                 505                 510

Gly Cys Phe Glu Phe Tyr His Lys Cys Asp Asn Glu Cys Met Glu Ser
            515                 520                 525

Val Arg Asn Gly Thr Tyr Asp Tyr Pro Gln Tyr Ser Glu Glu Ala Arg
            530                 535                 540

Leu Lys Arg Glu Glu Ile Ser Ser Gly Arg Leu Val Pro Arg Gly Ser
```

```
                  545                 550                 555                 560
Pro Gly Ser Gly Tyr Ile Pro Glu Ala Pro Arg Asp Gly Gln Ala Tyr
                        565                 570                 575

Val Arg Lys Asp Gly Glu Trp Val Leu Leu Ser Thr Phe Leu
                580                 585                 590
```

<210> SEQ ID NO 175
<211> LENGTH: 18
<212> TYPE: PRT
<213> ORGANISM: Artificial Sequence
<220> FEATURE:
<223> OTHER INFORMATION: Bip signal for synthetic PADRE HA or HA foldon

<400> SEQUENCE: 175

```
Met Lys Leu Cys Ile Leu Leu Ala Val Val Ala Phe Val Gly Leu Ser
1               5                   10                  15

Leu Gly
```

<210> SEQ ID NO 176
<211> LENGTH: 14
<212> TYPE: PRT
<213> ORGANISM: Artificial Sequence
<220> FEATURE:
<223> OTHER INFORMATION: UNIHIS for synthetic PADRE HA or HA foldon

<400> SEQUENCE: 176

```
Met Lys His Gln His Gln His Gln His Gln His Gln
1               5                   10
```

<210> SEQ ID NO 177
<211> LENGTH: 13
<212> TYPE: PRT
<213> ORGANISM: Artificial Sequence
<220> FEATURE:
<223> OTHER INFORMATION: Synthetic PADRE

<400> SEQUENCE: 177

```
Ala Lys Phe Val Ala Ala Trp Thr Leu Lys Ala Ala Ala
1               5                   10
```

<210> SEQ ID NO 178
<211> LENGTH: 13
<212> TYPE: PRT
<213> ORGANISM: Artificial Sequence
<220> FEATURE:
<223> OTHER INFORMATION: Thrombin cleavage site for synthetic PADRE HA
      or HA foldon

<400> SEQUENCE: 178

```
Ser Ser Gly Arg Leu Val Pro Arg Gly Ser Pro Gly Ser
1               5                   10
```

<210> SEQ ID NO 179
<211> LENGTH: 27
<212> TYPE: PRT
<213> ORGANISM: Artificial Sequence
<220> FEATURE:
<223> OTHER INFORMATION: Foldon for synthetic PADRE HA or HA sequence

<400> SEQUENCE: 179

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
                20                  25
```

<210> SEQ ID NO 180
<211> LENGTH: 1782
<212> TYPE: DNA
<213> ORGANISM: Artificial Sequence
<220> FEATURE:
<223> OTHER INFORMATION: Synthetic HA construct

<400> SEQUENCE: 180

```
atgccgctct acaaattgct aaacgtgtta tggttagtcg ctgtgtccaa cgcgattcct      60
ggcagctatt accatcacca tcaccatcac gactacgata ttccgacgac cgaaaacttg     120
tattttcaag gcgcggatca aatttgtata ggttaccatg cgaacaatag cacggaacaa     180
gtagatacca ttatggaaaa gaacgtgaca gttacacatg cgcaggacat tttggaaaaa     240
aagcacaatg gaaagttgtg tgatcttgac ggggtcaaac cactaatctt acgtgactgt     300
tcagtggcgg gttggttgtt aggcaacccg atgtgcgatg aatttattaa tgtaccggag     360
tggtcatata tcgtggaaaa agccaacccc gttaacgact tgtgttatcc tggtgatttt     420
aatgactacg aggaattaaa acacttgctg tcacgtatca atcactttga gaaaatacaa     480
ataatcccca atcttcctg gagtagccat gaggcttcgt tgggcgtgag tagcgcctgc     540
ccctaccaag gcaaatcgag ttttttccga acgtggtat ggctaataaa aaagaactcg     600
acgtacccga cgatcaaaag atcgtataac aatacgaacc aggaagactt gcttgtcttg     660
tggggtatcc accatccgaa cgacgccgct gaacagacaa aattatatca aaaccccact     720
acctacattt cagtaggcac gagtacgctg aaccagcgcc ttgtgccacg aatagccact     780
aggtctaagg ttaatggcca gtctggtcgc atggaatttt tctggactat actcaaacct     840
aacgatgcta tcaactttga gtctaatggc aactttattg cccctgaata cgcgtataag     900
attgttaaaa agggcgattc gacgattatg aaatcggaac tcgaatatgg taattgcaac     960
accaaatgtc aaactcccat gggcgctatt aacagctcca tgccatttca caatattcac    1020
ccgttgacta taggcgaatg tccaaaatat gtgaagtcca atcgcttggt actcgccacc    1080
ggcttgagga atagcccgca acgtgagaga cggagaaaaa agcggggatt gtttggcgcc    1140
atcgccggat ttatagaagg tggctggcaa ggaatggtgg atggctggta tggataccac    1200
cattccaacg aacaaggttc aggctacgcg gcagacaaag aatctactca aaaagcaata    1260
gacggcgtga caaataaagt aaatagtata attgacaaaa tgaatacgca gtttgaagcc    1320
gtcggccgtg agttcaataa cctggagcgc agaattgaaa atctaaacaa aaagatggag    1380
gacgggtttt tagacgtttg gacgtacaat gcagaattgt tagttttgat ggaaaacgaa    1440
cgcaccttgg attttcacga ctcgaacgtt aaaaacctgt acgataaagt ccgactgcaa    1500
ttacgcgata tgcaaaagaa actgggaaac ggctgcttcg aattttatca taaatgcgac    1560
aatgaatgca tggaatctgt acgaaatggt acatacgact atccccaata ctcggaggaa    1620
gcgcgtctaa acgcgaaga gattagcggg gtgaaattag agagtattgg aatttaccaa    1680
attttgagca tttatagcac cgttgcatcg agtcttgcgt tggcaataat ggtcgcgggc    1740
ttatctttgt ggatgtgcag caacggaagc cttcaatgta ga                       1782
```

<210> SEQ ID NO 181
<211> LENGTH: 594
<212> TYPE: PRT
<213> ORGANISM: Artificial Sequence
<220> FEATURE:
<223> OTHER INFORMATION: Synthetic HA construct

<400> SEQUENCE: 181

-continued

```
Met Pro Leu Tyr Lys Leu Leu Asn Val Leu Trp Leu Val Ala Val Ser
1               5                   10                  15

Asn Ala Ile Pro Gly Ser Tyr Tyr His His His His His Asp Tyr
            20              25                  30

Asp Ile Pro Thr Thr Glu Asn Leu Tyr Phe Gln Gly Ala Asp Gln Ile
        35                  40                  45

Cys Ile Gly Tyr His Ala Asn Asn Ser Thr Glu Gln Val Asp Thr Ile
    50                  55                  60

Met Glu Lys Asn Val Thr Val Thr His Ala Gln Asp Ile Leu Glu Lys
65                  70                  75                  80

Lys His Asn Gly Lys Leu Cys Asp Leu Asp Gly Val Lys Pro Leu Ile
                85                  90                  95

Leu Arg Asp Cys Ser Val Ala Gly Trp Leu Leu Gly Asn Pro Met Cys
                100                 105                 110

Asp Glu Phe Ile Asn Val Pro Glu Trp Ser Tyr Ile Val Glu Lys Ala
                115                 120                 125

Asn Pro Val Asn Asp Leu Cys Tyr Pro Gly Asp Phe Asn Asp Tyr Glu
    130                 135                 140

Glu Leu Lys His Leu Leu Ser Arg Ile Asn His Phe Glu Lys Ile Gln
145                 150                 155                 160

Ile Ile Pro Lys Ser Ser Trp Ser Ser His Glu Ala Ser Leu Gly Val
                165                 170                 175

Ser Ser Ala Cys Pro Tyr Gln Gly Lys Ser Ser Phe Phe Arg Asn Val
                180                 185                 190

Val Trp Leu Ile Lys Lys Asn Ser Thr Tyr Pro Thr Ile Lys Arg Ser
            195                 200                 205

Tyr Asn Asn Thr Asn Gln Glu Asp Leu Leu Val Leu Trp Gly Ile His
    210                 215                 220

His Pro Asn Asp Ala Ala Glu Gln Thr Lys Leu Tyr Gln Asn Pro Thr
225                 230                 235                 240

Thr Tyr Ile Ser Val Gly Thr Ser Thr Leu Asn Gln Arg Leu Val Pro
                245                 250                 255

Arg Ile Ala Thr Arg Ser Lys Val Asn Gly Gln Ser Gly Arg Met Glu
                260                 265                 270

Phe Phe Trp Thr Ile Leu Lys Pro Asn Asp Ala Ile Asn Phe Glu Ser
            275                 280                 285

Asn Gly Asn Phe Ile Ala Pro Glu Tyr Ala Tyr Lys Ile Val Lys Lys
    290                 295                 300

Gly Asp Ser Thr Ile Met Lys Ser Glu Leu Glu Tyr Gly Asn Cys Asn
305                 310                 315                 320

Thr Lys Cys Gln Thr Pro Met Gly Ala Ile Asn Ser Ser Met Pro Phe
                325                 330                 335

His Asn Ile His Pro Leu Thr Ile Gly Glu Cys Pro Lys Tyr Val Lys
                340                 345                 350

Ser Asn Arg Leu Val Leu Ala Thr Gly Leu Arg Asn Ser Pro Gln Arg
            355                 360                 365

Glu Arg Arg Arg Lys Lys Arg Gly Leu Phe Gly Ala Ile Ala Gly Phe
    370                 375                 380

Ile Glu Gly Gly Trp Gln Gly Met Val Asp Gly Trp Tyr Gly Tyr His
385                 390                 395                 400

His Ser Asn Glu Gln Gly Ser Gly Tyr Ala Ala Asp Lys Glu Ser Thr
                405                 410                 415
```

```
Gln Lys Ala Ile Asp Gly Val Thr Asn Lys Val Asn Ser Ile Ile Asp
                420                 425                 430
Lys Met Asn Thr Gln Phe Glu Ala Val Gly Arg Glu Phe Asn Asn Leu
            435                 440                 445
Glu Arg Arg Ile Glu Asn Leu Asn Lys Lys Met Glu Asp Gly Phe Leu
450                 455                 460
Asp Val Trp Thr Tyr Asn Ala Glu Leu Leu Val Leu Met Glu Asn Glu
465                 470                 475                 480
Arg Thr Leu Asp Phe His Asp Ser Asn Val Lys Asn Leu Tyr Asp Lys
                485                 490                 495
Val Arg Leu Gln Leu Arg Asp Asn Ala Lys Glu Leu Gly Asn Gly Cys
            500                 505                 510
Phe Glu Phe Tyr His Lys Cys Asp Asn Glu Cys Met Glu Ser Val Arg
        515                 520                 525
Asn Gly Thr Tyr Asp Tyr Pro Gln Tyr Ser Glu Glu Ala Arg Leu Lys
    530                 535                 540
Arg Glu Glu Ile Ser Gly Val Lys Leu Glu Ser Ile Gly Ile Tyr Gln
545                 550                 555                 560
Ile Leu Ser Ile Tyr Ser Thr Val Ala Ser Ser Leu Ala Leu Ala Ile
                565                 570                 575
Met Val Ala Gly Leu Ser Leu Trp Met Cys Ser Asn Gly Ser Leu Gln
            580                 585                 590
Cys Arg

<210> SEQ ID NO 182
<211> LENGTH: 1821
<212> TYPE: PRT
<213> ORGANISM: Artificial Sequence
<220> FEATURE:
<223> OTHER INFORMATION: Synthetic PADRE HA construct

<400> SEQUENCE: 182

Ala Thr Gly Cys Cys Gly Cys Thr Cys Thr Ala Cys Ala Ala Ala Thr
1               5                   10                  15
Thr Gly Cys Thr Ala Ala Ala Cys Gly Thr Gly Thr Thr Ala Thr Gly
            20                  25                  30
Gly Thr Thr Ala Gly Thr Cys Gly Cys Thr Gly Thr Gly Thr Cys Cys
        35                  40                  45
Ala Ala Cys Gly Cys Gly Ala Thr Cys Thr Gly Gly Cys Gly Cys Ala
    50                  55                  60
Gly Cys Thr Ala Thr Thr Ala Cys Cys Ala Thr Cys Ala Cys Cys Ala
65                  70                  75                  80
Thr Cys Ala Cys Cys Ala Thr Cys Ala Cys Gly Ala Cys Thr Ala Cys
                85                  90                  95
Gly Ala Thr Ala Thr Cys Cys Gly Ala Cys Gly Ala Cys Cys Gly
            100                 105                 110
Ala Ala Ala Ala Cys Thr Thr Gly Thr Ala Thr Thr Thr Cys Ala
        115                 120                 125
Ala Gly Gly Cys Gly Gly Cys Ala Ala Ala Thr Thr
    130                 135                 140
Gly Thr Gly Gly Cys Cys Gly Cys Gly Thr Gly Gly Ala Cys Ala Cys
145                 150                 155                 160
Thr Gly Ala Ala Ala Gly Cys Thr Gly Cys Gly Gly Cys Thr Gly Ala
                165                 170                 175
Thr Cys Ala Ala Ala Thr Thr Thr Gly Thr Ala Thr Ala Gly Gly Thr
```

-continued

```
            180                 185                 190

Thr Ala Cys Cys Ala Thr Gly Cys Gly Ala Ala Cys Ala Ala Thr Ala
        195                 200                 205

Gly Cys Ala Cys Gly Gly Ala Ala Cys Ala Ala Gly Thr Ala Gly Ala
    210                 215                 220

Thr Ala Cys Cys Ala Thr Thr Ala Thr Gly Gly Ala Ala Ala Ala Gly
225                 230                 235                 240

Ala Ala Cys Gly Thr Gly Ala Cys Ala Gly Thr Thr Ala Cys Ala Cys
                245                 250                 255
Ala Thr Gly Cys Gly Cys Ala Gly Gly Ala Cys Ala Thr Thr Thr Thr
            260                 265                 270

Gly Gly Ala Ala Ala Ala Ala Ala Ala Gly Cys Ala Cys Ala Ala Thr
        275                 280                 285

Gly Gly Ala Ala Ala Gly Thr Thr Gly Thr Gly Thr Gly Ala Thr Cys
    290                 295                 300

Thr Thr Gly Ala Cys Gly Gly Gly Gly Thr Cys Ala Ala Ala Cys Cys
305                 310                 315                 320
Ala Cys Thr Ala Ala Thr Cys Thr Thr Ala Cys Gly Thr Gly Ala Cys
                325                 330                 335
Thr Gly Thr Thr Cys Ala Gly Thr Gly Gly Cys Gly Gly Gly Thr Thr
            340                 345                 350

Gly Gly Thr Thr Gly Thr Thr Ala Gly Gly Cys Ala Ala Cys Cys Cys
        355                 360                 365

Gly Ala Thr Gly Thr Gly Cys Gly Ala Thr Gly Ala Ala Thr Thr Thr
    370                 375                 380

Ala Thr Thr Ala Ala Thr Gly Thr Ala Cys Cys Gly Gly Ala Gly Thr
385                 390                 395                 400

Gly Gly Thr Cys Ala Thr Ala Thr Ala Thr Cys Gly Thr Gly Gly Ala
                405                 410                 415

Ala Ala Ala Ala Gly Cys Cys Ala Ala Cys Cys Cys Cys Gly Thr Thr
            420                 425                 430

Ala Ala Cys Gly Ala Cys Thr Thr Gly Thr Gly Thr Thr Ala Thr Cys
        435                 440                 445

Cys Thr Gly Gly Thr Gly Ala Thr Thr Thr Thr Ala Ala Thr Gly Ala
    450                 455                 460

Cys Thr Ala Cys Gly Ala Gly Gly Ala Ala Thr Thr Ala Ala Ala Ala
465                 470                 475                 480

Cys Ala Cys Thr Thr Gly Cys Thr Gly Thr Cys Ala Cys Gly Thr Ala
                485                 490                 495

Thr Cys Ala Ala Thr Cys Ala Cys Thr Thr Thr Gly Ala Gly Ala Ala
            500                 505                 510

Ala Ala Thr Ala Cys Ala Ala Ala Thr Ala Ala Thr Cys Cys Cys Cys
        515                 520                 525

Ala Ala Ala Thr Cys Thr Thr Cys Cys Thr Gly Gly Ala Gly Thr Ala
    530                 535                 540

Gly Cys Cys Ala Thr Gly Ala Gly Gly Cys Thr Thr Cys Gly Thr Thr
545                 550                 555                 560

Gly Gly Gly Cys Gly Thr Gly Ala Gly Thr Ala Gly Cys Gly Cys Cys
                565                 570                 575

Thr Gly Cys Cys Cys Cys Thr Ala Cys Cys Ala Ala Gly Gly Cys Ala
            580                 585                 590

Ala Ala Thr Cys Gly Ala Gly Thr Thr Thr Thr Thr Thr Cys Cys Gly
        595                 600                 605
```

```
Ala Ala Ala Cys Gly Thr Gly Thr Ala Thr Gly Cys Thr Ala
    610             615             620
Ala Thr Ala Ala Ala Ala Ala Gly Ala Ala Cys Thr Cys Gly Ala
625             630             635             640
Cys Gly Thr Ala Cys Cys Gly Ala Cys Gly Ala Thr Cys Ala Ala
                645             650             655
Ala Ala Gly Ala Thr Cys Gly Thr Ala Thr Ala Ala Cys Ala Ala Thr
            660             665             670
Ala Cys Gly Ala Ala Cys Cys Ala Gly Gly Ala Ala Gly Ala Cys Thr
            675             680             685
Thr Gly Cys Thr Thr Gly Thr Cys Thr Thr Gly Thr Gly Gly Gly
    690             695             700
Thr Ala Thr Cys Cys Ala Cys Cys Ala Thr Cys Cys Gly Ala Ala Cys
705             710             715             720
Gly Ala Cys Gly Cys Cys Gly Cys Thr Gly Ala Ala Cys Ala Gly Ala
                725             730             735
Cys Ala Ala Ala Ala Thr Thr Ala Thr Ala Thr Cys Ala Ala Ala Ala
            740             745             750
Cys Cys Cys Cys Ala Cys Thr Ala Cys Cys Thr Ala Cys Ala Thr Thr
            755             760             765
Thr Cys Ala Gly Thr Ala Gly Gly Cys Ala Cys Gly Ala Gly Thr Ala
    770             775             780
Cys Gly Cys Thr Gly Ala Ala Cys Cys Ala Gly Cys Gly Cys Cys Thr
785             790             795             800
Thr Gly Thr Gly Cys Cys Ala Cys Gly Ala Ala Thr Ala Gly Cys Cys
                805             810             815
Ala Cys Thr Ala Gly Gly Thr Cys Thr Ala Ala Gly Gly Thr Thr Ala
            820             825             830
Ala Thr Gly Gly Cys Cys Ala Gly Thr Cys Thr Gly Gly Thr Cys Gly
            835             840             845
Cys Ala Thr Gly Gly Ala Ala Thr Thr Thr Thr Thr Cys Thr Gly Gly
            850             855             860
Ala Cys Thr Ala Thr Ala Cys Thr Cys Ala Ala Ala Cys Cys Thr Ala
865             870             875             880
Ala Cys Gly Ala Thr Gly Cys Thr Ala Thr Cys Ala Ala Cys Thr Thr
            885             890             895
Thr Gly Ala Gly Thr Cys Thr Ala Ala Thr Gly Gly Cys Ala Ala Cys
        900             905             910
Thr Thr Thr Ala Thr Thr Gly Cys Cys Cys Thr Gly Ala Ala Thr
        915             920             925
Ala Cys Gly Cys Gly Thr Ala Thr Ala Gly Ala Thr Thr Gly Thr
    930             935             940
Thr Ala Ala Ala Ala Gly Gly Gly Cys Gly Ala Thr Thr Cys Gly
945             950             955             960
Ala Cys Gly Ala Thr Thr Ala Thr Gly Ala Ala Thr Cys Gly Gly
        965             970             975
Ala Ala Cys Thr Cys Gly Ala Cys Thr Ala Thr Gly Gly Thr Ala Ala
            980             985             990
Thr Thr Gly Cys Ala Ala Cys Ala  Cys Cys Ala Ala Ala  Thr Gly Thr
        995             1000            1005
Cys Ala  Ala Ala Cys Thr Cys  Cys Cys Ala Thr Gly  Gly Gly Cys
    1010            1015            1020
```

```
Gly Cys Thr Ala Thr Thr Ala Ala Cys Ala Gly Cys Thr Cys Cys
    1025                1030                1035

Ala Thr Gly Cys Cys Ala Thr Thr Thr Cys Ala Cys Ala Ala Thr
    1040                1045                1050

Ala Thr Thr Cys Ala Cys Cys Gly Thr Thr Gly Ala Cys Thr
    1055                1060                1065

Ala Thr Ala Gly Gly Cys Gly Ala Ala Thr Gly Cys Cys Ala
    1070                1075                1080

Ala Ala Ala Thr Ala Thr Gly Thr Gly Ala Ala Gly Thr Cys Cys
    1085                1090                1095

Ala Ala Thr Cys Gly Cys Thr Thr Gly Gly Thr Ala Cys Thr Cys
    1100                1105                1110

Gly Cys Cys Ala Cys Gly Gly Cys Thr Thr Gly Ala Gly Gly
    1115                1120                1125

Ala Ala Thr Ala Gly Cys Cys Cys Gly Cys Ala Ala Cys Gly Thr
    1130                1135                1140

Gly Ala Gly Ala Gly Ala Cys Gly Gly Ala Gly Ala Ala Ala
    1145                1150                1155

Ala Ala Gly Cys Gly Gly Gly Gly Ala Thr Thr Gly Thr Thr Thr
    1160                1165                1170

Gly Gly Cys Gly Cys Cys Ala Thr Cys Gly Cys Cys Gly Gly Ala
    1175                1180                1185

Thr Thr Thr Ala Thr Ala Gly Ala Ala Gly Gly Thr Gly Gly Cys
    1190                1195                1200

Thr Gly Gly Cys Ala Ala Gly Gly Ala Ala Thr Gly Gly Thr Gly
    1205                1210                1215

Gly Ala Thr Gly Gly Cys Thr Gly Gly Thr Ala Thr Gly Gly Ala
    1220                1225                1230

Thr Ala Cys Cys Ala Cys Cys Ala Thr Thr Cys Cys Ala Ala Cys
    1235                1240                1245

Gly Ala Ala Cys Ala Ala Gly Gly Thr Thr Cys Ala Gly Gly Cys
    1250                1255                1260

Thr Ala Cys Gly Cys Gly Gly Cys Ala Gly Ala Cys Ala Ala Ala
    1265                1270                1275

Gly Ala Ala Thr Cys Thr Ala Cys Thr Cys Ala Ala Ala Ala Ala
    1280                1285                1290

Gly Cys Ala Ala Thr Ala Gly Ala Cys Gly Gly Cys Gly Thr Gly
    1295                1300                1305

Ala Cys Ala Ala Ala Thr Ala Ala Ala Gly Thr Ala Ala Ala Thr
    1310                1315                1320

Ala Gly Thr Ala Thr Ala Ala Thr Thr Gly Ala Cys Ala Ala Ala
    1325                1330                1335

Ala Thr Gly Ala Ala Thr Ala Cys Gly Cys Ala Gly Thr Thr Thr
    1340                1345                1350

Gly Ala Ala Gly Cys Cys Gly Thr Cys Gly Gly Cys Cys Gly Thr
    1355                1360                1365

Gly Ala Gly Thr Thr Cys Ala Thr Ala Ala Cys Cys Thr Gly
    1370                1375                1380

Gly Ala Gly Cys Gly Cys Ala Gly Ala Ala Thr Gly Ala Ala
    1385                1390                1395

Ala Ala Thr Cys Thr Ala Ala Cys Ala Ala Ala Ala Ala Gly
    1400                1405                1410

Ala Thr Gly Gly Ala Gly Gly Ala Cys Gly Gly Gly Thr Thr Thr
```

-continued

```
            1415                1420                1425
Thr Thr Ala Gly Ala Cys Gly Thr Thr Gly Gly Ala Cys Gly
            1430                1435                1440
Thr Ala Cys Ala Ala Thr Gly Cys Ala Gly Ala Ala Thr Thr Gly
            1445                1450                1455
Thr Thr Ala Gly Thr Thr Thr Thr Gly Ala Thr Gly Gly Ala Ala
            1460                1465                1470
Ala Ala Cys Gly Ala Ala Cys Gly Cys Ala Cys Cys Thr Thr Gly
            1475                1480                1485
Gly Ala Thr Thr Thr Thr Cys Ala Cys Gly Ala Cys Thr Cys Gly
            1490                1495                1500
Ala Ala Cys Gly Thr Thr Ala Ala Ala Ala Cys Cys Thr Gly
            1505                1510                1515
Thr Ala Cys Gly Ala Thr Ala Ala Ala Gly Thr Cys Cys Gly Ala
            1520                1525                1530
Cys Thr Gly Cys Ala Ala Thr Thr Ala Cys Gly Cys Gly Ala Thr
            1535                1540                1545
Ala Ala Thr Gly Cys Ala Ala Ala Gly Ala Ala Cys Thr Gly
            1550                1555                1560
Gly Gly Ala Ala Ala Cys Gly Gly Cys Thr Gly Cys Thr Thr Cys
            1565                1570                1575
Gly Ala Ala Thr Thr Thr Thr Ala Thr Cys Ala Thr Ala Ala Ala
            1580                1585                1590
Thr Gly Cys Gly Ala Cys Ala Ala Thr Gly Ala Ala Thr Gly Cys
            1595                1600                1605
Ala Thr Gly Gly Ala Ala Thr Cys Thr Gly Thr Ala Cys Gly Ala
            1610                1615                1620
Ala Ala Thr Gly Gly Thr Ala Cys Ala Thr Ala Cys Gly Ala Cys
            1625                1630                1635
Thr Ala Thr Cys Cys Cys Cys Ala Ala Thr Ala Cys Thr Cys Gly
            1640                1645                1650
Gly Ala Gly Gly Ala Ala Gly Cys Gly Cys Gly Thr Cys Thr Ala
            1655                1660                1665
Ala Ala Ala Cys Gly Cys Gly Ala Ala Gly Ala Gly Ala Thr Thr
            1670                1675                1680
Ala Gly Cys Gly Gly Gly Gly Thr Gly Ala Ala Ala Thr Thr Ala
            1685                1690                1695
Gly Ala Gly Ala Gly Thr Ala Thr Thr Gly Gly Ala Ala Thr Thr
            1700                1705                1710
Thr Ala Cys Cys Ala Ala Ala Thr Thr Thr Thr Gly Ala Gly Cys
            1715                1720                1725
Ala Thr Thr Thr Ala Thr Ala Gly Cys Ala Cys Cys Gly Thr Thr
            1730                1735                1740
Gly Cys Ala Thr Cys Gly Ala Gly Thr Cys Thr Thr Gly Cys Gly
            1745                1750                1755
Thr Thr Gly Gly Cys Ala Ala Thr Ala Ala Thr Gly Gly Thr Cys
            1760                1765                1770
Gly Cys Gly Gly Gly Cys Thr Thr Ala Thr Cys Thr Thr Thr Gly
            1775                1780                1785
Thr Gly Gly Ala Thr Gly Gly Cys Ala Gly Cys Ala Ala Cys
            1790                1795                1800
Gly Gly Ala Ala Gly Cys Cys Thr Thr Cys Ala Ala Thr Gly Thr
            1805                1810                1815
```

Ala Gly Ala
    1820

<210> SEQ ID NO 183
<211> LENGTH: 607
<212> TYPE: PRT
<213> ORGANISM: Artificial Sequence
<220> FEATURE:
<223> OTHER INFORMATION: Synthetic PADRE HA construct

<400> SEQUENCE: 183

Met Pro Leu Tyr Lys Leu Leu Asn Val Leu Trp Leu Val Ala Val Ser
1               5                   10                  15

Asn Ala Ile Pro Gly Ser Tyr Tyr His His His His His Asp Tyr
            20                  25                  30

Asp Ile Pro Thr Thr Glu Asn Leu Tyr Phe Gln Gly Ala Ala Lys Phe
        35                  40                  45

Val Ala Ala Trp Thr Leu Lys Ala Ala Ala Asp Gln Ile Cys Ile Gly
    50                  55                  60

Tyr His Ala Asn Asn Ser Thr Glu Gln Val Asp Thr Ile Met Glu Lys
65                  70                  75                  80

Asn Val Thr Val Thr His Ala Gln Asp Ile Leu Glu Lys Lys His Asn
                85                  90                  95

Gly Lys Leu Cys Asp Leu Asp Gly Val Lys Pro Leu Ile Leu Arg Asp
            100                 105                 110

Cys Ser Val Ala Gly Trp Leu Leu Gly Asn Pro Met Cys Asp Glu Phe
        115                 120                 125

Ile Asn Val Pro Glu Trp Ser Tyr Ile Val Glu Lys Ala Asn Pro Val
    130                 135                 140

Asn Asp Leu Cys Tyr Pro Gly Asp Phe Asn Asp Tyr Glu Glu Leu Lys
145                 150                 155                 160

His Leu Leu Ser Arg Ile Asn His Phe Glu Lys Ile Gln Ile Ile Pro
                165                 170                 175

Lys Ser Ser Trp Ser Ser His Glu Ala Ser Leu Gly Val Ser Ser Ala
            180                 185                 190

Cys Pro Tyr Gln Gly Lys Ser Ser Phe Phe Arg Asn Val Val Trp Leu
        195                 200                 205

Ile Lys Lys Asn Ser Thr Tyr Pro Thr Ile Lys Arg Ser Tyr Asn Asn
    210                 215                 220

Thr Asn Gln Glu Asp Leu Leu Val Leu Trp Gly Ile His His Pro Asn
225                 230                 235                 240

Asp Ala Ala Glu Gln Thr Lys Leu Tyr Gln Asn Pro Thr Thr Tyr Ile
                245                 250                 255

Ser Val Gly Thr Ser Thr Leu Asn Gln Arg Leu Val Pro Arg Ile Ala
            260                 265                 270

Thr Arg Ser Lys Val Asn Gly Gln Ser Gly Arg Met Glu Phe Phe Trp
        275                 280                 285

Thr Ile Leu Lys Pro Asn Asp Ala Ile Asn Phe Glu Ser Asn Gly Asn
    290                 295                 300

Phe Ile Ala Pro Glu Tyr Ala Tyr Lys Ile Val Lys Lys Gly Asp Ser
305                 310                 315                 320

Thr Ile Met Lys Ser Glu Leu Glu Tyr Gly Asn Cys Asn Thr Lys Cys
                325                 330                 335

Gln Thr Pro Met Gly Ala Ile Asn Ser Ser Met Pro Phe His Asn Ile
            340                 345                 350

```
His Pro Leu Thr Ile Gly Glu Cys Pro Lys Tyr Val Lys Ser Asn Arg
            355                 360                 365
Leu Val Leu Ala Thr Gly Leu Arg Asn Ser Pro Gln Arg Glu Arg Arg
        370                 375                 380
Arg Lys Lys Arg Gly Leu Phe Gly Ala Ile Ala Gly Phe Ile Glu Gly
385                 390                 395                 400
Gly Trp Gln Gly Met Val Asp Gly Trp Tyr Gly Tyr His His Ser Asn
                405                 410                 415
Glu Gln Gly Ser Gly Tyr Ala Ala Asp Lys Glu Ser Thr Gln Lys Ala
            420                 425                 430
Ile Asp Gly Val Thr Asn Lys Val Asn Ser Ile Ile Asp Lys Met Asn
            435                 440                 445
Thr Gln Phe Glu Ala Val Gly Arg Glu Phe Asn Asn Leu Glu Arg Arg
        450                 455                 460
Ile Glu Asn Leu Asn Lys Lys Met Glu Asp Gly Phe Leu Asp Val Trp
465                 470                 475                 480
Thr Tyr Asn Ala Glu Leu Leu Val Leu Met Glu Asn Glu Arg Thr Leu
                485                 490                 495
Asp Phe His Asp Ser Asn Val Lys Asn Leu Tyr Asp Lys Val Arg Leu
            500                 505                 510
Gln Leu Arg Asp Asn Ala Lys Glu Leu Gly Asn Gly Cys Phe Glu Phe
        515                 520                 525
Tyr His Lys Cys Asp Asn Glu Cys Met Glu Ser Val Arg Asn Gly Thr
530                 535                 540
Tyr Asp Tyr Pro Gln Tyr Ser Glu Glu Ala Arg Leu Lys Arg Glu Glu
545                 550                 555                 560
Ile Ser Gly Val Lys Leu Glu Ser Ile Gly Ile Tyr Gln Ile Leu Ser
                565                 570                 575
Ile Tyr Ser Thr Val Ala Ser Ser Leu Ala Leu Ala Ile Met Val Ala
            580                 585                 590
Gly Leu Ser Leu Trp Met Cys Ser Asn Gly Ser Leu Gln Cys Arg
        595                 600                 605

<210> SEQ ID NO 184
<211> LENGTH: 1731
<212> TYPE: DNA
<213> ORGANISM: Artificial Sequence
<220> FEATURE:
<223> OTHER INFORMATION: Synthetic HA foldon sequence

<400> SEQUENCE: 184
atgaagttgt gcatcttgct ggccgtcgtg gccttcgtgg gcctgtcgct gggcatgaag      60
caccaacacc aacatcaaca tcaacatcaa catcaagccc ccgatcaaat ttgtataggt     120
taccatgcga acaatagcac ggaacaagta gataccatta tggaaaagaa cgtgacagtt     180
acacatgcgc aggacatttt ggaaaaaaag cacaatggaa agttgtgtga tcttgacggg     240
gtcaaaccac taatcttacg tgactgttca gtggcgggtt ggttgttagg caacccgatg     300
tgcgatgaat ttattaatgt accggagtgg tcatatatcg tggaaaaagc caaccccgtt     360
aacgacttgt gttatcctgg tgattttaat gactacgagg aattaaaaca cttgctgtca     420
cgtatcaatc actttgagaa aatacaaata atccccaaat cttcctggag tagccatgag     480
gcttcgttgg gcgtgagtag cgcctgcccc taccaaggca atcgagtttt tttccgaaac     540
gtggtatggc taataaaaaa gaactcgacg tacccgacga tcaaaagatc gtataacaat     600
```

```
acgaaccagg aagacttgct tgtcttgtgg ggtatccacc atccgaacga cgccgctgaa    660
cagacaaaat tatatcaaaa ccccactacc tacatttcag taggcacgag tacgctgaac    720
cagcgccttg tgccacgaat agccactagg tctaaggtta atggccagtc tggtcgcatg    780 gaattttct ggactatact caaacctaac gatgctatca actttgagtc taatggcaac     840
tttattgccc ctgaatacgc gtataagatt gttaaaaagg gcgattcgac gattatgaaa    900
tcggaactcg aatatggtaa ttgcaacacc aaatgtcaaa ctcccatggg cgctattaac    960
agctccatgc catttcacaa tattcacccg ttgactatag gcgaatgtcc aaaatatgtg   1020
aagtccaatc gcttggtact cgccaccggc ttgaggaata gcccgcaacg tgagagacgg   1080
agaaaaaagc ggggattgtt tggcgccatc gccggattta tagaaggtgg ctggcaagga   1140
atggtggatg gctggtatgg ataccaccat tccaacgaac aaggttcagg ctacgcggca   1200
gacaaagaat ctactcaaaa agcaatagac ggcgtgacaa ataaagtaaa tagtataatt   1260
gacaaaatga atcgcagtt tgaagccgtc ggccgtgagt tcaataacct ggagcgcaga    1320
attgaaaatc taaacaaaaa gatggaggac gggtttttag acgtttggac gtacaatgca   1380
gaattgttag ttttgatgga aaacgaacgc accttggatt ttcacgactc gaacgttaaa   1440
aacctgtacg ataaagtccg actgcaatta cgcgataatg caaagaact gggaaacggc    1500 tgcttcgaat tttatcataa atgcgacaat gaatgcatgg aatctgtacg aaatggtaca   1560
tacgactatc cccaatactc ggaggaagcg cgtctaaaac gcgaagagat tagcagtggc   1620
cgcctggtgc cccgcggcag ccccggcagc ggctacatcc ccgaggcccc ccgcgatggc   1680
caggcctacg tgcgcaagga tggcgagtgg gtgctgctga gcaccttcct g            1731
```

<210> SEQ ID NO 185
<211> LENGTH: 577
<212> TYPE: PRT
<213> ORGANISM: Artificial Sequence
<220> FEATURE:
<223> OTHER INFORMATION: Synthetic HA foldon sequence

<400> SEQUENCE: 185

```
Met Lys Leu Cys Ile Leu Leu Ala Val Val Ala Phe Val Gly Leu Ser
1               5                   10                  15

Leu Gly Met Lys His Gln His Gln His Gln His Gln His Gln His Gln
                20                  25                  30

Ala Pro Asp Gln Ile Cys Ile Gly Tyr His Ala Asn Asn Ser Thr Glu
            35                  40                  45

Gln Val Asp Thr Ile Met Glu Lys Asn Val Thr Val Thr His Ala Gln
        50                  55                  60

Asp Ile Leu Glu Lys Lys His Asn Gly Lys Leu Cys Asp Leu Asp Gly
65                  70                  75                  80

Val Lys Pro Leu Ile Leu Arg Asp Cys Ser Val Ala Gly Trp Leu Leu
                85                  90                  95

Gly Asn Pro Met Cys Asp Glu Phe Ile Asn Val Pro Glu Trp Ser Tyr
            100                 105                 110

Ile Val Glu Lys Ala Asn Pro Val Asn Asp Leu Cys Tyr Pro Gly Asp
        115                 120                 125

Phe Asn Asp Tyr Glu Glu Leu Lys His Leu Leu Ser Arg Ile Asn His
    130                 135                 140

Phe Glu Lys Ile Gln Ile Ile Pro Lys Ser Ser Trp Ser Ser His Glu
145                 150                 155                 160

Ala Ser Leu Gly Val Ser Ser Ala Cys Pro Tyr Gln Gly Lys Ser Ser
```

```
                  165                 170                 175
        Phe Phe Arg Asn Val Val Trp Leu Ile Lys Lys Asn Ser Thr Tyr Pro
                      180                 185                 190

Thr Ile Lys Arg Ser Tyr Asn Thr Asn Gln Glu Asp Leu Leu Val
                      195                 200                 205

Leu Trp Gly Ile His His Pro Asn Asp Ala Ala Glu Gln Thr Lys Leu
                      210                 215                 220

Tyr Gln Asn Pro Thr Thr Tyr Ile Ser Val Gly Thr Ser Thr Leu Asn
        225                 230                 235                 240

Gln Arg Leu Val Pro Arg Ile Ala Thr Arg Ser Lys Val Asn Gly Gln
                            245                 250                 255

Ser Gly Arg Met Glu Phe Phe Trp Thr Ile Leu Lys Pro Asn Asp Ala
                        260                 265                 270

Ile Asn Phe Glu Ser Asn Gly Asn Phe Ile Ala Pro Glu Tyr Ala Tyr
                        275                 280                 285

Lys Ile Val Lys Lys Gly Asp Ser Thr Ile Met Lys Ser Glu Leu Glu
                        290                 295                 300

Tyr Gly Asn Cys Asn Thr Lys Cys Gln Thr Pro Met Gly Ala Ile Asn
        305                 310                 315                 320

Ser Ser Met Pro Phe His Asn Ile His Pro Leu Thr Ile Gly Glu Cys
                            325                 330                 335

Pro Lys Tyr Val Lys Ser Asn Arg Leu Val Leu Ala Thr Gly Leu Arg
                        340                 345                 350

Asn Ser Pro Gln Arg Glu Arg Arg Lys Lys Arg Gly Leu Phe Gly
                        355                 360                 365

Ala Ile Ala Gly Phe Ile Glu Gly Gly Trp Gln Gly Met Val Asp Gly
                        370                 375                 380

Trp Tyr Gly Tyr His His Ser Asn Glu Gln Gly Ser Gly Tyr Ala Ala
        385                 390                 395                 400

Asp Lys Glu Ser Thr Gln Lys Ala Ile Asp Gly Val Thr Asn Lys Val
                        405                 410                 415

Asn Ser Ile Ile Asp Lys Met Asn Thr Gln Phe Glu Ala Val Gly Arg
                        420                 425                 430

Glu Phe Asn Asn Leu Glu Arg Arg Ile Glu Asn Leu Asn Lys Lys Met
                        435                 440                 445

Glu Asp Gly Phe Leu Asp Val Trp Thr Tyr Asn Ala Glu Leu Leu Val
                        450                 455                 460

Leu Met Glu Asn Glu Arg Thr Leu Asp Phe His Asp Ser Asn Val Lys
        465                 470                 475                 480

Asn Leu Tyr Asp Lys Val Arg Leu Gln Leu Arg Asp Asn Ala Lys Glu
                        485                 490                 495

Leu Gly Asn Gly Cys Phe Glu Phe Tyr His Lys Cys Asp Asn Glu Cys
                        500                 505                 510

Met Glu Ser Val Arg Asn Gly Thr Tyr Asp Tyr Pro Gln Tyr Ser Glu
                        515                 520                 525

Glu Ala Arg Leu Lys Arg Glu Glu Ile Ser Ser Gly Arg Leu Val Pro
                        530                 535                 540

Arg Gly Ser Pro Gly Ser Gly Tyr Ile Pro Glu Ala Pro Arg Asp Gly
        545                 550                 555                 560

Gln Ala Tyr Val Arg Lys Asp Gly Glu Trp Val Leu Leu Ser Thr Phe
                        565                 570                 575

Leu
```

```
<210> SEQ ID NO 186
<211> LENGTH: 16
<212> TYPE: PRT
<213> ORGANISM: Influenza A virus

<400> SEQUENCE: 186

Pro Gln Arg Glu Arg Arg Arg Lys Lys Arg Gly Leu Phe Gly Ala Ile
1               5                   10                  15

<210> SEQ ID NO 187
<211> LENGTH: 12
<212> TYPE: PRT
<213> ORGANISM: Artificial Sequence
<220> FEATURE:
<223> OTHER INFORMATION: Mutated Influenza A Virus polybasic cleavage
      site

<400> SEQUENCE: 187

Pro Gln Arg Glu Thr Gln Gly Leu Phe Gly Ala Ile
1               5                   10

<210> SEQ ID NO 188
<211> LENGTH: 15
<212> TYPE: PRT
<213> ORGANISM: Artificial Sequence
<220> FEATURE:
<223> OTHER INFORMATION: Synthetic TEV protease cleavage site

<400> SEQUENCE: 188

Asp Tyr Asp Ile Pro Thr Thr Glu Asn Leu Tyr Phe Gln Gly Ala
1               5                   10                  15

<210> SEQ ID NO 189
<211> LENGTH: 23
<212> TYPE: PRT
<213> ORGANISM: Artificial Sequence
<220> FEATURE:
<223> OTHER INFORMATION: Influenza epitope

<400> SEQUENCE: 189

Ser Leu Leu Thr Glu Val Glu Thr Pro Thr Arg Asn Glu Trp Gly Cys
1               5                   10                  15

Arg Cys Asn Asp Ser Ser Asp
                20

<210> SEQ ID NO 190
<211> LENGTH: 23
<212> TYPE: PRT
<213> ORGANISM: Artificial Sequence
<220> FEATURE:
<223> OTHER INFORMATION: Influenza epitope

<400> SEQUENCE: 190

Ser Leu Leu Thr Glu Val Glu Thr Pro Ile Arg Asn Glu Trp Gly Cys
1               5                   10                  15

Arg Cys Asn Gly Ser Ser Asp
                20

<210> SEQ ID NO 191
<211> LENGTH: 23
<212> TYPE: PRT
<213> ORGANISM: Artificial Sequence
<220> FEATURE:
<223> OTHER INFORMATION: Influenza epitope

<400> SEQUENCE: 191
```

Ser Leu Leu Thr Glu Val Glu Thr Pro Ile Arg Asn Glu Trp Gly Cys
1               5                   10                  15

Arg Cys Asn Asp Ser Asn Asp
            20

<210> SEQ ID NO 192
<211> LENGTH: 23
<212> TYPE: PRT
<213> ORGANISM: Artificial Sequence
<220> FEATURE:
<223> OTHER INFORMATION: Influenza epitope

<400> SEQUENCE: 192

Ser Leu Leu Thr Glu Val Glu Thr Pro Thr Arg Asn Gly Trp Glu Cys
1               5                   10                  15

Lys Cys Ser Asp Ser Ser Asp
            20

<210> SEQ ID NO 193
<211> LENGTH: 23
<212> TYPE: PRT
<213> ORGANISM: Artificial Sequence
<220> FEATURE:
<223> OTHER INFORMATION: Influenza epitope

<400> SEQUENCE: 193

Ser Leu Leu Thr Glu Val Glu Thr Leu Thr Arg Asn Gly Trp Glu Cys
1               5                   10                  15

Lys Cys Ser Asp Ser Ser Asp
            20

<210> SEQ ID NO 194
<211> LENGTH: 23
<212> TYPE: PRT
<213> ORGANISM: Artificial Sequence
<220> FEATURE:
<223> OTHER INFORMATION: Influenza epitope

<400> SEQUENCE: 194

Ser Leu Leu Thr Glu Val Glu Thr Pro Thr Arg Asn Gly Trp Glu Cys
1               5                   10                  15

Lys Cys Ser Asp Ser Ser Glu
            20

<210> SEQ ID NO 195
<211> LENGTH: 23
<212> TYPE: PRT
<213> ORGANISM: Artificial Sequence
<220> FEATURE:
<223> OTHER INFORMATION: Influenza epitope

<400> SEQUENCE: 195

Ser Leu Leu Thr Glu Val Glu Thr Leu Thr Arg Asn Gly Trp Glu Cys
1               5                   10                  15

Lys Cys Arg Asp Ser Ser Asp
            20

<210> SEQ ID NO 196
<211> LENGTH: 23
<212> TYPE: PRT
<213> ORGANISM: Artificial Sequence
<220> FEATURE:
<223> OTHER INFORMATION: Influenza epitope

```
<400> SEQUENCE: 196

Ser Leu Leu Thr Glu Val Glu Thr Pro Thr Arg Asn Gly Trp Glu Cys
1               5                   10                  15

Lys Cys Asn Asp Ser Ser Asp
            20

<210> SEQ ID NO 197
<211> LENGTH: 23
<212> TYPE: PRT
<213> ORGANISM: Artificial Sequence
<220> FEATURE:
<223> OTHER INFORMATION: Influenza epitope

<400> SEQUENCE: 197

Ser Leu Leu Thr Glu Val Glu Thr Pro Ile Arg Asn Gly Trp Glu Cys
1               5                   10                  15

Lys Cys Asn Asp Ser Ser Asp
            20

<210> SEQ ID NO 198
<211> LENGTH: 23
<212> TYPE: PRT
<213> ORGANISM: Artificial Sequence
<220> FEATURE:
<223> OTHER INFORMATION: Influenza epitope

<400> SEQUENCE: 198

Ser Leu Leu Thr Glu Val Glu Thr Pro Ile Arg Ser Gly Trp Glu Cys
1               5                   10                  15

Lys Cys Asn Asp Ser Ser Asp
            20

<210> SEQ ID NO 199
<211> LENGTH: 23
<212> TYPE: PRT
<213> ORGANISM: Artificial Sequence
<220> FEATURE:
<223> OTHER INFORMATION: Influenza epitope

<400> SEQUENCE: 199

Ser Leu Leu Thr Glu Val Glu Thr Pro Thr Lys Asn Glu Trp Glu Cys
1               5                   10                  15

Lys Cys Ser Asp Ser Ser Asp
            20

<210> SEQ ID NO 200
<211> LENGTH: 23
<212> TYPE: PRT
<213> ORGANISM: Artificial Sequence
<220> FEATURE:
<223> OTHER INFORMATION: Influenza epitope

<400> SEQUENCE: 200

Ser Leu Leu Thr Glu Val Glu Thr Pro Thr Arg Asn Gly Trp Glu Cys
1               5                   10                  15

Ser Cys Ser Asp Ser Ser Asp
            20

<210> SEQ ID NO 201
<211> LENGTH: 23
<212> TYPE: PRT
<213> ORGANISM: Artificial Sequence
<220> FEATURE:
<223> OTHER INFORMATION: Influenza epitope
```

-continued

<400> SEQUENCE: 201

Ser Leu Leu Thr Glu Val Glu Thr Pro Thr Arg Asn Gly Trp Glu Cys
1               5                   10                  15

Arg Cys Ser Asp Ser Ser Asp
            20

<210> SEQ ID NO 202
<211> LENGTH: 23
<212> TYPE: PRT
<213> ORGANISM: Artificial Sequence
<220> FEATURE:
<223> OTHER INFORMATION: Influenza epitope

<400> SEQUENCE: 202

Val Leu Leu Thr Glu Val Glu Thr Pro Thr Arg Asn Gly Trp Glu Cys
1               5                   10                  15

Arg Tyr Ser Asp Ser Asn Asp
            20

<210> SEQ ID NO 203
<211> LENGTH: 23
<212> TYPE: PRT
<213> ORGANISM: Artificial Sequence
<220> FEATURE:
<223> OTHER INFORMATION: Influenza epitope

<400> SEQUENCE: 203

Ser Leu Leu Thr Glu Val Glu Thr Pro Thr Arg Asn Gly Trp Glu Cys
1               5                   10                  15

Arg Tyr Ser Gly Ser Ser Asp
            20

<210> SEQ ID NO 204
<211> LENGTH: 23
<212> TYPE: PRT
<213> ORGANISM: Artificial Sequence
<220> FEATURE:
<223> OTHER INFORMATION: Influenza epitope

<400> SEQUENCE: 204

Ser Leu Leu Thr Glu Val Glu Thr Pro Thr Arg Asn Gly Trp Glu Cys
1               5                   10                  15

Arg Cys Ser Asp Leu Ser Asp
            20

<210> SEQ ID NO 205
<211> LENGTH: 23
<212> TYPE: PRT
<213> ORGANISM: Artificial Sequence
<220> FEATURE:
<223> OTHER INFORMATION: Influenza epitope

<400> SEQUENCE: 205

Ser Leu Leu Thr Glu Val Glu Thr Leu Thr Arg Asn Gly Trp Glu Cys
1               5                   10                  15

Arg Cys Ser Gly Ser Ser Asp
            20

<210> SEQ ID NO 206
<211> LENGTH: 23
<212> TYPE: PRT
<213> ORGANISM: Artificial Sequence
<220> FEATURE:

```
<223> OTHER INFORMATION: Influenza epitope

<400> SEQUENCE: 206

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 207
<211> LENGTH: 23
<212> TYPE: PRT
<213> ORGANISM: Artificial Sequence
<220> FEATURE:
<223> OTHER INFORMATION: Influenza epitope

<400> SEQUENCE: 207

Ser Leu Leu Thr Glu Val Glu Thr His Thr Arg Asn Glu Trp Glu Cys
1               5                   10                  15

Arg Cys Ser Asp Ser Ser Asp
            20

<210> SEQ ID NO 208
<211> LENGTH: 23
<212> TYPE: PRT
<213> ORGANISM: Artificial Sequence
<220> FEATURE:
<223> OTHER INFORMATION: Influenza epitope

<400> SEQUENCE: 208

Ser Leu Leu Thr Glu Val Glu Thr Pro Thr Arg Asn Glu Trp Glu Cys
1               5                   10                  15

Arg Tyr Ser Asp Ser Ser Asp
            20

<210> SEQ ID NO 209
<211> LENGTH: 23
<212> TYPE: PRT
<213> ORGANISM: Artificial Sequence
<220> FEATURE:
<223> OTHER INFORMATION: Influenza epitope

<400> SEQUENCE: 209

Ser Leu Leu Thr Glu Val Glu Thr Leu Thr Arg Asn Gly Trp Gly Cys
1               5                   10                  15

Arg Cys Ser Asp Ser Ser Asp
            20

<210> SEQ ID NO 210
<211> LENGTH: 23
<212> TYPE: PRT
<213> ORGANISM: Artificial Sequence
<220> FEATURE:
<223> OTHER INFORMATION: Influenza epitope

<400> SEQUENCE: 210

Ser Leu Leu Thr Glu Val Glu Thr His Thr Arg Asn Gly Trp Gly Cys
1               5                   10                  15

Arg Cys Ser Asp Ser Ser Asp
            20

<210> SEQ ID NO 211
<211> LENGTH: 23
<212> TYPE: PRT
<213> ORGANISM: Artificial Sequence
```

```
<220> FEATURE:
<223> OTHER INFORMATION: Influenza epitope

<400> SEQUENCE: 211

Ser Leu Leu Thr Glu Val Glu Thr Pro Thr Arg Asn Gly Trp Gly Cys
1               5                   10                  15

Arg Cys Ser Gly Ser Ser Asp
            20

<210> SEQ ID NO 212
<211> LENGTH: 23
<212> TYPE: PRT
<213> ORGANISM: Artificial Sequence
<220> FEATURE:
<223> OTHER INFORMATION: Influenza epitope

<400> SEQUENCE: 212

Ser Leu Leu Thr Glu Val Glu Thr Pro Thr Arg Asn Gly Trp Gly Cys
1               5                   10                  15

Arg Tyr Ser Asp Ser Ser Asp
            20

<210> SEQ ID NO 213
<211> LENGTH: 36
<212> TYPE: PRT
<213> ORGANISM: Artificial Sequence
<220> FEATURE:
<223> OTHER INFORMATION: Influenza epitope

<400> SEQUENCE: 213

Ala Lys Phe Val Ala Ala Trp Thr Leu Lys Ala Ala Ala Ser Leu Leu
1               5                   10                  15

Thr Glu Val Glu Thr Pro Ile Arg Asn Glu Trp Gly Cys Arg Cys Asn
            20                  25                  30

Asp Ser Ser Asp
        35

<210> SEQ ID NO 214
<211> LENGTH: 36
<212> TYPE: PRT
<213> ORGANISM: Artificial Sequence
<220> FEATURE:
<223> OTHER INFORMATION: Influenza epitope

<400> SEQUENCE: 214

Ala Lys Phe Val Ala Ala Trp Thr Leu Lys Ala Ala Ala Ser Leu Leu
1               5                   10                  15

Thr Glu Val Glu Thr Pro Thr Arg Asn Glu Trp Glu Cys Arg Cys Ser
            20                  25                  30

Asp Ser Ser Asp
        35

<210> SEQ ID NO 215
<211> LENGTH: 36
<212> TYPE: PRT
<213> ORGANISM: Artificial Sequence
<220> FEATURE:
<223> OTHER INFORMATION: Influenza epitope

<400> SEQUENCE: 215

Ala Lys Phe Val Ala Ala Trp Thr Leu Lys Ala Ala Ala Ser Leu Leu
1               5                   10                  15

Thr Glu Val Glu Thr Pro Thr Arg Asn Gly Trp Glu Cys Arg Cys Ser
```

```
<210> SEQ ID NO 216
<211> LENGTH: 36
<212> TYPE: PRT
<213> ORGANISM: Artificial Sequence
<220> FEATURE:
<223> OTHER INFORMATION: Influenza epitope

<400> SEQUENCE: 216

Ala Lys Phe Val Ala Ala Trp Thr Leu Lys Ala Ala Ser Leu Le